US012571000B2

(12) United States Patent
Chuah et al.

(10) Patent No.: US 12,571,000 B2
(45) Date of Patent: Mar. 10, 2026

(54) DIAPHRAGM-SPECIFIC NUCLEIC ACID REGULATORY ELEMENTS AND METHODS AND USE THEREOF

(71) Applicant: VRIJE UNIVERSITEIT BRUSSEL, Brussels (BE)

(72) Inventors: Lay Khim Chuah, Bierbeek (BE); Thierry Vandendriessche, Bierbeek (BE); Warut Tulalamba, Brussels (BE)

(73) Assignee: VRIJE UNIVERSITEIT BRUSSEL, Brussell (BE)

( * ) Notice: Subject to any disclaimer, the term of this patent is extended or adjusted under 35 U.S.C. 154(b) by 23 days.

(21) Appl. No.: 18/417,465

(22) Filed: Jan. 19, 2024

(65) Prior Publication Data

US 2024/0327864 A1 Oct. 3, 2024

Related U.S. Application Data

(62) Division of application No. 16/498,690, filed as application No. PCT/EP2018/057753 on Mar. 27, 2018, now Pat. No. 11,920,149.

(30) Foreign Application Priority Data

Mar. 27, 2017 (EP) .................................... 17163080

(51) Int. Cl.

| | |
|---|---|
| *C12N 15/86* | (2006.01) |
| *A61K 48/00* | (2006.01) |
| *A61P 21/00* | (2006.01) |
| *C12N 9/26* | (2006.01) |

(52) U.S. Cl.
CPC .............. *C12N 15/86* (2013.01); *A61K 48/00* (2013.01); *A61P 21/00* (2018.01); *C12N 9/2408* (2013.01); *C12Y 302/0102* (2013.01); *C12N 2750/14143* (2013.01); *C12N 2800/22* (2013.01); *C12N 2830/008* (2013.01)

(58) Field of Classification Search
None
See application file for complete search history.

(56) References Cited

U.S. PATENT DOCUMENTS

| | | | |
|---|---|---|---|
| 7,655,700 | B2 | 2/2010 | Jordan et al. |
| 2007/0161031 | A1 | 7/2007 | Trinklein |

FOREIGN PATENT DOCUMENTS

| | | |
|---|---|---|
| JP | 2009-519710 | 5/2009 |
| JP | 2017-505126 | 2/2017 |
| JP | 2017-521492 | 8/2017 |
| WO | 2007/025269 | 3/2007 |
| WO | 2007/078599 | 7/2007 |
| WO | 2008/073303 | 6/2008 |
| WO | 2015/110449 | 7/2015 |
| WO | 2015/197869 | 12/2015 |
| WO | 2016/016119 | 2/2016 |

OTHER PUBLICATIONS

Sato et al., "Resequencing of the common marmoset genome improves genome assemblies and gene-coding sequence analysis", Scientific Reports, 2015, vol. 5, No. 1, pp. 1-8.
Sequence 1 from Jordan et al., "Transgenic mouse model and methods for treatment of neuro muscular disease by interfering with androgen-androgen receptor interaction in skeletal muscles", U.S. Pat. No. 7,655,700, issued Feb. 2, 2010, 2 pages.
Sequence from Slepak et al., "Control of cardiac-specific transcription by p300 through myocyte enhancer factor-2D", Journal of Biological Chemistry, 2000, vol. 276, No. 10, pp. 7575-7585, 1 page.
Sequence 4138 from Trinklein et al., "Functional Arrays for High Throughput Characterization of Gene Expression Regulatory Elements", EP Patent 2021499 published as WO 2007/078599 (cited above), 2013, 1 page.
"Alpha-actin promoter-Vp16-Bagly gene fusion", SEQ ID 84, Mar. 24, 2016. 2 pages.
"Human DNA sequence from clone RP5-1068B5 on chromosome 1q42. 11-43", Mar. 8, 2000, 2 pages.
"Human transcriptional regulatory element SEQ ID No. 7044", Dec. 11, 2008, 3 pages.
Bishopric et al., "Adrenergic regulation of the skeletal a-actin gene promoter during myocardial cell hypertrophy", Proceedings National Academy of Sciences PNAS, 1991, vol. 88, No. 6, pp. 2132-2136.
"Callithrix jacchus DNA, clone: CJB1-183K21, sequence_id: CJB1-183K21.b.", Aug. 25, 2015, 2 pages.
Mogalle et al., "Quantification of Diaphragm Mechanics in Pompe Disease Using Dynamic 3D MRI", PLOS ONE, 2016, vol. 11, No. 7, pp. 1-24.
International Search Report issued Jul. 23, 2018 in International (PCT) Application No. PCT/EP2018/057753.
Slepak et al., "Control of Cardiac-specific Transcription by p300 through Myocyte Enhancer Factor-2D", Journal of Biological Chemistry, 2000, vol. 276, No. 10, pp. 7575-7585.
Rasowo et al., European Scientific Journal, Jun. 2-14, 10(18):23-37. (Year:2014).
Stuart et al., Am J Physiol Cell Physiol. Mar. 1, 2-16; 310(5): C381-C389. (Year: 2016).
Wei et al., Gene, May 2016, 582(1): 1-13. (Year: 2016).
International Preliminary Report on Patentability issued Oct. 10, 2019 in International Application No. PCT/EP2018/057753.

(Continued)

*Primary Examiner* — Nicole Kinsey White
(74) *Attorney, Agent, or Firm* — Porter Wright Morris & Arthur LLP

(57) ABSTRACT

The present invention relates to nucleic acid regulatory elements that are able to enhance diaphragm-specific expression of genes, in particular expression in diaphragm as such, or in combination with expression in cardiac muscle and/or skeletal muscle, methods employing these regulatory elements and uses of these elements. Expression cassettes and vectors containing these nucleic acid regulatory elements are also disclosed. The present invention is particularly useful for applications using gene therapy, more particularly diaphragm-directed gene therapy, and for vaccination purposes.

19 Claims, 31 Drawing Sheets

Specification includes a Sequence Listing.

(56)　　　　　　References Cited

OTHER PUBLICATIONS

Office Action issued Mar. 8, 2022 in corresponding Japanese Patent Application No. 2019-553082, with English Translation, 12 pages.
Jaenecke and Diaz, Int Microbiol, Mar. 1999, 2(1):29-32. (Year: 1999).
Powell et al., Discov Med., Jan. 2015, 19(102):49-57. (Year: 2015).

A

B

C

D

E

F

G

TNNT1

H

TNNI2

I

J

K

L

M

MYBPC1

N

ENO3

O

P

Q

A

MYL2

B

MB

C

D

E

F

G

ALDOA

H

TPM1

SEQUENCE LISTING

```
Sequence total quantity: 147
SEQ ID NO: 1             moltype = DNA  length = 328
FEATURE                  Location/Qualifiers
misc_feature             1..328
```

```
                         note = Dph-CRE01
source                   1..328
                         mol_type = other DNA
                         organism = synthetic construct
SEQUENCE: 1
ggagacactc catatacggc ccggcccgcg ttacctggga ccgggccaac ccgctccttc   60
tttggtcaac gcaggggacc cgggcggggg cccaggccgc gaaccggccg agggaggggg  120
ctctagtgcc caacacccaa atatggctcg agaagggcag cgacattcct gcggggtggc  180
gcggagggaa tgcccgcggg ctatataaaa cctgagcaga gggacaagcg gccaccgcag  240
cggacagcgc caagtgaagc ctcgcttccc ctccgcggcg accagggccc gagccgagag  300
tagcagttgt agctacccgc ccaggtag                                      328

SEQ ID NO: 2               moltype = DNA   length = 452
FEATURE                    Location/Qualifiers
misc_feature               1..452
                           note = Dph-CRE02
source                     1..452
                           mol_type = other DNA
                           organism = synthetic construct
SEQUENCE: 2
gacaggtgcg gttcccggag cgcaggcgca cacatgcacc caccggcgaa cgcggtgacc   60
ctcgccccac cccatcccct ccggcggggca actgggtcgg gtcaggaggg gcaaacccgc  120
tagggagaca ctccatatac ggcccggccc gcgttacctg ggaccgggcc aacccgctcc  180
ttctttggtc aacgcagggg acccgggcgg gggcccaggc cgcgaaccgg ccgagggagg  240
gggctctagt gcccaacacc caaatatggc tcgagaaggg cagcgacatt cctgcggggt  300
ggcgcggagg gaatgcccgc gggctatata aaacctgagc agagggacaa gcggccaccg  360
cagcggacag cgccaagtga agcctcgctt ccctccgcg gcgaccaggg cccgagccga  420
gagtagcagt tgtagctacc cgcccaggta gg                                 452

SEQ ID NO: 3               moltype = DNA   length = 239
FEATURE                    Location/Qualifiers
misc_feature               1..239
                           note = Dph-CRE03
source                     1..239
                           mol_type = other DNA
                           organism = synthetic construct
SEQUENCE: 3
agagagaggg acaggcacca actgggtaac ctctgctgac ccccactcta ctttaccata   60
agtagctcca aatccttcta gaaaatctga aaggcatagc cccatatatc agtgatataa  120
atagaacctg cagcaggctc tggtaaatga tgactacaag gtggactggg aggcagcccg  180
gccttggcag gcatcatcct ctaaatataa agatgagttt gttcagcctt tgcagaagg   239

SEQ ID NO: 4               moltype = DNA   length = 509
FEATURE                    Location/Qualifiers
misc_feature               1..509
                           note = Dph-CRE04
source                     1..509
                           mol_type = other DNA
                           organism = synthetic construct
SEQUENCE: 4
cctttagag aatccacacc tgtcccagtt gctgggttcc actaccaaaa gtgaattgca    60
actattttag gagcacttaa gcacatccga aaaatgagtg attctgttct ggcccacacc  120
acatcactga tgtacccct taaagcatgt ccctgagttc atcacagaag actgctcctc   180
ctgtgccctc cacaaggtta gaactgtcct tgtcttaggg aaaaaggaga gagagagaga  240
gagagagaga gagagagaga gagagagaga caggcaccaa ctgggtaacc                300
tctgctgacc cccactctac tttaccataa gtagctccaa atccttctag aaaatctgaa  360
aggcatagcc ccatatatca gtgatataaa tagaacctgc agcaggctct ggtaaatgat  420
gactacaagg tggactggga ggcagcccgg ccttggcagg catcatcctc taaatataaa  480
gatgagtttg ttcagccttt gcagaagga                                     509

SEQ ID NO: 5               moltype = DNA   length = 169
FEATURE                    Location/Qualifiers
misc_feature               1..169
                           note = Dph-CRE05
source                     1..169
                           mol_type = other DNA
                           organism = synthetic construct
SEQUENCE: 5
cctttagag aatccacacc tgtcccagtt gctgggttcc actaccaaaa gtgaattgca    60
actattttag gagcacttaa gcacatccga aaaatgagtg attctgttct ggcccacacc  120
acatcactga tgtacccct taaagcatgt ccctgagttc atcacagaa                 169

SEQ ID NO: 6               moltype = DNA   length = 400
FEATURE                    Location/Qualifiers
misc_feature               1..400
                           note = Dph-CRE06
source                     1..400
                           mol_type = other DNA
                           organism = synthetic construct
```

-continued

```
SEQUENCE: 6
gggccagggg acggtggctt ctacgtgctt gggacgttcc cagccaccgt cccatgttcc      60
cggcgggggg ccagctgtcc ccaccgccag cccaactcag cacttggtca gggtatcagc     120
ttggtgggg gggcgtgagcc cagccctgg ggcggctcag cccatacaag gccatggggc      180
tgggcgcaaa gcatgcctgg gttcagggtg ggtatggtgc gggagcaggg aggtgagagg     240
ctcagctgcc ctccagaact cctccctggg gacaacccct cccagccaat agcacagcct     300
aggtcccct atataaggcc acggctgctg gcccttcctt tgggtcagtg tcacctccag      360
gatacagaca gcccccttc agcccagccc agccaggtac                           400

SEQ ID NO: 7              moltype = DNA   length = 255
FEATURE                   Location/Qualifiers
misc_feature             1..255
                          note = Dph-CRE07
source                   1..255
                          mol_type = other DNA
                          organism = synthetic construct
SEQUENCE: 7
cccagccccc ttcccggga ggtgggagcg gccacccagg gccccgtggc tgcccttgta       60
aggaggcgag gcccgaggac acccgagacg cccggttata attaaccagg acacgtggcg     120
aacccccctc caacacctgc ccccgaaccc ccccataccc agcgcctcgg gtctcggcct     180
ttgcggcaga ggagacagca aagcgccctc taaaaataac tcctttcccg gcgaccgaga     240
ccctccctgt ccccc                                                     255

SEQ ID NO: 8              moltype = DNA   length = 354
FEATURE                   Location/Qualifiers
misc_feature             1..354
                          note = Dph-CRE08
source                   1..354
                          mol_type = other DNA
                          organism = synthetic construct
SEQUENCE: 8
ctcctgggct cgagcaattc tcctgccttg acctcccaaa gtgctgggat tacaggcatg       60
agccactaca ccctgcccta gtgtgcttta tatcaaaggg gaaaccattt ggggcttcca     120
aacaggaaat gaacagtcgt accttttgtc ctcactaaca ttcagattgc aggaatgccg     180
tgtcccatag ggaaagagaa attcctgagg caagtgtcat atctgaactt gagatagtca     240
ccttccaggc agaaagctac acccgcctct tttcccagcc tctggcatca gctgccggcg     300
gtgtgggtaa gggatgcaaa gaactcaaaa catgtagcca ggattcccca tttg          354

SEQ ID NO: 9              moltype = DNA   length = 297
FEATURE                   Location/Qualifiers
misc_feature             1..297
                          note = Dph-CRE09
source                   1..297
                          mol_type = other DNA
                          organism = synthetic construct
SEQUENCE: 9
tgacaagcac aagtgtcccc ggcccaagca ccgcagagag cgcgcagcat ctctcccgt        60
gaccatgacc cagctactgc ctctttaacc ttgaatgcct ttttgggggc tcacgtgtca     120
cccagtggcg agtgagccac ccttacttca gaagaacggc atggggtggg ggggccttag     180
gtggtgcccc cctcacctat gactgccaaa agcggtcatg gggttatttt taaacatggg     240
gaggaagtat ttattgttcc tgggctgcag agagctgggc ggagtgtgga attcttc        297

SEQ ID NO: 10             moltype = DNA   length = 608
FEATURE                   Location/Qualifiers
misc_feature             1..608
                          note = Dph-CRE10
source                   1..608
                          mol_type = other DNA
                          organism = synthetic construct
SEQUENCE: 10
actcagggta aactgaggca ctcaaactgc cgaggagctc cgcctcccga gagacattta       60
atccgggggg atttgcagga aacttctaaa ttaagggtag cggctgctgc agctgagggg     120
gggcacgccg gtccctgcgc ccgggcagct gccgtgagct cacgcccga aatagcccca      180
ggggccccag ccgcagctgc cactgggtcc ggctgtcact cagaggaagc acggagcccc     240
cagcccaagg gtccctccc cttcgcatcg ccggggtttt tccagccgac cgtcggccac      300
tttttcctcc gacggctggc agggaagagg gggatggggg cgggacccca agggaggcgg     360
tccccagtgg gtgggcgaag ggggcggccg cacccccccgg ccgggccgtg cttctgcccc     420
tacaaggttt gggccgaggt gggggaggggt cctggttgcc ggccccgccc ggtccctccc     480
cgccttttag gcgcccgcgt ggcgggacg tcccagtccc gctccgtcct cctcgcctgc      540
caccggtgca cccagtccgc tcacccagcc cagtccgtcc ggtcctcacc gcctgccggc     600
cggcccac                                                             608

SEQ ID NO: 11             moltype = DNA   length = 308
FEATURE                   Location/Qualifiers
misc_feature             1..308
                          note = Dph-CRE11
source                   1..308
                          mol_type = other DNA
                          organism = synthetic construct
```

-continued

```
SEQUENCE: 11
tttttcctcc gacggctggc agggaagagg gggatggggg cgggacccca agggaggcgg    60
tccccagtgg gtgggcgaag ggggcggccg caccccccgg ccgggccgtg cttctgcccc   120
tacaaggttt gggccgaggt gggggagggt cctggttgcc ggccccgccc ggtccctccc   180
cgccttttag gcgcccgcgt ggccgggacg tcccagtccc gctccgtcct cctcgcctgc   240
caccggtgca cccagtccgc tcacccagcc cagtccgtcc ggtcctcacc gcctgccggc   300
cggcccac                                                            308

SEQ ID NO: 12            moltype = DNA   length = 263
FEATURE                  Location/Qualifiers
misc_feature            1..263
                         note = Dph-CRE12
source                  1..263
                         mol_type = other DNA
                         organism = synthetic construct
SEQUENCE: 12
gactcagggt aaactgaggc actcaaactg ccgaggagct ccgcctcccg agagacattt    60
aatccggggg gatttgcagg aaacttctaa attaagggta gcggctgctg cagctgaggg   120
ggggcacgcc ggtccctgcg cccgggcagc tgccgtgagc tcacgccccg aaatagcccc   180
aggggcccca gccgcagctg ccactgggtc cggctgtcac tcagaggaag cacggagccc   240
ccagcccaag ggtcccctcc cct                                           263

SEQ ID NO: 13            moltype = DNA   length = 324
FEATURE                  Location/Qualifiers
misc_feature            1..324
                         note = Dph-CRE13
source                  1..324
                         mol_type = other DNA
                         organism = synthetic construct
SEQUENCE: 13
ctcagggaat gagctggata caactaaaaa tcagcacatt tttgtttggt taaaacattc    60
tttgtggtca atttctttct aacagatcga gttctctaag gaacagcagg atggtaagtt   120
taaaagctat ggttcttaaa tgtgcacact cataaagatg gcatgtgtga aaaccaactc   180
ccttgggatg agtttagctc ttcctaatta tccccactgg tgttgccatt ctgaatataa   240
attgctctcg atcactctaa atataaatta gctcaatctg aaacccttgc tgatactcag   300
taatcaaagg tttaacaaac aaaa                                          324

SEQ ID NO: 14            moltype = DNA   length = 326
FEATURE                  Location/Qualifiers
misc_feature            1..326
                         note = Dph-CRE14
source                  1..326
                         mol_type = other DNA
                         organism = synthetic construct
SEQUENCE: 14
catttagtta aatcattaag atgcagaaag atattcccta attatctttt gcaatagctt    60
tttatgttcc tagattcaaa agtatcctaa ggcaaccttc taatgccaag acacctacat   120
agcttcctaa aaatctcaga gcaaccagca ctcattcttc tgtcaatgca tttgaaaagat   180
tactagtttt ttttctttct ttctcttctt cgccactgca gtccttcagt gctgaccaga   240
ttgctggtaa gtgaattgag tttgtctgct acagatgtag gcacagcact gcctagtttc   300
tgcaatatta cttatcttca aggcat                                        326

SEQ ID NO: 15            moltype = DNA   length = 596
FEATURE                  Location/Qualifiers
misc_feature            1..596
                         note = Dph-CRE15
source                  1..596
                         mol_type = other DNA
                         organism = synthetic construct
SEQUENCE: 15
tttgtttgtt aaacctttga ttactgagta tcagcaaggg tttcagattg agctaattta    60
tatttagagt gatcgagagc aatttatatt cagaatggca acaccagtgg ggataattag   120
gaagagctaa actcatccca agggagttgg ttttcacaca tgccatcttt atgagtgtgc   180
acatttaaga accatagctt ttaaacttac catcctgctg ttccttagag aactcgatct   240
gttagaaaga aattgaccac aaagaatgtt ttaaccaaac aaaaatgtgc tgattttttag   300
ttgtatccag ctcattccct gagtaatctt caaagtaagc tccaaaagtc agcctacttt   360
tcagagttca ggcgtagctt ggacactaac aggttaagcc atagtgtaac atgccttgaa   420
gataagtaat attgcagaaa ctaggcagtg ctgtgcctac atctgtagca gacaaactca   480
attcacttac cagcaatctg gtcagcactg aaggactgca gtggcgaaga agagaaagaa   540
agaaaaaaaa ctagtactct ttcaaatgca ttgacagaag aatgagtgct ggttgc       596

SEQ ID NO: 16            moltype = DNA   length = 290
FEATURE                  Location/Qualifiers
misc_feature            1..290
                         note = Dph-CRE16
source                  1..290
                         mol_type = other DNA
                         organism = synthetic construct
SEQUENCE: 16
```

-continued

```
agaccataaa agtaccggca ggcttccatc tcactatggc tgtctactcc aaggttctgg    60
tcatctaaaa atagctctca gggtacagat ccatctttcc ctttgcccta agaaagctaa   120
agaactctcc aagggtgtg gcaacttatc tctgaaacct gatgctagct gtgaggtcaa    180
agcttgccca gaaataaaag gaagcctcag ccagggatga ccccactcag ggaccggagc   240
agccctcaac tcactcttca gcttccctgc tgtgttgcag cccagccgct              290

SEQ ID NO: 17            moltype = DNA   length = 632
FEATURE                  Location/Qualifiers
misc_feature             1..632
                         note = Dph-CRE17
source                   1..632
                         mol_type = other DNA
                         organism = synthetic construct
SEQUENCE: 17
gtgctcccta gaagggaagc cactttaaga catgatgggc tttccttata cgtctgcttt    60
tttattttta accaccacca cctctttgct gaccaacatt tccttgcaaa ttatggcaag   120
ggggggaggag catgagcaaa ggagctgtgt gaaagttggt gatactccct gccaaaattc   180
caagttgaaa tggaatcctt cagtaaagtc tcttaggcaa ggtgggaaaa aaagatttac   240
aacttcagca gaactgtaat ctaccaaga aaaagtacag tcaatctacc tcactgtcac   300
caaaggatct gaagctggct ttgtcatata tctttctcct ttatatatgg aggtgggggg   360
gggagaaaaa aaggaaagag agttaaaaaa aattgatgaa gccctgaccc tttagattcc   420
atttatagtc tgagccggaa tgccatcccc cttgactaga gactgtcca atccagccgc   480
atgtgtcaag attctattag gcactaagtg aaatatatat gcatgccctt atgccgttta   540
acactctggg tccatcttca agacactggg ctgtggatca acccaaccac cactcctctt   600
ccaagaatca ttttgacagg ttcttttgga gg                                 632

SEQ ID NO: 18            moltype = DNA   length = 297
FEATURE                  Location/Qualifiers
misc_feature             1..297
                         note = Dph-CRE18
source                   1..297
                         mol_type = other DNA
                         organism = synthetic construct
SEQUENCE: 18
cctttgactt ttcttgaaag gggagggctg ggatattcca gagattgatc cttaaggctt    60
gctgactgcc tactcacttc tggaaacttc cagcagtgtc attcatagac ctgtgaagag   120
ctcttagctt gtttccttca cacagtgggg actctgaggg gtcagagtga gtcacccagc   180
aggccagtgg caggggtgag ccagaagcct ggccaaaccc tcctatcatc atggagagaa   240
gaaagcctcc tccagaagac gggaggccgg caggcgtgg ggcctgctca gatgcag       297

SEQ ID NO: 19            moltype = DNA   length = 309
FEATURE                  Location/Qualifiers
misc_feature             1..309
                         note = Dph-CRE19
source                   1..309
                         mol_type = other DNA
                         organism = synthetic construct
SEQUENCE: 19
ggaacagggc aggccttcct cacaagaatc taggacgtca aggcctgcca cctgcttgga    60
ggcttaaatt tctctgcaag ggcccttggc taaattaggt aatgggttca gactgtggga   120
ggggtgggac tcgctgaccc caggatctga ttgggcaggg tctccagtgc tggggagcag   180
ggaggtggga ggggagggtg cccctacaaa tcccgggggc tagagcaggc caggtcatct   240
ttgggtggtg gagtgcaaag gaggcgacct gcaacagagg agtcccggtc accagcaacc   300
atggtaagg                                                           309

SEQ ID NO: 20            moltype = DNA   length = 267
FEATURE                  Location/Qualifiers
misc_feature             1..267
                         note = Dph-CRE20
source                   1..267
                         mol_type = other DNA
                         organism = synthetic construct
SEQUENCE: 20
aattgtgaca tttaagcagt gactttgcaa aattggacgt gtcagtagga aaaagtactc    60
ttcccacctt aaagattgac aggaacatga gatggctgaa gctgttctga gcttttttct   120
ggcaagagta cataggacaa gaaatactct ggagagctca acattgaatc acatcatatc   180
atagtgcatg actagttgcc ttaatcttgc agttggactc actcaggaga aattgttggc   240
agagggatta agtagcctga caaaatt                                       267

SEQ ID NO: 21            moltype = DNA   length = 493
FEATURE                  Location/Qualifiers
misc_feature             1..493
                         note = Dph-CRE21
source                   1..493
                         mol_type = other DNA
                         organism = synthetic construct
SEQUENCE: 21
cttttctttt ctaattaggt cagttacttc atgtctgttt ttctttttg acatggtttc     60
ttctggcttt ggcaccacat attttcccca tatgtcattg cctctggagc ttcatgttgc   120
```

```
aatagttttt caaggggaac ggagagcaca ttgctaaggg tgggggatgg cttttgcctc    180
ttttgcctgc cctttgcttc agtgagtgtt cgtatttctg ttgggcctag ttctgtttgg    240
ttttgtagtc ttcagagtca gttatgtttg gactgaaaga tacttaagta aaaataatgg    300
caagtcagag atatgtctgg caaaggtgca gcacatttgt taaggttact ggtttattta    360
tctcccttgt ctctatggtg actaaatctg ggtctgggat ttaatggact tagttttgac    420
ctcttgtaac atctcctaac ttttcccagc ctctgattta gaaagaattc attttcactt    480
gaggagagaa act                                                       493

SEQ ID NO: 22            moltype = DNA   length = 197
FEATURE                  Location/Qualifiers
misc_feature             1..197
                         note = Dph-CRE22
source                   1..197
                         mol_type = other DNA
                         organism = synthetic construct
SEQUENCE: 22
tcatttgttt tgattacccg ggtgattgcc aaatgttaat ttaaaactga aataggccat    60
gagctcactc ccctaacaat gctgagtgtt tgagctaata cggcttgata atgagggagc    120
cagatccact gccagtgctc atgttatatg ataaacagac atttggagaa gtatgcagaa    180
catcttggca gttttcc                                                   197

SEQ ID NO: 23            moltype = DNA   length = 637
FEATURE                  Location/Qualifiers
misc_feature             1..637
                         note = Dph-CRE23
source                   1..637
                         mol_type = other DNA
                         organism = synthetic construct
SEQUENCE: 23
aaaaattggc tttaaggtca tgagcctcct tacagcagtc cctctcacct tcagctgtat    60
tccctatttc agatatactt gtttctctgc tgtaagtaca cttttctttt ctaattaggt    120
cagttacttc atgtctgttt ttcttttttg acatggtttc ttctggcttt ggcaccacat    180
attttcccca tatgtcattg cctctggagc ttcatgttgc aatagttttt caaggggaac    240
ggagagcaca ttgctaaggg tgggggatgg cttttgcctc ttttgcctgc cctttgcttc    300
agtgagtgtt cgtatttctg ttgggcctag ttctgtttgg ttttgtagtc ttcagagtca    360
gttatgtttg gactgaaaga tacttaagta aaaataatgg caagtcagag atatgtctgg    420
caaaggtgca gcacatttgt taaggttact ggtttattta tctcccttgt ctctatggtg    480
actaaatctg ggtctgggat ttaatggact tagttttgac ctcttgtaac atctcctaac    540
ttttcccagc ctctgattta gaaagaattc attttcactt gaggagagaa actgtctcac    600
ttagaaaagg ggtcctaact ggactctcga aaagtgg                             637

SEQ ID NO: 24            moltype = DNA   length = 561
FEATURE                  Location/Qualifiers
misc_feature             1..561
                         note = Dph-CRE24
source                   1..561
                         mol_type = other DNA
                         organism = synthetic construct
SEQUENCE: 24
gtctgcatcc taatcctgct gttgattgga gataacttca gcggtcacag ggcacctcgt    60
ctccatggca acccctctaa atattcctct agtgacttgt gctctacatt ctggctggat    120
cagagccctc ctgtggcaaa atattctaaa gatgttaaaa gagagagaga gaaaaaaaaa    180
ggctcaacta ataaatctat tctaaacgac tgagtcattt gttttgatta cccgggtgat    240
tgccaaatgt taatttaaaa ctgaaatagg ccatgagctc actcccctaa caatgctgag    300
tgtttgagct aatacggctt gataatgagg gagccagatc cactgccagt gctcatgtta    360
tatgataaac agacatttgg agaagtatgc agaacatctt ggcagttttc ctttaactct    420
aagggttgta aatacaaagt agaatgtgtt accatgagcc atttcatagg aagttgactt    480
tattttttta gaattcagaa ctttgcttct aaaaaggtaa ctttgcctct tgattctcat    540
ttttttccct aacttaggca c                                              561

SEQ ID NO: 25            moltype = DNA   length = 511
FEATURE                  Location/Qualifiers
misc_feature             1..511
                         note = Dph-CRE25
source                   1..511
                         mol_type = other DNA
                         organism = synthetic construct
SEQUENCE: 25
aaagacaggg aggtgcaatc taagttagga aattggtgac aaatagtcat agaacatggg    60
tcacctggct tcaattagtt atgtgacctt taagaaaaca agtgcccgtt tcagaaaaga    120
ctgacctttg aggctagaga catcaagcta ctcctctact tttaggaaaa aacaatgaca    180
gggttaattt aaaactctga tgcagacaga gttgaaaaat ccatgacaga tttatataac    240
gaacgtggat ggtgtttttgt tttcccagaa tgcagtttta aggtcagacc tatgactcag    300
agctgcgcac ttccctggtg gtatgcatca gtgacatgtt gccagtctaa tcgtccagaa    360
gggcttgtgc ccagctcggc ttgctccatt ataatcccca gctgagaagc cacctttcat    420
ttttttttaaa tagataagga agacagcatg aacatttgaa actcaaatac tatatgtagt    480
ttataacttt tcagcctgaa gacttgatgc a                                   511

SEQ ID NO: 26            moltype = DNA   length = 399
```

```
FEATURE           Location/Qualifiers
misc_feature      1..399
                  note = Dph-CRE26
source            1..399
                  mol_type = other DNA
                  organism = synthetic construct
SEQUENCE: 26
aatgcagcat accagtgaag ttgctaatta cattgaatca ttctgtacac gttctatttt     60
gaagggaaaa aacactttct gattttttgta tgaaattgta tgaaagacta cttttcagcc    120
gtgactcatg agctccgtct cattgcagct acttaggtat ttattcccaa atgtctgacg    180
acacctccag gtgcattagc atgtctatta cacaagtgtc ctattcattg gctaaggctt    240
tgctccatct gttgaatgtt ctgaggaaag cattataccc tttctttaga agccagtgtt    300
tatatgtgga gtcactaatg tactggtagg ttggatttag tgaagaacag atctgaaata    360
acctgatttt tttccatttg ggttgttgtt cattgttta                          399

SEQ ID NO: 27     moltype = DNA   length = 360
FEATURE           Location/Qualifiers
misc_feature      1..360
                  note = Dph-CRE27
source            1..360
                  mol_type = other DNA
                  organism = synthetic construct
SEQUENCE: 27
cccaaccttt gaatgtatat gggggagaaa ataacagaca aggttggagg cgaagataag     60
gggggatggg gtggtgcttc tccgcaaaca tccaacccttt ctgtaaagat tcctccagac    120
tggggaagaa ggcttgggtg tcggtccctt taagaaggaa gggaaagggt taaagccact    180
gcggggccat ttccttccc ggccccgaga gggcgcagga gctctcaggg gcttaaagga    240
ccgggcctgg gggcggggtta tggggcggga gggaggggaa ggtggtcttg gaggttgggg    300
cccgaggata tcgggggtcc ccccgggccc ccgacatcgg tctcgggaag cgaagcagcc    360

SEQ ID NO: 28     moltype = DNA   length = 471
FEATURE           Location/Qualifiers
misc_feature      1..471
                  note = Dph-CRE28
source            1..471
                  mol_type = other DNA
                  organism = synthetic construct
SEQUENCE: 28
ctcaccttcc tcctcctcct ccgcagcctc ctctggagat ggggggcacag aagagaaggc    60
gttaggagct gggggaggga tggggggcggt ggccagagac cagggttcca gtctctgctg    120
gacgggggtc cctctggcct cggctgcgat gggcacgttc ccctggcgg tgcagggatg    180
gcgcgaggag acgctccaga cccggagagg gcgggcgagg gcccgaggggc tgagccgccc    240
cttcccgcc aaagtgccac actcctcgcc tcccctccca agagctcctg ggcgtgtccg    300
catcccatag ggccggccca ctccctactc accttccggc tgctccctgc ggacgggtgt    360
ggggagagag gagggagggg agagttagac ctggggtggg agagcctctc caccactgca    420
cgccccaacc cctcccagtg cagcactcac tcctcatatt cctgctcctc g             471

SEQ ID NO: 29     moltype = DNA   length = 393
FEATURE           Location/Qualifiers
misc_feature      1..393
                  note = Dph-CRE29
source            1..393
                  mol_type = other DNA
                  organism = synthetic construct
SEQUENCE: 29
ggccgcctgg gaagaccggg gaggtggggg ccagagagtc gggaccacat gggatggggc    60
gggctagagc cagccctgta gggacagagt gggcaatggt gtctgggggc tggtgagcat    120
ggagggagga cccccaacac ctcagagacc tgtgctgcag ggccttccct gcatgagcag    180
caggggggcag cagatgccatt cggaagccgc tggggccttt aggggctcag tcctggccgg    240
atgcccctcc cagtccccac acatctgggc tgccttagcg tgctggggcct ccacgctgct    300
gtctcctctg atcctcccca cggggctgcg aagccggcag ggctggggcc aagagccccc    360
actccgagag ggtgccaagt cacggtccag ggg                                393

SEQ ID NO: 30     moltype = DNA   length = 331
FEATURE           Location/Qualifiers
misc_feature      1..331
                  note = Dph-CRE30
source            1..331
                  mol_type = other DNA
                  organism = synthetic construct
SEQUENCE: 30
ctgtcctcag gctccttacg agaacgacag aggcatctcc agcgcgtcac cgagccctaa    60
atagagtagc ccagccacgg caccccccac caagacttct tggactgggc ggcagcacgc    120
ggccaggcca ggccgccgga caggtggggga ggtctctgtg gctctccacg cccccattgg    180
tctgaggagg actctatgcc ctttctgagc aggggcccag cctggggggag gccatttata    240
cccctccccc tgggcccacc agccaactc gccgctgccg gcctgacctc gctcccagcc    300
ctgctgccca gattctaggt gaggcccagc c                                  331

SEQ ID NO: 31     moltype = DNA   length = 306
```

```
FEATURE              Location/Qualifiers
misc_feature         1..306
                     note = Dph-CRE31
source               1..306
                     mol_type = other DNA
                     organism = synthetic construct
SEQUENCE: 31
gctcccccaa ctcagcatag gtcataggtc acagcctcaa ggccctaagg cccagagaag   60
atggcctggc cctccccgct ggcaaaagtg ccccacccac ccaccaagac gctgctgaaa  120
gagaggaagt ggctgcccca agccttctgg ggcaggggaa gtgtggctgt ggcctggtca  180
caggggaatc acttcttctt tctgattcct gcacttcccg cccccacctc accggccgac  240
ctgcccccaa ctggccctcc tctccccag cctctggcct cccagcacca tgtgccacct  300
ggcaaa                                                             306

SEQ ID NO: 32        moltype = DNA   length = 268
FEATURE              Location/Qualifiers
misc_feature         1..268
                     note = Dph-CRE32
source               1..268
                     mol_type = other DNA
                     organism = synthetic construct
SEQUENCE: 32
aactctggca cattccagcc cctctttggg agaaagaaca tctcttcttg cccaggccct   60
agtgagacat gcatcgcaag acatgctccc cccttcctcc ccgctgggct ccagctgctg  120
ccagccctcc aagaaaggag aggccctgag ttgggctatt ttggtatctg gggtgggcac  180
ccgcagggct aaggttacct tggtatgtta agggctccct ggggcaggac tatataaccc  240
cagagggact gccccatgct gactcctt                                     268

SEQ ID NO: 33        moltype = DNA   length = 214
FEATURE              Location/Qualifiers
misc_feature         1..214
                     note = Dph-CRE33
source               1..214
                     mol_type = other DNA
                     organism = synthetic construct
SEQUENCE: 33
tacctggtgc aggccctcga ggccgctggt gcctgctctg tgcagtccct gctacgcctc   60
aggcccagcg cccgagggg aggtcgccga tacccaaaat aaaacctgcc ctatccctct   120
gacctcagct ggctgggcgg agagcgcctg ccaaagctcc aggagctggg cgggcagcac  180
cttcccctgc tggccacacg gggccagtgc aggg                              214

SEQ ID NO: 34        moltype = DNA   length = 129
FEATURE              Location/Qualifiers
misc_feature         1..129
                     note = Dph-CRE34
source               1..129
                     mol_type = other DNA
                     organism = synthetic construct
SEQUENCE: 34
tcttgggttt ctgggcagaa acgtcttgcc tatttctgga cacctcagct gccactggct   60
ccttataaat aacccacccc aggcgagggc cacgctgccc ccatcttgtg gcagccgaca  120
ggtgtctgc                                                          129

SEQ ID NO: 35        moltype = DNA   length = 403
FEATURE              Location/Qualifiers
misc_feature         1..403
                     note = Dph-CRE35
source               1..403
                     mol_type = other DNA
                     organism = synthetic construct
SEQUENCE: 35
ttacctggtg caggccctcg aggccgctgg tgcctgctct gtgcagtccc tgctacgcct   60
caggcccagc gcccgagggg gaggtcgccg atacccaaaa taaaacctgc cctatccctc  120
tgacctcagc tggctgggcg gagagcgcct gccaaagctc caggagctgg gcgggcagca  180
ccttcccctg ctggccacac ggggccagtg caggttatg gcacaccac cttcaggtgc   240
gcccctcagg accctggcc tgggtgaggg cttgggtggg cacaggcttc ctaggcctgc   300
agactgaacc acgtgtaacc agaatggtgg gctcagggct ccgttagaga agccggcaga  360
gcgagcctgg aaaaggaggt tggccccacc atgggagagg atg                    403

SEQ ID NO: 36        moltype = DNA   length = 415
FEATURE              Location/Qualifiers
misc_feature         1..415
                     note = Dph-CRE36
source               1..415
                     mol_type = other DNA
                     organism = synthetic construct
SEQUENCE: 36
agagtgaatg catgggaatg aatagatggg tggatgaatg acaactgtg tgaaatagca    60
gacagcctgg ggacaccctc cctcctgtcc ctcctctccc aggtcttgca ctgggccctg   120
```

-continued

```
acactcagcc ctgcagcctt cagcgtctgg gaagtccctt cgaggagcag caccccagac   180
tctgatgttc tggacttcac tttgccattc ccttgggtcc tcacagccac tattttctga   240
aggcttcatg tcaaaccctg cttgcctcat gaatacacac agttcagaaa agcaaaacct   300
cgacagagcc accacccaca caagggaggt gacgtgcccc catcctttct cagatgcccc   360
agccactgag agaggatcca ggccaccctc cccagctggg gaaccaccca gtgac        415

SEQ ID NO: 37           moltype = DNA   length = 352
FEATURE                 Location/Qualifiers
misc_feature            1..352
                        note = Dph-CRE37
source                  1..352
                        mol_type = other DNA
                        organism = synthetic construct
SEQUENCE: 37
accaatctgt gcctgaaccg aagagttccg cagacaccac cgcccacgct cagcctgtgg   60
ggtctgaggg gagtgagggg gtgggtcagg gtgccagact gctctccccc acctggtgcc   120
tcagtttccc tgatccaaga ggcagggtta tccaatctgg tggcctcact ggccagcata   180
caggccatca gaggccagga aggatgtctg ctagtcggac ggtgccacct ggagtcctga   240
ggaaagaaaa ccagtctcca cacgccacaa tgagcctgtg ggagatgctg gcacagatgg   300
taacggccac tgcgagtgcc cagggtgggg ccccagggtt agaaagggcc ta            352

SEQ ID NO: 38           moltype = DNA   length = 349
FEATURE                 Location/Qualifiers
misc_feature            1..349
                        note = Dph-CRE38
source                  1..349
                        mol_type = other DNA
                        organism = synthetic construct
SEQUENCE: 38
ctcctcagcc catccagaat gtacccgctg ctgggagtaa aaatagcagc tgacacctcc   60
tggaggcgga gggaggacct tgcctccttc tccaagcacg tcctctgcat cctggcctcc   120
ttcagcctcc tcctctggcc attcctatac ttggtaaggg gcctgcacgg gcatagcccc   180
ccccagcaag actccgcaca caccccggcc acccagtcac tggccaatgg gctcctagga   240
agatcaaatg tcactataac acgagggtgt gagccgggcg ccagtgcctg cagccggtgc   300
tgtccacagg gagctccagc ccttctcaca ctcgacccgc aggtgggta              349

SEQ ID NO: 39           moltype = DNA   length = 380
FEATURE                 Location/Qualifiers
misc_feature            1..380
                        note = Dph-CRE39
source                  1..380
                        mol_type = other DNA
                        organism = synthetic construct
SEQUENCE: 39
taactatgtt taatgtgctg agagaaagcc atttgtttac agaatcttat tatagaacag   60
aaatatactt gttccagaga agaggagttt aattggttcc aagtcaaatg atgctaacag   120
gcgtcacctc accaatccag gacttaagat gggttattat aaataggagt aacacatatt   180
ttttttggct cttttttccca cctgttatgc aagactgcat accactatga tgttcctcct   240
gattatttcc agcaactttg ggggtggctc acgtgtgctc atgaacaagt actgtcaggt   300
atcacatacg gtctgtcatt ttcttgctct tgagctctgg cacttctctg ctgctgtctg   360
ctgctgaggc ctgcagagat                                            380

SEQ ID NO: 40           moltype = DNA   length = 575
FEATURE                 Location/Qualifiers
misc_feature            1..575
                        note = Dph-CRE40
source                  1..575
                        mol_type = other DNA
                        organism = synthetic construct
SEQUENCE: 40
ttctctctca ctgtaaaagt gtaaaaggtt aggttactcc ccagcctgtc gaacatgtgc   60
ctgattgcct tctgagatag cacatcccta atccaaaaga aaacctagcc tggagcttgc   120
atccagctaa tcttcttcca cattgctcca aacagggagt tcagtttttct cattactcat   180
acagagagca gagatagatt ttcatgattc ttcaggactc tgttctctct gctttaatag   240
ccaaaagcta aagccaaatg aacttcttca cagagaacaa caagcaattt tatctaatcc   300
ttattattct tgctgtaact gcaattgtgt tattctgact gacagattcc cagaagagat   360
tcagtgaaaa taccctttgat cagattcaca aaggaacagc atatttcaag tgggcgtgtc   420
tggctagaat ctccctggac agttcagtaa cagcacatca acagactgct gaattcttat   480
ttccccgtcc aaaaaataac aaagccaatc tgaaatctgg aagtgttctg agggcagatg   540
gtattagccc agtagtaaac atatttttgg ctgct                           575

SEQ ID NO: 41           moltype = DNA   length = 463
FEATURE                 Location/Qualifiers
misc_feature            1..463
                        note = Dph-CRE41
source                  1..463
                        mol_type = other DNA
                        organism = synthetic construct
SEQUENCE: 41
```

-continued

```
ctacaataaa tatataactt ttttaatttg acaaaaaata attttgagtg gttacaaaaa    60
gggacaggtg tggcttggta actagaaaaa cattcccagc ctgggaaaca atctagtgag   120
agcttggagg cagaagacag aactctgatt acattcaagg agtttgccag atggcaacag   180
ataactgcca atgttcggtt gcactataat tattatacac tctctgtcac ttcagcaagc   240
gctcttttca caagacaagt ggtgacagaa tgttgtatta agattacccg ttgctaagct   300
tatgttaaaa tgaggaaatg aaatggaaag tcttgttttg gtaatgtctc tggggtatga   360
ggaatggagg gaaaggtttg actatgagca taactgcata gagaattttg tttgtttatg   420
ccttttggga atgcattatt ttgattgacc ctaattggga att                    463

SEQ ID NO: 42             moltype = DNA   length = 379
FEATURE                   Location/Qualifiers
misc_feature              1..379
                          note = Dph-CRE42
source                    1..379
                          mol_type = other DNA
                          organism = synthetic construct
SEQUENCE: 42
attcatgaag atgtaaaaga cacatttaaa acccacatca attgcactaa aagtcaactg    60
gaaacagaag gtttttaaat cctggtggtg gcaaattggc agccaaagga acaaagtctt   120
agtcaacata tttccatgtc ccccgaacac aaatagcctc gaaccttcgg agggtgttcc   180
tttgagatgt ttcatcagtg acatcacagt gattgccagc ttccacggac tactttaggc   240
gctgcccaga gtccaggagt ccagacagcc tgggagggga gaaggagttg gagctcaagt   300
tggagacagc gaggagaaac ctgccatagc cagggtgtgt ctttgatcct cttcaggtaa   360
ctgcaggatt tttatgcttt                                               379

SEQ ID NO: 43             moltype = DNA   length = 250
FEATURE                   Location/Qualifiers
misc_feature              1..250
                          note = Dph-CRE43
source                    1..250
                          mol_type = other DNA
                          organism = synthetic construct
SEQUENCE: 43
aagaaggaat accctagggc aaatgcgtgc tagaggggct taatacttgg cagaatcctt    60
ctttttcagt agcctgcttt tatgactgct ccgactgcac ctgttaggaa gataaataaa   120
ggactggcca attctttcct ctgaagcgcc ctaaatatat cactttaaaa agactttgga   180
aaaacaagtt gtatccttac ttctcaccca gtaaatctaa agaaattccc tcttgttccc   240
aggcctttca                                                          250

SEQ ID NO: 44             moltype = DNA   length = 194
FEATURE                   Location/Qualifiers
misc_feature              1..194
                          note = Dph-CRE44
source                    1..194
                          mol_type = other DNA
                          organism = synthetic construct
SEQUENCE: 44
ccacataact aaagcatgat gctattgagt tctaagtcta gtttccaccc ttatatgaaa    60
agtcagcttg gcacagagtt tggtagagct aagtctgacc agctgcactc tcagccacaa   120
gggaaattag acgagacagt gtggctgctt cagtaccaat caatcaaagt ttttgaaaat   180
tatcttgaaa acac                                                     194

SEQ ID NO: 45             moltype = DNA   length = 264
FEATURE                   Location/Qualifiers
misc_feature              1..264
                          note = Dph-CRE45
source                    1..264
                          mol_type = other DNA
                          organism = synthetic construct
SEQUENCE: 45
actttctctg tggattgcaa tatttcctgg catatgttca cttcagtaag acgatcagtg    60
tattaaaaac ccaatggggt ttctgcagaa gccaatgatg gcatggcacc tcttttgtgg   120
catgtgtgaa atctgccctt cgctgtaaac attcttatgc aacatgacac tctgccctat   180
gtccatttca tatgtggtgt tcagtgtgct gggaatgctg aaaaaaacaa ttctctctta   240
gagatttccc aagtagaatc acag                                          264

SEQ ID NO: 46             moltype = DNA   length = 427
FEATURE                   Location/Qualifiers
misc_feature              1..427
                          note = Dph-CRE46
source                    1..427
                          mol_type = other DNA
                          organism = synthetic construct
SEQUENCE: 46
agaaggaata ccctagggca aatgcgtgct agaggggctt aatacttggc agaatccttc    60
tttttcagta gcctgctttt atgactgctc cgactgcacc tgttaggaag ataaataaag   120
gactggccaa ttctttcctc tgaagcgccc taaatatatc actttaaaaa gactttggaa   180
aaacaagttg tatccttact tctcacccag taaatctaaa gaaattccct cttgttccca   240
ggcctttcaa acagtgaagt caggagtaag ggagactgtg gactggtcaa aggtggaagt   300
```

-continued

```
tagactcact agctggtcta aggaatccag gagggtggaa aacatgaaga acttacaatc  360
ctttatgctc tcaatgactc actttatttt ggccatgaga cacagccttg aaactttttt  420
ttttttt                                                            427

SEQ ID NO: 47          moltype = DNA   length = 436
FEATURE                Location/Qualifiers
misc_feature           1..436
                       note = Dph-CRE47
source                 1..436
                       mol_type = other DNA
                       organism = synthetic construct
SEQUENCE: 47
ggtcataaaa tactttctct gtggattgca atatttcctg gcatatgttc acttcagtaa  60
gacgatcagt gtattaaaaa cccaatgggg tttctgcaga agccatgat ggcatggcac   120
ctcttttgtg gcatgtgtga aatctgccct tcgctgtaaa cattcttatg caacatgaca  180
ctctgcccta tgtccatttc atatgtggtg ttcagtgtgc tgggaatgct gaaaaaaaca  240
attctctctt agagatttcc caagtagaat cacagtgtta aacctatcag cagcctccaa  300
gatcattttt tttaagcccc tcattttaca caaaaagaaa ctgaggccca gaaagccccc  360
tgactttctc agagtaacta agctggttaa tgatagatcc agaaatagaa cccaagggac  420
caacttcaga ttctag                                                  436

SEQ ID NO: 48          moltype = DNA   length = 359
FEATURE                Location/Qualifiers
misc_feature           1..359
                       note = Dph-CRE48
source                 1..359
                       mol_type = other DNA
                       organism = synthetic construct
SEQUENCE: 48
ctgagtcagc acatgcatct gtcagagaga gaagagcaag acggagcacg aggctgcagc  60
tgaatttaga aagttagagg tgttctcatc agccacatga gatgggcagg agattccttc   120
cagtaggcga gagagcagag tgcagacaac agatgtgaga aaggtcccca tagctgtcaa  180
gttcctgcat ccttgtgctg aagaaaggga ggtgccatca tgattgatgt tcagaggcag  240
tataaaagca ctgggtttct ccccaactgc ttgtcacacc gacctgcacc atctctcgcc  300
tgcctgtggg gtttctgtca actagtcgtg gagggaagga gactctttaa agaataaca   359

SEQ ID NO: 49          moltype = DNA   length = 353
FEATURE                Location/Qualifiers
misc_feature           1..353
                       note = Dph-CRE49
source                 1..353
                       mol_type = other DNA
                       organism = synthetic construct
SEQUENCE: 49
gagatttcat cacattttaa agttttgcca agccaaaaag ctacctgaat gtagagcagc  60
attcatcccc tcttgcctat ttctaagcat ttctcagggc ttagtcatcc atcagaaaag   120
gacctccctt gatgggaaaa ctccttctca tatctcttct ttgaccttca gtttctacct  180
gcaagagagt gaatggccta tttcaaacac cgaaatcaat ttgtctttgg aaagtcatct  240
tatatacaaa tattatcctt acctcaaatt ggggaaaggt taataattta tgcagaaaac  300
taagagaaag gaatagggga ggaggaaaga tagtttatca agggcaattg ttt          353

SEQ ID NO: 50          moltype = DNA   length = 354
FEATURE                Location/Qualifiers
misc_feature           1..354
                       note = Dph-CRE50
source                 1..354
                       mol_type = other DNA
                       organism = synthetic construct
SEQUENCE: 50
tcaaaagtct tttaaacata ttttctttat ataattaagt aaccagtgtt gacaggctgt  60
ggtgatcagt ttacaggttg gccttactta gtggcagagg gcattgatgg atgaagtctt   120
tcacccaaaa taaccacacc aaatgcatgt attaatatgg gaacttaatc ctgactgtca  180
ggcagggagt ccaacccctg ctaaagtatc ttatttgtaa tgcaaatgat ttacgtgtgt  240
actaagtgtc cttttatct gctctgtcac tttaacctct ccgaagtgta cccagaagca   300
atacattcta ccatgtttcc aaactggaaa cacaatattg ttttaattat tctg         354

SEQ ID NO: 51          moltype = DNA   length = 351
FEATURE                Location/Qualifiers
misc_feature           1..351
                       note = Dph-CRE51
source                 1..351
                       mol_type = other DNA
                       organism = synthetic construct
SEQUENCE: 51
gctgtcccag cgttatcagt cgggcgcctt gccagccgaa agggcctgtc taaattcgtt  60
tcctgtcccc taactcatcc cggcgctggc tggcctggag agggtaggat ggggcggcgc   120
cgagaatggc cgttatgagg accctaagag gtgagaccct ctcgccttct gggggtggggg  180
gtcccgtcct ttcccccact gaggacagag gcccgcccag cgatctgagc atgtgtggac  240
gtcaatcttc agcccctct tccaggcccc ctccccagcc ttgcagggct caggttaccc    300
```

-continued

```
ctggcctttc ctaaaggtca ctcattcctc ttgacgtttg caaaaggggg a              351

SEQ ID NO: 52             moltype = DNA   length = 607
FEATURE                   Location/Qualifiers
misc_feature              1..607
                          note = Dph-CRE52
source                    1..607
                          mol_type = other DNA
                          organism = synthetic construct
SEQUENCE: 52
tgtcccagcg ttatcagtcg ggcgccttgc cagccgaaag ggcctgtcta aattcgtttc      60
ctgtcccta  actcatcccg gcgctggctg gcctggagag ggtaggatgg ggcggcgccg      120
agaatggccg ttatgaggac cctaagaggt gagaccctct cgccttctgg ggtgggggt       180
cccgtccttt cccccactga ggacagaggc ccgcccagcg atctgagcat gtgtggacgt      240
caatcttgca gccctcttc  caggcccct  ccccagcctt gcagggctca ggttacccct      300
ggcctttcct aaaggtcact cattcctctt gacgtttgca aaaggggaat gtaatcctgg      360
ggtggggga  gacccctcat ctgtagcccc tcccttgctc ctcccaaagg gtggaattag      420
aacagggact gttattggga gacagaaagt gggggatagt agttgacctt tggtaagggg      480
gcaggtgccc agggccagag gcttctgctt caggctgtag tgggcacttg gctgccagcc      540
cagtgtgaag ggggaggat  ggagagaaag agaggcgggg ctggctgggg accgagtggc      600
tcaggga                                                               607

SEQ ID NO: 53             moltype = DNA   length = 469
FEATURE                   Location/Qualifiers
misc_feature              1..469
                          note = Dph-CRE53
source                    1..469
                          mol_type = other DNA
                          organism = synthetic construct
SEQUENCE: 53
agggctgggc ggcttccgga gcctgggcta ggggcaaggg gtcaccgagc gcggcccggg      60
cggaaagggg gttggtttc  tctctcctcc cgagcgcggc gcgcatccct ggcgtccacg      120
ccgaatccca cagtccccga cgccctcga  gtccgtgttc ctcgacagcc gcgcggctga      180
gtcactggcg ggctcgggcg gggccgcacc cgggcacgtg gcggcgctcc ccgcccgcca      240
tctcctgacc cctggcccac cgcacccta  ccccagggtg gaaaaatccc gggaggagcg      300
gcctgagatg aggggcgggg gcgagagggg agactggacg ggtggcgggg caggtggcct      360
ggggtggggg ctgggaggcc gcgcgggccg gcggggcggg gagcaggggt ggggagaggg      420
cggcgggggt gagtcaccgg gcgcgcgctg ccccggcgcc gacgggaag                 469

SEQ ID NO: 54             moltype = DNA   length = 332
FEATURE                   Location/Qualifiers
misc_feature              1..332
                          note = Dph-CRE54
source                    1..332
                          mol_type = other DNA
                          organism = synthetic construct
SEQUENCE: 54
tgggttcacc agggcccatt ctcagtctag aggattgtcc cttctctgga tcggctctag      60
cccagggcct caccccacat cccagccccg cccgccccag gcaggcaatg tctggatcac      120
cggccgtgcc ccttggcctg tgtctgcaga ggtcacagag cgcggacacc cgcgggcctt      180
aacagggcgg gctatttttc gaggcggaag aatactcaag ttgcaagagt ggcaacttt       240
tcaagaaggg gaaagtccca cttcgggcc  tttgggtttc ttcgcagtca gatgtgcgct      300
cacagccacc tggggagggc gggacgggcg gg                                   332

SEQ ID NO: 55             moltype = DNA   length = 206
FEATURE                   Location/Qualifiers
misc_feature              1..206
                          note = Dph-CRE55
source                    1..206
                          mol_type = other DNA
                          organism = synthetic construct
SEQUENCE: 55
tacattccag ggagggagac cagttgggac aaggcctagg ctgctctcct acaaatttgc      60
catgaacagg agccaaactc taagacctga ttcaagtggc ccagctgtca ctggtgacac      120
actcaggggc tgggcctatc atgttcttat acaacctagt gagtcaagct ttggaaaata      180
acattgtcag ggaagaacgt aaaagt                                          206

SEQ ID NO: 56             moltype = DNA   length = 289
FEATURE                   Location/Qualifiers
misc_feature              1..289
                          note = Dph-CRE56
source                    1..289
                          mol_type = other DNA
                          organism = synthetic construct
SEQUENCE: 56
ggagctgaga gtttaagggc atttgtttac tatgtttgct tggattttcc gaactgcctt      60
agttcctgat tccacactgc tattgtgtgg atcaaataat cccttgtcac aaaaataccc      120
tggggaatga ctccctggc  gtccaggtta tgagtgtggt cagtcattcc acatgcctta      180
gggatgagct atctgtgcca tgacgagcga tttcctttc  gagtttgta  atccccaaat      240
```

-continued

```
actaaatact attatcaata aaagttaatt aaggaaatgt atatcgaaa         289

SEQ ID NO: 57              moltype = DNA   length = 195
FEATURE                    Location/Qualifiers
misc_feature               1..195
                           note = Dph-CRE57
source                     1..195
                           mol_type = other DNA
                           organism = synthetic construct
SEQUENCE: 57
gacagctgtc ccgctcttgg aattcattgg cttcctctac ccggcctccc aaacaccacc    60
ccaatctagt ttagcccccc gccccaccct cgctgaccta ataaggccat gcagtgtgcg   120
ggggagctac ataaaagcgc gggctcgcgg cgactctgca ccacgcaggg gaagagaaag   180
caggagccgt ccagc                                                    195

SEQ ID NO: 58              moltype = DNA   length = 345
FEATURE                    Location/Qualifiers
misc_feature               1..345
                           note = Dph-CRE58
source                     1..345
                           mol_type = other DNA
                           organism = synthetic construct
SEQUENCE: 58
cccctcagct tcagcccca cctccaggag gccctaccca cgctcatgac cttgctattc     60
tgggccttgt gtcctgtagg gagatggaca ggagacagct gggcttccag gccacccagg   120
cgggggggcta gccgagggaa gcctgctggc tctcctgctt gctctaattt ctggggctcc   180
ccaaaccttg gcctcaggag actgggggata ggaccggcct tgaaagtggg ggaagctttg   240
gagagccggg tgctgggttc ttagtgagat ggccagtgaa ggctgtggtg ccccgaggta   300
agcagggcct gatcccctcc taatcttcca gcagcaactg gtgct                   345

SEQ ID NO: 59              moltype = DNA   length = 220
FEATURE                    Location/Qualifiers
misc_feature               1..220
                           note = Dph-CRE59
source                     1..220
                           mol_type = other DNA
                           organism = synthetic construct
SEQUENCE: 59
ctcctccagc agctgccctg gtggtaacca agagacgccc ccatcctgga gcaggggtgg     60
ggaggggcag ctcagagcag ctgcttctct gaggaagctg acaccaaggc cagcattcag   120
caacaacttg tggctttgca cccagcgccg gggtccccgc ccacctggct ccctgctgtc   180
cctcttcccc actgctgctc ggacttccct ctgaccctgg                         220

SEQ ID NO: 60              moltype = DNA   length = 663
FEATURE                    Location/Qualifiers
misc_feature               1..663
                           note = Dph-CRE60
source                     1..663
                           mol_type = other DNA
                           organism = synthetic construct
SEQUENCE: 60
ctttgctccc tgggagggcc tggccctgtg ggcatttgag tttataacac caccccatt      60
gtggcacacc cctccacccc gtaaaacaca ggctctgctc ttggaatcag tcttcctgat   120
ctgtggctgt gccctccaac agagggcacc cctgggcttc ccagctctgg gggtagtggg   180
tgccaacaag gagggggcctg gggctgaaga atcccacccg ctgagctcgg ccttctccct   240
tccccactgt ccagctccgc ctttcagcat cctgcctcac tccccgccca ggcagcaagg   300
agcccacacc ctcatgcccc tcagcttcag cccccacctc caggaggccc tacccacgct   360
catgaccttg ctattctggg ccttgtgtcc tgtagggaga tggacaggag acagctgggc   420
ttccaggcca cccaggcggg gggctagccg agggaagcct gctggctctc ctgcttgctc   480
taatttctgg ggctccccaa accttggcct caggagactg ggggatagac cggccttgaa   540
agtgggggaa gctttggaga gccgggtgct gggttcttag tgagatggcc agtgaaggct   600
gtggtgcccc gaggtaagca gggcctgatc ccctcctaat cttccagcag caactggtgc   660
tct                                                                 663

SEQ ID NO: 61              moltype = DNA   length = 594
FEATURE                    Location/Qualifiers
misc_feature               1..594
                           note = Dph-CRE61
source                     1..594
                           mol_type = other DNA
                           organism = synthetic construct
SEQUENCE: 61
cagcagctgc cctggtggta accaagagac gcccccatcc tggagcaggg gtggggaggg     60
gcagctcaga gcagctgctt ctctgaggaa gctgacacca aggccagcat tcagcaacaa   120
cttgtggctt tgcacccagc gccgggggtcc ccgcccacct ggctccctgc tgtccctctt   180
ccccactgct gctcggactt ccctctgacc ctggtggctc tgtgtctctg ctcccttttcc   240
ccctaggtct agacatctgt ccttatttcc cccagacctg tccccagaag tccaccccttc   300
cccattcctt tggtctggag cccctgcttg gtccagcttc ccaggcccc gacacctttc   360
tgtgggggtct gcctagctcc tgcacgcaca cagcatgggc ctgatcctgt tccctctgtg   420
```

-continued

```
gacagatgca gcagggcaga gtgcagcgca gaccacaggc ctctggggct ggccacagaa   480
accccgttgg ttagagcaca gtgtgggatg aggtgaccct cagtgcacga cttggggtga   540
cccctgcccc catcctgaga cagttacccc tccccctctg ccatcagcac attc         594

SEQ ID NO: 62          moltype = DNA  length = 634
FEATURE                Location/Qualifiers
misc_feature           1..634
                       note = Dph-CRE62
source                 1..634
                       mol_type = other DNA
                       organism = synthetic construct
SEQUENCE: 62
ccttccccat tcctttggtc tggagcccct gcttggtcca gcttccccag gccccgacac    60
ctttctgtgg ggtctgccta gctcctgcac gcacacagca tgggcctgat cctgttcccc   120
tcgtggacag atgcagcagg gcagagtgca gcgcagacca caggcctctg gggctggcca   180
cagaaacccc gttggttaga gcacagtgtg ggatgaggtg accctcagtg cacgacttgg   240
ggtgacccct gccccatcc tgagacagtt accctcccc ctctgccatc agcacattct    300
gtagccctctt gggttacttg gctgccttgg tgtcccattt tcttgggggt ggggtggggc   360
ttccctatcc aggatggggg ggccctcagg gctctgttcc cagaggctga gttagagcga   420
tggggaaggg ggggggcagt tttggggaga gacaggcagt gctggctttg ctcaccaggg   480
cctggacact aaatcccttg ttgatggctg tggcaaacccc tccctagggt agggttacca   540
tcttcggccc tgtcccttg actctctccc ctcacttccc cttgtccctc taggagccac   600
tcacttcctc tagcccccaa aagatgttct ccct                               634

SEQ ID NO: 63          moltype = DNA  length = 445
FEATURE                Location/Qualifiers
misc_feature           1..445
                       note = Dph-CRE63
source                 1..445
                       mol_type = other DNA
                       organism = synthetic construct
SEQUENCE: 63
cctcccctgc accccagagg caggtttat tttaagcttt aagggtgttc tcagccaaaa     60
caccgaagct aagccaccct cgcggcttca agagcttgga gagtcgggt tacccacccg    120
aactccgggc tccgggtccc gccgcgatgc cggctgcggc gcgggggggcc actgccactc   180
ccggcatgcg ccgggcggac ggccgctcca ccaatccccg cgcccgtcgg cgcccctgcc   240
ccgccctccc cagcctcctg acgctgattg gtcgagggga ggactcgctc ctagtggcgg   300
gaaagcgcgc cggtgtgatg atgactccaa ggagcccggc gcccggtcag ggagggcact   360
ggcatccctc attacccgcc cagcctggcc ttagcccttc cccgcgctcc ctaggcaccc   420
ccacccccgc agggcatctc caggg                                         445

SEQ ID NO: 64          moltype = DNA  length = 408
FEATURE                Location/Qualifiers
misc_feature           1..408
                       note = Dph-CRE64
source                 1..408
                       mol_type = other DNA
                       organism = synthetic construct
SEQUENCE: 64
gtctccgaac gcaggccccg tcgcgttaag cacaagctgg cagggcctct cctctccctt    60
ctcagatttg ctccttgaca tttgcctgct gcctggcggt ggcaacagct ggggcggggc   120
gcgcgcagga ggccccgtaa ccctatcccc gctccggctc cctcgtgaaa ccggagcttc   180
cctgccttgg ccgagggggga gggctgcggg ggccagaccg cctgcgaaga ccacaggggtt   240
tttcctctcg ggttttggct cccgtgggat ggatgtggct gtgcgggggg ttggcctgag   300
cttcgcttct aagccagcag cttggtcagg gaaacctgaa agcattccca gctaatcccc   360
caagtggtgc aagtctgtgc gcgcccatcc cgctgagtaa ggcggtgg                408

SEQ ID NO: 65          moltype = DNA  length = 496
FEATURE                Location/Qualifiers
misc_feature           1..496
                       note = Dph-CRE65
source                 1..496
                       mol_type = other DNA
                       organism = synthetic construct
SEQUENCE: 65
ggcaacaaag tccagggatt ccagaactta gctgtctttg aaacaacacc ttacattcca    60
aaggccaaca actttaagat tgccaacgac tcaaattatt tataggagat tgattcatat   120
acttaaccca atatgagagg aaatatttct aattatatcc aaacatcttt aatatgaggg   180
gaattaggct tggagacctt caatgccaaa aacatgtttt gccaaatatg ttttaagaaa   240
gaggaggagg ttacgtgttt tccatatttg agcctataaa agtacccttg gaatgagtat   300
gacttgtctc tcctcataaa gcttcaaggt aagtgtgtgt gaggacaggg ctctgtctgg   360
aggacggtaa gggatgtctg gctgcccgcg tgcatgccac acatcctggc tcccactgtc   420
cctggcagcc ctgccagtga agcaccagct tactcctag caattttaat tagatgttgt   480
agtcttccca gtcatt                                                   496

SEQ ID NO: 66          moltype = DNA  length = 319
FEATURE                Location/Qualifiers
misc_feature           1..319
                       note = Dph-CRE66
```

```
source                  1..319
                        mol_type = other DNA
                        organism = synthetic construct
SEQUENCE: 66
ccaggtgaca ggtggatggt ggagctggag gagccactcg gagcctccaa ggctgggggag   60
ggtggagggg ggaggcaggt cggtgtccca ggccacacct gttgactaag ggattaggat   120
gttgtgtccc tgccagccct cctccaataa gcccctctgg gcctgcaggg agaggaggag   180
ccttgccatg taaactgtat ttttagttcc ctgtgcctct ccccggctgc tataagacac   240
ctctccccac cccagccct ggccgcttgg ctggaggctc tgcgaggaca gctggggaga   300
aggggagctg tggtcagta                                                319

SEQ ID NO: 67          moltype = DNA   length = 372
FEATURE                Location/Qualifiers
misc_feature           1..372
                        note = Dph-CRE67
source                  1..372
                        mol_type = other DNA
                        organism = synthetic construct
SEQUENCE: 67
tcatcttcta ataatttggc aagccatcca tggtcttcta agcaaggcgc catgaatata   60
acgaatatag agacagaaaa agacccctcc ccactggctg ggttgaggga ctggagagcc   120
cagatggaag ggcagaggtg caggcttttt tccttgttgc cactagatgg cagtagggca   180
cccgttgtca gccctggggc aaggtcaccg actgtctttg cctttgcctc cagcaagcca   240
aaaccctggg cagactcaat ccaaaaataa acaatcaaag agcatgttgg cctggtcctt   300
tgctaggtac tgtagagcag gtgagagagt gaggggggaag gactccaaat tagaccagtt   360
cttagccatg aa                                                       372

SEQ ID NO: 68          moltype = DNA   length = 293
FEATURE                Location/Qualifiers
misc_feature           1..293
                        note = Dph-CRE68
source                  1..293
                        mol_type = other DNA
                        organism = synthetic construct
SEQUENCE: 68
agaaaggagc tgccctgggg atggctgtgt atccctacaa ctgccaggca catgcccctt   60
gaacacccga tgctacgtgt cccaaaggaa actggtctcc acccaccccc ggcccgtcct   120
cgtcctgggt accccacctt agtaaatggc gccaccatcg gcccggtcac tcagcgagaa   180
actcaactcc tggcagcaga tgacgggcac tctggttaaa tgactctctc cagcctccaa   240
gttcaacctg cagggaagcc ctggaaatcc tgtctccctc tgccctgcct ctc          293

SEQ ID NO: 69          moltype = DNA   length = 482
FEATURE                Location/Qualifiers
misc_feature           1..482
                        note = Dph-CRE69
source                  1..482
                        mol_type = other DNA
                        organism = synthetic construct
SEQUENCE: 69
gaaacatggc ttccacaggt tccagttgaa gaatcccagt tccgtctata aattccaggg   60
aaggtctctg attggccctg ctcattccca ggccattcc ttgacccagt cactgaagtc   120
agggagatgc agtaataaga ctggctggaa tcagggtctt tagggggtgga gggatgggga   180
ggaggcacag catgtcatca aaataaggaa attgcaaaag aaagcttgca ggctactttg   240
aatgacaatg agaaagacgg tgctgcctga gtgtgttaag gatccacatg gtctccaaaa   300
tcctccagga gcatacagtc tagtctggga gatgagacac aaaaataacc agaacacaac   360
agcttgcact gactcgaggg ctggataaga atatctggaaag ctccccatc tatttcagaa   420
gcttgtctct tggatgaaaa ttagacactt aatgggaaag ggctttgaaa agagtgcagt   480
aa                                                                  482

SEQ ID NO: 70          moltype = DNA   length = 398
FEATURE                Location/Qualifiers
misc_feature           1..398
                        note = Dph-CRE70
source                  1..398
                        mol_type = other DNA
                        organism = synthetic construct
SEQUENCE: 70
cctcaggtac cccctgcccc ccacagctcc tctcctgtgc cttgtttccc agccatgcgt   60
tctcctctat aaatacccgc tctggtattt ggggttggca gctgttgctg ccagggagat   120
ggttgggttg acatgcggct cctgacaaaa cacaaacccc tggtgtgtgt gggcgtgggt   180
ggtgtgagta ggggggatgaa tcagggaggg ggcggggggac ccaggggggca ggagccacac   240
aaagtctgtg cggggggtggg agcgcacata gcaattggaa actgaaagct tatcagaccc   300
tttctggaaa tcagcccact gtttataaac ttgaggcccc accctcgaca gtaccgggga   360
ggaagagggc ctgcactagt ccagaggggaa actgaggc                          398

SEQ ID NO: 71          moltype = DNA   length = 241
FEATURE                Location/Qualifiers
misc_feature           1..241
                        note = Dph-CRE71
```

-continued

```
source                    1..241
                          mol_type = other DNA
                          organism = synthetic construct
SEQUENCE: 71
cagggggcgca ggcctcttgc gggggagctg gcctccccgc ccccacggcc acgggccgcc   60
ctttcctggc aggacagcgg gatcttgcag ctgtcagggg aggggaggcg ggggctgatg   120
tcaggaggga tacaaatagt gccgacggct ggggggccctg tctcccctcg ccgcatccac   180
tctccggccg gccgcctgcc cgccgcctcc tccgtgcgcc cgccagcctc gcccgcgccg   240
t                                                                     241

SEQ ID NO: 72             moltype = DNA   length = 238
FEATURE                   Location/Qualifiers
misc_feature              1..238
                          note = Dph-CRE72
source                    1..238
                          mol_type = other DNA
                          organism = synthetic construct
SEQUENCE: 72
cccccaggca gcggcacggt ggactttgat gagttcctgg tcatgatggt tcggtgcatg   60
aaggacgaca gcaaagggaa atctgaggag gagctgtctg acctcttccg catgtttgac   120
aagtgagcac gtgaccctg acctctgacc ctgacccaca ctcaagccga gctgtacagg   180
agggcagtct cagattccag gcctaggac cctgtggcct ctgcctgata ggggagag      238

SEQ ID NO: 73             moltype = DNA   length = 465
FEATURE                   Location/Qualifiers
misc_feature              1..465
                          note = Dph-CRE73
source                    1..465
                          mol_type = other DNA
                          organism = synthetic construct
SEQUENCE: 73
agccagctct gggggcacgc ctgcttatcc tgtgggagtc catggagccg gggttgggac   60
agccctccac ccagtgccca tacaaggcct ggcggagttg gggactaatt ttggcttctg   120
aggcggcact agcaggccag ggggccagat aacgctgccc cacccctgc atgccaaagt   180
ccccagaaca atcaccaggt ttaactttgt tcctcgttaa aaatagccca gtggccaccc   240
tggtcaggtt accgtgggtg gcttgcctgc ctccacactg gttttattat cccaacttga   300
gggacagctg tccttcgggc cacccagctt gagtttcatc aggggccgaa agggcattga   360
gtggtcactg actattgtta ctgagggtca ccttggtcct gaaggggggtg cccacctgtc   420
accctggccc tgagcccagt cgcagtgagg ccagctgggg cacgt                    465

SEQ ID NO: 74             moltype = DNA   length = 285
FEATURE                   Location/Qualifiers
misc_feature              1..285
                          note = Dph-CRE74
source                    1..285
                          mol_type = other DNA
                          organism = synthetic construct
SEQUENCE: 74
ttttcattca ttccagaaac cttttcagag agtccctttg gggagtgtgg gggacaggag   60
ggaaagaaac ctggtccttg tagccgttcg tctgctccct gccctgggca gaggacgtgg   120
ggactcaggc cagcctgaga tcactggac cagaggaggg gctggaggat actacacgca   180
ggggtgggct gggctggggct gggctgggcc aggaatgcag cggggcaggg ctatttaagt   240
caagggccgg ctggcaaccc cagcaagctg tcctgtgagc cgcca                    285

SEQ ID NO: 75             moltype = DNA   length = 332
FEATURE                   Location/Qualifiers
misc_feature              1..332
                          note = Dph-CRE75
source                    1..332
                          mol_type = other DNA
                          organism = synthetic construct
SEQUENCE: 75
tgctctgttt acagacaagc tgctgtcctc cctgcaaagg ggagtgggtg gggcagaggg   60
caagtgccag gggggcacaa ggctgggcat gtggctggca tgagacggtg tctgagtaat   120
gtcaggcacc tggaggcatt gaccccagga ccttggaccc cagacctctg accgggggggc   180
agccagcgtc caggtacccc aacccctgcc ctgggtccgg cgtccccccca ttagtgagtc   240
ttggctctac ttatagcatc tgacaccaga ggggccgaaa atagcccctg gagaaggggg   300
aggaggggggc tatttaaagg gcctgggagg gg                                  332

SEQ ID NO: 76             moltype = DNA   length = 381
FEATURE                   Location/Qualifiers
misc_feature              1..381
                          note = Dph-CRE76
source                    1..381
                          mol_type = other DNA
                          organism = synthetic construct
SEQUENCE: 76
gcctgtggtc ttggtggtcg tggtcagttc cctctcctgc cagctgtgga atgtgaggcc   60
tggcctggga gatatttttg ctgcactttg agccaccccg ccccctggaa ctcagaccct   120
```

-continued

```
gcacagtcca tgccataaca atgacgacca cttccaattg tttcctagct ggagaggcgg    180
ggaggggagc actgtttggg aagggggggga gcctgggggga aatgcttcta gtgacaacag  240
cccctttctaa atccggctag ggactgggtg ccgttgggggg tgggggtgcc ctgctgcccc   300
atatatacag cccctgagac caggtctggc tccacagctc tgtcctgctc tgtgtctttc    360
cctgctgctc tcaggtagga g                                             381

SEQ ID NO: 77             moltype = DNA   length = 316
FEATURE                   Location/Qualifiers
misc_feature              1..316
                          note = Dph-CRE77
source                    1..316
                          mol_type = other DNA
                          organism = synthetic construct
SEQUENCE: 77
ggataccct accttaaaaa caaaacaaac cgtgctactt ggccctcttc ccttgagttg    60
ttgtctaatc tcattcattt cactgccaaa ctccctcaaat gcatggtgta cacccactgc   120
ttccacttcc tgtccactca tctttttcct cattaactcc ctgtggcctg gctttgcctg   180
tgacactaca caagctgctt gctccaagat aatccaagtt ctttttctctg tcttcctgat  240
acacaggctt tctttggcat ctgacactgc tggccacctg ctcttcttga aatgcttctt   300
ttggcttcta ggaaac                                                  316

SEQ ID NO: 78             moltype = DNA   length = 401
FEATURE                   Location/Qualifiers
misc_feature              1..401
                          note = Dph-CRE78
source                    1..401
                          mol_type = other DNA
                          organism = synthetic construct
SEQUENCE: 78
ccaagtggtg ggtgtagcct gggggttcaa tcctcctgtg gcgccccaga acccggtgcc    60
tcctccaacg tccggcatct gatgaggatc cgacccaggc gggcggcggc gggattcgct    120
cttccccttc gctccccgcg agaaagcccc gagggccgcg gcggcgcaga gccggtgaca    180
gttgaagctt aggcgggaag aggggaggcgc gaggcgggaa gagggagttt gggcctcggc    240
agccgccgta caaacaccgc tctggtcacc atggcaacag cgggatgccg cgaacggctt    300
ctgggcgggg ccggtccctc ggacgattgg acctagcttg gcgcggaatc cgtgaattgc    360
ccgcggcccg agggtgcagg tgatgggtgc tgaccgactg g                      401

SEQ ID NO: 79             moltype = DNA   length = 281
FEATURE                   Location/Qualifiers
misc_feature              1..281
                          note = Dph-CRE79
source                    1..281
                          mol_type = other DNA
                          organism = synthetic construct
SEQUENCE: 79
gactacaacc tgccagctca ggacgagagc tgtcaggaag agtccaggaa tggacttccc    60
acgggagggc acatttctgg tattcctggc aagataagga gttgactaag taatccacga    120
gaaaaggcat ttccggcaga ggaaacagtc tgggggtgag agggaggctg cagcatttgg    180
ggaactgcta gggctatcgt gtgtttggaa gaggggggagg gagagaggta ggcagggcta   240
aattgggaat tttgtcactg acataaattt taagtgccag g                      281

SEQ ID NO: 80             moltype = DNA   length = 393
FEATURE                   Location/Qualifiers
misc_feature              1..393
                          note = Dph-CRE80
source                    1..393
                          mol_type = other DNA
                          organism = synthetic construct
SEQUENCE: 80
cgttttgtgg taccaggggg tccctcctct cctgtcccca gccaaacctt ttcctttccc    60
ctcgggaaag ctgccttggc tgtcactacc tgctgcctat tccacatcct gaaccctgtg    120
acctaggccc agggctgctg cgcggacggt agctccccct gcaggaagca aggttcctcc    180
gggccccag actgctgctg gacctgtgca gaagcctgca actttcctct gcctagcccg    240
gcccacttcc tggatgcttg ctgccccag cccaccagag ctgtgagttc cattcctacc     300
ccctgcccca ctgagccctg atctaggtat gatcggtgca ttcatttttt tgctcaacaa   360
catttattac tgagcacctt ctcaaggcca ggc                               393

SEQ ID NO: 81             moltype = DNA   length = 169
FEATURE                   Location/Qualifiers
misc_feature              1..169
                          note = Dph-CRE81
source                    1..169
                          mol_type = other DNA
                          organism = synthetic construct
SEQUENCE: 81
cctaggccca gggctgctgc gcggacggta gctccccctg caggaagcaa ggttcctccg    60
ggccccaga ctgctgctgg acctgtgcag aagcctgcaa ctttcctctg cctagcccgg    120
cccacttcct ggatgcttgc tgcccccagc ccaccagagc tgtgagttc                169
```

```
SEQ ID NO: 82          moltype = DNA   length = 390
FEATURE                Location/Qualifiers
misc_feature           1..390
                       note = Dph-CRE82
source                 1..390
                       mol_type = other DNA
                       organism = synthetic construct
SEQUENCE: 82
gaagccaggt atcctggctg cccagccact gcctttatcc accagccttga ctctttcaga   60
tcatcttctc aaattatcca taggagattt atccacatac tcaataagaa aaatatttct  120
aattatatcc aaccattctt aatatgaatg agaattatgc ggggacgcta gattgccaag  180
aggtattttg ccaaacaatt ccttttgact taagaaagaa gaggcagctg cattgtttcc  240
atagctatcc atataaaaga gcccttggaa tgaggctgac tcgtcctgct ttaaaaagct  300
ccaaggtaag tgggagcagg acgggccttt caagagggac actggtcaca ccgcccagtg  360
tcagcagcag ctgctagttc tggtactgct                                   390

SEQ ID NO: 83          moltype = DNA   length = 294
FEATURE                Location/Qualifiers
misc_feature           1..294
                       note = Dph-CRE83
source                 1..294
                       mol_type = other DNA
                       organism = synthetic construct
SEQUENCE: 83
cagctgctag ttctggtact gctccttctg gaactgcacg ttttacctct atgaattttg   60
ttacttctgt ttacaatagc aagccatgcc ataaatggaa ttttttcccc ctcttttttgg  120
tcaactaatc aagtgctttt ccctttttctt ttatagaact gtctcactcc caggctacat  180
cttctcactt gctaacaagg taagatttgg actaaccagt tcctggagga gaatgcaaga  240
ggctctggga tggatttctg tcacttagca acctttcaga aagtgcttgt ctca         294

SEQ ID NO: 84          moltype = DNA   length = 460
FEATURE                Location/Qualifiers
misc_feature           1..460
                       note = Dph-CRE84
source                 1..460
                       mol_type = other DNA
                       organism = synthetic construct
SEQUENCE: 84
taaagacctt tctcagagat ccaaaccagc cccacccccc gccccaggga agcatagcat   60
attttctgtg aggccttgat ggtagcatca caaacccttg ggaaacacaa ctcccagtgt  120
ttgaggagag catgccgtat cttgttccag ggacactgag tcgtgagcat aaaacgctgc  180
attccaaaag agacgaagaa gcagtcgtct ctccatttaa ttatagattc ttcactttcc  240
cttaattgct tcagtcagca ctgttgactc tgggggagtc acagtacacc ggcagggcta  300
ttgctgttaa acaaggggtg actatcaggt aatgaggttt tcattttgtt ttttcaaaca  360
aacaaaccct gatgtacata ttcaagtggg cattcctgtt aaaggtgtca cattgggaaa  420
tgatgctcat gttgactctc ctttgtaacc aaatattgat                        460

SEQ ID NO: 85          moltype = DNA   length = 292
FEATURE                Location/Qualifiers
misc_feature           1..292
                       note = Dph-CRE85
source                 1..292
                       mol_type = other DNA
                       organism = synthetic construct
SEQUENCE: 85
taggaaggaa caagaagagg tagaaatgaa atggctccca aaagaaaaac ctcccttggg   60
tggtatttta ggacattagc tcaggctgcc ttgtcctcag tcatctcagt ggcatttaag  120
tagccccttg ggttacagat cacggcaggt gctgggaagt gaagaaggcc atgctaaaaa  180
tactggcctc ttctggaact ctgccggcag ccctgatgga gctccctcct caagcagcag  240
tacctcagca aagaacagt tcctccgcc ttaagcagta agaaaagtct gg             292

SEQ ID NO: 86          moltype = DNA   length = 472
FEATURE                Location/Qualifiers
misc_feature           1..472
                       note = Dph-CRE86
source                 1..472
                       mol_type = other DNA
                       organism = synthetic construct
SEQUENCE: 86
aagaaagggt ctttacaaaa ccaaaagaaa gcccattgct tacttttaat aacctaggcc   60
cacccatagg cctctaaatc aaataacctc cactgagaat taagctgtta gcactaggtc  120
tggcataggt gcagaaacaa aagtttagaa atcctaatct tgaatttacc taacacggct  180
gcctcctaga gcctgagtgg gttgtagcga gacctcaag agaggagagg cacctgggcc  240
atccgcctcc atgggctttt tttttttttgc atcgaatttc atggtctgca aagtaaggt  300
ggggctttac ttgccattca ggaggttgca aaggtcacct ccacatatgt tcctgttaag  360
gacatcagca gaaacttgag aagcaagtat aaaaatataa aaatgagcag gtggcattca  420
ataggaaaag aatgcagggt ttgctgggaa gtcatgattg aaaccagtcc aa           472

SEQ ID NO: 87          moltype = DNA   length = 476
```

-continued

```
FEATURE              Location/Qualifiers
misc_feature         1..476
                     note = Dph-CRE87
source               1..476
                     mol_type = other DNA
                     organism = synthetic construct
SEQUENCE: 87
aaggaagtga ccaggccagg tctggatccc tggaactgac tcctaactcc ctattcttgc    60
ctcctctgct gagctccaac ctggggagtc agctccctgg agtccacgca tctggatatc   120
gtccacatgc ctggaacttt gtcactgttc cggtggctgg gttgacacac cgtgattaaa   180
gggctctggt caatttctgt gccacgcagc ccctatgcta atggtcagat ctaatgttct   240
gaccattagg tcagtgtatc ttttccctcc tgggcagtta ggttagtgga agaaacccga   300
taaaatcttg gagaggaatt tgatcattct ctgaaggact tacaagttgt ttggcctgcc   360
taatctgctc agataccgtc cggggaatat ttggtaacca tcagtacag actgtgaatt    420
attctgtggg gactattaac aagaccctca ccaaccctgc ctcagctgat ctcagg       476

SEQ ID NO: 88       moltype = DNA  length = 459
FEATURE              Location/Qualifiers
misc_feature         1..459
                     note = Dph-CRE88
source               1..459
                     mol_type = other DNA
                     organism = synthetic construct
SEQUENCE: 88
acagaccaaa ttgcctgagt ctaaactcaa tgttctttcc ccttagactg ccacccgcac    60
acacacgcac acatgcacac cttttggag gcactgcaca gcaagcacag aagtacgcca    120
ctgagtcctg tgtccctaaa gtatttgact gtccctccgc tggggaaag ggcaggcaga    180
aaacaagact ccgtgtgctg tcgctgtgcc gccccctgcc tctctgaccc gcgcccgcag   240
agaaagtctc aagagccgcc ccaggctttc tcccacgttc tcccttttctc tgctgcagtt   300
gagtttccag agcgtgagcg cgcaggatga cacctggctg gctgagagct gccgggggagg  360
cgctggcggg tgccgagagc gcactgaccc tgacgcgggg tgcagcacgg ctgggaagcc   420
cccgggcctt tggctaagcg cgccggggga cggcacagg                          459

SEQ ID NO: 89       moltype = DNA  length = 378
FEATURE              Location/Qualifiers
misc_feature         1..378
                     note = Dph-CRE89
source               1..378
                     mol_type = other DNA
                     organism = synthetic construct
SEQUENCE: 89
gccccaacgc cctctccctg gcgcgcaggt ttagaaacag ggcggcctct ccggccgccg    60
cctcggcggc tcgggtcccc atatatagtc atatccaccg tcaactggga ggccggcggc   120
cggcagcgaa tgggcgagcg gcccccgcgg gaggagcggg gaggggggcac ggggcggagg   180
gaggagagga ggaaggggggg caggagaaaa aagcttttcc aaaaaagtat tggctgtctt   240
gaggaatgcg gtcgcccct tgggaaagta catatctggg agaagcaggc ggctccgcgc    300
tcgcactccc gctcctccgc ccgaccgcgc gctcgccccg ccgctcctgc tgcagcccca   360
gggccctcg ccgccgcc                                                  378

SEQ ID NO: 90       moltype = DNA  length = 983
FEATURE              Location/Qualifiers
misc_feature         1..983
                     note = mouse desmin promotor
source               1..983
                     mol_type = other DNA
                     organism = synthetic construct
SEQUENCE: 90
accttgcttc ctagctgggc ctttccttct cctctataaa taccagctct ggtatttcgc    60
cttggcagct gttgctgcta gggagacggc tggcttgaca tgcatctcct gacaaaacac   120
aaacccgtgg tgtgagtggg tgtgggcggt gtgagtaggg ggatgaatca gagagggggc   180
gagggagaca ggggcgcagg agtcaggcaa aggcgatgcg ggggtgcgac tacacgcagt   240
tggaaacagt cgtcagaaga ttctggaaac tatcttgctg gctataaact tgagggaagc   300
agaaggccaa cattcctccc aagggaaact gaggctcaga gttaaaaccc aggtatcagt   360
gatatgcatg tgccccggcc agggtcactc tctgactaac cggtacctac cctacaggcc   420
tacctagaga ctcttttgaa aggatggtag agacctgtcc gggctttgcc cacagtcgtt   480
ggaaacctca gcattttcta ggcaacttgt gcgaataaaa cacttcgggg gtccttcttg   540
ttcattccaa taacctaaaa cctctcctcg gagaaaatag ggggcctcaa acaaacgaaa   600
ttctctagcc cgctttcccc aggataaggc aggcatccaa atggaaaaaa aggggccggc   660
cggggggtctc ctgtcagctc cttgccctgt gaaacccagc aggcctgcct tgcttctgtc   720
ctcttggggc tgtccagggg cgcaggcctc ttgcggggga gctggcctcc ccgcccctc    780
gcctgtggcc gcccttttcc tggcaggaca gaggggatcct gcagctgtca ggggagggc    840
gccggggggt gatgtcagga gggctacaaa tagtgcagac agctaagggg ctccgtcacc    900
catcttcaca tccactccag ccggctgccc gcccgctgcc tcctctgtgc gtccgcccag   960
ccagcctcgt ccacgccgcc acc                                           983

SEQ ID NO: 91       moltype = DNA  length = 1099
FEATURE              Location/Qualifiers
misc_feature         1..1099
                     note = human 1.0kb desmin promotor
```

-continued

```
source                   1..1099
                         mol_type = other DNA
                         organism = synthetic construct
SEQUENCE: 91
tgtacaacgc gttacgcctc aggtaccccc tgcccccac  agctcctctc ctgtgccttg    60
tttcccagcc atgcgttctc ctctataaat acccgctctg gtatttgggg ttggcagctg   120
ttgctgccag ggagatggtt gggttgacat gcggctcctg acaaaacaca aaccctggt    180
gtgtgtgggc gtgggtggtg tgagtagggg gatgaatcag ggaggggcg  ggggacccag   240
ggggcaggag ccacacaaag tctgtgcggg ggtgggagcg cacatagcaa ttggaaactg   300
aaagcttatc agacccttc  tggaaatcag cccactgtt  ataaacttga ggccccaccc   360
tcgacagtac cggggaggaa gagggcctgc actagtccag agggaaactg aggctcaggg   420
ctagctcgcc catagacata catggcaggc aggctttggc caggatccct ccgcctgcca   480
ggcgtctccc tgcctccct  tcctgcctag agaccccac  cctcaagcct ggctggtctt   540
tgcctgagac ccaaacctct tcgacttcaa gagaatattt aggaacaagg tggtttaggg   600
cctttcctgg gaacaggcct tgacccttta agaaatgacc caaagtctct ccttgaccaa   660
aaaggggacc ctcaaactaa agggaagcct ctcttctgct gtctcccctg accccactcc   720
cccccacccc aggacgagga gataaccagg gctgaaagag gcccgcctgg gggctgcaga   780
catgcttgct gcctgccctg gcgaaggatt ggcaggcttg cccgtcacag gacccccgct   840
ggctgactca ggggcgcagg cctcttgcgg gggagctggc ctcccgccc  ccacggccac   900
gggccgccct ttcctggcag gacagcggga tcttgcagct gtcaggggag gggaggcggg   960
ggctgatgtc aggagggata caaatagtgc cgacggctgg gggccctgtc tccctcgcc  1020
gcatccactc tccggccggc cgcctgcccg ccgcctcctc cgtgcgcccg ccagcctcgc  1080
ccgcgccgtc acctctaga                                                1099

SEQ ID NO: 92             moltype = DNA   length = 1426
FEATURE                   Location/Qualifiers
misc_feature             1..1426
                         note = human 1.4kb desmin promotor
source                   1..1426
                         mol_type = other DNA
                         organism = synthetic construct
SEQUENCE: 92
acacacctac tagtaacccc tccagctggt gatggcaggt ctagggtagg accagtgact    60
ggctcctaat cgagcactct attttcaggg tttgcattcc aaaagggtca ggtccaagag   120
ggacctggag tgccaagtgg aggtgtagag gcacggccag tacccatgga gaatggtgga   180
tgtccttagg ggttagcaag tgccgtgtgc taaggagggg gctttggagg ttgggcaggc   240
cctctgtggg gctccatttt tgtggggtg  ggggctggag cattataggg ggtgggaagt   300
gattggggct gtcaccctag ccttccttat ctgacgccca cccatgcctc ctcaggtacc   360
ccctgccccc cacagctcct ctcctgtgcc ttgtttccca gccatgcgtt ctcctctata   420
aataccgct  ctggtatttg gggttggcag ctgttgctgc cagggagatg gttgggttga   480
catgcggctc ctgacaaaac acaaaccct  ggtgtgtgtg ggcgtgggtg gtgtgagtag   540
ggggatgaat caggggagggg gcggggggacc caggggggcag gagccacaca aagtctgtgc   600
ggggggtggga gcgcacatag caattggaaa ctgaaagctt atcagacccct ttctggaaat   660
cagcccactg tttataaaact tgaggcccca ccctcgacag taccggggag gaagaggggcc   720
tgcactagtc cagagggaaa ctgaggctca gggctagctc gcccatagac atacatggca   780
ggcaggcttt ggccaggatc cctccgcctg ccaggcgtct ccctgccctc ccttcctgcc   840
tagagacccc cacccctcaag cctggctggt ctttgcctga gaccccaaacc tcttcgactt   900
caagagaata tttaggaaca aggtggttta gggcctttcc tgggaacagg ccttgaccct   960
ttaagaaatg acccaaagtc tctccttgac caaaaagggg accctcaaac taaagggaag  1020
cctctcttct gctgtctccc ctgaccccac tccccccac  cccaggacga ggagataacc  1080
agggctgaaa gaggcccgcc tgggggctgc agacatgctt gctgcctgcc ctggcgaagg  1140
attggcaggc ttgcccgtca caggaccccc gctggctgac tcaggggcgc aggcctcttg  1200
cgggggagct ggcctccccg ccccacggc  cacgggccgc cctttcctgg caggacagcg  1260
ggatcttgca gctgtcaggg gaggggaggc ggggggctgat gtcaggaggg atacaaatag  1320
tgccgacggc tggggggccct gtctcccctc gccgcatcca ctctccggcc ggccgcctgc  1380
ccgcgccgcctc ctccgtgcgc cgccagcct cgccgcgcgc gtcacc                 1426

SEQ ID NO: 93             moltype = DNA   length = 2859
FEATURE                   Location/Qualifiers
misc_feature             1..2859
                         note = human GAA sequence
source                   1..2859
                         mol_type = other DNA
                         organism = synthetic construct
SEQUENCE: 93
atgggagtga ggcacccgcc ctgctcccac cggctcctgg ccgtctgcgc cctcgtgtcc    60
ttggcaaccg ctgcactcct ggggcacatc ctactccatg atttcctgct ggttccccga   120
gagctgagtg gctcctcccc agtcctggag gagactcacc cagctcacca gcagggagcc   180
agcagaccag ggccccggga tgcccaggca caccccggcc gtcccagagc agtgcccaca   240
cagtgcgacg tccccccaa  cagccgcttc gattgcgccc ctgacaaggc catcacccag   300
gaacagtgcg aggcccgcgg ctgttgctac atccctgcaa agcaggggct gcagggagcc   360
cagatggggc agcctggtg  cttcttccca cccagctacc ccagctacaa gctggagaac   420
ctgagctcct ctgaaatggg ctacacggcc accctgaccc gtaccacccc caccttcttc   480
cccaaggaca tcctgaccct gcggctggac gtgatgatgg agactgagaa ccgcctgcac   540
ttcacgatca agatccagc  taacaggcgc tacgaggtgc ccttggagac cccgcatgtc   600
cacagccggg gaccgtcccc actctacagc gtggagttct ccgaggagcc cttcggggtg   660
atcgtgcgcc ggcagctgga cggccgcgtg ctgctgaaca cgacggtggc cccctgttc   720
tttgcggacc agttccttca gctgtccacc tcgctgcct  cgcagtatat cacaggcctc   780
gccgagcacc tcagtcccct gatgctcagc accagctgga ccaggatcac cctgtggaac   840
```

```
cgggaccttg cgcccacgcc cggtgcgaac ctctacgggt ctcacccttt ctacctggcg  900
ctggaggacg gcgggtcggc acacggggtg ttcctgctaa acagcaatgc catggatgtg  960
gtcctgcagc cgagccctgc ccttagctgg aggtcgacag gtgggatcct ggatgtctac 1020
atcttcctgg gcccagagcc caagagcgtg gtgcagcagt acctggacgt tgtgggatac 1080
ccgttcatgc cgccatactg gggcctgggc ttccacctgt gccgctgggg ctactcctcc 1140
accgctatca cccgccaggt ggtggagaac atgaccaggg cccacttccc cctggacgtc 1200
cagtggaacg acctggacta catggactcc cggagggact tcacgttcaa caaggatggc 1260
ttccgggact tcccggccat ggtgcaggag ctgcaccagg cggccggcg ctacatgatg 1320
atcgtggatc ctgccatcag cagctcgggc cctgccggga gctacaggcc ctacgacgag 1380
ggtctgcgga ggggggtttt catcaccaac gagaccgggc agccgctgat tgggaaggta 1440
tggcccgggt ccactgcctt ccccgacttc accaacccca cagccctggc ctggtgggag 1500
gacatggtg ctgagttcca tgaccaggtg cccttcgacg gcatgtggat tgacatgaac 1560
gagccttcca acttcatcag gggctctgag gacggctgcc ccaacaatga gctggagaac 1620
ccacccTACG tgcctggggt ggttggggggg accctccagg cggccaccat ctgtgcctcc 1680
agccaccagt ttctctccac acactacaac ctgcacaacc tctacggcct gaccgaagcc 1740
atcgcctccc acagggcgct ggtgaaggct cgggggacac gcccatttgt gatctcccgc 1800
tcgacctttg ctggccacgg ccgatacgcc ggccactgga cggggggacgt gtggagctcc 1860
tgggagcagc tcgcctcctc cgtgccagaa atcctgcagt ttaacctgct ggggggtgcct 1920
ctggtcgggg ccgacgtctg cggcttcctg ggcaacacct cagaggagct ggtgtgtcgc 1980
tggacccagc tgggggggcctt ctaccccttc atgcggaacc acaacagcct gctcagtctg 2040
ccccaggagc cgtacagctt cagcgagccg gcccagcagg ccatgaggaa ggccctcacc 2100
ctgcgctacg cactcctccc ccacctctac acactgttcc accagcccca cgtcgcgggg 2160
gagaccgtgg cccggcccct cttcctggag ttccccaagg actctagcac ctggactgtg 2220
gaccaccagc tcctgtgggg ggaggccctg ctcatcaccc cagtgctcca ggccgggaag 2280
gccgaagtga ctggctactt cccccttgggc acatggtacg acctgcagac ggtgccagta 2340
gaggcccttg gcagcctccc accccccacct gcagctcccc gtgagccagc catccacagc 2400
gaggggcagt gggtgacgct gccggcccccc ctggacacca tcaacgtcca cctccgggct 2460
gggtacatca tccccctgca gggccctggc ctcacaacca cagtcccg ccagcagccc 2520
atggccctgg ctgtggccct gaccaagggg ggggggaggccc gaggggagct gttctgggac 2580
gatggaagt gctggagcga ggggcctaca cacaggtcat cttcctggcc 2640
aggaataaca cgatcgtgaa tgagctggta cgtgtgacca gtgagggagc tggcctgcag 2700
ctgcagaagg tgactgtcct gggcgtggcc acggcgcccc agcaggtcct ctccaacggt 2760
gtccctgtct ccaacttcac ctacagcccc gacaccaagg tcctggacat ctgtgtctcg 2820
ctgttgatgg gagagcagtt tctcgtcagc tggtgttag            2859
```

SEQ ID NO: 94           moltype = DNA   length = 2859
FEATURE                 Location/Qualifiers
misc_feature            1..2859
                        note = human GAAco sequence
source                  1..2859
                        mol_type = other DNA
                        organism = synthetic construct SEQUENCE: 94
```
atgggcgtca gacatcctcc atgttctcac agactgctgg ccgtgtgtgc tctggtgtct   60
cttgctacag ctgccctgct gggacatatc ctgctgcacg attttctgct ggtgcccaga  120
gagctgtctg gcagctctcc tgtgctggaa gaaacacacc ctgcacatca gcagggcgc  180
tctagacctg gacctagaga tgctcaagcc catcctgca gacctagagc cgtgcctaca  240
cagtgtgacg tgccacctaa cagcagattc gactgcgccc ctgacaaggc catcacacaa  300
gagcagtgtg aagccagagg ctgctgctac attcctgcca aacaaggact gcagggcgct  360
cagatgggac agccttggtg cttcttccca ccatcttacc ccagctacaa gctggaaaac  420
ctgagcagca gcgagatggg ctacaccgcc acactgacca gaaccacacc tacattcttc  480
ccaaaggaca tcctgacact gcggctggac gtgatgatgg aaaccgagaa ccggctgcac  540
ttcaccatca aggaccccgc caatagaaga tacgaggtgc ccctggaaac ccctcacgtg  600
cactctagag ccccatctcc actgtacagc gtggaattca gcgaggaacc ctttggcgtg  660
atcgtgcgga gacagtgga tggcagagtg ctgctgaata ccacagtggc ccctctgttc  720
ttcgccgacc agtttctgca gctgagcaca agcctgccta gccagtatat cacaggcctg  780
gccgaacacc tgtctccact gatgctgagc accagctgga ccagaatcac cctgtggaac  840
agagatctgg ccctacacc tggcgccaat ctgtacggct ctcacccttt ttatctggcc  900
ctggaagatg gcggaagcgc ccacggtgtc tttctgctga acagcaacgc catggacgtg  960
gtgctgcaac catctcctgc tctgtcttgg agaagcaccg gcggcatcct ggacgtgtac  1020
atctttctgg acccgagcc taagagcgtg gtgcagcagt atctggatgt cgtgggctac  1080
cccttcatgc ctcctattg gggcctgggc ttccacctgt gtagatgggg atacagctcc  1140
accgccatca ccagacaggt ggtggaaaac atgacccggg ctcacttccc actggatgtg  1200
cagtggaacg acctggacta catggactcc agacgggact tcacctttaa caaggacggc  1260
ttcagagact ccccgccat ggtgcaagaa ctgcatcaag cggcagacg gtacatgatg  1320
atcgtggatc ctgccatctc ttctagcggc cctgccggaa gctacagacc ttatgatgag  1380
ggcctgagaa gaggcgtgtt catcaccaat gagacaggcc agcctctgat cggcaaagtg  1440
tggcctggaa gcaccgcctt tccagacttc accaatccaa ccgctctggc ttggtgggaa  1500
gatatggtgg ccgagttcca cgatcaggtg cccttcgatg gcatgtggat cgacatgaac  1560
gagcccagca acttcatcag gggcagcgag gatggctgcc ccaacaacga actggaaaat  1620
cctccttacg tgcaggcgt tgtcggagga acactgcagg ccgccacaat ttgtgccagc  1680
agccatcagt ttctgagcac ccactacaac ctgcacaacc tgtacggcct gaccgaggcc  1740
attgcctctc atagagccct ggttaaggcc agaggcaccg gccttttgt gatcagcaga  1800
agcacatttg ccggccacgg cagatatgcc ggacattgga cgggggacgt ttggtctagt  1860
tgggagcagc tggcctctag cgtgcccgag atcctgcagt ttaatctgct gggagtgccc  1920
ctcgtgggag ccgatgtttg tggatttctg ggcaacacct ccgaggaact gtgcgtcaga  1980
tggacacagc tgggcgcctt ctatcccttc atgagaaacc acaacagcct gctgagcctg  2040
cctcaagagc cttacagctt tagcgaaccc gcacagcagg ccatgagaaa ggccctgact  2100
ctgagatacg ctctgctgcc ccacctgtac accctgtttc atcaagctca tgtggccggc  2160
```

```
gagacagtgg ccagaccact gtttctggaa ttccccaagg acagcagcac ctggacagtg   2220
gatcatcagc tgctctgggg agaagccctg ctcattacac ctgtgctgca ggctggcaag   2280
gccgaagtga caggatactt tcccctcggc acttggtacg acctgcagac agttcctgtg   2340
gaagctctgg gatctctgcc tccacctcct gctgctccta gagagcctgc cattcactct   2400
gaaggccagt gggttacact gcccgctcca ctggacacca tcaatgtgca cctgagagcc   2460
ggctacatca tccctctgca aggccctgga ctgaccacaa ccgaaagcag acagcagcca   2520
atggctctgg ccgtggctct gacaaaaggc ggagaagcta gaggcgaact gttctgggat   2580
gacggcgaga gcctggaagt gctggaacgg ggagcctaca cacaagtgat ctttctcgcc   2640
cggaacaaca ccatcgtgaa cgaactcgtc agagtgacca gtgaaggtgc cggactgcag   2700
ctccagaaag tgacagtgct tggagtggcc acagcacccc agcaggtttt gtctaatggc   2760
gtgcccgtgt ccaacttcac atacagccct gacaccaagg tgctggacat ctgtgtgtct   2820
ctgctgatgg gcgagcagtt cctggtgtcc tggtgttga   2859
```

```
SEQ ID NO: 95          moltype = DNA  length = 1812
FEATURE                Location/Qualifiers
misc_feature           1..1812
                       note = human MTM1 sequence
source                 1..1812
                       mol_type = other DNA
                       organism = synthetic construct
SEQUENCE: 95
atggcttctg catcaacttc taaatataat tcacactcct tggagaatga gtctattaag   60
aggacgtctc gagatggagt caatcgagat ctcactgagg ctgttcctcg acttccagga   120
gaaacactaa tcactgacaa agaagttatt tacatatgtc ctttcaatgg ccccattaag   180
ggaagagttt acatcacaaa ttatcgtctt tatttaagaa gtttggaaac ggattcttct   240
ctaatacttg atgttcctct gggtgtgatc tcgagaattg aaaaaatggg aggcgcgaca   300
agtagaggag aaaattccta tggtctagat attacttgta aagacatgaa aaacctgagg   360
ttcgctttga aacaggaagg ccacagcaga agagatatgt ttgagatcct cacgagatac   420
gcgtttcccc tggctcacag tctgccatta tttgcatttt taaatgaaga aaagtttaac   480
gtggatggat ggacagttta caatccagtg gaagaataca gaggcaggg cttgcccaat   540
caccattgga gaataacttt tattaataag tgctatgagc tctgtgacac ttaccctgct   600
cttttggtgg ttccgtatcg tgcctcagat gatgacctcc ggagagttgc aacttttagg   660
tcccgaaatc gaattccagt gctgtcatgg attcatccag aaaataagac ggtcattgtg   720
cgttgcagtc agcctcttgt cggtatgagt gggaaacgaa ataaagatga tgagaaatat   780
ctcgatgtta tcaggagac taataaacaa atttctaaac tcaccattta tgatgcaaga   840
cccagcgtaa atgcagtggc caacaaggca acaggaggag gatatgaaag tgatgatgca   900
tatcataacg ccgaactttt cttcttagac attcataata ttcatgttat gcgggaatct   960
ttaaaaaaag tgaaggacat tgtttatcct aatgtagaag aatctcattg gttgtccagt   1020
ttggagtcta ctcattggtt agaacatatc aagctcgttt tgacaggagc cattcaagta   1080
gcagacaaag tttcttcagg gaagagttca gtgcttgtgc attgcagtga cggatgggac   1140
aggactgctc agctgacatc cttggccatg ctgatgttgg atagcttcta taggagcatt   1200
gaagggttcg aaatactggt acaaaaaaaa tggataagtt ttggacataa atttgcatct   1260
cgaataggtc atggtgataa aaaccacacc gatgctgacc gttctcctat ttttctccag   1320
tttattgatt gtgtgtggca aatgtcaaaa cagttcccta cagcttttga attcaatgaa   1380
caatttttga ttataatttt ggatcatctg tatagttgcc gatttggtac tttcttattc   1440
aactgtgaat ctgctcgaga aagacagaag gttacagaaa ggactgtttc tttatggtca   1500
ctgataaaca gtaataaaga aaaattcaaa aacccccttct atactaaaga aatcaatcga   1560
gttttatatc cagttgccag tatgcgtcac ttggaactct gggtgaatta ctacattaga   1620
tggaacccca ggatcaagca acaacagccg aatccagtgg agcagcgtta catggagctc   1680
ttagccttac gcgacgaata cataaagcgg cttgaggaac tgcagctcgc caactctgcc   1740
aagctttctg atcccccaac ttcaccttcc agtccttcgc aaatgatgcc ccatgtgcaa   1800
actcacttct ga   1812
```

```
SEQ ID NO: 96          moltype = DNA  length = 1812
FEATURE                Location/Qualifiers
misc_feature           1..1812
                       note = human MTM1co sequence
source                 1..1812
                       mol_type = other DNA
                       organism = synthetic construct
SEQUENCE: 96
atggccagcg ccagcacaag caagtacaac agccacagcc tggaaaacga gagcatcaag   60
cggaccagca gagatggcgt gaacagagat ctgaccgagg ccgttcctag actgcctggc   120
gagacactga tcaccgacaa agaagtgatc tacatctgcc ccttcaacgg ccccatcaag   180
ggaagagtgt acatcaccaa ctaccggctg tacctgcggt ccctggaaac cgatagcagc   240
ctgattctgg atgtgcccct gggcgtgatc agccggattg aaaaaatggg cggagccacc   300
tccgaggcg agaatagcta tggcctggat atcacatgca aggacatgcg gaacctgaga   360
ttcgccctga gcaagagggg ccacagcaga cgggacatgt tcgagatcct gaccagatac   420
gcctttcctc tggctcactc tctgcccctg ttcgccttcc tgaacgaaga agttcaac   480
gtggacggct ggaccgtgta caaccccgtg aagagtata gacggcaggg actgcccaat   540
caccactggc ggatcacctt catcaacaag tgctacgagc tgtgcgacac ataccccgca   600
ctgctggtgg tgccttacag agcctctgac gacgatctga aagagtggc cacctttcgg   660
agccggaaca gaatccctgt gctgagctgg attcaccccg agaacaagac cgtgatcgtg   720
cggtgttctc agcctctcgt gggcatgagc ggcaagagaa acaaggacga gaagtac   780
ctggacgtga tccgcgagac aaacaagcag atcagcaagc tgaccatcta cgacgccaga   840
ccttctgtga cgccgtggc caacaaagcc acaggcggcg gatatgagtc cgacgatgcc   900
tatcacaacg ccgagctgtt cttcctggac attcacaaca tccatgtgat gcgcgagagc   960
ctgaagaaag tgaaggacat cgtgtacccc aatgtggaag agccactg gctgtctagc   1020
ctggaatcca cacactggct ggaacacatc aagctggtgc tgacaggcgc catccaggtg   1080
```

-continued

```
gcagacaaag tgtctagcgg caagtctagc gtgctggtgc actgtagcga cggatgggat    1140
agaacagccc agctgacatc cctggccatg ctgatgctgg acagcttcta cagatccatc    1200
gagggctttg agatcctggt gcagaagaag tggatcagct tcggccacaa gttcgcctct    1260
agaatcggac acggcgacaa gaaccacacc gacgccgata gaagccccat cttcctgcag    1320
ttcatcgact gcgtgtggca gatgtccaag cagttcccta ccgccttcga gttcaacgag    1380
cagttcctga tcatcatcct ggaccacctg tactcttgca gattcggcac cttcctgttc    1440
aactgcgaga gcgccagaga acggcagaaa gtgaccgaga gaaccgtgtc tctgtggtcc    1500
ctgatcaaca gcaacaaaga gaaattcaag aaccccttct acaccaaaga aatcaaccgg    1560
gtgctgtacc ccgtggccag catgagacat ctggaactgt gggtcaacta ctacatccgg    1620
tggaacccca gaatcaagca gcagcagccc aatcctgtgg aacagcggta tatggaactg    1680
ctggccctgc gggacgagta catcaagaga ctggaagaac tgcagctggc caacagcgcc    1740
aagctgagcg atcctcctac aagccctagc agccctctc agatgatgcc ccatgtgcag    1800
acccactttt ga                                                        1812
```

```
SEQ ID NO: 97              moltype = DNA   length = 6024
FEATURE                    Location/Qualifiers
misc_feature               1..6024
                           note = plasmid pAAVss-CRE02-CSkSH5-SPc5-12_GTRM-Luc2
source                     1..6024
                           mol_type = other DNA
                           organism = synthetic construct
SEQUENCE: 97
cctgcaggca gctgcgcgct cgctcgctca ctgaggccgc ccgggcaaag cccgggcgtc    60
gggcgacctt tggtcgcccg gcctcagtga gcgagcgagc gcgcagagag ggagtggcca    120
actccatcac taggggttcc tgcggccgac aggtgcggtt cccggagcgc aggcgcacac    180
atgcacccac cggcgaacgc ggtgaccctc gccccaccc atcccctccg gcgggcaact    240
gggtcgggtc aggaggggca aaccgctag ggagacactc catatacggc ccggcccgcg    300
ttacctggga ccgggccaac ccgctccttc tttggtcaac gcaggggacc cgggcggggg    360
cccaggccgc gaaccggccg agggaggggg ctctagtgcc caacacccaa atatggctcg    420
agaagggcag cgacattcct gcggggtggc gcggagggga tgcccgcggg ctatataaaa    480
cctgagcaga gggacaagcg gccaccgcag cggacagcgc caagtgaagc ctcgcttccc    540
ctccgcggcg accagggccc gagccgagag tagcagttgt agctaccgc ccaggtaggg    600
gcgcgccacg cgtcagttta ctcaccaggg attcagaggc agcactgctg aaccctgagc    660
ccttggcaca tcaggttggc tgtcagaagt cggcctttgt acatacacag ttcccttgtg    720
aggcccagct gcgtgtccta ggagcggggc ctctctccac agcagagctc agcctctcaa    780
gtgtatggac agcacgggtg cctgatgggt ggatttagcc atgagttgaa ggtggcttgg    840
ggagaatgag agttctagag ataggggaaa ggggttgcca ataggagagt ggaattcctg    900
agcacctcgt cacaggcagc cgacagaaca tgagccgcag ggcccaggct atttatacct    960
cgcctgtcac tatcagggtc cccacagctc ccccaccc cagccacaca cagcaggtcc    1020
ttttgctctt tctggtccct tctctactcc tccccctccc tacctaaggt acccaacgcg    1080
ttacgtggcc accgccttcg gcaccatcct cacgacaccc aaatatggcg acgggtgagg    1140
aatggtgggg agttatttt agagcggtga ggaaggtggg caggcagcag gtgttggcgc    1200
tctaaaaata actcccggga gttatttta gagcggtga atggtggaca cccaaatatg    1260
gcgacggttc ctcacccgtc gccatatttg ggtgtccgcc ctcggccggg gccgcattcc    1320
tggggggccgg gcggtgctcc cgcccgcctc gataaaaggc tccggggccg gcggcggccc    1380
acgagctacc cggaggagcg ggaggcgcca agctctagat ctagaaagag gtaagggttt    1440
aagggatggt tggttggtgg ggtattaatg tttaattacc tggagcacct gcctgaaatc    1500
acttttttc aggttggaag cttatggaag atgccaaaaa cattaagaag ggcccagcgc    1560
cattctaccc actcgaggac gggaccgccg gcgagcagct gcacaaagcc atgaagcgct    1620
acgccctggt gcccggcacc atcgccttta ccgacgcaca tatcgaggtg gacattacct    1680
acgccgagta cttcgagatg agcgttcggc tggcagaagc tatgaagcgc tatgggctga    1740
atacaaacca tcggatcgtg gtgtgcagcg agaatagctt gcagttcttc atgcccgtgt    1800
tgggtgccct gttcatcggt gtggctgtgg ccccagctaa cgacatctac aacgagcgcg    1860
agctgctgaa cagcatgggc atcagccagc ccaccgtcgt attcgtgagc aagaaagggc    1920
tgcaaaagat cctcaacgtg caaaagaagt accgatcat acaaaagatc atcatcatgg    1980
atagcaagac cgactaccag ggcttccaaa gcatgtacac cttcgtgact tccatttgc    2040
cacccggctt caacgagtac gacttcgtgc ccgagagctt cgaccgggac aaaaccatcg    2100
ccctgatcat gaacagtagt ggcagtaccg gattgcccaa gggcgtagcc ctaccgcacc    2160
gcaccgcttg tgtccgattc agtcatgccc gcgaccccat cttcggcaac cagatcatcc    2220
ccgacaccgc tatcctcagc gtggtgccat ttcaccacgg cttcggcatg ttcaccacgc    2280
tgggctactt gatctgcggc tttcgggtcg tgctcatgta ccgcttcgag gaggagctat    2340
tcttgcgcag cttgcaagac tataagattc aatctgccct gctggtgccc acactattta    2400
gcttcttcgc taagagcact ctcatcgaca gtacgacct aagcaacttg cacgagatcg    2460
ccagcggcgg ggcgccgctc agcaaggagg taggtgaggc cgtggccaaa cgcttccacc    2520
taccaggcat ccgccagggc tacggcctga cagaaacaac cagcgccatt ctgatcacc    2580
ccgaagggga cgacaagcct ggcgcagtag gcaaggtggt gcccttcttc gaggctaagg    2640
tggtggactt ggacaccggt aagacactgg gtgtgaacca gcgcggcgag ctgtgcgtcc    2700
gtggcccat gatcatgagc ggctacgtta acaacccga ggctacaaac gctctcatcg    2760
acaaggacgg ctggctgcac tcgggcgaca tcgcctactg ggacgaggac gagcacttct    2820
tcatcgtgga ccggctgaag agcctgatca aatacaaggg ctaccaggta gccccagccg    2880
aactggagag catcctgctg caacacccca acatcttcga cgccgggtc gccggcctgc    2940
ccgacgacga tgcggcgag ctgccgccg cagtcgtcgt gctggaacac ggtaaaacca    3000
tgaccgagaa ggagatcgtg gactatgtgg ccagccaggt tacaaccgcc aagaagctgc    3060
gcggtggtgt tgtgttcgtg gacgaggtgc ctaaaggact gaccggcaag ttggacgccc    3120
gcaagatccg cgagattctc attaaggcca agaagggcgg caagatcgcc gtgtaattgc    3180
aaacgtcaag tccatcttga gcatctgact tctggctaaa taaaagatct ttattttcat    3240
tagatctgtg tgttggtttt ttgtgtgcgt cgagatccac ggccgcagga accctagtg    3300
atggagttgg ccactccctc tctgcgcgct cgctcgctca ctgaggccgg cgaccaaag    3360
gtcgcccgac gcccgggctt tgcccgggcg gcctcagtga gcgagcgagc gcgcagctgc    3420
```

-continued

```
ctgcaggggc gcctgatgcg gtattttctc cttacgcatc tgtgcggtat ttcacaccgc   3480
atacgtcaaa gcaaccatag tacgcgccct gtagcggcgc attaagcgcg gcgggtgtgg   3540
tggttacgcg cagcgtgacc gctacacttg ccagcgccct agcgcccgct cctttcgctt   3600
tcttcccttc ctttctcgcc acgttcgccg gctttccccg tcaagctcta aatcggggggc   3660
tcccctttagg gttccgattt agtgctttac ggcacctcga ccccaaaaaa cttgatttgg   3720
gtgatggttc acgtagtggg ccatcgccct gatagacggt ttttcgccct ttgacgttgg   3780
agtccacgtt ctttaatagt ggactcttgt tccaaactgg aacaacactc aaccctatct   3840
cgggctattc ttttgattta taagggattt tgccgatttc ggcctattgg ttaaaaaatg   3900
agctgattta acaaaaattt aacgcgaatt ttaacaaaat attaacgttt acaattttat   3960
ggtgcactct cagtacaatc tgctctgatg ccgcatagtt aagccagccc cgacacccgc   4020
caacacccgc tgacgcgccc tgacgggctt gtctgctccc ggcatccgct tacagacaag   4080
ctgtgaccgt ctccgggagc tgcatgtgtc agaggttttc accgtcatca ccgaaacgcg   4140
cgagacgaaa gggcctcgtg atacgcctat ttttataggt taatgtcatg ataataatgg   4200
tttcttagac gtcaggtggc acttttcggg gaaatgtgcg cggaacccct atttgtttat   4260
ttttctaaat acattcaaat atgtatccgc tcatgagaca ataaccctga taaatgcttc   4320
aataatattg aaaaaggaag agtatgagta ttcaacattt ccgtgtcgcc cttattccct   4380
tttttgcggc attttgcctt cctgtttttg ctcacccaga aacgctggtg aaagtaaaag   4440
atgctgaaga tcagttgggt gcacgagtgg gttacatcga actggatctc aacagcggta   4500
agatccttga gagttttcgc cccgaagaac gttttccaat gatgagcact tttaaagttc   4560
tgctatgtgg cgcggtatta tcccgtattg acgccgggca agagcaactc ggtcgccgca   4620
tacactattc tcagaatgac ttggttgagt actcaccagt cacagaaaag catcttacgg   4680
atggcatgac agtaagagaa ttatgcagtg ctgccataac catgagtgat aacactgcgg   4740
ccaacttact tctgacaacg atcggaggac cgaaggagct aaccgctttt ttgcacaaca   4800
tgggggatca tgtaactcgc cttgatcgtt gggaaccgga gctgaatgaa gccataccaa   4860
acgacgagcg tgacaccacg atgcctgtag caatggcaac aacgttgcgc aaactattaa   4920
ctggcgaact acttactcta gcttcccggc aacaattaat agactggatg gaggcggata   4980
aagttgcagg accacttctg cgctcggccc ttccggctgg ctggtttatt gctgataaat   5040
ctggagccgg tgagcgtggg tctcgcggta tcattgcagc actggggcca gatggtaagc   5100
cctcccgtat cgtagttatc tacacgacgg ggagtcaggc aactatggat gaacgaaata   5160
gacagatcgc tgagataggt gcctcactga ttaagcattg gtaactgtca gaccaagttt   5220
actcatatat actttagatt gatttaaaac ttcattttta atttaaaagg atctaggtga   5280
agatcctttt tgataatctc atgaccaaaa tcccttaacg tgagttttcg ttccactgag   5340
cgtcagaccc cgtagaaaag atcaaaggat cttcttgaga tcctttttttt ctgcgcgtaa   5400
tctgctgctt gcaaacaaaa aaaccaccgc taccagcggt ggtttgtttg ccggatcaag   5460
agctaccaac tctttttccg aaggtaactg gcttcagcag agcgcagata ccaaatactg   5520
tccttctagt gtagccgtag ttaggccacc acttcaagaa ctctgtagca ccgcctacat   5580
acctcgctct gctaatcctg ttaccagtgg ctgctgccag tggcgataag tcgtgtctta   5640
ccgggttgga ctcaagacga tagttaccgg ataaggcgca gcggtcgggc tgaacggggg   5700
gttcgtgcac acagcccagc ttggagcgaa cgacctacaa caccgaactg acacttctct   5760
gtgagctatg agaaagcgcc acgcttcccg aagggagaaa ggcggacagg tatccggtaa   5820
gcggcagggt cggaacagga gagcgcacga gggagcttcc agggggaaac gcctggtatc   5880
tttatagtcc tgtcgggttt cgccacctct gacttgagcg tcgatttttg tgatgctcgt   5940
caggggggcg gagcctatgg aaaaacgcca gcaacgcggc cttttttacgg ttcctggcct   6000
tttgctggcc ttttgctcac atgt   6024
```

```
SEQ ID NO: 98         moltype = DNA  length = 6081
FEATURE               Location/Qualifiers
misc_feature          1..6081
                      note = plasmid pAAVss-CRE04-CSkSH5-SPc5-12_GTRM-Luc2
source                1..6081
                      mol_type = other DNA
                      organism = synthetic construct
SEQUENCE: 98
acatgtcctg caggcagctg cgcgctcgct cgctcactga ggccgcccgg gcaaagcccg   60
gggcgtcggc gacctttggt cgcccggcct cagtgagcga gcgagcgcgc agagagggag   120
tggccaactc catcactagg ggttcctgcg gccccttta gagaatccac acctgtccca   180
gttgctgggt tccactacca aaagtgaatt gcaactattt taggagcact aagcacatc   240
cgaaaaatga gtgattctgt tctggcccac accacatcac tgatgtaccc ccttaaagca   300
tgtccctgag ttcatcacag aagactgctc ctcctgtgcc ctccacaagg ttagaactat   360
ccttgtctta gggaaaaagg agagagagag agagagagag agagagagag agagagagag   420
agagagagag ggacaggcac caactgggta acctctgctg acccccactc tactttacca   480
taagtagctc caaatccttc tagaaaatct gaaaggcata gccccatata tcagtgatat   540
aaatagaacc tgcagcaggc tctggtaaat gatgactaca aggtggactg ggaggcagcc   600
cggccttggc aggcatcatc ctctaaatat aaagatgaat ttgttcagcc tttgcagaag   660
gaggcgcgcc acgcgtcagt ttactcacca gggattcaga ggcagcactg ctgaaccctg   720
agcccttggc acatcaggtt ggctgtcaga agtcggcctt tgtacataca cagttccctt   780
gtgaggccca gctgcgtgtc ctaggagcgg ggcctctctc cacagcagag ctcagcctct   840
caagtgtatg gacagcacgg gtgcctgatg ggtggatta gccatgagtt gaaggtggct   900
tggggagaat gagagttcta gagatagggag gaaggggttg ccaataggag agtggaattc   960
ctgagcacct cgtcacaggc agccgacaga acatgagccg cagggcccag gctatttata   1020
cctcgcctgt cactatcagg gtccccacag ctcccccac ctccagccac acacagcagg   1080
tccttttgct ctttctggtc ccttctctac tcctccccct ccctacctaa ggtacccaac   1140
gcgttacgtg gccaccgcct tcggcaccat cctcacgaca cccaaatatg gcgacggggtg   1200
aggaatggtg gggagttatt tttagagcgg tgaggaaggt ggcaggcag caggtgttgg   1260
cgctctaaaa ataactcccg ggagttattt ttagagcgga ggaatggtgg acacccaaat   1320
atggcgacgt tcctcacccc gtcgccatat ttgggtgtcc gccctcggcc ggggccgcat   1380
tcctggggggc cggcggtgc tccgcccgc ctcgataaaa ggctccgggg ccggcggcgg   1440
cccacgagct acccggagga gcgggaggcg ccaagctcta gatctagaaa gaggtaaggg   1500
tttaagggat ggttggttgg tggggtatta atgtttaatt acctggagca cctgcctgaa   1560
```

-continued

```
atcactttt  ttcaggttgg  aagcttatgg  aagatgccaa  aaacattaag  aagggcccag  1620
cgccattcta  cccactcgag  gacgggaccg  ccggcgagca  gctgcacaaa  gccatgaagc  1680
gctacgccct  ggtgcccggc  accatcgcct  ttaccgacgc  acatatcgag  gtggacatta  1740
cctacgccga  gtacttcgag  atgagcgttc  ggctggcaga  agctatgaag  cgctatgggc  1800
tgaatacaaa  ccatcggatc  gtggtgtgca  gcgagaatag  cttgcagttc  ttcatgcccg  1860
tgttgggtgc  cctgttcatc  ggtgtggctg  tggcccagc   taacgacatc  tacaacgagc  1920
gcgagctgct  gaacagcatg  ggcatcagcc  agcccaccgt  cgtattcgtg  agcaagaaag  1980
ggctgcaaaa  gatcctcaac  gtgcaaaaga  agctaccgat  catacaaaag  atcatcatca  2040
tggatagcaa  gaccgactac  cagggcttcc  aaagcatgta  caccttcgtg  acttcccatt  2100
tgccacccgg  cttcaacgag  tacgacttcg  tgcccgagag  cttcgaccgg  gacaaaacca  2160
tcgccctgat  catgaacagt  agtggcagta  ccggattgcc  caagggcgta  gccctaccgc  2220
accgcaccgc  ttgtgtccga  ttcagtcatg  cccgcgaccc  catcttcggc  aaccagatca  2280
tcccgacac   cgctatcctc  agcgtggtgc  catttcacca  cggcttcggc  atgttcacca  2340
cgctgggcta  cttgatctgc  ggctttcggg  tcgtgctcat  gtaccgcttc  gaggaggagc  2400
tattcttgcg  cagcttgcaa  gactataaga  ttcaatctgc  cctgctggtg  cccacactat  2460
ttagcttctt  cgctaagagc  actctcatcg  acaagtacga  cctaagcaac  ttgcacgaga  2520
tcgccagcgg  cggggcgccg  ctcagcaagg  aggtaggtga  ggccgtggcc  aaacgcttcc  2580
acctaccagg  catccgccag  ggctacggcc  tgacagaaac  aaccagcgcc  attctgatca  2640
cccccgaagg  ggacgacaag  cctggcgcag  taggcaaggt  ggtgcccttc  ttcgaggcta  2700
aggtggtgga  cttggacacc  ggtaagacac  tgggtgtgaa  ccagcgcggc  gagctgtgcg  2760
tccgtggccc  catgatcatg  agcggctacg  ttaacaaccc  cgaggctaca  aacgctctca  2820
tcgacaagga  cggctggctg  cacagcggcg  acatcgctca  ctggacgacg  gacgagcact  2880
tcttcatcgt  ggaccggctg  aagagcctga  tcaaatacaa  gggctaccag  gtagccccag  2940
ccgaactgga  gagcatcctg  ctgcaacacc  ccaacatctt  cgacgccggg  gtcgccggcc  3000
tgcccgacga  cgatgccggc  gagctgcccg  ccgcagtcgt  cgtgctggaa  cacggtaaaa  3060
ccatgaccga  gaaggagatc  gtggactatg  tggccagcca  ggttacaacc  gccaagaagc  3120
tgcgcggtgg  tgttgtgttc  gtggacgagg  tgcctaaagg  actgaccggc  aagttggacg  3180
cccgcaagat  ccgcgagatt  ctcattaagg  ccaagaaggg  cggcaagatc  gccgtgtaat  3240
tcgaaacgtc  acgtccatct  tgagcatctg  acttctggct  aaataaaaga  tctttatttt  3300
cattagatct  gtgtgttggt  tttttgtgtg  cgtcgagatc  cacggccgca  ggaacccta   3360
gtgatggagt  tggccactcc  ctctctgcgc  gctcgctcgc  tcactgaggc  cgggcgacca  3420
aaggtcgccc  gacgcccggg  ctttgcccgg  gcggcctcag  tgagcgagcg  agcgcgcagc  3480
tgcctgcagg  ggcgcctgat  gcggtatttt  ctccttacgc  atctgtgcgg  tatttcacac  3540
cgcatacgtc  aaagcaacca  tagtacgcgc  cctgtagcgg  cgcattaagc  gcggcgggtg  3600
tggtggttac  gcgcagcgtg  accgctacac  ttgccagcgc  cctagcgccc  gctcctttcg  3660
ctttcttccc  ttcctttctc  gccacgttcg  ccggctttcc  ccgtcaagct  ctaaatcggg  3720
ggctcccttt  agggttccga  tttagtgctt  tacggcacct  cgaccccaaa  aaacttgatt  3780
tgggtgatgg  ttcacgtagt  gggccatcgc  cctgatagac  ggtttttcgc  cctttgacgt  3840
tggagtccac  gttctttaat  agtggactct  tgttccaaac  tggaacaaca  ctcaacccta  3900
tctcgggcta  ttcttttgat  ttataaggga  ttttgccgat  ttcggcctat  tggttaaaaa  3960
atgagctgat  ttaacaaaaa  tttaacgcga  attttaacaa  aatattaacg  tttacaattt  4020
tatggtgcac  tctcagtaca  atctgctctg  atgccgcata  gttaagccag  ccccgacacc  4080
cgccaacacc  cgctgacgcg  ccctgacggg  cttgtctgct  cccggcatcc  gcttacagac  4140
aagctgtgac  cgtctccggg  agctgcatgt  gtcagaggtt  ttcaccgtca  tcaccgaaac  4200
gcgcgagacg  aaagggcctc  gtgatacgcc  tatttttata  ggttaatgtc  atgataataa  4260
tggtttctta  gacgtcaggt  ggcactttc   ggggaaatgt  gcgcggaacc  cctatttgtt  4320
tatttttcta  aatacattca  aatatgtatc  cgctcatgag  acaataaccc  tgataaatgc  4380
ttcaataata  ttgaaaaagg  aagagtatga  gtattcaaca  tttccgtgtc  gcccttattc  4440
ccttttttgc  ggcatttgc   cttcctgttt  ttgctcaccc  agaaacgctg  gtgaaagtaa  4500
aagatgctga  gatcagttg   ggtgcacgag  tgggttacat  cgaactggat  ctcaacagcg  4560
gtaagatcct  tgagagtttt  cgccccgaag  aacgttttcc  aatgatgagc  acttttaaag  4620
ttctgctatg  tggcgcggta  ttatcccgta  ttgacgccgg  gcaagagcaa  ctcggtcgcc  4680
gcatacacta  ttctcagaat  gacttggttg  agtactcacc  agtcacagaa  aagcatctta  4740
cggatggcat  gacagtaaga  gaattatgca  gtgctgccat  aaccatgagt  gataacactg  4800
cggccaactt  acttctgaca  acgatcggag  gaccgaagga  gctaaccgct  tttttgcaca  4860
acatggggga  tcatgtaact  cgccttgatc  gttgggaacc  ggagctgaat  gaagccatac  4920
caaacgacga  gcgtgacacc  acgatgcctg  tagcaatggc  aacaacgttg  cgcaaactat  4980
taactggcga  actacttact  ctagcttccc  ggcaacaatt  aatagactgg  atggaggcgg  5040
ataaagttgc  aggaccactt  ctgcgctcgg  cccttccggc  tggctggttt  attgctgata  5100
aatctggagc  cggtgagcgt  gggtctcgcg  gtatcattgc  agcactgggg  ccagatggta  5160
agccctcccg  tatcgtagtt  atctacacga  cggggagtca  ggcaactatg  gatgaacgaa  5220
atagacagat  cgctgagata  ggtgcctcac  tgattaagca  ttggtaactg  tcagaccaag  5280
tttactcata  tatactttag  attgatttaa  aacttcattt  ttaatttaaa  aggatctagg  5340
tgaagatcct  ttttgataat  ctcatgacca  aaatccctta  acgtgagttt  tcgttccact  5400
gagcgtcaga  ccccgtagaa  aagatcaaag  gatcttcttg  agatcctttt  tttctgcgcg  5460
taatctgctg  cttgcaaaca  aaaaaaccac  cgctaccagc  ggtggtttgt  ttgccggatc  5520
aagagctacc  aactcttttt  ccgaaggtaa  ctggcttcag  cagagcgcag  ataccaaata  5580
ctgtccttct  agtgtagccg  tagttaggcc  accacttcaa  gaactctgta  gcaccgccta  5640
catacctcgc  tctgctaatc  ctgttaccag  tggctgctgc  cagtggcgat  aagtcgtgtc  5700
ttaccgggtt  ggactcaaga  cgatagttac  cggataaggc  gcagcggtcg  ggctgaacgg  5760
ggggttcgtg  cacacagccc  agcttggagc  gaacgaccta  caccgaactg  agatacctac  5820
agcgtgagct  atgagaaagc  gccacgcttc  cgaagggag   aaaggcggac  aggtatccgg  5880
taagcggcag  ggtcggaaca  ggagagcgca  cgagggagct  tccaggggga  aacgcctggt  5940
atctttatag  tcctgtcggg  tttcgccacc  tctgacttga  gcgtcgattt  ttgtgatgct  6000
cgtcagggggg  gcggagccta  tggaaaaacg  ccagcaacgc  ggcctttta   cggttcctgg  6060
ccttttgctg  gccttttgct  c                                            6081
```

SEQ ID NO: 99      moltype = DNA  length = 5972
FEATURE            Location/Qualifiers -continued

```
misc_feature         1..5972
                     note = plasmid pAAVss-CRE06-CSkSH5-SPc5-12_GTRM-Luc2
source               1..5972
                     mol_type = other DNA
                     organism = synthetic construct
SEQUENCE: 99
cctgcaggca gctgcgcgct cgctcgctca ctgaggccgc ccgggcaaag cccgggcgtc  60
gggcgacctt tggtcgcccg gcctcagtga gcgagcgagc gcgcagagag ggagtggcca  120
actccatcac taggggttcc tgcggccggg ccaggggacg gtggcttcta cgtgcttggg  180
acgttcccag ccaccgtccc atgttcccgg cgggggggcca gctgtcccca ccgccagccc  240
aactcagcac ttggtcaggg tatcagcttg gtgggggggc gtgagcccag ccctgggggc  300
ggctcagccc atacaaggcc atggggctgg gcgcaaagca tgcctggggtt cagggtgggt  360
atggtgcggg agcagggagg tgagaggctc agctgccctc cagaactcct ccctgggggac  420
aacccctccc agccaatagc acagcctagg tcccctata taaggccacg gctgctggcc  480
cttcctttgg gtcagtgtca cctccaggat acagacagcc cccttcagc ccagcccagc  540
caggtacggc gcgccacgcg tcagtttact caccagggat tcagaggcag cactgctgaa  600
ccctgagccc ttggcacatc aggttggctg tcagaagtcg gcctttgtac atacacagtt  660
ccctgtgag gcccagctgc gtgtcctagg agcggggcct ctctccacag cagagctcag  720
cctctcaagt gtatggacag cacgggtgcc tgatggtgg atttagccat gagttgaagg  780
tggcttgggg agaatgagag ttctagagat agggagaagg ggttgccaat aggagagtgg  840
aattcctgag cacctcgtca caggcagccg acagaacatg agccgcaggg cccaggctat  900
ttatacctcg cctgtcacta tcagggtccc cacagctcca cccacctcca cacacacaca  960
gcaggtcctt ttgctctttc tggtcccttc tctactcctc cccctcccta cctaaggtac  1020
ccaacgcgtt acgtggccac cgccttcggc accatcctca cgacacccaa atatggcgac  1080
gggtgaggaa tggtgggggag ttattttag agcggtgagg aaggtgggca ggcagcaggt  1140
gttggcgctc taaaaataac tcccgggagt tatttttaga gcggaggaat ggtggacacc  1200
caaatatggc gacggttcct cacccgtcgc catatttggg tgtccgccct cggccggggc  1260
cgcattcctg ggggccgggc ggtgctcccg cccgcctcga taaaaggctc cggggccggc  1320
ggcggcccac gagctacccg gaggagcggg aggcgccaag ctctagatct agaaagaggt  1380
aagggtttaa gggatggttg gttggtgggg tattaatgtt taattacctg gagcacctgc  1440
ctgaaatcac ttttttttcag gttggaagct tatggaagat gccaaaaaca ttaagaaggg  1500
cccagcgcca ttctacccac tcgaggacg gaccgcggc gagcagctgc acaaagccat  1560
gaagcgctac gccctggtgc ccggcaccat cgcctttacc gacgcacata tcgaggtgga  1620
cattacctac gccgagtact tcgagatgag cgttcggctg gcagaagcta tgaagcgcta  1680
tgggctgaat acaaaccatc ggatcgtggt gtgcagcgag aatagcttgc agttcttcat  1740
gcccgtgttg ggtgccctgt tcatcggtgt ggctgtggcc ccagctaacg acatctacaa  1800
cgagcgcgag ctgctgaaca gcatgggcat cagccagccc accgtcgtat tcgtgagcaa  1860
gaaagggctg caaaagatcc tcaacgtgca aaagaagcta ccgatcatac aaaagatcat  1920
catcatggat agcaagaccg actaccaggg cttccacagc atgtacacct tcgtgacttc  1980
ccatttgcca cccggcttca acgagtacga cttcgtgccc gagagcttcg accgggacaa  2040
aaccatcgcc ctgatcatga cagtagtgg cagtaccgga ttgcccaagg gcgtagccct  2100
accgcaccgc accgcttgtg tccgattcag tcatgcccgc gaccccatct tcggcaacca  2160
gatcatcccc gacaccgcta tcctcagcgt ggtgccattt caccacggct tcggcatgtt  2220
caccacgctg ggctacttga tctgcgggctt tcgggtcgtg ctcatgtacc gcttcgagga  2280
ggagctattc ttgcgcagct tgcaagacta taagattcaa tctgccctgc tggtgcccac  2340
actatttagc ttcttcgcta agagcactct catcgacaag tacgacctaa gcaacttgca  2400
cgagatcgcc agcggcgggg cgccgctcag caaggaggta ggtgaggccg tggccaaacg  2460
cttccaccta ccaggcatcc gccagggcta cggcctgaca gaaacaacca gcgccattct  2520
gatcacccc gaaggggacg acaagcctgg cgcagtaggc aaggtggtgc ccttcttcga  2580
ggctaaggt gtggacttgg acaccggtaa gacactgggt gtgaaccagc gcggcgagct  2640
gtgcgtccgt ggccccatga tcatgagcgg ctacgttaac aaccccgagg ctacaaacgc  2700
tctcatcgac aaggacggct ggctgcacag cggcgacatc gcctactggg acgaggacga  2760
gcacttcttc atcgtggacc ggctgaagag cctgatcaaa tacaagggct accaggtagc  2820
cccagccgaa ctggagagca tcctgctgca acaccccaac atcttcgacg ccggggtcgc  2880
cggcctgccc gacgacgatg ccggcgagct gcccgccgtgt gtcgtcgtgc tggaacacgg  2940
taaaaccatg accgagaagg agatcgtgga ctatgtggcc agccaggtta caaccgccaa  3000
gaagctgcgc ggtggtgttg tgttcgtgga cgaggtgcct aaaggactga ccggcaagtt  3060
ggacgcccgc aagatccgcg agattctcat taaggccaag aagggcggca agatcgccgt  3120
gtaattcgaa acgtctagtc catcttgagc atctgacttc tggctaaata aaagatcttt  3180
attttcatta gatctgtgtg ttggtttttt gtgtgcgtcg agatccacgg ccgcaggaac  3240
ccctagtgat ggagttggcc actccctctc tgcgcgctcg ctcgctcact gaggccgggc  3300
gaccaaaggt cgcccgacgc ccgggctttg cccgggcggc ctcagtgagc gagcgagcgc  3360
gcagctgcct gcaggggcgc ctgatgcggt attttctcct tacgcatctg tgcggtattt  3420
cacaccgcat acgtcaaagc aaccatagta cgcgccctgt agcggcgcat taagcgcggc  3480
gggtgtggtg gttacgcgca gcgtgaccgc tacacttgcc agcgccctag cgcccgctcc  3540
tttcgctttc ttcccttcct ttctcgccac gttcgccggc tttccccgtc aagctctaaa  3600
tcggggggctc cctttagggt tccgatttag tgctttacgg cacctcgacc ccaaaaaact  3660
tgatttgggt gatggttcac gtagtgggcc atcgccctga tagacggttt ttcgcccttt  3720
gacgttggag tccacgttct ttaatagtgg actcttgttc caaactggaa caacactcaa  3780
ccctatctcg ggctattctt ttgatttata agggattttg ccgatttcgg cctattggtt  3840
aaaaaatgag ctgatttaac aaaaatttaa cgcgaatttt aacaaatat taacgtttac  3900
aatttttatgt tgcactctca gtacaatctg ctctgatgcc gcatagttaa gccagccccg  3960
acacccgcca acacccgctg acgcgccctg acgggcttgt ctgctcccgg catccgctta  4020
cagacaagct gtgaccgtct ccgggagctg catgtgtcag aggttttcac cgtcatcacc  4080
gaaacgcgcg agacgaaagg gcctcgtgat acgcctattt ttataggtta atgtcatgat  4140
aataatggtt tcttagacgt caggtggcac ttttcgggga aatgtgcgcg gaaccccctat  4200
ttgtttattt ttctaaatac attcaaatat gtatccgctc atgagacaat aaccctgata  4260
aatgcttcaa taatattgaa aaaggaagag tatgagtatt caacatttcc gtgtcgccct  4320
tattcccttt tttgcggcat tttgccttcc tgttttttgct cacccagaaa cgctggtgaa  4380
```

```
agtaaaagat gctgaagatc agttgggtgc acgagtgggt tacatcgaac tggatctcaa   4440
cagcggtaag atccttgaga gttttcgccc cgaagaacgt tttccaatga tgagcacttt   4500
taaagttctg ctatgtggcg cggtattatc ccgtattgac gccgggcaag agcaactcgg   4560
tcgccgcata cactattctc agaatgactt ggttgagtac tcaccagtca cagaaaagca   4620
tcttacggat ggcatgacag taagagaatt atgcagtgct gccataacca tgagtgataa   4680
cactgcggcc aacttacttc tgacaacgat cggaggaccg aaggagctaa ccgctttttt   4740
gcacaacatg ggggatcatg taactcgcct tgatcgttgg gaaccggagc tgaatgaagc   4800
cataccaaac gacgagcgtg acaccacgat gcctgtagca atggcaacaa cgttgcgcaa   4860
actattaact ggcgaactac ttactctagc ttcccggcaa caattaatag actggatgga   4920
ggcggataaa gttgcaggac cacttctgcg ctcggccctt ccggctggct ggtttattgc   4980
tgataaatct ggagccggtg agcgtgggtc tcgcggtatc attgcagcac tggggccaga   5040
tggtaagccc tcccgtatcg tagttatcta cacgacgggg agtcaggcaa ctatggatga   5100
acgaaataga cagatcgctg agataggtgc ctcactgatt aagcattggt aactgtcaga   5160
ccaagtttac tcatatatac tttagattga tttaaaactt catttttaat ttaaaaggat   5220
ctaggtgaag atcctttttg ataatctcat gaccaaaatc ccttaacgtg agttttcgtt   5280
ccactgagcg tcagaccccg tagaaaagat caaaggatct tcttgagatc ctttttttct   5340
gcgcgtaatc tgctgcttgc aaacaaaaaa accaccgcta ccagcggtgg tttgtttgcc   5400
ggatcaagag ctaccaactc tttttccgaa ggtaactggc ttcagcagag cgcagatacc   5460
aaatactgtc cttctagtgt agccgtagtt aggccaccac ttcaagaact ctgtagcacc   5520
gcctacatac ctcgctctgc taatcctgtt accagtggct gctgccagtg gcgataagtc   5580
gtgtcttacc gggttggact caagacgata gttaccggat aaggcgcagc ggtcgggctg   5640
aacggggggt tcgtgcacac agcccagctt ggagcgaacg acctacaccg aactgagata   5700
cctacagcgt gagctatgag aaagcgccac gcttcccgaa gggagaaagg cggacaggta   5760
tccggtaagc ggcagggtcg gaacaggaga gcgcacgagg gagcttccag ggggaaacgc   5820
ctggtatctt tatagtcctg tcgggtttcg ccacctctga cttgagcgtc gatttttgtg   5880
atgctcgtca gggggcgga gcctatgaa aaacgccagc aacgcggcct ttttacggtt   5940
cctggccttt tgctggcctt ttgctcacat gt   5972
```

```
SEQ ID NO: 100              moltype = DNA  length = 5827
FEATURE                    Location/Qualifiers
misc_feature              1..5827
                           note = plasmid pAAVss-CRE07-CSkSH5-SPc5-12_GTRM-Luc2
source                     1..5827
                           mol_type = other DNA
                           organism = synthetic construct
SEQUENCE: 100
cctgcaggca gctgcgcgct cgctcgctca ctgaggccgc ccgggcaaag cccgggcgtc   60
gggcgacctt tggtcgcccg gcctcagtga gcgagcgagc gcgcagagag ggagtggcca   120
actccatcac taggggttcc tgcggccccc agcccccttc cccgggaggt ggagcggcc   180
acccagggcc ccgtggctgc ccttgtaagg aggcgaggcc cgaggacacc cgagacgccc   240
ggttataatt aaccaggaca cgtggcgaac cccctccaa cacctgcccc cgaaccccc   300
catacccagc gcctcgggtc tcggcctttg cggcagagga gacagcaaag cgccctctaa   360
aaataactcc tttcccggcg accgagaccc tccctgtccc ccgcgcgcc acgcgtcagt   420
ttactcacca gggattcaga ggcagcactg ctgaaccctg agcccttggc acatcaggtt   480
ggctgtcaga agtcggcctt tgtacataca cagttccctt gtgaggccca gctgcgtgtc   540
ctaggagcgg ggcctctctc cacagcagag ctcagcctct caagtgtatg gacagcacgg   600
gtgcctgatg ggtggattta gccatgagtt gaaggtggtt tggggagaat gagagttcta   660
gagataggga gaaggggttg ccaataggag agtggaattc ctgagcacct cgtcacaggc   720
agccgacaga acatgagccg cagggcccag gctatttata cctcgcctgt cactatcagg   780
gtccccacag ctcccccac ctccagccac acacagcagg tccttttgct ctttctggtc   840
ccttctctac tcctccccct ccctacctaa ggtacccaac gcgttacgtg gccaccgcct   900
tcggcaccat cctcacgaca cccaaatatg gcgacgggtg aggaatggtg gggagttatt   960
tttagagcgg tgaggaaggt gggcaggcag caggtgttgg cgctctaaaa ataactcccg   1020
ggagttattt ttagagcgga ggaatggtgg acacccaaat atggcgacgg ttcctcaccc   1080
gtcgccatat ttgggtgtcc gccctcggcc ggggccgcat tcctgggggc cgggcggtgc   1140
tcccgcccgc ctcgataaaa ggctccgggg ccggcggcgg cccacgagct accggagga   1200
gcgggaggcg ccaagctcta gatctagaaa gaggtaaggg tttaagggat ggttggttgg   1260
tggggtatta atgtttaatt acctggagca cctgcctgaa atcactttt ttcaggttgg   1320
aagcttatgg aagatgccaa aaacattaag aagggcccag cgccattcta cccactcgag   1380
gacgggaccg ccggcgagca gctgcacaaa gccatgaagc gctacgccct ggtgcccggc   1440
accatcgcct ttaccgacgc acatatcgag gtggacatta cctacgccga gtacttcgag   1500
atgagcgttc ggctggcaga agctatgaag cgctatgggc tgaatacaaa ccatcggatc   1560
gtggtgtgca cgagaatag cttgcagttc ttcatgcccg tgttgggtgc cctgttcatc   1620
ggtgtggctg tggcccagc taacgacatc tacaacgagc gcgagctgct gaacatgatg   1680
ggcatcagcc agcccaccgt cgtattcgtg agcaagaaag ggctgcaaaa gatcctcaac   1740
gtgcaaaaga agtaccgat catacaaaag atcatcatca tggatagcaa gaccgactac   1800
cagggcttcc aaagcatgta caccttcgtg acttccatt tgccaccgg cttcaacgag   1860
tacgacttcg tgcccgagag cttcgaccgg gacaaaacca tcgccctgat catgaacagt   1920
agtggcagta ccggattgcc caagggcgta gccctaccgg accgcaccg ttgtgtccga   1980
ttcagtcatg cccgcgaccc catcttcggc aaccagatca tccccgacac cgctatcctc   2040
agcgtggtgc catttcacca cggcttcggc atgttcacca cgctgggcta cttgatctgc   2100
ggctttcggt cgtgctcat gtaccgcttc gaggaggagc tattcttgcg cagcttgcaa   2160
gactataaga ttcaatctgc cctgctggtg cccacactat ttagcttctt cgctaagagc   2220
actctcatcg acaagtacga cctaagcaac ttgcacgaga tcgccggcgg cggggagacg   2280
ctcagcaagg aggtaggtga ggccgtggc aaacgcttcc acctaccagg catccgccag   2340
ggctacggcc tgacagaaac aaccagcgcc attctgatca cccccgaagg ggacgacaag   2400
cctgcgcag taggcaaggt ggtgcccttc ttcgaggcta aggtggtgga cttggacacc   2460
ggtaagacac tgggtgtgaa ccagcgcggc gagctgtgcg tccgtggccc catgatcatg   2520
agcggctacg ttaacaaccc cgaggctaca aacgctctca tcgacaagga cggctggctg   2580
```

-continued

```
cacagcggcg acatcgccta ctgggacgag gacgagcact tcttcatcgt ggaccggctg    2640
aagagcctga tcaaatacaa gggctaccag gtagccccag ccgaactgga gagcatcctg    2700
ctgcaacacc ccaacatctt cgacgccggg gtcgccggcc tgcccgacga cgatgccggc    2760
gagctgcccg ccgcagtcgt cgtgctggaa cacggtaaaa ccatgaccga gaaggagatc    2820
gtggactatg tggccagcca ggttacaacc gccaagaagc tgcgcggtgg tgttgtgttc    2880
gtggacgagg tgcctaaagg actgaccggc aagttggacg cccgcaagat ccgcgagatt    2940
ctcattaagg ccaagaaggg cggcaagatc gccgtgtaat tcgaaacgtc ttgtccatct    3000
tgagcatctg acttctggct aaataaaaga tctttatttt cattagatct gtgtgttggt    3060
tttttgtgtg cgtcgagatc cacggccgca ggaacccta gtgatggagt tggccactcc    3120
ctctctgcgc gctcgctcgc tcactgaggc cgggcgacca aaggtcgccc gacgcccggg    3180
ctttgcccgg cgcggcctcag tgagcgagcg agcgcgcagc tgcctgcagg ggcgcctgat    3240
gcggtatttt ctccttacgc atctgtgcgg tatttcacac cgcatacgtc aaagcaacca    3300
tagtacgcgc cctgtagcgg cgcattaagc gcggcgggtg tggtggttac gcgcagcgtg    3360
accgctacac ttgccagcgc cctagcgccc gctcctttcg ctttcttccc ttcctttctc    3420
gccacgttcg ccggctttcc ccgtcaagct ctaaatcggg ggctccctt agggttccga    3480
tttagtgctt tacggcacct cgaccccaaa aaacttgatt tgggtgatgg ttcacgtagt    3540
gggccatcgc cctgatagac ggtttttcgc cctttgacgt tggagtccac gttctttaat    3600
agtggactct tgttccaaac tggaacaaca ctcaacccta tctcgggcta ttctttttgat    3660
ttataaggga ttttgccgat ttcggcctat tggttaaaaa atgagctgat ttaacaaaaa    3720
tttaacgcga attttaacaa aatattaacg tttacaattt tatggtgcac tctcagtaca    3780
atctgctctg atgccgcata gttaagccag ccccgacacc cgccaacacc cgctgacgcg    3840
ccctgacggg cttgtctgct cccggcatcc gcttacagac aagctgtgac cgtctccggg    3900
agctgcatgt gtcagaggtt ttcaccgtca tcaccgaaac gcgcgagacg aaagggcctc    3960
gtgatacgcc tattttttata ggttaatgtc atgataataa tggtttctta gacgtcaggt    4020
ggcactttc ggggaaatgt gcgcggaacc cctatttgtt tatttttcta aatacattca    4080
aatatgtatc cgctcatgag acaataaccc tgataaatgc ttcaataata ttgaaaaagg    4140
aagagtatga gtattcaaca tttccgtgtc gcccttattc ccttttttgc ggcattttgc    4200
cttcctgttt ttgctcaccc agaaacgctg gtgaaagtaa aagatgctga gatcagttg    4260
ggtgcacgag tgggttacat cgaactggat ctcaacagcg gtaagatcct tgagagtttt    4320
cgccccgaag aacgttttcc aatgatgagc acttttaaag ttctgctatg tggcgcggta    4380
ttatcccgta ttgacgccgg gcaagagcaa ctcggtcgc gcatacacta ttctcagaat    4440
gacttggttg agtactcacc agtcacagaa aagcatctta cggatggcat gacagtaaga    4500
gaattatgca gtgctgccat aaccatgagt gataacactg cggccaactt acttctgaca    4560
acgatcggag gaccgaagga gctaaccgct ttttttgcaca acatggggga tcatgtaact    4620
cgccttgatc gttgggaacc ggagctgaat gaagccatac caaacgacga gcgtgacacc    4680
acgatgcctg tagcaatggc aacaacgttg cgcaaactat taactggcga actacttact    4740
ctagcttccc ggcaacaatt aatagactgg atggaggcgg ataaagttgc aggaccactt    4800
ctgcgctcgg cccttccggc tggctggttt attgctgata aatctggagc cggtgagcgt    4860
gggtctcgcg gtatcattgc agcactgggg ccagatggta gccctcccg tatcgtagtt    4920
atctacacga cggggagtca ggcaactatg gatgaacga atagacagat cgctgagata    4980
ggtgcctcac tgattaagca ttggtaactg tcagaccaag tttactcata tatactttag    5040
attgatttaa aacttcattt ttaatttaaa aggatctagg tgaagatcct ttttgataat    5100
ctcatgacca aaatccctta acgtgagttt tcgttccact gagcgtcaga ccccgtagaa    5160
aagatcaaag gatcttcttg agatcctttt tttctgcgcg taatctgctg cttgcaaaca    5220
aaaaaaccac cgctaccagc ggtggtttgt ttgccggatc aagagctacc aactctttttt    5280
ccgaaggtaa ctggcttcag cagagcgcag ataccaaata ctgtccttct agtgtagccg    5340
tagttaggcc accacttcaa gaactctgta gcaccgccta cataccgtgc tctgctaatc    5400
ctgttaccag tggctgctgc cagtggcgat aagtcgtgtc ttaccgggtt ggactcaaga    5460
cgatagttac cggataaggc gcagcggtcg ggctgaacgg ggggttcgtg cacacagccc    5520
agcttggagc gaacgaccta caccgaactg agatacctac agcgtgagct atgagaaagc    5580
gccacgcttc ccgaagggag aaaggcggac aggtatccgg taagcggcag ggtcggaaca    5640
ggagagcgca cgagggagct tccaggggga aacgcctggt atctttatag tcctgtcggg    5700
tttcgccacc tctgacttga gcgtcgattt ttgtgatgct cgtcaggggg cggagcctta    5760
tggaaaaacg ccagcaacgc ggcctttttta cggttcctgg ccttttgctg ccttttgct    5820
cacatgt                                                              5827
```

```
SEQ ID NO: 101          moltype = DNA   length = 5891
FEATURE                 Location/Qualifiers
misc_feature            1..5891
                        note = plasmid pAAVss-CRE66-CSkSH5-SPc5-12_GTRM-Luc2
source                  1..5891
                        mol_type = other DNA
                        organism = synthetic construct
SEQUENCE: 101
cctgcaggca gctgcgcgct cgctcgctca ctgaggccgc ccgggcaaag cccgggcgtc    60
gggcgacctt tggtcgcccg gcctcagtga gcgagcgagc gcgcagagag ggagtggcca    120
actccatcac taggggttcc tgcggcccca ggtgacaggt ggatggtgga gctggaggag    180
ccactcggag cctccaaggc tggggagggt ggaggggga ggcaggtcgg tgtcccaggc    240
cacacctgtt gactaaggga ttaggatgtt gtgtccctgc cagccctcct ccaataagcc    300
cctctgggcc tgcagggaga ggaggagcct tgccatgtaa actgtatttt tagttccctg    360
tgcctctccc cggctgctat aagacacctc tccccacccc cagccctggc cgcttggctg    420
gaggctctgc gaggacagct ggggagaagg ggagctgtgg tcagtaggcg cgccacgcgt    480
cagtttactc accaggggatt cagaggcagc actgctgaac cctgagccct tggcacatca    540
ggttggctgt cagaagtcgg cctttgtaca tacacagttc cctgtgagg cagccagctg    600
tgtcctagga gcggggcctc tctccacagc agagctcagc ctctcaagtg tatggacagc    660
acgggtgcct gatgggtgga tttagccatg agttgaaggt ggcttgggga gaatgagagt    720
tctagagata gggagaaggg gttgccaata ggagagtgga attcctgagc acctcgtcac    780
aggcagccga cagaacatga gccgcagggc ccaggctatt tatacctcgc ctgtcactat    840
cagggtcccc acagctcccc ccacctccag ccacacacag caggtccttt tgctctttct    900
```

-continued

```
ggtcccttct ctactcctcc ccctccctac ctaaggtacc caacgcgtta cgtggccacc   960
gccttcggca ccatcctcac gacacccaaa tatggcgacg ggtgaggaat ggtgggggagt  1020
tattttaga gcggtgagga aggtgggcag gcagcaggtg ttggcgctct aaaaataact  1080
cccgggagtt attttagag cggaggaatg gtggacaccc aaatatggcg acggttcctc  1140
acccgtcgcc atatttgggt gtccgccctc ggccggggcc gcattcctgg gggccgggcg  1200
gtgctcccgc ccgcctcgat aaaaggctcc ggggccggcg gcggcccacg agctacccgg  1260
aggagcggga ggcgccaagc tctagatcta gaaagaggta agggtttaag ggatggttgg  1320
ttggtggggt attaatgttt aattacctgg agcacctgcc tgaaatcact ttttttcagg  1380
ttggaagctt atggaagatg ccaaaaacat taagaagggc ccagcgccat tctacccact  1440
cgaggacggg accgccggcg agcagctgca caaagccatg aagcgctacg ccctggtgcc  1500
cggcaccatc gcctttaccg acgcacatat cgaggtggac attacctacg ccgagtactt  1560
cgagatgagc gttcggctgg cagaagctat gaagcgctat gggctgaata caaaccatcg  1620
gatcgtggtg tgcagcgaga atagcttgca gttcttcatg cccgtgttgg gtgccctgtt  1680
catcggtgtg gctgtggccc cagctaacga catctacaac ggagcgcgagc tgctgaacag  1740
catgggcatc agccagccca ccgtcgtatt cgtgagcaag aaaggggctgc aaaagatcct  1800
caacgtgcaa aagaagctac cgatcataca aaagatcatc atcatggata gcaagaccga  1860
ctaccagggc ttccaaagca tgtacacctt cgtgacttcc catttgccac ccggcttcaa  1920
cgagtacgac ttcgtgcccg agagcttcga ccgggacaaa accatcgccc tgatcatgaa  1980
cagtagtggc agtaccggat tgcccaaggg cgtagcccta ccgcaccgca ccgcttgtgt  2040
ccgattcagt catgcccgcg accccatctt cggcaaccag atcatccccg acaccgctat  2100
cctcagcgtg gtgccatttc accacggctt cggcatgttc accacgctgg gctacttgat  2160
ctgcggcttt cgggtcgtgc tcatgtaccg cttcgaggag gagctattct tgcgcagctt  2220
gcaagactat aagattcaat ctgccctgct ggtgcccaca ctatttagct tcttcgctaa  2280
gagcactctc atcgacaagt acgacctaag caacttgcac gagatcgcca gcggcggggc  2340
gccgctcagc aaggaggtag gtgaggccgt ggccaaacgc ttccacctac caggcatccg  2400
ccagggctac ggcctgacag aaacaaccag cgccattctg atcaccccg aagggacga  2460
caagcctggc gcagtaggca aggtggtgcc cttcttcgag gctaaggtgg tggacttgga  2520
caccggtaag acactgggtg tgaaccagcc cggccgagctg tgcgtccgtg gccccatgat  2580
catgagcggc tacgttaaca accccgaggc tacaaacgct ctcatcgaca aggacggctg  2640
gctgcacagc ggcgacatcg cctactggga cgaggacgag cacttcttca tcgtggaccg  2700
gctgaagagc ctgatcaaat acaagggcta ccaggtagcc ccagccgaac tggagagcat  2760
cctgctgcaa caccccaaca tcttcgacgc cggggtcgcc ggcctgcccg acgacgatgc  2820
cggcgagctg cccgccgcag tcgtcgtgct ggaaacggt aaaaaccatga ccgagaagga  2880
gatcgtggac tatgtggcca gccaggttac aaccgccaag aagctgcgcg gtggtgttgt  2940
gttcgtggac gaggtgccta aaggactgac cggcaagttg gacgcccgca agatccgcga  3000
gattctcatt aaggccaaga agggcggcaa gatcgccgtg taattcgaaa cgtactgtcc  3060
atcttgagca tctgacttct ggctaaataa aagatcttta tttttcattag atctgtgtgt  3120
tggtttttg tgtgcgtcga gatccacggc cgcaggaacc cctagtgatg gagttggcca  3180
ctccctctct gcgcgctcgc tcgctcactg aggccgggga accaaaggtc gcccgacgcc  3240
cgggctttgc ccgggcggcc tcagtgagcg agcgagcgcg cagctgcctg caggggcgcc  3300
tgatgcggta ttttctcctt acgcatctgt gcggtatttc acaccgcata cgtcaaagca  3360
accatagtac gcgccctgta gcggcgcatt aagcgcggcg ggtgtggtgg ttacgcgcag  3420
cgtgaccgct acacttgcca gcgccctagc gcccgctcct ttcgctttct tcccttcctt  3480
tctcgccacg ttcgccggct ttccccgtca agctctaaat cggggctcc ctttagggtt  3540
ccgatttagt gctttacggc acctcgaccc caaaaaactt gatttgggtg atggttcacg  3600
tagtgggcca tcgccctgat agacggtttt tcgcccttg acgttggagt ccacgttctt  3660
taatagtgga ctcttgttcc aaactggaac aacactcaac cctatctgg gctattcttt  3720
tgatttataa gggattttgc cgatttcggc ctattggtta aaaaatgagc tgatttaaca  3780
aaaatttaac gcgaatttta acaaaatatt aacgtttaca attttatggt gcactctcag  3840
tacaatctgc tctgatgccg catagttaag ccagccccga cacccgccaa cacccgctga  3900
cgcgccctga cgggcttgtc tgctcccggc atccgcttac agacaagctg tgaccgtctc  3960
cgggagctgc atgtgtcaga ggttttcacc gtcatcaccg aaacgcgcga gacgaaaggg  4020
cctcgtgata cgcctatttt tataggttaa tgtcatgata ataatggttt cttagacgtc  4080
aggtggcact tttcggggaa atgtgcgcgg aacccctatt tgtttatttt tctaaataca  4140
ttcaaatatg tatccgctca tgagacaata accctgataa agcttcaat aatattgaaa  4200
aaggaagagt atgagtattc aacatttccg tgtcgccctt attccctttt ttgcggcatt  4260
ttgccttcct gttttgctc acccagaaac gctggtgaaa gtaaaagatg ctgaagatca  4320
gttgggtgca cgagtgggtt acatcgaact ggatctcaac agcggtaaga tccttgagag  4380
ttttcgcccc gaagaacgtt ttccaatgat gagcacttt aaagttctgc tatgtggcgc  4440
ggtattatcc cgtattgacg ccgggcaaga gcaactcggt cgccgcatac actattctca  4500
gaatgacttg gttgagtact caccagtcac agaaaagcat cttacggatg gcatgacagt  4560
aagagaatta tgcagtgctg ccataaccat gagtgataac actgcggcca acttacttct  4620
gacaacgatc ggaggaccga aggagctaac cgcttttttg cacaacatgg gggatcatgt  4680
aactcgcctt gatcgttggg aaccggagct gaatgaagcc ataccaaacg acgagcgtga  4740
caccacgatg cctgtagcaa tggcaacaac gttgcgcaaa ctattaactg gcgaactact  4800
tactctagct tcccggcaac aattaataga ctggatggag gcggataaag ttgcaggacc  4860
acttctgcgc tcggcccttc cggctggctg gtttattgct gataaatctg gagccggtga  4920
gcgtgggtct cgcggtatca ttgcagcact ggggccagat ggtaagccct cccgtatcgt  4980
agttatctac acgacgggga gtcaggcaac tatggatgaa cgaaatagac agatcgctga  5040
gataggtgcc tcactgatta agcattggta actgtcagac caagtttact catatatact  5100
ttagattgat ttaaaacttc attttttaatt taaaaggatc taggtgaaga tcctttttga  5160
taatctcatg accaaaatcc cttaacgtga gttttcgttc cactgagcgt cagaccccgt  5220
agaaaagatc aaaggatctt cttgagatcc ttttttttctg cgcgtaatct gctgcttgca  5280
aacaaaaaaa ccaccgctac cagcggtggt ttgtttgccg gatcaagagc taccaactct  5340
ttttccgaag gtaactggct tcagcagagc gcagatacca atactgtcc ttctagtgta  5400
gccgtagtta ggccaccact tcaagaactc tgtagcaccg cctacatacc tcgctctgct  5460
aatcctgtta ccagtggctg ctgccagtgg cgataagtcg tgtcttaccg ggttggactc  5520
aagacgatag ttaccggata aggcgcagcg gtcgggctga acggggggtt cgtgcacaca  5580
gcccagcttg gagcgaacga cctacaccga actgagatac ctacagcgtg agctatgaga  5640
```

-continued

```
aagcgccacg cttcccgaag ggagaaaggc ggacaggtat ccggtaagcg gcagggtcgg   5700
aacaggagag cgcacgaggg agcttccagg gggaaacgcc tggtatcttt atagtcctgt   5760
cgggtttcgc cacctctgac ttgagcgtcg atttttgtga tgctcgtcag gggggcggag   5820
cctatggaaa aacgccagca acgcggcctt tttacggttc ctggcctttt gctggccttt   5880
tgctcacatg t                                                        5891
```

```
SEQ ID NO: 102          moltype = DNA  length = 5865
FEATURE                 Location/Qualifiers
misc_feature            1..5865
                        note = plasmid pAAVss-CRE68-CSkSH5-SPc5-12_GTRM-Luc2
source                  1..5865
                        mol_type = other DNA
                        organism = synthetic construct
SEQUENCE: 102
cctgcaggca gctgcgcgct cgctcgctca ctgaggccgc ccgggcaaag cccgggcgtc   60
gggcgacctt tggtcgcccg gcctcagtga gcgagcgagc gcgcagagag ggagtggcca   120
actccatcac taggggttcc tgcggccaga aaggagctgc cctggggatg gctgtgtatc   180
cctacaactg ccaggcacat gcccccttgaa cacccgatgc tacgtgtccc aaaggaaact   240
ggtctccacc cacccccggc ccgtcctcgt cctgggtacc ccaccttagt aaatggcgcc   300
accatctgcc cggtcactca gcgagaaact caactcctgg cagcagatga cgggcactct   360
ggttaaatga ctctctccag cctccaagtt caacctgcag ggaagccctg gaaatcctgt   420
ctccctctgc cctgccttctc ggcgcgccac gcgtcagttt actcaccagg gattcagagg   480
cagcactgct gaaccctgag cccttggcac atcaggttgg ctgtcagaag tcggcctttg   540
tacatacaca gttcccttgt gaggcccagc tgcgtgtcct aggagcgggg cctctctcca   600
cagcagagct cagcctctca agtgtatgga cagcacgggt gcctgatggg tggatttagc   660
catgagttga aggtggcttg gggagaatga gagttctaga gataggagga aggggttgcc   720
aataggagag tggaattcct gagcacctcg tcacaggcag ccgacagaac atgagccgca   780
gggcccaggc tatttatacc tcgcctgtca ctatcagggt ccccacagct cccccacct   840
ccagccacac acagcaggtc cttttgctct ttctggtccc ttctctactc ctcccctcc   900
ctacctaagg tacccaacgc gttacgtggc caccgcctc ggcaccatcc tcacgacacc   960
caaatatggc gacgggtgag gaatggtggg gagttatttt tagagcggtg aggaaggtgg   1020
gcaggcagca ggtgttggcg ctctaaaaat aactcccggg agttattttt agagcggagg   1080
aatggtggac acccaaatat ggcgacggtt cctcacccgt cgccatattt gggtgtccgc   1140
cctcggccgg ggccgcgcattc ctgggggccg ggcggtgctc ccgcccgcct cgataaaagg   1200
ctccggggcc ggcggcgggcc cacgagctac ccggaggagc gggaggcgcc aagctctaga   1260
tctagaaaga ggtaagggtt taagggatgg ttggttggtg gggtattaat gtttaattac   1320
ctggagcacc tgcctgaaat cactttttt caggttggaa gcttatggaa gatgccaaaa   1380
acattaagaa gggcccagcg ccattctacc cactcgagga cgggaccgcc ggcgagcagc   1440
tgcacaaagc catgaagcgc tacgccctgg tgcccgtgac catcgccttt accgacgcac   1500
atatcgaggt ggacattacc tacgccgagt acttcgagat gagcgttcgg ctggcagaag   1560
ctatgaagcg ctatgggctg aatacaaacc atcggatcgt ggtgtgcagc gagaatagct   1620
tgcagttctt catgcccgtg ttgggtgccc tgttcatcgg tgtggctgtg gccccagcta   1680
acgacatcta caacgagcgc gagctgctga acagcatgga cacccacca cccaccgtcg   1740
tattcgtgag caagaaaggg ctgcaaaaga tcctcaacgt gcaaaagaag ctaccgatca   1800
tacaaaagat catcatcatg gatagcaaga ccgactacca gggcttccaa agcatgtaca   1860
ccttcgtgac ttcccatttg ccaccggct tcaacgagta cgacttcgtg cccgagagct   1920
tcgaccggga caaaaccatc gccctgatca tgaacagtag tggcagtacc ggattgccca   1980
agggcgtagc cctaccgcac cgcaccgctt gtgtccgatt cagtcatgcc cgcgacccca   2040
tcttcggcaa ccagatcatc cccgacaccg ctatcctcag cgtggtgcca tttcaccacg   2100
gcttcggcat gttcaccacg ctgggctact tgatctgcgg ctttcgggtc gtgctcatgt   2160
accgcttcga ggaggagcta ttcttgcgca gcttgcaaga ctataagatt caatctgtg   2220
tgctggtgcc cacactattt agcttcttcg ctaagagcac tctcatcgac aagtacgacc   2280
taagcaactt gcacgagatc gccagcggcg gggcgccgct cagcaaggag gtaggtgagg   2340
ccgtggccaa acgcttccac ctaccaggca tccgccaggg ctacgccctg acagaaacaa   2400
ccagcgccat tctgatcacc cccgaagggg acgacaagcc tggcgcagta ggcaaggtgg   2460
tgcccttctt cgaggctaag gtggtggact tggacaccgg taagacactg ggtgtgaacc   2520
agcgcggcga gctgtgcgtc cgtggcccca tgatcatgag cggctacgtt aacaaccccg   2580
aggctacaaa cgctctcatc gacaaggacg gctggctgca cagcggcgac atcgcctact   2640
gggacgagga cgagcacttc ttcatcgtgg accggctgaa gagcctgatc aaatacaagg   2700
gctaccaggt agccccagcc gaactgtgaga gcatcctgct gcaacacccc aacatcttcg   2760
acgccgggt cgccggcctg cccgacacg atgccggcga gctgcccgcc gcagtcgtcg   2820
tgctggaaca cggtaaaacc atgaccgaga aggagatcgt ggactatgtg gccagccagg   2880
ttacaaccgc caagaagctg cgcggtggtg ttgtgttcgt ggacgaggtg cctaaaggac   2940
tgaccgagca gttggacgcc cgcaagatcc gcgagattct cattaaggcc aagaagggca   3000
gcaagatcgc cgtgtaattc gaaacgtacg gtccatcttg agcatctgac ttctggctaa   3060
ataaaagatc tttattttca ttagatctgt gtgttggttt tttgtgtgcg tcagatcca   3120
cggccgcagg aaccccctagt gatggagttg gccactccct ctctgcgcgc tcgctcgctc   3180
actgaggccg ggcgaccaaa ggtcgcccga cgcccgggc ttgcccgggc ggcctcagtg   3240
agcgagcgag cgcgcagctg cctgcagggg cgcctgatgc ggtattttct ccttacgcat   3300
ctgtgcggta tttcacaccg catacgtcaa agcaaccata gtacgcgccc tgtagcggcg   3360
cattaagcgc ggcgggtgtg gtggttacgc gcagcgtgac cgctacactt gccagcgccc   3420
tagcgcccgc tcctttcgct ttcttccctt cctttctcgc cacgttcgcc ggctttcccc   3480
gtcaagctct aaatcggggg ctccctttag ggttccgatt tagtgcttta cggcacctcg   3540
accccaaaaa acttgattttg ggtgatggtt cacgtagtgg gccatcgccc tgatagacgg   3600
tttttcgccc tttgacgttg gagtccacgt tctttaatag tggactcttg ttccaaactg   3660
gaacaacact caaccctatc tcgggctatt cttttgattt ataagggatt ttgccgattt   3720
cggcctattg gttaaaaaat gagctgattt aacaaaaatt taacgcgaat tttaacaaaa   3780
tattaacgtt tacaatttta tggtgcactc tcagtacaat ctgctctgat gccgcatagt   3840
taagccagcc ccgacacccg ccaacacccg ctgacgcgcc ctgacgggct tgtctgctcc   3900
```

-continued

```
cggcatccgc ttacagacaa gctgtgaccg tctccgggag ctgcatgtgt cagaggtttt   3960
caccgtcatc accgaaacgc gcgagacgaa agggcctcgt gatacgccta ttttatagg    4020
ttaatgtcat gataataatg gtttcttaga cgtcaggtgg cacttttcgg ggaaatgtgc   4080
gcggaacccc tatttgttta tttttctaaa tacattcaaa tatgtatccg ctcatgagac   4140
aataaccctg ataaatgctt caataatatt gaaaaaggaa gagtatgagt attcaacatt   4200
tccgtgtcgc ccttattccc tttttttgcgg cattttgcct tcctgttttt gctcacccag   4260
aaacgctggt gaaagtaaaa gatgctgaag atcagttggg tgcacgagtg ggttacatcg   4320
aactggatct caacagcggt aagatccttg agagttttcg ccccgaagaa cgttttccaa   4380
tgatgagcac ttttaaagtt ctgctatgtg gcgcggtatt atcccgtatt gacgccgggc   4440
aagagcaact cggtcgccgc atacactatt ctcagaatga cttggttgag tactcaccag   4500
tcacagaaaa gcatcttacg gatggcatga cagtaagaga attatgcagt gctgccataa   4560
ccatgagtga taacactgcg gccaacttac ttctgacaac gatcggagga ccgaaggagc   4620
taaccgcttt tttgcacaac atgggggatc atgtaactcg ccttgatcgt tgggaaccgg   4680
agctgaatga agccatacca aacgacgagc gtgacaccac gatgcctgta gcaatggcaa   4740
caacgttgcg caaactatta actggcgaac tacttactct agcttcccgg caacaattaa   4800
tagactggat ggaggcggat aaagttgcag gaccacttct gcgctcggcc cttccggctg   4860
gctggtttat tgctgataaa tctggagccg gtgagcgtgg gtctcgcggt atcattgcag   4920
cactggggcc agatggtaag ccctcccgta tcgtagttat ctacacgacg gggagtcagg   4980
caactatgga tgaacgaaat agacagatcg ctgagatagg tgcctcactg attaagcatt   5040
ggtaactgtc agaccaagtt tactcatata tactttagat tgatttaaaa cttcattttt   5100
aatttaaaag gatctaggtg aagatccttt ttgataatct catgaccaaa atcccttaac   5160
gtgagttttc gttccactga gcgtcagacc ccgtagaaaa gatcaaagga tcttcttgag   5220
atccttttttt tctgcgcgta atctgctgct tgcaaacaaa aaaaccaccg ctaccagcgg   5280
tggtttgttt gccggatcaa gagctaccaa ctctttttcc gaaggtaact ggcttcagca   5340
gagcgcagat accaaatact gtccttctag tgtagccgta gttaggccac cacttcaaga   5400
actctgtagc accgcctaca tacctcgctc tgctaatcct gttaccagtg gctgctgcca   5460
gtggcgataa gtcgtgtctt accgggttgg actcaagacg atagttaccg gataaggcgc   5520
agcggtcggg ctgaacgggg ggttcgtgca cacagcccag cttggagcga acgacctaca   5580
ccgaactgag atacctacag cgtgagctat gagaaagcgc cacgcttccc gaagggagaa   5640
aggcggacag gtatccggta agcggcaggg tcggaacagg agagcgcacg agggagcttc   5700
cagggggaaa cgcctggtat ctttatagtc ctgtcgggtt cgccacctc tgacttgagc    5760
gtcgattttt gtgatgctcg tcaggggggc ggagcctatg gaaaaacgcc agcaacgcgg   5820
ccttttttacg gttcctggcc ttttgctggc cttttgctca catgt                 5865
```

```
SEQ ID NO: 103        moltype = DNA  length = 6054
FEATURE               Location/Qualifiers
misc_feature         1..6054
                      note = plasmid pAAVss-CRE69-CSkSH5-SPc5-12_GTRM-Luc2
source               1..6054
                      mol_type = other DNA
                      organism = synthetic construct SEQUENCE: 103
cctgcaggca gctgcgcgct cgctcgctca ctgaggccgc ccgggcaaag cccgggcgtc   60
gggcgacctt tggtcgcccg gcctcagtga gcgagcgagc gcggcagagag ggagtggcca   120
actccatcac taggggttcc tgcggccgaa acatggcttc cacagttcc agttgaagaa     180
tcccagttcc gtctataaat tccagggaag gtctctgatt ggccctgctc attcccaggc   240
ccattccttg acccagtcac tgaagtcagg gagatgcaat aataagactg gctggaatca    300
gggtctttag gggtggaggg atggggagga ggcacagcat gtcatcaaaa taaggaaatt   360
gcaaaagaaa gcttgcaggc tactttgaat gacaatgaga aagacggtgc tgcctgagtg   420
tgttaaggat ccacatggtc tccaaaatcc tccaggagca tacagtctag tctgggagat   480
gagacacaaa aataaccaga acacaacagc ttgcactgac tcgagggctg gataagaata   540
tctggaactc ccccatctat ttcagaagct gtgtctcttgg atgaaaatta gacacttaat   600
gggaaagggc tttgaaaaga gtgcagtaag gcgcgccacg cgtcagttta ctcaccaggg   660
attcagaggc agcactgctg aaccctgagc ccttggcaca tcaggttggc tgtcagaagt   720
cggcctttgt acatacacag ttcccttgtg aggcccagct gcgtgtccta ggagcgggga   780
ctctctccac agcagagctc agcctctcaa gtgtatggac agcacgggtg cctgatgggt   840
ggatttagcc atgagttgaa ggtggcttgg ggagaatgag agttctagag atagggagaa   900
ggggttgcca ataggagagt ggaattcctg agcacctcgt cacaggcagc cgacagaaca   960
tgagccgcag ggcccaggct atttatacct cgcctgtcac tatcagggtc cccacagctc   1020
ccccacctc cagccacaca cagcaggtcc ttttgctctt tctggtccct tctctactcc   1080
tcccctccc tacctaaggt acccaacgcg ttacgtggcc accgccttcg gcaccatcct   1140
cacgacaccc aaatatgcg acgggtgagg aatggtgggg agttatttt agagcggtga     1200
ggaaggtggg caggcagcag gtgttggcgc tctaaaaata actcccggga gttatttta    1260
gagcggagga atggtggaca cccaaatatg gcgacgggtc ctcacccgtc gccatatttg   1320
ggtgtccgcc ctcggccggg gccgcattcc tggggggccgg gcggtgctcc cgcccgcctc   1380
gataaaaggc tccggggccg gcggcggccc acgagctacc cggaggagcg ggaggcgcca   1440
agctctagat ctagaaagag gtaagggttt aagggatggt tggttggtgg ggtattaatg   1500
tttaattacc tggagcacct gcctgaaatc acttttttc aggttggaag cttatggaag   1560
atgccaaaaa cattaagaag ggcccagcgc cattctaccc actcgaggac gggaccgccg   1620
gcgagcagct gcacaaagcc atgaagcgct acgccctggt gcccggcacc atcgcctttta   1680
ccgacgcaca tatcgaggtg gacattacct acgccgagta cttcgagatg agcgttcggc    1740
tggcagaagc tatgaagcgc tatgggctga atacaaacca tcggatcgtg gtgtgcagcg    1800
agaatagctt gcagttcttc atgcccgtgt tgggtgccct gttcatcggt gtggctgtgg   1860
ccccagctaa cgacatctac aacgagcgcg agctgctgaa cagcatgggc atcagccgcaa  1920
ccaccgtcgt attcgtgagc aagaaagggc tgcaaaagat cctcaacgtg caaaagaagc   1980
taccgatcat acaaaagatc atcatcatgg atagcaagac cgactaccag ggcttccaa    2040
gcatgtacac cttcgtgact tcccatttgc caccccggctt caacgagtac gacttcgtgc   2100
ccgagagctt cgaccgggac aaaaccatcg ccctgatcat gaacagtagt ggcagtaccg   2160
gattgcccaa gggcgtagcc ctaccgcacc gcaccgcttg tgtccgattc agtcatgccc   2220
```

```
gcgaccccat cttcggcaac cagatcatcc ccgacaccgc tatcctcagc gtggtgccat   2280
ttcaccacgg cttcggcatg ttcaccacgc tgggctactt gatctgcggc tttcgggtcg   2340
tgctcatgta ccgcttcgag gaggagctat tcttgcgcag cttgcaagac tataagattc   2400
aatctgccct gctggtgccc acactattta gcttcttcgc taagagcact ctcatcgaca   2460
agtacgacct aagcaacttg cacgagatcg ccagcggcgg ggcgccgctc agcaaggagg   2520
taggtgaggc cgtggccaaa cgcttccacc taccaggcat ccgccagggc tacggcctga   2580
cagaaacaac cagcgccatt ctgatcaccc ccgaagggga cgacaagcct ggcgcagtag   2640
gcaaggtggt gcccttcttc gaggctaagg tggtggactt ggacaccggt aagacactgg   2700
gtgtgaacca gcgcggcgag ctgtgcgtcc gtggccccat gatcatgagc ggctacgtta   2760
acaaccccga ggctacaaac gctctcatcg acaaggacgg ctggctgcac agcggcgaca   2820
tcgcctactg ggacgaggac gagcacttct tcatcgtgga ccggctgaag agcctgatca   2880
aatacaaggg ctaccaggta gcccagccg aactggagag catcctgctg caacacccca    2940
acatcttcga cgccggggtc gccggcctgc ccgacgacga tgccggcgag ctgcccgccg   3000
cagtcgtcgt gctggaacac ggtaaaacca tgaccgagaa gcggatcgtg gactatgtgg   3060
ccagccaggt tacaaccgcc aagaagctgc gcggtggtgt tgtgttcgtg gacgaggtgc   3120
ctaaaggact gaccggcaag ttggacgccc gcaagatccg cgagattctc attaaggcca   3180
agaagggcgg caagatcgcc gtgtaattcg aaacgtatcg tccatcttga gcatctgact   3240
tctggctaaa taaaagatct ttattttcat tagatctgtg tgttggtttt ttgtgtgcgt   3300
cgagatccac ggccgcagga accctagtg atggagttgg ccactcctc tctgcgcgct     3360
cgctcgctca ctgaggccgg gcgaccaaag gtcgcccgac gcccgggctt tgcccggggcg   3420
gcctcagtga gcgagcgagc gcgcagctgc ctgcaggggc gcctgatgcg gtattttctc   3480
cttacgcatc tgtgcggtat ttcacaccgc atacgtcaaa gcaaccatag tacgcgccct   3540
gtagcggcgc attaagcgcg gcgggtgtgg tggttacgcg cagcgtgacc gctacacttg   3600
ccagcgccct agcgcccgct cctttcgctt tcttcccttc ctttctcgcc acgttcgccg   3660
gctttccccg tcaagctcta aatcgggggc tccctttagg gttccgattt agtgctttac   3720
ggcacctcga ccccaaaaaa cttgatttgg gtgatggttc acgtagtggg ccatcgccct   3780
gatagacggt ttttcgccct ttgacgttgg agtccacgtt ctttaatagt ggactcttgt   3840
tccaaactgg aacaacactc aaccctatct cgggctattc ttttgattta taagggattt   3900
tgccgatttc ggcctattgg ttaaaaaatg agctgattta acaaaaattt aacgcgaatt   3960
ttaacaaaat attaacgttt acaatttat ggtgcactct cagtacaatc tgctctgatg    4020
ccgcatagtt aagccagccc cgacacccgc caacacccgc tgacgcgccc tgacgggctt   4080
gtctgctccc ggcatccgct tacagacaag ctgtgaccgt ctccgggagc tgcatgtgtc   4140
agaggttttc accgtcatca ccgaaacgcg cgagacgaaa gggcctcgtg atacgcctat   4200
ttttataggt taatgtcatg ataataatgg tttcttagac gtcaggtggc acttttcggg   4260
gaaatgtgcg cggaacccct atttgtttat ttttctaaat acattcaaat atgtatccgc   4320
tcatgagaca ataaccctga taaatgcttc aataatattg aaaaaggaag agtatgagta   4380
ttcaacattt ccgtgtcgcc cttattccct tttttgcggc attttgcctt cctgtttttg   4440
ctcacccaga aacgctggtg aaagtaaaag atgctgaaga tcagttgggt gcacgagtgg   4500
gttacatcga actggatctc aacagcggta agatccttga gagtttttcgc cccgaagaac   4560
gttttccaat gatgagcact tttaaagttc tgctatgtgg cgcggtatta tcccgtattg   4620
acgccgggca agagcaactc ggtcgccgca tacactattc tcagaatgac ttggttgagt   4680
actcaccagt cacagaaaag catcttacgg atggcatgac agtaagagaa ttatgcagtg   4740
ctgccataac catgagtgat aacactgcgg ccaacttact tctgacaacg atcggaggac   4800
cgaaggagct aaccgctttt ttgcacaaca tgggggatca tgtaactcgc cttgatcgtt   4860
gggaaccgga gctgaatgaa gccataccaa acgacgagcg tgacaccacg atgcctgtag   4920
caatggcaac aacgttgcgc aaactattaa ctggcgaact acttactcta gcttcccggc   4980
aacaattaat agactggatg gaggcggata aagttgcagg accacttctg cgctcggccc   5040
ttccggctgg ctggtttatt gctgataaat ctggagccgg tgagcgtggg tctcgcggta   5100
tcattgcagc actggggcca gatggtaagc cctcccgtat cgtagttatc tacacgacgg   5160
ggagtcaggc aactatggat gaacgaaata gacagatcgc tgagataggt gcctcactga   5220
ttaagcattg gtaactgtca gaccaagttt actcatatat actttagatt gatttaaaac   5280
ttcatttttta atttaaaagg atctaggtga agatcctttt tgataatctc atgaccaaaa   5340
tcccttaacg tgagttttcg ttccactgag cgtcagaccc cgtagaaaag atcaaaggat   5400
cttcttgaga tcctttttttt ctgcgcgtaa tctgctgctt gcaaacaaaa aaaccaccgc   5460
taccagcggt ggtttgtttg ccggatcaag agctaccaac tctttttccg aaggtaactg   5520
gcttcagcag agcgcagata ccaaatactg tccttctagt gtagccgtag ttaggccacc   5580
acttcaagaa ctctgtagca ccgcctacat acctcgctct gctaatcctg ttaccagtgg   5640
ctgctgccag tggcgataag tcgtgtctta ccgggttgga ctcaagacga tagttaccgg   5700
ataaggcgca gcggtcgggc tgaacggggg gttcgtgcac acagcccagc ttggagcgaa   5760
cgacctacac cgaactgaga tacctacagc gtgagctatg agaaagcgcc acgcttcccg   5820
aagggagaaa ggcggacagg tatccggtaa gcggcagggt cggaacagga gagcgcacga   5880
gggagcttcc agggggaaac gcctggtatc tttatagtcc tgtcgggttt cgccacctct   5940
gacttgagcg tcgatttttg tgatgctcgt caggggggcg gagcctatgg aaaaacgcca   6000
gcaacgcggc ctttttacgg ttcctggcct tttgctggcc ttttgctcac atgt          6054
```

```
SEQ ID NO: 104          moltype = DNA   length = 5970
FEATURE                 Location/Qualifiers
misc_feature            1..5970
                        note = plasmid pAAVss-CRE70-CSkSH5-SPc5-12_GTRM-Luc2
source                  1..5970
                        mol_type = other DNA
                        organism = synthetic construct
SEQUENCE: 104
cctgcaggca gctgcgcgct cgctcgctca ctgaggccgc ccgggcaaag cccgggcgtc   60
gggcgacctt tggtcgcccg gcctcagtga gcgagcgagc gcgcagagag ggagtggcca   120
actccatcac tagggggttcc tgcggcccct caggtacccc ctgcccccca cagctcctct   180
cctgtgcctt gtttcccagc catgcgttct cctctataaa tacccgctct ggtatttggg   240
gttggcagct gttgctgcca gggagatggt tgggttgaca tgcggctcct gacaaaaacac   300
aaaccctgg tgtgtgtggg cgtgggtggt gtgagtaggg ggatgaatca gggagggggc    360
```

-continued

```
gggggaccca gggggcagga gccacacaaa gtctgtgcgg gggtgggagc gcacatagca    420
attggaaact gaaagcttat cagacccttt ctggaaatca gcccactgtt tataaacttg    480
aggccccacc ctcgacagta ccggggagga agagggcctg cactagtcca gagggaaact    540
gaggcggcgc gccacgcgtc agtttactca ccagggattc agaggcagca ctgctgaacc    600
ctgagccctt ggcacatcag gttggctgtc agaagtcggc ctttgtacat acacagttcc    660
cttgtgaggc ccagctgcgt gtcctaggag cggggcctct ctccacagca gagctcagcc    720
tctcaagtgt atggacagca cgggtgcctg atgggtggat ttagccatga gttgaaggtg    780
gcttggggag aatgagagtt ctagagatag ggagaagggg ttgccaatag gagagtggaa    840
ttcctgagca cctcgtcaca ggcagccgac agaacatgag ccgcagggcc caggctattt    900
atacctcgcc tgtcactatc agggtcccca cagctccccc cacctccagc cacacacagc    960
aggtcctttt gctctttctg gtcccttctc tactcctccc cctccctacc taaggtaccc   1020
aacgcgttac gtggccaccg ccttcggcac catcctcacg acacccaaat atggcgacgg   1080
gtgaggaatg gtgggggagtt attttttagag cggtgaggaa ggtgggcagg cagcaggtgt   1140
tggcgctcta aaaataactc ccgggagtta ttttttagagc ggaggaaatgg tggacaccca   1200
aatatggcga cggttcctca cccgtcgcca tatttgggtg tccgccctcg gccgggggccg   1260
cattcctggg ggccgggcgg tgctcccgcc cgcctcgata aaaggctccg gggccggcgg   1320
cggcccacga gctacccgga ggagcgggag gcgccaagct ctagatctag aaagaggtaa   1380
gggtttaagg gatggttggt tggtggggta ttaatgttta attacctgga gcacctgcct   1440
gaaatcactt tttttcaggt tggaagctta tggaagatgc caaaaacatt aagaagggcc   1500
cagcgccatt ctacccactc gaggacggga ccgccggcga gcagctgcac aaaagccatga   1560
agcgctacgc cctggtgccc ggcaccatcg cctttaccga cgcacatatc gaggtggaca   1620
ttacctacgc cgagtacttc gagatgagcg ttcggctggc agaagctatg aagcgctatg   1680
ggctgaatac aaaccatcgg atcgtggtgt gcagcgagaa tagcttgcag ttcttcatgc   1740
ccgtgttggg tgccctgttc atcggtgtgg ctgtggcccc agctaacgac atctacaacg   1800
agcgcgagct gctgaacagc atgggcatca gccagcccac cgtcgtattc gtgagcaaga   1860
aagggctgca aaagatcctc aacgtgcaaa agaagctacc gatcatacaa aagatcatca   1920
tcatggatag caagaccgac taccagggct tccaaagcat gtacaccttc gtgacttccc   1980
atttgccacc cggcttcaac gagtacgact tcgtgcccga gagcttcgac cgggacaaaa   2040
ccatcgccct gatcatgaac agtagtggca gtaccggatt gcccaagggc gtagccctac   2100
cgcaccgcac cgcttgtgtc cgattcagtc atgcccgcga ccccatcttc ggcaaccaga   2160
tcatccccga caccgctatc ctcagcgtgg tgccatttca ccacggcttc ggcatgttca   2220
ccacgctggg ctacttgatc tgcggctttc gggtcgtgct catgtaccgc ttcgaggagg   2280
agctattctt gcgcagcttg caagactata agattcaatc tgccctgctg gtgcccacac   2340
tatttagctt cttcgctaag agcactctca tcgacaagta cgacctaagc aacttgcacg   2400
agatcgccag cggcggggcg ccgctcagca aggaggtagg tgaggccgtg gccaaacgct   2460
tccacctacc aggcatccgc cagggctacg gcctgacaga aacaaccagc gccattctga   2520
tcacccccga aggggacgac aagcctggcg cagtaggcaa ggtggtgccc ttcttcgagg   2580
ctaaggtggt ggacttggac accggtaaga cactgggtgt gaaccagcgc ggcgagctgt   2640
gcgtccgtgg ccccatgatc atgagcggct acgttaacaa ccccgaggct acaaacgctg   2700
tcatcgacaa ggacggctgg ctgcacagcg gcgacatcgc ctactgggac gaggacgagc   2760
acttcttcat cgtggaccgg ctgaagagcc tgatcaaata caagggctac caggtagccc   2820
cagccgaact ggagagcatc ctgctgcaac accccaacat cttcgacgcc ggggtcgccg   2880
gcctgcccga cgacgatgcc ggcgagctgc ccgccgcatg cgtcgtgctg gaacacggta   2940
aaaccatgac cgagaaggag atcgtggact atgtggccag ccaggttaca accgccaaga   3000
agctgcgcgg tggtgttgtg ttcgtggacg aggtgcctaa aggactgacc ggcaagttgg   3060
acgcccgcaa gatccgcgag attctcatta aggccaagaa gggcggcaag atcgccgtgt   3120
aattcgaaac gtatggtcca tcttgagcat ctgacttctg gctaaataaa agatctttat   3180
tttcattaga tctgtgtgtt ggttttttgt gtgcgtcgag atccacggcc gcaggaaccc   3240
ctagtgatgg agttggccac tccctctctg cgcgctcgct cgctcactga ggccgggcga   3300
ccaaaggtcg cccgacgccc gggctttgcc cgggcggcct cagtgagcga gcgagcgcgc   3360
agctgcctgc aggggcgcct gatgcggtat tttctcctta cgcatctgtg cggtatttca   3420
caccgcatac gtcaaagcaa ccatagtacg cgccctgtag cggcgcatta agcgcggcgg   3480
gtgtggtggt tacgcgcagc gtgaccgcta cacttgccag cgccctagcg cccgctcctt   3540
tcgctttctt cccttccttt ctcgccacgt tcgccggctt tccccgtcaa gctctaaatc   3600
ggggctccc tttaggggtc cgatttagtg ctttacggca cctcgacccc aaaaaacttg   3660
atttgggtga tggttcacgt agtgggccat cgccctgata gacggttttt cgcccttga   3720
cgttggagtc cacgttcttt aatagtggac tcttgttcca aactggaaca acactcaacc   3780
ctatctcggg ctattctttt gatttataag ggattttgcc gatttcggcc tattggttaa   3840
aaaatgagct gatttaacaa aaatttaacg cgaattttaa caaaatatta acgtttacaa   3900
ttttatggtg cactctcagt acaatctgct ctgatgccgc atagttaagc cagccccgac   3960
acccgccaac acccgctgac gcgccctgac gggcttgtct gctcccggca tccgcttaca   4020
gacaagctgt gaccgtctcc gggagctgca tgtgtcagag gttttcaccg tcatcaccga   4080
aacgcgcgag acgaaagggc ctcgtgatac gcctattttt ataggttaat gtcatgataa   4140
taatggtttc ttagacgtca ggtggcactt ttcgggggaaa tgtgcgcgga acccctattt   4200
gtttatttt ctaaatacat tcaaatatgt atccgctcat gagacaataa ccctgataaa   4260
tgcttcaata atattgaaaa aggaagagta tgagtattca acatttccgt gtcgccctta   4320
ttcccttttt tgcggcattt tgccttcctg tttttgctca cccagaaacg ctggtgaaag   4380
taaaagatgc tgaagatcag ttgggtgcac gagtgggtta catcgaactg gatctcaaca   4440
gcggtaagat ccttgagagt tttcgccccg aagaacgttt tccaatgatg agcactttta   4500
aagttctgct atgtggcgcg gtattatccc gtattgacgc cgggcaagag caactcggtc   4560
gccgcataca ctattctcag aatgacttgg ttgagtactc accagtcaca gaaaagcatc   4620
ttacggatgg catgacagta agagaattat gcagtgctgc cataaccatg agtgataaca   4680
ctgcggccaa cttacttctg acaacgatcg gaggaccgaa ggagctaacc gctttttttgc   4740
acaacatggg ggatcatgta actcgccttg atcgttggga accggagctg aatgaagcca   4800
taccaaacga cgagcgtgac accacgatgc ctgtagcaat ggcaacaacg ttgcgcaaac   4860
tattaactgg cgaactactt actctagctt cccggcaaca attaatagac tggatggagg   4920
cggataaagt tgcaggacca cttctgcgct cggcccttcc ggctggctgg tttattgctg   4980
ataaatctgg agccggtgag cgtgggtctc gcggtatcat tgcagcactg gggccagatg   5040
gtaagccctc ccgtatcgta gttatctaca cgacggggag tcaggcaact atggatgaac   5100
```

```
gaaatagaca gatcgctgag ataggtgcct cactgattaa gcattggtaa ctgtcagacc    5160
aagtttactc atatatactt tagattgatt taaaacttca ttttaatttt aaaaggatct    5220
aggtgaagat cctttttgat aatctcatga ccaaaatccc ttaacgtgag ttttcgttcc    5280
actgagcgtc agaccccgta gaaaagatca aaggatcttc ttgagatcct tttttctgc     5340
gcgtaatctg ctgcttgcaa acaaaaaaac caccgctacc agcggtggt tgtttgccgg     5400
atcaagagct accaactctt tttccgaagg taactggctt cagcagagcg cagataccaa     5460
atactgtcct tctagtgtag ccgtagttag gccaccactt caagaactct gtagcaccgc     5520
ctacatacct cgctctgcta atcctgttac cagtggctgc tgccagtggc gataagtcgt     5580
gtcttaccgg gttggactca agacgatagt taccggataa ggcgcagcgg tcgggctcac     5640
cgggggggttc gtgcacacag cccagcttgg agcgaacgac ctacaccgaa ctgagatacc     5700
tacagcgtga gctatgagaa agcgccacgc ttcccgaagg gagaaaggcg gacaggtatc     5760
cggtaagcgg cagggtcgga acaggagagc gcacgaggga gcttccaggg ggaaacgcct     5820
ggtatcttta tagtcctgtc gggtttcgcc acctctgact tgagcgtcga ttttttgtgat    5880
gctcgtcagg ggggcggagc ctatggaaaa acgccagcaa cgcggccttt ttacggttcc     5940
tggccttttg ctggcctttt gctcacatgt                                     5970

SEQ ID NO: 105       moltype = DNA  length = 5813
FEATURE              Location/Qualifiers
misc_feature        1..5813
                     note = plasmid pAAVss-CRE71-CSkSH5-SPc5-12_GTRM-Luc2
source               1..5813
                     mol_type = other DNA
                     organism = synthetic construct
SEQUENCE: 105
cctgcaggca gctgcgcgct cgctcgctca ctgaggccgc ccgggcaaag cccgggcgtc     60
gggcgacctt tggtcgcccg gcctcagtga gcgagcgagc gcgcagagag ggagtggcca    120
actccatcac taggggttcc tgcggcccag gggcgcaggc ctcttgcggg ggagctggcc    180
tccccgcccc cacggccacg ggcgcgcctt tcctggcagg acagcgggat cttgcagctg    240
tcaggggagg ggaggcgggg gctgatgtca ggagggatac aaatagtgcc gacggctggg    300
ggcctgtct cccctcgccg catccactct ccggccggcc gcctgcccgc cgcctcctcc     360
gtgcgcccgc cagcctcgcc cgcgccgtgg cgcgccacgc gtcagtttac tcaccaggga    420
ttcagaggca gcactgctga accctgagcc cttggcacat caggttggct gtcagaagtc    480
ggcctttgta catacacagt tcccttgtga ggcccagctg cgtgtcctag gagcggggc     540
tctctccaca gcagagctca gcctctcaag tgtatggaca gcacgggtgc ctgatggggt    600
gatttagcca tgagttgaag gtggcttggg gagaatgaga gttctagaga tagggagaag   660
gggttgccaa taggagagtg gaattcctga gcacctcgtc acaggcagcc gacagaacat    720
gagccgcagg gcccaggcta tttataccct cgcctgtcact atcagggtcc ccacagctcc   780
ccccacctcc agcacacac agcaggtcct tttgctcttt ctggtccctt ctctactcct     840
ccccctcccct acctaaggta cccaacgcgt tacgtggcca ccgccttcgg caccatcctc    900
acgacaccca aatatggcga cgggtgagga atggtgggga gttatttta gagcggtgag     960
gaaggtgggc aggcagcagg tgttggcgct ctaaaaataa ctcccgggag ttattttag    1020
agcggaggaa tggtggacac ccaaaatatgg cgacggttcc tcaccgtcg ccatatttgg   1080
gtgtccgccc tcggccgggg ccgcattcct gggggcgggg cggtgctccc gcccgcctcg   1140
ataaaaggct ccggggccgg cggcggccca cgagctaccc ggaggagcgg gaggcgccaa    1200
gctctagatc tagaaagagg taaggggttta agggatggtt ggttggtggg gtattaatgt   1260
ttaattacct ggagcacctg cctgaaatca cttttttta ggttgaagc ttatggaaga     1320
tgccaaaaac attaagaagg gcccagcgcc attctaccca ctcgaggacg ggacccgccg   1380
cgagcagctg cacaaagcca tgaagcgcta cgccctggtg cccggcacca tcgcctttac   1440
cgacgcacat atcgaggtgg acattaccta cgccgagtac ttcgagatga gcgttcggct   1500
ggcagaagct atgaagcgct atgggctgaa tacaaaccat cggatcgtgg tgtgcagcga   1560
gaatagcttg cagttcttca tgcccgtgtt gggtgccctg ttcatcggtg tggctgtcgg   1620
cccagctaac gacatctaca acgagcgcga gctgctgaac agcatgggca tcagccagcc   1680
caccgtcgta ttcgtgagca agaaagggct gcaaagatc ctcaacgtgc aaaagaagct    1740
accgatcata caaaagatca tcatcatgga tagcaagacc gactaccagg cttccaaag    1800
catgtacacc ttcgtgactt cccatttgcc acccggcttc aacgagtacg acttcgtgcc   1860
cgagagcttc gaccgggaca aaaccatcgc cctgatcatg aacagtagtg gcagtaccgg   1920
attgcccaag ggcgtagccc taccgcaccg caccgcttgt gtccgattca gtcatgcccg   1980
cgaccccatc ttcggcaacc agatcatccc cgacaccgct atcctcagcg tggtgccatt   2040
tcaccacggc ttcggcatgt tcaccacgct gggctacttg atctgcggct ttcgggtcgt   2100
gctcatgtac cgcttcgagg aggagctatt cttgcgcagc ttgcaagact ataagattca   2160
atctgccctg ctggtgccca cactatttag cttcttcgct aagagcactc tcatcgacaa   2220
gtacgaccta agcaacttgc acgagatcgc cagcggcggg gcgccgctca gcaaggaggt   2280
aggtgaggcc gtggccaaac gcttccacct accaggcatc cgccagggct acggcctgac   2340
agaaacaaacc agcgccattc tgatcacccc cgaagggcac gcgcagtaga   2400
caaggtggtg cccttcttcg aggctaaggt ggtggacttg gacaccggta agacactggg   2460
tgtgaaccag cgcggcgagc tgtgcgtccg tggccccatg atcatgagcg gctacgttaa   2520
caaccccgag gctacaaacg ctctcatcga caaggacggc tggctgcaca gcggcgacat   2580
cgcctactgg gacgaggacg agcacttctt catcgtggac cggctgaaga gcctgatcaa   2640
atacaagggc taccaggtag ccccagccga actggagatc atcctgctgc aacaccccaa   2700
catcttcgac gccggggtcg ccggcctgcc cgacgacgat gccggcgagc tgcccgccgc   2760
agtcgtcgtg ctggaacacg gtaaaaccat gaccgagaag gagatcgtgg actatgtggc   2820
cagccaggtt acaaccgcca gaagctgcg cggtggtgtt gtgttcgtgg acgaggtgcc   2880
taaaggactg accggcaagt ggacgcccg caagatccgc gagattctca ttaaggcaa    2940
gaagggctgg aagatcgccg tgtaattcga aacgtacagt ccatcttgag catctgactt   3000
ctggctaaat aaaaagatct tatttcatt agatctgtgt gttggttttt tgtgtgcgtc   3060
gagatccacg gccgcaggaa cccctagtga tggagttggc cactccctct ctgcgcgctc   3120
gctcgctcac tgaggccggg cgaccaaagg tcgcccgacg cccgggcttt gcccggcggg   3180
cctcagtgag cgagcgagcg cgcagctgcc tgcaggggcg cctgatgcgg tatttttctcc   3240
ttacgcatct gtgcggtatt tcacaccgca tacgtcaaag caaccatagt acgcgccctg   3300
```

```
tagcggcgca ttaagcgcgg cgggtgtggt ggttacgcgc agcgtgaccg ctacacttgc    3360
cagcgcccta gcgccgctc  cttcgcttt  cttcccttcc tttctcgcca cgttcgccgg    3420
ctttcccgt  caagctctaa atcggggct  cccttaggg  ttccgattta gtgctttacg    3480
gcacctcgac cccaaaaaac ttgatttggg tgatggttca cgtagtgggc catcgccctg    3540
atagacggtt tttcgccctt tgacgttgga gtccacgttc tttaatagtg gactcttgtt    3600
ccaaactgga acaacactca accctatctc gggctattct tttgatttat aagggatttt    3660
gccgatttcg gcctattggt taaaaaatga gctgatttaa caaaaattta acgcgaattt    3720
taacaaaata ttaacgttta caattttatg gtgcactctc agtacaatct gctctgatgc    3780
cgcatagtta agccagcccc gacacccgcc aacacccgct gacgcgccct gacgggcttg    3840
tctgctcccg gcatccgctt acagacaagc tgtgaccgtc tccgggagct gcatgtgtca    3900
gaggttttca ccgtcatcac cgaaacgcgc gagacgaaag ggcctcgtga tacgcctatt    3960
tttataggtt aatgtcatga taataatggt ttcttagacg tcaggtggca cttttcgggg    4020
aaatgtgcgc ggaacccta  tttgtttatt tttctaaata cattcaaata tgtatccgct    4080
catgagacaa taaccctgat aaatgcttca ataatattga aaaaggaaga gtatgagtat    4140
tcaacatttc cgtgtcgccc ttattccctt ttttgcggca ttttgccttc ctgttttttgc    4200
tcacccagaa acgctggtga agtaaaaga  tgctgaagat cagttgggtg cacgagtggg    4260
ttacatcgaa ctggatctca acagcggtaa gatccttgag agttttcgcc ccgaagaacg    4320
ttttccaatg atgagcactt ttaaagttct gctatgtggc gcggtattat cccgtattga    4380
cgccgggcaa gagcaactcg gtcgccgcat acactattct cagaatgact tggttgagta    4440
ctcaccagtc acagaaaagc atcttacgga tggcatgaca gtaagagaat tatgcagtgc    4500
tgccataacc atgagtgata acactgcggc caacttactt ctgacaacga tcggaggacc    4560
gaaggagcta accgcttttt tgcacaacat ggggdatcat gtaactcgcc ttgatcgttg    4620
ggaaccggag ctgaatgaag ccataccaaa cgacgagcgt gacaccacga tgcctgtagc    4680
aatggcaaca acgttgcgca aactattaac tggcgaacta cttactctag cttcccggca    4740
acaattaata gactggatgg aggcggataa agttgcagga ccacttctgc gctcggccct    4800
tccggctggc tggtttattg ctgataaatc tggagccggt gagcgtgggt ctcgcggtat    4860
cattgcagca ctggggccag atggtaagcc ctcccgtatc gtagttatct acacgacggg    4920
gagtcaggca actatggatg aacgaaatag acagatcgct gagataggtg cctcactgat    4980
taagcattgg taactgtcag accaagttta ctcatatata ctttagattg atttaaaact    5040
tcatttttaa tttaaaagga tctaggtgaa gatcctttt  gataatctca tgaccaaaat    5100
cccttaacgt gagttttcgt tccactgagc gtcagacccc gtagaaaaga tcaaaggatc    5160
ttcttgagat cctttttttc tgcgcgtaat ctgctgcttg caaacaaaaa aaccaccgct    5220
accagcggtg gtttgtttgc cggatcaaga gctaccaact ctttttccga aggtaactgg    5280
cttcagcaga gcgcagatac caaatactgt ccttctagtg tagccgtagt taggccacca    5340
cttcaagaac tctgtagcac cgcctacata cctcgctcta tctctta cctcgctcta ctaatcctgt taccagtggc    5400
tgctgccagt ggcgataagt cgtgtcttac cgggttggac tcaagacgat agttaccgga    5460
taaggcgcag cggtcgggct gaacgggggg ttcgtgcaca cagcccagct tggagcgaac    5520
gacctacacc gaactgagat acctacagcg tgagctatga gaaagcgcca cgcttcccga    5580
agggagaaag gcggacaggt atccggtaag cggcagggtc ggaacaggag agcgcacgag    5640
ggagcttcca gggggaaacg cctggtatct ttatagtcct gtcgggtttc gccacctctg    5700
acttgagcgt cgatttttgt gatgctcgtc aggggggcgg agcctatgga aaaacgccag    5760
caacgcggcc tttttacggt tcctggcctt ttgctggcct tttgctcaca tgt           5813
```

```
SEQ ID NO: 106         moltype = DNA  length = 5888
FEATURE                Location/Qualifiers
misc_feature           1..5888
                       note = plasmid pAAVss-CRE77-CSkSH5-SPc5-12_GTRM-Luc2
source                 1..5888
                       mol_type = other DNA
                       organism = synthetic construct
SEQUENCE: 106
acatgtcctg caggcagctg cgcgctcgct cgctcactga ggccgcccgg gcaaagcccg    60
ggcgtcgggc gacctttggt cgcccggcct cagtgagcga gcgagcgcgc agagagggag    120
tggccaactc catcactagg ggttcctgcg gccggaatac cctaccttaa aaacaaaaca    180
aaccgtgcta cttggccctc ttcccttgag ttgttgtcta atctcattca tttcactgct    240
aaactcctca aatgcatggt gtacacccac tgcttccact tcctgtccac tcatcttttt    300
cctcattaac tccctgtggc ctggctttgc ctgtgacact acacaagctg cttgctccaa    360
gataatccaa gttctttct  ctgtcttcct gatacacagg ctttctttgg catctgacac    420
tgctggccac ctgctcttct tgaaatgctt cttttggctt ctaggaaacg gcgcgccaca    480
cgtcagttta ctcaccaggg attcagaggc agcactgctg aaccctgagc ccttggcaca    540
tcaggttggc tgtcagaagt cggcctttgt acatacacag ttcccttgtg aggcccagct    600
gcgtgtccta ggagcggggc ctctctccac agcagagctc agcctctcaa gtgtatggac    660
agcacgggtg cctgatgggt ggatttagcc atgagttgaa ggtggcttgg ggagaatgag    720
agttctagag ataggagaa  ggggttgcca ataggagagt ggaattcctg agcacctcgt    780
cacaggcagc cgacagaaca tgagccgcag ggcccaggct atttatacct cgcctgtcac    840
tatcagggtc cccacagctc cccccacctc cagccacaca cagcaggtcc ttttgctctt    900
tctggtccct tctctactcc tccccctccc tacctaaggt acccaacgcg ttacgtggcc    960
accgccttcg gcaccatcct cacgacaccc aaatatggcc acgggtgagg aatggtgggg    1020
agttatttt  agagcggtga ggaaggtggg caggcagcag gtgttggcgc tctaaaaata    1080
actcccggga gttatttta  gagcggagga atggtggaca cccaaatatg gcgacggttc    1140
ctcaccgtc  gccatatttg ggtgtccgcc ctcggccggg gccgcattcc tggggggccgg    1200
gcggtgctcc cgcccgcctc gataaaaggc tccggggccg gcggcggccc acgagctacc    1260
cggaggagcg ggaggcgcca agctctagat ctagaaaag  gtaagggttt aagggatggt    1320
tggttggtgg ggtattaatg tttaattacc tggagcacct cgtgaaatc  acttttttc    1380
aggttggaag cttatggaag atgccaaaaa cattaagaag ggcccagcgc cattctaccc    1440
actcgaggac gggaccgccg cgagcagct  gcacaaagcc atgaagcgct acgccctggt    1500
gcccggcacc atcgccttta ccgacgcaca tatcgaggtg gacattacct acgccgagta    1560
cttcgagatg agcgttcggc tggcagaagc tatgaagcgc tatgggctga atacaaacca    1620
tcggatcgtg gtgtgcagcg agaatagctt gcagttcttc atgcccgtgt ggggtgccct    1680
```

```
gttcatcggt gtggctgtgg ccccagctaa cgacatctac aacgagcgcg agctgctgaa    1740
cagcatgggc atcagccagc ccaccgtcgt attcgtgagc aagaaagggc tgcaaaagat    1800
cctcaacgtg caaaagaagc taccgatcat acaaaagatc atcatcatgg atagcaagac    1860
cgactaccag ggcttccaaa gcatgtacac cttcgtgact tcccatttgc cacccggctt    1920
caacgagtac gacttcgtgc ccgagagctt cgaccggcag aaaaccatcg ccctgatcat    1980
gaacagtagt ggcagtaccg gattgcccaa gggcgtagcc ctaccgcacc gcaccgcttg    2040
tgtccgattc agtcatgccc gcgacccat cttcggcaac cagatcatcc ccgacaccgc    2100
tatcctcagc gtggtgccat ttcaccacgg cttcggcatg ttcaccacgc tgggctactt    2160
gatctgcggc tttcgggtcg tgctcatgta ccgcttcgag gaggagctat tcttgcgcag    2220
cttgcaagac tataagattc aatctgccct gctggtgccc acactattta gcttcttcgc    2280
taagagcact ctcatcgaca agtacgacct aagcaacttg cacgagatcg ccagcggcgg    2340
ggcgccgctc agcaaggagg taggtgaggc cgtggccaaa cgcttccacc taccaggcat    2400
ccgccagggc tacggcctga cagaaacaac cagcgccatt ctgatcaccc ccgaagggga    2460
cgacaagcct ggcgcagtag gcaaggtggt gcccttcttc gaggctaagg tggtggactt    2520
ggacaccggg aagacactgg gtgtgaacca gcgcggcgag ctgtgcgtcc gtggccccat    2580
gatcatgagc ggctacgtta acaaccccga ggctacaaac gctctcatcg acaaggacgg    2640
ctggctgcac agcggcgaca tcgcctactg ggacgaggac gagcacttct tcatcgtgga    2700
ccggctgaag agcctgatca aatacaaggg ctaccaggta gccccagccg aactggaagg    2760
catcctgctg caacacccca acatcttcga cgccggggtc gccggcctgc ccgacgacga    2820
tgccggcgag ctgcccgccg cagtcgtcgt gctggaacac ggtaaaacca tgaccgagaa    2880
ggagatcgtg gactatgtgg ccagccaggt tacaaccgcc aagaagctgc gcggtggtgt    2940
tgtgttcgtg gacgaggtgc ctaaaggact gaccggcaag ttggacgccc aagatccg    3000
cgagattctc attaaggcca agaagggcgg caagatcgcc gtgtaattcg aaacgtaggg    3060
tccatcttga gcatctgact tctggctaaa taaaagatct ttattttcat tagatctgtg    3120
tgttggtttt ttgtgtgcgt cgagatccac ggccgcagga accctagtg atggagttgg    3180
ccactccctc tctgcgcgct cgctcgctca ctgaggccg cgaccaaag gtcgcccgac    3240
gcccgggctt tgcccgggcg gcctcagtga gcgagcgagc gcgcagctgc ctgcaggggc    3300
gcctgatgcg gtattttctc cttacgcatc tgtgcggtat ttcacaccgc atacgtcaaa    3360
gcaaccatag tacgcgccct gtagcggcgc attaagcgcg gcgggtgtgg tggttacgcg    3420
cagcgtgacc gctacacttg ccagcgccgt agcgcccgct cctttcgctt tcttcccttc    3480
ctttctcgcc acgttcgccg gctttccccg tcaagctcta aatcggggggc tccctttagg    3540
gttccgattt agtgctttac ggcacctcga ccccaaaaaa cttgatttgg gtgatggttc    3600
acgtagtggg ccatcgccct gatagacggt ttttcgccct ttgacgttgg agtccacgtt    3660
ctttaatagt ggactcttgt tccaaactgg aacaacactc aaccctatct cgggctattc    3720
ttttgattta taagggattt tgccgatttc ggcctattgg ttaaaaaatg agctgattta    3780
acaaaaattt aacgcgaatt ttaacaaaat attaacgttt acaattttat ggtgcactct    3840
cagtacaatc tgctctgatg ccgcatagtt aagccagccc cgacaccgc caacaccgc    3900
tgacgcgccc tgacgggctt gtctgctccc ggcatccgct tacagacaag ctgtgaccgt    3960
ctccggagagc tgcatgtgtc agaggttttc accgtcatca ccgaaacgcg cgagacgaaa    4020
gggcctcgtg atacgcctat ttttataggt taatgtcatg ataataatgg tttcttagac    4080
gtcaggtggc acttttcggg gaaatgtgcg cggaacccct atttgtttat ttttctaaat    4140
acattcaaat atgtatccgc tcatgagaca ataaccctga taaatgcttc aataatattg    4200
aaaaaggaag agtatgagta ttcaacattt ccgtgtcgcc cttattccct tttttgcggc    4260
attttgcctt cctgttttg ctcacccaga aacgctggtg aaagtaaaag atgctgaaga    4320
tcagttgggt gcacgagtgg gttacatcga actggatctc aacagcggta agatccttga    4380
gagttttcgc cccgaagaac gttttccaat gatgagcact tttaaagttc tgctatgtgg    4440
cgcggtatta tcccgtattg acgccgggca agagcaactc ggtcgccgca tacactattc    4500
tcagaatgac ttggttgagt actcaccagt cacagaaaag catcttacgg atggcatgac    4560
agtaagagaa ttatgcagtg ctgccataac catgagtgat aacactgcgg ccaacttact    4620
tctgacaacg atcggaggac cgaaggagct aaccgctttt ttgcacaaca tgggggatca    4680
tgtaactcgc cttgatcgtt gggaaccgga gctgaatgaa gccataccaa acgacgagcg    4740
tgacaccacg atgcctgtag caatggcaac aacgttgcgc aaactattaa ctggcgaact    4800
acttactcta gcttcccggc aacaattaat agactggatg gaggcggata aagttgcagg    4860
accacttctg cgctcggccc ttccggctgg ctggtttatt gctgataaat ctggagccgg    4920
tgagcgtggg tctcgcggta tcattgcagc actggggcca gatggtaagc cctcccgtat    4980
cgtagttatc tacacgacgg ggagtcaggc aactatggat gaacgaaata gacagatcgc    5040
tgagataggt gcctcactga ttaagcattg gtaactgtca gaccaagttt actcatatat    5100
actttagatt gatttaaaac ttcatttta atttaaaagg atctaggtga agatcctttt    5160
tgataatctc atgaccaaaa tcccttaacg tgagttttcg ttccactgag cgtcagaccc    5220
cgtagaaaag atcaaaggat cttcttgaga tcctttttt ctgcgcgtaa tctgctgctt    5280
gcaaacaaaa aaaccaccgc taccagcggt ggtttgtttg ccggatcaag agctaccaac    5340
tctttttccg aaggtaactg gcttcagcag agcgcagata ccaaatactg tccttctagt    5400
gtagccgtag ttaggccacc acttcaagaa ctctgtagca ccgcctacat acctcgctct    5460
gctaatcctg ttaccagtgg ctgctgccag tggcgataag tcgtgtctta ccgggttgga    5520
ctcaagacga tagttaccgg ataaggcgca gcggtcgggc tgaacggggg gttcgtgcac    5580
acagcccagc ttggagcgaa cgacctacac cgaactgaga tacctacagc gtgagctatg    5640
agaaagcgcc acgcttcccg aagggagaaa ggcggacagg tatccggtaa gcggcagggt    5700
cggaacagga gagcgcacga gggagcttcc aggggggaaac gcctggtatc tttatagtcc    5760
tgtcgggttt cgccacctct gacttgagcg tcgatttttg tgatgctcgt caggggggcg    5820
gagcctatgg aaaaacgcca gcaacgcggc ctttttacgg ttcctggcct tttgctggcc    5880
ttttgctc                                                            5888

SEQ ID NO: 107         moltype = DNA  length = 5572
FEATURE                Location/Qualifiers
misc_feature          1..5572
                      note = plasmid pAAVss-CSkSH5-SPc5-12_GTRM-Luc2
source                1..5572
                      mol_type = other DNA
                      organism = synthetic construct
```

```
SEQUENCE: 107
acatgtcctg caggcagctg cgcgctcgct cgctcactga ggccgcccgg gcaaagcccg   60
ggcgtcgggc gacctttggt cgcccggcct cagtgagcga gcgagcgcgc agagagggag  120
tggccaactc catcactagg ggttcctgcg gccggcgcgc cacgcgtcag tttactcacc  180
agggattcag aggcagcact gctgaaccct gagcccttgg cacatcaggt tggctgtcag  240
aagtcggcct ttgtacatac acagttccct tgtgaggccc agctgcgtgt cctaggagcg  300
gggcctctct ccacagcaga gctcagcctc tcaagtgtat ggacagcacg ggtgcctgat  360
gggtggattt agccatgagt tgaaggtggc ttggggagaa tgagagttct agagataggg  420
agaaggggtt gccaatagga gagtggaatt cctgagcacc tcgtcacagg cagccgacag  480
aacatgagcc gcagggccca ggctatttat acctcgcctg tcactatcag ggtccccaca  540
gctcccccca cctccagcca cacacagcag gtcctttgc tctttctggt cccttctcta  600
ctcctcccc tccctaccta aggtacccaa cgcgttacgt ggccaccgcc ttcggcacca  660
tcctcacgac acccaaatat ggcgacgggt gaggaatggt ggggagttat ttttagagcg  720
gtgaggaagg tgggcaggca gcaggtgttg gcgctctaaa aataactccc gggagttatt  780
tttagagcgg aggaatggtg gacacccaaa tatggcgacg gttcctcacc cgtcgccata  840
tttgggtgtc cgccctcggc cggggccgca ttcctggggg ccgggcggtg ctcccgcccg  900
cctcgataaa aggctccggg gccggcggcg gcccacgagc tacccggagg agcgggaggc  960
gccaagctct agatctagaa agaggtaagg gtttaaggga tggttggttg gtggggtatt 1020
aatgtttaat tacctggagc acctgcctga aatcactttt tttcaggttg gaagcttatg 1080
gaagatgcca aaaacattaa gaagggccca gcgccattct acccactcga ggacgggacc 1140
gccggcgagc agctgcacaa agccatgaag cgctacgccc tggtgcccgg caccatcgcc 1200
tttaccgacg cacatatcga ggtggacatt acctacgccg agtacttcga gatgagcgtt 1260
cggctggcag aagctatgaa gcgctatggg ctgaatacaa accatcggat cgtggtgtgc 1320
agcgagaata gcttgcagtt cttcatgccc gtgttgggtg ccctgttcat cggtgtggct 1380
gtggccccag ctaacgacat ctacaacgag cgcgagctgc tgaacagcat gggcatcagc 1440
cagcccaccg tcgtattcgt gagcaagaaa gggctgcaaa agatcctcaa cgtgcaaaag 1500
aagctaccga tcatacaaaa gatcatcatc atggatagca agaccgacta ccagggcttc 1560
caaagcatgt acaccttcgt gacttcccat ttgccacccg gcttcaacga gtacgacttc 1620
gtgcccgaga gcttcgaccg ggacaaaacc atcgccctga tcatgaacag tagtggcagt 1680
accggattgc ccaagggcgt agccctaccg caccgcaccg cttgtgtccg attcagtcat 1740
gcccgcgacc ccatcttcgg caaccagatc atcccccgaca ccgctatcct cagcgtggtg 1800
ccatttcacc acggcttcgg catgttcacc acgctgggct acttgatctg cggctttcgg 1860
gtcgtgctca tgtaccgctt cgaggaggag ctattcttgc gcagcttgca agactataag 1920
attcaatctg ccctgctggt gcccacacta tttagcttct tcgctaagag cactctcata 1980
gacaagtacg acctaagcaa cttgcacagg atcgccagcg gcggggcgcc gctcagcaag 2040
gaggtaggtg aggccgtggc caaacgcttc cacctaccag gcatccgcca gggctacggc 2100
ctgacagaaa caaccagcgc cattctgatc accccccgaag gggacgacaa gcctggcgca 2160
gtaggcaagg tggtgcccctt cttcgaggct aaggtggtgg acttggacac cggtaagaca 2220
ctgggtgtga accagcgcgg cgagctgtgc gtccgtggcc ccatgatcat gagcggctac 2280
gttaacaacc ccgaggctac aaacgctctc atcgacaagg acggctggct gcacagcggc 2340
gacatcgcct actgggacga ggacgagcac ttcttcatcg tggaccggct gaagagcctg 2400
atcaaataca agggctacca ggtagcccca gccgaactgg agagcatcct gctgcaacac 2460
cccaacatct tcgacgccgg ggtcgccggc ctgcccgacg acgtgccgca cgagctgccc 2520
gccgcagtcg tcgtgctgga acacggtaaa accatgaccg agaaggagat cgtggactat 2580
gtggccagcc aggttacaac cgccaagaag ctgcgcggtg gtgttgtgtt cgtggacgag 2640
gtgcctaaag gactgaccgg caagttggac gcccgcaaga tccgcgagat tctcattaag 2700
gccaagaagg gcggcaagat cgccgtgtaa ttcgaaacgt tcggtccatc ttgagcatct 2760
gacttctggc taaataaaag atctttattt tcattagatc tgtgtgttgg ttttttgtgt 2820
gcgtcgagat ccacggccgc aggaacccct agtgatggag ttggccactc cctctctgcg 2880
cgctcgctcg ctcactgagg ccgggcgacc aaaggtcgcc cgacgcccgg gctttgcccg 2940
ggcggcctca gtgagcgagc gagcgcgcag ctgcctgcag gggcgcctga tgcggtattt 3000
tctccttacg catctgtgcg gtatttcaca ccgcatacgt caaagcaacc atagtacgcg 3060
ccctgtagcg gcgcattaag cgcggcgggt gtggtggtta cgcgcagcgt gaccgctaca 3120
cttgccagcg ccctagcgcc cgctcctttc gctttcttcc cttcctttct cgccacgttc 3180
gccggctttc cccgtcaagc tctaaatcgg gggctccctt tagggttccg atttagtgct 3240
ttacggcacc tcgaccccaa aaaacttgat ttgggtgatg gttcacgtag tgggccatcg 3300
ccctgataga cggtttttcg ccctttgacg ttggagtcca cgttctttaa tagtggactc 3360
ttgttccaaa ctggaacaac actcaaccct atctcgggct attctttttga tttataaggg 3420
attttgccga tttcggccta ttggttaaaa aatgagctga tttaacaaaa atttaacgcg 3480
aattttaaca aaatattaac gtttacaatt ttatggtgca ctctcagtac aatctgctct 3540
gatgccgcat agttaagcca gccccgacac ccgccaacac ccgctgacgc gccctgacgg 3600
gcttgtctgc tcccggcatc cgcttacaga caagctgtga ccgtctccgg gagctgcatg 3660
tgtcagaggt tttcaccgtc atcaccgaaa cgcgcgagac gaaagggcct cgtgatacgc 3720
ctatttttat aggttaatgt catgataata atggtttctt agacgtcagg tggcactttt 3780
cggggaaatg tgcgcggaac ccctatttgt ttatttttct aaatacattc aaatatgtat 3840
ccgctcatga caataaccct gataaatgct tcaataat attgaaaaag gaagagtatg 3900
agtattcaac atttccgtgt cgcccttatt ccctttttg cggcattttg ccttcctgtt 3960
tttgctcacc cagaaacgct ggtgaaagta aaagatgctg aagatcagtt gggtgcacga 4020
gtgggttaca tcgaactgga tctcaacagc ggtaagatcc ttgagagttt tcgccccgaa 4080
gaacgttttc caatgatgag cacttttaaa gttctgctat gtggcgcggt attatcccgt 4140
attgacgccg ggcaagagca actcggtcgc cgcatacact attctcagaa tgacttggtt 4200
gagtactcac cagtcacaga aaagcatctt acggatggca tgacagtaag agaattatgc 4260
agtgctgcca taaccatgag tgataacact gcggccaact tacttctgac aacgatcgga 4320
ggaccgaagg agctaaccgc ttttttgcac aacatgggga tcatgtaac tcgccttgat 4380
cgttgggaac cggagctgaa tgaagccata ccaaacgacg agcgtgacac cacgatgcct 4440
gtagcaatgg caacaacgtt gcgcaaacta ttaactggcg aactacttac tctagcttcc 4500
cggcaacaat taatagactg gatggaggcg gataaagttg caggaccact tctgcgctcg 4560
gcccttccgg ctggctggtt tattgctgat aaatctggag ccggtgagcg tgggtctcgc 4620
ggtatcattg cagcactggg gccagatggt aagccctccc gtatcgtagt tatctacacg 4680
```

-continued

```
acggggagtc aggcaactat ggatgaacga aatagacaga tcgctgagat aggtgcctca  4740
ctgattaagc attggtaact gtcagaccaa gtttactcat atatacttta gattgattta  4800
aaacttcatt tttaatttaa aaggatctag gtgaagatcc tttttgataa tctcatgacc  4860
aaaatccctt aacgtgagtt ttcgttccac tgagcgtcag accccgtaga aaagatcaaa  4920
ggatcttctt gagatccttt ttttctgcgc gtaatctgct gcttgcaaac aaaaaaacca  4980
ccgctaccag cggtggtttg tttgccggat caagagctac caactctttt ccgaaggta   5040
actggcttca gcagagcgca gataccaaat actgtccttc tagtgtagcc gtagttaggc  5100
caccacttca agaactctgt agcaccgcct acatacctcg ctctgctaat cctgttacca  5160
gtggctgctg ccagtggcga taagtcgtgt cttaccgggt tggactcaag acgatagtta  5220
ccggataagg cgcagcggtc gggctgaacg gggggttcgt gcacacagcc cagcttggag  5280
cgaacgacct acaccgaact gagatacctal cagcgtgagc tatgagaaag cgccacgctt  5340
cccgaaggga gaaaggcgga caggtatccg gtaagcggca gggtcggaac aggagagcgc  5400
acgagggagc ttccaggggg aaacgcctgg tatctttata gtcctgtcgg gtttcgccac  5460
ctctgacttg agcgtcgatt tttgtgatgc tcgtcagggg gcggagcct atggaaaaac  5520
gccagcaacg cggccttttt acggttcctg gccttttgc ggccttttgc tc            5572
```

SEQ ID NO: 108          moltype = DNA  length = 5118
FEATURE                 Location/Qualifiers
misc_feature            1..5118
                        note = plasmid pAAVss-SPc5-12_GTRM-Luc2
source                  1..5118
                        mol_type = other DNA
                        organism = synthetic construct
SEQUENCE: 108

```
acatgtcctg caggcagctg cgcgctcgct cgctcactga ggccgcccgg gcaaagcccg  60
ggcgtcgggc gacctttggt cgcccggcct cagtgagcga ggagcgcgc agagagggag   120
tggccaactc catcactagg ggttcctgcg gccggcgcgc cacgcgtggt acccaacgcg   180
ttacgtggcc accgccttcg gcaccatcct cacgacaccc aaaatatggcg acgggtgagg  240
aatggtgggg agttattttt agagcggtga ggaaggtggg caggcagcag gtgttggcgc   300
tctaaaaata actcccggga gttatttta gagcggagga atggtggaca cccaaatatg    360
gcgacggttc ctcacccgtc gccatatttg ggtgtccgcc ctcggccggg gccgcattcc   420
tggggggccgg gcggtgctcc cgcccgcctc gataaaaggc tccggggccg gcggcggccc   480
acgagctacc cggaggagcg ggaggcgcca agctctagat ctagaaagag gtaagggttt   540
aaggatggt tggttggtgg ggtattaatg tttaattacc tggagcacct gcctgaaatc    600
acttttttc aggttggaag cttatggaag atgccaaaaa cattaagaag ggcccagcgc    660
cattctaccc actcgaagac gggaccgccg gcgagcagct gcacaaagcc atgaagcgct   720
acgcctggt gcccggcacc atcgccttta ccgacgcaca tatcgaggtg gacattacct    780
acgccgagta cttcgagatg agcgttcggc tggcagaagc tatgaagcgc tatgggctga   840
atacaaacca tcggatcgtg gtgtgcagcg agaatagtct gcagttcttc atgcccgtgt    900
tgggtgccct gttcatcggt gtggctgtgg ccccagctaa cgacatctac aacgagcgcg   960
agctgctgaa cagcatgggc atcagccagc ccaccgtcgt attcgtgagc aagaaagggc   1020
tgcaaaagat cctcaacgtg caaaagaagc taccgatcat acaaaagatc atcatcatgg   1080
atagcaagac cgactaccag ggcttccaaa gcatgtacac cttcgtact tcccatttgc    1140
cacccggctt caacgagtac gacttcgtgc ccgagagctt cgaccgggac aaaaaccatcg  1200
ccctgatcat gaacagtagt ggcagtaccg gattgcccaa gggcgtagcc ctaccgcacc   1260
gcaccgcttg tgtccgattc agtcatgccc gcgaccccat cttcggcaac cagatcatcc   1320
ccgacaccgc tatcctcagc gtggtgccat ttcaccagg cattgttcaccacgc          1380
tgggctactt gatctgcggc tttcgggtcg tgctcatgta ccgcttcgag gaggagctat    1440
tcttgcgcag cttgcaagac tataagattc aatctgccct gctggtgccc acactattta    1500
gcttcttcgc taagagcact ctcatcgaca agtacgacct aagcaacttg cacgagatcg    1560
ccagcggagg ggcgccgctc agcaaggagg taggtgagc cgtggccaaa cgcttccacc     1620
taccaggcat ccgccagggc tacggcctga cagaaacaac cagcgccatt ctgatcaccc    1680
ccgaaggggacgacaagcct ggcgcagtag gcaaggtggt gcccttcttc gaggctaagg     1740
tggtggactt ggacaccggt aagacactgg gtgtgaacca cgcgcggcgag ctgtgcgtcc   1800
gtggccccat gatcatgagc ggctacgtta acaaccccga ggctacaaac gctctcatcg    1860
acaaggacgg ctggctgcac agcggcgaca tcgcctactg ggacgaggac gagcacttct    1920
tcatcgtgga ccggctgaag agcctgatca aatacaaggg ctaccaggta gccccagccg    1980
aactggagag catcctgctg caacacccca acatcttcga cgccgggtc gccggcctgc     2040
ccgacgacga tgccggcgag ctgcccgccg cagtcgtcgt gctggaacac ggtaaaacca   2100
tgaccgagaa ggagatcgtg gactatgtgg ccagccaggt tacaaccgcc aagaagctgc    2160
gcggtggtgt tgtgttcgtg gacgaggtgc ctaaaggact gaccggcaag ttggacgccc   2220
gcaagatccg cgagattctc attaaggcca agaaggggcgg caagatcgcc gtgtaattcg    2280
aaacgttgtg tccatcttga gcatctgact tctggctaaa taaaagatct ttatttcat    2340
tagatctgtg tgttggtttt ttgtgtgcgt cgagatccac ggccgcagga accctagtg    2400
atggagttgg ccactccctc tctgcgcgct cgctcgctca ctgaggccgg ggaccaaag    2460
gtcgcccgac gcccgggctt tgcccgggcg gcctcagtga gcgagcgagc gcgcagctgc    2520
ctgcagggc gcctgatgcg gtattttctc cttacgcatc tgtgcggtat ttcacaccgc     2580
atacgtcaaa gcaaccatag tacgcgccct gtagcggcgc attaagcgcg gcgggtgtgg   2640
tggttacgcg cagcgtgacc gctacacttg ccagcgccct agcgcccgct cctttcgctt    2700
tcttcccttc ctttctcgcc acgttcgccg gctttcccg tcaagctcta aatcgggggc    2760
tccctttagg gttccgattt agtgctttac ggcacctcga ccccaaaaaa cttgatttgg    2820
gtgatggttc acgtagtggg ccatcgccct gatagacggt ttttcgccct ttgacgttgg    2880
agtccacgtt ctttaatagt ggactcttgt tccaaactgg aacaacactc aaccctatct   2940
cgggctattc ttttgattta taggatttt tgccgattc ggcctattgg ttaaaaaatg     3000
agctgattta acaaaaattt aacgcgaatt ttaacaaaat attaacgttt acaatttat     3060
ggtgcactct cagtacaatc tgctctgatg ccgcatagtt aagccagccc cgacacccgc   3120
caacaccgc tgacgcgccc tgacgggctt gtctgctccc ggcatccgct tacagacaag    3180
ctgtgaccgt ctccgggagc tgcatgtgtc agaggttttc accgtcatca ccgaaacgcg    3240
cgagacgaaa gggcctcgtg atacgcctat ttttataggt taatgtcatg ataataatgg   3300
```

-continued

```
tttcttagac gtcaggtggc acttttcggg gaaatgtgcg cggaaccccct atttgtttat   3360
ttttctaaat acattcaaat atgtatccgc tcatgagaca ataaccctga taaatgcttc   3420
aataatattg aaaaaggaag agtatgagta ttcaacattt ccgtgtcgcc cttattccct   3480
tttttgcggc attttgcctt cctgtttttg ctcacccaga aacgctggtg aaagtaaaag   3540
atgctgaaga tcagttgggg gcacgagtgg gttacatcga actggatctc aacagcggta   3600
agatccttga gagtttttcgc cccgaagaac gttttccaat gatgagcact tttaaagttc   3660
tgctatgtgg cgcggtatta tcccgtattg acgccgggca agagcaactc ggtcgccgca   3720
tacactattc tcagaatgac ttggttgagt actcaccagt cacagaaaag catcttacgg   3780
atggcatgac agtaagagaa ttatgcagtg ctgccataac catgagtgat aacactgcgg   3840
ccaacttact tctgacaacg atcggaggac cgaaggagct aaccgctttt ttgcacaaca   3900
tgggggatca tgtaactcgc cttgatcgtt gggaaccgga gctgaatgaa gccataccaa   3960
acgacgagcg tgacaccacg atgcctgtag caatggcaac aacgttgcgc aaactattaa   4020
ctggcgaact acttactcta gcttcccggc aacaattaat agactggatg gaggcggata   4080
aagttgcagg accacttctg cgctcggccc ttccggctgg ctggtttatt gctgataaat   4140
ctggagccgg tgagcgtggg tctcgcggta tcattgcagc actggggcca gatggtaagc   4200
cctcccgtat cgtagttatc tacacgacgg ggagtcaggc aactatggat gaacgaaata   4260
gacagatcgc tgagataggt gcctcactga ttaagcattg gtaactgtca gaccaagttt   4320
actcatatat actttagatt gatttaaaac ttcattttta atttaaaagg atctaggtga   4380
agatcctttt tgataatctc atgaccaaaa tcccttaacg tgagttttcg ttccactgag   4440
cgtcagaccc cgtagaaaag atcaaaggat cttcttgaga tcctttttttt ctgcgcgtaa   4500
tctgctgctt gcaaacaaaa aaaccaccgc taccagcggt ggtttgtttg ccggatcaag   4560
agctaccaac tctttttccg aaggtaactg gcttcagcag agcgcagata ccaaatactg   4620
tccttctagt gtagccgtag ttaggccacc acttcaagaa ctctgtagca ccgcctacat   4680
acctcgctct gctaatcctg ttaccagtgg ctgctgccag tggcgataag tcgtgtctta   4740
ccgggttgga ctcaagacga tagttaccgg ataaggcgca gcggtcgggc tgaacggggg   4800
gttcgtgcac acagcccagc ttggagcgaa cgacctacaa cgaactgaga tacctacagc   4860
gtgagctatg agaaagcgcc acgcttcccg aagggagaaa ggcggacagg tatccggtaa   4920
gcggcagggt cggaacagga gagcgcacga gggagcttcc agggggaaac gcctggtatc   4980
tttatagtcc tgtcgggttt cgccacctct gacttgagcg tcgatttttg tgatgctcgt   5040
caggggggcg gagcctatgg aaaaacgcca gcaacgcggc cttttttacgg ttcctggcct   5100
tttgctggcc ttttgctc                                                  5118
```

```
SEQ ID NO: 109          moltype = DNA  length = 7097
FEATURE                 Location/Qualifiers
misc_feature            1..7097
                        note = plasmid pAAVss-CRE02-SkSH4-hDES1.4kb-Luc2
source                  1..7097
                        mol_type = other DNA
                        organism = synthetic construct
SEQUENCE: 109
cctgcaggca gctgcgcgct cgctcgctca ctgaggccgc ccgggcaaag cccgggcgtc   60
gggcgacctt tggtcgcccg gcctcagtga gcgagcgagc gcgcagagag ggagtggcca   120
actccatcac tagggggttcc tgcggccgcac aggtgcggtt cccggagcgc aggcgcacac   180
atgcacccac cggcgaacgc ggtgaccctc gccccacccc atccccctccg gcgggcaact   240
gggtcgggtc aggaggggca aacccgctag ggagacactc catatacggc ccggcccgcg   300
ttacctggga ccgggccaac ccgctccttc tttggtcaac gcaggggacc cgggcggggg   360
cccaggccgc gaaccggccg aggggagggg ctctagtgcc caacacccaa atatggctcg   420
agaagggcag cgacattcct gcggggtggc gcggagggaa tgcccgcggg ctatataaaa   480
cctgagcaga gggacaagcg gccaccgcag cggacagcgc caagtgaagc ctcgcttccc   540
ctccgcggcg accagggccc gagccgagag tagcagttgt agctaccgc ccaggtaggg   600
gcgcgcacg cgtttctgag tcctctaagg tccctcactc ccaactcagc cccatgtcct   660
gtcaattccc actcagtgtc tgatctcctt ctcctcacct ttcccatctc ccgtttgacc   720
caagcttcct gagctctcct cccattcccc tttttggagt cctcctcctc tcccagaacc   780
cagtaataag tgggctcctc cctggcctgg accccgtgg taaccctata aggcgaggca   840
gctgctgtct gaggcaggga gggggctggtg tgggaggcta agggcagctg ctaagtttag   900
ggtggctcct tctctcttct tagagacaac aggtggctgg ggcctcagtg cccagaaaag   960
aaaatgtctt agaggtatcg gcatgggcct ggaggagggg ggacagggca gggggaggca   1020
tcttcctcag gacatcgggt cctagagggg tacccaacgg gttacgacac acctactagt   1080
aaccccctcca gctggtgatg gcaggtctag ggtaggaccca gtgactggct cctaatcgag   1140
cactctattt tcagggtttg cattccaaaa gggtcaggtc caagagggac ctggagtgcc   1200
aagtggaggt gtagaggcac ggccagtacc catggagaat ggtggatgtc cttagggtt   1260
agcaagtgcc gtgtgctaag gagggggctt tggaggttgg gcaggccctc tgtgggggctc   1320
cattttgtg ggggtgggg ctggagcatt ataggggtg ggaagtgatt ggggctgtca   1380
ccctagcctt ccttatctga cgcccaccca tgcctcctca ggtaccccct gcccccacca   1440
gctcctctcc tgtgccttgt ttcccagcca tgcgttctcc tctataaata cccgctctg   1500
tatttggggt tggcagctgt tgctgccagg gagatggttg ggttgacatg cggctcctga   1560
caaaacacaa acccctggtg tgtgtgggcg tgggtggtgt gagtaggggg atgaatcagg   1620
gagggggcgg gggacccagg gggcaggagc cacacaaagt ctgtgcgggg gtgggagcgc   1680
acatagcaat tggaaactga aagcttatca gaccctttct ggaaatcagc ccactgtttta   1740
taaacttgag gccccaccct cgacagtacc ggggaggaag agggcctgca ctagtccaga   1800
gggaaactga ggctcaggggc tagctcgccc atagacatac atggcaggca ggctttggcc   1860
aggatccctc cgcctgccag gcgtctcctt gccctccctt cctgcctaga gacccccacc   1920
ctcaagcctg gctggtcttt gcctgagacc caaacctctt cgacttcaag agaatattta   1980
ggaacaaggt ggtttagggc ctttcctggg aacaggcctt gaccctttaa gaaatgaccc   2040
aaagtctctc cttgaccaaa aaggggaccc tcaaactaaa gggaagcctc tcttctgctg   2100
tctcccctga ccccactccc cccacccca ggacgaggag ataaccaggg ctgaaagagg   2160
cccgcctggg ggctgcagac atgcttgctg cctgccctgg cgaaggattg gcaggcttgc   2220
ccgtcacagg accccgctg gctgactcag gggcgcaggc ctcttgcggg ggagctggcc   2280
tccccgcccc cacggccacg ggcgcgcctt tcctggcagg acagcgggat cttgcagctg   2340
```

-continued

```
tcaggggagg ggaggcgggg gctgatgtca ggagggatac aaatagtgcc gacggctggg   2400
ggccctgtct cccctcgccg catccactct ccggccggcc gcctgcccgc cgcctcctcc   2460
gtgcgcccgc cagcctcgcc cgcgccgtca cctctagaaa gaggtaaggg tttaagggat   2520
ggttggttgg tggggtatta atgtttaatt acctggagca cctgcctgaa atcacttttt   2580
ttcaggttgg aagcttatgg aagatgccaa aaacattaag aagggcccag cgccattcta   2640
cccactcgag gacgggaccg ccggcgagca gctgcacaaa gccatgaagc gctacgccct   2700
ggtgcccggc accatcgcct ttaccgacgc acatatcgag gtggacatta cctacgccga   2760
gtacttcgag atgagcgttc ggctggcaga agctatgaag cgctatgggc tgaatacaaa   2820
ccatcggatc gtggtgtgca gcgagaatag cttgcagttc ttcatgcccg tgttgggtgc   2880
cctgttcatc ggtgtggctg tggccccagc taacgacatc tacaacgagc gcgagctgct   2940
gaacagcatg ggcatcagcc agcccaccgt cgtattcgtg agcaagaaag ggctgcaaaa   3000
gatcctcaac gtgcaaaaga agctaccgat catacaaaag atcatcatca tggatagcaa   3060
gaccgactac cagggcttcc aaagcatgta caccttcgtg acttcccatt tgccacccgg   3120
cttcaacgag tacgacttcg tgcccgagag cttcgaccgg gacaaaacca tcgccctgat   3180
catgaacagt agtggcagta ccggattgcc caagggcgta gccctaccgc accgcaccgc   3240
ttgtgtccga ttcagtcatg cccgcgaccc catcttcggc aaccagatca tccccgacac   3300
cgctatcctc agcgtggtgc catttccacca cggcttcggc atgttcacca cgctcgggcta   3360
cttgatctgc ggctttcggg tcgtgctcat gtaccgcttc gaggaggagc tattcttgcg   3420
cagcttgcaa gactataaga ttcaatctgc cctgctggtg cccacactat ttagcttctt   3480
cgctaagagc actctcatcg acaagtacga cctaagcaac ttgcacgaga tcgccagcgg   3540
cggggcgccg ctcagcaagg aggtaggtga ggccgtggcc aaacgcttcc acctaccagg   3600
catccgccag ggctacggcc tgacagaaac aaccagcgcc attctgatca ccccgaagg   3660
ggacgacaag cctggcgcag taggcaaggt ggtgcccttc ttcgaggcta aggtggtgga   3720
cttggacacc ggtaagacac tgggtgtgaa ccagcgcggc gagctgtgcg tccgtggccc   3780
catgatcatg agcggctacg ttaacaaccc cgaggctaca aacgctctca tcgacaagga   3840
cggctggctg cacagcgggc acatcgccta ctgggacgag gacgagcact tcttcatcgt   3900
ggaccggctg aagagcctga tcaaatacaa gggctaccag gtagcccag ccgaactgga   3960
gagcatcctg ctgcaacacc ccaacatctt cgacgccggg gtcgccggcc tgcccgacga   4020
cgatgccggc gagctgcccg ccgcagtcgt cgtgctggaa cacggtaaaa ccatgaccga   4080
gaaggagatc gtggactatg tggccagcca ggttacaacc gccaagaagc tgcgcggtga   4140
tgttgtgttc gtggacgagg tgcctaaagg actgaccggc aagttggacg cccgcaagat   4200
ccgcgagatt ctcattaagg ccaagaaggg cggcaagatc gccgtgtaat cgaaacgaa   4260
atgtccatct tgagcatctg acttctggct aaataaaaga tctttatttt cattagatct   4320
gtgtgttggt tttttgtgtg cgtcgagatc cacggccgca ggaaccccta gtgatggagt   4380
tggccactcc ctctctcgcg gctcgctcgc tcactgaggc cgggcgacca aaggtcgccc   4440
gacgcccggg ctttgcccgg gcggcctcag tgagcgagcg agcgcgcagc tgcctgcagg   4500
ggcgcctgat gcggtatttt ctccttacgc atctgtgcgg tatttcacac cgcatacgtc   4560
aaagcaacca tagtacgcgc cctgtagcgg cgcattaagc gcggcgggtg tggtggttac   4620
gcgcagcgtg accgctacac ttgccagcgc cctagcgccc gctcctttcg ctttcttccc   4680
ttcctttctc gccacgttcg ccggctttcc ccgtcaagct ctaaatcggg ggctcccttt   4740
agggttccga tttagtgctt tacggcacct cgaccccaaa aaacttgatt tgggtgatgg   4800
ttcacgtagt gggccatcgc cctgatagac ggtttttcgc cctttgacgt tggagtccac   4860
gttctttaat agtggactct tgttccaaac tggaacaaca ctcaacccta tctcgggcta   4920
ttcttttgat ttataaggga ttttgccgat ttcggcctat tggttaaaaa atgagctgat   4980
ttaacaaaaa tttaacgcga attttaacaa aatattaacg tttacaattt tatggtgcac   5040
tctcagtaca atctgctctg atgccgcata gttaagccag ccccgacacc cgccaacacc   5100
cgctgacgcg ccctgacggg cttgtctgct cccggcatcc gcttacagac aagctgtgac   5160
cgtctccggg agctgcatgt gtcagaggtt ttcaccgtca tcaccgaaac gcgcgagacg   5220
aaagggcctc gtgatacgcc tatttttata ggttaatgtc atgataataa tggtttctta   5280
gacgtcaggt ggcactttc ggggaaatgt gcgcggaacc cctatttgtt tatttttcta   5340
aatacattca aatatgtatc cgctcatgag acaataaccc tgataaatgc ttcaataata   5400
ttgaaaaagg aagagtatga gtattcaaca tttccgtgtc gcccttattc ccttttttgc   5460
ggcattttgc cttcctgttt ttgctcaccc agaaacgctg gtgaaagtaa aagatgctga   5520
agatcagttg ggtgcacgag tgggttacat cgaactggat ctcaacagcg gtaagatcct   5580
tgagagtttt cgccccgaag aacgttttcc aatgatgagc acttttaaag ttctgctatg   5640
tggcgcggta ttatcccgta ttgacgccgg gcaagagcaa ctcggtcgcc gcatacacta   5700
ttctcagaat gacttggttg agtactcacc agtcacagaa aagcatctta cggatggcat   5760
gacagtaaga gaattatgca gtgctgccat aaccatgagt gataacactg cggccaactt   5820
acttctgaca acgatcggag gaccgaagga gctaaccgct tttttgcaca acatgggga   5880
tcatgtaact cgccttgatc gttgggaacc ggagctgaat gaagccatac caaacgacga   5940
gcgtgacacc acgatgcctg tagcaatggc aacaacgttg cgcaaactat taactggcga   6000
actacttact ctagcttccc ggcaacaatt aatagactgg atggaggcgg ataaagttgc   6060
aggaccactt ctgcgctcgg cccttccggc tggctggttt attgctgata atctggagc   6120
cggtgagcgt gggtctcgcg gtatcattgc agcactgggg ccagatggta agccctcccg   6180
tatcgtagtt atctacacga cggggagtca ggcaactatg gatgaacgaa atagacagat   6240
cgctgagata ggtgcctcac tgattaagca ttggtaactg tcagaccaag tttactcata   6300
tatactttag attgatttaa aacttcattt ttaatttaaa aggatctagg tgaagatcct   6360
ttttgataat ctcatgacca aaatccctta acgtgagttt tcgttccact gagcgtcaga   6420
ccccgtagaa aagatcaaag gatcttcttg agatcctttt tttctgcgcg taatctgctg   6480
cttgcaaaca aaaaaaccac cgctaccagc ggtggtttgt ttgccggatc aagagctacc   6540
aactcttttt ccgaaggtaa ctggcttcag cagagcgcag ataccaaata ctgtccttct   6600
agtgtagccg tagttaggcc accacttcaa gaactctgta gcaccgccta catacctcgc   6660
tctgctaatc ctgttaccag tggctgctgc cagtggcgat aagtcgtgtc ttaccgggtt   6720
ggactcaaga cgatagttac cggataaggc gcagcggtcg ggctgaacgg ggggttcgtg   6780
cacacagccc agcttggagc gaacgaccta caccgaactg agatacctac agcgtgagct   6840
atgagaaagc gccacgcttc ccgaagggag aaaggcggac aggtatccgg taagcggcag   6900
ggtcggaaca ggagagcgca cgagggagct tccaggggga aacgcctggt atctttatag   6960
tcctgtcggg tttcgccacc tctgacttga gcgtcgattt ttgtgatgct cgtcaggggg   7020
gcggagccta tggaaaaacg ccagcaacgc ggcctttta cggttcctgg ccttttgctg   7080
```

```
gccttttgct cacatgt                                                  7097

SEQ ID NO: 110        moltype = DNA  length = 7154
FEATURE               Location/Qualifiers
misc_feature          1..7154
                      note = plasmid pAAVss-CRE04-SkSH4-hDES1.4kb-Luc2
source                1..7154
                      mol_type = other DNA
                      organism = synthetic construct
SEQUENCE: 110
acatgtcctg caggcagctg cgcgctcgct cgctcactga ggccgcccgg gcaaagcccg   60
ggcgtcgggc gacctttggt cgcccggcct cagtgagcga gcgagcgcgc agagagggag  120
tggccaactc catcactagg ggttcctgcg gccccttta gagaatccac acctgtccca  180
gttgctgggt tccactacca aaagtgaatt gcaactattt taggagcact taagcacatc  240
cgaaaaatga gtgattctgt tctggcccac accacatcac tgatgtaccc ccttaaagca  300
tgtccctgag ttcatcacag aagactgctc ctcctgtgcc ctccacaagg ttagaactgt  360
ccttgtctta gggaaaaagg agagagagag agagagagag agagagagag agagagagag  420
agagagagag ggacaggcac caactgggta acctctgctg accccactc tactttacca  480
taagtagctc caaatccttc tagaaaatct gaaaggcata gccccatata tcagtgatat  540
aaatagaacc tgcagcaggc tctggtaaat gatgactaca aggtggactg ggaggcagcc  600
cggccttggc aggcatcatc ctctaaatat aaagatgagt ttgttcagcc tttgcagaag  660
gaggcgcgcc acgcgtttct gagtcctcta aggtccctca ctcccaactc agccccatgt  720
cctgtcaatt cccactcagt gtctgatctc cttctcctca cctttcccat ctcccgtttg  780
acccaagctt cctgagctct cctcccattc ccctttttgg agtcctcctc ctctcccaga  840
acccagtaat aagtgggctc ctccctggcc tggaccccccg tggtaaccct ataaggcgag  900
gcagctgctg tctgaggcag ggaggggctg gtgtgggagg ctaagggcag ctgctaagtt  960
tagggtggct ccttctctct tcttagagac aacaggtggc tggggcctca gtgcccagaa 1020
aagaaaatgt cttagaggta tcggcatggg cctggaggag gggggacagg gcaggggggag 1080
gcatcttcct caggacatcg ggtcctagag gggtacccaa cgggttacga cacacctact 1140
agtaacccct ccagctggtg atggcaggtc tagggtagga ccagtgactg gctcctaatc 1200
gagcactcta ttttcagggt ttgcattcca aaagggtcag gtccaagagg gacctggagt 1260
gccaagtgga ggtgtagagg cacggccagt acccatggag aatggtggat gtccttaggg 1320
gttagcaagt gccgtgtgct aaggagggggg cttttggaggt tgggcaggcc ctctgtgggg 1380
ctccatttttt gtgggggtgg gggctggagc attatagggg gtgggaagtg attgggggctg 1440
tcaccctagc cttccttatc tgacgcccac ccatgcctcc tcaggtaccc cctgccccca 1500
acagctcctc tcctgtgcct tgtttcccag ccatgcgttc tcctctataa atacccgctc 1560
tggtatttgg ggttggcagc tgttgctgcc agggagatgg ttgggttgac atgcggctcc 1620
tgacaaaaca caaaccccctg gtgtgtgtgg gcgtgggtgg tgtgagtagg gggatgaatc 1680
agggagggggg cggggggaccc aggggggcagg agccacacaa agtctgtgcg ggggtggggg 1740
cgcacatagc aattggaaac tgaaagctta tcagacccctt tctggaaatc agcccactgt 1800
ttataaactt gaggccccac cctcgacagt accggggagg aagagggcct gcactagtcc 1860
agagggaaac tgaggctcag ggctagctcg cccatagaca tacatggcag gcaggctttg 1920
gccaggatcc ctccgcctgc caggcgtctc cctgccctcc cttcctgcct agagaccccc 1980
accctcaagc ctggctggtc tttgcctgag acccaaacct cttcgacttc aagagaaatt 2040
ttaggaacaa ggtggtttag ggcctttcct gggaacaggc cttgacccctt taagaaatga 2100
cccaaagtct ctccttgacc aaaaagggga ccctcaaact aaagggaagc ctctcttctg 2160
ctgtctcccc tgaccccact ccccccccacc ccaggacgag gagataacca gggctgaaag 2220
aggcccgcct gggggctgca gacatgcttg ctgcctgccc tggcgaagga ttggcaggct 2280
tgcccgtcac aggaccccccg ctggctgact caggggcgca ggcctcttgc gggggagctg 2340
gcctccccgc ccccacggcc acgggccgcc ctttcctggc aggacagcgg gatcttgcag 2400
ctgtcagggg aggggaggcg ggggctgatg tcaggaggga tacaaatagt gccgacggct 2460
ggggggccctg tctcccctcg ccgcatccac tctccggccg gccgcctgcc cgccgcctcc 2520
tccgtgcgcc cgccagcctc gcccgcgccg tcacctctag aaagaggtaa gggtttaagg 2580
gatggttggt tggtggggta ttaatgttta attacctgga gcacctgcct gaaatcactt 2640
tttttcaggt tggaagctta tggaagatgc caaaaacatt aagaagggcc cagcgccatt 2700
ctacccactc gaggacggga ccgccggcga gcagctgcac aaagccatga gcgctacgc 2760
cctggtgccc ggcaccatcg cctttaccga cgcacatatc gaggtggaca ttacctacgc 2820
cgagtacttc gagatgagcg ttcggctggc agaagctatg aagcgctatg gctgaatac 2880
aaaccatcgg atcgtggtgt gcagcgagaa tagcttgcag ttcttcatgc ccgtgttggg 2940
tgccctgttc atcggtgtgg ctgtggcccc agctaacgac atctacaacg agcgcgagct 3000
gctgaacagc atgggcatca gccagcccac cgtcgtattc gtgagcaaga aagggctgca 3060
aaagatcctc aacgtgcaaa agaagctacc gatcatacaa aagatcatca tcatgtatag 3120
caagaccgac taccagggct tccaaagcat gtacaccttc gtgacttccc atttgccacc 3180
cggcttcaac gagtacgact tcgtgcccga gagcttcgac cgggacaaaa ccatcgccct 3240
gatcatgaac agtagtggca gtaccggatt gcccaagggc gtagccctac cgcaccgcac 3300
cgcttgtgtc cgattcagtc atgcccgcga ccccatcttc ggcaaccaga tcatccccga 3360
caccgctatc ctcagcgtgg tgccatttca ccacggcttc ggcatgttca ccacgctggg 3420
ctacttgatc tgcggctttc gggtcgtgct catgtaccgc ttcgaggagg agctattctt 3480
gcgcagcttg caagactata gattcaatc tgccctgcg gtgcccacac tatttagctt 3540
cttcgctaag agcactctca tcgacaagta cgacctaagc aacttgcacg agatcgccag 3600
cggcggggcg ccgctcagca aggaggtagg tgaggccgtg gccaaacgct tccacctacc 3660
aggcatccgc cagggctacg gcctgacaga acaaccagc gccattctga tcaccccccga 3720
aggggacgac aagcctggcg cagtaggcaa ggtggtgccc ttcttcgagg ctaaggtggt 3780
ggacttggac accggtaaga cactgggtgt gaaccagcga ggcgagctgt gcgtccgtgg 3840
ccccatgatc atgagcggct acgttaacaa ccccgaggct acaaacgctc tcatcgacaa 3900
ggacggctgg ctgcacagcg gcgacatcgc ctactgggac gaggacgagc acttcttcat 3960
cgtgaccgct ctgaagagcc tgatcaaata caagggctac caggtagccc cagccgaact 4020
ggagagcatc ctgctgcaac accccaacat cttcgacgcc ggggtcgccg gctgcccga 4080
cgacgatgcc ggcgagctgc cgccgcagt cgtcgtgctg gaacacggta aaaccatgac 4140
```

```
cgagaaggag atcgtggact atgtggccag ccaggttaca accgccaaga agctgcgcgg   4200
tggtgttgtg ttcgtggacg aggtgcctaa aggactgacc ggcaagttgg acgcccgcaa   4260
gatccgcgca gattctcatta aggccaagaa gggcggcaag atcgccgtgt aattcgaaac   4320
gaaaggtcca tcttgagcat ctgacttctg gctaaataaa agatctttat tttcattaga   4380
tctgtgtgtt ggttttttgt gtgcgtcgag atccacggcc gcaggaaccc ctagtgatgg   4440
agttggccac tccctctctg cgcgctcgct cgctcactga ggccgggcga ccaaaggtcc   4500
cccgacgccc gggctttgcc cgggcggcct cagtgagcga gcgagcgcgc agctgcctgc   4560
aggggcgcct gatgcggtat tttctcctta cgcatctgtg cggtatttca caccgcatac   4620
gtcaaagcaa ccatagtacg cgccctgtag cggcgcatta agcgcggcgg gtgtggtggt   4680
tacgcgcagc gtgaccgcta cacttgccag cgccctagcg cccgctcctt tcgctttctt   4740
cccttccttt ctcgccacgt tcgccggctt tccccgtcaa gctctaaatc gggggctccc   4800
tttagggttc cgatttagtg ctttacggca cctcgacccc aaaaaacttg atttgggtga   4860
tggttcacgt agtgggccat cgccctgata gacggttttt cgccctttga cgttggagtc   4920
cacgttcttt aatagtggac tcttgttcca aactggaaca acactcaacc ctatctcggg   4980
ctattctttt gatttataag ggattttgcc gatttcggcc tattggttaa aaaatgagct   5040
gatttaacaa aaatttaacg cgaattttaa caaaatatta acgtttacaa ttttatggtg   5100
cactctcagt acaatctgct ctgatgccgc atagttaagc cagccccgac accgccaac   5160
accgctgac gcgccctgac gggcttgtct gctcccggca tccgcttaca gacaagctgt   5220
gaccgtctcc gggagctgca tgtgtcagag gttttcaccg tcatcaccga aacgcgcgag   5280
acgaaagggc ctcgtgatac gcctattttt ataggttaat gtcatgataa taatggtttc   5340
ttagacgtca ggtggcactt ttcggggaaa tgtgcgcgga acccctattt gtttattttt   5400
ctaaatacat tcaaatatgt atccgctcat gagacaataa ccctgataaa tgcttcaata   5460
atattgaaaa aggaagagta tgagtattca acatttccgt gtcgccctta ttccctttt   5520
tgcggcattt tgccttcctg tttttgctca cccagaaacg ctggtgaaag taaaagatgc   5580
tgaagatcag ttgggtgcac gagtgggtta catcgaactg gatctcaaca gcggtaagat   5640
ccttgagagt tttcgccccg aagaacgttt tccaatgatg agcacttttta aagttctgct   5700
atgtggcgcg gtattatccc gtattgacgc cgggcaagag caactcggtc gccgcataca   5760
ctattctcag aatgacttgg ttgagtactc accagtcaca gaaaagcatc ttacggatgg   5820
catgacagta agagaattat gcagtgctgc cataaccatg agtgataaca ctgcggccaa   5880
cttacttctg acaacgatcg gaggaccgaa ggagctaacc gcttttttgc acaacatggg   5940
ggatcatgta actcgccttg atcgttggga accggagctg aatgaagcca taccaaacga   6000
cgagcgtgac accacgatgc ctgtagcaat ggcaacaacg ttgcgcaaac tattaactgg   6060
cgaactactt actctagctt cccggcaaca attaatagac tggatggagg cggataaagt   6120
tgcaggacca cttctgcgct cggcccttcc ggctggctgg tttattgctg ataaatctgg   6180
agccggtgag cgtgggtctc gcggtatcat tgcagcactg gggccagatg gtaagccctc   6240
ccgtatcgta gttatctaca cgacggggag tcaggcaact atggatgaac gaaatagaca   6300
gatcgctgag ataggtgcct cactgattaa gcattggtaa ctgtcagacc aagtttactc   6360
atatatactt tagattgatt taaaacttca ttttttaattt aaaaggatct aggtgaagat   6420
cctttttgat aatctcatga ccaaaatccc ttaacgtgag ttttcgttcc actgagcgtc   6480
agaccccgta gaaaagatca aaggatcttc ttgagatcct tttttttctgc gcgtaatctg   6540
ctgcttgcaa acaaaaaaac caccgctacc agcggtggtt tgtttgccgg atcaagagct   6600
accaactctt tttccgaagg taactggctt cagcagagcg cagataccaa atactgtcct   6660
tctagtgtag ccgtagttag gccaccactt caagaactct gtagcaccgc ctacatacct   6720
cgctctgcta atcctgttac cagtggctgc tgccagtggc gataagtcgt gtcttaccgg   6780
gttggactca agacgatagt taccggataa ggcgcagcgg tcgggctgaa cggggggttc   6840
gtgcacacag cccagcttgg agcgaacgac ctacaccgaa ctgagatacc tacagcgtga   6900
gctatgagaa agcgccacgc ttcccgaagg gagaaaggcg gacaggtatc cggtaagcgg   6960
cagggtcgga acaggagagc gcacgaggga gcttccaggg ggaaacgcct ggtatcttta   7020
tagtcctgtc gggtttcgcc acctctgact tgagcgtcga tttttgtgat gctcgtcagg   7080
gggcggagc ctatggaaaa acgccagcaa cgcggccttt ttacggttcc tggcctttg    7140
ctggcctttt gctc                                                     7154
```

```
SEQ ID NO: 111       moltype = DNA   length = 7045
FEATURE              Location/Qualifiers
misc_feature        1..7045
                     note = plasmid pAAVss-CRE06-SkSH4-hDES1.4kb-Luc2
source              1..7045
                     mol_type = other DNA
                     organism = synthetic construct
SEQUENCE: 111
cctgcaggca gctgcgcgct cgctcgctca ctgaggccgc ccgggcaaag cccgggcgtc   60
gggcgacctt tggtcgcccg gcctcagtga gcgagcgagc gcgcagagag ggagtggcca   120
actccatcac taggggttcc tgcggccggg ccaggggacg gtggcttcta cgtgcttggg   180
acgttcccag ccaccgtccc atgttcccgg cgggggcc gctgtcccca ccgccagccc    240
aactcagcac ttggtcaggg tatcagcttg gtgggggggc gtgagcccag ccctcgggc    300
ggctcagccc atacaaggcc atggggctgg gcgcaaagca tgcctggggtt cagggtgggt   360
atggtgcggg agcaggagg tgagaggctc agctgccctc cagaactcct ccctggggac    420
aacccctccc agccaatagc acagcctagg tccccctata taaggccacg gctgctggcc    480
cttcctttgg gtcagtgtca cctccaggat acagacagcc cccttcagc ccagcccagc    540
caggtacggc gcgccacgcg tttctgagtc ctctaaggtc cctcactccc aactcagccc   600
catgtcctgt caattcccac tcagtgtctg atctccttct cctcaccttt cccatctccc   660
gtttgaccca agcttcctga gctctcctcc cattcccctt tttggagtcc tcctcctctc   720
ccagaaccca gtaataagtg ggctcctccc tggcctggac cccgtggta accctataag    780
gcgaggcagc tgctgtctga ggcagggagg ggctggtgtg ggaggctaag ggcagctgct   840
aagtttaggg tggctccttc tctcttctta gagacaacag gtggctgggg cctcagtgcc   900
cagaaaagaa aatgtcttag aggtatcggc atgggcctgg aggaggggg acagggcagg   960
gggaggcatc ttcctcagga catcgggtcc tagagggta cccaacgggt tacgacacac   1020
ctactagtaa ccctccagc tggtgatggc aggtctaggt taggaccagt gactggctcc    1080
taatcgagca ctctattttc agggtttgca ttccaaaagg gtcaggtcca agaggggacct   1140
```

-continued

```
ggagtgccaa gtggaggtgt agaggcacgg ccagtaccca tggagaatgg tggatgtcct    1200
taggggttag caagtgccgt gtgctaagga gggggctttg gaggttgggc aggccctctg    1260
tggggctcca tttttgtggg ggtgggggct ggagcattat agggggtggg aagtgattgg    1320
ggctgtcacc ctagccttcc ttatctgacg cccacccatg cctcctcagg taccccctgc    1380
cccccacagc tcctctcctg tgccttgttt cccagccatg cgttctcctc tataaatacc    1440
cgctctggta tttgggggttg gcagctgttg ctgccaggga gatggttggg ttgacatgcg    1500
gctcctgaca aaacacaaac ccctggtgtg tgtgggcgtg ggtggtgtga gtaggggggat    1560
gaatcaggga gggggcgggg gacccagggg gcaggagcca cacaaagtct gtgcgggggt    1620
gggagcgcac atagcaattg gaaactgaaa gcttatcaga cccttctgg aaatcagccc    1680
actgtttata aacttgaggc cccaccctcg acagtaccgg ggaggaagag ggcctgcact    1740
agtccagagg gaaactgagg ctcagggcta gctcgcccat agacatacat ggcaggcagg    1800
ctttggccag gatccctccg cctgccaggc gtctccctgc cctcccttcc tgcctagaga    1860
cccccaccct caagcctggc tggtctttgc ctgagaccca aacctcttcg acttcaagag    1920
aatatttagg aacaaggtgg tttaggggcct ttcctgggaa caggccttga cccttttaaga   1980
aatgacccaa agtctctcct tgaccaaaaa ggggaccctc aaactaaagg gaagcctctc    2040
ttctgctgtc tcccctgacc ccactcccc ccacccagg acgaggagat aaccagggct    2100
gaaagaggcc cgcctggggg ctgcagacat gcttgctgcc tgccctggcg aaggattggc    2160
aggcttgccc gtcacaggac ccccgctggc tgactcaggg gcgcaggcct cttgcggggg    2220
agctggcctc cccgccccca cggccacggg ccgcccttc ctggcaggac agcgggatct    2280
tgcagctgtc aggggagggg aggcggggggc tgatgtcagg agggatacaa atagtgccga   2340
cggctggggg ccctgtctcc cctcgccgca tccactctcc ggccggccgc ctgcccgccg    2400
cctcctccgt gcgcccgcca gcctcgcccg cgccgtcacc tctagaaaga ggtaaggggtt   2460
taagggatgg ttggttggtg gggtattaat gtttaattac ctggagcacc tgcctgaaat    2520
cacttttttt caggttggaa gcttatggaa gatgccaaaa acattaagaa gggcccagcg   2580
ccattctacc cactcgagga cgggaccgcc ggcgagcagc tgcacaaagc catgaagcgc    2640
tacgccctgg tgcccggcac catcgccttt accgacgcac atatcgaggt ggacattacc    2700
tacgccgagt acttcgagat gagcgttcgg ctggcagaag ctatgaagcg ctatgggctg    2760
aatacaaacc atcggatcgt ggtgtgcagc gagaatagct tgcagttctt catgcccgtg   2820
ttgggtgccc tgttcatcgg tgtggctgtg gccccagcta acgacatcta caacgagcgc    2880
gagctgctga acagcatggg catcagccag cccaccgtcg tattcgtgag caagaaaggg   2940
ctgcaaaaga tcctcaacgt gcaaaagaag ctaccgatca tacaaaagat catcatcatg    3000
gatagcaaga ccgactacca gggcttccaa agcatgtaca ccttcgtgac ttcccatttg    3060
ccacccggct tcaacgagta cgacttcgtg cccgagagct tcgaccggga caaaaccatc    3120
gccctgatca tgaacagtag tggcagtacc ggattgccca agggcgtagc cctaccgcac    3180
cgcaccgctt gtgtccgatt cagtcatgcc cggcgacccca tcttcggcaa ccagatcatc    3240
cccgacaccg ctatcctcag cgtggtgcca tttcaccacg gcttcggcat gttcaccacg    3300
ctgggctact tgatctgcgg cttttcgggtc gtgctcatgt accgcttcga ggaggagcta    3360
ttcttgcgca gcttgcaaga ctataagatt caatctgccc tgctggtgcc cacactattt    3420
agcttcttcg ctaagagcac tctcatcgac aagtacgacc taagcaactt gcacgagatc    3480
gccagcggcg gggcgccgct cagcaaggag gtaggtgagg ccgtggccaa acgcttccac    3540
ctaccaggca tccgccaggg ctacggcctg acagaaacaa ccagcgccat tctgatcacc    3600
cccgaaggggg acgacaagcc tggcgcagta ggcaaggtgg tgcccttctt cgaggctaag    3660
gtggtggact tggacaccgg taagacactg ggtgtgaacc agcgcggcga gctgtgcgtc    3720
cgtggcccca tgatcatgag cggctacgtt aacaaccccg aggctacaaa cgctctcatc    3780
gacaaggacg gctggctgca cagcggcgac atcgcctact gggacgagga cgagcacttc    3840
ttcatcgtgg accggctgaa gagcctgatc aaatacaagg gctaccaggt agccccagcc    3900
gaactggaga gcatcctgct gcaacacccc aacatcttcg acgccggggt cgccggcctg    3960
cccgacgacg atgccggcga gctgcccgcc gcagtcgtcg tgctggaaca cggtaaaacc    4020
atgaccgaga aggagatcgt ggactatgtg gccagccagg ttacaaccgc caagaagctg    4080
cgcggtggtg ttgtgttcgt ggacgaggtg cctaaaggac tgaccggcaa gttggacgcc    4140
cgcaagatcc gcgagattct cattaaggcc aagaagggcg gcaagatcgc cgtgtaattc    4200
gaaacgaagg gtccatcttg agcatctgac ttctggctaa ataaaagatc tttatttttca    4260
ttagatctgt gtgttggttt tttgtgtgcg tcgagatcca cggccgcagg aacccctagt    4320
gatggagttg gccactccct ctctgcgcgc tcgctcgctc actgaggccg ggcgaccaaa    4380
ggtcgcccga cgcccgggct ttgcccgggc ggcctcagtg agcgagcgag cgcgcagcctg   4440
cctgcagggg cgcctgatgc ggtattttct ccttacgcat ctgtgcggta tttcacaccg    4500
catacgtcaa agcaaccata gtacgcgccc tgtagcggcg cattaagcgc ggcgggtgtg    4560
gtggttacgc gcagcgtgac cgctacactt gccagcgccc tagcgcccgc tcctttcgct    4620
ttcttccctt cctttctcgc cacgttcgcc ggctttcccc gtcaagctct aaatcggggg    4680
ctcccttttag ggttccgatt tagtgcttta cggcacctcg accccaaaaa acttgatttg    4740
ggtgatggtt cacgtagtgg gccatcgccc tgatagacgg tttttcgccc tttgacgttg    4800
gagtccacgt tctttaatag tggactcttg ttccaaactg gaacaacact caaccctatc    4860
tcgggctatt cttttgattt ataagggatt ttgccgattt cggcctattg gttaaaaaat    4920
gagctgattt aacaaaaatt taacgcgaat tttaacaaaa tattaacgtt tacaatttta    4980
tggtgcactc tcagtacaat ctgctctgat gccgcatagt taagccagcc ccgacacccg   5040
ccaacacccg ctgacgcgcc ctgacgggct tgtctgctcc cggcatccgc ttacagacaa    5100
gctgtgaccg tctccgggag ctgcatgtgt cagaggtttt caccgtcatc accgaaacgc    5160
gcgagacgaa agggcctcgt gatacgccta tttttatagg ttaatgtcat gataataatg    5220
gtttcttaga cgtcaggtgg cacttttcgg ggaaatgtga gcggaacccc tatttgttta    5280
tttttctaaa tacattcaaa tatgtatccg ctcatgagac aataaccctg ataaatgctt    5340
caataatatt gaaaaaggaa gagtatgagt attcaacatt tccgtgtcgc ccttattccc    5400
ttttttgcgg cattttgcct tcctgttttt gctcacccag aaacgctggt gaaagtaaaa    5460
gatgctgaag atcagttggg tgcacgagtg ggttacatcg aactggatct caacagcggt    5520
aagatccttg agagttttcg ccccgaagaa cgttttaaagtu tctatcgcat gataataatg    5580
ctgctatgtg gcgcggtatt atcccgtatt gacgccgggc aagagcaact cggtcgccgc    5640
atacactatt ctcagaatga cttggttgag tactcaccag tcacagaaaa gcatcttacg    5700
gatggcatga cagtaagaga attatgcagt gctgccataa ccatgagtga taacactgcg    5760
gccaacttac ttctgacaac gatcggagga ccgaaggagc taaccgcttt tttgcacaac    5820
atgggggatc atgtaactcg ccttgatcgt tgggaaccgg agctgaatga agccatacca    5880
```

```
aacgacgagc gtgacaccac gatgcctgta gcaatggcaa caacgttgcg caaactatta   5940
actggcgaac tacttactct agcttcccgg caacaattaa tagactggat ggaggcggat   6000
aaagttgcag gaccacttct gcgctcggcc cttccggctg gctggtttat tgctgataaa   6060
tctggagccg gtgagcgtgg gtctcgcggt atcattgcag cactgggcc agatggtaag   6120
ccctcccgta tcgtagttat ctacacgacg gggagtcagg caactatgga tgaacgaaat   6180
agacagatcg ctgagatagg tgcctcactg attaagcatt ggtaactgtc agaccaagtt   6240
tactcatata tactttagat tgatttaaaa cttcattttt aatttaaaag gatctaggtg   6300
aagatccttt ttgataatct catgaccaaa atcccttaac gtgagttttc gttccactga   6360
gcgtcagacc ccgtagaaaa gatcaaagga tcttcttgag atcctttttt tctgcgcgta   6420
atctgctgct tgcaaacaaa aaaaccaccg ctaccagcgg tggtttgttt gccggatcaa   6480
gagctaccaa ctcttttttcc gaaggtaact ggcttcagca gagcgcagat accaaatact   6540
gtccttctag tgtagccgta gttaggccac cacttcaaga actctgtagc accgcctaca   6600
tacctcgctc tgctaatcct gttaccagtg gctgctgcca gtggcgataa gtcgtgtctt   6660
accgggttgg actcaagacg atagttaccg gataaggcgc agcggtcggg ctgaacgggg   6720
ggttcgtgca cacagcccag cttggagcga acgacctaca ccgaactgag atacctacag   6780
cgtgagctat gagaaagcgc cacgcttccc gaagggagaa aggcggacag gtatccggta   6840
agcggcaggg tcggaacagg agagcgcacg agggagcttc caggggggaaa cgcctggtat   6900
ctttatagtc ctgtcgggtt tcgccacctc tgacttgagc gtcgatttt gtgatgctcg   6960
tcagggggggc ggagcctatg gaaaaacgcc agcaacgcgg ccttttttacg gttcctggcc   7020
ttttgctggc ctttttgctca catgt                                          7045

SEQ ID NO: 112          moltype = DNA   length = 6942
FEATURE                 Location/Qualifiers
misc_feature           1..6942
                        note = plasmid pAAVss-CRE18-SkSH4-hDES1.4kb-Luc2
source                 1..6942
                        mol_type = other DNA
                        organism = synthetic construct SEQUENCE: 112
cctgcaggca gctgcgcgct cgctcgctca ctgaggccgc ccgggcaaag cccgggcgtc   60
gggcgacctt tggtcgcccg gcctcagtga gcgagcgagc gcgcagagag ggagtggcca   120
actccatcac taggggttcc tgcggcccct ttgactttc ttgaaagggg agggctggga   180
tattccagag attgatcctt aaggcttgct gactgcctac tcacttctgg aaacttccag   240
cagtgtcatt catagacctg tgaagagctc ttagcttgtt ctcacac agtgggggact   300
ctgaggggtc agagtgagtc acccagcagg ccagtggcag gggtgagcca gaagcctggc   360
caaaccctcc tatcatcatg gagagaagaa agcctcctcc agaagacggg aggccggcag   420
ggcgtggggc ctgctcagat gcagggcgcg ccacgcgttt ctgagtcctc taaggtccct   480
cactcccaac tcagccccat gtcctgtcaa ttcccactca gtgtctgatc tccttctcct   540
caccttttcc atctcccgtt tgacccaagc ttcctgagct ctcctcccat tcccctttt   600
ggagtcctcc tcctctccca gaacccagta ataagtgggc tcctccctgg cctggacccc   660
cgtggtaacc ctataaggcg aggcagctgc tgtctgaggc agggaggggc tggtgtggga   720
ggctaaggggc agctgctaag tttagggtgg ctccttctct cttcttagag acaacaggtg   780
gctggggcct cagtgcccag aaaagaaaat gtcttagagg tatcggcatg ggcctggagg   840
aggggggaca gggcagggggg aggcatcttc ctcaggacat cgggtcctag aggggtaccc   900
aacgggttac gacacaccta ctagtaaccc ctccagctgg tgatggcagg tctagggtag   960
gaccagtgac tggctcctaa tcgagcactc tattttcagg gtttgcattc caaaagggtc   1020
aggtccaaga gggacctgga gtgccaagtg gaggtgtaga ggcacggcca gtacccatgg   1080
agaatggtgg atgtccttag gggttagcaa gtgccgtgtg ctaaggaggg ggctttggag   1140
gttgggcagg ccctctgtgg ggctccattt ttgtgggggt gggggctgga gcattatagg   1200
gggtgggaag tgattggggc tgtcacccta gccttcctta tctgacgccc acccatgcct   1260
cctcaggtac cccctgcccc ccacagctcc tctcctgtgc cttgtttccc agccatgcgt   1320
tctcctctat aaataccogc tctggtattt gggggttggca gctgttgctg ccagggagat   1380
ggttgggttg acatgcggct cctgacaaaa cacaaacccc tggtgtgtgt gggcgtgggt   1440
ggtgtgagta gggggatgaa tcaggagggg ggcgggggac ccagggggca ggagccacac   1500
aaagtctgtg cgggggtggg agcgcacata gcaattgaaa actgaaagct tatcagaccc   1560
tttctggaaa tcagcccact gtttataaac ttgaggcccc accctcgaca gtaccgggga   1620
ggaagaggggc ctgcactagt ccagagggaa actgaggctc agggctagct cgcccataga   1680
catacatggg aggcaggctt tggccaggat ccctccgcct gccaggcgtc tccctgccct   1740
ccottcctgc ctagagaccc ccaccctcaa gcctggctgg tctttgcctg agacccaaac   1800
ctcttcgact tcaagagaat atttaggaac aaggtggttt agggcctttc ctggaacag    1860
gccttgaccc tttaagaaat gacccaaagt ctctccttga ccaaaaaggg gaccctcaaa   1920
ctaaagggaa gcctctcttc tgctgtctcc cctgaccccca ctccccccca ccccaggacg   1980
aggagataac cagggctgaa agaggcccgc ctgggggctg cagacatgct tgctgcctgc   2040
cctggcgaag gattggcagg cttgcccgtc acaggacccc ggtgctga ctcaggggcg    2100
caggcctctt gcggggggagc tggcctcccc gccccacgg ccacgggccg cccttttcctg    2160
gcaggacagc gggatcttgc agctgtcagg ggaggggag cggggggctga tgtcaggagg    2220
gatacaaata gtgccgacgg ctgggggccc tgtctcccct cgccgcatcc actctccggc   2280
cggccgcctg cccgccgcct cctccgtgcg cccgccagcc tcgcccgcgc cgtcacctct   2340
agaaagaggt aagggtttaa gggatggttg gttggtgggg tattaatgtt taattacctg   2400
gagcacctgc ctgaaatcac ttttttttcag gttggaagct tatggaagat gccaaaaaca   2460
ttaagaaggg cccagcgcca ttctacccac tcgaggacgg gaccgccggc gagcagctgc   2520
acaaagccat gaagcgctac gccctggtgc ccggcaccat cgcctttacc gacgcacata   2580
tcgaggtgga cattacctac gccgagtact tcgatgag cgttcggctg gcagaagcta   2640
tgaagcgcta tgggctgaat acaaaccatc ggatcgtgat gtgcagcgag aatagcttgc   2700
agttcttcat gcccgtgttg ggtgccctgt tcatcggtgt ggctgtggcc ccagctaacg   2760
acatctacaa cgagcgcgag ctgctgaaca catggcat cagccagccc accgtcgtat   2820
tcgtgagcaa gaaagggctg caaaagatcc tcaacgtgca aaagaagcta ccgatcatac   2880
aaaagatcat catcatggat agcaagaccg actaccaggg cttccaaagc atgtacacct   2940
tcgtgacttc ccatttgcca cccggcttca acgagtacga cttcgtgccc gagagcttcg   3000
```

```
accgggacaa aaccatcgcc ctgatcatga acagtagtgg cagtaccgga ttgcccaagg   3060
gcgtagccct accgcaccgc accgcttgtg tccgattcag tcatgcccgc gacccccatct  3120
tcggcaacca gatcatcccc gacaccgcta tcctcagcgt ggtgccattt caccacggct   3180
tcggcatgtt caccacgctg ggctacttga tctgcggctt tcgggtcgtg ctcatgtacc   3240
gcttcgagga ggagctattc ttgcgcagct tgcaagacta taagattcaa tctgccctgc   3300
tggtgcccac actatttagc ttcttcgcta agagcactct catcgacaag tacgacctaa   3360
gcaacttgca cgagatcgcc agcggcgggg cgccgctcag caaggaggta ggtgaggccg   3420
tggccaaacg cttccaccta ccaggcatcc gccaggggcta cggcctgaca gaaacaacca  3480
gcgccattct gatcacccccc gaaggggacg acaagcctgg cgcagtaggc aaggtggtgc   3540
ccttcttcga ggctaaggtg gtggacttgg acaccggtaa gacactgggt gtgaaccagc   3600
gcggcgagct gtgcgtccgt ggcccccatga tcatgagcgg ctacgttaac aaccccgagg   3660
ctacaaacgc tctcatcgac aaggacgct ggctgcacag cggcgacatc gcctactggg    3720
acgaggacga gcacttcttc atcgtggacc ggctgaagag cctgatcaaa tacaagggct   3780
accaggtagc cccagccgaa ctggaagca tcctgctgca acaccccaac atcttcgacg    3840
ccggggtcgc cggcctgccc gacgacgatg ccggcgagct gcccgccgca gtcgtcgtgc   3900
tggaacacgg taaaaccatg accgagaagg agatcgtgga ctatgtggcc agccaggtta   3960
caaccgccaa gaagctgcgc ggtggtgttg tgttcgtgga cgaggtgcct aaaggactga   4020
ccggcaagtt ggacgcccgc aagatccgcg agattctcat taaggccaag aagggcggca   4080
agatcgccgt gtaattcgaa acgagacgtc catcttgagc atctgacttc tggctaaata   4140
aaagatcttt attttcatta gatctgtgtg ttggtttttt gtgtgcgtcg agatccacgg   4200
ccgcaggaac ccctagtgat ggagttggcc actccctctc tgcgcgctcg ctcgctcact   4260
gaggccgggc gaccaaaggt cgcccgacgc ccgggcttg cccgggcggc ctcagtgagc    4320
gagcgagcgc gcagctgcct gcaggggcgc ctgatgcggt attttctcct tacgcatctg   4380
tgcggtattt cacaccgcat acgtcaaagc aaccatagta cgcgccctgt agcggcgcat   4440
taagcgcggc gggtgtggtg gttacgcgca gcgtgaccgc tacacttgcc agcgccctag   4500
cgcccgctcc tttcgctttc ttcccttcct tctcgccac gttcgccggc tttccccgtc    4560
aagctctaaa tcgggggctc cctttagggt tccgatttag tgctttacgg cacctcgacc   4620
ccaaaaaact tgatttgggt gatggttcac gtagtgggcc atcgccctga tagacggttt   4680
ttcgcccttt gacgttggag tccacgttct ttaatagtgg actcttgttc caaactggaa   4740
caacactcaa ccctatctcg ggctattctt ttgatttata agggattttg ccgatttcgg   4800
cctattggtt aaaaaatgag ctgatttaac aaaaatttaa cgcgaatttt aacaaaatat   4860
taacgtttac aattttatgg tgcactctca gtacaatctg ctctgatgcc gcatagttaa   4920
gccagccccg acacccgcca acacccgctg acgcgccctg acgggcttgt ctgctcccgg    4980
catccgctta cagacaagct gtgaccgtct ccgggagctg catgtgtcag aggttttcac   5040
cgtcatcacc gaaacgcgcg agacgaaagg gcctcgtgat acgcctattt ttataggtta   5100
atgtcatgat aataatggtt tcttagacgt caggtggcac ttttcgggga aatgtgcgcg   5160
gaaccccctat ttgtttattt ttctaaatac attcaaatat gtatccgctc atgagacaat   5220
aaccctgata aatgcttcaa taatattgaa aaaggaagag tatgagtatt caacatttcc   5280
gtgtcgccct tattcccttt tttgcggcat tttgccttcc tgtttttgct cacccagaaa   5340
cgctggtgaa agtaaaagat gctgaagatc agttgggtgc acgagtgggt tacatcgaac   5400
tggatctcaa cagcggtaag atccttgaga gttttcgccc cgaagaacgt tttccaatga   5460
tgagcacttt taaagttctg ctatgtggcg cggtattatc ccgtattgac gccgggcaag   5520
agcaactcgg tcgccgcata cactattctc agaatgactt ggttgagtac tcaccagtca   5580
cagaaaagca tcttacggat ggcatgacag taagagaatt atgcagtgct gccataacca   5640
tgagtgataa cactgcggcc aacttacttc tgacaacgat cggaggaccg aaggagctaa   5700
ccgctttttt gcacaacatg ggggatcatg taactcgcct tgatcgttgg gaaccggagc   5760
tgaatgaagc cataccaaac gacgagcgtg acaccacgat gcctgtagca atggcaacaa   5820
cgttgcgcaa actattaact ggcgaactac ttactctagc ttcccggcaa caattaatag   5880
actggatgga ggcggataaa gttgcaggac cacttctgcg ctcggccctt ccggctggct   5940
ggtttattgc tgataaatct ggagccggtg agcgtgggtc tcgcggtatc attgcagcac   6000
tggggccaga tggtaagccc tcccgtatcg tagttatcta cacgacgggg agtcaggcaa   6060
ctatggatga acgaaataga cagatcgctg agataggtgc ctcactgatt aagcattggt   6120
aactgtcaga ccaagtttac tcatatatac tttagattga tttaaaactt catttttaat   6180
ttaaaaggat ctaggtgaag atccttttg ataatctcat gaccaaaatc ccttaacgtg    6240
agttttcgtt ccactgagcg tcagaccccg tagaaaagat caaaggatct tcttgagatc   6300
ctttttttct gcgcgtaatc tgctgcttgc aaacaaaaaa accaccgcta ccagcggtgg   6360
tttgtttgcc ggatcaagag ctaccaactc tttttccgaa ggtaactggc ttcagcagag   6420
cgcagatacc aaatactgtc cttctagtgt agccgtagtt aggccaccac ttcaagaact   6480
ctgtagcacc gcctacatac ctcgctctgc taatcctgtt accatggct gctgccagtg    6540
gcgataagtc gtgtcttacc gggttggact caagacgata gttaccggat aaggcgcagc   6600
ggtcgggctg aacggggggt tcgtgcacac agcccagctt ggagcgaacg acctacaccg   6660
aactgagata cctacagcgt gagctatgag aaagcgccac gcttcccgaa gggagaaagg   6720
cggacaggta tccggtaagc ggcagggtcg aacaggaga gcgcacgagg gagcttccag    6780
ggggaaacgc ctggtatctt tatagtcctg tcgggtttcg ccacctctga cttgagcgtc   6840
gatttttgtg atgctcgtca ggggggcgga gcctatggaa aaacgccagc aacgcggcct   6900
ttttacggtt cctggccttt tgctggcctt ttgctcacat gt                      6942
```

```
SEQ ID NO: 113      moltype = DNA  length = 7138
FEATURE             Location/Qualifiers
misc_feature        1..7138
                    note = plasmid pAAVss-CRE21-SkSH4-hDES1.4kb-Luc2
source              1..7138
                    mol_type = other DNA
                    organism = synthetic construct
SEQUENCE: 113
acatgtcctg caggcagctg cgcgctcgct cgctcactga ggccgcccgg gcaaagcccg   60
ggcgtcgggc gacctttggt cgcccggcct cagtgagcga gcgagcgcgc agagaggggag  120
tggccaactc catcactagg ggttcctgcg gcccttttct tttctaatta ggtcagttac   180
ttcatgtctg ttttttcttt ttgacatggt ttcttctggc tttggcacca catatttcc    240
```

-continued

```
ccatatgtca ttgcctctgg agcttcatgt tgcaatagtt tttcaagggg aacggagagc  300
acattgctaa gggtgggggga tggcttttgc ctcttttgcc tgcccttttgc ttcagtgagt  360
gttcgtattt ctgttgggcc tagttctgtt tggttttgta gtcttcagag tcagttatgt  420
ttggactgaa agatacttaa gtaaaaataa tggcaagtca gagatatgtc tggcaaaggt  480
gcagcacatt tgttaaggtt actggtttat ttatctccct tgtctctatg gtgactaaat  540
ctgggtctgg gatttaatgg acttagtttt gacctcttgt aacatctcct aacttttccc  600
agcctctgat ttagaaagaa ttcattttca cttgaggaga gaaactggcg cgccacgcgt  660
ttctgagtcc tctaaggtcc ctcactccca actcagcccc atgtcctgtc aattcccact  720
cagtgtctga tctccttctc ctcacctttc ccatctcccg tttgacccaa gcttcctgga  780
ctctcctccc attccccttt ttggagtcct cctcctctcc cagaacccag taataagtag  840
gctcctccct ggcctggacc cccgtggtaa ccctataagg cgaggcagct gctgtctgag  900
gcagggaggg gctggtgtgg gaggctaagg gcagctgcta agtttagggt ggctccttct  960
ctcttcttag agacaacagg tggctggggc ctcagtgccc agaaaagaaa atgtcttaga  1020
ggtatcggca tgggcctgga ggagggggga cagggcaggg ggaggcatct tcctcaggac  1080
atcgggtcct agagggggtac ccaacggggtt acgacacacc tactagtaac ccctccagct  1140
ggtgatggca ggtctagggt aggaccagtg actggctcct aatcgagcac tctattttca  1200
gggtttgcat tccaaaaggg tcaggtccaa gagggacctg gagtgccaag tggaggtgta  1260
gaggcacggc cagtacccat ggagaatggt ggatgtcctt aggggttagc aagtgccgtg  1320
tgctaaggag ggggctttgg aggttgggca ggccctctgt ggggctccat ttttgtgggg  1380
gtgggggctg gagcattata gggggtggga agtgattggg gctgtcaccc tagccttcct  1440
tatctgacgc ccacccatgc ctcctcaggt acccctgcc ccacagct cctctcctgt  1500
gccttgtttc ccagccatgc gttctcctct ataaatacct gctctggtat ttggggttgg  1560
cagctgttgc tgccaggag atggttgggt tgacatgcgg ctcctgacaa aacacaaacc  1620
cctggtgtgt gtgggcgtgg gtggtgtgag taggggggatg aatcaggggag ggggcggggg  1680
acccagggggg caggagccac acaaagtctg tgcgggggtg ggagcgcaca tagcaattgg  1740
aaactgaaag cttatcagac cctttctgga aatcagccca ctgtttataa acttgaggcc  1800
ccaccctcga cagtaccggg gaggaagagg gcctgcacta gtccagaggg aaactgaggc  1860
tcagggctag ctcgcccata gacatacatg gcaggcaggc tttggccagg atccctccgc  1920
ctgccaggcg tctccctgcc ctcccttcct gcctagagac cccacccctc aagcctggct  1980
ggtctttgcc tgagacccaa acctcttcga cttcaagaga atatttagga acaaggtggt  2040
ttagggcctt tcctgggaac aggccttgac cctttaagaa atgacccaaa gtctctcctt  2100
gaccaaaaag gggaccctca aactaaaggg aagcctctct tctgctgtct ccctgaccc  2160
cactcccccc caccccagga cgaggagata accaggggctg aaagagggccc gcctgggggc  2220
tgcagacatg cttgctgcct gccctggcga aggattggca ggcttgcccg tcacaggacc  2280
cccgctggct gactcagggg cgcaggcctc ttgcggggga gctggcctcc ccgcccccac  2340
ggccacgggc cgcccttttcc tggcaggaca gcgggatctt gcagctgtca gggggagggga  2400
ggcggggggct gatgtcagga gggatacaaa tagtgccgac ggctgggggc cctgtctccc  2460
ctcgccgcat ccactctccg gccggccgcc tgcccgccgc ctcctccgtg cgcccgccag  2520
cctcgccgc gccgtcacct ctagaaagag gtaaggggttt aagggatggt tggttggtgg  2580
ggtattaatg tttaattacc tggagcacct gcctgaaatc actttttttc aggttggaag  2640
cttatggaag atgccaaaaa cattaagaag ggcccagccgc cattctaccc actcgaggac  2700
gggaccgccg gcgagcagct gcacaaagcc atgaagcgct acgccctggt gcccggcacc  2760
atcgcctttta ccgacgcaca tatcgaggtg gacattacct acgccgagta cttcgagatg  2820
agcgttcggc tggcagaagc tatgaagcgc tatgggctga atacaaacca tcggatcgtg  2880
gtgtgcagcg agaatagctt gcagttcttc atgcccgtgt tgggtgccct gttcatcggt  2940
gtggctgtgg ccccagctaa cgacatctac aacgagcgcg agctgctgaa cagcatgggc  3000
atcagccagc ccaccgtcgt attcgtgagc aagaaagggc tgcaaaagat cctcaacgtg  3060
caaaagaagc taccgatcat acaaaagatc atcatcatgg atagcaagac cgactaccag  3120
ggcttccaaa gcatgtacac cttcgtgact tcccatttgc cacccggctt caacgagtac  3180
gacttcgtgc ccgagagctt cgaccgggac aaaaccatcg ccctgatcat gaacagtagt  3240
ggcagtaccg gattgcccaa gggcgtagcc ctaccgcacc gcaccgcttg tgtccgattc  3300
agtcatgccc gcgacccat cttcggcaac cagatcatcc ccgacaccgc tatcctcagc  3360
gtggtgccat ttcaccacgg cttcggcatg ttcaccacgc tgggctactt gatctgcggc  3420
tttcgggtcg tgctcatgta ccgcttcgag gaggagctat tcttgcgcag cttgcaagac  3480
tataagattc aatctgccct gctggtgccc cacactattta gcttcttcgc taagagcact  3540
ctcatcgaca agtacgacct aagcaacttg cacgagatcg ccagcggcgg ggcgccgctc  3600
agcaaggagg taggtgaggc cgtggccaaa cgcttccacc taccaggcat ccgcagggc  3660
tacgcctga cagaaacaac cagcgccatt ctgatcaccc ccgaagggga cgacaagcct  3720
ggcgcagtag gcaaggtggt gcccttcttc gaggctaagg tggtggactt ggacaccggt  3780
aagacactgg gtgtgaacca gcgcggcgag ctgtgcgtcc gtggccccat gatcatgagc  3840
ggctacgtta acaacccga ggctacaaac gctctcatcg acaaggacgg ctggctgcac  3900
agcggcgaca tcgcctactg ggacgaggac gagcacttct tcatcgtgga ccggctgaag  3960
agcctgatca aatacaaggg ctaccaggta gccccagccg aactggagag catcctgctg  4020
caacacccca acatcttcga cgccggggtc gccggcgtgc ccgacgacga tgcccgggag  4080
ctgcccgccg cagtcgtcgt gctggaacac ggtaaaacca tgaccgagaa ggagatcgtg  4140
gactatgtgg ccagccaggt tacaaccgcc aagaagctgc gcggtggtgt tgtgttcgtg  4200
gacgaggtgc ctaaaggact gaccggcaag ttggacgccc gcaagatccg cgagattctc  4260
attaaggcca agaagggcgg caagatcgcc gtgtaattcg aaacgattcg tccatcttga  4320
gcatctgact tctggctaaa taaaagatct ttattttcat tagatctgtg tgttggtttt  4380
ttgtgtgcgt cgagatccac ggccgcagga accctagtg atggagttgg ccactccctc  4440
tctgcgcgct cgctcgctca ctgaggccgg gcgaccaaag gtcgcccgac gcccgggctt  4500
tgcccgggcg gcctcagtga gcgagcgagc gcgcagctgc ctgcaggggc gcctgatgcg  4560
gtatttttctc cttacgcatc tgtgcggtat ttcacaccgc atacgtcaaa gcaaccatag  4620
tacgcgccct gtagcggcgc attaagcgcg gcgggtgtgg tggttacgcg cagcgtgacc  4680
gctacacttg ccagcgccct agcgcccgct cctttcgctt tcttcccttc ctttctcgcc  4740
acgttcgccg gctttccccg tcaagctcta aatcggggggc tccctttagg gttccgattt  4800
agtgctttac ggcacctcga ccccaaaaaa cttgatttgg gtgatggttc acgtagtggg  4860
ccatcgccct gatagacggt ttttcgccct ttgacgttgg agtccacgtt ctttaatagt  4920
ggactcttgt tccaaactgg aacaacactc aaccctatct cgggctattc ttttgattta  4980
```

```
taagggattt tgccgatttc ggcctattgg ttaaaaaatg agctgattta acaaaaattt   5040
aacgcgaatt ttaacaaaat attaacgttt acaattttat ggtgcactct cagtacaatc   5100
tgctctgatg ccgcatagtt aagccagccc cgacacccgc caacaccgc tgacgcgccc    5160
tgacgggctt gtctgctccc ggcatccgct tacagacaag ctgtgaccgt ctccgggagc   5220
tgcatgtgtc agaggttttc accgtcatca ccgaaacgcg cgagacgaaa gggcctcgtg   5280
atacgcctat ttttataggt taatgtcatg ataataatgg tttcttagac gtcaggtggc   5340
acttttcggg gaaatgtgcg cggaacccct atttgtttat ttttctaaat acattcaaat   5400
atgtatccgc tcatgagaca ataaccctga taaatgcttc aataatattg aaaaaggaag   5460
agtatgagta ttcaacattt ccgtgtcgcc cttattccct tttttgcggc attttgcctt   5520
cctgtttttg ctcacccaga aacgctggtg aaagtaaaag atgctgaaga tcagttgggt   5580
gcacgagtgg gttacatcga actggatctc aacagcggta agatccttga gagttttcgc   5640
cccgaagaac gttttccaat gatgagcact tttaaagttc tgctatgtgg cgcggtatta   5700
tcccgtattg acgccgggca agagcaactc ggtcgccgca tacactattc tcagaatgac   5760
ttggttgagt actcaccagt cacagaaaag catcttacgg atggcatgac agtaagagaa   5820
ttatgcagtg ctgccataac catgagtgat aacactgcgg ccaacttact tctgacaacg   5880
atcggaggac cgaaggagct aaccgctttt ttgcacaaca tgggggatca tgtaactcgc   5940
cttgatcgtt gggaaccgga gctgaatgaa gccataccaa acgacgagcg tgacaccacg   6000
atgcctgtag caatggcaac aacgttgcgc aaactattaa ctggcgaact acttactcta   6060
gcttcccggc aacaattaat agactggatg gaggcggata aagttgcagg accacttctg   6120
cgctcggccc ttccggctgg ctggtttatt gctgataaat ctggagccgg tgagcgtggg   6180
tctcgcggta tcattgcagc actggggcca gatggtaagc cctcccgtat cgtagttatc   6240
tacacgacgg ggagtcaggc aactatggat gaacgaaata gacagatcgc tgagataggt   6300
gcctcactga ttaagcattg gtaactgtca gaccaagttt actcatatat actttagatt   6360
gatttaaaac ttcattttta atttaaaagg atctaggtga agatccttt tgataatctc    6420
atgaccaaaa tcccttaacg tgagttttcg ttccactgag cgtcagaccc cgtagaaaag   6480
atcaaaggat cttcttgaga tcctttttt ctgcgcgtaa tctgctgctt gcaaacaaaa    6540
aaaccaccgc taccagcggt ggtttgtttg ccggatcaag agctaccaac tctttttccg   6600
aaggtaactg gcttcagcag agcgcagata ccaaatactg tccttctagt gtagccgtag   6660
ttaggccacc acttcaagaa ctctgtagca ccgcctacat acctcgctct gctaatcctg   6720
ttaccagtgg ctgctgccag tggcgataag tcgtgtctta ccgggttgga ctcaagacga   6780
tagttaccgg ataaggcgca gcggtcgggc tgaacggggg gttcgtgcac acagcccagc   6840
ttggagcgaa cgacctacac cgaactgaga tacctacagc gtgagctatg agaaagcgcc   6900
acgcttcccg aagggagaaa ggcggacagg tatccggtaa gcggcaggt cggaacagga    6960
gagcgcacga gggagcttcc aggggggaaac gcctggtatc tttatagtcc tgtcgggttt   7020
cgccacctct gacttgagcg tcgatttttg tgatgctcgt caggggggcg gagcctatgg   7080
aaaaacgcca gcaacgcggc ctttttacgg ttcctggcct tttgctc                  7138
```

```
SEQ ID NO: 114        moltype = DNA   length = 7108
FEATURE               Location/Qualifiers
misc_feature         1..7108
                      note = plasmid pAAVss-CRE41-SkSH4-hDES1.4kb-Luc2
source               1..7108
                      mol_type = other DNA
                      organism = synthetic construct
SEQUENCE: 114
acatgtcctg caggcagctg cgcgctcgct cgctcactga ggccgcccgg gcaaagcccg    60
ggcgtcgggc gacctttggt cgcccggcct cagtgagcga gagcgcgc agagaggag      120
tggccaactc catcactagg ggttcctgcg gccctacaat aaatatataa ctttttaat    180
ttgacaaaaa ataattttga gtggttacaa aaagggacag gtgtggcttg gtaactagaa   240
aaacattccc agcctgggaa acaatctagt gagagcttgg aggcagaaga cagaactctg   300
attacattca aggagtttgc cagatggcaa cagataactg ccaatgttcg gttgcactat   360
aattattata cactctctgt cacttcagca agcgctcttt tcacaagaca agtggtgaca   420
gaatgttgta ttaagattac ccgttgctaa gcttatgtta aaatgaggaa atgaaatgga   480
aagtcttgtt ttggtaatgt ctctgggta tgaggaatgg agggaaaggt ttgactatga    540
gcataactgc atagagaatt ttgtttgttt atgcctttg ggaatgcatt attttgattg    600
accctaattg ggaattggcg cgccacgcgt ttctgagtcc tctaaggtcc ctcactccca   660
actcagcccc atgtcctgtc aattcccact cagtgtctga tctccttctc ctcacctttc   720
ccatctcccg tttgacccaa gcttcctgag ctctcctccc attcccctt ttggagtcct    780
cctcctctcc cagaacccag taataagtgg gctcctccct ggcctggacc ccgtggtaa    840
ccctataagg cgaggcagct gctgtctgag gcagggaggg gctggtgtgg gaggctaagg   900
gcagctgcta agtttagggt ggctccttct ctcttcttag agacaacagg tggctgggc    960
ctcagtgccc agaaaagaaa atgtcttaga ggtatcggca tgggcctgga ggagggggga   1020
cagggcaggg ggaggcatct tcctcaggac atcgggtcct agaggggtac ccaacgggtt   1080
acgacacacc tactagtaac ccctccagct ggtgatggca ggtctaggt aggaccagtg    1140
actggctcct aatcgagcac tctattttca gggtttgcat tccaaaaggg tcaggtccaa   1200
gagggacctg gagtgccaag tggaggtgta gaggcacggc cagtacccat ggagaatggt   1260
ggatgtcctt aggggttagc aagtgccgtg tgctaaggag ggggctttgg aggttgggca   1320
ggccctctgt ggggctccat ttttgtgggg gtgggggctg gagcattata gggggtggga   1380
agtgattggg gctgtcaccc tagccttcct tatctgacgc caccccatgc tcctcaggt    1440
accccctgcc ccccacagct cctctcctgt gccttgtttc ccagccatgc gttctcctct   1500
ataaataccc gctctggtat ttggggttgg cagctgttgc tgccaggag atggctgggt    1560
tgacatgcgc ctcctgacaa aacacaaacc cctggtgtgt gtgggcgtgg gtggtgtgag   1620
tagggggatg aatcagggag ggggcggggg acccaggggg caggagccac acaaagtctg   1680
tgcggggggtg ggagcgcaca tagcaattgg aaactgaaga cttatcagac cctttctgga   1740
aatcagccca ctgtttataa acttgaggcc ccaccctcga cagtaccggg gaggaagagg   1800
gcctgcacta gtccagaggg aaactgaggc tcagggctag ctcgcccata gacatacatg   1860
gcaggcaggc tttggccagg atccctccgc ctgccaggcg tctccctgcc ctccttcct    1920
gcctagagac ccccaccctc aagcctggct ggtcttgcc tgagacccaa acctcttcga     1980
cttcaagaga atatttagga acaaggtggt ttagggcctt tcctgggaac aggccttgac   2040
```

-continued

```
cctttaagaa atgacccaaa gtctctcctt gaccaaaaag gggaccctca aactaaaggg  2100
aagcctctct tctgctgtct cccctgaccc cactcccccc caccccagga cgaggagata  2160
accagggctg aaagaggccc gcctgggggc tgcagacatg cttgctgcct gccctggcga  2220
aggattggca ggcttgcccg tcacaggacc cccgctggct gactcagggg cgcaggcctc  2280
ttgcggggga gctggcctcc ccgcccccac ggccacgggc cgcccttttcc tggcaggaca  2340
gcgggatctt gcagctgtca ggggagggga ggcgggggct gatgtcagga gggatacaaa  2400
tagtgccgac ggctgggggc cctgtctccc ctcgccgcat ccactctccg gccggccgcc  2460
tgcccgccgc ctcctccgtg cgcccgccag cctcgcccgc gccgtcacct ctagaaagag  2520
gtaagggttt aagggatggt tggttggtgg ggtattaatg tttaattacc tggagcacct  2580
gcctgaaatc actttttttc aggttggaag cttatggaag atgccaaaaa cattaagaag  2640
ggcccagcgc cattctaccc actcgaggac gggaccgccg gcgagcagct gcacaaagcc  2700
atgaagcgct acgccctggt gcccggcacc atcgccttta ccgacgcaca tatcgaggtg  2760
gacattacct acgccgagta cttcgagatg agcgttcggc tggcagaagc tatgaagcgc  2820
tatgggctga atacaaacca tcggatcgtg gtgtgcaggc agaatagctt gcagttcttc  2880
atgcccgtgt tgggtgccct gttcatcggt gtggctgtgg ccccagctaa cgacatctac  2940
aacgagcgcg agctgctgaa cagcatgggc atcagccagc ccaccgtcgt attcgtgagc  3000
aagaaagggc tgcaaaagat cctcaacgtg caaaagaagc taccgatcat acaaaagatc  3060
atcatcatgg atagcaagac cgactaccag ggcttccaaa ggctgtacac cttcgtgact  3120
tcccatttgc cacccggctt caacgagtac gacttcgtgc ccgagagctt cgaccgggac  3180
aaaaccatcg ccctgatcat gaacagtagt ggcagtaccg gattgcccaa gggcgtagcc  3240
ctaccgcacc gcaccgcttg tgtccgattc agtcatgccc gcgaccccat cttcggcaac  3300
cagatcatcc ccgacaccgc tatcctcagc gtggtgccat ttcaccacgg cttcggcatg  3360
ttcaccacgc tgggctactt gatctgcggc tttcgggtcg tgctcatgta ccgcttcgag  3420
gaggagctat tcttgcgcag cttgcaagac tataagattc aatctgccct gctggtgccc  3480
acactattta gcttcttcgc taagagcact ctcatcgaca agtacgacct aagcaacttg  3540
cacgagatcg ccagcggcgg ggcgccgctc agcaaggagg taggtgaggc cgtggccaaa  3600
cgcttccacc taccaggcat ccgccagggc tacggcctga cagaaacaac cagcgccatt  3660
ctgatcaccc ccgaaggggga cgacaagcct ggcgcagtag gcaaggtggt gcccttcttc  3720
gaggctaagg tggtggactt ggacaccggt aagacactgg gtgtgaacca gcgcggcgag  3780
ctgtgcgtcc gtggccccat gatcatgagc ggctacgtta acaacccga ggctacaaac  3840
gctctcatcg acaaggacgg ctggctgcac agcggcgaca tcgcctactg ggacgaggac  3900
gagcacttct tcatcgtgga ccggctgaag agcctgatca aatacaaggg ctaccaggta  3960
gccccagccg aactggagag catcctgctg caacacccca acatcttcga cgccggggtc  4020
gccggcctgc ccgacgacga tgccggcgag ctgcccgccg cagtcgtcgt gctggaacac  4080
ggtaaaaacca tgaccgagaa ggagatcgtg gactatgtgg ccagccaggt tacaaccgcc  4140
aagaagctgc gcggtggtgt tgtgttcgtg gacgaggtgc ctaaaggact gaccggcaag  4200
ttggacgccc gcaagatccg cgagattctc attaaggcca agaagggcgg caagatcgcc  4260
gtgtaattcg aaacgagaag tccatcttga gcatctgact tctggctaaa taaaagatct  4320
ttatttttcat tagatctgtg tgttggtttt ttgtgtgcgat cgagatccac ggccgcagga  4380
accctagtg atggagttgg ccactccctc tctgcgcgct cgctcgctca ctgaggccgg  4440
gcgaccaaag gtcgcccgac gcccgggctt tgccgggggg gcctcagtga gcgagcgagc  4500
gcgcagctgc ctgcagggggc gcctgatgcg gtattttctc cttacgcatc tgtgcggtat  4560
ttcacaccgc atacgtcaaa gcaaccatag tacgcgccct gtagcggcgc attaagcgcg  4620
gcgggtgtgg tggttacgcg cagcgtgacc gctacacttg ccagcgccct agcgcccgct  4680
cctttcgctt tcttcccttc ctttctcgcc acgttcgccg gctttccccg tcaagctcta  4740
aatcgggggc tcccttagg gttccgattt agtgctttac ggcacctcga ccccaaaaa  4800
cttgatttgg gtgatggttc acgtagtggg ccatcgccct gatagacggt ttttcgccct  4860
ttgacgttgg agtccacgtt ctttaatagt ggactcttgt tccaaactgg aacaacactc  4920
aaccctatct cgggctattc ttttgattta taagggattt tgccgatttc ggcctattgg  4980
ttaaaaaatg agctgattta acaaaaattt aacgcgaatt ttaacaaaat attaacgttt  5040
acaattttat ggtgcactct cagtacaatc tgctctgatg ccgcatagtt aagccagccc  5100
cgacacccgc caacacccgc tgacgcgccc tgacgggctt gtctgctccc ggcatccgct  5160
tacagacaag ctgtgaccgt ctccgggagc tgcatgtgtc agaggttttc accgtcatca  5220
ccgaaacgcg cgagacgaaa gggcctcgtg atacgcctat ttttataggt taatgtcatg  5280
ataataatgg tttcttagac gtcaggtggc acttttcggg gaaatgtgcg cggaacccct  5340
atttgtttat ttttctaaat acattcaaat atgtatccgc tcatgagaca ataaccctga  5400
taaatgcttc aataatattg aaaaaggaag agtatgagta ttcaacattt ccgtgtcgcc  5460
cttattccct tttttgcggc attttgcctt cctgtttttg ctcacccaga aacgctggtg  5520
aaagtaaaag atgctgaaga tcagttgggt gcacgagtgg gttacatcga actggatctc  5580
aacagcggta agatccttga gagttttcgc cccgaagaac gttttccaat gatgagcact  5640
tttaaagttc tgctatgtgg cgcggtatta tcccgtattg acgccgggca agagcaactc  5700
ggtcgccgca tacactattc tcagaatgac ttggttgagt actcaccagt cacagaaaag  5760
catcttacgg atggcatgac agtaagagaa ttatgcagtg ctgccataac catgagtgat  5820
aacactgcgg ccaacttact tctgacaacg atcggaggac cgaaggagct aaccgctttt  5880
ttgcacaaca tgggggatca tgtaactcgc cttgatcgtt gggaaccgga gctgaatgaa  5940
gccataccaa acgacgagcg tgacaccacg atgcctgtag caatggcaac aacgttgcgc  6000
aaactattaa ctggcgaact acttactcta gcttcccggc aacaattaat agactggatg  6060
gaggcggata aagttgcagg accacttctg cgctcggccc ttccggctgg ctggtttatt  6120
gctgataaat ctggagccgg tgagcgtggg tctcgcggta tcattgcagc actggggcca  6180
gatggtaagc cctcccgtat cgtagttatc tacacgacgg ggagtcaggc aactatggat  6240
gaacgaaata gacagatcgc tgagataggg gcctcactga ttaagcattg gtaactgtca  6300
gaccaagttt actcatatat actttagatt gatttaaaac ttcattttta atttaaaagg  6360
atctaggtga agatccttttt tgataatctc atgaccaaaa tcccttaacg tgagttttcg  6420
ttccactgag cgtcagaccc cgtagaaaag atcaaaggat cttcttgaga tcctttttttc  6480
ctgcgcgtaa tctgctgctt gcaaacaaaa aaaccaccgc taccagcggt ggtttgtttg  6540
ccggatcaag agctaccaac tctttttttccg aaggtaactg gcttcagcag agcgcagata  6600
ccaaatactg tccttctagt gtagccgtag ttaggccacc acttcaagaa ctctgtagca  6660
ccgcctacat acctcgctct gctaatcctg ttaccagtgg ctgctgccag tggcgataag  6720
tcgtgtctta ccgggttgga ctcaagacga tagttaccgg ataaggcgca gcggtcgggc  6780
```

```
tgaacgggggg gttcgtgcac acagcccagc ttggagcgaa cgacctacac cgaactgaga  6840
tacctacagc gtgagctatg agaaagcgcc acgcttcccg aagggagaaa ggcggacagg  6900
tatccggtaa gcggcagggt cggaacagga gagcgcacga gggagcttcc aggggggaaac  6960
gcctggtatc tttatagtcc tgtcgggttt cgccacctct gacttgagcg tcgatttttg  7020
tgatgctcgt cagggggggcg gagcctatgg aaaaacgcca gcaacgcggc ctttttacgg  7080
ttcctggcct tttgctggcc ttttgctc                                    7108
```

```
SEQ ID NO: 115              moltype = DNA   length = 6990
FEATURE                     Location/Qualifiers
misc_feature                1..6990
                            note = plasmid pAAVss-CRE58-SkSH4-hDES1.4kb-Luc2
source                      1..6990
                            mol_type = other DNA
                            organism = synthetic construct
SEQUENCE: 115
cctgcaggca gctgcgcgct cgctcgctca ctgaggccgc ccgggcaaag cccgggcgtc   60
gggcgacctt tggtcgcccg gcctcagtga gcgagcgagc gcgcagagag ggagtggcca  120
actccatcac taggggttcc tgcggccccc ctcagcttca gcccccacct ccaggaggcc  180
ctacccacgc tcatgacctt gctattctgt gccttgtgtc ctgtagggag atggacagga  240
gacagctggg cttccaggcc acccaggcgg ggggctagcc gagggaagcc tgctggctct  300
cctgcttgct ctaatttctg gggctcccca aaccttggcc tcaggagact ggggatagga  360
ccggccttga aagtggggga agctttggag agccgggtgc tggttctta gtgagatggc  420
cagtgaaggc tgtggtgccc cgaggtaagc agggcctgat cccctcctaa tcttccagca  480
gcaactggtg ctgcgcgcc acgcgtttct gagtcctcta aggtccctca ctcccaactc  540
agccccatgt cctgtcaatt cccactcagt gtctgatctc cttctcctca cctttcccat  600
ctcccgtttg acccaagctt cctgagctct cctcccattc ccctttttgg agtcctcctc  660
ctctcccagaa acccagtaat aagtgggctc ctccctggcc tggaccccccg tggtaaccct  720
ataaggcgag gcagctgctg tctgaggcag ggagggggctg gtgtgggagg ctaagggcag  780
ctgctaagtt tagggtggct ccttctctct tcttagagac aacaggtggc tggggcctca  840
gtgcccagaa aagaaaatgt cttagaggta tcggcatggg cctggaggag ggggggacagg  900
gcaggggggag gcatcttcct caggacatcg ggtcctagga gggtacccaa cgggttacga  960
cacacctact agtaacccct ccagctggtg atggcaggtc tagggtagga ccagtgactg  1020
gctcctaatc gagcactcta ttttcagggt ttgcattcca aaagggtcag gtccaagagg  1080
gacctggagt gccaagtgga ggtgtagagg cacggccagt acccatggag aatggtggat  1140
gtccttaggg gttagcaagt gccgtgtgct aaggaggggg ctttggaggt tgggcaggcc  1200
ctctgtgggg ctccattttt gtgggggtgg gggctggagc attataggg gtgggaagtg  1260
attggggctg tcaccctagc cttccttatc tgacgcccac ccatgcctcc tcaggtaccc  1320
cctgccccc acagctcctc tcctgtgcct tgtttcccag ccatgcgttc tcctctataa  1380
ataccgctc tggtatttgg ggttggcagc tgttgctgcc agggagatgg ttggggttgac  1440
atgcggctcc tgacaaaaca caaacccctg gtgtgtgtgg gcgtgggtgg tgtgagtagg  1500
gggatgaatc agggagggggg cggggggaccc aggggggcagg agccacacaa agtctgtgcg  1560
gggggtggggag cgcacatagc aattggaaac tgaaagctta tcagacccctt tctggaaatc  1620
agcccactgt ttataaactt gaggccccac cctcgacagt accggggagg aagagggcct  1680
gcactagtcc agaggggaaac tgaggctcag ggctagctcg cccatagaca tacatggcag  1740
gcaggcttttg gccaggatcc ctccgcctgc caggcgtctc cctgccctcc cttcctgcct  1800
agagacccccc accctcaagc ctggctggtc tttgcctgag acccaaacct cttcgacttc  1860
aagagaatat ttaggaacaa ggtggtttag ggccttttcct gggaacaggc cttgaccctt  1920
taagaaatga cccaaagtct ctccttgacc aaaaagggga ccctcaaact aaagggaagc  1980
ctctcttctg ctgtctcccc tgaccccact cccccccacc ccaggacgag gagataacca  2040
gggctgaaag aggcccgcct gggggctgca gacatgcttg ctgcctgccc tggcgaagga  2100
ttggcaggct tgcccgtcac aggacccccg ctggctgact caggggcgca ggcctcttga  2160
ggggggagctg gcctccccgc ccccacggcc acgggccgcc ctttcctggc aggacagcgg  2220
gatcttgcag ctgtcagggg aggggaggcg ggggctgatg tcaggaggga tacaaatagt  2280
gccgacggct ggggggccctg tctcccctcg ccgcatccac tctccggccg gccgcctgcc  2340
cgccgcctcc tccgtgcgcc cgccagcctc gcccgcgccg tcacctctag aaagaggtaa  2400
gggtttaagg gatggttggt tggtggggta ttaatgttta attacctgga gcacctgcct  2460
gaaatcactt tttttcaggt tggaagctta tggaagatgc caaaaacatt aagaagggcc  2520
cagcgccatt ctacccactc gaggacggga ccgccggcga gcagctgcac aaagccatga  2580
agcgctacgc cctggtgccc ggcaccatcg cctttaccga cgcacatatc gaggtggaca  2640
ttacctacgc cgagtacttc gagatgagcg ttcggctggc agaagctatg aagcgctatg  2700
ggctgaatac aaaccatcgg atcgtggtgt gcagcgagaa tagcttgcag ttcttcatgc  2760
ccgtgttggg tgccctgttc atcggtgtgg ctgtggcccc agctaacgac atctacaacg  2820
agcgcgagct gctgaacagc atgggcatca gccagcccac cgtcgtattc gtgagcaaga  2880
aagggctgca aaagatcctc aacgtgcaaa agaagctacc gatcatacaa aagatcatca  2940
tcatggatag caagaccgac taccaggggct tccaaagcat gtacaccttc gtgacttccc  3000
atttgccacc cggcttcaac gagtacgact tcgtgcccga gagcttcgac cgggacaaaa  3060
ccatcgccct gatcatgaac agtagtggca gtaccggatt gcccaagggc gtagccctac  3120
cgcaccgcac cgcttgtgtc cgattcagtc atgcccgcga cccatcttc ggcaaccaga  3180
tcatccccga caccgctatc ctcagcgtgg tgccatttca ccacggcttc ggcatgttca  3240
ccacgctggg ctacttgatc tgcggctttc gggtcgtgct catgtaccgc ttcgaggagg  3300
agctattctt gcgcagcttg caagactata agattcaatc tgccctgctg gtgcccacac  3360
tatttagctt cttcgctaag agcactctca tcgacaagta cgacctaagc aacttgcacg  3420
agatcgccag cggcggggcg ccgctcagca aggaggtagg tgaggccgtg gccaaacgct  3480
tccacctacc aggcatccgc caggcctacg gcctgacaga aacaaccagc gccattctga  3540
tcaccccccga aggggacgac aagcctggcg cagtaggcaa ggtggtgccc ttcttcgagg  3600
ctaaggtggt ggacttggac accggtaaga cactgggtgt gaaccagcgc ggcgagctgt  3660
gcgtccgtgg ccccatgatc atgagcggct acgttaacaa ccccgaggct acaaacgctc  3720
tcatcgacaa ggacggctgg ctgcacagcg gcgacatcgc ctactgggac gaggacgagc  3780
acttcttcat cgtggaccgg ctgaagagcc tgatcaaata caagggctac caggtagccc  3840
```

```
cagccgaact ggagagcatc ctgctgcaac accccaacat cttcgacgcc ggggtcgccg   3900
gcctgcccga cgacgatgcc ggcgagctgc ccgccgcagt cgtcgtgctg gaacacggta   3960
aaaccatgac cgagaaggag atcgtggact atgtggccag ccaggttaca accgccaaga   4020
agctgcgcgg tggtgttgtg ttcgtggacg aggtgcctaa aggactgacc ggcaagttgg   4080
acgccgcaa gatccgcgag attctcatta aggccaagaa gggcggcaag atcgccgtgt   4140
aattcgaaac gaattgtcca tcttgagcat ctgacttctg gctaaataaa agatctttat   4200
tttcattaga tctgtgtgtt ggttttttgt gtgcgtcgag atccacggcc gcaggaaccc   4260
ctagtgatgg agttggccac tccctctctg cgcgctcgct cgctcactga ggccgggcga   4320
ccaaaggtcg cccgacgccc gggctttgcc cgggcggcct cagtgagcga gcgagcgcgc   4380
agctgcctgc aggggcgcct gatgcggtat tttctcctta cgcatctgtg cggtatttca   4440
caccgcatac gtcaaagcaa ccatagtacg cgccctgtag cggcgcatta agcgcggcgg   4500
gtgtggtggt tacgcgcagc gtgaccgcta cacttgccag cgccctagcg cccgctcctt   4560
tcgctttctt cccttccttt ctcgccacgt tcgccggctt tccccgtcaa gctctaaatc   4620
gggggctccc tttagggttc cgatttagtg ctttacggca cctcgacccc aaaaaacttg   4680
atttgggtga tggttcacgt agtgggccat cgccctgata cacggttttt cgccctttga   4740
cgttggagtc cacgttcttt aatagtggac tcttgttcca aactggaaca acactcaacc   4800
ctatctcggg ctattctttt gatttataag ggattttgcc gatttcggcc tattggttaa   4860
aaaatgagct gatttaacaa aaatttaacg caatttttaa caaaatatta acgtttacaa   4920
ttttatggtg cactccagt acaatctgct ctgatgccgc atagttaagc cagccccgac   4980
acccgccaac acccgctgac gcgccctgac gggcttgtct gctcccggca tccgcttaca   5040
gacaagctgt gaccgtctcc gggagctgca tgtgtcagag gttttcaccg tcatcaccga   5100
aacgcgcgag acgaaagggc ctcgtgatac gcctattttt ataggttaat gtcatgataa   5160
taatggtttc ttagacgtca ggtggcactt ttcggggaaa tgtgcgcgga acccctattt   5220
gtttattttt ctaaatacat tcaaatatgt atccgctcat gagacaataa ccctgataaa   5280
tgcttcaata atattgaaaa aggaagagta tgagtattca acatttccgt gtcgcccta   5340
ttccctttt tgcggcattt tgccttcctg ttttgctca cccagaaacg ctggtgaaag   5400
taaaagatgc tgaagatcag ttgggtgcac gagtgggtta catcgaactg gatctcaaca   5460
gcggtaagat ccttgagagt tttcgccccg aagaacgttt tccaatgatg agcacttta   5520
aagttctgct atgtggcgcg gtattatccc gtattgacgc cgggcaagag caactcggtc   5580
gccgcataca ctattctcag aatgacttgg ttgagtactc accagtcaca gaaaagcatc   5640
ttacggatgg catgacagta agagaattat gcagtgctgc cataaccatg agtgataaca   5700
ctgcggccaa cttacttctg acaacgatcg gaggaccgaa ggagctaacc gcttttttgc   5760
acaacatggg ggatcatgta actcgccttg atcgttggga accggagctg aatgaagcca   5820
taccaaacga cgagcgtgac accacgatgc ctgtagcaat ggcaacaacg ttgcgcaaac   5880
tattaactgg cgaactactt actctagctt cccggcaaca attaatagac tggatggagg   5940
cggataaagt tgcaggacca cttctgcgct cggcccttcc ggctggctgg tttattgctg   6000
ataaatctgg agccggtgag cgtgggtctc gcggtatcat tgcagcactg gggccagatg   6060
gtaagccctc ccgtatcgta gttatctaca cgacggggag tcaggcaact atggatgaac   6120
gaaatagaca gatcgctgag ataggtgcct cactgattaa gcattggtaa ctgtcagacc   6180
aagtttactc atatatactt tagattgatt taaaacttca tttttaattt aaaaggatct   6240
aggtgaagat cctttttgat aatctcatga ccaaaatccc ttaacgtgag ttttcgttcc   6300
actgagcgtc agacccgta gaaaagatca aggatcttc ttgagatcct ttttttctg   6360
gcgtaatctg ctgcttgcaa acaaaaaaac caccgctacc agcggtggtt tgtttgccgg   6420
atcaagagct accaactctt tttccgaagg taactggctt cagcagagcg cagataccaa   6480
atactgtcct tctagtgtag ccgtagttag gccaccactt caagaactct gtagcaccgc   6540
ctacatacct cgctctgcta atcctgttac cagtggctgc tgccagtggc gataagtcgt   6600
gtcttaccgg gttggactca agacgatagt taccggataa ggcgcagcgg tcgggctgaa   6660
cggggggttc gtgcacacag cccagcttgg agcgaacgac ctacaccgaa ctgagatacc   6720
tacagcgtga gctatgagaa agcgccacgc ttcccgaagg gagaaaggcg gacaggtatc   6780
cggtaagcgg cagggtcgga acaggagagc gcacgaggga gcttccaggg ggaaacgcct   6840
ggtatcttta tagtcctgtc gggtttcgcc acctctgact tgagcgtcga ttttttgtgat   6900
gctcgtcagg ggggcggagc ctatggaaaa acgccagcaa cgcggccttt ttacggttcc   6960
tggccttttg ctggcctttt gctcacatgt                                    6990
```

```
SEQ ID NO: 116          moltype = DNA   length = 6865
FEATURE                 Location/Qualifiers
misc_feature            1..6865
                        note = plasmid pAAVss-CRE59-SkSH4-hDES1.4kb-Luc2
source                  1..6865
                        mol_type = other DNA
                        organism = synthetic construct
SEQUENCE: 116
cctgcaggca gctgcgcgct cgctcgctca ctgaggccgc ccgggcaaag cccggggcgtc   60
gggcgacctt tggtcgcccg gcctcagtga gcgagcgagc gcgcagaggg aggcgtcca   120
actccatcac taggggttcc tgcggccctc ctccagcagc tgccctggtg gtaaccaaga   180
gacgcccca tcctggagca ggggtgggga ggggcagctc agagcagctg cttctctgag   240
gaagctgaca ccaaggccag cattcagcaa caacttgtgg ctttgcaccc agcgccgggg   300
tccccgccca cctggctccc tgctgtccct cttcccact gctgctcgga cttccctctg   360
accctggggc gcgccacgcg tttctgagtc tctaaggtc ctcactccc aactcagccc   420
catgtcctgt caattcccac tcagtgtctg atctccttct cctcaccttt cccatctccc   480
gtttgaccca agcttcctga gctctcctcc cattcccctt tttggagtcc tcctcctctc   540
ccagaaccca gtaataagtg ggctcctccc tggcctggac ccccgtggta accctataag   600
gcgaggcagc tgctgtctga ggcagggagg ggctggtgtg ggaggctaag ggcagctgct   660
aagtttaggg tggctccttc tctcttctta gagacaacag gtggctgggg cctcagtgcc   720
cagaaaagaa aatgtcttag aggtatcggc atgggcctgg aggaggggg acagggcagg   780
gggaggcatc ttcctcagga catcgggtcc tagaggggta cccaacgggt tacgacacac   840
ctactagtaa cccctccagc tggtgatggc aggtctaggg taggaccagt gactggctcc   900
taatcgagca ctctattttc agggtttgca ttccaaaagg gtcaggtcca agagggacct   960
ggagtgccaa gtggaggtgt agaggcacgg ccagtaccca tggagaatgg tggatgtcct   1020
```

-continued

```
tagggggttag caagtgccgt gtgctaagga gggggctttg gaggttgggc aggccctctg    1080
tggggctcca tttttgtggg ggtgggggct ggagcattat aggggggtggg aagtgattgg    1140
ggctgtcacc ctagccttcc ttatctgacg cccacccatg cctcctcagg tacccccctgc    1200
cccccacagc tcctctcctg tgccttgttt cccagccatg cgttctcctc tataaatacc     1260
cgctctggta tttgggggttg gcagctgttg ctgccaggga gatggttggg ttgacatgcg    1320
gctcctgaca aaacacaaac ccctggtgtg tgtgggcgtg ggtggtgtga gtaggggggat    1380
gaatcaggga gggggcgggg gacccagggg gcaggagcca cacaaagtct gtgcggggggt    1440
gggagcgcac atagcaattg gaaactgaaa gcttatcaga ccctttctgg aaatcagccc     1500
actgtttata aacttgaggc cccacctcg acagtaccgg ggaggaagag ggcctgcact      1560
agtccagagg gaaactgagg ctcagggcta gctcgcccat agacatacat ggcaggcagg     1620
ctttggccag gatccctccg cctgccaggc gtctccctgc cctcccttcc tgcctagaga     1680
cccccaccct caagcctggc tggtctttgc ctgagaccca aacctcttcg acttcaagag     1740
aatatttagg aacaaggtgg tttagggcct ttcctgggaa caggccttga cccttttaaga    1800
aatgacccaa agtctctcct tgaccaaaaa ggggaccctc aaactaaagg gaagcctctc     1860
ttctgctgtc tcccctgacc ccactccccc ccacccagg acgaggagat aaccagggct      1920
gaaagaggcc cgcctggggg ctgcagacat gcttgctgcc tgccctggcg aaggattggc     1980
aggcttgccc gtcacaggac ccccgctggc tgactcaggg gcgcaggcct cttgcggggg     2040
agctggcctc cccgcccca cggccacggg ccgcccttc ctggcaggac agcgggatct       2100
tgcagctgtc agggggaggg aggcgggggc tgatgtcagg agggatacaa atagtgccga     2160
cggctggggg ccctgtctcc cctcgccgca tccactctcc ggccggccgc ctgcccgccg     2220
cctcctccgt gcgcccgcca gcctcgcccg cgccgtcacc tctagaaaga ggtaagggtt     2280
taagggatgg ttggttggtg gggtattaat gtttaattac ctggagcacc tgcctgaaat     2340
cactttttt caggttggaa gcttatggaa gatgccaaaa acattaagaa gggcccagcg      2400
ccattctacc cactcgagga cgggaccgcc ggcgagcagc tgcacaaagc catgaagcgc     2460
tacgccctg tgcccggcac catcgccttt accgacgcac atatcgaggt ggacattacc      2520
tacgccgagt acttcgagat gagcgttcgg ctggcagaag ctatgaagcg ctatggcgtc    2580
aatacaaacc atcggatcgt ggtgtgcagc gagaatagct tgcagttctt catgcccgtg     2640
ttgggtgccc tgttcatcgg tgtggctgtg gccccagcta acgacatcta caacgagcgc     2700
gagctgctga acagcatggg catcagccag cccaccgtcg tattcgtgag caagaaaggg     2760
ctgcaaaaga tcctcaacgt gcaaaagaag ctaccgatca tacaaaagat catcatcatg     2820
gatagcaaga ccgactacca gggcttccaa agcatgtaca ccttcgtgac ttcccatttg     2880
ccacccggct tcaacgagta cgacttcgtg cccgagagct tcgaccggga caaaaccatc     2940
gccctgatca tgaacagtag tggcagtacc ggattgccca agggcgtagc cctaccgcac     3000
cgcaccgctt gtgtccgatt cagtcatgcc cgcgaccca tcttcggcaa ccagatcatc      3060
cccgacaccg ctatcctcag cgtggtgcca tttcaccacg gcttcggcat gttcaccacg     3120
ctgggctact tgatctgcgg cttttcgggtc gtgctcatgt accgcttcga ggaggagcta     3180
ttcttgcgca gcttgcaaga ctataagatt caatctgccc tgctggtgcc cacactattt     3240
agcttcttcg ctaagagcac tctcatcgac aagtacgacc taagcaactt gcacgagatc     3300
gccagcgacg gggcgccgct cagcaaggag gtaggtgagg ccgtggccaa acgcttccac     3360
ctaccaggca tccgccaggg ctacggcctg acagaaacaa ccagcgccat tctgatcacc     3420
cccgaagggg acgacaagcc tggcgcagta ggcaaggtgg tgcccttctt cgaggctaag     3480
gtggtggact tggacaccgg taagacactg ggtgtgaacc agcgcggcga gctgtgcgtc     3540
cgtggcccca tgatcatgag cggctacgtt aacaacccg aggctacaaa cgctctcatc      3600
gacaaggacg gctggctgca cagcggcgac atcgcctact gggacgagga cgagcacttc     3660
ttcatcgtgg accggctgaa gagcctgatc aaatacaagg gctaccaggt agccccagcc     3720
gaactggaga gcatcctgct gcaacacccc aacatcttcg acgccgggt cgccggcctg      3780
cccgacgacg atgccggcga gctgcccgcc gcagtcgtcg tgctggaaca cggtaaaacc     3840
atgaccgaga aggagatcgt ggactatgtg gccagccagg ttacaaccgc caagaagctg     3900
cgcggtggtg ttgtgttcgt ggacgaggtg cctaaaggac tgaccggcaa gttggacgcc     3960
cgcaagatcc gcgagattct cattaaggcc aagaagggcg gcaagatcgc cgtgtaattc     4020
gaaacgaatc gtccatcttg agcatctgac ttctggctaa ataaaagatc tttatttca     4080
ttagatctgt gtgttggttt tttgtgtgcg tcgagatcca cggccgcagg aacccctagt     4140
gatggagttg gccactccct ctctgcgcgc tcgctcgctc actgaggccg ggcgaccaaa     4200
ggtcgcccga cgcccgggct ttgcccgggc ggcctcagtg agcgagcgag cgcgcagctg     4260
cctgcagggg cgcctgatgc ggtattttct ccttacgcat ctgtgcggta tttcacaccg     4320
catacgtcaa agcaaccata gtacgcgccc tgtagcggcg cattaagcgc ggcgggtgtg    4380
gtggttacgc gcagcgtgac cgctacactt gccagcgccc tagcgcccgc tcctttcgct     4440
ttcttccctt cctttctcgc cacgttcgcc ggctttcccc gtcaagctct aaatcgggggg    4500
ctcccttag ggttccgatt tagtgcttta cggcacctcg accccaaaaa acttgattttg     4560
ggtgatggtt cacgtagtgg gccatcgccc tgatagacgg ttttttcgccc tttgacgttg    4620
gagtccacgt tctttaatag tggactcttg ttccaaactg gaacaacact caaccctatc     4680
tcgggctatt cttttgattt ataagggatt ttgccgattt cggcctattg gttaaaaaat     4740
gagctgattt aacaaaaatt taacgcgaat tttaacaaa tattaacgtt tacaatttta     4800
tggtgcactc tcagtacaat ctgctctgat gccgcatagt taagccagcc ccgacacccg     4860
ccaacacccg ctgacgcgcc ctgacgggct tgtctgctcc cggcatccgc ttacagacaa     4920
gctgtgaccg tctccgggag ctgcatgtgt cagaggtttt caccgtcatc accgaaacgc     4980
gcgagacgaa agggcctcgt gatacgccta ttttttatagg ttaatgtcat gataataatg    5040
gtttcttaga cgtcaggtgg cactttttcgg ggaaatgtgc gcggaacccc tatttgttta    5100
tttttctaaa tacattcaaa tatgtatccg ctcatgagac aataaccctg ataaatgctt     5160
caataatatt gaaaaaggaa gagtatgagt attcaacatt tccgtgtcgc ccttattccc     5220
tttttttgcgg cattttgcct tcctgttttt gctcacccag aaacgctggt gaaagtaaaa    5280
gatgctgaag atcagttggg tgcacgagtg ggttacatcg aactggatct caacagcggt     5340
aagatccttg agagttttcg ccccgaagaa cgttttccaa tgatgagcac ttttaaagtt     5400
ctgctatgtg gcgcggtatt atcccgtatt gacgccgggc aagagcaact cggtcgccgc     5460
atacactatt ctcagaatga cttggttgag tactcaccag tcacagaaaa gcatcttacg     5520
gatggcatga cagtaagaga attatgcagt gctgccataa ccatgagtga taacactgcg     5580
gccaacttac ttctgacaac gatcggagga ccgaaggagc taaccgcttt tttgcacaac     5640
atgggggatc atgtaactcg ccttgatcgt tgggaaccgg agctgaatga agccatacca     5700
aacgacgagc gtgacaccac gatgcctgta gcaatggcaa caacgttgcg caaactatta     5760
```

-continued

```
actggcgaac tacttactct agcttcccgg caacaattaa tagactggat ggaggcggat 5820
aaagttgcag gaccacttct gcgctcggcc cttccggctg gctggtttat tgctgataaa 5880
tctggagccg gtgagcgtgg gtctcgcggt atcattgcag cactgggggcc agatggtaag 5940
ccctcccgta tcgtagttat ctacacgacg gggagtcagg caactatgga tgaacgaaat 6000
agacagatcg ctgagatagg tgcctcactg attaagcatt ggtaactgtc agaccaagtt 6060
tactcatata tactttagat tgatttaaaa cttcattttt aatttaaaag gatctaggtg 6120
aagatccttt ttgataatct catgaccaaa atcccttaac gtgagttttc gttccactga 6180
gcgtcagacc ccgtagaaaa gatcaaagga tcttcttgag atcctttttt tctgcgcgta 6240
atctgctgct tgcaaacaaa aaaaccaccg ctaccagcgg tggtttgttt gccggatcaa 6300
gagctaccaa ctcttttttcc gaaggtaact ggcttcagca gagcgcagat accaaatact 6360
gtccttctag tgtagccgta gttaggccac cacttcaaga actctgtagc accgcctaca 6420
tacctcgctc tgctaatcct gttaccagtg gctgctgcca gtggcgataa gtcgtgtctt 6480
accgggttgg actcaagacg atagttaccg gataaggcgc agcggtcggg ctgaacgggg 6540
ggttcgtgca cacagcccag cttggagcga acgacctaca ccgaactgag atacctacag 6600
cgtgagctat gagaaagcgc cacgcttccc gaagggagaa aggcggacag gtatccggta 6660
agcggcaggg tcggaacagg agagcgcacg agggagcttc caggggggaaa cgcctggtat 6720
ctttatagtc ctgtcgggtt tcgccacctc tgacttgagc gtcgattttt gtgatgctcg 6780
tcaggggggc ggagcctatg gaaaaacgcc agcaacgcgg cctttttacg gttcctggcc 6840
ttttgctggc cttttgctca catgt 6865
```

SEQ ID NO: 117 moltype = DNA length = 7308
FEATURE Location/Qualifiers
misc_feature 1..7308
  note = plasmid pAAVss-CRE60-SkSH4-hDES1.4kb-Luc2
source 1..7308
  mol_type = other DNA
  organism = synthetic construct
SEQUENCE: 117

```
acatgtcctg caggcagctg cgcgctcgct cgctcactga ggccgcccgg gcaaagcccg 60
ggcgtcgggc gacctttggt cgcccgggcct cagtgagcga gcgagcgcgc agagagggag 120
tggccaactc catcactagg ggttcctgcg gcccctttgct ccctgggagg gcctggccct 180
gtgggcattt gagtttataa caccacccccc attgtggcac accctccac cccgtaaaac 240
acaggctctg ctcttggaat cagtcttcct gatctgtggc tgtgccctcc aacagagggc 300
accccgtgggc ttcccagctc tggggggtagt gggtgccaac aaggagggggc ctggggctga 360
agaatcccac ccgctgagct cggccttctc ccttcecccac tgtccagctc cgcctttcag 420
catcctgcct cactccccgc ccaggcagca aggagcccac accctcatgc ccctcagctt 480
cagcccccac ctccaggagg ccctacccac gctcatgacc ttgctattct gggccttgtg 540
tcctgtaggg agatggacag gagacagctg ggcttccagg ccacccaggc gggggggctag 600
ccgagggaag cctgctggct ctcctgcttg ctctaatttc tggggctccc caaaccttag 660
cctcaggaga ctggggatag gaccggcctt gaaagtgggg gaagctttgg agagccgggt 720
gctgggttct tagtgagatg gccagtgaag gctgtggtgc cccgaggtaa gcagggcctg 780
atccctcct aatcttccag cagcaactgg tgctctggcg cgccacgcgt ttctgagtcc 840
tctaaggtcc ctcactccca actcagcccc atgtcctgtc aattcccact cagtgtctga 900
tctccttctc ctcacctttc ccatctcccg tttgacccaa gcttcctgag ctctcctccc 960
attcccctt ttggagtcct cctcctctcc cagaacccag taataagtgg gctcctccct 1020
ggcctggacc cccgtggtaa ccctataagg cgaggcagct gctgtctgag gcagggaggg 1080
gctggtgtgg gaggctaagg gcagctgcta agtttagggt ggctccttct ctcttcttag 1140
agacaacagg tggctggggc ctcagtgccc agaaaagaaa atgtcttaga ggtatcggca 1200
tgggcctgga ggaggggggga cagggcaggg ggaggcatct tcctcaggac atcgggtcct 1260
agaggggtac ccaacgggtt acgacacacc tactagtaac ccctccagct ggtgatggca 1320
ggtctagggt aggaccagtg actggctcct aatcgagcac tctattttca gggtttgcat 1380
tccaaaaggg tcaggtccaa gagggacctg gagtgccaag tggaggtgta gaggcacggc 1440
cagtacccat ggagaatggt ggatgtcctt aggggttagc aagtgccgtg tgctaaggag 1500
ggggctttgg aggttgggca ggccctctgt ggggctccat ttttgtgggg gtggggggctg 1560
gagcattata gggggtggga agtgattggg gctgtcaccc tagccttcct tatctgacgc 1620
ccacccatgc ctcctcaggt accccctgcc ccccacagct cctctcctgt gccttgtttc 1680
ccagccatgc gttctcctct ataaataccc gctctggtat ttggggttgg cagctgttgc 1740
tgccaggggag atggttgggt tgacatgcgc ctcctgacaa aacacaaacc cctggtgtgt 1800
gtgggcgtgg gtggtgtgag taggggggatg aatcaggggag ggggcggggg acccaggggg 1860
caggagccac acaaagtctg tgcgggggtg ggagcgccac tagcaattgg aaactgaaag 1920
cttatcagac cctttctgga aatcagccca ctgtttataa acttgaggcc ccaccctcga 1980
cagtaccggg gaggaagagg gcctgcacta gtccagaggg aaactgaggc tcagggctag 2040
ctcgcccata gacatacatg gcaggcaggc tttggccagg atccctccgc ctgccaggcg 2100
tctccctgcc ctcccttcct gcctagagac ccccaccctc aagcctgcct ggtctttgcc 2160
tgagacccaa acctcttcga cttcaagaga atatttagga acaaggtggt ttagggcctt 2220
tcctgggaac aggccttgac cctttaagaa atgacccaaa gtctctctt gaccaaaaag 2280
gggaccctca aactaaaggg aagcctctct tctgctgtct cccctgaccc cactcccccc 2340
caccccagga cgaggagata accagggctg aaagaggccc gcctgggggc tgcagacatg 2400
cttgctgcct gccctggcga aggattggca ggctgcccg tcacaggacc ccgcgctggct 2460
gactcaggggg cgcaggcctc ttgcggggga gctggcctcc ccgccccac ggccacgggc 2520
cgcccttttcc tggcaggaca gcgggatctt gcagctgtca ggggagggga ggcgggggct 2580
gatgtcagga gggatacaaa tagtgccgac ggctgggggc cctgtctccc ctcgccgcat 2640
ccactctccg gccggccgcc tgcccgccgc ctcctccgtg cgcccgccag cctcgcccgc 2700
gccgtcacct ctagaaagag gtaagggttt aagggatggt tggttggtgg ggtattaatg 2760
tttaattacc tggagcacct gcctgaaatc acttttttttc aggttggaag cttatggaag 2820
atgccaaaaa cattaagaag ggcccagcgc cattctaccc actcgaggac gggaccgccg 2880
gcgagcagc gcacaaagcc atgaagcgct acgccctggt gccggcacc atcgccttta 2940
ccgacgcaca tatcgaggtg gacattacct acgccgagta cttcgagatg agcgttcggc 3000
tggcagaagc tatgaagcgc tatgggctga atacaaacca tcggatcgtg gtgtgcagcg 3060
```

-continued

```
agaatagctt gcagttcttc atgcccgtgt tgggtgccct gttcatcggt gtggctgtgg   3120
ccccagctaa cgacatctac aacgagcgcg agctgctgaa cagcatgggc atcagccagc   3180
ccaccgtcgt attcgtgagc aagaaagggc tgcaaaagat cctcaacgtg caaaagaagc   3240
taccgatcat acaaaagatc atcatcatgg atagcaagac cgactaccag ggcttccaaa   3300
gcatgtacac cttcgtgact tcccatttgc cacccggctt caacgagtac gacttcgtgc   3360
ccgagagctt cgaccgggac aaaaccatcg ccctgatcat gaacagtagt ggcagtaccg   3420
gattgcccaa gggcgtagcc ctaccgcacc gcaccgcttg tgtccgattc agtcatgccc   3480
gcgaccccat cttcggcaac cagatcatcc ccgacaccgc tatcctcagc gtggtgccat   3540
ttcaccacgg cttcggcatg ttcaccacgc tgggctactt gatctgcggc tttcgggtcg   3600
tgctcatgta ccgcttcgag gaggagctat tcttgcgcag cttgcaagac tataagattc   3660
aatctgccct gctggtgccc acactattta gcttcttcgc taagagcact ctcatcgaca   3720
agtacgacct aagcaacttg cacgagatcg ccagcggcgg ggcgccgctc agcaaggagg   3780
taggtgaggc cgtggccaaa cgcttccacc taccaggcat ccgccagggc tacggcctga   3840
cagaaacaac cagcgccatt ctgatcaccc ccgaaggga cgacaagcct ggccgcagtag   3900
gcaaggtggt gcccttcttc gaggctaagg tggtggactt ggacaccggt aagacactgg   3960
gtgtgaacca gcgcggcgag ctgtgcgtcc gtggccccat gatcatgagc ggctacgtta   4020
acaacccga ggctacaaac gctctcatcg acaaggacgg ctggctgcac agcggcgaca   4080
tcgcctactg ggacgaggac gagcacttct tcatcgtgga ccggctgaag agcctgatca   4140
aatacaaggg ctaccaggta gccccagccg aactggagag catcctgctg caacacccca   4200
acatcttcga cgccggggtc gccggcctgc ccgacgacga tgccggcgag ctgcccgccg   4260
cagtcgtcgt gctggaacac ggtaaaacca tgaccgagaa ggagatcgtg gactatgtgg   4320
ccagccaggt tacaaccgcc aagaagctgc gcggtggtgt tgtgttcgtg gacgaggtgc   4380
ctaaaggact gaccggcaag ttggacgccc gcaagatccg cgagattctc attaaggcca   4440
agaagggcgg caagatcgcc gtgtaattcg aaacgaatgg tccatcttga gcatctgact   4500
tctggctaaa taaaagatct ttattttcat tagatctgtg tgttggtttt ttgtgtgcgt   4560
cgagatccac ggccgcagga acccctagtg atggagttgg ccactccctc tctgcgcgct   4620
cgctcgctca ctgaggccgg gcgaccaaag gtcgcccgac gcccgggctt tgcccgggcg   4680
gcctcagtga gcgagcgagc gcgcagctgc ctgcaggggc gcctgatgcg gtattttctc   4740
cttacgcatc tgtgcggtat ttcacaccgc atacgtcaaa gcaaccatag tacgcgccct   4800
gtagcgcgcg attaagcgcg gcgggtgtgg tggttacgcg cagcgtgacc gctacacttg   4860
ccagcgccct agcgcccgct cctttcgctt tcttcccttc ctttctcgcc acgttcgccg   4920
gctttccccg tcaagctcta aatcggggc tccctttagg gttccgattt agtgctttac   4980
ggcacctcga ccccaaaaaa cttgatttgg gtgatggttc acgtagtggg ccatcgccct   5040
gatagacggt tttgcccct ttgacgttgg agtccacgtt ctttaatagt ggactcttgt   5100
tccaaactgg aacaacactc aaccctatct cgggctattc ttttgattta taagggattt   5160
tgccgatttc ggcctattgg ttaaaaaatg agctgattta acaaaaattt aacgcgaatt   5220
ttaacaaaat attaacgttt acaattttat ggtgcactct cagtacaatc tgctctgatg   5280
ccgcatagtt aagccagccc cgacacccgc caacacccgc tgacgcgccc tgacgggctt   5340
gtctgctccc ggcatccgct tacagacaag ctgtgaccgt ctccgggagc tgcatgtgtc   5400
agaggttttc accgtcatca ccgaaacgcg cgagacgaaa gggcctcgtg atacgcctat   5460
ttttataggt taatgtcatg ataataatgg tttcttagac gtcaggtggc acttttcggg   5520
gaaatgtgcg cggaacccct atttgtttat ttttctaaat acattcaaat atgtatccgc   5580
tcatgagaca ataaccctga taaatgcttc aataatattg aaaaaggaag agtatgagta   5640
ttcaacattt ccgtgtcgcc cttattccct tttttgcggc attttgcctt cctgtttttg   5700
ctcacccaga aacgctggtg aaagtaaaag atgctgaaga tcagttgggt gcacgagtgg   5760
gttacatcga actggatctc aacagcggta agatccttga gttttcgc cccgaagaac   5820
gttttccaat gatgagcact tttaaagttc tgctatgtgg cgcggtatta tcccgtattg   5880
acgccgggca agagcaactc ggtcgccgca tacactattc tcagaatgac ttggttgagt   5940
actcaccagt cacagaaaag catcttacgg atggcatgac agtaagagaa ttatgcagtg   6000
ctgccataac catgagtgat aacactgcgg ccaacttact tctgacaacg atcggaggac   6060
cgaaggagct aaccgctttt ttgcacaaca tgggggatca tgtaactcgc cttgatcgtt   6120
gggaaccgga gctgaatgaa gccataccaa acgacgagcg tgacaccacg atgcctgtag   6180
caatggcaac aacgttgcgc aaactattaa ctggcgaact acttactcta gcttcccggc   6240
aacaattaat agactggatg gaggcggata aagttgcagg accacttctg cgctcggccc   6300
ttccggctgg ctggtttatt gctgataaat ctggagccgg tgagcgtggg tctcgcggta   6360
tcattgcagc actggggcca gatggtaagc cctcccgtat cgtagttatc tacacgacgg   6420
ggagtcaggc aactatggat gaacgaaata gacagatcgc tgagataggt gcctcactga   6480
ttaagcattg gtaactgtca gaccaagttt actcatatat actttagatt gatttaaaac   6540
ttcatttta atttaaaagg atctaggtga agatcctttt gataatctc atgaccaaaa   6600
tcccttaacg tgagttttcg ttccactgag cgtcagaccc cgtagaaaag atcaaaggat   6660
cttcttgaga tcctttttt ctgcgcgtaa tctgctgctt gcaaacaaaa aaaccaccgc   6720
taccagcggt ggtttgtttg ccggatcaag agctaccaac tctttttccg aaggtaactg   6780
gcttcagcag agcgcagata ccaaatactg tccttctagt gtagccgtag ttaggccacc   6840
acttcaagaa ctctgtagca ccgcctacat acctcgctct gctaatcctg ttaccagtgg   6900
ctgctgccag tggcgataag tcgtgtctta ccgggttgga ctcaagacga tagttaccgg   6960
ataaggcgca gcggtcgggc tgaacggggg gttcgtgcac acagcccagc ttggagcgaa   7020
cgacctacac cgaactgaga tacctacagc gtgagctatg agaaagcgcc acgcttcccg   7080
aagggagaaa ggcggacagg tatccggtaa gcggcagggt cggaacagga gcgcacga   7140
gggagcttcc agggggaaac gcctggtatc tttatagtcc tgtcgggttt cgccacctct   7200
gacttgagcg tcgatttttg tgatgctcgt caggggggcg gagcctatgg aaaaacgcca   7260
gcaacgcggc cttttacgg ttcctggcct tttgctggcc ttttgctc                7308
```

SEQ ID NO: 118          moltype = DNA   length = 7053
FEATURE                 Location/Qualifiers
misc_feature           1..7053
                       note = plasmid pAAVss-CRE64-SkSH4-hDES1.4kb-Luc2
source                 1..7053
                       mol_type = other DNA
                       organism = synthetic construct

```
SEQUENCE: 118
acatgtcctg caggcagctg cgcgctcgct cgctcactga ggccgccggg gcaaagcccg    60
ggcgtcgggc gacctttggt cgcccggcct cagtgagcga gcgagcgcgc agagagggag   120
tggccaactc catcactagg ggttcctgcg gccgtctccg aacgcaggcc ccgtcgcgtt   180
aagcacaagc tggcagggcc tctcctctcc cttctcagat ttgctccttg acatttgcct   240
gctgcctggc ggtggcaaca gctggggcgg ggcgcgcgca ggaggccccg taaccctatc   300
cccgctccgg ctccctcgtg aaaccggagc ttccctgcct tggccgaggg ggagggctgc   360
gggggccaga ccgcctgcga agaccacagg gtttttcctc tcgggttttg gctcccgtgg   420
gatggatgtg gctgtgcggg gggttggcct gagcttcgct tctaagccag cagcttggtc   480
agggaaacct gaaagcattc ccagctaatc ccccaagtgg tgcaagtctg tgcgcgccca   540
tcccgctgag taaggcggtg gggcgcgcca cgcgtttctg agtcctctaa ggtccctcac   600
tcccaactca gcccccatgtc ctgtcaattc ccactcagtg tctgatctcc ttctcctcac   660
ctttcccatc tcccgtttga cccaagcttc ctgagctctc ctcccattcc cctttttgga   720
gtcctcctcc tctcccagaa cccagtaata agtgggctcc tccctggcct ggacccccgt   780
ggtaacccta taaggcgagg cagctgctgt ctgaggcagg gaggggctgg tgtgggaggc   840
taagggcagc tgctaagttt agggtggctc cttctctctt cttagagaca acaggtggct   900
ggggcctcag tgcccagaaa agaaaatgtc ttagaggtat cggcatgggc ctggaggagg   960
ggggacaggg cagggggagg catcttcctc aggacatcgg gtcctagagg ggtacccaac  1020
gggttacgac acacctacta gtaacccctc cagctggtga tggcaggtct agggtaggac  1080
cagtgactgg ctcctaatcg agcactctat tttcagggtt tgcattccaa aagggtcagg  1140
tccaagaggg acctggagtg ccaagtggag gtgtagaggc acggccagta cccatggaga  1200
atggtggatg tccttagggg ttagcaagtg ccgtgtgcta aggagggggc tttggaggtt  1260
gggcaggccc tctgtggggc tccatttttg tgggggtggg ggctggagca ttataggggg  1320
tgggaagtga ttggggctgt caccctagcc ttccttatct gacgcccacc catgcctcct  1380
caggtaccc ctgccccca cagctcctct cctgtgcctt gtttcccagc catgcgttct  1440
cctctataaa tacccgctct ggtatttggg gttggcagct gttgctgcca gggagatggt  1500
tgggttgaca tgcggctcct gacaaaacac aaacccctgg tgtgtgtggg cgtgggtggt  1560
gtgagtaggg ggatgaatca gggaggggc ggggaccca gggggcagga gccacacaaa  1620
gtctgtgcgg gggtgggagc gcacatagca attggaaact gaaagcttat cagaccccttt  1680
ctggaaatca gcccactgtt tataaacttg aggccccacc ctcgacagta ccggggagga  1740
agagggcctg cactagtcca gagggaaact gaggctcagg gctagctcgc ccatagacat  1800
acatggcagg caggctttgg ccaggatccc tccgcctgcc aggcgtctcc ctgccctccc  1860
ttcctgccta gagacccca ccctcaagcc tggctggtct ttgcctgaga cccaaacctc  1920
ttcgacttca agagaatatt taggaacaag gtggtttagg gcctttcctg ggaacaggcc  1980
ttgacccttt aagaaatgac ccaaagtctc tccttgacca aaaaggggac cctcaaacta  2040
aagggaagcc tctcttctgc tgtctcccct gacccccactc ccccccaccc caggacgagg  2100
agataaccag ggctgaaaga ggcccgcctg ggggctgcag acatgcttgc tgcctgccct  2160
ggcgaaggat tggcaggctt gcccgtcaca ggaccccgc tggctgactc aggggcgcag  2220
gcctcttgcg ggggagctgg cctcccccgc cccacggcca ccggccgccc tttcctggca  2280
ggacagcggg atcttgcagc tgtcagggga ggggaggcgg gggctgatgt caggagggat  2340
acaaatagtg ccgacggctg ggggccctgt ctcccctcgc cgcatccact ctccggccgg  2400
ccgcctgccc gccgcctcct ccgtgcgccc gccagcctcg cccgcgccgt cacctctaga  2460
aagaggtaag ggtttaaggg atggttggtt ggtggggtat taatgtttaa ttacctggag  2520
cacctgcctg aaatcacttt tttcaggtt ggaagcttat ggaagatgcc aaaaacatta  2580
agaagggccc agcgccattc tacccactcg aggacgggac cgccggcgag cagctgcaca  2640
aagccatgaa gcgctacgcc ctggtgcccg gcaccatcgc ctttaccgac gcacatatcg  2700
aggtggacat tacctacgcc gagtacttcg agatgagcgt tcggctggca gaagctatga  2760
agcgctatgg gctgaataca aaccatcgga tcgtggtgtg cagcgagaat agcttgcagt  2820
tcttcatgcc cgtgttgggt gccctgttca tcggtgtggc tgtggcccca gctaacgaca  2880
tctacaacga gcgcgagctg ctgaacagca tgggcatcag ccagcccacc gtcgtattcg  2940
tgagcaagaa agggctgcaa aagatcctca acgtgcaaaa gaagctaccg atcatacaaa  3000
agatcatcat catggatagc aagaccgact accagggctt ccaaagcatg tacaccttcg  3060
tgacttccca tttgccaccc ggcttcaacg agtacgactt cgtgcccgag agcttcgacc  3120
gggacaaaac catcgccctg atcatgaaca gtagtggcag taccggattg cccaagggcg  3180
tagccctacc gcaccgcacc gcttgtgtcc gattcagtca gagccgcgac cccatcttcg  3240
gcaaccagat catccccgac accgctatcc tcagcgtggt gccatttcac cacggcttcg  3300
gcatgttcac cacgctgggc tacttgatct gcggctttcg ggtcgtgctc atgtaccgct  3360
tcgaggagga gctattcttg cgcagcttgc aagactataa gattcaatct gccctgctga  3420
tgcccacact atttagcttc ttcgctaaga gcactctcat cgacaagtac gacctaagca  3480
acttgcacga gatcgccagc ggcggggcgc cgctcagcag gagggtaggt gaggccgtgg  3540
ccaaacgctt ccacctacca ggcatccgcc agggctacgg cctgacagaa acaaccagcg  3600
ccattctgat cacccccgaa ggggacgaca gcctggcgc agtaggcaag gtggtgccct  3660
tcttcgaggc taaggtggtg gacttggaca ccggtaagac actgggtgtg aaccagcgcg  3720
gcgagctgtg cgtccgtggc cccatgatca tgagcggcta cgttaacaac ccgcaggcta  3780
caaacgctct catcgacaag gacggctggc tgcacagcgg cgacatcgcc tactgggacg  3840
aggacgagca cttcttcatc gtggaccggc tgaagagcct gatcaaatac aagggctacc  3900
aggtagcccc agccgaactg gagagcatcc tgctgcaaca ccccaacatc ttcgacgccg  3960
gggtcgccgg cctgcccgac gacgatgccg gcgagctgcc cgccgcagtc gtcgtgctgg  4020
aacacggtaa aaccatgacc gagaaggaga tcgtggacta tgtggccagc caggttacaa  4080
ccgccaagaa gctgcgcggt ggtgttgtgt tcgtggacga ggtgcctaaa ggactgaccg  4140
gcaagttgga cgcccgcaag atccgcgaga ttctcattaa ggccaagaag ggcggcaaga  4200
tcgccgtgta attcgaaacg aacggtccat cttgagcatc tgacttctgg ctaaataaaa  4260
gatctttatt ttcattagat ctgtgtgttg gtttttttgt gcgtcgaga tccacgccg  4320
caggaacccc tagtgatgga gttggccact ccctctctgc gcgctcgctc gctcactgag  4380
gccgggcgac caaaggtcgc ccgacgcccg ggctttgccc gggcggcctc agtgagcgag  4440
cgagcgcgca gctgcctgca ggggcgcctg atgcggtatt ttctccttac gcatctgtgc  4500
ggtatttcac accgcatacg tcaaagcaac catagtacgc gccctgtagc ggcgcattaa  4560
gcgcggcggg tgtggtggtt acgcgcagcg tgaccgctac acttgccagc gccctagcgc  4620
ccgctccttt cgctttcttc ccttcctttc tcgccacgtt cgccggcttt ccccgtcaag  4680
```

```
ctctaaatcg ggggctccct ttagggttcc gatttagtgc tttacggcac ctcgaccccca   4740
aaaaacttga tttgggtgat ggttcacgta gtgggccatc gccctgatag acggtttttc   4800
gccctttgac gttggagtcc acgttcttta atagtggact cttgttccaa actggaacaa   4860
cactcaaccc tatctcgggc tattcttttg atttataagg gattttgccg atttcggcct   4920
attggttaaa aaatgagctg atttaacaaa aatttaacgc gaattttaac aaaatattaa   4980
cgtttacaat tttatggtgc actctcagta caatctgctc tgatgccgca tagttaagcc   5040
agccccgaca cccgccaaca cccgctgacg cgccctgacg ggcttgtctg ctcccggcat   5100
ccgcttacag acaagctgtg accgtctccg ggagctgcat gtgtcagagg ttttcaccgt   5160
catcaccgaa acgcgcgaga cgaaagggcc tcgtgatacg cctattttta taggttaatg   5220
tcatgataat aatggtttct tagacgtcag gtggcacttt tcggggaaat gtgcgcggaa   5280
cccctatttg tttattttc taaatacatt caaatatgta tccgctcatg agacaataac   5340
cctgataaat gcttcaataa tattgaaaaa ggaagagtat gagtattcaa catttccgtg   5400
tcgcccttat tcccttttt gcggcatttt gccttcctgt ttttgctcac ccagaaacgc   5460
tggtgaaagt aaaagatgct gaagatcagt tgggtgcacg agtgggttac atcgaactgg   5520
atctcaacag cggtaagatc cttgagagtt ttcgccccga agaacgtttt ccaatgatga   5580
gcactttaa agttctgcta tgtggcgcgg tattatcccg tattgacgcc gggcaagagc   5640
aactcggtcg ccgcatacac tattctcaga atgacttggt tgagtactca ccagtcacag   5700
aaaagcatct tacggatggc atgacagtaa gagaattatg cagtgctgcc ataaccatga   5760
gtgataacac tgcggccaac ttacttctga caacgatcgg aggaccgaag gagctaaccg   5820
cttttttgca caacatgggg gatcatgtaa ctcgccttga tcgttgggaa ccggagctga   5880
atgaagccat accaaacgac gagcgtgaca ccacgatgcc tgtagcaatg gcaacaacgt   5940
tgcgcaaact attaactggc gaactactta ctctagcttc ccggcaacaa ttaatagact   6000
ggatggaggc ggataaagtt gcaggaccac ttctgcgctc ggcccttccg gctggctggt   6060
ttattgctga taaatctgga gccggtgagc gtgggtctcg cggtatcatt gcagcactgg   6120
ggccagatgg taagccctcc cgtatcgtag ttatctacac gacggggagt caggcaacta   6180
tggatgaacg aaatagacag atcgctgaga taggtgcctc actgattaag cattggtaac   6240
tgtcagacca agtttactca tatatacttt agattgattt aaaacttcat ttttaattta   6300
aaaggatcta ggtgaagatc cttttgata atctcatgac caaaatccct taacgtgagt   6360
tttcgttcca ctgagcgtca gaccccgtag aaaagatcaa aggatcttct tgagatcctt   6420
ttttctgcg cgtaatctgc tgcttgcaaa caaaaaaacc accgctacca gcggtggttt   6480
gtttgccgga tcaagagcta ccaactcttt ttccgaaggt aactggcttc agcagagcgc   6540
agataccaaa tactgtcctt ctagtgtagc cgtagttagg ccaccacttc aagaactctg   6600
tagcaccgcc tacatacctc gctctgctaa tcctgttacc agtggctgct gccagtggcg   6660
ataagtcgtg tcttaccggg ttggactcaa gacgatagtt accggataag gcgcagcggt   6720
cgggctgaac ggggggttcg tgcacacagc ccagcttgga gcgaacgacc tacaccgaac   6780
tgagatacct acagcgtgag ctatgagaaa gcgccacgct tcccgaaggg agaaaggcgg   6840
acaggtatcc ggtaagcggc agggtcggaa caggagagcg cacgagggag cttccagggg   6900
gaaacgcctg gtatctttat agtcctgtcg ggtttcgcca cctctgactt gagcgtcgat   6960
ttttgtgatg ctcgtcaggg gggcggagcc tatggaaaaa cgccagcaac gcggcctttt   7020
tacggttcct ggccttttgc tggccttttg ctc                                7053
```

```
SEQ ID NO: 119          moltype = DNA   length = 6210
FEATURE                 Location/Qualifiers
misc_feature            1..6210
                        note = plasmid pAAVss-hDES1.4kb-Luc2
source                  1..6210
                        mol_type = other DNA
                        organism = synthetic construct
SEQUENCE: 119
acatgtcctg caggcagctg cgcgctcgct cgctcactga ggccgcccgg gcaaagcccg   60
ggcgtcgggc gacctttggt cgcccggcct cagtgagcga gcgagcgcgc agagagggag   120
tggccaactc catcactagg ggttcctgcg gccggcgcgc cacgcgtggt acccaacggg   180
ttacgacaca cctactagta acccctccag ctggtgatgg caggtctagg gtaggaccag   240
tgactggctc ctaatcgagc actctatttt cagggtttgc attccaaaag ggtcaggtcc   300
aagaggaacc tggagtgcca agtggaggtg tagaggcacg gccagtaccc atggagaatg   360
gtggatgtcc ttaggggtta gcaagtgccg tgtgctaagg aggggggcttt ggaggttggg   420
caggccctct gtggggctcc atttttgtgg gggtgggggc tggagcatta tagggggtgg   480
gaagtgattg gggctgtcac cctagccttc cttatctgac gcccacccat gcctcctcag   540
gtaccccctg ccccccacag ctcctctcct gtgccttgtt tcccagccat gcgttctcct   600
ctataaatac ccgctctggt atttgggggtt ggcagctgtt gctgccaggg agatggttgg   660
gttgacatgc ggctcctgac aaaacacaaa cccctggtgt gtgtgggcgt gggtggtgtg   720
agtaggggga tgaatcaggg aggggcggg ggacccaggg ggcaggagcc acacaaagtc   780
tgtgcggggg tgggagcgca catagcaatt ggaaactgaa agcttatcag acccttctg   840
gaaatcagcc cactgtttat aaacttgagg ccccacccto gacagtaccg gggaggaaga   900
gggcctgcac tagtccagag ggaaactgag gctcagggct agctcgccca tagacataca   960
tggcaggcag gctttggcca ggatccctcc gcctgccagg cgtctccctg ccctcccttc   1020
ctgcctagag accccaccc tcaagcctgg ctggtctttg cctgagaccc aaacctcttc   1080
gacttcaaga gaatatttag gaacaaggtg gtttagggc tttcctggga acaggccttg   1140
acccttaag aaatgaccca aagtctctcc ttgaccaaaa aggggaccct caaactaaag   1200
ggaagcctct cttctgctgt ctcccctgac cccactcccc cccacccag gacgaggaga   1260
taaccagggc tgaaagaggc ccgcctgggg gctgcagaca tgcttgctgc ctgccctggc   1320
gaaggattgg caggcttgcc cgtcacagga ccccgctgg ctgactcagg ggcgcaggcc   1380
tcttgcgggg gagctggcct ccccgccccc acggccacgg gcgcgccttt cctggcagga   1440
cagcgggatc ttgcagctgt cagggaggg gagcgtgatg tcag gaggataca   1500
aatagtgccg acggctgggg gcctgtctc ccctcgccgc atccactctc cggccggccg   1560
cctgcccgcc gcctcctccg tgcgcccgcc agcctcgccc gcgccgtcac ctctagaaag   1620
aggtaagggt ttaaggggatg gttggttggt ggggtattaa tgtttaatta cctggagcac   1680
ctgcctgaaa tcactttttt tcaggttgga agcttatgga agatgccaaa aacattaaga   1740
agggcccagc gccattctac ccactcgaag acgggaccgc cggcgagcag ctgcacaaag   1800
```

```
ccatgaagcg ctacgccctg gtgcccggca ccatcgcctt taccgacgca catatcgagg   1860
tggacattac ctacgccgag tacttcgaga tgagcgttcg gctggcagaa gctatgaagc   1920
gctatgggct gaatacaaac catcggatcg tggtgtgcag cgagaatagc ttgcagttct   1980
tcatgcccgt gttgggtgcc ctgttcatcg gtgtggctgt ggccccagct aacgacatct   2040
acaacgagcg cgagctgctg aacagcatgg gcatcagcca gcccaccgtc gtattcgtga   2100
gcaagaaagg gctgcaaaag atcctcaacg tgcaaaagaa gctaccgatc atacaaaaga   2160
tcatcatcat ggatagcaag accgactacc agggcttcca aagcatgtac accttcgtga   2220
cttcccattt gccacccggc ttcaacgagt acgacttcgt gcccgagagc ttcgaccggg   2280
acaaaaccat cgccctgatc atgaacagta gtggcagtac cggattgccc aagggcgtag   2340
ccctaccgca ccgcaccgct tgtgtccgat tcagtcatgc ccgcgacccc atcttcggca   2400
accagatcat ccccgacacc gctatcctca gcgtggtgcc atttcaccac ggcttcggca   2460
tgttcaccac gctgggctac ttgatctgcg gctttcgggt cgtgctcatg taccgcttcg   2520
aggaggagct attcttgcgc agcttgcaag actataagat tcaatctgcc ctgctggtgc   2580
ccacactatt tagcttcttc gctaagagca ctctcatcga caagtacgac ctaagcaact   2640
tgcacgagat cgccagcggc ggggcgccgc tcagcaagga ggtaggtgag gccgtggcca   2700
aacgcttcca cctaccaggc atccgccagg gctacgacct gacagaaaca accagcgcca   2760
ttctgatcac ccccgaaggg gacgacaagc ctggcgcagt aggcaaggtg gtgcccttct   2820
tcgaggctaa ggtggtggac ttggacaccg gtaagacact gggtgtgaac cagcgcggcg   2880
agctgtgcgt ccgtggcccc atgatcatga gcggctacgt taacaacccc gaggctacaa   2940
acgctctcat cgacaaggac ggctggctgc acagcggcga catcgcctac tgggacgagg   3000
acgagcactt cttcatcgtg gaccggctga agagcctgat caaatacaag ggctaccagg   3060
tagccccagc cgaactggag agcatcctgc tgcaacaccc caacatcttc gacgccgggg   3120
tcgccggcct gcccgacgac gatgccggcg agctgcccgc cgcagtcgtc gtgctggaac   3180
acggtaaaac catgaccgag aaggagatcg tggactatgt ggccagccag gttacaaccg   3240
ccaagaagct gcgcggtggt gttgtgttcg tggacgaggt gcctaaagga ctgaccggca   3300
agttggacgc ccgcaagatc cgcgagattc tcattaaggc caagaagggc ggcaagatcg   3360
ccgtgtaatt cgaaacgttg agtccatctt gagcatctga cttctggcta aataaaaagat   3420
ctttattttc attagatctg tgtgttggtt ttttgtgtgc gtcgagatcc acggccgcag   3480
gaacccctag tgatggagtt ggccactccc tctctgcgcg ctcgctcgct cactgaggcc   3540
gggcgaccaa aggtcgcccg acgcccgggc tttgcccggg cggcctcagt gagcgagcga   3600
gcgcgcagct gcctgcaggg gcgcctgatg cggtattttc tccttacgca tctgtgcggt   3660
atttcacacc gcatacgtca aagcaaccat agtacgcgcc ctgtagcggc gcattaagcg   3720
cggcgggtgt ggtggttacg cgcagcgtga ccgctacact tgccagcgcc ctagcgcccg   3780
ctcctttcgc tttcttccct tcctttctcg ccacgttcgc cggctttccc cgtcaagctc   3840
taaatcgggg gctcccttta gggttccgat ttagtgcttt acggcacctc gaccccaaaa   3900
aacttgattt gggtgatggt tcacgtagtg ggccatcgcc ctgatagacg gtttttcgcc   3960
ctttgacgtt ggagtccacg ttctttaata gtggactctt gttccaaact ggaacaacac   4020
tcaaccctat ctcgggctat tcttttgatt tataagggat tttgccgatt tcggcctatt   4080
ggttaaaaaa tgagctgatt taacaaaaat ttaacgcgaa ttattaacgt ttacaatttt   4140
ttacaatttt atggtgcact ctcagtacaa tctgctctga tgccgcatag ttaagccagc   4200
cccgacaccc gccaacaccc gctgacgcgc cctgacgggc ttgtctgctc ccggcatccg   4260
cttacagaca agctgtgacc gtctccggga gctgcatgtg tcagaggttt tcaccgtcat   4320
caccgaaacg cgcgagacga aagggcctcg tgatacgcct atttttatag gttaatgtca   4380
tgataataat ggtttcttag acgtcaggtg gcacttttcg gggaaatgtg cgcggaaccc   4440
ctatttgttt atttttctaa atacattcaa atatgtatcc gctcatgaga caataaccct   4500
gataaatgct tcaataatat tgaaaaagga agagtatgag tattcaacat ttccgtgtcg   4560
cccttattcc cttttttgcg gcattttgcc ttcctgtttt tgctcaccca gaaacgctgg   4620
tgaaagtaaa agatgctgaa gatcagttgg gtgcacgagt gggttacatc gaactggatc   4680
tcaacagcgg taagatcctt gagagttttc gccccgaaga acgttttcca atgatgagca   4740
cttttaaagt tctgctatgt ggcgcggtat tatcccgtat tgacgccggg caagagcaac   4800
tcggtcgccg catacactat tctcagaatg acttggttga gtactcacca gtcacagaaa   4860
agcatcttac ggatggcatg acagtaagag aattatgcag tgctgccata accatgagtg   4920
ataacactgc ggccaactta cttctgacaa cgatcggagg accgaaggag ctaaccgctt   4980
ttttgcacaa catgggggat catgtaactc gccttgatcg ttgggaaccg gagctgaatg   5040
aagccatacc aaacgacgag cgtgacacca cgatgcctgt agcaatggca acaacgttgc   5100
gcaaactatt aactggcgaa ctacttactc tagcttcccg gcaacaatta atagactgga   5160
tggaggcgga taaagttgca ggaccacttc tgcgctcggc ccttccggct ggctggttta   5220
ttgctgataa atctggagcc ggtgagcgtg ggtctcgcgg tatcattgca gcactggggc   5280
cagatggtaa gccctcccgt atcgtagtta tctacacgac ggggagtcag gcaactatgg   5340
atgaacgaaa tagacagatc gctgagatag gtgcctcact gattaagcat tggtaactgt   5400
cagaccaagt ttactcatat atactttaga ttgatttaaa acttcatttt taatttaaaa   5460
ggatctaggt gaagatcctt tttgataatc tcatgaccaa aatcccttaa cgtgagtttt   5520
cgttccactg agcgtcagac cccgtagaaa agatcaaagg atcttcttga tccttttt    5580
ttctgcgcgt aatctgctgc ttgcaaacaa aaaaaccacc gctaccagcg gtggtttgtt   5640
tgccggatca agagctacca actctttttc cgaaggtaac tggcttcagc agagcgcaga   5700
taccaaatac tgtccttcta gtgtagccgt agttaggcca ccacttcaag aactctgtag   5760
caccgcctac atacctcgct ctgctaatcc tgttaccagt ggctgctgcc agtggcgata   5820
agtcgtgtct taccgggttg gactcaagac gatagttacc ggataaggcg cagcggtcgg   5880
gctgaacggg gggttcgtgc acacagccca gcttggagcg aacgacctac accgaactga   5940
gatacctaca gcgtgagcta tgagaaagcg ccacgcttcc cgaagggaga aaggcggaca   6000
ggtatccggt aagcggcagg gtcggaacag gagagcgcac gagggagctt ccaggggaa    6060
acgcctggta tctttatagt cctgtcgggt ttcgccacct ctgacttgag cgtcgatttt   6120
tgtgatgctc gtcaggnggg cggagcctat ggaaaaacgc cagcaacgcg gccttttta c  6180
ggttcctggc cttttgctgg cctttgctc                                     6210
```

```
SEQ ID NO: 120        moltype = DNA   length = 6645
FEATURE               Location/Qualifiers
misc_feature          1..6645
                      note = plasmid pAAVss-SkSH4-hDES1.4kb-Luc2
```

```
source                  1..6645
                        mol_type = other DNA
                        organism = synthetic construct
SEQUENCE: 120
acatgtcctg caggcagctg cgcgctcgct cgctcactga ggccgcccgg gcaaagcccg   60
ggcgtcgggc gacctttggt cgcccggcct cagtgagcga gcgagcgcgc agagagggag   120
tggccaactc catcactagg ggttcctgcg gccggcgcgc cacgcgtttc tgagtcctct   180
aaggtccctc actcccaact cagccccatg tcctgtcaat tcccactcag tgtctgatct   240
ccttctcctc acctttccca tctcccgttt gacccaagct tcctgagctc tcctcccatt   300
cccctttttg gagtcctcct cctctcccag aacccagtaa taagtgggct cctccctggc   360
ctggaccccc gtggtaaccc tataaggcga ggcagctgct gtctgaggca gggagggggct   420
ggtgtgggag gctaagggca gctgctaagt ttagggtggc tccttctctc ttcttagaga   480
caacaggtgg ctgggcctc agtgcccaga aaagaaaatg tcttagaggt atcggcatgg   540
gcctggagga ggggggacag ggcagggga ggcatcttcc tcaggacatc gggtcctaga   600
ggggtaccca acgggttacg acacacctac tagtaacccc tccagctggt gatggcaggt   660
ctagggtagg accagtgact ggctcctaat cgagcactct attttcaggg tttgcattcc   720
aaaagggtca ggtccaagag ggacctggag tgccaagtgg aggtgtagag gcacggccag   780
tacccatgga gaatggtgga tgtccttagg ggttagcaag tgccgtgtgc taaggagggg   840
gctttggagg ttgggcaggc cctctgtggg gctccatttt tgtgggggtg ggggctggag   900
cattataggg ggtgggaagt gattggggct gtcaccctag ccttccttat ctgacgccca   960
cccatgcctc ctcaggtacc ccctgccccc cacagctcct ctcctgtgcc ttgtttccca   1020
gccatgcgtt ctcctctata aatacccgct ctggtatttg gggttggcag ctgttgctgc   1080
cagggagatg gttgggttga catgcggctc ctgacaaaac acaaacccct ggtgtgtgtg   1140
ggcgtgggtg gtgtgagtag ggggatgaat cagggagggg gcgggggacc caggggcag   1200
gagccacaca aagtctgtgc gggggtggga gcgcacatag caattggaaa ctgaaagctt   1260
atcagaccct ttctggaaat cagcccactg tttataaact tgaggcccca ccctcgacag   1320
taccggggag gaagagggcc tgcactagtc cagagggaaa ctgaggctca gggctagctc   1380
gcccatagac atacatggca ggcaggcttt ggccaggatc cctccgcctg ccaggcgtct   1440
ccctgccctc ccttcctgcc tagagacccc caccctcaag cctggctggt ctttgcctga   1500
gacccaaacc tcttcgactt caagagaata tttaggacaa aggtggttta gggcctttcc   1560
tgggaacagg ccttgaccct ttaagaaatg acccaaagtc tctccttgac caaaaagggg   1620
accctcaaac taaagggaag cctctcttct gctgtctccc ctgaccccac tccccccac   1680
cccaggacga ggagataacc agggctgaaa gaggcccgcc tggggggctgc agacatgctt   1740
gctgcctgcc ctggcgaagg attggcaggc ttgcccgtca caggacccccc gctggctgac   1800
tcagggcgc aggcctcttg cggggggagct ggcctccccg ccccacggc cacgggccgc   1860
cctttcctgg caggacagcg ggatcttgca gctgtcaggg gaggggaggc ggggggctgat   1920
gtcaggaggg atacaaatag tgccgacggc tggggggccct gtctccccctc gccgcatcca   1980
ctctccggcc ggccgcctgc ccgccgcctc ctccgtgcgc ccgccagcct cgcccgcgcc   2040
gtcacctcta gaaagaggta agggtttaag ggatggttgg ttggtggggt attaatgttt   2100
aattacctgg agcacctgcc tgaaatcact tttttcagg ttggaagctt atggaagatg   2160
ccaaaaacat taagaagggc ccagcgccat tctacccact cgaggacggg accgccggcg   2220
agcagctgca caaagccatg aagcgctacg ccctggtgcc cggcaccatc gcctttaccg   2280
acgcacatat cgaggtggac attacctacg ccgagtactt cgagatgagc gttcggctgg   2340
cagaagctat gaagcgctat gggctgaata caaaccatcg gatcgtggtg tgcagcgaga   2400
atagcttgca gttcttcatg cccgtgttgg gtgcccgtt catcggtgtg gctgtggccc   2460
cagctaacga catctacaac gagcgcgagc tgctgaacag catgggcatc agccagccca   2520
ccgtcgtatt cgtgagcaag aaagggctgc aaaagatcct caacgtgcaa aagaagctac   2580
cgatcataca aaagatcatc atcatggata gcaagaccga ctaccagggc ttccaaagca   2640
tgtacacctt cgtgacttcc catttgccac ccggcttcaa cgagtacgac ttcgtgcccg   2700
agagcttcga ccgggacaaa accatcgccc tgatcatgaa cagtagtggc agtaccggat   2760
tgcccaaggg cgtagcccta ccgcaccgca ccgcttgtgt ccgattcagt catgcccgacg   2820
acccatctt cggcaaccag atcatccccg acaccgctat cctcagcgtg gtgccatttc   2880
accacggctt cggcatgttc accacgctgg gctacttgat ctgcggcttt cgggtcgtgc   2940
tcatgtaccg cttcgaggag gagctattct tgcgcagctt gcaagactat aagattcaat   3000
ctgccctgct ggtgcccaca ctatttagct tcttcgctaa gagcactctc atcgacaagt   3060
acgacctaag caacttgcac gagatcgcca gcggcgggc gccgctcagc aaggaggtag   3120
gtgaggccgt ggccaaacgc ttccacctac caggcatccg ccaggctac ggcctgacag   3180
aaacaaccag cgccattctg atcaccccccg aaggggacga caagcctggc gcagtaggca   3240
aggtggtgcc cttcttcgag gctaaggtgg tggacttgaa caccggtaag acactgggtg   3300
tgaaccagcg cggcgagctg tgcgtccgtg gccccatgat catgagcggc tacgttaaca   3360
accccgaggc tacaaacgct ctcatcgaca aggacggctg gctgcacagc ggcgacatcg   3420
cctactggga cgaggacgag cacttcttca tcgtggaccg gctgaagagc ctgatcaaat   3480
acaagggcta ccaggtagcc ccagccgaac tggagagcat cctgctgcaa caccccaaca   3540
tcttcgacgc cggggtcgcc ggcctgcccg acgacgatgc cggcgagctg cccgccgcag   3600
tcgtcgtgct ggaacacggt aaaaccatga ccgagaagga tcgcggac tatgtggcca   3660
gccaggttac aaccgccaag aagctgcgcg gtggtgttgt gttcgtggac gaggtgccta   3720
aaggactgac cggcaagttg gacgcccgca gatccgcga gattctcatt aaggccaaga   3780
agggcggcaa gatcgccgtg taattcgaaa cgttccgtcc atcttgagca tctgacttct   3840
ggctaaataa aagatcttta ttttcattag atctgtgtgt tggttttttg tgtgcgtcga   3900
gatccacggc cgcaggaacc cctagtgatg gagttggcca ctccctctct gcgcgctcgc   3960
tcgctcactg aggccgggcg accaaaggtc gcccgacgcc cgggctttgc ccgggcggcc   4020
tcagtgagcg agcgagcgcg cagctgcctg caggggcgcc tgatgcggta ttttctcctt   4080
acgcatctgt gcggtatttc acaccgcata cgtcaaagca accatagtac gcgccctgta   4140
gcggcgcatt aagcgcggcg ggtgtggtgg ttacgcgcag cgtgaccgct acacttgcca   4200
gcgccctagc gcccgctcct ttcgctttct tcccttcctt tctcgccacg ttcgccggct   4260
ttccccgtca gctctaaat cggggggctcc ctttagggtt ccgatttagt gctttacggc   4320
acctcgaccc caaaaaactt gatttgggtg atggttcacg tagtgggcca tcgccctgat   4380
agacggtttt tcgccctttg acgttggagt ccacgttctt taatagtgga ctcttgttcc   4440
aaactggaac aacactcaac cctatctcgg gctattcttt tgatttataa gggatttttgc   4500
```

```
cgatttcggc ctattggtta aaaaatgagc tgatttaaca aaaatttaac gcgaatttta   4560
acaaaatatt aacgtttaca attttatggt gcactctcag tacaatctgc tctgatgccg   4620
catagttaag ccagccccga cacccgccaa cacccgctga cgcgccctga cgggcttgtc   4680
tgctcccggc atccgcttac agacaagctg tgaccgtctc cgggagctgc atgtgtcaga   4740
ggttttcacc gtcatcaccg aaacgcgcga gacgaaaggg cctcgtgata cgcctatttt   4800
tataggttaa tgtcatgata ataatggttt cttagacgtc aggtggcact tttcggggaa   4860
atgtgcgcgg aacccctatt tgtttatttt tctaaataca ttcaaatatg tatccgctca   4920
tgagacaata accctgataa atgcttcaat aatattgaaa aaggaagagt atgagtattc   4980
aacatttccg tgtcgccctt attccctttt ttgcggcatt ttgccttcct gtttttgctc   5040
acccagaaac gctggtgaaa gtaaaagatg ctgaagatca gttgggtgca cgagtgggtt   5100
acatcgaact ggatctcaac agcggtaaga tccttgagag ttttcgcccc gaagaacgtt   5160
ttccaatgat gagcactttt aaagttctgc tatgtggcgc ggtattatcc cgtattgacg   5220
ccgggcaaga gcaactcggt cgccgcatac actattctca gaatgacttg gttgagtact   5280
caccagtcac agaaaagcat cttacggatg gcatgacagt aagagaatta tgcagtgctg   5340
ccataaccat gagtgataac actgcggcca acttacttct gacaacgatc ggaggaccga   5400
aggagctaac cgcttttttg cacaacatgg gggatcatgt aactcgcctt gatcgttggg   5460
aaccggagct gaatgaagcc ataccaaacg acgagcgtga caccacgatg cctgtagcaa   5520
tggcaacaac gttgcgcaaa ctattaactg gcgaactact tactctagct tcccggcaac   5580
aattaataga ctggatggag gcggataaag ttgcaggacc acttctgcgc tcggcccttc   5640
cggctggctg gtttattgct gataaatctg gagccggtga gcgtgggtct cgcggtatca   5700
ttgcagcact ggggccagat ggtaagccct cccgtatcgt agttatctac acgacgggga   5760
gtcaggcaac tatggatgaa cgaaatagac agatcgctga gataggtgcc tcactgatta   5820
agcattggta actgtcagac caagtttact catatatact ttagattgat ttaaaacttc   5880
attttaatt taaaaggatc taggtgaaga tcctttttga taatctcatg accaaaatcc   5940
cttaacgtga gttttcgttc cactgagcgt cagaccccgt agaaaagatc aaaggatctt   6000
cttgagatcc tttttttctg cgcgtaatct gctgcttgca aacaaaaaaa ccaccgctac   6060
cagcggtggt ttgtttgccg gatcaagagc taccaactct ttttccgaag gtaactggct   6120
tcagcagagc gcagatacca aatactgtcc ttctagtgta gccgtagtta ggccaccact   6180
tcaagaactc tgtagcaccg cctacatacc tcgctctgct aatcctgtta ccagtggctg   6240
ctgccagtgg cgataagtcg tgtcttaccg ggttggactc aagacgatag ttaccggata   6300
aggcgcagcg tcgggctga acggggggtt cgtgcacaca gcccagcttg gagcgaacga   6360
cctacaccga actgagatac ctacagcgtg agctatgaga aagcgccacg cttcccgaag   6420
ggagaaaggc ggacaggtat ccggtaagcg gcagggtcgg aacaggagag cgcacgaggg   6480
agcttccagg gggaaacgcc tggtatcttt atagtcctgt cgggtttcgc cacctctgac   6540
ttgagcgtcg atttttgtga tgctcgtcag ggggcggag cctatggaaa aacgccagca   6600
acgcggcctc tttacggtc ctggcctttt gctggccttt tgctc   6645
```

```
SEQ ID NO: 121          moltype = DNA  length = 435
FEATURE                 Location/Qualifiers
misc_feature            1..435
                        note = Muscle CRE Sk-SH4
source                  1..435
                        mol_type = other DNA
                        organism = synthetic construct
SEQUENCE: 121
ttctgagtcc tctaaggtcc ctcactccca actcagcccc atgtcctgtc aattcccact   60
cagtgtctga tctccttctc ctcacctttc ccatctccg tttgacccaa gcttcctgag   120
ctctcctccc attccccttt ttggagtcct cctcctctcc cagaacccag taataagtgg   180
gctcctccct ggcctggacc cccgtggtaa ccctataagg cgaggcagct gctgtctgag   240
gcagggaggg gctggtgtgg gaggctaagg gcagctgcta agtttagggt ggctccttct   300
ctcttcttag agacaacagg tggctggggc ctcagtgccc agaaaagaaa atgtcttaga   360
ggtatcggca tgggcctgga ggagggggga cagggcaggg ggaggcatct tcctcaggac   420
atcgggtcct agagg   435
```

```
SEQ ID NO: 122          moltype = DNA  length = 454
FEATURE                 Location/Qualifiers
misc_feature            1..454
                        note = Heart-Muscle CRE CSk-SH5
source                  1..454
                        mol_type = other DNA
                        organism = synthetic construct
SEQUENCE: 122
cagtttactc accagggatt cagaggcagc actgctgaac cctgagccct tggcacatca   60
ggttggctgt cagaagtcgg cctttgtaca tacacagttc ccttgtgagg cccagctgcg   120
tgtcctagga gcggggcctc tctccacagc agagctcagc ctctcaagtg tatggacagc   180
acgggtgcct gatgggtgga tttagccatg agttgaaggt ggcttgggga gaatgagagt   240
tctagagata gggagaaggg gttgccaata ggagagtgga attcctgagc acctcgtcac   300
aggcagccga cagaacatga gccgcagggc ccaggctatt tatacctcgc ctgtcactat   360
cagggtcccc acagctcccc ccacctccag ccacacacag caggtccttt tgctctttct   420
ggtcccttct ctactcctcc ccctccctac ctaa   454
```

```
SEQ ID NO: 123          moltype = DNA  length = 495
FEATURE                 Location/Qualifiers
misc_feature            1..495
                        note = Heart-Muscle CRE CSk-SH1
source                  1..495
                        mol_type = other DNA
                        organism = synthetic construct
SEQUENCE: 123
```

-continued

```
ctcactcccc gcccaggcag caaggagccc acaccctcat gcccctcagc ttcagccccc    60
acctccagga ggccctaccc acgctcatga ccttgctatt ctgggccttg tgtcctgtag   120
ggagatggac aggagacagc tgggcttcca ggccacccag gcgggggggct agccgaggga   180
agcctgctgg ctctcctgct tgctctaatt tctggggctc cccaaacctt ggcctcagga   240
gactggggat aggaccggcc ttgaaagtgg gggaagcttt gggagagccgg gtgctgggtt   300
cttagtgaga tggccagtga aggctgtggg gccccgaggt aagcagggcc tgatcccctc   360
ctaatcttcc agcagcaact ggtgctctga ggctcccct cccccagccc tgccagcctt   420
cagggacctg ccttccaaag atgggcaggg gaggggggacg aggacacccca cccactcctc   480
agaccagcat gtctt                                                     495
```

```
SEQ ID NO: 124            moltype = DNA   length = 334
FEATURE                   Location/Qualifiers
misc_feature              1..334
                          note = SPc-5-12 promotor
source                    1..334
                          mol_type = other DNA
                          organism = synthetic construct
SEQUENCE: 124
tggccaccgc cttcggcacc atcctcacga cacccaaata tggcgacggg tgaggaatgg    60
tggggagtta tttttagagc ggtgaggaag gtgggcaggc agcaggtgtt ggcgctctaa   120
aaataactcc cggagttat tttttagagcg gaggaatggt ggacacccaa atatggcgac   180
ggttcctcac ccgtcgccat atttgggtgt ccgccctcgg ccgggggccgc attcctgggg   240
gccgggcggt gctcccgccc gcctcgataa aaggctccgg ggcgggcggc ggcccacgag   300
ctacccggag gagcgggagg cgccaagctc taga                               334
```

```
SEQ ID NO: 125            moltype = DNA   length = 92
FEATURE                   Location/Qualifiers
misc_feature              1..92
                          note = MVM intron
source                    1..92
                          mol_type = other DNA
                          organism = synthetic construct
SEQUENCE: 125
aagaggtaag ggtttaaggg atggttggtt ggtggggtat taatgtttaa ttacctggag    60
cacctgcctg aaatcacttt ttttcaggtt gg                                  92
```

```
SEQ ID NO: 126            moltype = DNA   length = 134
FEATURE                   Location/Qualifiers
misc_feature              1..134
                          note = SV40 Polyadenylation signal
source                    1..134
                          mol_type = other DNA
                          organism = synthetic construct
SEQUENCE: 126
atgctttatt tgtgaaattt gtgatgctat tgctttattt gtaaccatta taagctgcaa    60
taaacaagtt aacaacaaca attgcattca ttttatgttt caggttcagg gggaggtgtg   120
ggaggttttt taaa                                                     134
```

```
SEQ ID NO: 127            moltype = DNA   length = 49
FEATURE                   Location/Qualifiers
misc_feature              1..49
                          note = synthetic Polyadenylation signal
source                    1..49
                          mol_type = other DNA
                          organism = synthetic construct
SEQUENCE: 127
aataaaagat ctttattttc attagatctg tgtgttggtt ttttgtgtg               49
```

```
SEQ ID NO: 128            moltype = DNA   length = 20
FEATURE                   Location/Qualifiers
misc_feature              1..20
                          note = forward primer luciferase
source                    1..20
                          mol_type = other DNA
                          organism = synthetic construct
SEQUENCE: 128
cccaccgtcg tattcgtgag                                                20
```

```
SEQ ID NO: 129            moltype = DNA   length = 21
FEATURE                   Location/Qualifiers
misc_feature              1..21
                          note = reverse primer luciferase
source                    1..21
                          mol_type = other DNA
                          organism = synthetic construct
SEQUENCE: 129
tcagggcgat ggttttgtcc c                                              21
```

```
SEQ ID NO: 130            moltype = DNA   length = 7303
```

```
FEATURE            Location/Qualifiers
misc_feature       1..7303
                   note = plasmid
                   pAAVss-CRE04-CSkSH5-SPc5-12GTRM-MVM-hGAAco-SynthpA
source             1..7303
                   mol_type = other DNA
                   organism = synthetic construct SEQUENCE: 130
cctgcaggca gctgcgcgct cgctcgctca ctgaggccgc ccgggcaaag cccgggcgtc   60
gggcgacctt tggtcgcccg gcctcagtga gcgagcgagc gcgcagagag ggagtggcca  120
actccatcac taggggttcc tgcggccgca cgcgtaccgg tccttttaga gaatccacac  180
ctgtcccagt tgctgggttc cactaccaaa agtgaattgc aactatttta ggagcactta  240
agcacatccg aaaaatgagt gattctgttc tggcccacac cacatcactg atgtaccccc  300
ttaaagcatg tccctgagtt catcacagaa gactgctcct cctgtgccct ccacaaggtt  360
agaactgtcc ttgtcttagg gaaaaaggag agagagagca agagagagag agagagagag  420
agagagagag agagagaggg acaggcacca actgggtaac ctctgctgac ccccactcta  480
ctttaccata agtagctcca aatccttcta gaaaatctga aaggcatagc cccatatatc  540
agtgatataa atagaacctg cagcaggctc tggtaaatga tgactacaag gtggactggg  600
aggcagcccg gccttggcag gcatcatcct ctaaatataa agatgagttt gttcagcctt  660
tgcagaagga ggcgcgccac gcgtcagttt actcaccagg gattcagagg cagcactgct  720
gaaccctgag cccttggcac atcaggttgg ctgtcagaag tcggcctttg tacatacaca  780
gttcccttgt gaggcccagc tgcgtgtcct aggagcgggt cctctctcca cagcagagct  840
cagcctctca agtgtatgga cagcacgggt gcctgatggg tggatttagc catgagttga  900
aggtggcttg gggagaatga gagttctaga gataggagag aggggttgcc aataggagag  960
tggaattcct gagcacctcg tcacaggcag ccgacagaac atgagccgca gggcccaggc 1020
tatttatacc tcgcctgtca ctatcagggt ccccacagct cccccacct ccagccacac 1080
acagcaggtc cttttgctct ttctggtccc ttctctactc ctcccctcc ctacctaagg 1140
tacccaaccc gttacgtggc caccgccttc ggcaccatcc tcacgacacc caaatatggc 1200
gacgggtgag gaatggtggg gagttatttt tagagcggtg aggaaggtgg gcaggcagca 1260
ggtgttggcg ctctaaaaat aactcccggg agttatttt agagcggagg aatggtggac 1320
acccaaatat ggcgacggtt cctcaccgt cgccatattt gggtgtccgc cctcggccgg 1380
ggccgcattc ctgggggccg ggcggtgctc ccgcccgcct cgataaaagg ctccggggcc 1440
ggcggcggcc cacgagctac ccggaggagc gggaggcgcc aagctctaga tctagaacta 1500
gtaagaggta agggtttaag ggatggttgg ttggtggggt attaatgttt aattacctgg 1560
agcacctgcc tgaaatcact tttttcagg ttggcgtacg gccaccatgg gcgtcagaca 1620
tcctccatgt tctcacagac tgctggccgt gtgtgctctg gtgtctcttg ctacagctgc 1680
cctgctggga catatcctgc tgcacgattt tctgctggtg cccagagagc tgtctcggcag 1740
ctctcctgtg ctggaagaaa cacaccctgc acatcagcag ggcgcctcta gacctggacc 1800
tagagatgct caagcccatc ctggcagacc tagagccggt cctacacagt gtgacgtgcc 1860
acctaacagc agattcgact gcgcccctga caaggccatc acacaagagc agtgtgaagc 1920
cagaggctgc tgctacattc ctgccaaaca aggactgcag ggcgctcaga tgggacagcc 1980
ttggtgcttc ttcccaccat cttaccccag ctacaagctg gaaaacctga gcagcagcga 2040
gatgggctac accgccacac tgaccagaac cacacctaca ttcttcccaa aggacatcct 2100
gacactgcgg ctggacgtga tgatggaaac cgagaaccgg ctgcacttca ccatcaagga 2160
ccccgccaat agaagatacg aggtgccct ggaaacccct cacgtgcact ctagagcccc 2220
atctccactg tacagcgtgg aattcagcga ggaacccttt ggcgtgatcg tgcggagaca 2280
gctggatggc agagtgctgc tgaataccac agtggccct ctgttcttcg ccgaccagtt 2340
tctgcagctg agcacaagcc tgcctagcca gtatatcaca ggcctggccg aacacctgtc 2400
tccactgatg ctgagcacca gctggaccag aatcaccctg tggaacagag atctggcccc 2460
tacacctggc gccaatctgt acggctctca ccctttttat ctggccctgg aagatggcgg 2520
aagcgcccac ggtgtctttc tgctgaacag caacggccatg gacgtggtgc tgcaaccatc 2580
tcctgctctg tcttggagaa gcaccggcgg catcctggac gtgtacatct ttctgggacc 2640
cgagcctaag agcgtggtgc agcagtatct ggatgtcgtg ggctaccct tcatgcctcc 2700
ttattggggc ctgggcttcc acctgtgtag atggggatac agctccaccg ccatcaccag 2760
acaggtggtg gaaaacatga cccggggctca cttcccactg gatgtgcagt ggaacgacct 2820
ggactacatg gactcagac gggacttcac ctttaacaag gacggcttca gagacttccc 2880
cgccatggtg caagaactgc atcaaggcgg cagacggtac atgatgatcg tggatcctgc 2940
catctcttct agcggccctg ccggaagcta cagaccttat gatgagggcc tgagaagagg 3000
cgtgttcatc accaatgaga caggccagcc tctgatcggc aaagtgtggc ctggaagcac 3060
cgcctttcca gacttcacca tccaaccgc tctggcttgg tgggaagata tggtggccga 3120
gttccacgat caggtgccct tcgatggcat gtggatcgac atgaacgagc cagcaacttt 3180
catcaggggc agcgaggatg gctgcccaa caacgaactg gaaaatcctc cttacgtgcc 3240
aggcgttgtc ggaggaacac tgcaggccgc cacaatttgt gccagcagcc atcagtttct 3300
gagcacccac tacaacctga cggcccatt cggcctgaga aaacctgta cccctcatcag 3360
agccctggtt aaggcagag gcacccggcc ttttgtgatc agcagaagca catttgccgg 3420
ccacggcaga tatgccggac attggacagg ggacgtttgg tctagttggg agcagctggc 3480
ctctagcgtc cccgagatcc tgcagtttaa tctgctggga gtgccctcg tgggagccga 3540
tgtttgtgga tttctgggca acacctccga ggaactgtgc gtcagatgga cacagctggg 3600
cgccttctat cccttcatga gaaaccacaa cagcctgctc agcctgcctc aagagcctta 3660
cagctttagc gaaccgcac agcaggccat gagaaaggcc ctgactctga gatacgctct 3720
gctgcccccac ctgtacaccc tgtttcatca agctcatgtg gccggcgaga cagtggccag 3780
accactgttt ctggaattcc ccaaggacag cagcacctgg acagtggatc atcagctgct 3840
ctggggagaa gccctgctca ttacacctgt gctgcaggct ggcaaggccg aagtgacagg 3900
atacttccc tccggcacgt ggtacgacct cagacagtt cagtgggatg tctgggataca 3960
tctgcctcca cctcctgctg ctccctagaga gcctgccatt cactctgaag gccagtgggt 4020
tacactgccc gctccactgg acaccatcaa tgtgcacctg agagcggct acatcatccc 4080
tctgcaaggc cctggactga ccacaaccga aagcagacag cagccaatgg ctctggccgt 4140
ggctctgaca aaggcggag aagctagagg cgaactgttc tgggatgacg gcgagagcct 4200
ggaagtgctg gaacggggag cctacacaca agtgatcttc ctcgcccgga acaacaccat 4260
```

-continued

```
cgtgaacgaa ctcgtcagag tgaccagtga aggtgccgga ctgcagctcc agaaagtgac   4320
agtgcttgga gtggccacag cacccccagca ggttttgtct aatggcgtgc ccgtgtccaa   4380
cttcacatac agccctgaca ccaaggtgct ggacatctgt gtgtctctgc tgatgggcga   4440
gcagttcctg gtgtcctggt gttgacctag gaataaaaga tctttatttt cattagatct   4500
gtgtgttggt tttttgtgtg acccgtctga ttttgtaggt aaccacgtgc ggaccgagcg   4560
gccgcaggaa cccctagtga tggagttggc cactccctct ctgcgcgctc gctcgctcac   4620
tgaggccggg cgaccaaagg tcgcccgacg cccgggcttt gcccgggcgg cctcagtgag   4680
cgagcgagcg cgcagctgcc tgcaggggcg cctgatgcgg tattttctcc ttacgcatct   4740
gtgcggtatt tcacaccgca tacgtcaaag caaccatagt acgcgccctg tagcggcgca   4800
ttaagcgcgg cgggtgtggt ggttacgcgc agcgtgaccg ctacacttgc cagcgcccta   4860
gcgcccgctc ctttcgcttt cttcccttcc tttctcgcca cgttcgccgg ctttccccgt   4920
caagctctaa atcgggggct ccctttaggg ttccgattta gtgctttacg gcacctcgac   4980
cccaaaaaac ttgatttggg tgatggttca cgtagtgggc catcgccctg atagacggtt   5040
tttcgccctt tgacgttgga gtccacgttc tttaatagtg gactcttgtt ccaaactgga   5100
acaacactca accctatctc gggctattct tttgatttat aagggatttt gccgatttcg   5160
gcctattggt taaaaaatga gctgatttaa caaaaattta acgcgaattt taacaaaata   5220
ttaacgttta caattttatg gtgcactctc agtacaatct gctctgatgc cgcatagtta   5280
agccagcccc gacacccgcc aacacccgct gacgcgccct gacgggcttg tctgctcccg   5340
gcatccgctt acagacaagc tgtgaccgtc tccgggagct gcatgtgtca gaggttttca   5400
ccgtcatcac cgaaacgcgc gagacgaaag ggcctcgtga tacgcctatt tttataggtt   5460
aatgtcatga taataatggt ttcttagacg tcaggtggca ctttttcgggg aaatgtgcgc   5520
ggaacccta tttgtttatt tttctaaata cattcaaata tgtatccgct catgagacaa   5580
taaccctgat aaatgcttca ataatattga aaaaggaaga gtatgagtat tcaacatttc   5640
cgtgtcgccc ttattccctt ttttgcggca ttttgccttc ctgtttttgc tcacccagaa   5700
acgctggtga aagtaaaaga tgctgaagat cagttgggtg cacgagtggg ttacatcgaa   5760
ctggatctca acagcggtaa gatccttgag agttttcgcc ccgaagaacg ttttccaatg   5820
atgagcactt ttaaagttct gctatgtggc gcggtattat cccgtattga cgccgggcaa   5880
gagcaactcg gtcgccgcat acactattct cagaatgact tggttgagta ctcaccagtc   5940
acagaaaagc atcttacgga tggcatgaca gtaagagaat tatgcagtgc tgccataacc   6000
atgagtgata acactgcggc caacttactt ctgacaacga tcggaggacc gaaggagcta   6060
accgcttttt tgcacaacat gggggatcat gtaactcgcc ttgatcgttg ggaaccggag   6120
ctgaatgaag ccataccaaa cgacgagcgt gacaccacga tgcctgtagc aatggcaaca   6180
acgttgcgca aactattaac tggcgaacta cttactctag cttcccggca acaattaata   6240
gactggatgg aggcggataa agttgcagga ccacttctgc gctcggccct tccggctggc   6300
tggtttattg ctgataaatc tggagccggt gagcgtgggt ctcgcggtat cattgcagca   6360
ctggggccag atggtaagcc ctcccgtatc gtagttatct acacgacggg gagtcaggca   6420
actatggatg aacgaaatag acagatcgct gagataggtg cctcactgat taagcattgg   6480
taactgtcag accaagttta ctcatatata ctttagattg atttaaaact tcattttaa   6540
tttaaaagga tctaggtgaa gatccttttt gataatctca tgaccaaaat cccttaacgt   6600
gagttttcgt tccactgagc gtcagacccc gtagaaaaga tcaaaggatc ttcttgagat   6660
ccttttttc tgcgcgtaat ctgctgcttg caaacaaaaa aaccaccgct accagcggtg   6720
gtttgtttgc cggatcaaga gctaccaact cttttttccga aggtaactgg cttcagcaga   6780
gcgcagatac caaatactgt ccttctagtg tagccgtagt taggccacca cttcaagaac   6840
tctgtagcac cgcctacata cctcgctctg ctaatcctgt taccagtggc tgctgccagt   6900
ggcgataagt cgtgtcttac cgggttggac tcaagacgat agttaccgga taaggcgcag   6960
cggtcgggct gaacgggggg ttcgtgcaca gcccagct tggagcgaac gacctacacc   7020
gaactgagat acctacagcg tgagctatga gaaagcgcca cgcttcccga agggagaaag   7080
gcggacaggt atccggtaag cggcagggtc ggaacaggag agcgcacgag ggagcttcca   7140
gggggaaacg cctggtatct ttatagtcct gtcgggtttc gccacctctg acttgagcgt   7200
cgatttttgt gatgctcgtc aggggggcgg agcctatgga aaaacgccag caacgcggcc   7260
tttttacggt tcctggcctt ttgctggcct tttgctcaca tgt                   7303
```

```
SEQ ID NO: 131         moltype = DNA   length = 7224
FEATURE                Location/Qualifiers
misc_feature           1..7224
                       note = plasmid
                       pAAVss-CRE64-SKCRM4-hDES1.4kb-MVM-hMTM1co-SynthpA
source                 1..7224
                       mol_type = other DNA
                       organism = synthetic construct
SEQUENCE: 131
cctgcaggca gctgcgcgct cgctcgctca ctgaggccgc ccgggcaaag cccgggcgtc   60
gggcgacctt tggtcgcccg gcctcagtga gcgagcgagc gcgcagagag ggagtggcca   120
actccatcac taggggttcc tgcggccgc caccggtgc tgcaacgca cgttaagcac   180
cgttaagcac aagctggcag ggcctctcct ctcccttctc agatttgctc cttgacattt   240
gcctgctgcc tggcggtggc aacagctggg gcggggcgcg cgcaggaggc cccgtaaccc   300
tatcccgct ccggctccct cgtgaaaccg gagcttccct gccttggccg aggggggaggg   360
ctgcggggc cagaccgcct gcgaagacca cagggttttt cctctcgggg tttggctccc   420
gtgggatgga tgtggctgtg cgggggggttg gcctgagctt cgcttctaag ccagcagctt   480
ggtcagggaa acctgaaagc attcccagct aatcccccaa gtggtgcaag tctgtgcgcg   540
cccatcccgc tgagtaaggc ggtggggcgc gccacgcgtt tctgagtcct ctaaggtccc   600
tcactcccaa ctcagcccca tgtcctgtca attcccactc agtgtctgat ctccttctcc   660
tcacctttcc catctcccgt ttgacccaag cttcctgagc tctcctccca ttcccctttt   720
tggagtcctc ctcctctccc agaacccagt aataagtggg ctctcccctg gcctgaaccc   780
ccgtggtaac cctataaggc gaggcagctg ctgtctgagg cagggagggg ctggtgtggg   840
aggctaaggg cagctgctaa gtttaggggt gctccttctc tcttcttaga caacaggt   900
ggctggggcc tcagtgccca gaaaagaaaa tgtcttagag gtatcggcat gggcctggag   960
gagggggac agggcagggg gaggcatctt cctcaggaca tcgggtccta gaggggtacc   1020
caacgggtta cgacacacct actagtaacc cctccagctg gtgatggcag gtctagggta   1080
```

-continued

```
ggaccagtga ctggctccta atcgagcact ctattttcag ggtttgcatt ccaaaagggt   1140
caggtccaag agggacctgg agtgccaagt ggaggtgtag aggcacggcc agtacccatg   1200
gagaatggtg gatgtcctta ggggttagca agtgccgtgt gctaaggagg gggctttgga   1260
ggttgggcag gccctctgtg gggctccatt tttgtggggg tgggggctgg agcattatag   1320
ggggtgggaa gtgattgggg ctgtcaccct agccttcctt atctgacgcc cacccatgcc   1380
tcctcaggta cccctgccc cccacagctc ctctcctgtg ccttgtttcc cagccatgcg   1440
ttctcctcta taaatacccg ctctggtatt tggggttggc agctgtttgct gccagggaga   1500
tggttgggtt gacatgcggc tcctgacaaa acacaaaccc ctggtgtgtg tgggcgtggg   1560
tggtgtgagt aggggatga atcagggagg gggcggggga cccaggggc aggagccaca   1620
caaagtctgt gcggggtgg gagcgcacat agcaattgga aactgaaagc ttatcagacc   1680
ctttctggaa atcagcccac tgtttataaa cttgaggccc caccctcgac agtaccgggg   1740
aggaagaggg cctgcactag tccagaggga aactgaggct cagggctagc tcgcccatag   1800
acatacatgg caggcaggct ttggccagga tccctccgcc tgccaggcgt ctccctgccc   1860
tcccttcctg cctagagacc cccaccctca agcctggctg gtctttgcct gagacccaaa   1920
cctcttcgac ttcaagagaa tatttaggaa caaggtggt tagggccttt cctgggaaca   1980
ggccttgacc ctttaagaaa tgacccaaag tctctccttg accaaaaagg ggaccctcaa   2040
actaaaggga agcctctctt ctgctgtctc ccctgacccc actcccccc accccaggac   2100
gaggagataa ccagggctga aagaggcccg cctgggggct gcagacatgc ttgctgcctg   2160
ccctggcgaa ggattggcag gcttgcccgt cacaggaccc ccgctggctg actcaggggc   2220
gcaggcctct tgcggggggag ctggcctccc cgccccacg gccacgggcc gcctttcct   2280
ggcaggacag cgggatcttg cagctgtcag gggaggggag gcggggggctg atgtcaggag   2340
ggatacaaat agtgccgacg gctggggggcc ctgtctcccc tcgccgcatc cactctccgg   2400
ccggccgcct gcccgccgcc tcctccgtgc gcccgccagc ctcgcccgcg ccgtcacctc   2460
tagaactagt aagaggtaag ggtttaaggg atggttggtt ggtgggggtat taatgtttaa   2520
ttacctggag cacctgcctg aaatcacttt ttttcaggtt ggcgtacggc caccatggcc   2580
agcgccacga caagcaagta caacagccac agcctggaaa acgagagcat caagcggacc   2640
agcagagatg gcgtgaacag agatctgacc gaggccgttc ctagactgcc tggcgagaca   2700
ctgatcaccg acaaagaagt gatctacatc tgcccccttca acggcccat caagggaaga   2760
gtgtacatca ccaactaccg gctgtacctg cggtccctgg aaaccgatag cagcctgatt   2820
ctggatgtgc ccctgggcgt gatcagccgg attgaaaaaa tgggcggagc cacctccaga   2880
ggcgagaata gctatggcct ggatatcaca tgcaaggaca tgcggaacct gagattcgcc   2940
ctgaagcaag agggccacag cagacgggac atgttcgaga tcctgaccag atacgccttt   3000
cctctggctc actctctgcc cctgttcgcc ttcctgaacg aagagaagtt caacgtggac   3060
ggctggaccg tgtacaaccc cgtggaagag tatagacggc agggactgcc caatcaccac   3120
tggcggatca ccttcatcaa caagtgctac gagctgtgcg acacataccc cgcactgctg   3180
gtggtgcctt acagagcctc tgacgacgat ctgagaagag tggccacctt tcggagccgg   3240
aacagaatcc ctgtgctgag ctggattcac cccgagaaca agaccgtgat cgtgcggtgt   3300
tctcagcctc tcgtgggcat gagcggcaag agaaacaagg acgacgagaa gtacctggac   3360
gtgatccgcg agacaaacaa gcagatcagc aagctgacca tctacgacgc cagaccttct   3420
gtgaacgccg tggccaacaa agccacaggc ggcggatatg agtccgacga tgcctatcac   3480
aacgccgagc tgttcttcct ggacattcac aacatccatg tgatgcgcga gagcctgaag   3540
aaagtgaagg acatcgtgta ccccaatgtg aagagagcc actggctgtc tagcctggaa   3600
tccacacact ggctggaaca catcaagctg gtgctgacag cgacatcca ggtggcaaac   3660
aaagtgtcta gcggcaagtc tagcgtgctg gtgcactgta gcgacggatg ggatagaaca   3720
gcccagctga catccctggc catgctgatg ctggacagct ctacagatc catcgagggc   3780
tttgagatcc tggtgcagaa gaagtggatc agcttcggcc acaagttcgc ctctagaatc   3840
ggacacggcg acaagaacca caccgacgcc gatagaaccc catcttcct gcagttcatc   3900
gactgcgtgt ggcagatgtc caagcagttc cctaccgcct tcgagttcaa cgagcagttc   3960
ctgatcatca tcctggacca cctgtactct tgcagattcg gcaccttcct gttcaactgc   4020
gagagcgcca gagaacggca gaaagtgacc gagagaaccg tgtctctgtg gtccctgatc   4080
aacagcaaca aagagaaatt caagaacccc ttctacacca aagaaatcaa ccgggtgcta   4140
taccccgtgg ccagcatgag acatctggaa ctgtgggtca actactacat ccggtggaac   4200
cccagaatca agcagcagca gcccaatcct gtggaacagc ggtatatgga actgctggcc   4260
ctgcgggacg agtacatcaa gagactggaa gaactgcagc tggccaacag cgccaagctg   4320
agcgatcctc ctacaagccc tagcagcccc tctcagatga tgccccatgt gcagacccac   4380
tttttgaccta ggaataaaag atctttattt tcattagatc tgtgtgttgg ttttttgtgt   4440
gacccgtctg attttgtagg taaccacgtg cggaccgagc ggccgcagga accctagtg   4500
atggagttgg ccactcctc tctgcgcgct cgctcgctca ctgaggccgg gcgaccaaag   4560
gtcgcccgac gcccgggctt tgcccggggcg gcctcagtga gcgagcgagc gcgcagctgc   4620
ctgcaggggc gcctgatgcg gtattttctc cttacgcatc tgtgcggtat ttcacaccgc   4680
atacgtcaaa gcaaccatag tacgcgccct gtagcggcgc attaagcgcg gcgggtgtgg   4740
tggttacgcg cagcgtgacc gctacacttg ccagcgccct agcgcccgct cctttcgctt   4800
tcttcccttc ctttctcgcc acgttcgccg gctttcccg tcaagctcta aatcgggggc   4860
tccctttagg gttccgattt agtgctttac ggcacctcga ccccaaaaaa cttgatttgg   4920
gtgatggttc acgtagtggg ccatcgccct gatagacggt ttttcgccct ttgacgttgg   4980
agtccacgtt ctttaatagt ggactcttgt tccaaactgg aacaacactc aaccctatct   5040
cgggctattc ttttgattta aaggggattt tgccgatttc ggcctattgg ttaaaaaatg   5100
agctgatttta acaaaaattt aacgcgaatt ttaacaaaat attaacgttt acaattttat   5160
ggtgcactct cagtacaatc tgctctgatg ccgcatagtt aagccagccc cgacacccgc   5220
caacacccgc tgacgcgccc tgacgggctt gtctgctccc ggcatccgct tacagacaag   5280
ctgtgaccgt ctccgggagc tgcatgtgtc agaggttttc accgtcatca ccgaaacgcg   5340
cgagacgaaa gggcctcgtg atacgcctat ttttataggt taatgtcatg ataataatgg   5400
tttcttagac gtcaggtggc actttcggg gaaatgtgcg cggaacccct atttgtttat   5460
ttttctaaat acattcaaat atgtatccgc tcatgagaca ataaccctga taaatgcttc   5520
aataatattg aaaaaggaag agtatgagta ttcaacattt ccgtgtcgcc cttattccct   5580
tttttgcggc attttgcctt cctgtttttg ctcacccaga aacgctggtg aaagtaaaag   5640
atgctgaaga tcagttgggt gcacgagtgg gttacatcga actggatctc aacagcggta   5700
agatccttga gagttttcgc cccgaagaac gttttccaat gatgagcact tttaaagttc   5760
tgctatgtgg cgcggtatta tcccgtattg acgccgggca agagcaactc ggtcgccgca   5820
```

-continued

```
tacactattc tcagaatgac ttggttgagt actcaccagt cacagaaaag catcttacgg  5880
atggcatgac agtaagagaa ttatgcagtg ctgccataac catgagtgat aacactgcgg  5940
ccaacttact tctgacaacg atcggaggac cgaaggagct aaccgctttt ttgcacaaca  6000
tgggggatca tgtaactcgc cttgatcgtt gggaaccgga gctgaatgaa gccataccaa  6060
acgacgagcg tgacaccacg atgcctgtag caatggcaac aacgttgcgc aaactattaa  6120
ctggcgaact acttactcta gcttcccggc aacaattaat agactggatg gaggcggata  6180
aagttgcagg accacttctg cgctcggccc ttccggctgg ctggtttatt gctgataaat  6240
ctggagccgg tgagcgtggg tctcgcggta tcattgcagc actggggcca gatggtaagc  6300
cctcccgtat cgtagttatc tacacgacgg ggagtcaggc aactatggat gaacgaaata  6360
gacagatcgc tgagataggt gcctcactga ttaagcattg gtaactgtca gaccaagttt  6420
actcatatat actttagatt gatttaaaac ttcattttta atttaaaagg atctaggtga  6480
agatcctttt tgataatctc atgaccaaaa tcccttaacg tgagttttcg ttccactgag  6540
cgtcagaccc cgtagaaaag atcaaaggat cttcttgaga tcctttttttt ctgcgcgtaa  6600
tctgctgctt gcaaacaaaa aaaccaccgc taccagcggt ggtttgtttg ccggatcaag  6660
agctaccaac tctttttccg aaggtaactg gcttcagcag agcgcagata ccaaatactg  6720
tccttctagt gtagccgtag ttaggccacc acttcaagaa ctctgtagca ccgcctacat  6780
acctcgctct gctaatcctg ttaccagtgg ctgctgccag tggcgataag tcgtgtctta  6840
ccgggttgga ctcaagacga tagttaccgg ataaggcgca gcggtcgggc tgaacggggg  6900
gttcgtgcac acagcccagc ttggagcgaa cgacctacac cgaactgaga tacctacagc  6960
gtgagctatg agaaagcgcc acgcttcccg aagggagaaa ggcggacagg tatccggtaa  7020
gcggcagggt cggaacagga gagcgcacga gggagcttcc agggggaaac gcctggtatc  7080
tttatagtcc tgtcgggttt cgccacctct gacttgagcg tcgatttttg tgatgctcgt  7140
caggggggcg gagcctatgg aaaaacgcca gcaacgcggc cttttacgg ttcctggcct  7200
tttgctggcc ttttgctcac atgt  7224
```

SEQ ID NO: 132        moltype = DNA   length = 6780
FEATURE               Location/Qualifiers
misc_feature         1..6780
                      note = plasmid pAAVss-CSkSH5-SPc5-12GTRM-MVM-hGAAco-SynthpA
source               1..6780
                      mol_type = other DNA
                      organism = synthetic construct
SEQUENCE: 132

```
cctgcaggca gctgcgcgct cgctcgctca ctgaggccgc ccgggcaaag cccgggcgtc  60
gggcgacctt tggtcgcccg gcctcagtga gcgagcgagc gcgcagagag ggagtggcca  120
actccatcac taggggttcc tgcggccgca cgcgtaccgg tcagtttact caccaggat  180
tcagaggcag cactgctgaa ccctgagccc ttggcacatc aggttggctg tcagaagtcg  240
gcctttgtac atacacagtt cccttgtgag gcccagctgc gtgtcctagg agcggggcct  300
ctctccacag cagagctcag cctctcaagt gtatggacag cacgggtgcc tgatgggtgg  360
atttagccat gagttgaagg tggcttgggg agaatgagag ttctagagat agggagaagg  420
ggttgccaat aggagagtgg aattcctgag cacctcgtca caggcagccg acagaacatg  480
agccgcaggg cccaggctat ttatacctcg cctgtcacta tcagggtccc cacagctccc  540
cccacctcca gccacacaca gcaggtcctt ttgctcttc tggtcccttc tctactcctc  600
ccctccctta cctaaggtac ccaacccgtt acgtggccac cgccttcggc accatcctca  660
cgacacccaa atatgcgac gggtgaggaa tggtggggag ttattttag agcggtgagg  720
aaggtgggca ggcagcaggt gttggcgctc taaaaataac tcccgggagt tattttaga  780
gcggaggaat ggtggacacc caaatatggc gacggttcct cacccgtcgc catatttggg  840
tgtccgccct cggccggggc cgcattcctg ggggccgggc ggtgctcccg cccgcctcga  900
taaaaggctc cggggccggc ggcggcccac gagctacccg gaggagcggg aggcgccaag  960
ctctagatct agaactagta agaggtaagg gtttaaggga tggttggttg gtggggtatt  1020
aatgtttaat tacctggagc acctgcctga aatcactttt tttcaggttg gcgtacggcc  1080
accatgggcg tcagacatcc tccatgttct cacagactgc tggccgtgtg tgctctggtg  1140
tctcttgcta cagctgccct gctgggacat atcctgctgc acgattttct gctggtgccc  1200
agagagctgt ctggcagctc tcctgtgctg gaagaaacac accctgcaca tcagcagggc  1260
gcctctagac ctggacctag agatgctcaa gcccatcctg cagacctagg accgtgcct  1320
acacagtgtg acgtgccacc taacagcaga ttcgactgcg ccctgacaa ggccatcaca  1380
caagagcagt gtgaagccag aggctgctgc tacattcctg ccaaacaagg actgcagggc  1440
gctcagatgg acagccttg gtgcttcttc ccaccatctt accccagcta caagctggaa  1500
aacctgagca gcagcgagat gggctacacc gccacactga ccagaaccac acctacattc  1560
ttcccaaagg acatcctgac actgcggctg gacgtgatga tggaaaccga gaaccggctg  1620
cacttcacca tcaaggaccc cgccaataga agatacgagg tgcccctgga aaccctcac  1680
gtgcactcta gagccccatc tccactgtac agcgtggaat tcagcgagga acctttggc  1740
gtgatcgtgc ggagacagct ggatggcaga gtgctgctga ataccacagt ggcccctctg  1800
ttcttcgccg accagttct gcagctgagc acaagcctgc ctagccagta tatcacaggc  1860
ctggccgaac acctgtctcc actgatgctg agcaccagct ggaccagaat caccctgtgg  1920
aacagagatc tggcccctac acctggcgcc aatctgtacg gctctcaccc ttttttatctg  1980
gccctggaag atggcggaag cgcccacggt gtctttctgc tgaacagcaa cgccatggac  2040
gtggtgctgc aaccatctcc tgctctgtct tggagaagca ccggcggcat cctggacgtg  2100
tacatctttc tgggacccga gcctaagagc gtggtgcagc agatactgga tgtcgtgggc  2160
taccccttca tgcctcctta ttggggcctg ggcttccacc tgtgtagatg gggatacagc  2220
tccaccgcca tcaccagaca ggtggtggaa aacatgaccc gggctcactt cccactggat  2280
gtgcagtgga acgacctgga ctacatggac tccagacggg acttcaccct taacaaggac  2340
ggcttcagag acttccccgc catggtgcaa gaactgcatc aaggcggcag acggtacatg  2400
atgatcgtgg atccgccat ctcttctagc gcccctgccg gaagctacag accttatgat  2460
gagggcctga aagaggcgt gttcatcacc aatgagacag gccagcctct gatcggcaaa  2520
gtgtggcctg gaagcaccgc ctttccagac ttcaccaatc caaccgctct ggcttggtgg  2580
gaagatatgg tggccgagtt ccacgatcag gtgcccttcg atggcatgtg gatcgacatg  2640
aacgagccca gcaacttcat caggggcagc gaggatggct gccccaacaa cgaactggaa  2700
aatcctcctt acgtgccagg cgttgtcgga ggaacactgc aggccgccac aatttgtgcc  2760
```

-continued

```
agcagccatc agtttctgag cacccactac aacctgcaca acctgtacgg cctgaccgag  2820
gccattgcct ctcatagagc cctggttaag gccagaggca cccggccttt tgtgatcagc  2880
agaagcacat ttgccggcca cggcagatat gccggacatt ggacagggga cgtttggtct  2940
agttgggagc agctggcctc tagcgtgccc gagatcctgc agtttaatct gctgggagtg  3000
cccctcgtgg gagccgatgt ttgtggattt ctgggcaaca cctccgaaga actgtgcgtc  3060
agatggacac agctgggcgc cttctatccc ttcatgagaa accacaacag cctgctgagc  3120
ctgcctcaag agccttacag ctttagcgaa cccgcacagc aggccatgag aaaggccctg  3180
actctgagat acgctctgct gccccacctg tacaccctgt ttcatcaagc tcatgtggcc  3240
ggcgagacag tggccagacc actgtttctg gaattcccca aggacagcag cacctggaca  3300
gtggatcatc agctgctctg gggagaagcc ctgctcatta cacctgtgct gcaggctggc  3360
aaggccgaag tgacaggata ctttcccctc ggcacttggt acgacctgca gacagttcct  3420
gtggaagctc tgggatctct gcctccacct cctgctgctc ctagagagcc tgccattcac  3480
tctgaaggcc agtgggttac actgcccgct ccactggaca ccatcaatgt gcacctgaga  3540
gccggctaca tcatccctct gcaaggccct ggactgacca caaccgaaag cagacagcag  3600
ccaatggctc tggccgtggc tctgacaaaa ggcggagaag ctagaggcga actgttctgg  3660
gatgacggcg agagcctgga agtgctgaa cggggagcct acacacaagt gatctttctc  3720
gcccggaaca acaccatcgt gaacgaactc gtcagagtga ccagtgaagg tgccggactg  3780
cagctcccaga aagtgacagt gcttggagtg gccacagcac ccagcaggt tttgtctaat  3840
ggcgtgcccg tgtccaactt cacatacagc cctgacacca aggtgctgga catctgtgtg  3900
tctctgctga tgggcgagca gttcctggtg tcctggtgtt gacctaggaa taaaagatct  3960
ttattttcat tagatctgtg tgttggtttt ttgtgtgacc cgtctgattt tgtaggtaac  4020
cacgtgcgga ccgagcggcc gcaggaaccc ctagtgatgg agttggccac tccctctctg  4080
cgcgctcgct cgctcactga ggccgggcga ccaaaggtcg cccgacgccc gggctttgcc  4140
cgggcggcct cagtgagcga gcgagcgcgc agctgcctgc aggggcgcct gatgcggtat  4200
tttctcctta cgcatctgtg cggtatttca caccgcatac gtcaaagcaa ccatagtacg  4260
cgccctgtag cggcgcatta agcgcggcgg gtgtggtggt tacgcgcagc gtgaccgcta  4320
cacttgccag cgccctagcg cccgctcctt tcgctttctt cccttccttt ctcgccacgt  4380
tcgccggctt tccccgtcaa gctctaaatc ggggggctccc tttagggttc cgatttagtg  4440
ctttacggca cctcgacccc aaaaaacttg atttgggtga tggttcacgt agtgggccat  4500
cgccctgata gacggttttt cgccctttga cgttggagtc cacgttcttt aatagtggac  4560
tcttgttcca aactggaaca acactcaacc ctatctcggg ctattctttt gatttataag  4620
ggattttgcc gatttcggcc tattggttaa aaaatgagct gatttaacaa aaatttaacg  4680
cgaatttaa caaaatatta acgtttacaa ttttatggtg cactctcagt acaatctgct  4740
ctgatgccgc atagttaagc cagccccgac acccgccaac acccgctgac gcgccctgac  4800
gggcttgtct gctcccggca tccgcttaca gacaagctgt gaccgtctcc gggagctgca  4860
tgtgtcagag gttttcaccg tcatcaccga aacgcgcgag acgaaagggc ctcgtgatac  4920
gcctattttt ataggttaat gtcatgataa taatggtttc ttagacgtca ggtggcactt  4980
ttcggggaaa tgtgcgcgga acccctattt gtttattttt ctaaatacat tcaaatatgt  5040
atccgctcat gagacaataa ccctgataaa tgcttcaata atattgaaaa aggaagagta  5100
tgagtattca acatttccgt gtcgccctta ttcccttttt tgcggcattt tgccttcctg  5160
tttttgctca cccagaaacg ctggtgaaag taaaagatgc tgaagatcag ttgggtgcac  5220
gagtgggtta catcgaactg gatctcaaca gcggtaagat ccttgagagt tttcgccccg  5280
aagaacgttt tccaatgatg agcacttttta aagttctgct atgtggcgcg gtattatccc  5340
gtattgacgc cgggcaagag caactcggtc gccgcataca ctattctcag aatgacttgg  5400
ttgagtactc accagtcaca gaaaagcatc ttacggatgg catgacagta agagaattat  5460
gcagtgctgc cataaccatg agtgataaca ctgcggccaa cttacttctg acaacgatcg  5520
gaggaccgaa ggagctaacc gcttttttgc acaacatggg ggatcatgta actcgccttg  5580
atcgttggga accggagctg aatgaagcca taccaaacga cgagcgtgac accacgatgc  5640
ctgtagcaat ggcaacaacg ttgcgcaaac tattaactgg cgaactactt actctagctt  5700
cccggcaaca attaatagac tggatggagg cggataaagt tgcaggacca cttctgcgct  5760
cggcccttcc ggctggctgg tttattgctg ataaatctg agccggtgag cgtgggtctc  5820
gcggtatcat tgcagcactg gggccagatg gtaagccctc ccgtatcgta gttatctaca  5880
cgacgggag tcaggcaact atggatgaac gaaatagaca gatcgctgag ataggtgcct  5940
cactgattaa gcattggtaa ctgtcagacc aagtttactc atatatactt tagattgatt  6000
taaaacttca ttttttaattt aaaaggatct aggtgaagat cctttttgat aatctcatga  6060
ccaaaatccc ttaacgtgag ttttcgttcc actgagcgtc agaccccgta gaaaagatca  6120
aaggatcttc ttgagatcct tttttttctgc gcgtaatctg ctgcttgcaa acaaaaaaac  6180
caccgctacc agcggtggtt tgtttgccgg atcaagagct accaactctt tttccgaagg  6240
taactggctt cagcagagcg cagataccaa atactgtag tctagtgtag ccgtagttag  6300
gccaccactt caagaactct gtagcaccgc ctacatacct cgctctgcta atcctgttac  6360
cagtggctgc tgccagtggc gataagtcgt gtcttaccgg gttggactca agacgatagt  6420
taccggataa ggcgcagcgg tcgggctgaa cggggggttc gtgcacacag cccagcttgg  6480
agcgaacgac ctacaccgaa ctgagatacc tacagcgtga gctatgagaa agcgccacg  6540
ttcccgaagg gagaaaggcg gacaggtatc cggtaagcgg cagggtcgga acaggagagc  6600
gcacgaggga gcttccaggg ggaaacgcct ggtatcttta gtgtcctgtc gggtttcgcc  6660
acctctgact tgagcgtcga tttttgtgat gctcgtcagg ggggcggagc ctatggaaaa  6720
acgccagcaa cgcggccttt ttacggttcc tggccttttg ctggcctttt gctcacatgt  6780
```

```
SEQ ID NO: 133       moltype = DNA  length = 6780
FEATURE              Location/Qualifiers
misc_feature        1..6780
                    note = plasmid pAAVss-CSkSH5-SPc5-12GTRM-MVM-hGAA-SynthpA
source              1..6780
                    mol_type = other DNA
                    organism = synthetic construct
SEQUENCE: 133
cctgcaggca gctgcgcgct cgctcgctca ctgaggccgc ccgggcaaag cccggcgtc  60
gggcgacctt tggtcgcccg gcctcagtga gcgagcgagc gcgcagagag ggagtggcca  120
actccatcac taggggttcc tgcggccgca cgcgtaccgg tcagtttact caccagggat  180
```

-continued

```
tcagaggcag cactgctgaa ccctgagccc ttggcacatc aggttggctg tcagaagtcg    240
gcctttgtac atacacagtt cccttgtgag gcccagctgc gtgtcctagg agcggggcct    300
ctctccacag cagagctcag cctctcaagt gtatggacag cacgggtgcc tgatgggtgg    360
atttagccat gagttgaagg tggcttgggg agaatgagag ttctagagat agggagaagg    420
ggttgccaat aggagagtgg aattcctgag cacctcgtca caggcagccg acagaacatg    480
agccgcaggg cccaggctat ttataccctcg cctgtcacta tcagggtccc cacagctccc    540
cccacctcca gccacacaca gcaggtcctt ttgctctttc tggtcccttc tctactcctc    600
cccctcccta cctaaggtac ccaacccgtt acgtggccac cgccttcggc accatcctca    660
cgacacccaa atatggcgac gggtgaggaa tggtggggag ttattttag agcggtgagg    720
aaggtgggca ggcagcaggt gttggcgctc taaaaataac tcccgggagt tattttaga    780
gcggaggaat ggtggacacc caaatatggc gacggttcct caccctcgtcgc catatttggg    840
tgtccgccct cggccggggc cgcattcctg ggggccgggc ggtgctcccg cccgcctcga    900
taaaaggctc cggggccggc ggcggccac gagctacccg gaggagcggg aggcgccaag    960
ctctagatct agaactagta agaggtaagg gtttaaggga tggttggttg gtggggtatt    1020
aatgtttaat tacctggagc acctgcctga aatcactttt tttcaggttg gcgtacggcc    1080
accatgggag tgaggcaccc gccctgctcc caccggctcc tggccgtctg cgccctcgtg    1140
tccttggcaa ccgctgcact cctggggcac atcctactcc atgatttcct gctggttccc    1200
cgagagctga gtggctcctc cccagtcctg gaggagactc acccagctca ccagcaggga    1260
gccagcagac cagggccccg ggatgcccag gcacaccccg gccgtcccag agcagtgccc    1320
acacagtgcg acgtcccccc caacagccgc ttcgattgcg cccctgacaa ggccatcacc    1380
caggaacagt gcgaggcccg cggctgttgc tacatccctg caaagcaggg gctgcaggga    1440
gcccagatgg ggcagccctg gtgcttcttc ccacccagct accccagcta caagctggag    1500
aacctgagct cctctgaaat gggctacacg gccaccctga cccgtaccac ccccacctc    1560
ttccccaagg acatcctgac cctgcggctg gacgtgatga tggagactga gaaccgcctc    1620
cacttcacga tcaaagatcc agctaacagg cgctacgagg tgcccttgga gacccccat    1680
gtccacagcc gggcaccgtc cccactctac agcgtgaagt tctccgagga gcccttcggg    1740
gtgatcgtgc gccggcagct ggacggccgc gtgctgctga acacgacggt ggcgcccctg    1800
ttctttgcgg accagttcct tcagctgtcc acctcgctgc cctcgcagta tatcacaggc    1860
ctcgccgagc acctcagtcc cctgatgctc agcaccagct ggaccaggat caccctgtgg    1920
aaccgagacc ttgcgcccac gcccggtgcg aacctctacg ggtctcaccc tttctacctg    1980
gcgctggagg acggcgggtc ggcacacggg gtgttcctgc taaacagcaa tgccatggat    2040
gtggtcctgc agccgagccc tgccccttagc tggaggtcga caggtgggat cctggatgtc    2100
tacatcttcc tgggcccaga gcccaagagc gtggtcagc agtacctgga cgttgtggga    2160
tacccgttca tgcgccgcata ctggggcctg ggcttccacc tgtgccgctg gggctactcc    2220
tccaccgcta tcacccgcca ggtggtggag aacatgacca gggcccactt ccccctggac    2280
gtccagtgga acgacctgga ctacatggac tcccggaggg acttcacgtt caacaaggat    2340
ggcttccggg acttcccggc catggtgcag gagctgcacc agggcggccg gcgctacatg    2400
atgatcgtgg atcctgccat cagcagctcg ggccctgccg ggagctacag gccctacgac    2460
gagggtctgc ggaggggggt tttcatcacc aacgagaccg gccagccgct gattgggaag    2520
gtatggcccg ggtccactgc cttccccgac ttcaccaacc ccacagccct ggcctggtgg    2580
gaggacatgg tggctgagtt ccatgaccag gtgcccttcg acggcatgtg gattgacatg    2640
aacgagcctt ccaacttcat caggggctct gaggacggct gccccaacaa tgagctggag    2700
aacccaccct acgtgcctgg ggtggttggg gggaccctcc aggcggccac catctgtgcc    2760
tccagccacc agtttctctc cacacactac aacctgcaca acctctacgg cctgaccgaa    2820
gccatcgcct cccacaggggc gctggtgaag gctcggggga cacgcccatt tgtgatctcc    2880
cgctcgacct ttgctggcca cggccgatac gccggccact ggacgggga cgtgtggagc    2940
tcctgggagc agctcgcctc ctccgtgcca gaaatcctgc agtttaacct gctggggggtg    3000
cctctggtcg gggccgacgt ctgcggcttc ctgggcaaca cctcagagga gctgtgtgtg    3060
cgctggaccc agctgggggc cttctacccc ttcatgcgga accacaacag cctgctcagt    3120
ctgcccagg agccgtacag cttcagcgag ccggcccagc aggccatgag gaaggccctc    3180
acctgcgct acgcactcct cccccacctc tacacactgt tccaccagge ccacgtgcgg    3240
ggggagaccg tggcccggcc cctcttcctg gagttcccca aggactctag cacctggact    3300
gtggaccacc agctcctgtg ggggggggggc ctgctcatca ccccagtgct ccaggccggg    3360
aaggccgaag tgactggcta cttccccttg ggcacatggt acgacctgca gacggtgcca    3420
gtagagcgcc ttggcagcct cccacccca cctgcagctc cccgtgagcc agccatccac    3480
agcgaggggc agtgggtgac gctgccggcc cccctggaca ccatcaacgt ccacctccgg    3540
gctgggtaca tcatccccct gcagggccct ggcctcacaa ccacagagtc ccgccagcag    3600
cccatgggcc tggctgtggc cctgaccaag ggtgggggagg cccgagggga gctgttctgg    3660
gacgatggag agagcctgga agtgctggag cgagggggct acacacaggt catcttcctg    3720
gccaggaata acacgatcgt gaatgactg gtacgtgtga cagtgaggg agctggcctg    3780
cagctgcaga aggtgactgt cctgggcgtg gccacggcgc cccagcaggt cctctccaac    3840
ggtgtccctg tctccaactt cacctacagc cccgacacca aggtcctgga catctgtgtc    3900
tcgctgttga tgggagagca gtttctcgtc agctggtgtt agcctaggaa taaaagatct    3960
ttattttcat tagatctgtg tgttggtttt ttgtgtgaac cgtctgattt tgtaggtaac    4020
cacgtgcgga ccgagcggcc gcaggaaccc ctagtgatgg agttggccac tccctctctg    4080
cgcgctcgct cgctcactga ggccgggcga ccaaaggtcg cccgacgccc gggctttgcc    4140
cgggcggcct cagtgagcga gcgagcgcgc agctgcctgc aggggcgcct gatgcggtat    4200
tttctcctta cgcatctgtg cggtatttca caccgcatac gtcaaagcaa ccatagtacg    4260
cgccctgtag cggcgcatta agcgcggcgg gtgtggtggt tacgcgcagc gtgaccgcta    4320
cacttgccag cgccctagcg cccgctcctt cgctttctt cccttccttt ctcgccacgt    4380
tcgccggctt tccccgtcaa gctctaaatc ggggctccc tttagggttc cgatttagtg    4440
ctttacggca cctcgacccc aaaaaacttg atttgggtga tggttcacgt agtgggccat    4500
cgccctgata gacggttttt cgccctttga cgttggagtc cacgttcttt aatagtggac    4560
tcttgttcca aactggaaca acactcaacc ctatctcggg ctattctttt gatttataag    4620
ggattttgcc gatttcggcc tattggttaa aaaatgagct gatttaacaa aaatttaacg    4680
cgaatttaa caaaatatta acgtttacaa ttttatggtg cactctcagt acaatctgct    4740
ctgatgccgc atagttaagc cagccccgac acccgccaac acccgctgac gcgccctgac    4800
gggcttgtct gctcccggca tccgcttaca gacaagctgt gaccgtctcc gggagctgca    4860
tgtgtcagag gttttcaccg tcatcaccga aacgcgcgag acgaaagggc ctcgtgatac    4920
```

```
gcctattttt ataggttaat gtcatgataa taatggtttc ttagacgtca ggtggcactt   4980
ttcggggaaa tgtgcgcgga acccctattt gtttattttt ctaaatacat tcaaatatgt   5040
atccgctcat gagacaataa ccctgataaa tgcttcaata atattgaaaa aggaagagta   5100
tgagtattca acatttccgt gtcgccctta ttcccttttt tgcggcattt tgccttcctg   5160
tttttgctca cccagaaacg ctggtgaaag taaaagatgc tgaagatcag ttgggtgcac   5220
gagtgggtta catcgaactg gatctcaaca gcggtaagat ccttgagagt tttcgccccg   5280
aagaacgttt tccaatgatg agcactttta aagttctgct atgtggcgcg gtattatccc   5340
gtattgacgc cgggcaagag caactcggtc gccgcataca ctattctcag aatgacttgg   5400
ttgagtactc accagtcaca gaaaagcatc ttacggatgg catgacagta agagaattat   5460
gcagtgctgc cataaccatg agtgataaca ctgcggccaa cttacttctg acaacgatcg   5520
gaggaccgaa ggagctaacc gcttttttgc acaacatggg ggatcatgta actcgccttg   5580
atcgttggga accggagctg aatgaagcca taccaaacga cgagcgtgac accacgatgc   5640
ctgtagcaat ggcaacaacg ttgcgcaaac tattaactgg cgaactactt actctagctt   5700
cccggcaaca attaatagac tggatggagg cggataaagt tgcaggacca cttctgcgct   5760
cggcccttcc ggctggctgg tttattgctg ataaatctgg agccggtgag cgtgggtctc   5820
gcggtatcat tgcagcactg gggccagatg gtaagccctc ccgtatcgta gttatctaca   5880
cgacggggag tcaggcaact atggatgaac gaaatagaca gatcgctgag ataggtgcct   5940
cactgattaa gcattggtaa ctgtcagacc aagtttactc atatatactt tagattgatt   6000
taaaacttca tttttaattt aaaaggatct aggtgaagat cctttttgat aatctcatga   6060
ccaaaatccc ttaacgtgag ttttcgttcc actgagcgtc agacccgta gaaaagatca   6120
aaggatcttc ttgagatcct ttttttctgc gcgtaatctg ctgcttgcaa acaaaaaaac   6180
caccgctacc agcggtggtt tgtttgccgg atcaagagct accaactctt tttccgaagg   6240
taactggctt cagcagagcg cagataccaa atactgtcct tctagtgtag ccgtagttag   6300
gccaccactt caagaactct gtagcaccgc ctacatacct cgctctgcta tcctgttac    6360
cagtggctgc tgccagtggc gataagtcgt gtcttaccgg gttggactca agacgatagt   6420
taccggataa ggcgcagcgg tcgggctgaa cggggggttc gtgcacacag cccagcttgg   6480
agcgaacgac ctacaccgaa ctgagatacc tacagcgtga gctatgagaa agcgccacgc   6540
ttcccgaagg gagaaaggcg gacaggtatc cggtaagcgg cagggtcgga acaggagagc   6600
gcacgaggga gcttccaggg ggaaacgcct ggtatcttta tagtcctgtc gggtttcgcc   6660
acctctgact tgagcgtcga tttttgtgat gctcgtcagg ggggcggagc ctatggaaaa   6720
acgccagcaa cgcggccttt ttacggttcc tggccttttg ctggcctttt gctcacatgt   6780
```

```
SEQ ID NO: 134           moltype = DNA   length = 6355
FEATURE                  Location/Qualifiers
misc_feature             1..6355
                         note = plasmid pAAVss-hDES1.4kb-MVM-hMTM1co-SynthpA
source                   1..6355
                         mol_type = other DNA
                         organism = synthetic construct
SEQUENCE: 134
cctgcaggca gctgcgcgct cgctcgctca ctgaggccgc ccgggcaaag cccgggcgtc   60
gggcgacctt tggtcgcccg gcctcagtga gcgagcgagc gcgcagagag ggagtggcca   120
actccatcac taggggttcc tgcggccgcg gcgcgccacc ggtacacacc tactagtaac   180
ccctccagct ggtgatggca ggtctagggt aggaccagtg actggctcct aatcgagcac   240
tctattttca gggtttgcat tccaaaaggg tcaggtccaa gagggacctg gagtgccaag   300
tggaggtgta gaggcacggc cagtacccat ggagaatggt ggatgtcctt aggggttagc   360
aagtgccgtg tgctaaggag ggggctttgg aggttgggac ggccctctgt ggggctccat   420
ttttgtgggg gtgggggctg gagcattata gggggtggga agtgattggg gctgtcaccc   480
tagccttcct tatctgacgc ccacccatgc ctcctcaggt accccctgcc ccccacagct   540
cctctcctgt gccttgtttc ccagccatgc gttctcctct ataaataccc gctctggtat   600
ttggggttgg cagctgttgc tgccagggag atggttaggt tgacatgcgg ctcctgacaa   660
aacacaaacc cctggtgtgt gtgggcgtgg gtgggtgtgag taggggatg aatcagggag   720
ggggcggggg acccaggggg caggagccac acaaagtctg tgcgggggtg ggagcgcaca   780
tagcaattgg aaactgaaag cttatcagac cctttctgga aatcagccca ctgtttataa   840
acttgaggcc ccaccctcga cagtaccggg gaggaagagg gcctgcacta gtccagaggg   900
aaactgaggc tcagggctag ctcgcccata gacatacatg gcaggcaggc tttggccagg   960
atccctccgc ctgccaggcg tctccctgcc ctcccttcct gcctagagac ccccacccctc   1020
aagcctggct ggtctttgcc tgagacccaa acctcttcga cttcaagaga atatttagga   1080
acaaggtggt ttagggcctt tcctgggaac aggccttgac cctttaagaa atgacccaaa   1140
gtctctcctt gaccaaaaag gggaccctca aactaaaggg aagcctctct tctgctgtct   1200
cccctgaccc cactccccccc caccccagga cgaggagata accagggctg aaagaggccc   1260
gcctgggggc tgcagacatg cttgctgcct gccctggcga aggattggca ggcttgcccg   1320
tcacaggacc cccgctggct gactcagggg cgcaggcctc ttgcggggga gctggcctcc   1380
ccgccccac ggccacgggc cgccttttcc tggcaggaca gggggatctt gcagctgtca   1440
ggggagggga ggcgggggct gatgtcagga gggatacaaa tagtgccgac ggctggggc    1500
cctgtctccc ctcgccgcat ccactctccg gccggccgcc tgcccgccgc ctcctccgtg   1560
cgcccgccag cctcgcccgc gccgtcacct ctagaactag taagaggtaa gggtttaagg   1620
gatggttggt tggtggggta ttaatgttta attacctgga gcacctgcct gaaatcactt   1680
tttttcaggt tggcgtacgg ccaccatggc cagcgccaac acaagcaagt acaacagcca   1740
cagcctggaa aacgagagca tcaagcggac cagcagagat ggcgtgaaca gagatctgac   1800
cgaggccgtt cctagactgc ctggcgagac actgatcacc gacaaagaag tgatctacat   1860
ctgccccttc aacggcccca tcaagggaag agtgtacatc accaactacc ggctgtacct   1920
gcggtccctg gaaccgata gcagcctgat tctggatgtg ccctgggcg tgatcagccg   1980
gattgaaaaa atgggcggag ccacctccag aggcgagaat agctatggcc tggatatcac   2040
atgcaaggac atgcggaacc tgagattcgc cctgaagcaa gagggccaca gcagacggga   2100
catgttcgag atcctgacca gatacgcctt tcctctggct cactctctgc ccctgttcgc   2160
cttcctgaac gaagagaagt tcaacgtgga cggctggacc gtgtacaacc ccgtggaaga   2220
gtatagacgc agggagtgc ccaatcacca ctggcggatc accttcatca acaagtgcta   2280
cgagctgtgc gacacatacc ccgcactgct ggtggtgcct tacagagcct ctgacgacga   2340
```

-continued

```
tctgagaaga gtggccacct ttcggagccg gaacagaatc cctgtgctga gctggattca   2400
ccccgagaac aagaccgtga tcgtgcggtg ttctcagcct ctcgtgggca tgagcggcaa   2460
gagaaacaag gacgacgaga agtacctgga cgtgatccgc gagacaaaca agcagatcag   2520
caagctgacc atctacgacg ccagaccttc tgtgaacgcc gtggccaaca aagccacagg   2580
cggcggatat gagtccgacg atgcctatca caacgccgag ctgttcttcc tggacattca   2640
caacatccat gtgatgcgcg agagcctgaa gaaagtgaag gacatcgtgt accccaatgt   2700
ggaagagagc cactggctgt ctagcctgga atccacacac tggctggaac acatcaagct   2760
ggtgctgaca ggcgccatcc aggtggcaga caaagtgtct agcggcaagt ctagcgtgct   2820
ggtgcactgt agcgacggat gggatagaac agcccagctg acatccctgg ccatgctgat   2880
gctggacagc ttctacagat ccatcgaggg ctttgagatc ctggtgcaga agaagtggat   2940
cagcttcggc cacaagttcg cctctagaat cggacacggc gacaagaacc acaccgacgc   3000
cgatagaagc cccatcttcc tgcagttcat cgactgcgtg tggcagatgt ccaagcagtt   3060
ccctaccgcc ttcgagttca acgagcagtt cctgatcatc atcctggacc acctgtactc   3120
ttgcagattc ggcaccttcc tgttcaactg cgagagcgcc agagaacggc agaaagtgac   3180
cgagagaacc gtgtctctgt ggtccctgat caacagcaac aaagagaaat tcaagaaccc   3240
cttctacacc aaagaaatca accgggtgct gtaccccgtg gccagcatga gacatctgga   3300
actgtgggtc aactactaca tccggtggaa ccccagaatc aagcagcagc agcccaatcc   3360
tgtggaacag cggtatatgg aactgctggc cctgcgggac gagtacatca agagactgga   3420
agaactgcag ctggccaaca gcgccaagct gagcgatcct cctacaagcc ctagcagccc   3480
ctctcagatg atgccccatg tgcagaccca cttttgacct aggaataaaa gatctttatt   3540
ttcattagat ctgtgtgttg gttttttgtg tgacccgtct gattttgtag gtaaccacgt   3600
gcggaccgag cggccgcagg aacccctagt gatggagttg ccactccct ctctgcgcgc   3660
tcgctcgctc actgaggccg ggcgaccaaa ggtcgcccga cgcccgggct ttgcccgggc   3720
ggcctcagtg agcgagcgag cgcgcagctg cctgcagggg cgcctgatgc ggtattttct   3780
ccttacgcat ctgtgcggta tttcacaccg catacgtcaa agcaaccata gtacgcgccc   3840
tgtagcggcg cattaagcgc ggcgggtgtg gtggttacgc gcagcgtgac cgctacactt   3900
gccagcgccc tagcgcccgc tcctttcgct ttcttccctt cctttctcgc cacgttcgcc   3960
ggctttcccc gtcaagctct aaatcggggg ctccctttag ggttccgatt tagtgcttta   4020
cggcacctcg accccaaaaa acttgatttg ggtgatggtt cacgtagtgg gccatcgccc   4080
tgatagacgg tttttcgccc tttgacgttg gagtccacgt tctttaatag tggactcttg   4140
ttccaaactg gaacaacact caaccctatc tcgggctatt cttttgattt ataagggatt   4200
ttgccgattt cggcctattg gttaaaaaat gagctgattt aacaaaaatt taacgcgaat   4260
tttaacaaaa tattaacgtt tacaatttta tggtgcactc tcagtacaat ctgctctgat   4320
gccgcatagt taagccagcc ccgacacccg ccaacacccg ctgacgcgcc ctgacgggct   4380
tgtctgctcc cggcatccgc ttacagacaa gctgtgaccg tctccgggag ctgcatgtgt   4440
cagaggtttt caccgtcatc accgaaacgc gcgagacgaa agggcctcgt gatacgccta   4500
ttttttatagg ttaatgtcat gataataatg gtttcttaga cgtcaggtgg cacttttcgg   4560
ggaaatgtgc gcggaacccc tatttgttta ttttctaaat acattcaaa tatgtatccg   4620
ctcatgagac aataaccctg ataaatgctt caataatatt gaaaaaggaa gagtatgagt   4680
attcaacatt tccgtgtcgc ccttattccc ttttttgcgg cattttgcct tcctgttttt   4740
gctcacccag aaacgctggt gaaagtaaaa gatgctgaag atcagttggg tgcacgagtg   4800
ggttacatcg aactggatct caacagcggt aagatccttg agagttttcg ccccgaagaa   4860
cgttttccaa tgatgagcac ttttaaagtt ctgctatgtg gcgcggtatt atcccgtatt   4920
gacgccgggc aagagcaact cggtcgccgc atacactatt ctcagaatga cttggttgag   4980
tactcaccag tcacagaaaa gcatcttacg gatggcatga cagtaagaga attatgcagt   5040
gctgccataa ccatgagtga taacactgcg gccaacttac ttctgacaac gatcggagga   5100
ccgaaggagc taaccgcttt tttgcacaac atgggggatc atgtaactcg ccttgatcgt   5160
tgggaaccgg agctgaatga agccatacca aacgacgagc gtgacaccac gatgcctgta   5220
gcaatggcaa caacgttgcg caaactatta actggcgaac tacttactct agcttcccgg   5280
caacaattaa tagactggat ggaggcggat aaagttgcag gaccacttct gcgctcggcc   5340
cttccggctg gctggtttat tgctgataaa tctggagccg gtgagcgtgg gtctcgcggt   5400
atcattgcag cactggggcc agatggtaag ccctcccgta tcgtagttat ctacacgacg   5460
gggagtcagg caactatgga tgaacgaaat agacagatcg ctgagatagg tgcctcactg   5520
attaagcatt ggtaactgtc agaccaagtt tactcatata tactttagat tgatttaaaa   5580
cttcattttt aatttaaaag gatctaggtg aagatccttt ttgataatct catgaccaaa   5640
atcccttaac gtgagttttc gttccactga gcgtcagacc ccgtagaaaa gatcaaagga   5700
tcttcttgag atcctttttt tctgcgcgta atctgctgct tgcaaacaaa aaaaccaccg   5760
ctaccagcgg tggtttgttt gccggatcaa gagctaccaa ctctttttcc gaaggtaact   5820
ggcttcagca gagcgcagat accaaatact gtccttctag tgtagccgta gttaggccac   5880
cacttcaaga actctgtagc accgcctaca tacctcgctc tgctaatcct gttaccagtg   5940
gctgctgcca gtggcgataa gtcgtgtctt accgggttgg actcaagacg atagttaccg   6000
gataaggcgc agcggtcggg ctgaacgggg ggttcgtgca cacagcccag cttggagcga   6060
acgacctaca ccgaactgag atacctacag cgtgagctat gagaaagcgc cacgcttccc   6120
gaagggagaa aggcggacag gtatccggta agcggcaggg tcggaacagg agagcgcacg   6180
agggagcttc caggggggaaa cgcctggtat ctttatagtc ctgtcgggtt tcgccacctc   6240
tgacttgagc gtcgatttt gtgatgctcg tcaggggggc ggagcctatg gaaaaacgcc   6300
agcaacgcgg cctttttacg gttcctggcc ttttgctggc cttttgctca catgt        6355
```

```
SEQ ID NO: 135          moltype = DNA  length = 6355
FEATURE                 Location/Qualifiers
misc_feature            1..6355
                        note = plasmid pAAVss-hDES1.4kb-MVM-hMTM1-SynthpA
source                  1..6355
                        mol_type = other DNA
                        organism = synthetic construct
SEQUENCE: 135
cctgcaggca gctgcgcgct cgctcgctca ctgaggccgc ccgggcaaag cccgggcgtc   60
gggcgacctt tggtcgcccg gcctcagtga gcgagcgagc gcgcagagag ggagtggcca   120
actccatcac taggggttcc tgcggccgcg gcgcgccacc ggtacacacc tactagtaac   180
```

-continued

```
ccctccagct ggtgatggca ggtctagggt aggaccagtg actggctcct aatcgagcac  240
tctattttca gggtttgcat tccaaaaggg tcaggtccaa gagggacctg gagtgccaag  300
tggaggtgta gaggcacggc cagtacccat ggagaatggt ggatgtcctt aggggttagc  360
aagtgccgtg tgctaaggag ggggctttgg aggttgggca ggccctctgt ggggctccat  420
ttttgtgggg gtgggggctg gagcattata gggggtggga agtgattggg gctgtcaccc  480
tagccttcct tatctgacgc ccacccatgc ctcctcaggt accccctgcc ccccacagct  540
cctctcctgt gccttgtttc ccagccatgc gttctcctct ataaataccc gctctggtat  600
ttggggttgg cagctgttgc tgccagggag atggttgggt tgacatgcgg ctcctgacaa  660
aacacaaacc cctggtgtgt gtgggcgtgg gtggtgtgag taggggatgg aatcagggag  720
ggggcggggg acccaggggg caggagccac acaaagtctg tgcggggtg ggagcgcaca  780
tagcaattgg aaactgaaag cttatcagac ccttctgga aatcagccca ctgtttataa  840
acttgaggcc ccaccctcga cagtaccggg gaggaagagg gcctgcacta gtccagaggg  900
aaactgaggc tcagggctag ctcgcccata gacatacatg gcaggcaggc tttggccagg  960
atccctccgc ctgccaggcg tctccctgcc ctccctccct gcctagagac ccccaccctc  1020
aagcctggct ggtctttgcc tgagacccaa acctcttcga cttcaagaga atatttagga  1080
acaaggtggt ttagggcctt tcctgggaac aggccttgac cctttaagaa atgacccaaa  1140
gtctctcctt gaccaaaaag gggaccctca aactaaaggg aagcctctct tctgctgtct  1200
ccctgaccc cactccccc cacccagga cgaggagata accagggctg aaagaggccc  1260
gcctgggggc tgcagacatg cttgctgcct gccctggcga aggattggca ggcttgcccg  1320
tcacaggacc cccgctggct gactcagggg cgcaggcctc ttgcggggga gctggcctcc  1380
ccgcccccac ggccacgggc cgcccttttc tggcaggaca gcgggatctt gcagctgtca  1440
gggggaggga ggcgggggct gatgtcagga gggatacaaa tagtgccgac ggctgggggc  1500
cctgtctccc ctcgccgcat ccactctccg gccggccgcc tgcccgccgc ctcctccgtg  1560
cgcccgccag cctcgcccgc gccgtcacct ctagaactag taagaggtaa gggtttaagg  1620
gatggttggt tggtgggta ttaatgttta attacctgga gcacctgcct gaaatcactt  1680
tttttcaggt tggcgtacgg ccaccatggc ttctgcatca acttctaaat ataattcaca  1740
ctccttggag aatgagtcta ttaagaggac gtctcgagat ggagtcaatc gagatctcac  1800
tgaggctgtt cctcgacttc caggagaaac actaatcact gacaaagaag ttatttacat  1860
atgtcctttc aatggcccca ttaagggaag agtttacatc acaaattatc gtctttattt  1920
aagaagtttg gaaacggatt cttctctaat acttgatgt cctctgggtg tgatctcgag  1980
aattgaaaaa atgggaggcg cgacaagtag aggagaaaat tcctatggtc tagatattac  2040
ttgtaaagac atgagaaacc tgaggttcgc tttgaaacag gaaggccaca gcagaagaga  2100
tatgtttgag atcctcacga gatacgcgtt tcccctggct cacagtctgc cattatttgc  2160
attttaaat gaagaaaagt ttaacgtgga tggatggaca gtttacaatc cagtggaaga  2220
atacaggagg cagggcttgc ccaatcacca ttggagaata acttttatta ataagtgcta  2280
tgagctctgt gacacttacc ctgctctttt ggtggttccg tatcgtgcct cagatgatga  2340
cctccggaga gttgcaactt ttaggtcccg aaatcgaatt ccagtgctgt catggattca  2400
tccagaaaat aagacggtca ttgtgcgttg cagtcagcct cttgtcggta tgagtgggaa  2460
acgaaataaa gatgatgaga aatatctcga tgttatcagg gagactaata aacaaatttc  2520
taaactcacc atttatgatg caagacccag cgtaaatgca gtggccaaca aggcaacagg  2580
aggaggatat gaaagtgatg atgcatatca taacgccgaa ctttctttt tagacattca  2640
taatattcat gttatgcggg aatctttaaa aaaagtgaag gacattgttt atcctaatgt  2700
agaagaatct cattggttgt ccagtttgga gtctactcat tggttagaac atatcaagct  2760
cgttttgaca ggagccattc aagtagcaga caaagtttct tcaggaagag gttcagtgct  2820
tgtgcattgc agtgacggat gggacaggac tgctcagctg acatccttgg ccatgctgat  2880
gttggatagc ttctatagga gcattgaagg gttcgaaata ctggtacaaa aaaatggat  2940
aagtttggga cataaatttg catctcgaat aggtcatggt gataaaaacc acaccgatgc  3000
tgaccgttct cctattttttc tccagtttat tgattgtgtg tggcaaatgt caaaacagtt  3060
ccctacagct ttttgaattca atgaacaatt tttgattata attttggatc atctgtatag  3120
ttgccgattt ggtactttct tattcaactg tgaatctgct cgagaaagac agaaggttac  3180
agaaagatct gtttctttat ggtcactgat aaacagtaat aaagaaaaat tcaaaaaccc  3240
cttctatact aaagaaatca atcgagtttt atatccagtt gccagtatgc gtcacttgga  3300
actctgggtg aattactaca ttagatggaa ccccaggatc aagcaacaac agccgaatcc  3360
agtggagcag cgttacatgg agctcttagc cttacgcgac gaatacataa agcggcttga  3420
ggaactgcag ctcgccaact ctgccaagct ttctgatccc ccaacttcac cttccagtcc  3480
ttcgcaaatg atgccccatg tgcaaactca cttctgacct aggaataaaa gatctttatt  3540
ttcattagat ctgtgtgttg gttttttgtg tgacccgtct gattttgtag gtaaccacgt  3600
gcggaccgag cggccgcagg aacccctagt gatggagttg gccactccct ctctgcgcgc  3660
tcgctcgctc actgaggccg ggcgaccaaa ggtcgcccga cgcccgggct ttgcccgggc  3720
ggcctcagtg agcgagcgag cgcgcagctg cctgcagggg cgcctgatgc ggtattttct  3780
ccttacgcat ctgtgcggta tttcacaccg catacgtcaa agcaaccata gtacgcgccc  3840
tgtagcggcg cattaagcgc ggcgggtgtg gtggttacgc gcagcgtgac cgctacactt  3900
gccagcgccc tagcgcccgc tcctttcgct ttcttccctt cctttctcgc cacgttcgcc  3960
ggctttcccc gtcaagctct aaatcggggg ctccctttag ggttccgatt tagtgcttta  4020
cggcacctcg accccaaaaa acttgatttg ggtgatggtt cacgtagtgg gccatcgccc  4080
tgatagacgg tttttcgccc tttgacgttg gagtccacgt tctttaatag tggactcttg  4140
ttccaaactg gaacaacact caaccctatc tcgggctatt cttttgattt ataagggatt  4200
ttgccgattt cggcctattg gttaaaaaat gagctgattt aacaaaaatt taacgcgaat  4260
tttaacaaaa tattaacgtt tacaatttta tggtgcactc tcagtacaat ctgctctgat  4320
gccgcatagt taagccagcc ccgacacccg ccaacacccg ctgacgcgcc ctgacgggct  4380
tgtctgctcc cggcatccgc ttacagacaa gctgtgaccg tctccgggag ctgcatgtgt  4440
cagaggtttt caccgtcatc accgaaacgc gcgagacgaa agggcctcgt gatacgccta  4500
tttttatagg ttaatgtcat gataataatg gtttcttaga cgtcaggtgg cacttttcgg  4560
ggaaatgtgc gcggaacccc tatttgttta tttttctaaa tacattcaaa tatgtatccg  4620
ctcatgagac aataaccctg ataaatgctt caataatatt gaaaaaggaa gagtatgagt  4680
attcaacatt tccgtgtcgc ccttattccc tttttgcgg cattttgcct tcctgttttt  4740
gctcacccag aaacgctggt gaaagtaaaa gatgctgaag atcagttggg tgcacgagtg  4800
ggttacatcg aactggatct caacagcggt aagatccttg agagttttcg ccccgaagaa  4860
cgttttccaa tgatgagcac ttttaaagtt ctgctatgtg gcgcggtatt atcccgtatt  4920
```

```
gacgccgggc aagagcaact cggtcgccgc atacactatt ctcagaatga cttggttgag    4980
tactcaccag tcacagaaaa gcatcttacg gatggcatga cagtaagaga attatgcagt    5040
gctgccataa ccatgagtga taacactgcg gccaacttac ttctgacaac gatcggagga    5100
ccgaaggagc taaccgcttt tttgcacaac atggggatc atgtaactcg ccttgatcgt    5160
tgggaaccgg agctgaatga agccatacca aacgacgagc gtgacaccac gatgcctgta    5220
gcaatggcaa caacgttgcg caaactatta actggcgaac tacttactct agcttcccgg    5280
caacaattaa tagactggat ggaggcggat aaagttgcag gaccacttct gcgctcggcc    5340
cttccggctg gctggtttat tgctgataaa tctggagccg gtgagcgtgg gtctcgcggt    5400
atcattgcag cactgggggc agatggtaag ccctcccgta tcgtagttat ctacacgacg    5460
gggagtcagg caactatgga tgaacgaaat agacagatcg ctgagatagg tgcctcactg    5520
attaagcatt ggtaactgtc agaccaagtt tactcatata tactttagat tgatttaaaa    5580
cttcattttt aatttaaaag gatctaggtg aagatccttt ttgataatct catgaccaaa    5640
atcccttaac gtgagttttc gttccactga gcgtcagacc ccgtagaaaa gatcaaagga    5700
tcttcttgag atcctttttt tctgcgcgta atctgctgct tgcaaacaaa aaaaccaccg    5760
ctaccagcgg tggtttgttt gccggatcaa gagctaccaa ctcttttttcc gaaggtaact    5820
ggcttcagca gagcgcagat accaaatact gtccttctag tgtagccgta gttaggccac    5880
cacttcaaga actctgtagc accgcctaca tacctcgctc tgctaatcct gttaccagtg    5940
gctgctgcca gtggcgataa gtcgtgtctt accgggttgg actcaagacg atagttaccg    6000
gataaggcgc agcggtcggg ctgaacgggg ggttcgtgca cacagcccag cttggagcga    6060
acgacctaca ccgaactgag atacctacag cgtgagctat gagaaagcgc cacgcttccc    6120
gaagggagaa aggcggacag gtatccgta agcggcaggg tcggaacagg agagcgcacg    6180
agggagcttc caggggggaaa cgcctggtat ctttatagtc ctgtcgggtt tcgccacctc    6240
tgacttgagc gtcgatttttt gtgatgctcg tcaggggggg ggagcctatg gaaaaacgcc    6300
agcaacgcgg cctttttacg gttcctggcc ttttgctggc ctttttgctca catgt         6355
```

SEQ ID NO: 136          moltype = DNA   length = 6808
FEATURE                 Location/Qualifiers
misc_feature           1..6808
                        note = plasmid pAAVss-SKCRM4-hDES1.4kb-MVM-hMTM1co-SynthpA
source                 1..6808
                        mol_type = other DNA
                        organism = synthetic construct
SEQUENCE: 136

```
cctgcaggca gctgcgcgct cgctcgctca ctgaggccgc ccgggcaaag cccgggcgtc    60
gggcgacctt tggtcgcccg gcctcagtga gcgagcgagc gcgcagagag ggagtggcca    120
actccatcac taggggttcc tgcggccgcg cgcgccacc ggtttctgag tcctctaagg    180
tccctcactc ccaactcagc cccatgtcct gtcaattccc actcagtgtc tgatctcctt    240
ctcctcacct ttcccatctc ccgtttgacc caagcttcct gagctctcct cccattcccc    300
tttttggagt cctcctcctc tcccagaacc cagtaataag tgggctcctc cctggcctgg    360
accccgtgg taaccctata aggcgaggca gctgctgtct gaggcaggga ggggctggtg    420
tgggaggcta agggcagctg ctaagtttag ggtggctcct tctctcttct tagagacaac    480
aggtggctgg ggcctcagtg cccagaaaag aaaatgtctt agaggtatcg gcatgggcct    540
ggaggagggca ggacagggca gggggaggca tcttcctcag gacatcgggt cctagagggg    600
tacccaacgg gttacgacac acctactagt aaccctcca gctggtgatg gcaggtctag    660
ggtaggacca gtgactggct cctaatcgag cactctattt tcagggtttg cattccaaaa    720
gggtcaggtc aagagggac ctggagtgcc aagtggaggt gtagaggcac ggccagtacc    780
catggagaat ggtggatgtc cttaggggtt agcaagtgcc gtgtgctaag gaggggggctt    840
tggaggttgg gcaggccctc tgtgggggctc cattttttgtg ggggtgggggg ctggagcatt    900
ataggggggtg ggaagtgatt ggggctgtca ccctagcctt ccttatctga cgcccaccca    960
tgcctcctca ggtaccccct gcccccaca gctcctctcc tgtgccttgt ttcccagcca    1020
tgcgttctcc tctataaata cccgctctgg tatttgggggt tggcagctgt tgctgccagg    1080
gagatggttg ggttgacatg cggctcctga caaaacacaa accctggtg tgtgtgggcg    1140
tgggtggtgt gagtaggggg atgaatcagg gaggggggcg gggacccagg gggcaggagc    1200
cacacaaagt ctgtgcgggg gtgggagcgc acatagcaat tggaaactga agcttatca    1260
gacccttttct ggaaatcagc ccactgttta taaacttgag gcccaccct cgacagtacc    1320
ggggaggaag agggcctgca ctagtccaga gggaaactga ggctcagggc tagctcgccc    1380
atagacatac atggcaggca ggctttggcc aggatcccc cgcctgccag gcgtctccct    1440
gccctccctt cctgcctaga gacccccacc ctcaagcctg gctggtcttt gcctgagacc    1500
caaacctctt cgacttcaag agaatatttta ggaacaaggt ggtttagggc ctttcctggg    1560
aacaggcctt gacccctttaa gaaatgaccc aaagtctctc cttgaccaaa aagggggaccc    1620
tcaaactaaa gggaagcctc tcttctgctt tctcccctga ccccactccc ccccacccca    1680
ggacgaggag ataaccaggg ctgaaagagg cccgcctggg ggctgcagac atgcttgctg    1740
cctgccctgg cgaaggattg gcaggcttgc ccgtcacagg accccgctg gctgactcag    1800
gggcgcaggc ctcttgcggg ggagctggcc tcccgcacg gccgccctt    1860
tcctggcagg acagcgggat cttgcagctg tcagggggagg ggaggcgggg gctgatgtca    1920
ggagggatac aaatagtgcc gacggctggg ggccctgtct ccctcgccg catccactct    1980
ccggccggcc gcctgcccgc cgcctcctcc gtgcgcccgc cagcctcgcc cgcgccgtca    2040
cctctagaac tagtaagagg taaggggttta agggatggt ggttggtggg gtattaatgt    2100
ttaattacct ggagcacctg cctgaaatca cttttttttca ggttggcgta cgtgaccacat    2160
ggccagcgcc agcacaagca agtacaacag ccacagcctg gaaaacgaga gcatccagcg    2220
gaccagcaga gatggcgtga acagagatct gaccgaggcc gttcctagac tgcctggcga    2280
gacactgatc accgacaaag aagtgatcta catctgcccc ttcaacgcc ccatcaaggg    2340
aagagtgtac atcaccaact accggctgta cctgcggtcc ctggaaaccg atagcagcct    2400
gattctggat gtgcccctgg gcgtgatcag ccggattgaa aaatgggac ggccgcaccttc    2460
cagaggcgag aatagctatg cctggatat cacatgcaag gacatgcgga acctgagatt    2520
cgccctgaag caagagggcc acagcagacg ggacatgttc gagatcctga ccagatacgc    2580
ctttcctctg gctcactctc tgcccctgtt cgccttcctg aacgaagaga gttcaacgt    2640
ggacggctgg accgtgtaca accccgtgga agagtataga cggcagggac tgcccaatca    2700
ccactggcgg atcaccttca tcaacaagtg ctacgagctg tgcgacacat accccgcact    2760
```

```
gctggtggtg ccttacagag cctctgacga cgatctgaga agagtggcca cctttcggag  2820
ccggaacaga atccctgtgc tgagctggat tcaccccgag aacaagaccg tgatcgtgcg  2880
gtgttctcag cctctcgtgg gcatgagcgg caagagaaac aaggacgacg agaagtacct  2940
ggacgtgatc cgcgagacaa acaagcagat cagcaagctg accatctacg acgccagacc  3000
ttctgtgaac gccgtggcca acaaagccac aggcggcgga tatgagtccg acgatgccta  3060
tcacaacgcc gagctgttct tcctggacat tcacaacatc catgtgatgc gcgagagcct  3120
gaagaaagtg aaggacatcg tgtaccccaa tgtgtggaag agccactggc tgtctagcct  3180
ggaatccaca cactggctgg aacacatcaa gctggtgctg acaggcgcca tccaggtggc  3240
agacaaagtg tctagcggca agtctagcgt gctggtgcac tgtagcgacg gatgggatag  3300
aacagcccag ctgacatccc tggccatgct gatgctggac agcttctaca gatccatcga  3360
gggctttgag atcctggtgc agaagaagtg gatcagcttc ggccacaagt tcgcctctag  3420
aatcggacac ggcgacaaga accacaccga cgccgataga agccccatct tcctgcagtt  3480
catcgactgc gtgtggcaga tgtccaagca gttccctacc gccttcgagt tcaacgagca  3540
gttcctgatc atcatcctgg accacctgta ctcttgcaga ttcggcacct tcctgttcaa  3600
ctgcgagagc gccagagaac ggcagaaagt gaccgagaga accgtgtctc tgtggtccct  3660
gatcaacagc aacaaagaga aattcaagaa cccccttctac accaaagaaa tcaaccgggt  3720
gctgtacccc gtggccagca tgagacatct ggaactgtgg gtcaactact acatccggtg  3780
gaaccccaga atcaagcagc agcagcccaa tcctgtggaa caggtata tggaactgct  3840
ggccctgcgg gacgagtaca tcaagagact ggaagaactg cagctggcca acagcgccaa  3900
gctgagcgat cctcctacaa gccctagcag ccctctcag atgatgcccc atgtgcagac  3960
ccacttttga cctaggaata aaagatcttt attttcatta gatctgtgtg ttggtttttt  4020
gtgtgacccg tctgattttg taggtaacca cgtgcggacc gggacgccgc aggaaccct  4080
agtgatggag ttggccactc cctctctgcg cgctcgctcg ctcactgagg ccgggcgacc  4140
aaaggtcgcc cgacgcccgg gctttgcccg ggcggcctca gtgagcgagc gagcgcgcag  4200
ctgcctgcag gggcgcctga tgcggtattt tctccttacg catctgtgcg gtatttcaca  4260
ccgcatacgt caaagcaacc atagtacggc ccctgtatcg gcgcattaag cgcggcgggt  4320
gtggtggtta cgcgcagcgt gaccgctaca cttgccagcg ccctagcgcc cgctcctttc  4380
gctttcttcc cttcctttct cgccacgttc gccggctttc cccgtcaagc tctaaatcgg  4440
gggctccctt tagggttccg atttagtgct ttacggcacc tcgaccccaa aaaacttgat  4500
ttgggtgatg gttcacgtag tgggccatcg ccctgataga cggttttcg cccttttgacg  4560
ttggagtcca cgttctttaa tagtggactc ttgttccaaa ctggaacaac actcaaccct  4620
atctcgggct attctttga tttataaggg attttgccga tttcggccta ttggttaaaa  4680
aatgagctga tttaacaaaa atttaacgcg aattttaaca aaatattaac gtttacaatt  4740
ttatggtgca ctctcagtac aatctgctct gatgccgcat agttaagcca gccccgacac  4800
ccgccaacac ccgctgacgc gccctgacgg gcttgtctgc tcccggcatc cgcttacaga  4860
caagctgtga ccgtctccgg gagctgcatg tgtcagaggt tttcaccgtc atcaccgaaa  4920
cgcgcgagac gaaagggcct cgtgatacgc ctatttttat aggttaatgt catgataata  4980
atggtttctt agacgtcagg tggcactttt cggggaaatg tgcgcggaac ccctatttgt  5040
ttatttttct aaatacattc aaatatgtat ccgctcatga gacaataacc ctgataaatg  5100
cttcaataat attgaaaaag gaagagtatg agtattcaac atttccgtgt cgcccttatt  5160
ccctttttttg cggcatttttg ccttcctgtt tttgctcacc cagaaacgct ggtgaaagta  5220
aaagatgctg aagatcagtt gggtgcacga gtgggttaca tcgaactgga tctcaacagc  5280
ggtaagatcc ttgagagttt tcgccccgaa gaacgttttc caatgatgag cacttttaaa  5340
gttctgctat gtggcgcggt attatcccgt attgacgccg ggcaagagca actcggtcgc  5400
cgcatacact attctcagaa tgacttggtt gagtactcac cagtcacaga aaagcatctt  5460
acggatggca tgacagtaag agaattatgc agtgctgcca taaccatgag tgataacact  5520
gcggccaact tacttctgac aacgatcgga ggaccgaagg agctaaccgc ttttttgcac  5580
aacatggggg atcatgtaac tcgccttgat cgttgggaac cggagctgaa tgaagccata  5640
ccaaacgacg agcgtgacac cacgatgcct gtagcaatgg caacaacgtt gcgcaaacta  5700
ttaactggcg aactacttac tctagcttcc cggcaacaat taatagactg gatggaggcg  5760
gataaagttg caggaccact tctgcgctcg gcccttccgg ctggctggtt tattgctgac  5820
aaatctggag ccggtgagcg tgggtctcgc ggtatcattg cagcactggg gccagatggt  5880
aagccctccc gtatcgtagt tatctacacg acggggagtc aggcaactat ggatgaacga  5940
aatagacaga tcgctgagat aggtgcctca ctgattaagc attggtaact gtcagaccaa  6000
gtttactcat atatacttta gattgattta aaacttcatt tttaatttaa aaggatctag  6060
gtgaagatcc tttttgataa tctcatgacc aaaatccctt aacgtgagtt ttcgttccac  6120
tgagcgtcag accccgtaga aaagatcaaa ggatcttctt gagatccttt ttttctgcgc  6180
gtaatctgct gcttgcaaac aaaaaaacca ccgctaccag cggtggtttg tttgccggat  6240
caagagctac caactctttt tccgaaggta actggcttca gcagagcgca gataccaaat  6300
actgtccttc tagtgtagcc gtagttaggc caccacttca agaactctgt agcaccgcct  6360
acatacctcg ctctgctaat cctgttacca gtggctgctg ccagtggcga taagtcgtgt  6420
cttaccgggt tggactcaag acgatagtta ccggataagg cgcagcggtc gggctgaacg  6480
gggggttcgt gcacacagcc cagcttggag cgaacgacct acaccgaact gagatacccta  6540
cagcgtgagc tatgagaaag cgccacgctt cccgaagggag aaaggcggaca caggtatccg  6600
gtaagcggca gggtcggaac aggagagcgc acgagggagc ttccaggggg aaacgcctgg  6660
tatctttata gtcctgtcgg gtttcgccac ctctgacttg agcgtcgatt tttgtgatgc  6720
tcgtcagggg ggcggagcct atggaaaaac gccagcaacg cggccttttt acggttcctg  6780
gccttttgct ggccttttgc tcacatgt                                      6808
```

```
SEQ ID NO: 137        moltype = DNA   length = 6808
FEATURE               Location/Qualifiers
misc_feature          1..6808
                      note = plasmid pAAVss-SKCRM4-hDES1.4kb-MVM-hMTM1-SynthpA
source                1..6808
                      mol_type = other DNA
                      organism = synthetic construct
SEQUENCE: 137
cctgcaggca gctgcgcgct cgctcgctca ctgaggccgc ccgggcaaag cccgggcgtc  60
gggcgacctt tggtcgcccg gcctcagtga gcgagcgagc gcgcagagag ggagtggcca  120
```

```
actccatcac tagggggttcc tgcggccgcg gcgcgccacc ggtttctgag tcctctaagg    180
tccctcactc ccaactcagc cccatgtcct gtcaattccc actcagtgtc tgatctcctt    240
ctcctcacct ttcccatctc ccgtttgacc caagcttcct gagctctcct cccattcccc    300
tttttggagt cctcctcctc tcccagaacc cagtaataag tgggctcctc cctggcctgg    360
accccgtgg taaccctata aggcgaggca gctgctgtct gaggcaggga ggggctggtg    420
tgggaggcta agggcagctg ctaagtttag ggtggctcct tctctcttct tagagacaac    480
aggtggctgg ggcctcagtg cccagaaaag aaaatgtctt agaggtatcg gcatgggcct    540
ggaggagggg ggacagggca gggggaggca tcttcctcag gacatcgggt cctagagggg    600
tacccaacgg gttacgacac acctactagt aacccctcca gctggtgatg gcaggtctag    660
ggtaggacca gtgactggct cctaatcgag cactctattt tcagggtttg cattccaaaa    720
gggtcaggtc caagagggac ctggagtgcc aagtggaggt gtagaggcac ggccagtacc    780
catggagaat ggtggatgtc cttaggggtt agcaagtgcc gtgtgctaag gagggggctt    840
tggaggttgg gcaggccctc tgtggggctc cattttttgtg ggggtggggg ctggagcatt    900
atagggggtg ggaagtgatt ggggctgtca ccctagcctt cctttatctga cgcccaccca    960
tgcctcctca ggtacccccct gccccccaca gctcctctcc tgtgccttgt ttcccagcca   1020
tgcgttctcc tctataaata cccgctctgg tatttggggt tggcagctgt tgctgccagg   1080
gagatggttg ggttgacatg cggctcctga caaaacacaa acccctggtg tgtgtgggcg   1140
tgggtggtgt gagtaggggg atgaatcagg gagggggcag gggacccagg gggcaggagc   1200
cacacaaagt ctgtgcgggg gtgggagcgc acatagcaat tggaaactga aagcttatca   1260
gacccttct ggaaatcagc ccactgttta taaacttgag gccccaccct cgacagtacc   1320
ggggaggaag agggcctgca ctagtccaga gggaaactga ggctcagggc tagctcgccc   1380
atagacatac atggcaggca ggctttggcc aggatccctc cgcctgccag gcgtctccct   1440
gccctccctt cctgcctaga gaccccacc ctcaagcctg gctggtcttt gcctgagacc   1500
caaacctctt cgacttcaag agaatattta ggaacaaggt ggtttagggc ctttcctggg   1560
aacaggcctt gacccttaa gaaatgaccc aaagtctctc cttgaccaaa aaggggaccc   1620
tcaaactaaa gggaagcctc tcttctgctg tctcccctga ccccactccc ccccacccca   1680
ggacgaggag ataaccaggg ctgaaagagg cccgcctggg ggctgcagac atgcttgctg   1740
cctgccctgg cgaaggattg gcaggcttgc ccgtcacagg accccgctg gctgactcag   1800
gggcgcaggc ctcttgcggg ggagctggcc tccccgcccc cacggccacg ggccgccctt   1860
tcctggcagg acagcgggat cttgcagctg tcaggggagg gggacgcggg gctgatgtca   1920
ggagggatac aaatagtgcc gacggctggg ggccctgtct ccccctcgccg catccactct   1980
ccggccggcc gcctgcccgc cgcctcctcc gtgcgcccgc cagcctcgcc cgcgcgcgtca   2040
cctctagaac tagtaagagg taagggttta agggatggtt ggttggtggg gtattaatgt   2100
ttaattacct ggagcacctg cctgaaatca ctttttttca ggttggcgta cggccaccat   2160
ggcttctgca tcaacttcta aatataattc acactccttg gagaatgagt ctattaagag   2220
gacgtctcga gatggagtca atcgagatct cactgaggct gttcctcgac ttccaggaga   2280
aacactaatc actgacaaag aagttatta catatgtcct ttcaatggcc ccattaaggg   2340
aagagtttac atcacaaatt atcgtcttta tttaagaagt ttggaaacgg attcttctct   2400
aatacttgat gttcctctgg gtgtgatctc gagaattgaa aaaatgggag gcgcgacaag   2460
tagaggagaa aattcctatg gtctagatat tacttgtaaa gacatgagaa acctgaggtt   2520
cgctttgaaa caggaaggcc acagcagaag agatatgttt gagatcctca cgagatacgc   2580
gtttcccctg gctcacagtc tgccattatt tgcattttta aatgaagaaa agtttaacgt   2640
ggatggatgg acagtttaca atccagtgga agaatacagg aggcagggct tgcccaatca   2700
ccattggaga ataacttta ttaataagtg ctatgagctc tgtgacactt accctgctct   2760
tttggtggtt ccgtatcgtg cctcagatga tgacctccgg agagttgcaa cttttaggtc   2820
ccgaaatcga attccagtgc tgtcatggat tcatccagaa aataagacgg tcattgtgcg   2880
ttgcagtcag cctcttgtcg gtatgagtgg gaaacgaaat aaagatgatg agaaatatct   2940
cgatgttatc agggagacta ataaacaaat ttctaaactc accatttatg atgcaagacc   3000
cagcgtaaat gcagtggcca acaaggcaac aggaggagga tatgaaagtg atgatgcata   3060
tcataacgcc gaacttttct tcttagacat tcataatatt catgttatgc gggaatcttt   3120
aaaaaaagtg aaggacattg tttatcctaa tgtagaagaa tctcattggt tgtccagttt   3180
ggagtctact cattggttag aacatatcaa gctcgttttg acaggagcca ttcaagtagc   3240
agacaaagtt tcttcaggga agagttcagt gcttgtgcat tgcagtgacg gatgggacag   3300
gactgctcag ctgacatcct tggccatgct gatgttggat agcttctata ggagcattga   3360
agggtcgaa atactggtac aaaaaaaatg gataagtttt ggacataaat ttgcatctcg   3420
aataggtcat ggtgataaaa accacaccga tgctgaccgt tctcctattt ttctccagtt   3480
tattgattgt gtgtggcaaa tgtcaaaaca gttccctaca gcttttgaat tcaatgaaca   3540
attttttgatt ataattttgg atcatctgta tagttgccga tttggtactt tcttattcaa   3600
ctgtgaatct gctcgagaaa gacagaaggt tacagaaagg actgtttctt tatggtcact   3660
gataaacagt aataaagaaa aattcaaaaa ccccttctat actaaagaaa tcaatcgagt   3720
tttatatcca gttgccagta tgcgtcactt ggaactctgg gtgaattact acattagatg   3780
gaaccccagg atcaagcaac aacagccgaa tccagtggag cagcgttaca tggagctctt   3840
agccttacgc gacgaataca taaagcggct tgaggaactg cagctcgcca actctgccaa   3900
gctttctgat cccccaactt caccttccag tccttcgcaa atgatgccaa atgtgcaaac   3960
tcacttctga cctaggaata aaagatcttt attttcatta gatctgtgtg ttggtttttt   4020
gtgtgacccg tctgattttg taggtaacca cgtgcggacc gagcggccgc aggaacccct   4080
agtgatggag ttggccactc cctctctgcg cgctcgctcg ctcactgagg ccgggcgacc   4140
aaaggtcgcc cgacgcccgg gctttgcccg ggcggcctca gtgagcgagc gagcgcgcag   4200
ctgcctgcag gggcgcctga tgcggtattt tctccttacg catctgtgcg gtatttcaca   4260
ccgcatacgt caaagcaacc atagtacgcg ccctgtagcg gcgcattaag cgcggcgggt   4320
gtggtggtta cgcgcagcgt gaccgctaca cttgccagcg ccctagcgcc cgctcctttc   4380
gctttcttcc cttcctttct cgccacgttc gccggctttc cccgtcaagc tctaaatcgg   4440
gggctccctt tagggttccg atttagtgct ttacggcacc tcgaccccaa aaaacttgat   4500
ttgggtgatg gttcacgtag tgggccatcg ccctgatag cggtttttcg ccctttgacg   4560
ttggagtcca cgttctttaa tagtggactc ttgttccaaa ctggaacaac actcaaccct   4620
atctcgggct attcttttga tttataaggg attttgccga tttcggccta ttggttaaaa   4680
aatgagctga tttaacaaaa atttaacgcg aatttttaaca aaatattaac gtttacaatt   4740
ttatggtgca ctctcagtac aatctgctct gatgccgcat agttaagcca gccccgacac   4800
ccgccaacac ccgctgacgc gccctgacgg gcttgtctgc tcccggcatc cgcttacaga   4860
```

-continued

```
caagctgtga ccgtctccgg gagctgcatg tgtcagaggt tttcaccgtc atcaccgaaa  4920
cgcgcgagac gaaagggcct cgtgatacgc ctattttat aggttaatgt catgataata  4980
atggtttctt agacgtcagg tggcactttt cggggaaatg tgcgcggaac ccctatttgt  5040
ttattttct aaatacattc aaatatgtat ccgctcatga gacaataacc ctgataaatg  5100
cttcaataat attgaaaaag gaagagtatg agtattcaac atttccgtgt cgcccttatt  5160
cccttttttg cggcattttg ccttcctgtt tttgctcacc cagaaacgct ggtgaaagta  5220
aaagatgctg aagatcagtt gggtgcacga gtggtttaca tcgaactgga tctcaacagc  5280
ggtaagatcc ttgagagttt tcgccccgaa gaacgttttc caatgatgag cactttaaa  5340
gttctgctat gtggcgcggt attatcccgt attgacgccg ggcaagagca actcggtcgc  5400
cgcatacact attctcagaa tgacttggtt gagtactcac cagtcacaga aaagcatctt  5460
acggatggca tgacagtaag agaattatgc agtgctgcca taaccatgag tgataacact  5520
gcggccaact tacttctgac aacgatcgga ggaccgaagg agctaaccgc ttttttgcac  5580
aacatggggg atcatgtaac tcgccttgat cgttgggaac cggagctgaa tgaagccata  5640
ccaaacgacg agcgtgacac cacgatgcct gtagcaatgg caacaacgtt gcgcaaacta  5700
ttaactggcg aactacttac tctagcttcc cggcaacaat taatagactg gatggaggcg  5760
gataaagttg caggaccact tctgcgctcg gcccttccgg ctggctggtt tattgctgat  5820
aaatctggag ccggtgagcg tgggtctcgc ggtatcattg cagcactggg gccagatggt  5880
aagccctccc gtatcgtagt tatctacacg acggggagtc aggcaactat ggatgaacga  5940
aatagacaga tcgctgagat aggtgcctca ctgattaagc attggtaact gtcagaccaa  6000
gtttactcat atatacttta gattgattta aaacttcatt tttaatttaa aaggatctag  6060
gtgaagatcc tttttgataa tctcatgacc aaaatccctt aacgtgagtt ttcgttccac  6120
tgagcgtcag accccgtaga aaagatcaaa ggatcttctt gagatccttt ttttctgcgc  6180
gtaatctgct gcttgcaaac aaaaaaacca ccgctaccag cggtggtttg tttgccggat  6240
caagagctac caactctttt tccgaaggta actggcttca gcagagcgca gataccaaat  6300
actgtccttc tagtgtagcc gtagttaggc caccacttca agaactctgt agcaccgcct  6360
acatacctcg ctctgctaat cctgttacca gtggctgctg ccagtggcga taagtcgtga  6420
cttaccgggt tggactcaag acgatagtta ccggataagg cgcagcggtc gggctgaacg  6480
gggggttcgt gcacacagcc cagcttggag cgaacgacct acaccgaact gagatacta  6540
cagcgtgagc tatgagaaag cgccacgctt cccgaaggga gaaaggcgga caggtatccg  6600
gtaagcggca gggtcggaac aggagagcgc acgagggagc ttccaggggg aaacgcctgg  6660
tatctttata gtcctgtcgg gtttcgccac ctctgacttg agcgtcgatt tttgtgatgc  6720
tcgtcagggg ggcggagcct atggaaaaac gccagcaacg cggcctttt acggttcctg  6780
gccttttgct ggccttttgc tcacatgt                                      6808
```

SEQ ID NO: 138          moltype = DNA   length = 6308
FEATURE                 Location/Qualifiers
misc_feature            1..6308
                        note = plasmid pAAVss-SPc5-12GTRM-MVM-hGAAco-SynthpA
source                  1..6308
                        mol_type = other DNA
                        organism = synthetic construct
SEQUENCE: 138

```
cctgcaggca gctgcgcgct cgctcgctca ctgaggccgc ccgggcaaag cccgggcgtc  60
gggcgacctt tggtcgcccg gcctcagtga gcgagcgagc gcgcagagag ggagtggcca  120
actccatcac taggggttcc tgcggccgca cgcgtaccgg ttggccaccg ccttcggcac  180
catcctcacg acacccaaat atggcgacgg gtgaggaatg gtgggagtt attttagag  240
cggtgaggaa ggtgggcagg cagcaggtgt tggcgctcta aaaataactc ccgggagtta  300
tttttagagc ggaggaatgg tggacaccca aatatggcga cggttcctca cccgtcgcca  360
tatttgggtg tccgccctcg gccggggccg cattctgggg ggcgggcggt tgctcccgcc  420
cgcctcgata aaaggctccg gggccggcgg cggcccacga gctacccgga ggagcgggag  480
gcgccaagct ctagatctag aactagtaag aggtaaggt ttaagggatg gttggttggt  540
ggggtattaa tgtttaatta cctggagcac ctgcctgaaa tcactttttt tcaggttggc  600
gtacggccac catgggcgtc agacatcctc catgttctca cagactgctg gccgtgtgtg  660
ctctggtgtc tcttgctaca gctgccctgc tgggacatat cctgctgcac gatttttctgc  720
tggtgcccag agagctgtct ggcagctctc ctgtgctgga agaaacacac cctgcacatc  780
agcagggcgc ctctagacct ggacctagag atgctcaagc ccatcctggc agacctagag  840
ccgtgcctac acagtgtgac gtgccaccta acagcagatt cgactgcgcc cctgacaagg  900
ccatcacaca agagcagtgt gaagccgag gctgctgcta cattcctgcc aaacaaggac  960
tgcagggcgc tcagatggga cagccttggt gcttcttccc accatcttac cccagctaca  1020
agctggaaaa cctgagcagc agcgagatgg gctacaccgc cacactgacc agaaccacac  1080
ctacattctt cccaaaggac atcctgcacac tgcggctgga cgtgatgatg gaaaccgaga  1140
accggctgca cttcaccatc aaggacccg ccaatagaag atacgaggtg cccctggaaa  1200
cccctcacgt gcactctaga gccccatctc cactgtacag cgtggaattc agcgaggaac  1260
cctttggagg gatcgtgcgg agacagctgg atggcagagt gctgctgaat accacagtgg  1320
cccctctgtt cttcgccgac cagtttctgc agctgagcac aagcctgcct agccagtata  1380
tcacaggcct ggccgaacac ctgtctccac tgatgctgag caccagctgg accagaatca  1440
ccctgtggaa cagagatctg gccccacac ctggcgccaa tctgtacggc tctcaccctt  1500
tttatctggc cctggaagat ggcggaagcg cccacggtgt ctttctgctg aacagcaacg  1560
ccatggacgt ggtgctgcaa ccatctcctg ctctgtctg gagaagcacc ggcgggatcc  1620
tggacgtgta catctttctg ggacccgagc ctaagagcgt ggtgcagcag tatctggatg  1680
tcgtgggcta cccccttcatg cctccttatt ggggcctggg cttccacctg tgtagatggg  1740
gatacagctc caccgccatc accagacagg tggtggaaaa catgacccgg gctcacttcc  1800
cactggatgt gcagtggaac gacctggact acatggactc cagacgggac ttcaccttta  1860
acaaggacgg cttcagagac ttccccgcca tggtgcagga actgcatcaa gcgggcagac  1920
ggtacatgat gatcgtggat cctgccatct cttctagcgg ccctgccgga agctacagac  1980
cttatgatga gggcctgaga agaggcgtgt tcatcaccaa tgagacaggc cagcctctga  2040
tcggcaaagt gtggcctgga agcaccgcct tccagacttt caccaatcca accgctctgg  2100
cttggtggga agatatggtg gccgagttcc acgatcaggt gcccttcgat ggcatgtgga  2160
tcgacatgaa cgagcccagc aacttcatca ggggcagcga ggatggctgc cccaacaacg  2220
```

-continued

```
aactggaaaa tcctccttac gtgccaggcg ttgtcggagg aacactgcag gccgccacaa  2280
tttgtgccag cagccatcag tttctgagca cccactacaa cctgcacaac ctgtacggcc  2340
tgaccgaggc cattgcctct catagagccc tggttaaggc cagaggcacc cggccttttg  2400
tgatcagcag aagcacattt gccggccacg gcagatatgc cggacattgg acaggggacg  2460
tttggtctag ttgggagcag ctggcctcta gcgtgcccga gatcctgcag tttaatctgc  2520
tgggagtgcc cctcgtggga gccgatgttt gtggatttct gggcaacacc tccgaggaac  2580
tgtgcgtcag atggacacag ctgggcgcct tctatccctt catgagaaac cacaacagcc  2640
tgctgagcct gcctcaagag ccttacagct ttagcgaacc cgcacagcag gccatgagaa  2700
aggccctgac tctgagatac gctctgctgc cccacctgta caccctgttt catcaagctc  2760
atgtggccgg cgagacagtg gccagaccac tgtttctgga attccccaag gacagcagca  2820
cctggacagt ggatcatcag ctgctctggg gagaagccct gctcattaca cctgtgctgc  2880
aggctggcaa ggccgaagtg acaggatact ttcccctcgg cacttggtac gacctgcaga  2940
cagttcctgt ggaagctctg ggatctctgc ctccacctcc tgctgctcct agagagcctg  3000
ccattcactc tgaaggccag tgggttacac tgcccgctcc actggacacc atcaatgtgc  3060
acctgagagc cggctacatc atccctctgc aaggccctgg actgaccaca accgaaagca  3120
gacagcagcc aatggctctg gccgtgggctc tgacaaaagg cggagaagct agaggcgaac  3180
tgttctggga tgacggcgag agcctggaag tgctggaacg gggagcctac acacaagtga  3240
tctttctcgc ccggaacaac accatcgtga acgaactcgt caggacctac agtgaaggtg  3300
ccggactgca gctccagaaa gtgacagtgc ttggagtggc cacagcaccc cagcaggttt  3360
tgtctaatgg cgtgcccgtg tccaacttca catacagccc tgacaccaag gtgctggaca  3420
tctgtgtgtc tctgctgatg ggcgagcagt tcctggtgtc ctggtgttga cctaggaata  3480
aaagatcttt attttcatta gatctgtgtg ttggtttttt gtgtgacccg tctgattttg  3540
taggtaacca cgtgcggacc gagcggccgc aggaaccct agtgatggag ttggccactc  3600
cctctctgcg cgctcgctcg ctcactgagg ccgggcgacc aaaggtcgcc cgacgcccgg  3660
gctttgcccg ggcggcctca gtgagcgagc gagcgcgcag ctgcctgcag gggcgcctga  3720
tgcggtattt tctccttacg catctgtgcg gtatttcaca ccgcatacgt caaagcaacc  3780
atagtacgcg ccctgtagcg gcgcattaag cgcggcgggt gtggtggtta cgcgcagcgt  3840
gaccgctaca cttgccagcg ccctagcgcc cgctcctttc gctttcttcc cttcctttct  3900
cgccacgttc gccggctttc cccgtcaagc tctaaatcgg gggctccctt tagggttccg  3960
atttagtgct ttacggcacc tcgaccccaa aaaacttgat ttgggtgatg gttcacgtag  4020
tgggccatcg ccctgataga cggtttttcg ccctttgacg ttggagtcca cgttctttaa  4080
tagtggactc ttgttccaaa ctggaacaac actcaaccct atctcgggct attcttttga  4140
tttataaggg attttgccga tttcggccta ttggttaaaa aatgagctga tttaacaaaa  4200
atttaacgcg aattttaaca aaatattaac gtttacaatt ttatggtgca ctctcagtac  4260
aatctgctct gatgccgcat agttaagcca gccccgacac ccgccaacac ccgctgacgc  4320
gccctgacgg gcttgtctgc tcccggcatc cgcttacaga caagctgtga ccgtctccgg  4380
gagctgcatg tgtcagaggt tttcaccgtc atcaccgaaa cgcgcgagac gaaagggcct  4440
cgtgatacgc ctatttttat aggttaatgt catgataata atggtttctt agacgtcagg  4500
tggcactttt cggggaaatg tgcgcggaac ccctatttgt ttatttttct aaatacattc  4560
aaatatgtat ccgctcatga caataacc ctgataaatg cttcaataat attgaaaaag  4620
gaagagtatg agtattcaac atttccgtgt cgccttatt cccttttttg cggcattttg  4680
ccttcctgtt tttgctcacc cagaaacgct ggtgaaagta aaagatgctg aagatcagtt  4740
gggtgcacga gtgggttaca tcgaactgga tctcaacagc ggtaagatcc ttgagagttt  4800
tcgccccgaa gaacgttttc caatgatgag cacttttaaa gttctgctat gtggcgcggt  4860
attatcccgt attgacgccg ggcaagagca actcggtcgc cgcatacact attctcagaa  4920
tgacttggtt gagtactcac cagtcacaga aaagcatctt acggatggca tgacagtaag  4980
agaattatgc agtgctgcca taaccatgag tgataacact gcggccaact tacttctgac  5040
aacgatcgga ggaccgaagg agctaaccgc ttttttgcac aacatggggg atcatgtaac  5100
tcgccttgat cgttgggaac cggagctgaa tgaagccata ccaaacgacg agcgtgacac  5160
cacgatgcct gtagcaatgg caacaacgtt gcgcaaacta ttaactggcg aactacttac  5220
tctagcttcc cggcaacaat taatagactg gatggaggcg gataaagttg caggaccact  5280
tctgcgctcg gcccttccgg ctggctggtt tattgctgat aaatctggag ccggtgagcg  5340
tgggtctcgc ggtatcattg cagcactggg gccagatggt aagccctccc gtatcgtagt  5400
tatctacacg acggggagtc aggcaactat ggatgaacga aatagacaga tcgctgagat  5460
aggtgcctca ctgattaagc attggtaact gtcagaccaa gtttactcat atatacttta  5520
gattgattta aaacttcatt tttaatttaa aaggatctag gtgaagatcc tttttgataa  5580
tctcatgacc aaaatccctt aacgtgagtt ttcgttccac tgagcgtcag accccgtaga  5640
aaagatcaaa ggatcttctt gagatccttt ttttctgcgc gtaatctgct gcttgcaaac  5700
aaaaaaacca ccgctaccag cggtggtttg tttgccggat caagagctac caactctttt  5760
tccgaaggta actggcttca gcagagcgca gataccaaat actgtccttc tagtgtagcc  5820
gtagttaggc caccacttca agaactctgt agcaccgcct acatacctcg ctctgctaat  5880
cctgttacca gtggctgctg ccagtggcga taagtcgtgt cttaccgggt tggactcaag  5940
acgatagtta ccggataagg cgcagcggtc gggctgaacg gggggttcgt gcacacagcc  6000
cagcttggag cgaacgacct acaccgaact gagatacct atggcgtgag tatgagaaag  6060
cgccacgctt cccgaaggga aaaggcgga caggtatccg gtaagcggca gggtcggaac  6120
aggagagcgc acgagggagc ttccaggggg aaacgcctgg tatctttata gtcctgtcgg  6180
gtttcgccac ctctgacttg agcgtcgatt tttgtgatgc tcgtcagggg ggcggagcct  6240
atggaaaaac gccagcaacg cggcctttt acggttcctg gccttttgct ggccttttgc  6300
tcacatgt                                                            6308
```

SEQ ID NO: 139           moltype = DNA   length = 6308
FEATURE                  Location/Qualifiers
misc_feature            1..6308
                         note = plasmid pAAVss-SPc5-12GTRM-MVM-hGAA-SynthpA
source                  1..6308
                         mol_type = other DNA
                         organism = synthetic construct
SEQUENCE: 139
cctgcaggca gctgcgcgct cgctcgctca ctgaggccgc ccgggcaaag cccgggcgtc  60

-continued

```
gggcgacctt tggtcgcccg gcctcagtga gcgagcgagc gcgcagagag ggagtggcca    120
actccatcac tagggggttcc tgcggccgca cgcgtaccgg ttggccaccg ccttcggcac    180
catcctcacg acacccaaat atggcgacgg gtgaggaatg gtgggagtt attttttagag    240
cggtgaggaa ggtgggcagg cagcaggtgt tggcgctcta aaaataactc ccgggagtta    300
tttttagagc ggaggaatgg tggacaccca aatatgcga cggttcctca cccgtcgcca    360
tatttgggtg tccgccctcg gccggggccg cattcctggg ggccgggcgg tgctcccgcc    420
cgcctcgata aaaggctccg gggccggcgg cggcccacga gctacccgga ggagcgggag    480
gcgccaagct ctagatctag aactagtaag aggtaagggt ttaagggatg gttggttggt    540
ggggtattaa tgtttaatta cctggagcac ctgcctgaaa tcacttttt tcaggttggc    600
gtacggccac catgggagtg aggcacccgc cctgctccca ccggctcctg gccgtctgcg    660
ccctcgtgtc cttggcaacc gctgcactcc tggggcacat cctactccat gatttcctgc    720
tggttccccg agagctgagt ggctcctccc cagtcctgga ggagactcac ccagctcacc    780
agcagggagc cagcagacca gggcccccggg atgcccaggc acaccccggc cgtcccagag    840
cagtgcccac acagtgcgac gtcccccca acagccgctt cgattgcgcc cctgacaagg    900
ccatcaccca ggaacagtgc gaggcccgcg gctgttgcta catccctgca aagcaggggc    960
tgcagggagc ccagatgggg cagccctggt gcttcttccc acccagctac cccagctaca   1020
agctggagaa cctgagctcc tctgaaatgg gctacacggc caccctgacc cgtaccaccc   1080
ccaccttctt ccccaaggac atcctgaccc tgcggctgga cgtgatgatg gagactgaga   1140
accgcctcca cttcacgatc aaagatccag ctaacaggcg ctacgaggtg cccttggaga   1200
ccccgcatgt ccacagccgg gcaccgtccc cactctacag cgtggagttc tccgaggagc   1260
ccttcgggt gatcgtgcgc cggcagctgg acggccgcgt gctgctgaac acgacggtgg   1320
cgccctgtt ctttgcggac cagttccttc agctgtccac ctcgctgcc tcgcagtata   1380
tcacaggcct cgccgagcac ctcagtcccc tgatgctcag caccagctgg accaggatca   1440
ccctgtggaa ccgggacctt gcgcccacgc ccggtgcgaa cctctacggg tctcacccctt   1500
tctacctggc gctggaggac ggcgggtcgg cacacggggg gttcctgcta aacagcaatg   1560
ccatggatgt ggtcctgcag ccgagccctg ccctttagctg gaggtcgaca ggtgggatcc   1620
tggatgtcta catcttcctg ggcccagagc ccaagagcgt ggtgcagcag tacctggacg   1680
ttgtgggata cccgttcatg ccgccatact ggggcctggg cttccaccctg tgccgctggg   1740
gctactcctc caccgctatc acccgccagg tggtggagaa catgaccagg gcccacttcc   1800
ccctggacgt ccagtggaac gacctggact acatggactc ccggaagggac ttcacgttca   1860
acaaggatgg cttccgggac ttccccgggcca tggtgcagga gctgcaccag ggcggccggc   1920
gctacatgat gatcgtggat cctgccatca gcagctcggg ccctgccggg agctacaggc   1980
cctacgacga gggtctgcgg aggggggtttt tcatcaccaa cgagaccggc cagccgctga   2040
ttgggaaggt atggcccggg tccactgcct tccccgactt caccaacccc acagccctgg   2100
cctggtggga ggacatggtg gctgagttcc atgaccaggt gcccttcgac ggcatgtgga   2160
ttgacatgaa cgagccttcc aacttcatca ggggctctga ggacggctgc cccaacaatg   2220
agctggagaa cccaccctac gtgcctgggg tggttggggg gaccctccag gcggccacca   2280
tctgtgcctc cagccaccag tttctctcca cacactacaa cctgcacaac ctctacggcc   2340
tgaccgaagc catcgcctcc cacagggcgc tggtgaagc tcgggggaca cgcccatttg   2400
tgatctcccg ctcgaccttt gctggccacg gccgatacgc cggccactgg acgggggacg   2460
tgtgagctc ctgggagcag ctcgcctcct ccgtgccaga aatcctgcag tttaacctgc   2520
tgggggtgcc tctggtcggg gccgacgtct gcggcttcct gggcaacacc tcagaggagc   2580
tgtgtgtgcg ctggaccaca ctgggggcct tctaccccctt catgcggaac cacaacaggcc   2640
tgctcagtct gccccaggag ccgtacagct tcagcgagcc ggcccagcag gccatgagga   2700
aggccctcac cctgcgctac gcactcctcc cccacctcta cacactgttc caccaggccc   2760
acgtcgcggg ggagaccgtg gcccggcccc tcttcctgga gttccccaag gactctagca   2820
cctggactgt ggaccaccag ctcctgtggg gggaggccct gctcatccac ccagtgctcc   2880
aggccgggaa ggccgaagtg actggctact tcccctttggg cacatggtac gacctgcaga   2940
cggtgccagt agaggcccctt ggcagcctcc caccccacc tgcagctccc cgtgagccag   3000
ccatccacag cgaggggcag tgggtgacgc tgccggcccc cctggacacc atcaacgtcc   3060
acctccggggc tgggtacatc atccccctgc agggccctcg cctcacaacc acagagtccc   3120
gccagcagcc catggcccctg gctgtggccc tgaccaaggg tggggaggcc cgaggggagc   3180
tgttctggga cgatggagag agcctggaag tgctggagcg aggggcctac acacaggtca   3240
tcttcctggc caggaataac acgatcgtga atgagctggt acgtgtgacc agtgagggag   3300
ctggcctgca gctgcagaag gtgactgtcc tgggcgtgagc cacggcgcc cagcaggtcc   3360
tctccaacgg tgtccctgtc tccaacttca cctacagcc cgacaccaag gtcctggaca   3420
tctgtgtctc gctgttgatg ggagagcagt ttctcgtcag ctggtgttag cctaggaata   3480
aaagatcttt attttcatta gatctgtgtg ttggtttttt gtgtgacccg tctgattttg   3540
taggtaacca cgtgcggacc gagcggccgc aggaaccct agtgatggag ttggccactc   3600
cctctctgcg cgctcgctcg ctcactgagg ccgggcgacc aaaggtcgcc cgacgcccgg   3660
gctttgcccg ggcggcctca ctgagcgagc gagcgcgcag ctgcctgcag gggcgcctga   3720
tgcggtattt tctccttacg catctgtgcg gtatttcaca ccgcatacgt caaagcaacc   3780
atagtacgcg ccctgtagcg gcgcattaag cgcggcgggt gtggtggtta cgcgcagcgt   3840
gaccgctaca cttgccagcg ccctagcgcc cgctcctttc gctttcttcc cttcctttct   3900
cgccacgttc gccggctttc cccgtcaagc tctaaatcgg gggctccctt tagggttccg   3960
atttagtgct ttacggcacc tcgacccca aaaaacttgat ttgggtgatg gttcacgtag   4020
tgggccatcg ccctgataga cggtttttcg ccctttgacg ttggagtcca cgttcttaa   4080
tagtggactc ttgttccaaa ctggaacaac actcaaccct atctcgggct attctttga   4140
tttataaggg attttgccga tttcggccta ttggttaaaa aatgagctga tttaacaaaa   4200
atttaacgcg aattttaaca aaatattaac gtttacaatt ttatggtgca ctctcagtac   4260
aatctgctct gatgccgcat agttaagcca gccccgacac ccgccaacac ccgctgacgc   4320
gccctgacgg gcttgtctgc tcccggcatc cgcttacaga caagctgtga ccgtctccgg   4380
gagctgcatg tgtcagaggt tttcaccgtc atcaccgaaa cgcgcgagac gaaagggcct   4440
cgtgatacgc ctatttttat aggttaatgt catgataata atggtttctt agacgtcagg   4500
tggcactttt cggggaaatg tgcgcggaac ccctatttgt ttatttttct aaatacattc   4560
aaatatgtat ccgctcatga acaataacc ctgataaatg cttcaataat attgaaaaag   4620
gaagagtatg agtattcaac atttccgtgt cgcccttatt cccttttttg cggcattttg   4680
ccttcctgtt tttgctcacc cagaaacgct ggtgaaagta aaagatgctg aagatcagtt   4740
gggtgcacga gtgggttaca tcgaactgga tctcaacagc ggtaagatcc ttgagagttt   4800
```

-continued

```
tcgccccgaa gaacgttttc caatgatgag cacttttaaa gttctgctat gtggcgcggt    4860
attatcccgt attgacgccg ggcaagagca actcggtcgc cgcatacact attctcagaa    4920
tgacttggtt gagtactcac cagtcacaga aaagcatctt acggatggca tgacagtaag    4980
agaattatgc agtgctgcca taaccatgag tgataacact gcggccaact tacttctgac    5040
aacgatcgga ggaccgaagg agctaaccgc ttttttgcac aacatggggg atcatgtaac    5100
tcgccttgat cgttgggaac cggagctgaa tgaagccata ccaaacgacg agcgtgacac    5160
cacgatgcct gtagcaatgg caacaacgtt gcgcaaacta ttaactggcg aactacttac    5220
tctagcttcc cggcaacaat taatagactg gatggaggcg gataaagttg caggaccact    5280
tctgcgctcg gcccttccgg ctggctggtt tattgctgat aaatctggag ccggtgagcg    5340
tgggtctcgc ggtatcattg cagcactggg gccagatggt aagccctccc gtatcgtagt    5400
tatctacacg acggggagtc aggcaactat ggatgaacga aatagacaga tcgctgagat    5460
aggtgcctca ctgattaagc attggtaact gtcagaccaa gtttactcat atatacttta    5520
gattgattta aaacttcatt tttaatttaa aaggatctag gtgaagatcc tttttgataa    5580
tctcatgacc aaaatccctt aacgtgagtt ttcgttccac tgagcgtcag accccgtaga    5640
aaagatcaaa ggatcttctt gagatccttt ttttctgcgc gtaatctgct gcttgcaaac    5700
aaaaaaacca ccgctaccag cggtggtttg tttgccggat caagagctac caactctttt    5760
tccgaaggta actggcttca gcagagcgca gataccaaat actgtccttc tagtgtagcc    5820
gtagttaggc caccacttca agaactctgt agcaccgcct acatacctcg ctctgctaat    5880
cctgttacca gtggctgctg ccagtggcga taagtcgtgt cttaccgggt tggactcaag    5940
acgatagtta ccggataagg cgcagcggtc gggctgaacg gggggttcgt gcacacagcc    6000
cagcttggag cgaacgacct acaccgaact gagatacct a cagcgtgagc tatgagaaag    6060
cgccacgctt cccgaaggga gaaaggcgga caggtatccg gtaagcggca gggtcggaac    6120
aggagagcgc acgagggagc ttccaggggg aaacgcctgg tatctttata gtcctgtcgg    6180
gtttcgccac ctctgacttg agcgtcgatt tttgtgatgc tcgtcagggg ggcggagcct    6240
atggaaaaac gccagcaacg cggcctttttt acggttcctg ccttttttgct ggccttttgc    6300
tcacatgt                                                             6308
```

```
SEQ ID NO: 140          moltype = DNA  length = 21
FEATURE                 Location/Qualifiers
misc_feature            1..21
                        note = Forward Primer hGAA
source                  1..21
                        mol_type = other DNA
                        organism = synthetic construct
SEQUENCE: 140
tgccctcgca gtatatcaca g                                                21

SEQ ID NO: 141          moltype = DNA  length = 19
FEATURE                 Location/Qualifiers
misc_feature            1..19
                        note = Reverse Primer hGAA
source                  1..19
                        mol_type = other DNA
                        organism = synthetic construct
SEQUENCE: 141
gagacccgta gaggttcgc                                                   19

SEQ ID NO: 142          moltype = DNA  length = 20
FEATURE                 Location/Qualifiers
misc_feature            1..20
                        note = Forward Primer hGAAco
source                  1..20
                        mol_type = other DNA
                        organism = synthetic construct
SEQUENCE: 142
acccccttcat gcctccttat                                                 20

SEQ ID NO: 143          moltype = DNA  length = 20
FEATURE                 Location/Qualifiers
misc_feature            1..20
                        note = Reverse Primer hGAAco
source                  1..20
                        mol_type = other DNA
                        organism = synthetic construct
SEQUENCE: 143
tccatgtagt ccaggtcgtt                                                  20

SEQ ID NO: 144          moltype = DNA  length = 23
FEATURE                 Location/Qualifiers
misc_feature            1..23
                        note = Forward Primer hMTM1
source                  1..23
                        mol_type = other DNA
                        organism = synthetic construct
SEQUENCE: 144
gtttgagatc ctcacgagat acg                                              23

SEQ ID NO: 145          moltype = DNA  length = 23
FEATURE                 Location/Qualifiers
```

-continued

```
misc_feature          1..23
                      note = Reverse Primer hMTM1
source                1..23
                      mol_type = other DNA
                      organism = synthetic construct
SEQUENCE: 145
gtccatccat ccacgttaaa ctt                                                          23

SEQ ID NO: 146        moltype = DNA   length = 20
FEATURE               Location/Qualifiers
misc_feature          1..20
                      note = Forward Primer hMTM1co
source                1..20
                      mol_type = other DNA
                      organism = synthetic construct
SEQUENCE: 146
ggcaagagaa acaaggacga                                                              20

SEQ ID NO: 147        moltype = DNA   length = 20
FEATURE               Location/Qualifiers
misc_feature          1..20
                      note = Reverse Primer hMTM1co
source                1..20
                      mol_type = other DNA
                      organism = synthetic construct
SEQUENCE: 147
ggcatcgtcg gactcatatc                                                              20
```

DIAPHRAGM-SPECIFIC NUCLEIC ACID REGULATORY ELEMENTS AND METHODS AND USE THEREOF

FIELD

The present invention relates to nucleic acid regulatory elements that are able to enhance diaphragm-specific expression of genes, methods employing these regulatory elements and use thereof. The invention further encompasses expression cassettes, vectors and pharmaceutical compositions comprising these regulatory elements. The present invention is particularly useful for applications using gene therapy, more particularly diaphragm-directed gene therapy, or gene editing, and for vaccination purposes.

BACKGROUND

The diaphragm is a sheet of internal skeletal muscle that extends across the bottom of the thoracic cavity. The diaphragm separates the thoracic cavity containing the heart and lungs, from the abdominal cavity and performs an important function in respiration: as the diaphragm contracts, the volume of the thoracic cavity increases, and air is drawn into the lungs. As with any organ or muscle, the diaphragm is subject to disorders and abnormalities, which come in many different forms and can stem from injury or illness. Consequently, diaphragm dysfunction can result in severe respiratory problems with potential fatal consequences. Diaphragmatic weakness and paralysis can be classified according to the anatomic region of abnormality. Diaphragmatic paralysis and weakness may be unilateral or bilateral, temporary or permanent, depending on the cause.

There are currently no effective cures available to treat the potential life-threatening diaphragm dysfunction in many of these and other muscle disorders. Hence, there is a need to establish effective cures by gene therapy to enable robust expression of the cognate therapeutic genes in the diaphragm. This requires the development of potent expression cassettes containing the genes of interest.

Consequently, there is a need to identify robust nucleic acid regulatory elements capable of substantially increasing transcription in the diaphragm. These nucleic acid regulatory elements are critically important for the regulation of gene expression in a tissue-specific manner. They are typically composed of clusters of transcription factor binding site (TFBS) motifs. The types and arrangement of TFBS and epigenetic modification patterns influence gene expression levels and specificity. Conventional methods of vector design relied on haphazard trial-and-error approaches whereby transcriptional enhancers were combined with promoters to boost expression levels. Though this could sometimes be effective, it often resulted in non-productive combinations that resulted in either modest or no increased expression levels of the gene of interest and/or loss of tissue specificity. Moreover, these conventional approaches did not take account of the importance of including evolutionary conserved regulatory motifs into the expression modules, which is particularly relevant for clinical translation.

There remains a need in the art for safe and efficient gene delivery to diaphragm, skeletal muscles and/or heart.

SUMMARY OF THE INVENTION

The present inventors have relied on a computational approach (cf. FIG. 1) to identify robust nucleic acid regulatory elements that boost gene expression at the transcriptional level in the diaphragm (i.e. diaphragm: Dph). This requires the following computational steps: (1) diaphragm-specific genes were identified that are highly and specifically expressed based on expression data from diaphragm; (2) publicly available databases (ENSEMBL) were used for extracting the sequences upstream of the Transcriptional Start Site (TSS) of the selected genes. 3) These sequences were then submitted into UCSC Genome Browser Database for locating the transcription start site in human genome. To extract the corresponding diaphragm nucleic acid regulatory elements, defined herein as nucleic acid regulatory elements, the sequences were selected based on the following criteria: a) rich TFBS content, b) epigenetic signatures associated with high DNase hypersensitivity or chromatin accessibility (i.e. histone modifications), and c) evolutionary conserved clusters of TFBS associated with highly expressed diaphragm-specific genes.

As shown in the experimental section, the inventors identified nucleic acid regulatory elements that will specifically enhance gene expression in diaphragm. In addition, the inventors identified nucleic acid regulatory elements with combined diaphragm-specific and other tissue-specific expression such as for skeletal muscle and cardiac and skeletal muscle expression. Exemplary, but not limiting, muscle- or heart-muscle-specific regulatory elements are those that identified previously in European Patent Applications WO2015/110449A1 and WO2011/051450A1.

This combination approach will hence allow robust expression in diaphragm as well as other tissues that are affected by particular diseases that affect both diaphragm and skeletal muscles such as e.g. MTM. However, for diseases such as GSD-II and DMD which affects different tissues such as the diaphragm, skeletal muscles and heart, a combination of diaphragm nucleic acid regulatory element with the skeletal muscle nucleic acid regulatory element and/or the cardiac nucleic acid element will be developed. The diaphragm regulatory elements and the combination of diaphragm and other tissues elements (skeletal muscle and/ or cardiac elements) will subsequently be validated in vivo yielding efficient and multiple tissue-specific gene expression. This approach hence, allows for the use of lower and thus safer vector doses, while maximizing therapeutic efficacy.

The invention therefore provides the following aspects:

In the screening, 89 regulatory elements were identified that can increase the expression of a transgene in a gene therapy delivery system such as in a vector system such as in an AAV vector system, increasing expression in diaphragm tissue. These elements are depicted in Tables 3 and 4 below. Table 3 depicts the Diaphragm cis regulatory elements (denominations "Dph-CREs", "CREs" or "CRMs" or "SH" used herein are the same and interchangeable) (Dph-CREs) which are particularly relevant for increasing expression in diaphragm and skeletal muscle, while Table 4 depicts the Diaphragm CREs (Dph-CREs) which are particularly relevant for increasing expression in diaphragm, skeletal muscle and heart tissue. Seven of these CREs are present in both groups.

In particular, Dph-CRE02, Dph-CRE04, Dph-CRE58, Dph-CRE59, Dph-CRE60, Dph-CRE64, Dph-CRE06, Dph-CRE21, Dph-CRE41 and Dph-CRE18 (Table 3 & FIGS. 5A to 5I) have been validated in vivo for their high expression in diaphragm and skeletal muscle tissue. More particularly, Dph-CRE-02 Dph-CRE-64 and Dph-CRE-21 are preferred. Even more preferably, Dph-CRE64 is used for treating diseases which require upregulation of transgene expression in Diaphragm and skeletal muscle, and less in heart. In a specific embodiment, these Dph-CREs, more preferably the Dph-CRE64 (or Dph-CRE02 or CRE-21) are combined with muscle specific CRE Sk-SH4 (SEQ ID NO; 121). In a more preferred embodiment, said combination of CREs is coupled to the human desmin promoter, more preferably the 1,4kb variant thereof (SEQ ID NO; 92). For treatment of MTM disease, said CRE-promoter combination is preferably driving the hMTM1 (SEQ ID NO: 95) or more preferably the codon optimized hMTM1 transgene (SEQ ID NO; 96).

Myotubular myopathy (MTM) affects primarily the skeletal muscles and diaphragm, whereas the heart is rarely affected. Hence, ideally expression of the therapeutic MTM1 transgene should be targeted to skeletal muscles and diaphragm but not the heart. Therefore the SK-SH4-hDes1.4kb expression cassette is referred since in this cassette expression in skeletal muscle is high, while it is much lower in heart when combined with the (Dph-CRE-64) compared to e.g. the CSk-SH5-SPc which result in widespread cardiac gene expression when combined with the top Dph-CREs such as the Dph-CRE-02, -04 & 06.

As an example, the most preferred AAV vector combination for treating MTM is defined by SEQ ID NO: 131, pAAVss-CRE64-Sk-SH4-hDES1.4kb-MVM-hMTM1co-SynthpA.

Alternatively, Dph-CRE69, 70, 71, 66, 68, 77, 02, 04, 06, 07 (Table 4 and FIGS. 5A to 5I) have been validated in vivo for their high expression in diaphragm, skeletal muscle and heart tissue. More particularly, Dph-CRE-02, Dph-CRE-04 and CRE-06 are preferred. In a specific embodiment, said Dph-CREs, more preferably Dph-CRE-02,Dph-CRE04 (or Dph-CRE06) are combined with skeletal muscle and heart specific CRE CSk-SH5 (SEQ ID NO: 122). In a more preferred embodiment, said combination of CREs is coupled to the SPc5-12 promoter (SEQ ID NO: 124). SPc5-12 (sometimes called SPC-5-12-GTRM, which term is interchangeable). For treatment of e.g. Pompe disease, said CRE-promoter combination is preferably driving the hGAA (SEQ ID NO: 93) or more preferably the codon optimized hGAAco transgene (SEQ ID NO; 94).

The rationale for this design is based on the fact that in Pompe disease the GAA transgene is defective, which affects mainly skeletal muscles, diaphragm and the heart. Hence, ideally expression of the therapeutic GAA gene should be targeted to these affected tissues. The CSk-SH5-SPc combination leads to robust and specific expression in diaphragm, the skeletal muscles and heart and is therefore well suited to target those tissues that are affected in Pompe. As an example, the most preferred AAV vector combination for treating Pompe disease is defined by SEQ ID NO: 130). pAAVss-CRE04-CSk-SH5-SPc5-12GTRM-MVM-hGAAco-SynthpA (SEQ ID NO: 130).

Based on the above arguments, the present invention provides 10 different AAV constructs which were tested for expressing therapeutic genes:

1) pAAVss-hDes1.4kb-MVM-hMTM1-SynthpA (no diaphragm CRE, no muscle CRE Sk-SH4, only Desmin1.4kb promoter driving the MTM1 gene expression+MTM1) (SEQ ID NO; 135)

2) pAAVss-hDes1.4kb-MVM-hMTM1co-SynthpA (no diaphragm CRE, no muscle CRE Sk-SH4, +Des1.4kb+ codon opt MTM1) (SEQ ID NO; 134)

3) pAAVss-Sk-SH4-hDes1.4kb-MVM-hMTM1-SynthpA (no diaphragm CRE, +muscle CRE Sk-SH4+ Des1.4kb+MTM1) (SEQ ID NO; 137)

4) pAAVss-Sk-SH4-hDes1.4kb-MVM-hMTM1co-Syn-thpA (no diaphragm CRE, +muscle CRE Sk-SH4+ Des1.4kb+codon opt MTM1) (SEQ ID NO; 136)

5) pAAVss-CRE64-Sk-SH4-hDes1.4kb-MVM-hMTM1co-SynthpA (contain best selected Diaphragm CRE64 combined with muscle CRE Sk-SH4) (SEQ ID NO; 131)

6) pAAVss-SPc5-12GTRM-MVM-hGAA-SynthpA (no diaphragm CRE, no muscle CRE, only SPc5-12-GTRM promoter driving the GAA gene expression)) (SEQ ID NO; 139)

7) pAAVss-SPc5-12GTRM-MVM-hGAAco-SynthpA (no diaphragm, no muscle CRE CSk-SH5, +SPc5-12-GTRM+codon opt GAA) (SEQ ID NO; 138)

8) pAAVss-CSK-SH5-SPc5-12GTRM-MVM-hGAA-SynthpA (no diaphragm CRE, +muscle CRE CSk-SH5+SPc5-12-GTRM+GAA) (SEQ ID NO; 133)

9) pAAVss-CSK-SH5-SPc-5-12GTRM-MVM-hGAAco-SynthpA ((no diaphragm CRE, +muscle CRE CSK-SH5+SPc5-12-GTRM+codon opt GAA) (SEQ ID NO; 132)

10) pAAVss-CRE04-CSk-SH5-SPc-5-12GTRM-MVM-hGAAco-SynthpA ((contain best selected Diaphragm CRE04 combined with muscle CRE CSk-SH5) (SEQ ID NO; 130)

The invention further provides the following aspects:

Aspect 1: a nucleic acid regulatory element for enhancing diaphragm-specific gene expression comprising, consisting essentially of, or consisting of the sequence selected from the group consisting of: SEQ ID NO:1 to 89, a sequence having at least 80%, preferably at least 85%, more preferably at least 90%, even more preferably at least 95%, such as 95%, 96%, 97%, 98%, or 99%, identity to any of these sequences. This aspect hence preferably provides for a nucleic acid regulatory element for enhancing gene expression in diaphragm, having a maximal length of 1000 nucleotides, preferably 800 nucleotides, more preferably 700 nucleotides, 600 nucleotides or 550 nucleotides, comprising the sequence defined by SEQ ID NO: 4, a sequence having at least 80%, preferably at least 85%, more preferably at least 90%, even more preferably at least 95%, such as 95%, 96%, 97%, 98%, or 99%, identity to any of these sequences, the complement of said sequence, or a sequence hybridizing under stringent conditions to said nucleic acid regulatory element, or the use thereof for enhancing diaphragm-specific gene expression. In either one of these embodiments, SEQ ID NO:4 can be replaced by either one of SEQ ID NO: 1-89.

Aspect 2: the nucleic acid regulatory element according to aspect 1 for enhancing gene expression in the diaphragm and skeletal muscle, comprising consisting essentially of, or consisting of the sequence selected from the group consisting of: SEQ ID NO:1 to 7 and 10 to 65, 82, and 83 (cf. Dph-CRE-1 to 7, 10 to 65, 82, and 83 in Table 3), or a sequence having at least 80%, preferably at least 85%, more preferably at least 90%, even more preferably at least 95%, such as 95%, 96%, 97%, 98%, or 99%, identity to any of these sequences, or the use thereof for enhancing gene expression in the diaphragm and skeletal muscle. In a preferred embodiment of said aspect, said regulatory element is Dph-CRE64 (SEQ ID NO: 64) or Dph-CRE02 (SEQ ID NO: 2) or Dph-CRE21 (SEQ ID NO: 21).

Aspect 3: the nucleic acid regulatory element according to aspect 1 or 2, having a maximal length of 1000 nucleotides, preferably 800 nucleotides, more preferably 700 nucleotides, still comprising the regulatory element defined by any one of SEQ ID NO: 1 to 7, 10 to 65, 82, and 83 (cf. Dph-CRE1 to 7, 10 to 65, 82, and 83 in Table 3). In a preferred embodiment of said aspect, said regulatory element is Dph-CRE64 (SEQ ID NO: 64) or Dph-CRE02 (SEQ ID NO: 2) or Dph-CRE21 (SEQ ID NO: 21).

Aspect 4: the nucleic acid regulatory element according to aspect 1 for enhancing gene expression in diaphragm, skeletal muscle and heart tissue comprising a functional fragment of a sequence selected from the group consisting of: SEQ ID NO: 1 to 9, 66 to 81, and 84 to 89, or a sequence having at least 80%, preferably at least 85%, more preferably at least 90%, even more preferably at least 95%, such as 95%, 96%, 97%, 98%, or 99%, identity to any of these sequences. (cf. Dph-CRE1 to 9, 66 to 81, and 84 to 89 in Table 4), or the use thereof for enhancing gene expression in diaphragm, skeletal muscle and heart tissue. In a preferred embodiment of said aspect, said regulatory element is Dph-CRE04 (SEQ ID NO: 4) or Dph-CRE06 (SEQ ID NO: 6) or Dph-CRE02 (SEQ ID NO: 2).

Aspect 5: the nucleic acid regulatory element according to aspect 1 or 4, having a maximal length of 1000 nucleotides, preferably 800 nucleotides, more preferably 700 nucleotides even more preferably 600 nucleotides, such as 500 nucleotides, still comprising the regulatory element defined by any one of SEQ ID No: 1 to 9, 66 to 81, and 84 to 89. (cf. Dph-CRE1 to 9, 66 to 81, and 84 to 89 in Table 4). In a preferred embodiment of said aspect, said regulatory element is Dph-CRE04 (SEQ ID NO: 4) or Dph-CRE06 (SEQ ID NO: 6) or Dph-CRE02 (SEQ ID NO: 2).

Aspect 6: a nucleic acid regulatory element for enhancing gene expression in diaphragm, skeletal muscle and heart tissue comprising, consisting essentially of, or consisting of the complement of a sequence as defined in any one of aspects 1 to 3, or hybridizing under stringent conditions to the nucleic acid regulatory element according to any one of aspects 1 to 3.

Aspect 7: a nucleic acid regulatory element for enhancing gene expression in diaphragm, skeletal muscle and heart tissue comprising, consisting essentially of, or consisting of the complement of a sequence as defined in any one of aspects 1, 4 or 5, or hybridizing under stringent conditions to the nucleic acid regulatory element according to any one of aspects 1, 4 or 5.

Aspect 8: use of the nucleic acid regulatory element according to any one aspects 1 to 3, and 6 in a nucleic acid expression cassette, or a vector, more particularly for enhancing gene expression in diaphragm and skeletal muscle of said nucleic acid expression cassette or vector.

Aspect 9: use of the nucleic acid regulatory element according to any one aspects 1, 4, 5, and 7 in a nucleic acid expression cassette, or a vector, more particularly for enhancing gene expression in diaphragm, skeletal muscle and heart tissue expression of said nucleic acid expression cassette or vector.

Aspect 10: a nucleic acid expression cassette comprising at least one, such as one, two, three, four, five or more, nucleic acid regulatory elements according to any one of aspects 1 to 7, operably linked to a promoter.

Aspect 11: the nucleic acid expression cassette according to aspect 10, wherein the nucleic acid regulatory element is operably linked to a promoter and a transgene.

Aspect 12: the nucleic acid expression cassette according any one of aspects 10 or 11, wherein the promoter is a diaphragm and skeletal muscle-specific promoter, such as the promotor of any one of the genes defined in Table 3, namely the ACTA1, CKM, TPM2, MYL1, TNNC2, FHL1, TNNT1, TNNI2, MYLPF, TNNT3, MYH2, SLN, MYBPC1, ENO3, CA3, ATP2A1, and MYH1 genes; or wherein the promoter is a diaphragm, skeletal muscle and heart-specific promoter, such as the promotor of any one of the genes defined in Table 4, namely ACTA1, CKM, MYL2, MB, DES, TNNC1, TCAP, MYH7, ALDOA, and TPM1 genes. In preferred embodiments of said aspect, and particularly of aspects 2 and 3, the promoter is the mouse or human Desmin promoter, more preferably the human 1.4kb Desmin promoter according to SEQ ID NO: 92. In preferred embodiments of said aspect and particularly of aspects 4 and 5, the promoter is the SPc5-12 promoter according to SEQ ID NO: 124.

Aspect 13: the nucleic acid expression cassette according to any one of aspects 10 to 12, wherein the transgene encodes a therapeutic protein or an immunogenic protein.

Aspect 14: the nucleic acid expression cassette according to any one of aspects 9 to 13, wherein the transgene encodes a secretable protein or a structural protein, such as myotubularin (MTM, SEQ ID NO: 95), acid glucosidase (GAA, SEQ ID NO: 93), follistatin, dystrophin, sarcoglycan, or dysferlin. In a preferred embodiment of said aspect, said transgenes are codon-optimised such as MTMco (SEQ ID NO: 96) or GAAco (SEQ ID NO: 94).

Additionally, the Dph-CRE can be supplemented by a further regulatory element (CRE) e.g. resulting in further expression in skeletal muscle or skeletal muscle and heart tissue such as the ones disclosed in WO2015/110449. Said additional CRE can be placed before or after the Dph-CRE (Exemplary vector backbones are depicted in FIG. 8). In a preferred embodiment, the skeletal muscle CRE Sk-SH4 (SEQ ID NO: 121), or the skeletal muscle and cardiac CREs CSk-SH5 (SEQ ID NO: 122) and CSk-SH1 (SEQ ID NO: 123) regulatory elements are used in combination with the Dph-CREs.

Specifically preferred is the combination of Dph-CRE64, 02 or 21 with CRE Sk-SH4, in particular the combination of Dph-CRE64 with CRE Sk-SH4. This embodiment is preferably coupled to the mouse or human Desmin promoter, more preferably the human 1.4kb Desmin promoter according to SEQ ID NO: 92. Even more preferred, said CRE-promoter combination is driving the MTM1 transgene (SEQ ID NO: 94) or its codon-optimised variant MTM1co (SEQ ID NO: 96). Said combination is particularly interesting for use in treating MTM disease.

Further specifically preferred is the combination of Dph-CRE04, 06 or 02 with CRE CSk-SH5, in particular the combination of Dph-CRE04 with CRE CSk-SH5. This embodiment is preferably coupled to the SPc5-12 promoter according to SEQ ID NO: 124. Even more preferred, said CRE-promoter combination is driving the hGAA (SEQ ID NO:93 transgene or its codon optimised variant hGAAco (SEQ ID NO: 94). Said combination is particularly interesting for use in treating Pompe disease.

Aspect 15: the nucleic acid expression cassette according to any one of aspects 9 to 14, further comprising an intron, preferably the Minute Virus of Mouse (MVM) intron (SEQ ID NO: 125).

Aspect 16: the nucleic acid expression cassette according to any one of aspects 9 to 15, further comprising a poly-adenylation signal, preferably the synthetic poly-A site (SEQ ID NO: 127) or the Simian Virus 40 (SV40) polyadenylation signal.

Aspect 17: a vector comprising the nucleic acid regulatory element according to any one of aspects 1 to 7, or the nucleic acid expression cassette according to any one of aspects 10 to 16.

Aspect 18: the vector according to aspect 17, which is a viral vector, preferably an adeno-associated viral (AAV) vector, more preferably an AAV9 vector.

Aspect 19: the vector according to aspect 17, which is a non-viral vector, preferably a plasmid, a minicircle, an episomal vector, or a transposon-based vector, such as a PiggyBac-based vector or a Sleeping Beauty-based vector.

Particularly interesting embodiments of said aspect are the vectors defined by SEQ ID NO: 131 (especially for use in treating MTM disease) or 130 (especially for use in treating Pompe disease).

Aspect 20: a pharmaceutical composition comprising the nucleic acid expression cassette according to any one of aspects 10 to 16, or the vector according to any one of aspects 17 to 19, and a pharmaceutically acceptable carrier.

Aspect 21: the nucleic acid regulatory element according to any one of aspects 1 to 7, the nucleic acid expression cassette according to any one of aspects 10 to 16, the vector according to any one of aspects 17 to 19, or the pharmaceutical composition according to aspect 20 for use in medicine, more preferably for use in gene therapy.

Aspect 22: the nucleic acid regulatory element according to any one of aspects 1 to 3, and 6, the nucleic acid expression cassette according to any one of aspects 10 to 16, the vector according to any one of aspects 17 to 19, or the pharmaceutical composition according to aspect 20, for use in treating MTM.

Aspect 23: the nucleic acid regulatory element according to any one of aspects 1, 4, 5, and 7, the nucleic acid expression cassette according to any one of aspects 10 to 16, the vector according to any one of aspects 17 to 19, or the pharmaceutical composition according to aspect 20, for use in treating Pompe disease.

Alternatively, either one of the following diseases could be treated using the nucleic acid regulatory element according to any one of aspects 1 to 7, the nucleic acid expression cassette according to any one of aspects 10 to 16, the vector according to any one of aspects 17 to 19, or the pharmaceutical composition according to aspect 20: neuromuscular disorders and heart diseases, such as Abetalipoproteinemia (Bassen Kornzwieg), Acetylcholine Receptor Deficiency (Congenital Myasthenic Syndrome), Charlevoix-Saguenay Syndrome/Disease, Benign Congenital Myopathy, Brody Disesase, Centronuclear Myopathy (Myotubular Myopathy), Chondrodystrophic Myotonia (Schwartz-Jampel Syndrome), Chudley Sydrome, Fingerprint Myopathy, Hereditary Neuralgic Amyotrophy (Parsonage-Turner Syndrome), Inclusion Body Myopathy (e.g. Type 2 or Type 3), Inclusion Body Myositis, Isaac's Syndrome (Neuromyotonia), Kennedy's Disease (Spinal Bulbar (Muscular) Atrophy), Macrophagic Myofascitis, McAdle's Disease (Myophosphorylase Deficiency/Glycogen Storage Type V), Mononeuritis Multiplex, Muscle-Eye-Brain Disease, Nemaline Myopathy, Nonaka Myopathy, Rippling Muscle Disease, Tibial Muscular Dystrophy (Udd Distal Myopathy), Welander's Distal Myopathy, Acid Maltase Deficiency (Pompe's Disease/Glycogen Storage Disease Type II), Danon Disease (Gylcogen Storage Disease Type IIb/Vacuolar Myopathies), Debranching Enzyme Deficiency (Glycogen Storage Disease Type III/Forbe's Disease), Andersen Disease/Syndrome (Glycogen Storage Disease Type IV/Branching Enzyme Deficiency), Tauri's Disease (Glycogen Storage Disease Type VII/Phosphofructokinase Deficiency), Desmin Storage Myopathy (Myofibrillar Myopathy), Myodenylate Deaminase Deficiency, Adrenoleukodystrophy, Arthrogryposis Multiplex Congenita, Ataxia with Congenital Glaucoma, Ataxia with Vitamin E Deficiency, Barth Syndrome, Bethlem Myopathy, Carnitine Palmityl Transferase Deficiency, Carnitine Deficiency, Central Core Disease, Hereditary Motor and Sensory Neuropathy (e.g. Charcot-Marie-Tooth Diseases (CMT) such as CMT Type I, CMT Type II, CMT Type III (Dejerine-Sottas Disease), CMT Type IV (Refsum's Disease), CMT Type V; Peroneal Muscular Atrophy; Neuronal Type of Peroneal Muscular Atrophy), Hereditary Sensory and Autonomic Neuropathy (e.g. Type I, Type III (Familial Dysautonomia/Riley-Day Syndrome), Type IV (Congenital insensitivity to pain and anhidrosis), Congenital Fibre Type Disproportion Myopathy, Distal Spinal Muscular Atrophy, Familial Amyloid Neuropathy, Familial Dilated Cardiomyopathy with Muscular Dystrophy, Friedreich's Ataxia, Hyperkalemic Periodic Paralysis (Gamstorp Disease), Giant Axonal Neuropathy, Guillain-Barre Syndrome (Acute inflammatory Demyelinating/Polyradiculoneuropathy), Hyperthermia (Malignant Hyperthermia), Hypokalemic Periodic Paralysis, Iatrogenic Myopathy, Kearns-Sayre Syndrome, Kugelberg Welander Disease (Spinal Muscular Atrophy Type III), Laing Distal Myopathy, Lambert-Eaton (Myasthenic) Syndrome, Leigh's Syndrome, Minicore Myopathy/Multicore Myopathy, Mitochondrial Myopathy and/or Neuropathy, Mixed Connective Tissue Overlap Disease, Miyoshi Myopathy, Multifocal Motor Neuropathy with Conduction Block, Myasthenia Gravis, Myotonia Congenita (Thomsen's Disease), Myotonic Muscular Dystrophy (e.g. Type I (Steinert's Disease), Type II (Proximal Myotonic Myopathy)), Oculopharyngeal Muscular Dystrophy, Olivopontocerebellar Atrophy, Paramyotonia Congenita, Paraneoplastic neuropathy, Polymyopsitis, Reducing Body Myopathy, Scapuloperoneal Muscular Atrophy, Tubular Aggregate Myopathy, Walker-Warburg Syndrome, Werdnig-Hoffman Disease (Spinal Muscular Atrophy Type I), Zebra Body Myopathy, Nuclear Envelop Disease, muscular dystrophy (e.g. Duchenne muscular dystrophy (DMD)/Becker muscular dystrophy (BMD)), motor neuron diseases (MND), such as e.g. Charcot-Marie-Tooth Diseases (CMT) such as CMT Type I, CMT Type II, CMT Type III (Dejerine-Sottas Disease), CMT Type IV (Refsum's Disease), CMT Type V, spinal muscular atrophy (SMA), and amyotrophic lateral sclerosis (ALS), Emery-Dreifuss muscular dystrophy, facioscapulohumeral muscular dystrophy (FSHD), congenital muscular dystrophies, congenital myopathies, limb girdle muscular dystrophy, metabolic myopathies, muscle inflammatory diseases, myasthenia, mitochondrial myopathies, anomalies of ionic channels, nuclear envelop diseases, cardiomyopathies, cardiac hypertrophy, heart failure, distal myopathies, cardiovascular diseases, hemophilia, including hemophilia A and B, and diabetes.

In one embodiment, the diseases and disorders that may benefit from gene therapy using the Dph-CRE Sk-SH4 CRE in combination with, the Desmin promoter (e.g. the human DES 1.4kb promoter (SEQ ID NO:92) are diseases that affect the skeletal muscle, and include Abetalipoproteinemia (Bassen Kornzwieg), Acetylcholine Receptor Deficiency (Congenital Myasthenic Syndrome), Charlevoix-Saguenay Syndrome/Disease, Benign Congenital Myopathy, Brody Disesase, Centronuclear Myopathy (Myotubular Myopathy), Chondrodystrophic Myotonia (Schwartz-Jampel Syndrome), Chudley Sydrome, Fingerprint Myopathy, Hereditary Neuralgic Amyotrophy (Parsonage-Turner Syndrome), Inclusion Body Myopathy (e.g. Type 2 or Type 3), Inclusion Body Myositis, Isaac's Syndrome (Neuromyotonia), Kennedy's Disease (Spinal Bulbar (Muscular) Atrophy), Macrophagic Myofascitis, McAdle's Disease (Myophosphorylase Deficiency/Glycogen Storage Type V), Mononeuritis Multiplex, Muscle-Eye-Brain Disease, Nemaline Myopathy, Nonaka Myopathy, Rippling Muscle Disease, Tibial Muscular Dystrophy (Udd Distal Myopathy) and Welander's Distal Myopathy. In another embodiment, the diseases and disorders that may benefit from gene therapy using the Dph-CRE CSk-SH5 CRE combination with e.g. the SPc5-

12 promoter are diseases that affect both the skeletal muscle and heart, and include Acid Maltase Deficiency (Pompe's Disease/Glycogen Storage Disease Type II), Danon Disease (Gylcogen Storage Disease Type IIb/Vacuolar Myopathies), Debranching Enzyme Deficiency (Glycogen Storage Disease Type III/Forbe's Disease), Andersen Disease/Syndrome (Glycogen Storage Disease Type IV/Branching Enzyme Deficiency), Tauri's Disease (Glycogen Storage Disease Type VII/Phosphofructokinase Deficiency), Desmin Storage Myopathy (Myofibrillar Myopathy), Myodenylate Deaminase Deficiency, Adrenoleukodystrophy, Arthrogryposis Multiplex Congenita, Ataxia with Congenital Glaucoma, Ataxia with Vitamin E Deficiency, Barth Syndrome, Bethlem Myopathy, Carnitine Palmityl Transferase Deficiency, Carnitine Deficiency, Central Core Disease, Hereditary Motor and Sensory Neuropathy (e.g. Charcot-Marie-Tooth Diseases (CMT) such as CMT Type I, CMT Type II, CMT Type III (Dejerine-Sottas Disease), CMT Type IV (Refsum's Disease), CMT Type V; Peroneal Muscular Atrophy; Neuronal Type of Peroneal Muscular Atrophy), Hereditary Sensory and Autonomic Neuropathy (e.g. Type I, Type III (Familial Dysautonomia/Riley-Day Syndrome), Type IV (Congenital insensitivity to pain and anhidrosis), Congenital Fibre Type Disproportion Myopathy, Distal Spinal Muscular Atrophy, Familial Amyloid Neuropathy, Familial Dilated Cardiomyopathy with Muscular Dystrophy, Friedreich's Ataxia, Hyperkalemic Periodic Paralysis (Gamstorp Disease), Giant Axonal Neuropathy, Guillain-Barre Syndrome (Acute inflammatory Demyelinating/Polyradiculoneuropathy), Hyperthermia (Malignant Hyperthermia), Hypokalemic Periodic Paralysis, Iatrogenic Myopathy, Kearns-Sayre Syndrome, Kugelberg Welander Disease (Spinal Muscular Atrophy Type III), Laing Distal Myopathy, Lambert-Eaton (Myasthenic) Syndrome, Leigh's Syndrome, Minicore Myopathy/Multicore Myopathy, Mitochondrial Myopathy and/or Neuropathy, Mixed Connective Tissue Overlap Disease, Miyoshi Myopathy, Multifocal Motor Neuropathy with Conduction Block, Myasthenia Gravis, Myotonia Congenita (Thomsen's Disease), Myotonic Muscular Dystrophy (e.g. Type I (Steinert's Disease), Type II (Proximal Myotonic Myopathy)), Oculopharyngeal Muscular Dystrophy, Olivopontocerebellar Atrophy, Paramyotonia Congenita, Paraneoplastic neuropathy, Polymyopsitis, Reducing Body Myopathy, Scapuloperoneal Muscular Atrophy, Tubular Aggregate Myopathy, Walker-Warburg Syndrome, Werdnig-Hoffman Disease (Spinal Muscular Atrophy Type I), Zebra Body Myopathy and Nuclear Envelop Disease.

Aspect 24: the nucleic acid regulatory element according to any one of aspects 1 to 7, the nucleic acid expression cassette according to any one of aspects 10 to 16, the vector according to any one of aspects 17 to 19, or the pharmaceutical composition according to aspect 20 for use as a vaccine, preferably a prophylactic vaccine, or for use in vaccination therapy, preferably prophylactic vaccination.

Aspect 25: A method, preferably an in vitro or ex vivo method, for expressing a transgene product in diaphragm and skeletal muscle cells, comprising:

introducing the nucleic acid expression cassette according to any one of aspects 10 to 16, or the vector according to any one of aspects 17 to 19, comprising the nucleic acid regulatory element according to any one of aspects 1 to 3 and 6, into the cells; and expressing the transgene product in the cells.

Aspect 26: A method, preferably an in vitro or ex vivo method, for expressing a transgene product in diaphragm, skeletal muscle, and heart cells, comprising:

introducing the nucleic acid expression cassette according to any one of aspects 10 to 16, or the vector according to any one of aspects 17 to 19, comprising the nucleic acid regulatory element according to any one of aspects 1, 4, 5, and 7, into the cells; and expressing the transgene product in the cells.

Aspect 27: a method for treating MTM comprising the administration of a therapeutically effective amount of the nucleic acid expression cassette according to any one of aspects 10 to 16, the vector according to any one of aspects 17 to 19, or the pharmaceutical composition according to aspect 20, each comprising the nucleic acid regulatory element according to any one of aspects 1 to 3, and 6, to a subject in need thereof.

Aspect 28: a method for treating Pompe disease comprising the administration of a therapeutically effective amount of the nucleic acid expression cassette according to any one of aspects 10 to 16, the vector according to any one of aspects 17 to 19, or the pharmaceutical composition according to aspect 20, each comprising the nucleic acid regulatory element according to any one of aspects 1, 4, 5, and 7, to a subject in need thereof.

Aspect 29: a method for treating any one of the diseases or disorders selected from the group comprising: muscular dystrophy (e.g. Duchenne muscular dystrophy (DMD)/Becker muscular dystrophy (BMD)), myotonic dystrophy, myotonic muscular dystrophy (DM), Duchenne dystrophinopathy, sarcoglycanopathies, Miyoshi myopathy, Fukuyama type congenital muscular dystrophy, dysferlinopathies, neuromuscular disease, motor neuron diseases (MND), such as e.g. Charcot-Marie-Tooth disease (CMT), spinal muscular atrophy (SMA), and amyotrophic lateral sclerosis (ALS), Emery-Dreifuss muscular dystrophy, facioscapulohumeral muscular dystrophy (FSHD), congenital muscular dystrophies, congenital myopathies, limb girdle muscular dystrophy, metabolic myopathies, muscle inflammatory diseases, myasthenia, mitochondrial myopathies, anomalies of ionic channels, nuclear envelop diseases, cardiomyopathies, cardiac hypertrophy, heart failure, distal myopathies, cardiovascular diseases, hemophilia, including hemophilia A and B, and diabetes, comprising the administration of a therapeutically effective amount of the nucleic acid expression cassette according to any one of aspects 10 to 16, the vector according to any one of aspects 17 to 19, or the pharmaceutical composition according to aspect 20, each comprising the nucleic acid regulatory element according to any one of aspects 1 to 7.

Aspect 30. A codon-optimised human GAA gene as defined in SEQ ID NO: 94 Aspect 31. The codon-optimised human GAA gene for use in gene therapy, more particularly for use in treatment of diseases requiring restoration of GAA expression or increase of GAA expression. More preferably, said disease is Pompe disease or Duchenne muscular dystrophy.

Aspect 32. A codon-optimised human MTM1 gene as defined in SEQ ID NO: 96 Aspect 33. The codon-optimised human MTM1 gene for use in gene therapy, more particularly for use in treatment of diseases requiring restoration of MTM1 expression or increase of MTM expression. More preferably, said disease is MTM disease or Duchenne muscular dystrophy.

Aspect 34. A vector comprising the codon-optimised human GAA gene of aspect 30.

Aspect 35. A vector comprising the codon-optimised human MTM1 gene of aspect 32.

Aspect 36. A pharmaceutical composition comprising the vector according to aspect 34 or 35.

Aspect 37. A vector according to any one of aspects 1, and 4 to 5, comprising the codon-optimised human GAA gene of aspect 30.

Aspect 38. A vector according to any one of aspects 1-3, and 5, comprising the codon-optimised human MTM1 gene of aspect 32.

Aspect 39. A method, preferably an in vitro or ex vivo method, for expressing a transgene product in diaphragm, skeletal muscle, and heart cells, comprising:

introducing the nucleic acid expression cassette according to aspects 10 to 16, or the vector according to any one of aspects 17 to 19, comprising a nucleic acid regulatory element having a maximal length of 1000 nucleotides, preferably 800 nucleotides, more preferably 700 nucleotides, 600 nucleotides or 550 nucleotides, comprising the sequence defined by SEQ ID NO: 4 or SEQ ID NO: 64, a sequence having at least 80%, preferably at least 85%, more preferably at least 90%, even more preferably at least 95%, such as 95%, 96%, 97%, 98%, or 99%, identity to said sequence, the complement of said sequence, or a sequence hybridizing under stringent conditions to said nucleic acid regulatory element, into the cells; and expressing the transgene product in the cells.

BRIEF DESCRIPTION OF DRAWINGS

FIG. 5A Expression in Diaphragm FIG. 5B Expression in Quadricep FIG. 5C Expression in Gastrocnemius FIG. 5D Expression in Tibialis FIG. 5E Expression in Bicep FIG. 5F Expression in Tricep FIG. 5G Expression in total skeletal muscle tissues FIG. 5H Expression in heart. In the left-hand graphs, the fold difference in expression of the different new Diaphragm CREs (Dph-CREs) in a vector backbone comprising the hDES1.4kb promotor and a muscle-specific CRE Sk-SH4 (SEQ ID NO: 121) is indicated versus the same vector backbone with hDES1.4kb promotor only (bottom numbers) and versus the same vector backbone without the new CREs (upper numbers). In the right-hand graphs, the fold difference in expression of the different new Diaphragm CREs in a vector backbone comprising the SPc5-12 promotor and a muscle-specific CRE CSk-SH5 (SEQ ID NO: 122) is indicated versus the same vector backbone with SPc5-12 promotor only (bottom numbers) and versus the same vector backbone without the new CRE's (upper numbers) FIG. 5I Specificity of Diaphragm CREs (mainly expressed in diaphragm, skeletal muscle and heart but not in other tissues. The numbers of the Diaphragm CREs correspond to the numbering of Tables 3 and 4.

FIG. 6A Effect of the muscle-specific CRE (CSk-SH5—SEQ ID NO: 122) on the mRNA expression of human codon optimized GAA gene. FIG. 5B The increasing of GAA protein expression. The total proteins from the mice organs were extracted according to the manufacturer's protocol. The total proteins were diluted with the samples buffer and loaded into the hGAA ELISA plate. The background was subtracted with non-injected mice. The results show that codon-optimized hGAA sequence can improve the translation efficiency resulting in 2-3 folds higher expression.

FIG. 7A Effect of the skeletal muscle specific CRE (Sk-SH4—SEQ ID NO: 121) on the mRNA expression of human codon optimized MTM1 gene. FIG. 7B Codon optimization led to an increase of 2.2 to 3.8 folds of hMTM1 protein expression in gastrocnemius and diaphragm respectively.

US 12,571,000 B2

Figure 11:
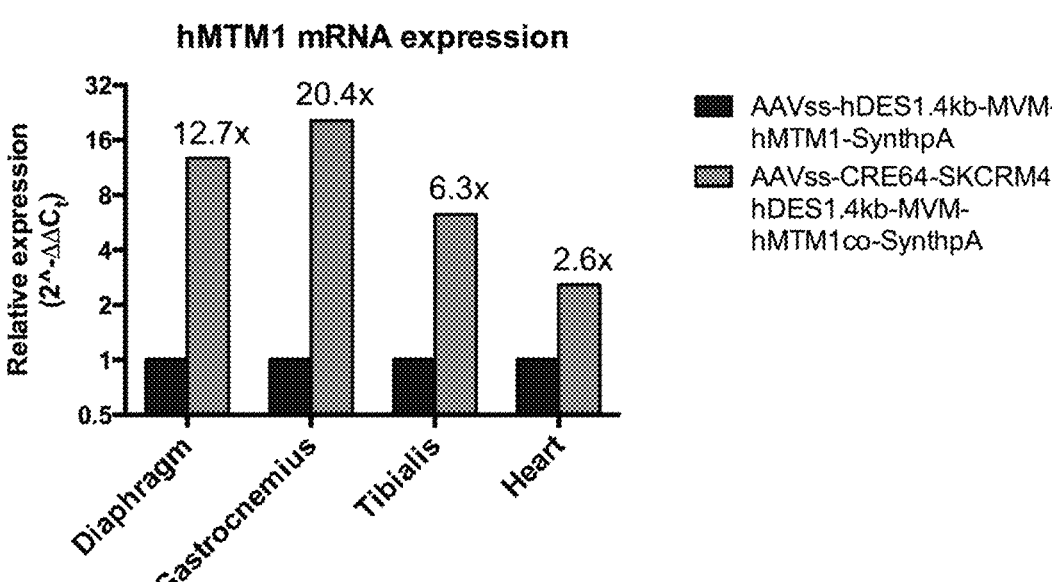

13                                                                    14 between Dph-CRE-containing AAV (dark gray) and its
control without Dph-CRE04 and CSk-SH5 (light gray).
    FIG. 11: Increase of MTM1 therapeutic gene transcription
using diaphragm-specific cis-regulatory element (Dph-
CRE) CRE64 (SEQ ID NO:64) in combination with Sk-SH4
(SEQ ID NO: 121—called SKCRM4 in the figure). The
fold-difference indicated on the top of each bar is calculated
from relative expression between Dph-CRE-containing
AAV (light gray) and its control without Dph-CRE64 and
Sk-SH4 (black).

DESCRIPTION

As used herein, the singular forms "a", "an", and "the"
include both singular and plural referents unless the context
clearly dictates otherwise.
    The terms "comprising", "comprises" and "comprised of"
as used herein are synonymous with "including", "includes"
or "containing", "contains", and are inclusive or open-ended
and do not exclude additional, non-recited members, ele-
ments or method steps. The terms also encompass "consist-
ing of" and "consisting essentially of", which enjoy well-
established meanings in patent terminology.
    The recitation of numerical ranges by endpoints includes
all numbers and fractions subsumed within the respective
ranges, as well as the recited endpoints.
    The terms "about" or "approximately" as used herein
when referring to a measurable value such as a parameter, an
amount, a temporal duration, and the like, are meant to
encompass variations of and from the specified value, such
as variations of +/−10% or less, preferably +/−5% or less,
more preferably +/−1% or less, and still more preferably
+/−0.1% or less of and from the specified value, insofar such
variations are appropriate to perform in the disclosed inven-
tion. It is to be understood that the value to which the
modifier "about" refers is itself also specifically, and pref-
erably, disclosed.
    Whereas the terms "one or more" or "at least one", such
as one or more members or at least one member of a group
of members, is clear per se, by means of further exempli-
fication, the term encompasses inter alia a reference to any
one of said members, or to any two or more of said members,
such as, e.g., any 3, 4, 5, 6 or 7 etc. of said members, and
up to all said members. In another example, "one or more"
or "at least one" may refer to 1, 2, 3, 4, 5, 6, 7 or more.
    The discussion of the background to the invention herein
is included to explain the context of the invention. This is not
to be taken as an admission that any of the material referred
to was published, known, or part of the common general
knowledge in any country as of the priority date of any of the
claims.
    Throughout this disclosure, various publications, patents
and published patent specifications are referenced by an
identifying citation. All documents cited in the present
specification are hereby incorporated by reference in their
entirety. In particular, the teachings or sections of such
documents herein specifically referred to are incorporated by
reference.
    Unless otherwise defined, all terms used in disclosing the
invention, including technical and scientific terms, have the
meaning as commonly understood by one of ordinary skill in the art to which this invention belongs. By means of
further guidance, term definitions are included to better
appreciate the teaching of the invention. When specific
terms are defined in connection with a particular aspect of
the invention or a particular embodiment of the invention,
such connotation is meant to apply throughout this specifi-
cation, i.e., also in the context of other aspects or embodi-
ments of the invention, unless otherwise defined.
    In the following passages, different aspects or embodi-
ments of the invention are defined in more detail. Each
aspect or embodiment so defined may be combined with any
other aspect(s) or embodiment(s) unless clearly indicated to
the contrary. In particular, any feature indicated as being
preferred or advantageous may be combined with any other
feature or features indicated as being preferred or advanta-
geous.
    Reference throughout this specification to "one embodi-
ment", "an embodiment" means that a particular feature,
structure or characteristic described in connection with the
embodiment is included in at least one embodiment of the
present invention. Thus, appearances of the phrases "in one
embodiment" or "in an embodiment" in various places
throughout this specification are not necessarily all referring
to the same embodiment, but may. Furthermore, the particu-
lar features, structures or characteristics may be combined in
any suitable manner, as would be apparent to a person
skilled in the art from this disclosure, in one or more
embodiments. Furthermore, while some embodiments
described herein include some but not other features
included in other embodiments, combinations of features of
different embodiments are meant to be within the scope of
the invention, and form different embodiments, as would be
understood by those in the art. For example, in the appended
claims, any of the claimed embodiments can be used in any
combination.
    For general methods relating to the invention, reference is
made inter alia to well-known textbooks, including, e.g.,
"Molecular Cloning: A Laboratory Manual, 2nd Ed." (Sam-
brook et al., 1989), "Current Protocols in Molecular Biol-
ogy" (Ausubel et al., 1987).
    In one aspect, the invention relates to a nucleic acid
regulatory element for enhancing gene expression in dia-
phragm and skeletal muscle cells or tissue or in diaphragm,
heart, and skeletal muscle cells or tissue comprising, con-
sisting essentially of (i.e., the regulatory element may for
instance additionally comprise sequences used for cloning
purposes, but the indicated sequences make up the essential
part of the regulatory element, e.g. they do not form part of
a larger regulatory region such as a promoter), or consisting
of a sequence selected from the group consisting of: SEQ ID
NO:1 to 89, a sequence having at least 80%, preferably at
least 85%, more preferably at least 90%, even more prefer-
ably at least 95%, such as 95%, 96%, 97%, 98%, or 99%,
identity to any of these sequences, or a functional fragment
of a sequence selected from the group consisting of: SEQ ID
NO:1 to 89.
    Table 3 below depicts the core nucleotide sequence of the
different nucleic acid regulatory elements for enhancing
gene expression in diaphragm and skeletal muscle cells or
tissue and their corresponding genes and lengths.

TABLE 3

<u>The CREs sequence for high expression in diaphragm and skeletal muscle.</u>

| SEQ ID NO. | Gene | Dph-CRE (CRE) | Size (bp) | Sequence |
|---|---|---|---|---|
| 1 | ACTA1 | Dph-CRE01 | 328 | GGAGACACTCCATATACGGCCCGGCCCGCGTTACCTGGG ACCGGGCCAACCCGCTCCTTCTTTGGTCAACGCAGGGGA CCCGGGCGGGGGCCCAGGCCGCGAACCGGCCGAGGGAGG GGGCTCTAGTGCCCAACACCCAAATATGGCTCGAGAAGG GCAGCGACATTCCTGCGGGGTGGCGCGGAGGGAATGCCC GCGGGCTATATAAAACCTGAGCAGAGGGACAAGCGGCCA CCGCAGCGGACAGCGCCAAGTGAAGCCTCGCTTCCCCTC CGCGGCGACCAGGGCCCGAGCCGAGAGTAGCAGTTGTAG CTACCCGCCCAGGTAG |
| 2 | ACTA1 | Dph-CRE02 | 452 | GACAGGTGCGGTTCCCGGAGCGCAGGCGCACACATGCAC CCACCGGCGAACGCGGTGACCCTCGCCCCACCCCATCCC CTCCGGCGGGCAACTGGGTCGGGTCAGGAGGGGCAAACC CGCTAGGGAGACACTCCATATACGGCCCGGCCCGCGTTA CCTGGGACCGGGCCAACCCGCTCCTTCTTTGGTCAACGC AGGGGACCCGGGCGGGGGCCCAGGCCGCGAACCGGCCGA GGGAGGGGGCTCTAGTGCCCAACACCCAAATATGGCTCG AGAAGGGCAGCGACATTCCTGCGGGGTGGCGCGGAGGGA ATGCCCGCGGGCTATATAAAACCTGAGCAGAGGGACAAG CGGCCACCGCAGCGGACAGCGCCAAGTGAAGCCTCGCTT CCCCTCCGCGGCGACCAGGGCCCGAGCCGAGAGTAGCAG TTGTAGCTACCCGCCCAGGTAGG |
| 3 | ACTA1 | Dph-CRE03 | 239 | AGAGAGAGGGACAGGCACCAACTGGGTAACCTCTGCTGA CCCCCACTCTACTTTACCATAAGTAGCTCCAAATCCTTC TAGAAAATCTGAAAGGCATAGCCCCATATATCAGTGATA TAAATAGAACCTGCAGCAGGCTCTGGTAAATGATGACTA CAAGGTGGACTGGGAGGCAGCCCGGCCTTGGCAGGCATC ATCCTCTAAATATAAAGATGAGTTTGTTCAGCCTTTGCA GAAGG |
| 4 | ACTA1 | Dph-CRE04 | 509 | CCTTTTAGAGAATCCACACCTGTCCCAGTTGCTGGGTTC CACTACCAAAAGTGAATTGCAACTATTTTAGGAGCACTT AAGCACATCCGAAAAATGAGTGATTCTGTTCTGGCCCAC ACCACATCACTGATGTACCCCCTTAAAGCATGTCCCTGA GTTCATCACAGAAGACTGCTCCTCCTGTGCCCTCCACAA GGTTAGAACTGTCCTTGTCTTAGGGAAAAAGGAGAGAGA GAGAGAGAGAGAGAGAGAGAGAGAGAGAGAGAGAGAGAG AGAGGGACAGGCACCAACTGGGTAACCTCTGCTGACCCC CACTCTACTTTACCATAAGTAGCTCCAAATCCTTCTAGA AAATCTGAAAGGCATAGCCCCATATATCAGTGATATAAA TAGAACCTGCAGCAGGCTCTGGTAAATGATGACTACAAG GTGGACTGGGAGGCAGCCCGGCCTTGGCAGGCATCATCC TCTAAATATAAAGATGAGTTTGTTCAGCCTTTGCAGAAG GA |
| 5 | ACTA1 | Dph-CRE05 | 169 | CCTTTTAGAGAATCCACACCTGTCCCAGTTGCTGGGTTC CACTACCAAAAGTGAATTGCAACTATTTTAGGAGCACTT AAGCACATCCGAAAAATGAGTGATTCTGTTCTGGCCCAC ACCACATCACTGATGTACCCCCTTAAAGCATGTCCCTGA GTTCATCACAGAA |
| 6 | CKM | Dph-CRE06 | 400 | GGGCCAGGGGACGGTGGCTTCTACGTGCTTGGGACGTTC CCAGCCACCGTCCCATGTTCCCGGCGGGGGGCCAGCTGT CCCCACCGCCAGCCCAACTCAGCACTTGGTCAGGGTATC AGCTTGGTGGGGGGGCGTGAGCCCAGCCCCTGGGCGGC TCAGCCCATACAAGGCCATGGGGCTGGGCGCAAAGCATG CCTGGGTTCAGGGTGGGTATGGTGCGGGAGCAGGGAGGT GAGAGGCTCAGCTGCCCTCCAGAACTCCTCCCTGGGGAC AACCCCTCCCAGCCAATAGCACAGCCTAGGTCCCCCTAT ATAAGGCCACGGCTGCTGGCCCTTCCTTTGGGTCAGTGT CACCTCCAGGATACAGACAGCCCCCCTTCAGCCCAGCCC AGCCAGGTAC |
| 7 | CKM | Dph-CRE07 | 255 | CCCAGCCCCCTTCCCCGGGAGGTGGGAGCGGCCACCCAG GGCCCCGTGGCTGCCCTTGTAAGGAGGCGAGGCCCGAGG ACACCCGAGACGCCCGGTTATAATTAACCAGGACACGTG GCGAACCCCCCTCCAACACCTGCCCCCGAACCCCCCCAT ACCCAGCGCCTCGGGTCTCGGCCTTTGCGGCAGAGGAGA CAGCAAAGCGCCCTCTAAAAATAACTCCTTTCCCGGCGA CCGAGACCCTCCCTGTCCCCC |
| 10 | TPM2 | Dph-CRE10 | 608 | ACTCAGGGTAAACTGAGGCACTCAAACTGCCGAGGAGCT CCGCCTCCCGAGAGACATTTAATCCGGGGGGATTTGCAG GAAACTTCTAAATTAAGGGTAGCGGCTGCTGCAGCTGAG |

TABLE 3-continued

The CREs sequence for high expression in diaphragm and skeletal muscle.

| SEQ ID NO. | Gene | Dph-CRE (CRE) | Size (bp) | Sequence |
|---|---|---|---|---|
| | | | | GGGGGGCACGCCGGTCCCTGCGCCCGGGCAGCTGCCGTG AGCTCACGCCCCGAAATAGCCCCAGGGGCCCCAGCCGCA GCTGCCACTGGGTCCGGCTGTCACTCAGAGGAAGCACGG AGCCCCCAGCCCAAGGGTCCCCTCCCCTTCGCATCGCCG GGGTTTTTCCAGCCGACCGTCGGCCACTTTTTCCTCCGA CGGCTGGCAGGGAAGAGGGGGATGGGGGCGGGACCCCAA GGGAGGCGGTCCCCAGTGGGTGGGCGAAGGGGGCGGCCG CACCCCCCGGCCGGGCCGTGCTTCTGCCCCTACAAGGTT TGGGCCGAGGTGGGGGAGGGTCCTGGTTGCCGGCCCCGC CCGGTCCCTCCCCGCCTTTTAGGCGCCCGCGTGGCCGGG ACGTCCCAGTCCCGCTCCGTCCTCCTCGCCTGCCACCGG TGCACCCAGTCCGCTCACCCAGCCCAGTCCGTCCGGTCC TCACCGCCTGCCGGCCGGCCCAC |
| 11 | TPM2 | Dph-CRE11 | 308 | TTTTTCCTCCGACGGCTGGCAGGGAAGAGGGGGATGGGG GCGGGACCCCAAGGGAGGCGGTCCCCAGTGGGTGGGCGA AGGGGGCGGCCGCACCCCCCGGCCGGGCCGTGCTTCTGC CCCTACAAGGTTTGGGCCGAGGTGGGGGAGGGTCCTGGT TGCCGGCCCCGCCCGGTCCCTCCCCGCCTTTTAGGCGCC CGCGTGGCCGGGACGTCCCAGTCCCGCTCCGTCCTCCTC GCCTGCCACCGGTGCACCCAGTCCGCTCACCCAGCCCAG TCCGTCCGGTCCTCACCGCCTGCCGGCCGGCCCAC |
| 12 | TPM2 | Dph-CRE12 | 263 | GACTCAGGGTAAACTGAGGCACTCAAACTGCCGAGGAGC TCCGCCTCCCGAGAGACATTTAATCCGGGGGGATTTGCA GGAAACTTCTAAATTAAGGGTAGCGGCTGCTGCAGCTGA GGGGGGGCACGCCGGTCCCTGCGCCCGGGCAGCTGCCGT GAGCTCACGCCCCGAAATAGCCCCAGGGGCCCCAGCCGC AGCTGCCACTGGGTCCGGCTGTCACTCAGAGGAAGCACG GAGCCCCCAGCCCAAGGGTCCCCTCCCCT |
| 13 | MYL1 | Dph-CRE13 | 324 | CTCAGGGAATGAGCTGGATACAACTAAAAATCAGCACAT TTTTGTTTGGTTAAAACATTCTTTGTGGTCAATTTCTTT CTAACAGATCGAGTTCTCTAAGGAACAGCAGGATGGTAA GTTTAAAAGCTATGGTTCTTAAATGTGCACACTCATAAA GATGGCATGTGTGAAAACCAACTCCCTTGGGATGAGTTT AGCTCTTCCTAATTATCCCCACTGGTGTTGCCATTCTGA ATATAAATTGCTCTCGATCACTCTAAATATAAATTAGCT CAATCTGAAACCCTTGCTGATACTCAGTAATCAAAGGTT TAACAAACAAAA |
| 14 | MYL1 | Dph-CRE14 | 326 | CATTTAGTTAAATCATTAAGATGCAGAAAGATATTCCCT AATTATCTTTTGCAATAGCTTTTTATGTTCCTAGATTCA AAAGTATCCTAAGGCAACCTTCTAATGCCAAGACACCTA CATAGCTTCCTAAAAATCTCAGAGCAACCAGCACTCATT CTTCTGTCAATGCATTTGAAAGAGTACTAGTTTTTTTTC TTTCTTTCTCTTCTTCGCCACTGCAGTCCTTCAGTGCTG ACCAGATTGCTGGTAAGTGAATTGAGTTTGTCTGCTACA GATGTAGGCACAGCACTGCCTAGTTTCTGCAATATTACT TATCTTCAAGGCAT |
| 15 | MYL1 | Dph-CRE15 | 596 | TTTGTTTGTTAAACCTTTGATTACTGAGTATCAGCAAGG GTTTCAGATTGAGCTAATTTATATTTAGAGTGATCGAGA GCAATTTATATTCAGAATGGCAACACCAGTGGGGATAAT TAGGAAGAGCTAAACTCATCCCAAGGGAGTTGGTTTTCA CACATGCCATCTTTATGAGTGTGCACATTTAAGAACCAT AGCTTTTAAACTTACCATCCTGCTGTTCCTTAGAGAACT CGATCTGTTAGAAAGAAATTGACCACAAAGAATGTTTTA ACCAAACAAAAATGTGCTGATTTTTAGTTGTATCCAGCT CATTCCCTGAGTAATCTTCAAAGTAAGCTCCAAAAGTCA GCCTACTTTTCAGAGTTCAGGCGTAGCTTGGACACTAAC AGGTTAAGCCATAGTGTAACATGCCTTGAAGATAAGTAA TATTGCAGAAACTAGGCAGTGCTGTGCCTACATCTGTAG CAGACAAACTCAATTCACTTACCAGCAATCTGGTCAGCA CTGAAGGACTGCAGTGGCGAAGAAGAGAAAGAAAGAAAA AAAACTAGTACTCTTTCAAATGCATTGACAGAAGAATGA GTGCTGGTTGC |
| 16 | MYL1 | Dph-CRE16 | 290 | AGACCATAAAAGTACCGGCAGGCTTCCATCTCACTATGG CTGTCTACTCCAAGGTTCTGGTCATCTAAAAATAGCTCT CAGGGTACAGATCCATCTTTCCCTTTGCCCTAAGAAAGC TAAAGAACTCTCCAAGGGGTGTGGCAACTTATCTCTGAA |

TABLE 3-continued

The CREs sequence for high expression in diaphragm and skeletal muscle.

| SEQ ID NO. | Gene | Dph-CRE (CRE) | Size (bp) | Sequence |
|---|---|---|---|---|
| | | | | ACCTGATGCTAGCTGTGAGGTCAAAGCTTGCCCAGAAAT AAAAGGAAGCCTCAGCCAGGGATGACCCCACTCAGGGAC CGGAGCAGCCCTCAACTCACTCTTCAGCTTCCCTGCTGT GTTGCAGCCCAGCCGCT |
| 17 | MYL1 | Dph-CRE17 | 632 | GTGCTCCCTAGAAGGGAAGCCACTTTAAGACATGATGGG CTTTCCTTATACGTCTGCTTTTTTATTTTTAACCACCAC CACCTCTTTGCTGACCAACATTTCCTTGCAAATTATGGC AAGGGGGGGAGGAGCATGAGCAAAGGAGCTGTGTGAAAGT TGGTGATACTCCCTGCCAAAATTCCAAGTTGAAATGGAA TCCTTCAGTAAAGTCTCTTAGGCAAGGTGGGAAAAAAAG ATTTACAACTTCAGCAGAACTGTAATTCTACCAAGAAAA AGTACAGTCAATCTACCTCACTGTCACCAAAGGATCTGA AGCTGGCTTTGTCATATATCTTTCTCCTTTATATATGGA GGTGGGGGGGGGAGAAAAAAAGGAAAGAGAGTTAAAAAA AATTGATGAAGCCCTGACCCTTTAGATTCCATTTATAGT CTGAGCCGGAATGCCATCCCCCTTGACTAGAGAACTGTC CAATCCAGCCGCATGTGTCAAGATTCTATTAGGCACTAA GTGAAATATATATGCATGCCCTTATGCCGTTTAACACTC TGGGTCCATCTTCAAGACACTGGGCTGTGGATCAACCCA ACCACCACTCCTCTTCCAAGAATCATTTTGACAGGTTCT TTTGGAGG |
| 18 | TNNC2 | Dph-CRE18 | 297 | CCTTTGACTTTTCTTGAAAGGGGAGGGCTGGGATATTCC AGAGATTGATCCTTAAGGCTTGCTGACTGCCTACTCACT TCTGGAAACTTCCAGCAGTGTCATTCATAGACCTGTGAA GAGCTCTTAGCTTGTTTCCTTCACACAGTGGGGACTCTG AGGGGTCAGAGTGAGTCACCCAGCAGGCCAGTGGCAGGG GTGAGCCAGAAGCCTGGCCAAACCCTCCTATCATCATGG AGAGAAGAAAGCCTCCTCCAGAAGACGGGAGGCCGGCAG GGCGTGGGGCCTGCTCAGATGCAG |
| 19 | TNNC2 | Dph-CRE19 | 309 | GGAACAGGGCAGGCCTTCCTCACAAGAATCTAGGACGTC AAGGCCTGCCACCTGCTTGGAGGCTTAAATTTCTCTGCA AGGGCCCTTGGCTAAATTAGGTAATGGGTTCAGACTGTG GGAGGGGTGGGACTCGCTGACCCCAGGATCTGATTGGGC AGGGTCTCCAGTGCTGGGGAGCAGGGAGGTGGGAGGGGA GGGTGCCCCTACAAATCCCGGGGGCTAGAGCAGGCCAGG TCATCTTTGGGTGGTGGAGTGCAAAGGAGGCGACCTGCA ACAGAGGAGTCCCGGTCACCAGCAACCATGGTAAGG |
| 20 | FHL1 | Dph-CRE20 | 267 | AATTGTGACATTTAAGCAGTGACTTTGCAAAATTGGACG TGTCAGTAGGAAAAAGTACTCTTCCCACCTTAAAGATTG ACAGGAACATGAGATGGCTGAAGCTGTTCTGAGCTTTTT TCTGGCAAGAGTACATAGGACAAGAAATACTCTGGAGAG CTCAACATTGAATCACATCATATCATAGTGCATGACTAG TTGCCTTAATCTTGCAGTTGGACTCACTCAGGAGAAATT GTTGGCAGAGGGATTAAGTAGCCTGACAAAATT |
| 21 | FHL1 | Dph-CRE21 | 493 | CTTTTCTTTTCTAATTAGGTCAGTTACTTCATGTCTGTT TTTCTTTTTTGACATGGTTTCTTCTGGCTTTGGCACCAC ATATTTTCCCCATATGTCATTGCCTCTGGAGCTTCATGT TGCAATAGTTTTTCAAGGGGAACGGAGAGCACATTGCTA AGGGTGGGGGATGGCTTTTGCCTCTTTTGCCTGCCCTTT GCTTCAGTGAGTGTTCGTATTTCTGTTGGGCCTAGTTCT GTTTGGTTTTGTAGTCTTCAGAGTCAGTTATGTTTGGAC TGAAAGATACTTAAGTAAAAATAATGGCAAGTCAGAGAT ATGTCTGGCAAAGGTGCAGCACATTTGTTAAGGTTACTG GTTTATTTATCTCCCTTGTCTCTATGGTGACTAAATCTG GGTCTGGGATTTAATGGACTTAGTTTTGACCTCTTGTAA CATCTCCTAACTTTTCCCAGCCTCTGATTTAGAAAGAAT TCATTTTCACTTGAGGAGAGAAACT |
| 22 | FHL1 | Dph-CRE22 | 197 | TCATTTGTTTTGATTACCCGGGTGATTGCCAAATGTTAA TTTAAAACTGAAATAGGCCATGAGCTCACTCCCCTAACA ATGCTGAGTGTTTGAGCTAATACGGCTTGATAATGAGGG AGCCAGATCCACTGCCAGTGCTCATGTTATATGATAAAC AGACATTTGGAGAAGTATGCAGAACATCTTGGCAGTTTT CC |
| 23 | FHL1 | Dph-CRE23 | 637 | AAAAATTGGCTTTAAGGTCATGAGCCTCCTTACAGCAGT CCCTCTCACCTTCAGCTGTATTCCCTATTTCAGATATAC TTGTTTCTCTGCTGTAAGTACACTTTTCTTTTCTAATTA GGTCAGTTACTTCATGTCTGTTTTTTCTTTTTTGACATGG TTTCTTCTGGCTTTGGCACCACATATTTTCCCCATATGT |

TABLE 3-continued

The CREs sequence for high expression in diaphragm and skeletal muscle.

| SEQ ID NO. | Gene | Dph-CRE (CRE) | Size (bp) | Sequence |
|---|---|---|---|---|
| | | | | CATTGCCTCTGGAGCTTCATGTTGCAATAGTTTTTCAAG GGGAACGGAGAGCACATTGCTAAGGGTGGGGGATGGCTT TTGCCTCTTTTGCCTGCCCTTTGCTTCAGTGAGTGTTCG TATTTCTGTTGGGCCTAGTTCTGTTTGGTTTTGTAGTCT TCAGAGTCAGTTATGTTTGGACTGAAAGATACTTAAGTA AAAATAATGGCAAGTCAGAGATATGTCTGGCAAAGGTGC AGCACATTTGTTAAGGTTACTGGTTTATTTATCTCCCTT GTCTCTATGGTGACTAAATCTGGGTCTGGGATTTAATGG ACTTAGTTTTGACCTCTTGTAACATCTCCTAACTTTTCC CAGCCTCTGATTTAGAAAGAATTCATTTTCACTTGAGGA GAGAAACTGTCTCACTTAGAAAAGGGGTCCTAACTGGAC TCTCGAAAAGTGG |
| 24 | FHL1 | Dph-CRE24 | 561 | GTCTGCATCCTAATCCTGCTGTTGATTGGAGATAACTTC AGCGGTCACAGGGCACCTCGTCTCCATGGCAACCCCTCT AAATATTCCTCTAGTGACTTGTGCTCTACATTCTGGCTG GATCAGAGCCCTCCTGTGGCAAAATATTCTAAAGATGTT AAAAGAGAGAGAGAGAAAAAAAAAGGCTCAACTAATAAA TCTATTCTAAACGACTGAGTCATTTGTTTTGATTACCCG GGTGATTGCCAAATGTTAATTTAAAACTGAAATAGGCCA TGAGCTCACTCCCCTAACAATGCTGAGTGTTTGAGCTAA TACGGCTTGATAATGAGGGAGCCAGATCCACTGCCAGTG CTCATGTTATATGATAAACAGACATTTGGAGAAGTATGC AGAACATCTTGGCAGTTTTCCTTTAACTCTAAGGGTTGT AAATACAAAGTAGAATGTGTTACCATGAGCCATTTCATA GGAAGTTGACTTTATTTTTTTAGAATTCAGAACTTTGCT TCTAAAAAGGTAACTTTGCCTCTTGATTCTCATTTTTTT CCCTAACTTAGGCAC |
| 25 | FHL1 | Dph-CRE25 | 511 | AAAGACAGGGAGGTGCAATCTAAGTTAGGAAATTGGTGA CAAATAGTCATAGAACATGGGTCACCTGGCTTCAATTAG TTATGTGACCTTTAAGAAAACAAGTGCCCGTTTCAGAAA AGACTGACCTTTGAGGCTAGAGACATCAAGCTACTCCTC TACTTTTAGGAAAAAACAATGACAGGGTTAATTTAAAAC TCTGATGCAGACAGAGTTGAAAAATCCATGACAGATTTA TATAACGAACGTGGATGGTGTTTTGTTTTCCCAGAATGC AGTTTTAAGGTCAGACCTATGACTCAGAGCTGTGCACTT CCCTGGTGGTATGCATCAGTGACATGTTGCCAGTCTAAT CGTCCAGAAGGGCTTGTGCCCAGCTCGGCTTGCTCCATT ATAATCCCCAGCTGAGAAGCCACCTTTCATTTTTTTTAA ATAGATAAGGAAGACAGCATGAACATTTGAAACTCAAAT ACTATATGTAGTTTATAACTTTTCAGCCTGAAGACTTGA TGCA |
| 26 | FHL1 | Dph-CRE26 | 399 | AATGCAGCATACCAGTGAAGTTGCTAATTACATTGAATC ATTCTGTACACGTTCTATTTTGAAGGGAAAAAACACTTT CTGATTTTTGTATGAAATTGTATGAAAGACTACTTTTCA GCCGTGACTCATGAGCTCCGTCTCATTGCAGCTACTTAG GTATTTATTCCCAAATGTCTGACGACACCTCCAGGTGCA TTAGCATGTCTATTACACAAGTGTCCTATTCATTGGCTA AGGCTTTGCTCCATCTGTTGAATGTTCTGAGGAAAGCAT TATACCCTTTCTTTAGAAGCCAGTGTTTATATGTGGAGT CACTAATGTACTGGTAGGTTGGATTTAGTGAAGAACAGA TCTGAAATAACCTGATTTTTTTCCATTTGGGTTGTTGTT CATTGTTTA |
| 27 | TNNT1 | Dph-CRE27 | 360 | CCCAACCTTTGAATGTATATGGGGGAGAAAATAACAGAC AAGGTTGGAGGCGAAGATAAGGGGGGATGGGGTGGTGCT TCTCCGCAAACATCCAACCCTTCTGTAAAGATTCCTCCA GACTGGGGAAGAAGGCTTGGGTGTCGGTCCCTTTAAGAA GGAAGGGAAAGGGTTAAAGCCACTGCGGGGCCATTTCCC TTCCCGGCCCCGAGAGGGCGCAGGAGCTCTCAGGGGCTT AAAGGACCGGGCCTGGGGGCGGGTTATGGGGGCGGAGGG AGGGAAGGGTGGTCTTGGAGGTTGGGGCCCGAGGGTATC GGGGGTCCCCCGGGCCCCCGACATCGGTCTCGGGAAGC GAAGCAGCC |
| 28 | TNNT1 | Dph-CRE28 | 471 | CTCACCTTCCTCCTCCTCCTCCGCAGCCTCCTCTGGAGA TGGGGGCACAGAAGAGAAGGCGTTAGGAGCTGGGGGAGG GATGGGGGCGGTGGCCAGAGACCAGGGTTCCAGTCTCTG CTGGACGGGGGTCCCTCTGGCCTCGGCTGCGATGGGCAC GTTCCCCCTGGCGGTGCAGGGATGGCGCGAGGAGACGCT CCAGACCCGGAGAGGGCGGGCGAGGGCCCGAGGGCTGAG CCGCCCCTTCCCCGCCAAAGTGCCACACTCCTCGCCTCC CCTCCCAAGAGCTCCTGGGCGTGTCCCCATCCCATAGGG |

TABLE 3-continued

The CREs sequence for high expression in diaphragm and skeletal muscle.

| SEQ ID NO. | Gene | Dph-CRE (CRE) | Size (bp) | Sequence |
|---|---|---|---|---|
| | | | | CCGGCCCACTCCCTACTCACCTTCCGGCTGCTCCCTGCG GACGGGTGTGGGGAGAGAGGAGGGAGGGGAGAGTTAGAC CTGGGGTGGGAGAGCCTCTCCACCACTGCACGCCCCAAC CCCTCCCAGTGCAGCACTCACTCCTCATATTCCTGCTCC TCG |
| 29 | TNNI2 | Dph-CRE29 | 393 | GGCCGCCTGGGAAGACCGGGGAGGTGGGGGCCAGAGAGT CGGGACCACATGGGATGGGGCGGGCTAGAGCCAGCCCTG TAGGGACAGAGTGGGCAATGGTGTCTGGGGGCTGGTGAG CATGGAGGGAGGACCCCCAACACCTCAGAGACCTGTGCT GCAGGGCCTTCCCTGCATGAGCAGCAGGGGGCAGCAGAT GCCTTCGGAAGCCGCTGGGGCCTTTAGGGGCTCAGTCCT GGCCGGATGCCCCTCCCAGTCCCCACACATCTGGGCTGC CTTAGCGGCTGGGGCCTCCACGCTGCTGTCTCCTCTGAT CCTCCCCACGGGGCTGCGAAGCCGGCAGGGCTGGGGCCA AGAGCCCCCACTCCGAGAGGGTGCCAAGTCACGGTCCAG GGG |
| 30 | TNNI2 | Dph-CRE30 | 331 | CTGTCCTCAGGCTCCTTACGAGAACGACAGAGGCATCTC CAGCGCGTCACCGAGCCCTAAATAGAGTAGCCCAGCCAC GGCACCCCCCACCAAGACTTCTTGGACTGGGCGGCAGCA CGCGGCCAGGCCAGGCGGCCGGACAGGTGGGGAGGTCTC TGTGGCTCTCCACGCCCCCATTGGTCTGAGGAGGACTCT ATGCCCTTTCTGAGCAGGGGCCCAGCCTGGGGGAGGCCA TTTATACCCCTCCCCCTGGGCCCACCAGCCCAACTCGCC GCTGCCGGCCTGACCTCGCTCCCAGCCCTGCTGCCCAGA TTCTAGGTGAGGCCCAGCC |
| 31 | TNNI2 | Dph-CRE31 | 306 | GCTCCCCCAACTCAGCATAGGTCATAGGTCACAGCCTCA AGGCCCTAAGGCCCAGAGAAGATGGCCTGGCCCTCCCCG CTGGCAAAAGTGCCCCACCCACCCACCAAGACGCTGCTG AAAGAGAGGAAGTGGCTGCCCCAAGCCTTCTGGGGCAGG GGAAGTGTGGCTGTGGCCTGGTCACAGGGGAATCACTTC TTCTTTCTGATTCCTGCACTTCCCGCCCCCACCTCACCG GCCGACCTGCCCCCAACTGGCCCTCCTCTCCCCCAGCCT CTGGCCTCCCAGCACCATGTGCCACCTGGCAAA |
| 32 | MYLPF | Dph-CRE32 | 268 | AACTCTGGCACATTCCAGCCCCTCTTTGGGAGAAAGAAC ATCTCTTCTTGCCCAGGCCCTAGTGAGACATGCATCGCA AGACATGCTCCCCCCTTCCTCCCCGCTGGGCTCCAGCTG CTGCCAGCCCTCCAAGAAAGGAGAGGCCCTGAGTTGGGC TATTTTGGTATCTGGGGTGGGCACCCGCAGGGCTAAGGT TACCTTGGTATGTTAAGGGCTCCCTGGGGCAGGACTATA TAACCCCAGAGGGACTGCCCCATGCTGACTCCTT |
| 33 | TNNT3 | Dph-CRE33 | 214 | TACCTGGTGCAGGCCCTCGAGGCCGCTGGTGCCTGCTCT GTGCAGTCCCTGCTACGCCTCAGGCCCAGCGCCCGAGGG GGAGGTCGCCGATACCCAAAATAAAACCTGCCCTATCCC TCTGACCTCAGCTGGCTGGGCGGAGAGCGCCTGCCAAAG CTCCAGGAGCTGGGCGGGCAGCACCTTCCCCTGCTGGCC ACACGGGGCCAGTGCAGGG |
| 34 | TNNT3 | Dph-CRE34 | 129 | TCTTGGGTTTCTGGGCAGAAACGTCTTGCCTATTTCTGG ACT+CCTCAGCTGCCACTGGCTCCTTATAAATAACCCACC CCAGGCGAGGGCCACGCTGCCCCCATCTTGTGGCAGCCG ACAGGTGTCTGC |
| 35 | TNNT3 | Dph-CRE35 | 403 | TTACCTGGTGCAGGCCCTCGAGGCCGCTGGTGCCTGCTC TGTGCAGTCCCTGCTACGCCTCAGGCCCAGCGCCCGAGG GGGAGGTCGCCGATACCCAAAATAAAACCTGCCCTATCC CTCTGACCTCAGCTGGCTGGGCGGAGAGCGCCTGCCAAA GCTCCAGGAGCTGGGCGGGCAGCACCTTCCCCTGCTGGC CACACGGGGCCAGTGCAGGGTTATGGCACACCCACCTTC AGGTGCGCCCCTCAGGACCCCTGGCCTGGGTGAGGGCTT GGGTGGGCACAGGCTTCCTAGGCCTGCAGACTGAACCAC GTGTAACCAGAATGGTGGGCTCAGGGCTCCGTTAGAGAA GCCGGCAGAGCGAGCCTGGAAAAGGAGGTTGGCCCCACC ATGGGAGAGGATG |
| 36 | TNNT3 | Dph-CRE36 | 415 | AGAGTGAATGCATGGGAATGAATAGATGGGTGGATGAAT GGACAACTGTGTGAAATAGCAGACAGCCTGGGGACACCC TCCCTCCTGTCCCTCCTCTCCCAGGTCTTGCACTGGGCC CTGACACTCAGCCCTGCAGCCTTCAGCGTCTGGGAAGTC CCTTCGAGGAGCAGCACCCCAGACTCTGATGTTCTGGAC TTCACTTTGCCATTCCCTTGGGTCCTCACAGCCACTATT |

TABLE 3-continued

The CREs sequence for high expression in diaphragm and skeletal muscle.

| SEQ ID NO. | Gene | Dph-CRE (CRE) | Size (bp) | Sequence |
|---|---|---|---|---|
| | | | | TTCTGAAGGCTTCATGTCAAACCCTGCTTGCCTCATGAA TACACACAGTTCAGAAAAGCAAAACCTCGACAGAGCGAC CACCCACACAAGGGAGGTGACGTGCCCCCATCCTTTCTC AGATGCCCCAGCCACTGAGAGAGGATCCAGGCCACCCTC CCCAGCTGGGGAACCACCCAGTGAC |
| 37 | TNNT3 | Dph-CRE37 | 352 | ACCAATCTGTGCCTGAACCGAAGAGTTCCGCAGACACCA CCGCCCACGCTCAGCCTGTGGGGTCTGAGGGGAGTGAGG GGGTGGGTCAGGGTGCCAGACTGCTCTCCCCCACCTGGT GCCTCAGTTTCCCTGATCCAAGAGGCAGGGTTATCCAAT CTGGTGGCCTCACTGGCCAGCATACAGGCCATCAGAGGC CAGGAAGGATGTCTGCTAGTCGGACGGTGCCACCTGGAG TCCTGAGGAAAGAAAACCAGTCTCCACACGCCACAATGA GCCTGTGGGAGATGCTGGCACAGATGGTAACGGCCACTG CGAGTGCCCAGGGTGGGGCCCCAGGGTTAGAAAGGGCCT A |
| 38 | TNNT3 | Dph-CRE38 | 349 | CTCCTCAGCCCATCCAGAATGTACCCGCTGCTGGGAGTA AAAATAGCAGCTGACACCTCCTGGAGGCGGAGGGGAGGAC CTTGCCTCCTTCTCCAAGCACGTCCTCTGCATCCTGGCC TCCTTCAGCCTCCTCCTCTGGCCATTCCTATACTTGGTA AGGGGCCTGCACGGGCATAGCCCCCCCCAGCAAGACTCC GCACACACCCCGGCCACCCAGTCACTGGCCAATGGGCTC CTAGGAAGATCAAATGTCACTATAACACGAGGGTGTGAG CCGGGCGCCAGTGCCTGCAGCCGGTGCTGTCCACAGGGA GCTCCAGCCCTTCTCACACTCGACCCGCAGGTGGGTA |
| 82 | MYH2 | Dph-CRE82 | 390 | GAAGCCAGGTATCCTGGCTGCCCAGCCACTGCCTTTATC CACCAGCTTGACTCTTTCAGATCATCTTCTCAAATTATC CATAGGAGATTTATCCACATACTCAATAAGAAAAATATT TCTAATTATATCCAACCATTCTTAATATGAATGAGAATT ATGCGGGGACGCTAGATTGCCAAGAGGTATTTTGCCAAA CAATTCCTTTTGACTTAAGAAAGAAGAGGCAGCTGCATT GTTTCCATAGCTATCCATATAAAAGAGCCCTTGGAATGA GGCTGACTCGTCCTGCTTTAAAAAGCTCCAAGGTAAGTG GGAGCAGGACGGGCCTTTCAAGAGGGACACTGGTCACAC CGCCCAGTGTCAGCAGCAGCTGCTAGTTCTGGTACTGCT |
| 83 | MYH2 | Dph-CRE83 | 294 | CAGCTGCTAGTTCTGGTACTGCTCCTTCTGGAACTGCAC GTTTTACCTCTATGAATTTTGTTACTTCTGTTTACAATA GCAAGCCATGCCATAAATGGGATTTTTTCCCCCTCTTTT TGGTCAACTAATCAAGTGCTTTTCCCTTTTCTTTTATAG AACTGTCTCACTCCCAGGCTACATCTTCTCACTTGCTAA CAAGGTAAGATTTGGACTAACCAGTTCCTGGAGGAGAAT GCAAGAGGCTCTGGGATGGATTTCTGTCACTTAGCAACC TTTCAGAAAGTGCTTGTCTCA |
| 39 | SLN | Dph-CRE39 | 380 | TAACTATGTTTAATGTGCTGAGAGAAAGCCATTTGTTTA CAGAATCTTATTATAGAACAGAAATATACTTGTTCCAGA GAAGAGGAGTTTAATTGGTTCCAAGTCAAATGATGCTAA CAGGCGTCACCTCACCAATCCAGGACTTAAGATGGGTTA TTATAAATAGGAGTAACACATATTTTTTTTGGCTCTTTT TCCCACCTGTTATGCAAGACTGCATACCACTATGATGTT CCTCCTGATTATTTCCAGGAACTTTGGGGGTGGCTCACG TGTGCTCATGAACAAGTACTGTCAGGTATCACATACGGT CTGTCATTTTCTTGCTCTTGAGCTCTGGCACTTCTCTGC TGCTGTCTGCTGCTGAGGCCTGCAGAGAT |
| 40 | SLN | Dph-CRE40 | 575 | TTCTCTCTCACTGTAAAAGTGTAAAAGGTTAGGTTACTC CCCAGCCTGTCGAACATGTGCCTGATTGCCTTCTGAGAT AGCACATCCCTAATCCAAAAGAAAACCTAGCCTGGAGCT TGCATCCAGCTAATCTTCTTCCACATTGCTCCAAACAGG GAGTTCAGTTTTCTCATTACTCATACAGAGAGCAGAGAT AGATTTTCATGATTCTTCAGGACTCTGTTCTCTCTGCTT TAATAGCCAAAAGCTAAAGCCAAATGAACTTCTTCACAG AGAACAACAAGCAATTTTATCTAATCCTTATTATTCTTG CTGTAACTGCAATTGTGTTATTCTGACTGACAGATTCCC AGAAGAGATTCAGTGAAAATACCCTTGATCAGATTCACA AAGGAACAGCATATTTCAAGTGGGCGTGTCTGGCTAGAA TCTCCCTGGACAGTTCAGTAACAGCACATCAACAGACTG CTGAATTCTTATTTCCCCGTCCAAAAAATAACAAAGCCA ATCTGAAATCTGGAAGTGTTCTGAGGGCAGATGGTATTA GCCCAGTAGTAAACATATTTTTGGCTGCT |

TABLE 3-continued

The CREs sequence for high expression in diaphragm and skeletal muscle.

| SEQ ID NO. | Gene | Dph-CRE (CRE) | Size (bp) | Sequence |
|---|---|---|---|---|
| 41 | SLN | Dph-CRE41 | 463 | CTACAATAAATATATAACTTTTTTAATTTGACAAAAAT<br>AATTTTGAGTGGTTACAAAAAGGGACAGGTGTGGCTTGG<br>TAACTAGAAAAACATTCCCAGCCTGGGAAACAATCTAGT<br>GAGAGCTTGGAGGCAGAAGACAGAACTCTGATTACATTC<br>AAGGAGTTTGCCAGATGGCAACAGATAACTGCCAATGTT<br>CGGTTGCACTATAATTATTATACACTCTCTGTCACTTCA<br>GCAAGCGCTCTTTTCACAAGACAAGTGGTGACAGAATGT<br>TGTATTAAGATTACCCGTTGCTAAGCTTATGTTAAAATG<br>AGGAAATGAAATGGAAAGTCTTGTTTTGGTAATGTCTCT<br>GGGGTATGAGGAATGGAGGGAAAGGTTTGACTATGAGCA<br>TAACTGCATAGAGAATTTTGTTTGTTTATGCCTTTTGGG<br>AATGCATTATTTTGATTGACCCTAATTGGGAATT |
| 42 | SLN | Dph-CRE42 | 379 | ATTCATGAAGATGTAAAAGACACATTTAAAACCCACATC<br>AATTGCACTAAAAGTCAACTGGAAACAGAAGGTTTTTAA<br>ATCCTGGTGGTGGCAAATTGGCAGCCAAAGGAACAAAGT<br>CTTAGTCAACATATTTCCATGTCCCCCGAACACAAATAG<br>CCTCGAACCTTCGGAGGGTGTTCCTTTGAGATGTTTCAT<br>CAGTGACATCACAGTGATTGCCAGCTTCCACGGACTACT<br>TTAGGCGCTGCCCAGAGTCCAGGAGTCCAGACAGCCTGG<br>GAGGGGAGAAGGAGTTGGAGCTCAAGTTGGAGACAGCGA<br>GGAGAAACCTGCCATAGCCAGGGTGTGTCTTTGATCCTC<br>TTCAGGTAACTGCAGGATTTTTATGCTT |
| 43 | MYBPC1 | Dph-CRE43 | 250 | AAGAAGGAATACCCTAGGGCAAATGCGTGCTAGAGGGGC<br>TTAATACTTGGCAGAATCCTTCTTTTTCAGTAGCCTGCT<br>TTTATGACTGCTCCGACTGCACCTGTTAGGAAGATAAAT<br>AAAGGACTGGCCAATTCTTTCCTCTGAAGCGCCCTAAAT<br>ATATCACTTTAAAAAGACTTTGGAAAAACAAGTTGTATC<br>CTTACTTCTCACCCAGTAAATCTAAAGAAATTCCCTCTT<br>GTTCCCAGGCCTTTCA |
| 44 | MYBPC1 | Dph-CRE44 | 194 | CCACATAACTAAAGCATGATGCTATTGAGTTCTAAGTCT<br>AGTTTCCACCCTTATATGAAAAGTCAGCTTGGCACAGAG<br>TTTGGTAGAGCTAAGTCTGACCAGCTGCACTCTCAGCCA<br>CAAGGGAAATTAGACGAGACAGTGTGGCTGCTTCAGTAC<br>CAATCAATCAAAGTTTTTGAAAATTATCTTGAAAACAC |
| 45 | MYBPC1 | Dph-CRE45 | 264 | ACTTTCTCTGTGGATTGCAATATTTCCTGGCATATGTTC<br>ACTTCAGTAAGACGATCAGTGTATTAAAAACCCAATGGG<br>GTTTCTGCAGAAGCCAATGATGGCATGGCACCTCTTTTG<br>TGGCATGTGTGAAATCTGCCCTTCGCTGTAAACATTCTT<br>ATGCAACATGACACTCTGCCCTATGTCCATTTCATATGT<br>GGTGTTCAGTGTGCTGGGAATGCTGAAAAAAACAATTCT<br>CTCTTAGAGATTTCCCAAGTAGAATCACAG |
| 46 | MYBPC1 | Dph-CRE46 | 427 | AGAAGGAATACCCTAGGGCAAATGCGTGCTAGAGGGGCT<br>TAATACTTGGCAGAATCCTTCTTTTTCAGTAGCCTGCTT<br>TTATGACTGCTCCGACTGCACCTGTTAGGAAGATAAATA<br>AAGGACTGGCCAATTCTTTCCTCTGAAGCGCCCTAAATA<br>TATCACTTTAAAAAGACTTTGGAAAAACAAGTTGTATCC<br>TTACTTCTCACCCAGTAAATCTAAAGAAATTCCCTCTTG<br>TTCCCAGGCCTTTCAAACAGTGAAGTCAGGAGTAAGGGA<br>GACTGTGGACTGGTCAAAGGTGGAAGTTAGACTCACTAG<br>CTGGTCTAAGGAATCCAGGAGGGTGGAAAACATGAAGAA<br>CTTACAATCCTTTATGCTCTCAATGACTCACTTTATTTT<br>GGCCATGAGACACAGCCTTGAAACTTTTTTTTTTTT |
| 47 | MYBPC1 | Dph-CRE47 | 436 | GGTCATAAAATACTTTCTCTGTGGATTGCAATATTTCCT<br>GGCATATGTTCACTTCAGTAAGACGATCAGTGTATTAAA<br>AACCCAATGGGGTTTCTGCAGAAGCCAATGATGGCATGG<br>CACCTCTTTTGTGGCATGTGTGAAATCTGCCCTTCGCTG<br>TAAACATTCTTATGCAACATGACACTCTGCCCTATGTCC<br>ATTTCATATGTGGTGTTCAGTGTGCTGGGAATGCTGAAA<br>AAAACAATTCTCTCTTAGAGATTTCCCAAGTAGAATCAC<br>AGTGTTAAACCTATCAGCAGCCTCCAAGATCATTTTTTT<br>TAAGCCCCTCATTTTACACAAAAAGAAACTGAGGCCCAG<br>AAAGCCCCCTGACTTTCTCAGAGTAACTAAGCTGGTTAA<br>TGATAGATCCAGAAATAGAACCCAAGGGACCAACTTCAG<br>ATTCTAG |
| 48 | MYBPC1 | Dph-CRE48 | 359 | CTGAGTCAGCACATGCATCTGTCAGAGAGAGAAGAGCAA<br>GACGGAGCACGAGGCTGCAGCTGAATTTAGAAAGTTAGA<br>GGTGTTCTCATCAGCCACATGAGATGGGCAGGAGATTCC |

TABLE 3-continued

The CREs sequence for high expression in diaphragm and skeletal muscle.

| SEQ ID NO. | Gene | Dph-CRE (CRE) | Size (bp) | Sequence |
|---|---|---|---|---|
| | | | | TTCCAGTAGGCGAGAGAGCAGAGTGCAGACAACAGATGT GAGAAAGGTCCCCATAGCTGTCAAGTTCCTGCATCCTTG TGCTGAAGAAAGGGAGGTGCCATCATGATTGATGTTCAG AGGCAGTATAAAAGCACTGGGTTTCTCCCCAACTGCTTG TCACACCGACCTGCACCATCTCTCGCCTGCCTGTGGGGT TTCTGTCAACTAGTCGTGGAGGGAAGGAGACTCTTTAAA GAATAACA |
| 49 | MYBPC1 | Dph-CRE49 | 353 | GAGATTTCATCACATTTTAAAGTTTTGCCAAGCCAAAAA GCTACCTGAATGTAGAGCAGCATTCATCCCTCTTGCCT ATTTCTAAGCATTTCTCAGGGCTTAGTCATCCATCAGAA AAGGACCTCCCTTGATGGGAAAACTCCTTCTCATATCTC TTCTTTGACCTTCAGTTTCTACCTGCAAGAGAGTGAATG GCCTATTTCAAACACCGAAATCAATTTGTCTTTGGAAAG TCATCTTATATACAAATATTATCCTTACCTCAAATTGGG GAAAGGTTAATAATTTATGCAGAAAACTAAGAGAAAGGA ATAGGGGAGGAGGAAAGATAGTTTATCAAGGGCAATTGT TT |
| 50 | MYBPC1 | Dph-CRE50 | 354 | TCAAAAGTCTTTTAAACATATTTTCTTTATATAATTAAG TAACCAGTGTTGACAGGCTGTGGTGATCAGTTTACAGGT TGGCCTTACTTAGTGGCAGAGGGCATTGATGGATGAAGT CTTTCACCCAAAATAACCACACCAAATGCATGTATTAAT ATGGGAACTTAATCCTGACTGTCAGGCAGGGAGTCCAAC CCCTGCTAAAGTATCTTATTTGTAATGCAAATGATTTAC GTGTGTACTAAGTGTCCTTTTTATCTGCTCTGTCACTTT AACCTCTCCGAAGTGTACCCAGAAGCAATACATTCTACC ATGTTTCCAAACTGGAAACACAATATTGTTTTAATTATT CTG |
| 51 | ENO3 | Dph-CRE51 | 351 | GCTGTCCCAGCGTTATCAGTCGGGCGCCTTGCCAGCCGA AAGGGCCTGTCTAAATTCGTTTCCTGTCCCTAACTCAT CCCGGCGCTGGCTGGCCTGGAGAGGGTAGGATGGGGCGG CGCCGAGAATGGCCGTTATGAGGACCCTAAGAGGTGAGA CCCTCTCGCCTTCTGGGGTGGGGGGTCCCGTCCTTTCCC CCACTGAGGACAGAGGCCCGCCCAGCGATCTGAGCATGT GTGGACGTCAATCTTGCAGCCCCTCTTCCAGGCCCCCTC CCCAGCCTTGCAGGGCTCAGGTTACCCCTGGCCTTTCCT AAAGGTCACTCATTCCTCTTGACGTTTGCAAAAGGGGAA |
| 52 | ENO3 | Dph-CRE52 | 607 | TGTCCCAGCGTTATCAGTCGGGCGCCTTGCCAGCCGAAA GGGCCTGTCTAAATTCGTTTCCTGTCCCTAACTCATCC CGGCGCTGGCTGGCCTGGAGAGGGTAGGATGGGGCGGCG CCGAGAATGGCCGTTATGAGGACCCTAAGAGGTGAGACC CTCTCGCCTTCTGGGGTGGGGGGTCCCGTCCTTTCCCCC ACTGAGGACAGAGGCCCGCCCAGCGATCTGAGCATGTGT GGACGTCAATCTTGCAGCCCCTCTTCCAGGCCCCCTCCC CAGCCTTGCAGGGCTCAGGTTACCCCTGGCCTTTCCTAA AGGTCACTCATTCCTCTTGACGTTTGCAAAAGGGGAATG TAATCCTGGGGTGGGGGGAGACCCCTCATCTGTAGCCCC TCCCTTGCTCCTCCCAAAGGGTGGAATTAGAACAGGGAC TGTTATTGGGAGACAGAAAGTGGGGGATAGTAGTTGACC TTTGGTAAGGGGGCAGGTGCCCAGGGCCAGAGGCTTCTG CTTCAGGCTGTAGTGGGCACTTGGCTGCCAGCCCAGTGT GAAGGGGGGAGGATGGAGAGAAAGAGAGGCGGGGCTGGC TGGGGACCGAGTGGCTCAGGGA |
| 53 | ENO3 | Dph-CRE53 | 469 | AGGGCTGGGCGGCTTCCGGAGCCTGGGCTAGGGGCAAGG GGTCACCGAGCGCGGCCCGGGCGGAAAGGGGGTTGGTTT TCTCTCTCCTCCCGAGCGCGGCGCGCATCCCTGGCGTCC ACGCCGAATCCCACAGTCCCCGACGCCCCTCGAGTCCGT GTTCCTCGACAGCCGCGCGGCTGAGTCACTGGCGGGCTC GGGCGGGGCCGCACCCGGGCACGTGGCGGCGCTCCCCGC CCGCCATCTCCTGACCCCTGGCCCACCGCACCCCTACCC CAGGGTGGAAAAATCCCGGGAGGAGCGGCCTGAGATGAG GGGGCGGGGCGAGAGGGGAGACTGGACGGGTGGCGGGGC AGGTGGCCTGGGGTGGGGGCTGGGAGGCCGCGCGGGCCG GCGGGGCGGGGAGCAGGGGTGGGGAGAGGGCGGCGGGGG TGAGTCACCGGGCGCGCGCTGCCCCGGCGCCGACGGGAA G |
| 54 | ENO3 | Dph-CRE54 | 332 | TGGGTTCACCCAGGGCCCATTCTCAGTCTAGAGGATTGTC CCTTCTCTGGATCGGCTCTAGCCCAGGGCCTCACCCGAC ATCCCAGCCCCGCCCGCCCCAGGCAGGCAATGTCTGGAT CACCGGCCGTGCCCCTTGGCCTGTGTCTGCAGAGGTCAC |

TABLE 3-continued

The CREs sequence for high expression in diaphragm and skeletal muscle.

| SEQ ID NO. | Gene | Dph-CRE (CRE) | Size (bp) | Sequence |
|---|---|---|---|---|
|  |  |  |  | AGAGCGCGGACACCCGCGGGGCTTAACAGGCGGGGCTAT |
|  |  |  |  | TTTTCGAGGCGGAAGAATACTCAAGTTGCAAGAGTGGCA |
|  |  |  |  | ACTTTTTCAAGAAGGGGAAAGTCCCACTTCGGGCCCTTT |
|  |  |  |  | GGGTTTCTTCGCAGTCAGATGTGCGCTCACAGCCACCTG |
|  |  |  |  | GGGAGGGCGGGACGGGCGGG |
| 55 | CA3 | Dph-CRE55 | 206 | TACATTCCAGGGAGGGGAGACCAGTTGGGACAAGGCCTAG |
|  |  |  |  | GCTGCTCTCCTACAAATTTGCCATGAACAGGAGCCAAAC |
|  |  |  |  | TCTAAGACCTGATTCAAGTGGCCCAGCTGTCACTGGTGA |
|  |  |  |  | CACACTCAGGGGCTGGGCCTATCATGTTCTTATACAACC |
|  |  |  |  | TAGTGAGTCAAGCTTTGGAAAATAACATTGTCAGGGAAG |
|  |  |  |  | AACGTAAAAGT |
| 56 | CA3 | Dph-CRE56 | 289 | GGAGCTGAGAGTTTAAGGGCATTTGTTTACTATGTTTGC |
|  |  |  |  | TTGGATTTTCCGAACTGCCTTAGTTCCTGATTCCACACT |
|  |  |  |  | GCTATTGTGTGGATCAAATAATCCCTTGTCACAAAAATA |
|  |  |  |  | CCCTGGGGAATGACTCCCCTGGCGTCCAGGTTATGAGTG |
|  |  |  |  | TGGTCAGTCATTCCACATGCCTTAGGGATGAGCTATCTG |
|  |  |  |  | TGCCATGACGAGCGATTTCCTTTTCGAGTTTTGTAATCC |
|  |  |  |  | CCAAATACTAAATACTATTATCAATAAAAGTTAATTAAG |
|  |  |  |  | GAAATGTATATCGAAA |
| 57 | CA3 | Dph-CRE57 | 195 | GACAGCTGTCCCGCTCTTGGAATTCATTGGCTTCCTCTA |
|  |  |  |  | CCCGGCCTCCCAAACACCACCCCAATCTAGTTTAGCCCC |
|  |  |  |  | CCGCCCCACCCTCGCTGACCTAATAAGGCCATGCAGTGT |
|  |  |  |  | GCGGGGGAGCTACATAAAAGCGCGGGCTCGCGGCGACTC |
|  |  |  |  | TGCACCACGCAGGGGAAGAGAAAGCAGGAGCCGTCCAGC |
| 58 | ATP2A1 | Dph-CRE58 | 345 | CCCCTCAGCTTCAGCCCCCACCTCCAGGAGGCCCTACCC |
|  |  |  |  | ACGCTCATGACCTTGCTATTCTGGGCCTTGTGTCCTGTA |
|  |  |  |  | GGGAGATGGACAGGAGACAGCTGGGCTTCCAGGCCACCC |
|  |  |  |  | AGGCGGGGGGCTAGCCGAGGGAAGCCTGCTGGCTCTCCT |
|  |  |  |  | GCTTGCTCTAATTTCTGGGGCTCCCCAAACCTTGGCCTC |
|  |  |  |  | AGGAGACTGGGGATAGGACCGGCCTTGAAAGTGGGGGAA |
|  |  |  |  | GCTTTGGAGAGCCGGGTGCTGGGTTCTTAGTGAGATGGC |
|  |  |  |  | CAGTGAAGGCTGTGGTGCCCCGAGGTAAGCAGGGCCTGA |
|  |  |  |  | TCCCCTCCTAATCTTCCAGCAGCAACTGGTGCT |
| 59 | ATP2A1 | Dph-CRE59 | 220 | CTCCTCCAGCAGCTGCCCTGGTGGTAACCAAGAGACGCC |
|  |  |  |  | CCCATCCTGGAGCAGGGGTGGGGAGGGGCAGCTCAGAGC |
|  |  |  |  | AGCTGCTTCTCTGAGGAAGCTGACACCAAGGCCAGCATT |
|  |  |  |  | CAGCAACAACTTGTGGCTTTGCACCCAGCGCCGGGGTCC |
|  |  |  |  | CCGCCCACCTGGCTCCCTGCTGTCCCTCTTCCCCACTGC |
|  |  |  |  | TGCTCGGACTTCCCTCTGACCCTGG |
| 60 | ATP2A1 | Dph-CRE60 | 663 | CTTTGCTCCCTGGGAGGGCCTGGCCCTGTGGGCATTTGA |
|  |  |  |  | GTTTATAACACCACCCCCATTGTGGCACACCCCTCCACC |
|  |  |  |  | CCGTAAAACACAGGCTCTGCTCTTGGAATCAGTCTTCCT |
|  |  |  |  | GATCTGTGGCTGTGCCCTCCAACAGAGGGCACCCCTGGG |
|  |  |  |  | CTTCCCAGCTCTGGGGGTAGTGGGTGCCAACAAGGAGGG |
|  |  |  |  | GCCTGGGGCTGAAGAATCCCACCCGCTGAGCTCGGCCTT |
|  |  |  |  | CTCCCTTCCCCACTGTCCAGCTCCGCCTTTCAGCATCCT |
|  |  |  |  | GCCTCACTCCCCGCCCAGGCAGCAAGGAGCCCACACCCT |
|  |  |  |  | CATGCCCCTCAGCTTCAGCCCCCACCTCCAGGAGGCCCT |
|  |  |  |  | ACCCACGCTCATGACCTTGCTATTCTGGGCCTTGTGTCC |
|  |  |  |  | TGTAGGGAGATGGACAGGAGACAGCTGGGCTTCCAGGCC |
|  |  |  |  | ACCCAGGCGGGGGGCTAGCCGAGGGAAGCCTGCTGGCTC |
|  |  |  |  | TCCTGCTTGCTCTAATTTCTGGGGCTCCCCAAACCTTGG |
|  |  |  |  | CCTCAGGAGACTGGGGATAGGACCGGCCTTGAAAGTGGG |
|  |  |  |  | GGAAGCTTTGGAGAGCCGGGTGCTGGGTTCTTAGTGAGA |
|  |  |  |  | TGGCCAGTGAAGGCTGTGGTGCCCCGAGGTAAGCAGGGC |
|  |  |  |  | CTGATCCCCTCCTAATCTTCCAGCAGCAACTGGTGCTCT |
| 61 | ATP2A1 | Dph-CRE61 | 594 | CAGCAGCTGCCCTGGTGGTAACCAAGAGACGCCCCCATC |
|  |  |  |  | CTGGAGCAGGGGTGGGGAGGGGCAGCTCAGAGCAGCTGC |
|  |  |  |  | TTCTCTGAGGAAGCTGACACCAAGGCCAGCATTCAGCAA |
|  |  |  |  | CAACTTGTGGCTTTGCACCCAGCGCCGGGGTCCCCGCCC |
|  |  |  |  | ACCTGGCTCCCTGCTGTCCCTCTTCCCCACTGCTGCTCG |
|  |  |  |  | GACTTCCCTCTGACCCTGGTGGCTCTGTGTCTCTGCTCC |
|  |  |  |  | CTTTCCCCCTAGGTCTAGACATCTGTCCTTATTTCCCCC |
|  |  |  |  | AGACCTGTCCCCAGAAGTCCACCCTTCCCCATTCCTTTG |
|  |  |  |  | GTCTGGAGCCCCTGCTTGGTCCAGCTTCCCCAGGCCCCG |
|  |  |  |  | ACACCTTTCTGTGGGGTCTGCCTAGCTCCTGCACGGACA |
|  |  |  |  | CAGCATGGGCCTGATCCTGTTCCCCTCGTGGACAGATGC |
|  |  |  |  | AGCAGGGCAGAGTGCAGCGCAGACCACAGGCCTCTGGGG |

TABLE 3-continued

The CREs sequence for high expression in diaphragm and skeletal muscle.

| SEQ ID NO. | Gene | Dph-CRE (CRE) | Size (bp) | Sequence |
|---|---|---|---|---|
| | | | | CTGGCCACAGAAACCCCGTTGGTTAGAGCACAGTGTGGG ATGAGGTGACCCTCAGTGCACGACTTGGGGTGACCCCTG CCCCCATCCTGAGACAGTTACCCCTCCCCCTCTGCCATC AGCACATTC |
| 62 | ATP2A1 | Dph-CRE62 | 634 | CCTTCCCCATTCCTTTGGTCTGGAGCCCCTGCTTGGTCC AGCTTCCCCAGGCCCCGACACCTTTCTGTGGGGTCTGCC TAGCTCCTGCACGCACACAGCATGGGCCTGATCCTGTTC CCCTCGTGGACAGATGCAGCAGGGCAGAGTGCAGCGCAG ACCACAGGCCTCTGGGGCTGGCCACAGAAACCCCGTTGG TTAGAGCACAGTGTGGGATGAGGTGACCCTCAGTGCACG ACTTGGGGTGACCCCTGCCCCCATCCTGAGACAGTTACC CCTCCCCCTCTGCCATCAGCACATTCTGTAGCCTCTTGG GTTACTTGGCTGCCTTGGTGTCCCATTTTCTTGGGGGTG GGGTGGGGATTCCCTATCCAGGATGGGGGGGCCCTCAGG GCTCTGTTCCCAGAGGCTGAGTTAGAGCGATGGGGAAGG GGGGGGGCAGTTTTGGGGAGAGACAGGCAGTGCTGGCTT TGCTCACCAGGGCCTGGACACTAAATCCCTTGTTGATGG CTGTGGCAACCCCTCCCTAGGGTAGGGTTACCATCTTCG GCCCTGTCCCCTTGACTCTCTCCCCTCACTTCCCCTTGT CCCTCTAGGAGCCACTCACTTCCTCTAGCCCCCAAAAGA TGTTCTCCCT |
| 63 | ATP2A1 | Dph-CRE63 | 445 | CCTCCCCTGCACCCCAGAGGCAGGTTTTATTTTAAGCTT TAAGGGTGTTCTCAGCCAAAACACCGAAGCTAAGCCACC CTCGCGGCTTCAAGAGCTTGGAGAGCTCGGGTTACCCAC CCGAACTCCGGGCTCCGGGTCCCGCCGCGATGCCGGCTG CGGCGCGGGGGGCCACTGCCACTCCCGGCATGCGCCGGG CGGACGGCCGCTCCACCAATCCCCGCGCCCGTCGGCGCC CCTGCCCCGCCCTCCCCAGCCTCCTGACGCTGATTGGTC GAGGGGAGGACTCGCTCCTAGTGGCGGGAAAGCGCGGCG GTGTGATGATGACTCCAAGGAGCCCGGCGCCCGGTCAGG GAGGGCACTGGCATCCCTCATTACCCGCCCAGCCTGGCC TTAGCCCTTCCCCGCGCTCCCTAGGCACCCCCACCCCCG CAGGGCATCTCCAGGG |
| 64 | ATP2A1 | Dph-CRE64 | 408 | GTCTCCGAACGCAGGCCCCGTCGCGTTAAGCACAAGCTG GCAGGGCCTCTCCTCTCCCTTCTCAGATTTGCTCCTTGA CATTTGCCTGCTGCCTGGCGGTGGCAACAGCTGGGGCGG GGCGCGCGCAGGAGGCCCCGTAACCCTATCCCCGCTCCG GCTCCCTCGTGAAACCGGAGCTTCCCTGCCTTGGCCGAG GGGGAGGGCTGCGGGGGCCAGACCGCCTGCGAAGACCAC AGGGTTTTTCCTCTCGGGTTTTGGCTCCCGTGGGATGGA TGTGGCTGTGCGGGGGGTTGGCCTGAGCTTCGCTTCTAA GCCAGCAGCTTGGTCAGGGAAACCTGAAAGCATTCCCAG CTAATCCCCCAAGTGGTGCAAGTCTGTGCGCGCCCATCC CGCTGAGTAAGGCGGTGG |
| 65 | MYH1 | Dph-CRE65 | 496 | GGCAACAAAGTCCAGGGATTCCAGAACTTAGCTGTCTTT GAAACAACACCTTACATTCCAAAGGCCAACAACTTTAAG ATTGCCAACGACTCAAATTATTTATAGGAGATTGATTCA TATACTTAACCCAATATGAGAGGAAATATTTCTAATTAT ATCCAAACATCTTTAATATGAGGGGAATTAGGCTTGGAG ACCTTCAATGCCAAAAACATGTTTTGCCAAATATGTTTT AAGAAAGAGGAGGAGGTTACGTGTTTTCCATATTTGAGC CTATAAAAGTACCCTTGGAATGAGTATGACTTGTCTCTC CTCATAAAGCTTCAAGGTAAGTGTGTGTGAGGACAGGGC TCTGTCTGGAGGACGGTAAGGGATGTCTGGCTGCCCGCG TGCATGCCACACATCCTGGCTCCCACTGTCCCTGGCAGC CCTGCCAGTGAAGCACCAGCTTACTCCGTAGCAATTTTA ATTAGATGTTGTAGTCTTCCCAGTCATT |

Table 4 below depicts the core nucleotide sequence of the different nucleic acid regulatory elements for enhancing gene expression in diaphragm, heart and skeletal muscle cells or tissue and their corresponding genes and lengths.

TABLE 4

| | The CREs sequence for highly expression in diaphragm, skeletal muscle, and heart. | | |
|---|---|---|---|
| SEQ ID NO. | Dph-CRE Gene (CRE) | Size (bp) | Sequence |
| 1 | ACTA1Dph-CRE01 | 328 | GGAGACACTCCATATACGGCCCGGCCCGCGTTACCTGG GACCGGGCCAACCCGCTCCTTCTTTGGTCAACGCAGGG GACCCGGGCGGGGGCCCAGGCCGCGAACCGGCCGAGGG AGGGGGCTCTAGTGCCCAACACCCAAATATGGCTCGAG AAGGGCAGCGACATTCCTGCGGGGTGGCGCGGAGGGAA TGCCCGCGGGCTATATAAAACCTGAGCAGAGGGACAAG CGGCCACCGCAGCGGACAGCGCCAAGTGAAGCCTCGCT TCCCCTCCGCGGCGACCAGGGCCCGAGCCGAGAGTAGC AGTTGTAGCTACCCGCCCAGGTAG |
| 2 | ACTA1Dph-CRE02 | 452 | GACAGGTGCGGTTCCCGGAGCGCAGGCGCACACATGCA CCCACCGGCGAACGCGGTGACCCTCGCCCCACCCCATC CCCTCCGGCGGGCAACTGGGTCGGGTCAGGAGGGGCAA ACCCGCTAGGGAGACACTCCATATACGGCCCGGCCCGC GTTACCTGGGACCGGGCCAACCCGCTCCTTCTTTGGTC AACGCAGGGGACCCGGGCGGGGGCCCAGGCCGCGAACC GGCCGAGGGAGGGGGCTCTAGTGCCCAACACCCAAATA TGGCTCGAGAAGGGCAGCGACATTCCTGCGGGGTGGCG CGGAGGGAATGCCCGCGGGCTATATAAAACCTGAGCAG AGGGACAAGCGGCCACCGCAGCGGACAGCGCCAAGTGA AGCCTCGCTTCCCCTCCGCGGCGACCAGGGCCCGAGCC GAGAGTAGCAGTTGTAGCTACCCGCCCAGGTAGG |
| 3 | ACTA1Dph-CRE03 | 239 | AGAGAGAGGGACAGGCACCAACTGGGTAACCTCTGCTG ACCCCCACTCTACTTTACCATAAGTAGCTCCAAATCCT TCTAGAAAATCTGAAAGGCATAGCCCCATATATCAGTG ATATAAATAGAACCTGCAGCAGGCTCTGGTAAATGATG ACTACAAGGTGGACTGGGAGGCAGCCCGGCCTTGGCAG GCATCATCCTCTAAATATAAAGATGAGTTTGTTCAGCC TTTGCAGAAGG |
| 4 | ACTA1Dph-CRE04 | 509 | CCTTTTAGAGAATCCACACCTGTCCCAGTTGCTGGGTT CCACTACCAAAAGTGAATTGCAACTATTTTAGGAGCAC TTAAGCACATCCGAAAAATGAGTGATTCTGTTCTGGCC CACACCACATCACTGATGTACCCCCTTAAAGCATGTCC CTGAGTTCATCACAGAAGACTGCTCCTCCTGTGCCCTC CACAAGGTTAGAACTGTCCTTGTCTTAGGGAAAAAGGA GAGAGAGAGAGAGAGAGAGAGAGAGAGAGAGAGAGAGA GAGAGAGAGAGGGACAGGCACCAACTGGGTAACCTCTG CTGACCCCCACTCTACTTTACCATAAGTAGCTCCAAAT CCTTCTAGAAAATCTGAAAGGCATAGCCCCATATATCA GTGATATAAATAGAACCTGCAGCAGGCTCTGGTAAATG ATGACTACAAGGTGGACTGGGAGGCAGCCCGGCCTTGG CAGGCATCATCCTCTAAATATAAAGATGAGTTTGTTCA GCCTTTGCAGAAGGA |
| 5 | ACTA1Dph-CRE05 | 169 | CCTTTTAGAGAATCCACACCTGTCCCAGTTGCTGGGTT CCACTACCAAAAGT1AATTGCAACTATTTTAGGAGCAC TTAAGCACATCCGAAAAATGAGTGATTCTGTTCTGGCC CACACCACATCACTGATGTACCCCCTTAAAGCATGTCC CTGAGTTCATCACAGAA |
| 6 | CKM Dph-CRE06 | 400 | GGGCCAGGGGACGGTGGCTTCTACGTGCTTGGGACGTT CCCAGCCACCGTCCCATGTTCCCGGCGGGGGGCCAGCT GTCCCCACCGCCAGCCCAACTCAGCACTTGGTCAGGGT ATCAGCTTGGTGGGGGGGCGTGAGCCCAGCCCCTGGGG CGGCTCAGCCCATACAAGGCCATGGGGCTGGGCGCAAA GCATGCCTGGGTTCAGGGTGGGTATGGTGCGGGAGCAG GGAGGTGAGAGGCTCAGCTGCCCTCCAGAACTCCTCCC TGGGGACAACCCCTCCCAGCCAATAGCACAGCCTAGGT CCCCCTATATAAGGCCACGGCTGCTGGCCCTTCCTTTG GGTCAGTGTCACCTCCAGGATACAGACAGCCCCCCTTC AGCCCAGCCCAGCCAGGTAC |
| 7 | CKM Dph-CRE07 | 255 | CCCAGCCCCCTTCCCCGGGAGGTGGGAGCGGCCACCCA GGGCCCCGTGGCTGCCCTTGTAAGGAGGCGAGGCCCGA GGACACCCGAGACGCCCGGTTATAATTAACCAGGACAC GTGGCGAACCCCCCTCCAACACCTGCCCCCGAACCCCC CCATACCCAGCGCCTCGGGTCTCGGCCTTTGCGGCAGA GGAGACAGCAAAGCGCCCTCTAAAAATAACTCCTTTCC CGGCGACCGAGACCCTCCCTGTCCCCC |

TABLE 4-continued

| | | | The CREs sequence for highly expression in diaphragm, skeletal muscle, and heart. |
|---|---|---|---|
| SEQ ID NO. | Gene | Dph-CRE (CRE) | Size (bp) Sequence |
| 8 | MYL2 | Dph-CRE08 | 354 CTCCTGGGCTCGAGCAATTCTCCTGCCTTGACCTCCCA AAGTGCTGGGATTACAGGCATGAGCCACTACACCCTGC CCTAGTGTGCTTTATATCAAAGGGGA/vACCATTTGGGG CTTCCAAACAGGAAATGAACAGTCGTACCTTTTGTCCT CACTAACATTCAGATTGCAGGAATGCCGTGTCCCATAG GGAAAGAGAAATTCCTGAGGCAAGTGTOYTATCTGAAC TTGAGATAGTCACCTTCCAGGCAGAAAGCTACACCCGC CTCTTTTCCCAGCCTCTGGCATCAGCTGCCGGCGGTGT GGGTAAGGGATGCAAAGAACTCAAAACATGTAGCCAGG ATTCCCCATTTG |
| 9 | MYL2 | Dph-CRE09 | 297 TGACAAGCACAAGTGTCCCCGGCCCAAGCACCGCAGAG AGCGCGCAGCATCTCTCCCCGTGACCATGACCCAGCTA CTGCCTCTTTAACCTTGAATGCCTTTTTGGGGGCTCAC GTGTCACCCAGTGGCGAGTGAGCCACCCTTACTTCAGA AGAACGGCATGGGGTGGGGGGGCCTTAGGTGGTGCCCG CCTCACCTATGACTGCCAAAAGCGGTCATGGGGTTATT TTTAAACATGGGGAGGAAGTATTTATTGTTCCTGGGCT GCAGAGAGCTGGGCGGAGTGTGGAATTCTTC |
| 66 | MB | Dph-CRE66 | 319 CCAGGTGACAGGTGGATGGTGGAGCTGGAGGAGCCACT CGGAGCCTCCAAGGCTGGGGAGGGTGGAGGGGGGAGGC AGGTCGGTGTCCCAGGCCACACCTGTTGACTAAGGGAT TAGGATGTTGTGTCCCTGCCAGCCCTCCTCCAATAAGC CCCTCTGGGCCTGCAGGGAGAGGAGGAGCCTTGCCATG TAAACTGTATTTTTAGTTCCCTGTGCCTCTCCCCGGCT GCTATAAGACACCTCTCCCCACCCCCAGCCCTGGCCGC TTGGCTGGAGGCTCTGCGAGGACAGCTGGGGAGAAGGG GAGCTGTGGTCAGTA |
| 67 | MB | Uph-CRE67 | 372 TCATCTTCTAATAATTTGGCAAGCCATCCATGGTCTTC TAAGCAAGGCGCCATGAATATAACGAATATAGAGACAG AAAAAGACCCCTCCCCACTGGCTGGGTTGAGGGACTGG AGAGCCCAGATGGAAGGGCAGAGGTGCAGGCTTTTTTC CTTGTTGCCACTAGATGGCAGTAGGGCACCCGTTGTCA GCCCTGGGGCAAGGTCACCGACTGTCTTTGCCTTTGCC TCCAGCAAGCCAAAACCCTGGGCAGACTCAATCCAAAA ATAAACAATCAAAGAGCATGTTGGCCTGGTCCTTTGCT AGGTACTGTAGAGCAGGTGAGAGAGTGAGGGGGAAGGA CTCCAAATTAGACCAGTTCTTAGCCATGAA |
| 68 | MB | Dph-CRE68 | 293 AGAAAGGAGCTGCCCTGGGGATGGCTGTGTATCCCTAC AACTGCCAGGCACATGCCCCTTGAACACCCGATGCTAC GTGTCCCAAAGGAAACTGGTCTCCACCCACCCCCGGCC CGTCCTCGTCCTGGGTACCCCACCTTAGTAAATGGCGC CACCATCTGCCCGGTCACTCAGCGAGAAACTCAACTCC TGGCAGCAGATGACGGGCACTCTGGTTAAATGACTCTC TCCAGCCTCCAAGTTCAACCTGCAGGGAAGCCCTGGAA ATCCTGTCTCCCTCTGCCCTGCCTCTC |
| 69 | DES | Dph-CRE69 | 482 GAAACATGGCTTCCACAGGTTCCAGTTGAAGAATCCCA GTTCCGTCTATAAATTCCAGGGAAGGTCTCTGATTGGC CCTGCTCATTCCCAGGCCCATTCCTTGACCCAGTCACT GAAGTCAGGGAGATGCAGTAATAAGACTGGCTGGAATC AGGGTCTTTAGGGGTGGAGGGATGGGGAGGGAGGCACAG CATGTCATCAAAATAAGGAAATTGCAAAAGAAAGCTTG CAGGCTACTTTGAATGACAATGAGAAAGACGGTGCTGC CTGAGTGTGTTAAGGATCCACATGGTCTCCAAAATCCT CCAGGAGCATACAGTCTAGTCTGGGAGATGAGACACAA AAATAACCAGAACACAACAGCTTGCACTGACTCGAGGG CTGGATAAGAATATCTGGAACTCCCCCATCTATTTCAG AAGCTTGTCTCTTGGATGAAAATTAGACACTTAATGGG AAAGGGCTTTGAAAAGAGTGCAGTAA |
| 70 | DES | Dph-CRE70 | 398 CCTCAGGTACCCCCTGCCCCCCACAGCTCCTCTCCTGT GCCTTGTTTCCCAGCGATGCGTTCTCCTCTATAAATAC CCGCTCTGGTATTTGGGGTTGGCAGCTGTTGCTGCCAG GGAGATGGTTGGGTTGACATGCGGCTCCTGACAAAACA CAAACCCCTGGTGTGTGTGGGCGTGGGTGGTGTGAGTA GGGGGATGAATCAGGGAGGGGGCGGGGGACCCAGGGGG CAGGAGCCACACAAAGTCTGTGCGGGGGGTGGGAGCGCA CATAGCAATTGGAAACTGAAAGCTTATCAGACCCTTTC TGGAAATCAGCCCACTGTTTATAAACTTGAGGCCCCAC |

TABLE 4-continued

The CREs sequence for highly expression in diaphragm,
skeletal muscle, and heart.

| SEQ ID NO. | Gene | Dph-CRE (CRE) | Size (bp) | Sequence |
|---|---|---|---|---|
| | | | | CCTCGACAGTACCGGGGAGGAAGAGGGCCTGCACTAGT CCAGAGGGAAACTGAGGC |
| 71 | DES | Dph-CRE71 | 241 | CAGGGGCGCAGGCCTCTTGCGGGGGAGCTGGCCTCCCC GCCCCCACGGCCACGGGCCGCCCTTTCCTGGCAGGACA GCGGGATCTTGCAGCTGTCAGGGGAGGGGAGGCGGGGG CTGATGTCAGGAGGGATACAAATAGTGCCGACGGCTGG GGGCCCTGTCTCCCCTCGCCGCATCCACTCTCCGGCCG GCCGCCTGCCCGCCGCCTCCTCCGTGCGCCCGCCAGCC TCGCCCGCGCCGT |
| 72 | TNNC1 | Dph-CRE72 | 238 | CCCCCAGGCAGCGGCACGGTGGACTTTGATGAGTTCCT GGTCATGATGGTTCGGTGCATGAAGGACGACAGCAAAG GGAAATCTGAGGAGGAGCTGTCTGACCTCTTCCGCATG TTTGACAAGTGAGCACGTGACCCTTGACCTCTGACCCT GACCCACACTCAAGCCGAGCTGTACAGGAGGGCAGTCT CAGATTCCAGGCCTAGGGACCCTGTGGCCTCTGCCTGA TAGGGGAGAG |
| 73 | TNNC1 | Dph-CRE73 | 465 | AGCCAGCTCTGGGGGCACGCCTGCTTATCCTGTGGGAG TCCATGGAGCCGGGGTTGGGACAGCCCTCCACCCAGTG CCCATACAAGGCCTGGCGGAGTTGGGGACTAATTTTGG CTTCTGAGGCGGCACTAGCAGGCCAGGGGGCCAGATAA CGCTGCCCCACCCCCTGCATGCCAAAGTCCCCAGAACA ATCACCAGGTTTAACTTTGTTCCTCGTTAAAAATAGCC CAGTGGCCACCCTGGTCAGGTTACCGTGGGTGGCTTGC CTGCCTCCACACTGGTTTTATTATCCCAACTTGAGGGA CAGCTGTCCTTCGGGCCCACCCAGCTTGAGTTTCATCAG GGGCCGAAAGGGCATTGAGTGGTCACTGACTATTGTTA CTGAGGGTCACCTTGGTCCTGAAGGGGGTGCCCACCTG TCACCCTGGCCCTGAGCCCAGTCGCAGTGAGGCCAGCT GGGTCACGT |
| 74 | TNNC1 | Dph-CRE74 | 285 | TTTTCATTCATTCCAGAAACCTTTTCAGAGAGTCCCTT TGGGGAGTGTGGGGGACAGGAGGGAAAGAAACCTGGTC CTTGTAGCCGTTCGTCTGCTCCCTGCCCTGGGCAGAGG ACGTGGGGACTCAGGCCAGCCTGAGATCACTGGGACCA GAGGAGGGGCTGGAGGATACTACACGCAGGGGTGGGCT GGGCTGGGCTGGGCTGGGCCAGGAATGCAGCGGGGCAG GGCTATTTAAGTCAAGGGCCGGCTGGCAACCCCAGCAA GCTGTCCTGTGAGCCGCCA |
| 75 | TCAP | Dph-CRE75 | 332 | TGCTCTGTTTACAGACAAGCTGCTGTCCTCCCTGCAAA GGGGAGTGGGTGGGGCAGAGGGCAAGTGCCAGGGGGGC ACAAGGCTGGGCATGTGGCTGGCATGAGACGGTGTCTG AGTAATGTCAGGCACCTGGAGGCATTGACCCCAGGACC TTGGACCCCAGACCTCTGACCGGGGGGGCAGCCAGCGTC CAGGTACCCCAACCCCTGCCCTGGGTCCGGCGTCCCCC CATTAGTGAGTCTTGGCTCTACTTATAGCATCTGACAC CAGAGGGGCCGAAAATAGCCCCTGGAGAAGGGGGAGGA GGGGGCTATTTAAAGGGCCTGGGAGGGG |
| 76 | MYH7 | Dph-CRE76 | 381 | GCCTGTGGTCTTGGTGGTCGTGGTCAGTTCCCTCTCCT GCCAGCTGTGGAATGTGAGGCCTGGCCTGGGAGATATT TTTGCTGCACTTTGAGCCACCCCGCCCCCTGGAACTCA GACCCTGCACAGTCCATGCCATAACAATGACGACCACT TCCAATTGTTTCCTAGCTGGAGAGGCGGGGAGGGGAGC ACTGTTTGGGAAGGGGGGGAGCCTGGGGGAAATGCTTC TAGTGACAACAGCCCTTTCTAAATCCGGCTAGGGACTG GGTGCCGTTGGGGGTGGGGGTGCCCTGCTGCCCCATAT ATACAGCCCCTGAGACCAGGTCTGGCTCCACAGCTCTG TCCTGCTCTGTGTCTTTCCCTGCTGCTCTCAGGTAGGA G |
| 77 | MYH7 | Dph-CRE77 | 316 | GGAATACCCTACCTTAAAAACAAAACAAACCGTGCTAC TTGGCCCTCTTCCCTTGAGTTGTTGTCTAATCTCATTC ATTTCACTGCCAAACTCCTCAAATGCATGGTGTACACC CACTGCTTCCACTTCCTGTCCACTCATCTTTTTCCTCA TTAACTCCCTGTGGCCTGGCTTTGCCTGTGACACTACA CAAGCTGCTTGCTCCAAGATAATCCAAGTTCTTTTCTC TGTCTTCCTGATACACAGGCTTTCTTTGGCATCTGACA CTGCTGGCCACCTGCTCTTCTTGAAATGCTTCTTTTGG CTTCTAGGAAAC |

TABLE 4-continued

| SEQ ID NO. | Dph-CRE Gene (CRE) | Size (bp) | Sequence |
|---|---|---|---|

The CREs sequence for highly expression in diaphragm,
skeletal muscle, and heart.

| SEQ ID NO. | Dph-CRE Gene (CRE) | Size (bp) | Sequence |
|---|---|---|---|
| 78 | ALDOADph-CRE78 | 401 | CCAAGTGGTGGGTGTAGCCTGGGGGTTCAATCCTCCTG<br>TGGCGCCCCAGAACCCGGTGCCTCCTCCAACGTCCGGC<br>ATCTGATGAGGATCCGACCCAGGCGGGCGGCGGCGGGA<br>TTCGCTCTTCCCCTTCGCTCCCCGCGAGAAAGCCCCGA<br>GGGCCGCGGCGGCGCAGAGCCGGTGACAGTTGAAGCTT<br>AGGCGGGAAGAGGGAGGCGCGAGGCGGGAAGAGGGAGT<br>TTGGGCCTCGGCAGCCGCCGTACAAACACCGCTCTGGT<br>CACCATGGCAACAGCGGGATGCCGCGAACGGCTTCTGG<br>GCGGGGCCGGTCCCTCGGACGATTGGACCTAGCTTGGC<br>GCGGAATCCGTGAATTGCCCGCGGCCCGAGGGTGCAGG<br>TGATGGGTGCTGACCGACTGG |
| 79 | ALDOADph-CRE79 | 281 | GACTACAACCTGCCAGCTCAGGACGAGAGCTGTCAGGA<br>AGAGTCCAGGAATGGACTTCCCACGGGAGGGCACATTT<br>CTGGTATTCCTGGCAAGATAAGGAGTTGACTAAGTAAT<br>CCACGAGAAAAGGCATTTCCGGCAGAGGAAACAGTCTG<br>GGGGTGAGAGGGAGGCTGCAGCATTTGGGGAACTGCTA<br>GGGCTATCGTGTGTTTGGAAGAGGGGGAGGGAGAGAGG<br>TAGGCAGGGCTAAATTGGGAATTTTGTCACTGACATAA<br>ATTTTAAGTGCCAGG |
| 80 | ALDOADph-CRE80 | 393 | CGTTTTGTGGTACCAGGGGGTCCCTCCTCTCCTGTCCC<br>CAGCCAAACCTTTTCCTTTCCCCTCGGGAAAGCTGCCT<br>TGGCTGTCACTACCTGCTGCCTATTCCACATCCTGAAC<br>CCTGTGACCTAGGCCCAGGGCTGCTGCGCGGACGGTAG<br>CTCCCCCTGCAGGAAGCAAGGTTCCTCCGGGCCCCCAG<br>ACTGCTGCTGGACCTGTGCAGAAGCCTGCAACTTTCCT<br>CTGCCTAGCCCGGCCCACTTCCTGGATGCTTGCTGCCC<br>CCAGCCCACCAGAGCTGTGAGTTCCATTCCTACCCCCT<br>GCCCCACTGAGCCCTGATCTAGGTATGATCGGTGCATT<br>CATTTTTTTGCTCAACAACATTTATTACTGAGCACCTT<br>CTCAAGGCCAGGC |
| 81 | ALDOADph-CRE81 | 169 | CCTAGGCCCAGGGCTGCTGCGCGGACGGTAGCTCCCCC<br>TGCAGGAAGCAAGGTTCCTCCGGGCCCCCAGACTGCTG<br>CTGGACCTGTGCAGAAGCCTGCAACTTTCCTCTGCCTA<br>GCCCGGCCCACTTCCTGGATGCTTGCTGCCCCCAGCCC<br>ACCAGAGCTGTGAGTTC |
| 84 | TPM1 Dph-CRE84 | 460 | TAAAGACCTTTCTCAGAGATCCAAACCAGCCCCACCCC<br>CCGCCCCCAGGAAGCATAGCATATTTTCTGTGAGGCCT<br>TGATGGTAGCATCACAAACCCTTGGGAAACACAACTCC<br>CAGTGTTTGAGGAGAGCATGCCGTATCTTGTTCCAGGG<br>ACACTGAGTCGTGAGCATAAAACGCTGCATTCCAAAAG<br>AGACGAAGAAGCAGTCGTCTCTCCATTTAATTATAGAT<br>TCTTCACTTTCCCTTAATTGCTTCAGTCAGCACTGTTG<br>ACTCTGGGGGAGTCACAGTACACCGGCAGGGCTATTGC<br>TGTTAAACAAGGGGTGACTATCAGGTAATGAGGTTTTC<br>ATTTTGTTTTTTCAAACAAACAAACCCTGATGTACATA<br>TTCAAGTGGGCATTCCTGTTAAAGGTGTCACATTGGGA<br>AATGATGCTCATGTTGACTCTCCTTTGTAACCAAATAT<br>TGAT |
| 85 | TPM1 Dph-CRE85 | 292 | TAGGAAGGAACAAGAAGAGGTAGAAATGAAATGGCTCC<br>CAAAAGAAAAACCTCCCTTGGGTGGTATTTTAGGACAT<br>TAGCTCAGGCTGCCTTGTCCTCAGTCATCTCAGTGGCA<br>TTTAAGTAGCCCCTTGGGTTACAGATCACGGCAGGTGC<br>TGGGAAGTGAAGAAGGCCATGCTAAAAATACTGGCCTC<br>TTCTGGAACTCTGCCGGCAGCCCTGATGGAGCTCCCTC<br>CTCAAGCAGCAGTACCTCAGCAAAAGAACAGTTTCCTC<br>CGCCTTAAGCAGTAAGAAAAGTCTGG |
| 86 | TPM1 Dph-CRE86 | 472 | AAGAAAGGGTCTTTACAAAACCAAAAGAAAGCCCATTG<br>CTTACTTTTAATAACCTAGGCCCACCCATAGGCCTCTA<br>AATCAAATAACCTCCACTGAGAATTAAGCTGTTAGCAC<br>TAGGTCTGGCATAGGTGCAGAAACAAAAGTTTAGAAAT<br>CCTAATCTTGAATTTACCTAACACGGCTGCCTCCTAGA<br>GCCTGAGTGGGTTGTAGCGAGACCTCAAGTAGAGGAGA<br>GGCACCTGGGCCATCCGCCTCCATGGGCTTTTTTTTTT<br>TTGCATCGAATTTCATGGTCTGCAAAGTAAGGGTGGGG<br>CTTTACTTGCCATTCAGGAGGTTGCAAAGGTCACCTCC |

TABLE 4-continued

The CREs sequence for highly expression in diaphragm,
skeletal muscle, and heart.

| SEQ ID NO. | Dph-CRE Gene (CRE) | Size (bp) | Sequence |
|---|---|---|---|
| | | | ACATATGTTCCTGTTAAGGACATCAGCAGAAACTTGAG AAGCAAGTATAAAAATATAAAAATGAGCAGGTGGCATT CAATAGGAAAAGAATGCAGGGTTTGCTGGGAAGTCATG ATTGAAACCAGTCCAA |
| 87 | TFM1 Dph-CRE87 | 476 | AAGGAAGTGACCAGGCCAGGTCTGGATCCCTGGAACTG ACTCCTAACTCCCTATTCTTGCCTCCTCTGCTGAGCTC CAACCTGGGGAGTCAGCTCCCTGGAGTCCACGCATCTG GATATCGTCCACATGCCTGGAACTTTGTCACTGTTCCG GTGGCTGGGTTGACACACCGTGATTAAAGGGCTCTGGT CAATTTCTGTGCCACGCAGCCCCTATGCTAATGGTCAG ATCTAATGTTCTGACCATTAGGTCAGTGTATCTTTTCC CTCCTGGGCAGTTAGGTTAGTGGAAGAAACCCGATAAA ATCTTGGAGAGGAATTTGATCATTCTCTGAAGGACTTA CAAGTTGTTTGGCCTGCCTAATCTGCTCAGATACCGTC CGGGGAATATTTGGTAACCATGCAGTACAGACTGTGAA TTATTCTGTGGGGACTATTAACAAGACCCTCACCAACC CTGCCTCAGCTGATCTCAGG |
| 88 | TPM1 Dph-CRE88 | 459 | ACAGACCAAATTGCCTGAGTCTAAACTCAATGTTCTTT CCCCTTAGACTGCCACCCGCACACACACGCACACATGC ACACCTTTTTGGAGGCACTGCACAGCAAGCACAGAAGT ACGCCACTGAGTCCTGTGTCCCTAAAGTATTTGACTGT CCCTCCGCTGGGGGAAAGGGCAGGCAGAAAACAAGACT CCGTGTGCTGTCGCTGTGCCGCCCCCTGCCTCTCTGAC CCGCGCCCGCAGAGAAAGTCTCAAGAGCCGCCCCAGGC TTTCTCCCACGTTCTCCCTTTCTCTGCTGCAGTTGAGT TTCCAGAGCGTGAGCGCGCAGGATGACACCTGGCTGGC TGAGAGCTGCCGGGGAGGCGCTGGCGGGTGCCGAGAGC GCACTGACCCTGACGCGGGGTGCAGCACGGCTGGGAAG CCCCCGGGCCTTTGGCTAAGCGCGCCGGGGGACGGCAC AGG |
| 89 | TPM1 Dph-CRE89 | 378 | GCCCCAACGCCCTCTCCCTGGCGCGCAGGTTTAGAAAC AGGGCGGCCTCTCCGGCCGCCGCCTCGGCGGCTCGGGT CCCCATATATAGTCATATCCACCGTCAACTGGGAGGCC GGCGGCCGGCAGCGAATGGGCGAGCGGCCCCCGCGGGA GGAGCGGGGAGGGGGCACGGGGCGGAGGGAGGAGAGGA GGAAGGGGGGCAGGAGAAAAAAGCTTTTCCAAAAAAGT ATTGGCTGTCTTGAGGAATGCGGTCGCCCCCTTGGGAA AGTACATATCTGGGAGAAGCAGGCGGCTCCGCGCTCGC ACTCCCGCTCCTCCGCCCGACCGCGCGCTCGCCCCGCC GCTCCTGCTGCAGCCCCAGGGCCCCTCGCCGCCGCC |

A 'nucleic acid regulatory element' or 'regulatory element', also called "CRE" (cis-regulatory element), "CRM" (cis-regulatory module), or "SH" as used herein refers to a transcriptional control element, in particular a non-coding cis-acting transcriptional control element, capable of regulating and/or controlling transcription of a gene, in particular tissue-specific transcription of a gene. Regulatory elements comprise at least one transcription factor binding site (TFBS), more in particular at least one binding site for a tissue-specific transcription factor, most particularly at least one binding site for a muscle-specific transcription factor. Typically, regulatory elements as used herein increase or enhance promoter-driven gene expression when compared to the transcription of the gene from the promoter alone, without the regulatory elements. Thus, regulatory elements particularly comprise enhancer sequences, although it is to be understood that the regulatory elements enhancing transcription are not limited to typical far upstream enhancer sequences, but may occur at any distance of the gene they regulate. Indeed, it is known in the art that sequences regulating transcription may be situated either upstream (e.g. in the promoter region) or downstream (e.g. in the 3'UTR) of the gene they regulate in vivo, and may be located in the immediate vicinity of the gene or further away. Of note, although regulatory elements as disclosed herein typically comprise naturally occurring sequences, combinations of (parts of) such regulatory elements or several copies of a regulatory element, i.e. regulatory elements comprising non-naturally occurring sequences, are themselves also envisaged as regulatory element. Regulatory elements as used herein may comprise part of a larger sequence involved in transcriptional control, e.g. part of a promoter sequence. However, regulatory elements alone are typically not sufficient to initiate transcription, but require a promoter to this end. The regulatory elements disclosed herein are provided as nucleic acid molecules, i.e. isolated nucleic acids, or isolated nucleic acid molecules. Said nucleic acid regulatory elements hence have a sequence which is only a small part of the naturally occurring genomic sequence and hence is not naturally occurring as such, but is isolated therefrom.

The term "nucleic acid" as used herein typically refers to an oligomer or polymer (preferably a linear polymer) of any length composed essentially of nucleotides. A nucleotide unit commonly includes a heterocyclic base, a sugar group, and at least one, e.g. one, two, or three, phosphate groups, including modified or substituted phosphate groups. Heterocyclic bases may include inter alia purine and pyrimidine bases such as adenine (A), guanine (G), cytosine (C), thymine (T) and uracil (U) which are widespread in naturally-occurring nucleic acids, other naturally-occurring bases (e.g., xanthine, inosine, hypoxanthine) as well as chemically or biochemically modified (e.g., methylated), non-natural or derivatised bases. Sugar groups may include inter alia pentose (pentofuranose) groups such as preferably ribose and/or 2-deoxyribose common in naturally-occurring nucleic acids, or arabinose, 2-deoxyarabinose, threose or hexose sugar groups, as well as modified or substituted sugar groups. Nucleic acids as intended herein may include naturally occurring nucleotides, modified nucleotides or mixtures thereof. A modified nucleotide may include a modified heterocyclic base, a modified sugar moiety, a modified phosphate group or a combination thereof. Modifications of phosphate groups or sugars may be introduced to improve stability, resistance to enzymatic degradation, or some other useful property. The term "nucleic acid" further preferably encompasses DNA, RNA and DNA/RNA hybrid molecules, specifically including hnRNA, pre-mRNA, mRNA, cDNA, genomic DNA, amplification products, oligonucleotides, and synthetic (e.g., chemically synthesised) DNA, RNA or DNA/RNA hybrids. A nucleic acid can be naturally occurring, e.g., present in or isolated from nature; or can be non-naturally occurring, e.g., recombinant, i.e., produced by recombinant DNA technology, and/or partly or entirely, chemically or biochemically synthesised. A "nucleic acid" can be double-stranded, partly double stranded, or single-stranded. Where single-stranded, the nucleic acid can be the sense strand or the antisense strand. In addition, nucleic acid can be circular or linear.

As used herein "transcription factor binding site", "transcription factor binding sequence" or "TFBS" refers to a sequence of a nucleic acid region to which transcription factors bind. Non-limiting examples of TFBS include binding sites for transcription factor 3, also known as TCF3 or E2A; binding sites for nuclear factor I, also known as NF1; binding sites for CCAAT-enhancer-binding protein, also known as C/EBP; binding sites for myogenic differentiation, also known as MyoD; binding sites for sterol regulatory element-binding protein, also known as SREBP; binding sites for leukemia/lymphoma-related factor, also known as LRF; binding sites for protein 53, also known as p53; binding sites for hepatocyte nuclear factor 3-alpha, also known as HNF3a; binding sites for hepatocyte nuclear factor 3-beta, also known as HNF3b; binding sites for hepatocyte nuclear factor 4, also known as HNF4; binding sites for myocyte-specific enhancer factor 2A, also known as MEF2A or RSRFC4; binding sites for peroxisome proliferator-activated receptor, also known as PPAR; binding sites for serum response factor, also known as SRF; binding sites for transcription activator-like protein 1b, also known as Tal1_b. Transcription factor binding sites may be found in databases such as Transfac®.

Sequences disclosed herein may be part of sequences of regulatory elements capable of controlling transcription of diaphragm-, and skeletal muscles-specific genes in vivo. Particular examples for diaphragm and skeletal muscle specific regulatory elements may in particular be controlling the following genes (cf. Table 2): ACTA1, CKM, TPM2, MYL1, TNNC2, FHL1, TNNT1, TNNI2, MYLPF, TNNT3, MYH2, SLN, MYBPC1, ENO3, CA3, ATP2A1, or MYH1.

Accordingly, in embodiments, the nucleic acid regulatory elements disclosed herein comprise a sequence from ACTA1 regulatory elements, i.e. regulatory elements that control expression of the ACTA1 gene (Alpha-actin-1 gene) in vivo, e.g. regulatory elements comprising any one or more of SEQ ID NOs: 1 to 5, or functional fragments thereof. In other embodiments, the nucleic acid regulatory elements disclosed herein comprise a sequence from CKM regulatory elements, i.e. regulatory elements that control expression of the CKM gene (Muscle Creatine Kinase gene) in vivo, e.g. regulatory elements comprising any one or more of SEQ ID NOs: 6 or 7, or functional fragments thereof. In other embodiments, the nucleic acid regulatory elements disclosed herein comprise a sequence from MYL2 regulatory elements, i.e. regulatory elements that control expression of the MYL2 (Myosin, Light Chain 2 gene) gene in vivo, e.g. regulatory elements comprising any one or more of SEQ ID NOs: 8 or 9, or functional fragments thereof. In other embodiments, the nucleic acid regulatory elements disclosed herein comprise a sequence from TPM2 regulatory elements, i.e. regulatory elements that control expression of the TPM2 gene (Tropomyosin 2 gene) in vivo, e.g. regulatory elements comprising any one or more of SEQ ID NOs: 10 to 12, or functional fragments thereof. In other embodiments, the nucleic acid regulatory elements disclosed herein comprise a sequence from MYL1 regulatory elements, i.e. regulatory elements that control expression of the MYL1 gene (gene) in vivo, e.g. regulatory elements comprising any one or more of SEQ ID NOs: 13 to 17, or functional fragments thereof. In other embodiments, the nucleic acid regulatory elements disclosed herein comprise a sequence from TNNC2 regulatory elements, i.e. regulatory elements that control expression of the TNNC2 gene (Troponin T2, Cardiac Type gene) in vivo, e.g. regulatory elements comprising any one or more of SEQ ID NOs: 18 or 19, or functional fragments thereof. In other embodiments, the nucleic acid regulatory elements disclosed herein comprise a sequence from FHL1 regulatory elements, i.e. regulatory elements that control expression of the FHL1 gene (Four And A Half LIM Domains 1 gene) in vivo, e.g. regulatory elements comprising any one or more of SEQ ID NOs: 20 to 26, or functional fragments thereof. In other embodiments, the nucleic acid regulatory elements disclosed herein comprise a sequence from TNNT1 regulatory elements, i.e. regulatory elements that control expression of the TNNT1 gene (Troponin T Type 1 gene) in vivo, e.g. regulatory elements comprising any one or more of SEQ ID NOs: 27 or 28, or functional fragments thereof. In other embodiments, the nucleic acid regulatory elements disclosed herein comprise a sequence from TNNI2 regulatory elements, i.e. regulatory elements that control expression of the TNNI2 gene (Troponin I Type 2 gene) in vivo, e.g. regulatory elements comprising any one or more of SEQ ID NOs: 29 to 31, or functional fragments thereof. In other embodiments, the nucleic acid regulatory elements disclosed herein comprise a sequence from MYLPF regulatory elements, i.e. regulatory elements that control expression of the MYLPF gene (Myosin Light Chain, Phosphorylatable, Fast Skeletal Muscle gene) in vivo, e.g. regulatory elements comprising SEQ ID NO: 32, or functional fragments thereof. In other embodiments, the nucleic acid regulatory elements disclosed herein comprise a sequence from TNNT3 regulatory elements, i.e. regulatory elements that control expression of the TNNT3 gene (Troponin T Type 3 gene) in vivo, e.g. regulatory elements comprising any one or more of SEQ ID NOs: 33 to 38, or functional fragments thereof. In other embodiments, the nucleic acid regulatory elements disclosed herein comprise a sequence from MYH2 regulatory elements, i.e. regulatory elements that control expression of the MYH2 gene (Myosin, Heavy Chain 2 gene) in vivo, e.g. regulatory elements comprising any one or more of SEQ ID NOs: 82 or 83, or functional fragments thereof. In other embodiments, the nucleic acid regulatory elements disclosed herein comprise a sequence from SLN regulatory elements, i.e. regulatory elements that control expression of the SLN gene (Sarcolipin gene) in vivo, e.g. regulatory elements comprising any one or more of SEQ ID NOs: 39 to 42, or functional fragments thereof. In other embodiments, the nucleic acid regulatory elements disclosed herein comprise a sequence from MYBPC1 regulatory elements, i.e. regulatory elements that control expression of the MYBPC1 gene (Myosin Binding Protein C, Slow Type gene) in vivo, e.g. regulatory elements comprising any one or more of SEQ ID NOs: 43 to 50, or functional fragments thereof. In other embodiments, the nucleic acid regulatory elements disclosed herein comprise a sequence from ENO3 regulatory elements, i.e. regulatory elements that control expression of the ENO3 gene (Enolase 3 gene) in vivo, e.g. regulatory elements comprising any one or more of SEQ ID NOs: 51 to 54, or functional fragments thereof. In other embodiments, the nucleic acid regulatory elements disclosed herein comprise a sequence from CA3 regulatory elements, i.e. regulatory elements that control expression of the CA3 gene (Carbonic Anhydrase III gene) in vivo, e.g. regulatory elements comprising any one or more of SEQ ID NOs: 55 to 57, or functional fragments thereof. In other embodiments, the nucleic acid regulatory elements disclosed herein comprise a sequence from ATP2A1 regulatory elements, i.e. regulatory elements that control expression of the ATP2A1 gene (ATPase, Ca++Transporting, Cardiac Muscle, Fast Twitch 1 gene or Sarcoplasmic/endoplasmic reticulum calcium ATPase 1 gene) in vivo, e.g. regulatory elements comprising any one or more of SEQ ID NOs: 58 to 64, or functional fragments thereof. In other embodiments, the nucleic acid regulatory elements disclosed herein comprise a sequence from MYH1 regulatory elements, i.e. regulatory elements that control expression of the MYH1 gene (Myosin, Heavy Chain 1 gene) in vivo, e.g. regulatory elements comprising SEQ ID NO: 65, or functional fragments thereof.

Sequences disclosed herein may be part of sequences of regulatory elements capable of controlling transcription of diaphragm-, skeletal muscle and heart-specific genes in vivo. Particular examples for diaphragm-, skeletal muscle and heart specific regulatory elements may in particular be controlling the following genes: ACTA1, CKM, MYL2, MB, DES, TNNC1, TCAP, MYH7, ALDOA, or TPM1. Accordingly, in embodiments, the nucleic acid regulatory elements disclosed herein comprise a sequence from ACTA1 regulatory elements, i.e. regulatory elements that control expression of the ACTA1 gene (Alpha-actin-1 gene) in vivo, e.g. regulatory elements comprising any one or more of SEQ ID NOs: 1 to 5, or functional fragments thereof. In other embodiments, the nucleic acid regulatory elements disclosed herein comprise a sequence from CKM regulatory elements, i.e. regulatory elements that control expression of the CKM gene (Muscle Creatine Kinase gene) in vivo, e.g. regulatory elements comprising any one or more of SEQ ID NOs: 6 or 7, or functional fragments thereof. In other embodiments, the nucleic acid regulatory elements disclosed herein comprise a sequence from MYL2 regulatory elements, i.e. regulatory elements that control expression of the MYL2 (Myosin, Light Chain 2 gene) gene in vivo, e.g. regulatory elements comprising any one or more of SEQ ID NOs: 8 or 9, or functional fragments thereof. In other embodiments, the nucleic acid regulatory elements disclosed herein comprise a sequence from MB regulatory elements, i.e. regulatory elements that control expression of the MB gene (Myoglobin gene) in vivo, e.g. regulatory elements comprising any one or more of SEQ ID NOs: 66 to 68, or functional fragments thereof. In other embodiments, the nucleic acid regulatory elements disclosed herein comprise a sequence from DES regulatory elements, i.e. regulatory elements that control expression of the DES gene (Desmin gene) in vivo, e.g. regulatory elements comprising any one or more of SEQ ID NOs: 69 to 71, or functional fragments thereof. In other embodiments, the nucleic acid regulatory elements disclosed herein comprise a sequence from TNNC1 regulatory elements, i.e. regulatory elements that control expression of the TNNC1 gene (Troponin C Type 1 gene) in vivo, e.g. regulatory elements comprising any one or more of SEQ ID NOs: 72 to 74, or functional fragments thereof. In other embodiments, the nucleic acid regulatory elements disclosed herein comprise a sequence from TCAP regulatory elements, i.e. regulatory elements that control expression of the TCAP gene (Titin-Cap gene) in vivo, e.g. regulatory elements comprising SEQ ID NOs: 75, or functional fragments thereof. In other embodiments, the nucleic acid regulatory elements disclosed herein comprise a sequence from MYH7 regulatory elements, i.e. regulatory elements that control expression of the MYH7 gene (Myosin, Heavy Chain 7 gene) in vivo, e.g. regulatory elements comprising any one or more of SEQ ID NOs: 76 or 77, or functional fragments thereof. In other embodiments, the nucleic acid regulatory elements disclosed herein comprise a sequence from ALDOA regulatory elements, i.e. regulatory elements that control expression of the ALDOA gene (Aldolase A gene) in vivo, e.g. regulatory elements comprising any one or more of SEQ ID NOs: 78 to 81, or functional fragments thereof. In other embodiments, the nucleic acid regulatory elements disclosed herein comprise a sequence from TPM1 regulatory elements, i.e. regulatory elements that control expression of the TPM1 gene (Tropomyosin 1 gene) in vivo, e.g. regulatory elements comprising any one or more of SEQ ID NOs: 84 to 89, or functional fragments thereof.

As used herein, the terms "identity" and "identical" and the like refer to the sequence similarity between two polymeric molecules, e.g., between two nucleic acid molecules, e.g., two DNA molecules. Sequence alignments and determination of sequence identity can be done, e.g., using the Basic Local Alignment Search Tool (BLAST) originally described by Altschul et al. 1990 (J Mol Biol 215: 403-10), such as the "Blast 2 sequences" algorithm described by Tatusova and Madden 1999 (FEMS Microbiol Lett 174: 247-250). Typically, the percentage sequence identity is calculated over the entire length of the sequence. As used herein, the term "substantially identical" denotes at least 90%, preferably at least 95%, such as 95%, 96%, 97%, 98% or 99%, sequence identity.

The term 'functional fragment' as used in the application refers to fragments of the regulatory element sequences disclosed herein that retain the capability of regulating muscle-specific expression, i.e. they can still confer tissue specificity and they are capable of regulating expression of a (trans)gene in the same way (although possibly not to the same extent) as the sequence from which they are derived. Functional fragments may preferably comprise at least 20, at least 25, at least 30, at least 35, at least 40, at least 45, at least 50, at least 60, at least 70, at least 80, at least 90, at least 100, at least 120, at least 150, at least 200, at least 250, at least 300, at least 350, or at least 400 contiguous nucleotides from the sequence from which they are derived. Also preferably, functional fragments may comprise at least 1, more preferably at least 2, at least 3, or at least 4, even more preferably at least 5, at least 10, or at least 15, of the transcription factor binding sites (TFBS) that are present in the sequence from which they are derived.

"Diaphragm and skeletal muscle-specific expression" as used in the application, refers to the preferential or predominant expression of a (trans)gene (as RNA and/or polypeptide) in diaphragm and skeletal muscle cells or diaphragm or skeletal muscle tissue, as compared to other (i.e. non-diaphragm or skeletal muscle) tissues. According to particular embodiments, at least 50%, more particularly at least 60%, at least 70%, at least 75%, at least 80%, at least 85%, at least 90%, at least 95%, at least 98%, at least 99% or 100% of the (trans)gene expression occurs within diaphragm and/or skeletal muscle cells or tissue. According to a particular embodiment, diaphragm and skeletal muscle specific expression entails that there is less than 10%, less than 5%, less than 2% or even less than 1% 'leakage' of expressed gene product to other organs or tissue than muscle, such as lung, liver, brain, kidney and/or spleen.

As used herein "diaphragm, skeletal muscle and cardiac-specific expression" refers to the preferential or predominant expression of a (trans)gene in diaphragm, heart, skeletal muscle cells or tissue and in particular heart muscle. According to particular embodiments, at least 50%, more particularly at least 60%, at least 70%, at least 75%, at least 80%, at least 85%, at least 90%, at least 95%, at least 98%, at least 99% or 100% of the (trans)gene expression occurs within diaphragm, skeletal muscle cells and heart tissue. Thus, according to particular embodiments, less than 10%, less than 5%, less than 2% or even less than 1% of the (trans)gene expression occurs in an organ or tissue other than diaphragm, heart and skeletal muscle.

The same applies mutatis mutandis for myocyte-specific and myoblast-specific expression, which may be considered as a particular form of muscle-specific expression. Throughout the application, where muscle-specific is mentioned in the context of expression, myocyte-specific and myoblast-specific expression are also explicitly envisaged. Similarly, where cardiac and skeletal muscle-specific expression is used in the application, cardiomyocyte and skeletal myocyte-specific expression and cardiac myoblast and skeletal myoblast-specific expression is also explicitly envisaged. Similarly, where skeletal muscle-specific expression is used in the application, skeletal myocyte-specific and skeletal myoblast-specific expression is also explicitly envisaged.

As used herein, the terms "heart muscle" or "cardiac muscle" refer to the autonomically regulated, striated muscle type found in the heart.

As used herein, the term "skeletal muscle" refers to the voluntarily controlled, striated muscle type that is attached to the skeleton. Non-limiting examples of skeletal muscle include the biceps, the triceps, the quadriceps, the tibialis interior, and the gastrocnemius muscle.

The term "myocyte," as used herein, refers to a cell that has been differentiated from a progenitor myoblast such that it is capable of expressing muscle-specific phenotype under appropriate conditions. Terminally differentiated myocytes fuse with one another to form myotubes, a major constituent of muscle fibers. The term "myocyte" also refers to myocytes that are de-differentiated. The term includes cells in vivo and cells cultured ex vivo regardless of whether such cells are primary or passaged.

The term "myoblast" as used herein, refers to an embryonic cell in the mesoderm that differentiates to give rise to a muscle cell or myocyte. The term includes cells in vivo and cells cultured ex vivo regardless of whether such cells are primary or passaged.

In embodiments, the invention relates to a nucleic acid regulatory element for enhancing gene expression in diaphragm and skeletal muscle comprising, consisting essentially of, or consisting of a sequence selected from the group consisting of: SEQ ID NO:1 to 7, 10 to 65, 82, and 83 (cf. Dph-CRE1 to 7, 10 to 65, 82, and 83 in Table 3); a sequence having at least 80%, preferably at least 85%, more preferably at least 90%, even more preferably at least 95%, such as 95%, 96%, 97%, 98%, or 99%, identity to any of the sequences selected from the group consisting of SEQ ID NO: 1 to 7, 10 to 65, 82, and 83 (cf. Dph-CRE1 to 7, 10 to 65, 82, and 83 in Table 3); or a functional fragment thereof, wherein said functional fragment comprises at least 20, preferably at least 25, more preferably at least 50, at least 100, at least 200 or at least 250, contiguous nucleotides from the sequence from which it is derived, and wherein said functional fragment comprises at least 1, preferably at least 5, more preferably at least 10 or at least 15, of the transcription factor binding sites (TFBS) that are present in the sequence from which it is derived.

In further embodiments, the invention relates to a nucleic acid regulatory element for enhancing gene expression in diaphragm, skeletal muscle and cardiac comprising, consisting essentially of, or consisting of a sequence selected from the group consisting of: SEQ ID No: 1 to 9, 66 to 81, and 84 to 89. (cf. Dph-CRE1 to 9, 66 to 81, and 84 to 89 in Table 4); or a sequence having at least 80%, preferably at least 85%, more preferably at least 90%, even more preferably at least 95%, such as 95%, 96%, 97%, 98%, or 99%, identity to any one of the sequences selected from the group consisting of SEQ ID No: 1 to 9, 66 to 81, and 84 to 89. (cf. Dph-CRE1 to 9, 66 to 81, and 84 to 89 in Table 4); or a functional fragment thereof, wherein said functional fragment comprise at least 20, preferably at least 25, more preferably at least 50, at least 100, at least 200 or at least 250, contiguous nucleotides from the sequence from which it is derived, and wherein said functional fragment comprises at least 1, preferably at least 5, more preferably at least 10 or at least 15, of the transcription factor binding sites (TFBS) that are present in the sequence from which it is derived.

It is also possible to make nucleic acid regulatory elements that comprise an artificial sequence by combining two or more identical or different sequences disclosed herein or functional fragments thereof. Accordingly, in certain embodiments a nucleic acid regulatory element for enhancing gene expression in diaphragm, and skeletal muscle cells or tissue is provided comprising at least two sequences selected from the group consisting of: SEQ ID NO:1 to 7, 10 to 65, 82, and 83 (cf. Dph-CRE1 to 7, 10 to 65, 82, and 83 in Table 3).

Alternatively, in certain embodiments a nucleic acid regulatory element for enhancing gene expression in diaphragm, skeletal muscle and heart cells or tissue is provided comprising at least two sequences selected from the group consisting of: SEQ ID No: 1 to 9, 66 to 81, and 84 to 89. (cf. Dph-CRE1 to 9, 66 to 81, and 84 to 89 in Table 4).

For example, disclosed herein is a nucleic acid regulatory element comprising, consisting essentially of, or consisting of 2, 3, 4, or 5 repeats, e.g. tandem repeats, of any one of SEQ ID NOs:1 to 89, or combinations thereof.

Particular examples of nucleic acid regulatory elements that comprise an artificial sequence include the regulatory elements that are obtained by rearranging the transcription factor binding sites (TFBS) that are present in the sequences disclosed herein. Said rearrangement may encompass changing the order of the TFBSs and/or changing the position of one or more TFBSs relative to the other TFBSs and/or changing the copy number of one or more of the TFBSs. For example, also disclosed herein is a nucleic acid regulatory element for enhancing muscle-specific gene expression, in particular cardiac and skeletal muscle-specific gene expression, comprising binding sites for E2A, HNH1, NF1, C/EBP, LRF, MyoD, and SREBP; or for E2A, NF1, p53, C/EBP, LRF, and SREBP; or for E2A, HNH1, HNF3a, HNF3b, NF1, C/EBP, LRF, MyoD, and SREBP; or E2A, HNF3a, NF1, C/EBP, LRF, MyoD, and SREBP; or for E2A, HNF3a, NF1, CEBP, LRF, MyoD, and SREBP; or for HNF4, NF1, RSRFC4, C/EBP, LRF, and MyoD, or NF1, PPAR, p53, C/EBP, LRF, and MyoD. Further for example, also disclosed herein is a nucleic acid regulatory element for enhancing diaphragm and skeletal muscle-specific gene expression, in particular comprising binding sites for one or more of: NFYA, SIN3A, TCF12, PHF8, IRF1 and combinations thereof, such as NFYA, SIN3A, TCF12, PHF8, and IRF1. Further for example, also disclosed herein is a nucleic acid regulatory element for enhancing diaphragm, heart, and skeletal muscle-specific gene expression, in particular comprising binding sites for one or more of: MAFF, FOXA2, TAL1, CEBPB, RFX5, HSF1, SRF and combinations thereof, such as MAFF, FOXA2, TAL1, CEBPB, RFX5, HSF1, and SRF. In some embodiments, these nucleic acid regulatory elements comprise at least two, such as 2, 3, 4, or more copies of any one or more of the recited TFBSs.

In case the regulatory element is provided as a single stranded nucleic acid, e.g. when using a single-stranded AAV vector, the complement strand is considered equivalent to the disclosed sequences. Hence, also disclosed herein is a nucleic acid regulatory element for enhancing muscle-specific gene expression comprising, consisting essentially of, or consisting of the complement of a sequence described herein, in particular a sequence selected from the group consisting of: SEQ ID NOs:1 to 89; a sequence having at least 80%, preferably at least 85%, more preferably at least 90%, even more preferably at least 95%, such as 95%, 96%, 97%, 98%, or 99%, identity to any of these sequences; or a functional fragment thereof.

Also disclosed herein is a nucleic acid regulatory element for enhancing muscle-specific gene expression hybridizing under stringent conditions to a nucleic acid regulatory element described herein, in particular to the nucleic acid regulatory element comprising, consisting essentially of, or consisting of a sequence selected from the group consisting of: SEQ ID NOs:1 to 89; a sequence having at least 90%, preferably at least 95%, such as 95%, 96%, 97%, 98%, or 99%, identity to any of these sequences; a functional fragment thereof; or to its complement. Said nucleic acid regulatory elements do not need to be of equal length as the sequence they hybridize to. In preferred embodiments, the size of said hybridizing nucleic acid regulatory element does not differ more than 25% in length, in particular 20% in length, more in particular 15% in length, most in particular 10% in length from the sequence it hybridizes to.

The expression 'hybridize under stringent conditions' refers to the ability of a nucleic acid molecule to hybridize to a target nucleic acid molecule under defined conditions of temperature and salt concentration. Typically, stringent hybridization conditions are no more than 25° C. to 30° C. (for example, 20° C., 15° C., 10° C. or 5° C.) below the melting temperature (Tm) of the native duplex. Methods of calculating Tm are well known in the art. By way of non-limiting example, representative salt and temperature conditions for achieving stringent hybridization are: 1×SSC, 0.5% SDS at 65° C. The abbreviation SSC refers to a buffer used in nucleic acid hybridization solutions. One liter of the 20× (twenty times concentrate) stock SSC buffer solution (pH 7.0) contains 175.3 g sodium chloride and 88.2 g sodium citrate. A representative time period for achieving hybridization is 12 hours.

Preferably the regulatory elements as described herein are fully functional while being only of limited length. This allows their use in vectors or nucleic acid expression cassettes without unduly restricting their payload capacity. Accordingly, in embodiments, the regulatory element disclosed herein is a nucleic acid of 1500 nucleotides or less, 1000 nucleotides or less, 900 nucleotides or less, 800 nucleotides or less, 700 nucleotides or less, more preferably 600 nucleotides or less, such as 550 nucleotides or less, 500 nucleotides or less, 450 nucleotides or less, 400 nucleotides or less, 350 nucleotides or less, or 300 nucleotides or less (i.e. the nucleic acid regulatory element has a maximal length of 1500 nucleotides, 1000 nucleotides, 900 nucleotides, 800 nucleotides, 700 nucleotides, preferably 600 nucleotides, such as 550 nucleotides, 500 nucleotides, 450 nucleotides, 400 nucleotides, 350 nucleotides, or 300 nucleotides).

However, it is to be understood that the disclosed nucleic acid regulatory elements retain regulatory activity (i.e. with regard to specificity and/or activity of transcription) and thus they particularly have a minimum length of 20 nucleotides, 25 nucleotides, 30 nucleotides, 35 nucleotides, 40 nucleotides, 45 nucleotides, 50 nucleotides, 100 nucleotides, 150 nucleotides, 200 nucleotides, 250 nucleotides, 300 nucleotides, 350 nucleotides or 400 nucleotides.

In certain embodiments, the invention provides for a nucleic acid regulatory element of 1000 nucleotides or less, preferably 900 nucleotides or less, preferably 800 nucleotides or less, preferably 700 nucleotides or less of a sequence selected from the group consisting of: SEQ ID NOs:1 to 89; a sequence having at least 80%, preferably at least 85%, more preferably at least 90%, even more preferably at least 95%, such as 95%, 96%, 97%, 98%, or 99%, identity to any of said sequences; or a functional fragment thereof.

The nucleic acid regulatory elements disclosed herein may be used in a nucleic acid expression cassette. Accordingly, in an aspect the invention provides for the use of the nucleic acid regulatory elements as described herein in a nucleic acid expression cassette.

In an aspect the invention provides a nucleic acid expression cassette comprising a nucleic acid regulatory element as described herein, operably linked to a promoter. In embodiments, the nucleic acid expression cassette does not contain a transgene. Such nucleic acid expression cassette may be used to drive expression of an endogenous gene. In preferred embodiments, the nucleic acid expression cassette comprises a nucleic acid regulatory element as described herein, operably linked to a promoter and a transgene.

As used herein, the term 'nucleic acid expression cassette' refers to nucleic acid molecules that include one or more transcriptional control elements (such as, but not limited to promoters, enhancers and/or regulatory elements, polyadenylation sequences, and introns) that direct (trans)gene expression in one or more desired cell types, tissues or organs. Typically, they will also contain a transgene, although it is also envisaged that a nucleic acid expression cassette directs expression of an endogenous gene in a cell into which the nucleic acid cassette is inserted.

The term 'operably linked' as used herein refers to the arrangement of various nucleic acid molecule elements relative to each such that the elements are functionally connected and are able to interact with each other. Such elements may include, without limitation, a promoter, an enhancer and/or a regulatory element, a polyadenylation sequence, one or more introns and/or exons, and a coding sequence of a gene of interest to be expressed (i.e., the transgene). The nucleic acid sequence elements, when properly oriented or operably linked, act together to modulate the activity of one another, and ultimately may affect the level of expression of the transgene. By modulate is meant increasing, decreasing, or maintaining the level of activity of a particular element. The position of each element relative to other elements may be expressed in terms of the 5' terminus and the 3' terminus of each element, and the distance between any particular elements may be referenced by the number of intervening nucleotides, or base pairs, between the elements. As understood by the skilled person, operably linked implies functional activity, and is not necessarily related to a natural positional link. Indeed, when used in nucleic acid expression cassettes, the regulatory elements will typically be located immediately upstream of the promoter (although this is generally the case, it should definitely not be interpreted as a limitation or exclusion of positions within the nucleic acid expression cassette), but this needs not be the case in vivo. E.g., a regulatory element sequence naturally occurring downstream of a gene whose transcription it affects is able to function in the same way when located upstream of the promoter. Hence, according to a specific embodiment, the regulatory or enhancing effect of the regulatory element is position-independent.

In particular embodiments, the nucleic acid expression cassette comprises one nucleic acid regulatory element as described herein. In alternative embodiments, the nucleic acid expression cassette comprises two or more, such as, e.g., 2, 3, 4, 5, 6, 7, 8, 9, or 10, nucleic acid regulatory elements as described herein, i.e. they are combined modularly to enhance their regulatory (and/or enhancing) effect. In further embodiments, at least two of the two or more nucleic acid regulatory elements are identical or substantially identical. In yet further embodiments, all of the two or more regulatory elements are identical or substantially identical. The copies of the identical or substantially identical nucleic acid regulatory elements may be provided as tandem repeats in the nucleic acid expression cassette. In alternative further embodiments, at least two of the two or more nucleic acid regulatory elements are different from each other, that is to say, are defined by a different SEQ ID NO. The nucleic acid expression cassette may also comprise a combination of identical and substantially identical nucleic acid regulatory elements and non-identical nucleic acid regulatory elements.

For example, the nucleic acid expression cassette may comprise a nucleic acid regulatory element comprising SEQ ID NO:1, and a nucleic acid regulatory element comprising any one or more of SEQ ID Nos: 2 to 689; or the nucleic acid expression cassette may comprise a nucleic acid regulatory element comprising any one or more of SEQ ID NO: 1-89 and a nucleic acid regulatory element (cis-regulatory element, CRE, CRM, or SH) specific for another tissue type such as e.g. the ones disclosed in previous applications from the same authors: WO2015110449; WO2009130208; WO2009071679; WO2011051450; WO2016146757; WO2014063753; or WO2014064277. Alternatively, this can be done for remaining regulatory elements defined by SEQ ID NOs: 2 to 89 respectively. In a specific embodiment, the muscle-specific regulatory element designated Sk-SH4 (SEQ ID NO:121) or CSk-SH5 (SEQ ID NO:122) can be used in combination with any one of the Diaphragm cis-regulatory elements defined by SEQ ID NOs: 1 to 89.

As used in the application, the term 'promoter' refers to nucleic acid sequences that regulate, either directly or indirectly, the transcription of corresponding nucleic acid coding sequences to which they are operably linked (e.g. a transgene or endogenous gene). A promoter may function alone to regulate transcription or may act in concert with one or more other regulatory sequences (e.g. enhancers or silencers, or regulatory elements). In the context of the present application, a promoter is typically operably linked to a regulatory element as disclosed herein to regulate transcription of a (trans)gene. When a regulatory element as described herein is operably linked to both a promoter and a transgene, the regulatory element can (1) confer a significant degree of diaphragm-specific, in particular diaphragm and skeletal muscle-specific or diaphragm, cardiac and skeletal muscle-specific, expression in vivo (and/or in vitro in cell lines derived from cardiac, diaphragm, and skeletal muscle cells or tissue) of the transgene, and/or (2) can increase the level of expression of the transgene in diaphragm and skeletal muscle or in diaphragm, cardiac and skeletal muscle (and/or in vitro in cell lines derived from cardiac, diaphragm, and skeletal muscle cells or tissue).

The promoter may be homologous (i.e. from the same species as the animal, in particular mammal, to be transfected with the nucleic acid expression cassette) or heterologous (i.e. from a source other than the species of the animal, in particular mammal, to be transfected with the expression cassette). As such, the source of the promoter may be any virus, any unicellular prokaryotic or eukaryotic organism, any vertebrate or invertebrate organism, or any plant, or may even be a synthetic promoter (i.e. having a non-naturally occurring sequence), provided that the promoter is functional in combination with the regulatory elements described herein. In preferred embodiments, the promoter is a mammalian promoter, in particular a murine or human promoter.

The promoter may be an inducible or constitutive promoter.

Non-limiting exemplary skeletal muscle and/or diaphragm-specific promoter are the Desmin promotor, other muscle specific promoters such as muscle creatine kinase promoter (MCK) (Wang B et al, Gene Ther, 2008), alpha-myosin heavy chain (a-MHC), myosin light chain (MLC-2), cardiac troponin C (cTnC), myogenin MYF4 promoters (Pacak C. A. et al., Genet Vaccines Ther, 2008), viral promoters such as murine stem cell virus (MSCV) promoter (Suga T et al., Plos One, 2011), and all potential promoters that can be used to cloned downstream of the diaphragm nucleic acid regulatory elements. The regulatory elements disclosed herein can be used in nucleic acid expression cassettes in conjunction with their natural promoter, as well as with another promoter. Preferably, the nucleic acid expression cassettes disclosed herein comprise a diaphragm, heart, and/or skeletal muscle-specific promoter, in order to increase diaphragm, heart, and/or skeletal muscle-specificity and/or avoid leakage of expression in other tissues. Examples of such promotors are diaphragm and/or skeletal muscle-specific promoters, such as the promotor of one of the genes defined in Table 3, namely the ACTA1, CKM, TPM2, MYL1, TNNC2, FHL1, TNNT1, TNNI2, MYLPF, TNNT3, MYH2, SLN, MYBPC1, ENO3, CA3, ATP2A1, and MYH1 genes; or diaphragm-, skeletal muscle- and heart-specific promoters, such as the promotor of any one of the genes defined in Table 4, namely ACTA1, CKM, MYL2, MB, DES, TNNC1, TCAP, MYH7, ALDOA, and TPM1 genes. Non-limiting examples of muscle-specific promoters include the desmin (DES) promoter, the synthetic SPc-5-12 promoter (SPc5-12-GTRM), the alpha-actin1 promoter (ACTA1), the Creatine kinase, muscle (CKM) promoter, the Four and a half LIM domains protein 1 (FHL1) promoter, the alpha 2 actinin (ACTN2) promoter, the filamin-C (FLNC) promoter, the sarcoplasmic/endoplasmic reticulum calcium ATPase 1 (ATP2A1) promoter, the troponin I type 1 (TNNI1) promoter, the myosin-1 (MYH1) promoter, the phosphorylatable, fast skeletal muscle myosin light chain (MYLPF) promoter, the alpha-3 chain tropomyosin (TPM3) promoter, the ankyrin repeat domain-containing protein 2 (ANKRD2) promoter the myosin heavy-chain (MHC) promoter, the myosin light-chain (MLC) promoter, the muscle creatine kinase (MCK) promoter, synthetic muscle promoters as described in Li et al. (1999, Nat Biotechnol. 17:241-245), such as the SPc5-12 promoter, the muscle creatine kinase (MCK) promoter, the dMCK promoter and the tMCK promoter consisting of respectively, a double or triple tandem of the MCK enhancer to the MCK basal promoter as described in Wang et al. (2008, Gene Ther, 15:1489-1499).

In particularly preferred embodiments, the promoter is a mammalian promoter, in particular a murine or human promoter.

In preferred embodiments, the promoter is from the desmin gene, in particular the murine desmin gene, such as the promoter as defined in SEQ ID NO: 90 (cf. FIG. 4), or the human desmin gene, such as the promoter as defined in SEQ ID NO: 91 (1,0kb) or SEQ ID NO: 92 (1,4kb). In preferred embodiments, the desmin promotor is the 1,4kb promotor of SEQ ID NO: 92 which has been shown to further increase expression levels (cf. examples) For example, the murine desmin promoter is commercially available as pDRIVE-mDesmin (Invivogen). The desmin promoter is expressed in both cardiac muscle and skeletal muscle. In embodiments, the promoter is a skeletal muscle-specific promoter, in particular a muscle creatine kinase (MCK) promoter, more particularly the double MCK promoter or triple MCK promoter consisting of a double or triple tandem of MCK enhancer and MCK basal promoter as described in Wang et al. (2008, Gene Ther, 15:1489-1499). Furthermore, the promoter does not need to be the promoter of the transgene in the nucleic acid expression cassette, although it is possible that the transgene is transcribed from its own promoter.

To minimize the length of the nucleic acid expression cassette, the regulatory elements may be linked to minimal promoters, or shortened versions of the promoters described herein. A 'minimal promoter' (also referred to as basal promoter or core promoter) as used herein is part of a full-size promoter still capable of driving expression, but lacking at least part of the sequence that contributes to regulating (e.g. tissue-specific) expression. This definition covers both promoters from which (tissue-specific) regulatory elements have been deleted—that are capable of driving expression of a gene but have lost their ability to express that gene in a tissue-specific fashion and promoters from which (tissue-specific) regulatory elements have been deleted that are capable of driving (possibly decreased) expression of a gene but have not necessarily lost their ability to express that gene in a tissue-specific fashion. Preferably, the promoter contained in the nucleic acid expression cassette disclosed herein is 1000 nucleotides or less in length, 900 nucleotides or less, 800 nucleotides or less, 700 nucleotides or less, 600 nucleotides or less, 500 nucleotides or less, 400 nucleotides or less, 300 nucleotides or less, or 250 nucleotides or less.

The term 'transgene' as used herein refers to particular nucleic acid sequences encoding a polypeptide or a portion of a polypeptide to be expressed in a cell into which the nucleic acid sequence is introduced. However, it is also possible that transgenes are expressed as RNA, typically to control (e.g. lower) the amount of a particular polypeptide in a cell into which the nucleic acid sequence is inserted. These RNA molecules include but are not limited to molecules that exert their function through RNA interference (shRNA, RNAi), micro-RNA regulation (miR) (which can be used to control expression of specific genes), catalytic RNA, anti-sense RNA, RNA aptamers, etc. How the nucleic acid sequence is introduced into a cell is not essential to the invention, it may for instance be through integration in the genome or as an episomal plasmid. Of note, expression of the transgene may be restricted to a subset of the cells into which the nucleic acid sequence is introduced. The term 'transgene' is meant to include (1) a nucleic acid sequence that is not naturally found in the cell (i.e., a heterologous nucleic acid sequence); (2) a nucleic acid sequence that is a mutant form of a nucleic acid sequence naturally found in the cell into which it has been introduced; (3) a nucleic acid sequence that serves to add additional copies of the same (i.e., homologous) or a similar nucleic acid sequence naturally occurring in the cell into which it has been introduced; or (4) a silent naturally occurring or homologous nucleic acid sequence whose expression is induced in the cell into which it has been introduced.

The transgene may be homologous or heterologous to the promoter (and/or to the animal, in particular a mammal or human, in which it is introduced, e.g. in cases where the nucleic acid expression cassette is used for gene therapy).

The transgene may be a full-length cDNA or genomic DNA sequence, or any fragment, subunit or mutant thereof that has at least some biological activity. In particular, the transgene may be a minigene, i.e. a gene sequence lacking part, most or all of its intronic sequences. The transgene thus optionally may contain intron sequences. Optionally, the transgene may be a hybrid nucleic acid sequence, i.e., one constructed from homologous and/or heterologous cDNA and/or genomic DNA fragments. By 'mutant form' is meant a nucleic acid sequence that contains one or more nucleotides that are different from the wild-type or naturally occurring sequence, i.e., the mutant nucleic acid sequence contains one or more nucleotide substitutions, deletions, and/or insertions. The nucleotide substitution, deletion, and/or insertion can give rise to a gene product (i.e. e., protein or nucleic acid) that is different in its amino acid/nucleic acid sequence from the wild type amino acid/nucleic acid sequence. Preparation of such mutants is well known in the art. In some cases, the transgene may also include a sequence encoding a leader peptide or signal sequence such that the transgene product will be secreted from the cell.

The transgene that may be contained in the nucleic acid expression cassettes described herein typically encodes a gene product such as RNA or a polypeptide (protein).

In embodiments, the transgene encodes a therapeutic protein. The therapeutic protein may be a secretable protein. Non-limiting examples of secretable proteins, in particular secretable therapeutic proteins, include glucosidase, follistatin, clotting factors, such as factor VIII or factor IX, insulin, erythropoietin, lipoprotein lipase, antibodies or nanobodies, growth factors, cytokines, chemokines, plasma factors etc. The therapeutic protein may also be a structural protein. Non-limiting examples of structural proteins, in particular structural therapeutic proteins, include myotubularin, dysferlin, follistatin, microdystrophin 1, dystrophin and sarcoglycans. In preferred embodiments, the transgene comprises the microdystrophin 1 (MD1 & MD2) gene or the follistatin (F57) gene, preferably the exon-skipping construct of follistatin. A non-exhaustive and non-limiting list of transgenes envisaged in the application includes angiogenic factors for therapeutic angiogenesis such as VEGF, PIGF, or guidance molecules such as ephrins, semaphorins, Slits and netrins or their cognate receptors; cytokines and/or growth factors such as erythropoietin (EPO), interferon-α, interferon-β, interferon-γ, interleukin 1 (IL-1), interleukin 2 (IL-2), interleukin 3 (IL-3), interleukin 4 (IL-4), interleukin 5 (IL-5), interleukin 6 (IL-6), interleukin 7 (IL-7), interleukin 8 (IL-8), interleukin 9 (IL-9), interleukin 10 (IL-10), interleukin 11 (IL-11), interleukin 12 (IL-12), chemokine (C-X-C motif) ligand 5 (CXCL5), granulocyte-colony stimulating factor (G-CSF), granulocyte-macrophage colony stimulating factor (GM-CSF), macrophage colony stimulating factor (M-CSF), stem cell factor (SCF), keratinocyte growth factor (KGF), monocyte chemoattractant protein-1 (MCP-1), tumor necrosis factor (TNF), proteins involved in calcium handling such as SERCA (Sarco/Endoplasmic Reticulum Ca2+-ATPase), calcineurin, microdystrophin 1 (MD1), follistatin (F57), alpha-glucosidase (GAA), myotubularin 1 (MTM1), transgenes encoding antibodies, nanobodies, antiviral dominant-negative proteins, and fragments, subunits or mutants thereof.

In embodiments, the transgene encodes an immunogenic protein. Non-limiting examples of immunogenic proteins include epitopes and antigens derived from a pathogen.

As used herein, the term "immunogenic" refers to a substance or composition capable of eliciting an immune response.

Other sequences may be incorporated in the nucleic acid expression cassette disclosed herein as well, typically to further increase or stabilize the expression of the transgene product (e.g. introns and/or polyadenylation sequences).

Any intron can be utilized in the expression cassettes described herein. The term "intron" encompasses any portion of a whole intron that is large enough to be recognized and spliced by the nuclear splicing apparatus. Typically, short, functional, intron sequences are preferred in order to keep the size of the expression cassette as small as possible which facilitates the construction and manipulation of the expression cassette. In some embodiments, the intron is obtained from a gene that encodes the protein that is encoded by the coding sequence within the expression cassette. The intron can be located 5' to the coding sequence, 3' to the coding sequence, or within the coding sequence. An advantage of locating the intron 5' to the coding sequence is to minimize the chance of the intron interfering with the function of the polyadenylation signal. In embodiments, the nucleic acid expression cassette disclosed herein further comprises an intron. Non-limiting examples of suitable introns are Minute Virus of Mice (MVM) intron, beta-globin intron (betaIVS-II), factor IX (FIX) intron A, Simian virus 40 (SV40) small-t intron, and beta-actin intron.

Preferably, the intron is MVM intron.

Any polyadenylation signal that directs the synthesis of a polyA tail is useful in the expression cassettes described herein, examples of those are well known to one of skill in the art. Exemplary polyadenylation signals include, but are not limited to, polyA sequences derived from the Simian virus 40 (SV40) late gene, the bovine growth hormone (BGH) polyadenylation signal, the minimal rabbit L-globin (mRBG) gene, and the synthetic polyA s(SPA) site as described in Levitt et al. (1989, Genes Dev 3:1019-1025).

Preferably, the polyadenylation signal is derived from SV40 (i.e. SV40 pA).

Figure 9:
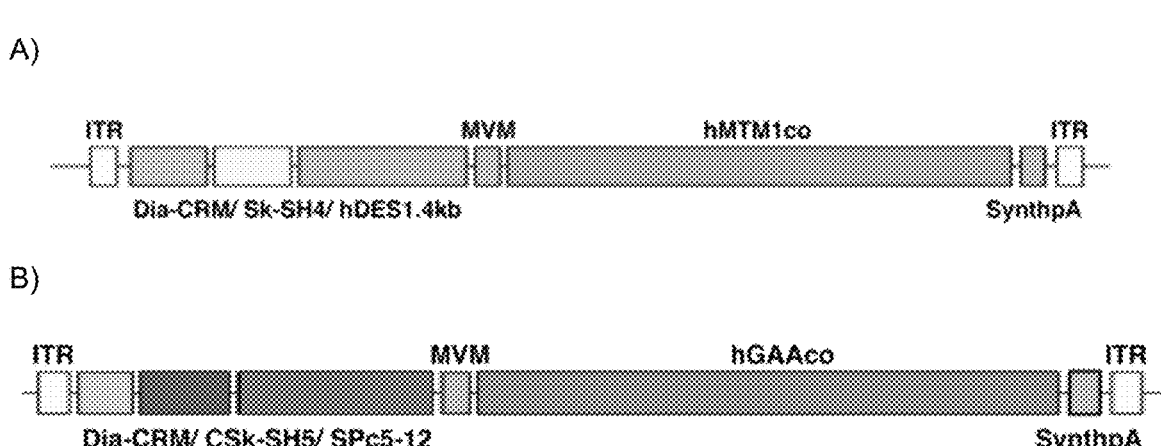
FIG. 9: Schematic view of AAV vectors for expression of A) hMTMco or B) hGAAco transgene. Vector A) further comprises one of the Dph-CREs (called Dia-CRM), the Sk-SH4-CRE (SEQ ID NO: 121), the hDes1,4kb promoter, the MVM intron, the hMTM1co transgene, and a synthetic poly-A site, cloned between the ITRs of an AAV vector. Vector B) further comprises one of the Dph-CREs (called Dia-CRM), the CSk-SH5-CRE (SEQ ID NO: 122), the SPc5-12 promoter, the MVM intron, the hGAAco transgene, and a synthetic poly-A site, cloned between the ITRs of an AAV vector.

In particular embodiments, the invention provides a nucleic acid expression cassette comprising, consisting essentially of, or consisting of a nucleic acid regulatory element selected from the group consisting of SEQ ID NO:

1 to 89 or a sequence having 95% identity to said sequence, operably linked to a promoter, preferably a promoter selected from the group consisting of the promoter from the desmin gene or the SPc5-12 promoter, and a transgene, preferably a transgene encoding a luciferase. In further embodiments, the nucleic acid expression cassette further comprises an MVM intron. In yet further embodiments the nucleic acid expression cassette further comprises a polyadenylation signal, preferably a polyadenylation signal derived from synthetic polyA (SynthpA: SEQ ID: 127 & FIGS. 9 A) and B)).

In particular embodiments, the invention provides a nucleic acid expression cassette comprising, consisting essentially of, or consisting of a nucleic acid regulatory element selected from the group consisting of SEQ ID NO: 1 to 89, or a sequence having 95% identity to said sequence, operably linked to a promoter, preferably the promoter from the desmin gene, and a transgene, preferably a transgene encoding microdystrophin, exon-skipping construct or follistatin. In further embodiments, the nucleic acid expression cassette further comprises an MVM intron. In yet further embodiments, the nucleic acid expression cassette further comprises a polyadenylation signal. Alternatively, any one of the following transgenes can be introduced: secretable proteins, in particular secretable therapeutic proteins, including glucosidase, follistatin, clotting factors, such as factor VIII or factor IX, insulin, erythropoietin, lipoprotein lipase, antibodies or nanobodies, growth factors, cytokines, chemokines, plasma factors etc.; or structural proteins such as structural therapeutic proteins, including myotubularin, dysferlin, follistatin, microdystrophin 1, dystrophin and sarcoglycans. In embodiments, the transgene comprises the microdystrophin 1 (MD1) gene or the follistatin (F57) gene, preferably the exon-skipping construct of follistatin.

The nucleic acid regulatory element and the nucleic acid expression cassette disclosed herein may be used as such, or typically, they may be part of a nucleic acid vector. Accordingly, a further aspect relates to the use of a nucleic acid regulatory element as described herein or a nucleic acid expression cassette as described herein in a vector, in particular a nucleic acid vector.

In an aspect, the invention also provides a vector comprising a nucleic acid regulatory element as disclosed herein. In further embodiments, the vector comprises a nucleic acid expression cassette as disclosed herein.

The term 'vector' as used in the application refers to nucleic acid molecules, e.g. double-stranded DNA, which may have inserted into it another nucleic acid molecule (the insert nucleic acid molecule) such as, but not limited to, a cDNA molecule. The vector is used to transport the insert nucleic acid molecule into a suitable host cell. A vector may contain the necessary elements that permit transcribing the insert nucleic acid molecule, and, optionally, translating the transcript into a polypeptide. The insert nucleic acid molecule may be derived from the host cell, or may be derived from a different cell or organism. Once in the host cell, the vector can replicate independently of, or coincidental with, the host chromosomal DNA, and several copies of the vector and its inserted nucleic acid molecule may be generated. The vectors can be episomal vectors (i.e., that do not integrate into the genome of a host cell), or can be vectors that integrate into the host cell genome. The term 'vector' may thus also be defined as a gene delivery vehicle that facilitates gene transfer into a target cell. This definition includes both non-viral and viral vectors. Non-viral vectors include but are not limited to cationic lipids, liposomes, nanoparticles, PEG, PEI, plasmid vectors (e.g. pUC vectors, bluescript vectors (pBS) and pBR322 or derivatives thereof that are devoid of bacterial sequences (minicircles)) transposons-based vectors (e.g. PiggyBac (PB) vectors or Sleeping Beauty (SB) vectors), etc. Viral vectors are derived from viruses and include but are not limited to retroviral, lentiviral, adeno-associated viral, adenoviral, herpes viral, hepatitis viral vectors or the like. Typically, but not necessarily, viral vectors are replication-deficient as they have lost the ability to propagate in a given cell since viral genes essential for replication have been eliminated from the viral vector. However, some viral vectors can also be adapted to replicate specifically in a given cell, such as e.g. a cancer cell, and are typically used to trigger the (cancer) cell-specific (onco)lysis. Virosomes are a non-limiting example of a vector that comprises both viral and non-viral elements, in particular they combine liposomes with an inactivated HIV or influenza virus (Yamada et al., 2003). Another example encompasses viral vectors mixed with cationic lipids.

In preferred embodiments, the vector is a viral vector, such as a retroviral, lentiviral, adenoviral, or adeno-associated viral (AAV) vector, more preferably an AAV vector. AAV vectors are preferably used as self-complementary, double-stranded AAV vectors (scAAV) in order to overcome one of the limiting steps in AAV transduction (i.e. single-stranded to double-stranded AAV conversion) (McCarty, 2001, 2003; Nathwani et al, 2002, 2006, 2011; Wu et al., 2008), and also the use of single-stranded AAV vectors (ssAAV) are also encompassed herein (FIGS. 9 A) and B)).

AAV serotype 9 (AAV9) is ideally suited to achieve efficient transduction in heart and skeletal muscle. Accordingly, in particularly preferred embodiments, the vector is an AAV9 vector.

Production of AAV vector particles can e.g. be achieved by transient co-transfection of AAV-reporter and AAV helper constructs, encoding AAV serotype 9 capsids into HEK293 cells, followed by a purification step based on cesium chloride (CsCl) density gradient ultracentrifugation, as described (Vanden Driessche et al., 2007).

Since the nucleic acid regulatory elements are de facto modular, also combinations of the best diaphragm-specific nucleic acid regulatory elements with any other muscle-specific and/or cardiac specific nucleic acid regulatory elements to maximize expression in the desired target tissue are tested. Consequently, this can lead to the generation of a versatile muscle-specific nucleic acid regulatory element platform tailor-made for diseases that affect skeletal muscle, diaphragm and in some cases also heart (e.g. MTM or GSD II). Furthermore, the diaphragm-specific nucleic acid regulatory elements can also be combined with other promoters or nucleic acid regulatory elements active in other target tissues.

In other embodiments, the vector is a non-viral vector, preferably a plasmid, a minicircle, or a transposon-based vector, such as a Sleeping Beauty(SB)-based vector or piggyBac(PB)-based vector.

In yet other embodiments, the vector comprises viral and non-viral elements.

In particular embodiments, the invention provides a vector comprising a nucleic acid expression cassette comprising a nucleic acid regulatory element comprising, consisting essentially of, or consisting of a nucleic acid regulatory element selected from the group consisting of SEQ ID NO:1 to 89 a promoter, preferably the promoter from the desmin gene, an MVM intron, a transgene, preferably a transgene encoding microdystrophin 1/2 or an exon-skipping construct thereof, and a polyadenylation signal. Alternatively, any one of the following transgenes can introduced: secretable proteins, in particular secretable therapeutic proteins, including glucosidase, follistatin, clotting factors, such as factor VIII or factor IX, insulin, erythropoietin, lipoprotein lipase, antibodies or nanobodies, growth factors, cytokines, chemokines, plasma factors etc.; or structural proteins such as structural therapeutic proteins, including myotubularin, dysferlin, follistatin, microdystrophin 1, dystrophin and sarcoglycans. In embodiments, the transgene comprises the microdystrophin 1 (MD1 or 2) gene or the follistatin (FS7) gene, preferably the exon-skipping construct of follistatin.

In particular embodiments, the invention provides a vector comprising a nucleic acid expression cassette comprising a nucleic acid regulatory element comprising, consisting essentially of, or consisting of a nucleic acid regulatory element selected from the group consisting of SEQ ID NO:1 to 89, a promoter, preferably the promoter from the desmin gene, an MVM intron, a transgene, preferably a transgene encoding follistatin, and a polyadenylation signal. Alternatively, any one of the following transgenes can introduced: secretable proteins, in particular secretable therapeutic proteins, including glucosidase, follistatin, clotting factors, such as factor VIII or factor IX, insulin, erythropoietin, lipoprotein lipase, antibodies or nanobodies, growth factors, cytokines, chemokines, plasma factors etc.; or structural proteins such as structural therapeutic proteins, including myotubularin, dysferlin, follistatin, microdystrophin 1, dystrophin and sarcoglycans. In embodiments, the transgene comprises the microdystrophin 1 (MD1 or 2) gene or the follistatin (FS7) gene, preferably the exon-skipping construct of follistatin.

The nucleic acid expression cassettes and vectors disclosed herein may be used, for example, to express proteins that are normally expressed and utilized in muscle (i.e. structural proteins), or to express proteins that are expressed in muscle and that are then exported to the blood stream for transport to other portions of the body (i.e. secretable proteins). For example, the expression cassettes and vectors disclosed herein may be used to express a therapeutic amount of a gene product (such as a polypeptide, in particular a therapeutic protein, or RNA) for therapeutic purposes, in particular for gene therapy. Typically, the gene product is encoded by the transgene within the expression cassette or vector, although in principle it is also possible to increase expression of an endogenous gene for therapeutic purposes. In an alternative example, the expression cassettes and vectors disclosed herein may be used to express an immunological amount of a gene product (such as a polypeptide, in particular an immunogenic protein, or RNA) for vaccination purposes.

The nucleic acid expression cassettes and vectors as taught herein may be formulated in a pharmaceutical composition with a pharmaceutically acceptable excipient, i.e., one or more pharmaceutically acceptable carrier substances and/or additives, e.g., buffers, carriers, excipients, stabilisers, etc. The pharmaceutical composition may be provided in the form of a kit.

The term "pharmaceutically acceptable" as used herein is consistent with the art and means compatible with the other ingredients of the pharmaceutical composition and not deleterious to the recipient thereof.

Accordingly, a further aspect of the invention relates to a pharmaceutical composition comprising a nucleic acid expression cassette or a vector described herein.

The use of nucleic acid regulatory elements described herein for the manufacture of these pharmaceutical compositions is also disclosed herein.

In embodiments, the pharmaceutical composition may be a vaccine. The vaccine may further comprise one or more adjuvants for enhancing the immune response. Suitable adjuvants include, for example, but without limitation, saponin, mineral gels such as aluminium hydroxide, surface active substances such as lysolecithin, pluronic polyols, polyanions, peptides, oil or hydrocarbon emulsions, bacilli Calmette-Guerin (BCG), *Corynebacterium parvum*, and the synthetic adjuvant QS-21. Optionally, the vaccine may further comprise one or more immunostimulatory molecules. Non-limiting examples of immunostimulatory molecules include various cytokines, lymphokines and chemokines with immunostimulatory, immunopotentiating, and pro-inflammatory activities, such as interleukins (e.g., IL-1, IL-2, IL-3, IL-4, IL-12, IL-13); growth factors (e.g., granulocyte-macrophage (GM)-colony stimulating factor (CSF)); and other immunostimulatory molecules, such as macrophage inflammatory factor, Flt3 ligand, B7.1; B7.2, etc.

In a further aspect, the invention relates to the nucleic acid regulatory elements, the nucleic acid expression cassettes, the vectors, or the pharmaceutical compositions described herein for use in medicine.

As used herein, the terms "treat" or "treatment" refer to both therapeutic treatment and prophylactic or preventative measures. Beneficial or desired clinical results include, but are not limited to, prevention of an undesired clinical state or disorder, reducing the incidence of a disorder, alleviation of symptoms associated with a disorder, diminishment of extent of a disorder, stabilized (i.e., not worsening) state of a disorder, delay or slowing of progression of a disorder, amelioration or palliation of the state of a disorder, remission (whether partial or total), whether detectable or undetectable, or combinations thereof. "Treatment" can also mean prolonging survival as compared to expected survival if not receiving treatment.

As used herein, the terms "therapeutic treatment" or "therapy" and the like, refer to treatments wherein the object is to bring a subjects body or an element thereof from an undesired physiological change or disorder to a desired state, such as a less severe or unpleasant state (e.g., amelioration or palliation), or back to its normal, healthy state (e.g., restoring the health, the physical integrity and the physical well-being of a subject), to keep it at said undesired physiological change or disorder (e.g., stabilization, or not worsening), or to prevent or slow down progression to a more severe or worse state compared to said undesired physiological change or disorder.

As used herein the terms "prevention", "preventive treatment" or "prophylactic treatment" and the like encompass preventing the onset of a disease or disorder, including reducing the severity of a disease or disorder or symptoms associated therewith prior to affliction with said disease or disorder. Such prevention or reduction prior to affliction refers to administration of the nucleic acid regulatory elements, the nucleic acid expression cassettes, the vectors, or the pharmaceutical compositions described herein to a patient that is not at the time of administration afflicted with clear symptoms of the disease or disorder. "Preventing" also encompasses preventing the recurrence or relapse-prevention of a disease or disorder for instance after a period of improvement. In embodiments, the nucleic acid regulatory elements according to any one of SEQ ID NO:1 to 7, 10 to 65, 82, and 83 (cf. Dph-CRE1 to 7, 10 to 65, 82, and 83 in Table 3), the nucleic acid expression cassettes, the vectors, or the pharmaceutical compositions described herein may be for use in gene therapy, in particular diaphragm and skeletal muscle-directed gene therapy. Alternatively, the nucleic acid regulatory elements according to any one of SEQ ID No: 1 to 9, 66 to 81, and 84 to 89. (cf. Dph-CRE1 to 9, 66 to 81, and 84 to 89 in Table 4). the nucleic acid expression cassettes, the vectors, or the pharmaceutical compositions described herein may be for use in gene therapy, in particular diaphragm-, skeletal muscle- and heart-directed gene therapy.

Also disclosed herein is the use of the nucleic acid regulatory elements according to any one of SEQ ID NO: 1 to 7, 10 to 65, 82, and 83 (cf. Dph-CRE1 to 7, 10 to 65, 82, and 83 in Table 3), the nucleic acid expression cassettes, the vectors, or the pharmaceutical compositions described herein for the manufacture of a medicament for gene therapy, in particular diaphragm and skeletal muscle-directed gene therapy.

Also disclosed herein is the use of the nucleic acid regulatory elements according to any one of SEQ ID No: 1 to 9, 66 to 81, and 84 to 89. (cf. Dph-CRE1 to 9, 66 to 81, and 84 to 89 in Table 4), the nucleic acid expression cassettes, the vectors, or the pharmaceutical compositions described herein for the manufacture of a medicament for gene therapy, in particular diaphragm-, skeletal muscle- and heart-directed gene therapy.

Also disclosed herein is a method for gene therapy, in particular diaphragm and skeletal muscle-directed gene therapy in a subject in need of said gene therapy comprising:

introducing in the subject, in particular in diaphragm and/or skeletal muscle tissue or cells of the subject, a nucleic acid expression cassette, a vector or a pharmaceutical composition described herein, wherein the nucleic acid expression cassette, the vector or the pharmaceutical composition comprises a nucleic acid regulatory element according to any one of SEQ ID NO: 1 to 7, 10 to 65, 82, and 83 (cf. Dph-CRE1 to 7, 10 to 65, 82, and 83 in Table 3), operably linked to a promoter and a transgene; and expressing a therapeutically effective amount of the transgene product in the subject, in particular in diaphragm and/or skeletal muscle tissue or cells of the subject.

Also disclosed herein is a method for gene therapy, in particular diaphragm-, skeletal muscle- and heart-directed gene therapy in a subject in need of said gene therapy comprising:

introducing in the subject, in particular in diaphragm-, skeletal muscle- and heart-tissue or cells of the subject a nucleic acid expression cassette, a vector or a pharmaceutical composition described herein, wherein the nucleic acid expression cassette, the vector or the pharmaceutical composition comprises a nucleic acid regulatory element according to any one of SEQ ID No: 1 to 9, 66 to 81, and 84 to 89. (cf. Dph-CRE1 to 9, 66 to 81, and 84 to 89 in Table 4), operably linked to a promoter and a transgene; and expressing a therapeutically effective amount of the transgene product in the subject, in particular in diaphragm-, skeletal muscle-, and heart-tissue or cells of the subject.

The transgene product may be any one of the following transgenes can introduced: secretable proteins, in particular secretable therapeutic proteins, including glucosidase, follistatin, clotting factors, such as factor VIII or factor IX, insulin, erythropoietin, lipoprotein lipase, antibodies or nanobodies, growth factors, cytokines, chemokines, plasma factors etc.; or structural proteins such as structural therapeutic proteins, including myotubularin, dysferlin, follistatin, microdystrophin 1, dystrophin and sarcoglycans. In embodiments, the transgene comprises the microdystrophin 1 (MD1 or 2) gene or the follistatin (FS7) gene, preferably the exon-skipping construct of follistatin. In particular embodiments, the transgene product is follistatin or micro-dystrophin, in particular microdystrophin 1 (MTM1). Alternatively, the transgene product may be RNA, such as siRNA.

Exemplary diseases and disorders that may benefit from gene therapy using the nucleic acid regulatory elements, the nucleic acid expression cassettes, the vectors, or the pharmaceutical compositions described herein include myotubular myopathy (MTM), Pompe disease, muscular dystrophy (e.g. Duchenne muscular dystrophy (DMD)/Becker muscular dystrophy (BMD)), myotonic dystrophy, Myotonic Muscular Dystrophy (DM), Miyoshi myopathy, Fukuyama type congenital, muscular dystrophy, dysferlinopathies neuromuscular disease, motor neuron diseases (MND), such as e.g. Charcot-Marie-Tooth disease (CMT), spinal muscular atrophy (SMA), and amyotrophic lateral sclerosis (ALS), Emery-Dreifuss muscular dystrophy, facioscapulohumeral muscular dystrophy (FSHD), congenital muscular dystrophies, congenital myopathies, limb girdle muscular dystrophy, metabolic myopathies, muscle inflammatory diseases, myasthenia, mitochondrial myopathies, anomalies of ionic channels, nuclear envelop diseases, cardiomyopathies, cardiac hypertrophy, heart failure, distal myopathies, cardiovascular diseases, hemophilia, including hemophilia A and B, and diabetes. In addition, many neuromuscular disorders affect respiratory function due to weakening of the diaphragm and respiratory muscles (www.medscape.com/viewarticle/805299_3) Semin Respir Crit Care Med. 2002 June; 23(3):191-200). Causes of diseases of the diaphragm vary, but they can be due to gene defects that influence diaphragm function directly. In particular, there are multiple genetic disorders that are due to mutations in genes that affect the function of the diaphragm, often in combination with abnormalities at the level of skeletal muscles and/or heart. For example, myotubular myopathy (MTM) is due to mutations in the myotubularin gene and affects the skeletal muscle and diaphragm. Patients suffering from MTM typically present with hypotonia, generalized muscle weakness and respiratory failure at birth. Survival beyond the postnatal period requires intensive support, often including gastrostomy feeding and mechanical ventilation. Because of their severe breathing problems, patients suffering from MTM typically do not live past age 2. For MTM, muscle-directed gene therapy is currently the only clinically relevant option. Alternatively, Pompe's disease (also referred to as glycogen storage disorder type II or GSD II) mainly affects skeletal muscle, diaphragm and heart. GSD II results in deficiency of the lysosomal enzyme acid α-glucosidase (GAA) that leads to a lysosomal storage defect. In GSD II patients, glycogen cannot be broken down effectively into glucose. The accumulation of glycogen in GSD II patients causes myopathy with progressive muscle weakness. Without medical intervention, patients suffering from the most severe form of GSD II die because of respiratory failure within the first year of life. Other muscle diseases such as Duchenne muscular dystrophy (DMD) afflicts approximately one in 3500 live male births. The disease leads to a progressive destruction of skeletal muscles, including the diaphragm, the most affected individuals die of ventilatory failure in the third decade of life. Many other myopathies also affect pulmonary function, including—but not limited to—polymyositis/dermatomyositis, hereditary channel disorders, mitochondrial encephalomyopathies, acid maltase deficiency, and congenital myopathy, disuse atrophy. Other diseases affecting diaphragm include Congenital Muscular Dystrophy (CMD), Becker Muscular Dystrophy (BMD), Facioscapulohumeral Muscular Dystrophy (FSHD), Limb Girdle Muscular Dystrophy (LGMD), Myotonic Muscular Dystrophy (DM), Miyoshi myopathy, Fukuyama type congenital muscular dystrophy, dysferlinopathies. Also many neuropathic disorders weaken the diaphragm and respiratory muscles. This includes amyotrophic lateral sclerosis, poliomyelitis, postpolio syndrome, Kennedy syndrome, stroke, multiple sclerosis, spinal muscular atrophy, syringomyelia, neuralgic neuropathy, and motor neuron diseases. Brachial plexitis and isolated unilateral or bilateral phrenic neuropathies can also weaken the diaphragm significantly. Peripheral neuropathies affecting respiration are primarily acute disorders such as Guillain-Barre syndrome, *porphyria*, and critical illness neuropathy, but chronic diseases such as chronic inflammatory demyelinating polyneuropathy (CIDP) and Charcot-Marie-Tooth disease (CMT) can also cause respiratory insufficiency. Disorders of neuromuscular transmission such as Lambert-Eaton syndrome, and myasthenia gravis often affect respiration. Alternatively, diaphragm dysfunction can be the result of congenital defects resulting in anatomical abnormalities (e.g. Arnold-Chiari malformation) or acquired defects, which occur as the result of an injury, trauma, infection (e.g. West Nile virus, botulism), exposure to, organophosphates, radiation therapy, malnutrition, tumour compression or surgery. Cold cardioplegia used in cardiac surgery is another common cause of phrenic nerve injury. In addition, radiation therapy can affect the phrenic nerve resulting in diaphragmatic dysfunction. Obstructive airway diseases that affect the lungs, such as chronic obstructive pulmonary disease (COPD) and asthma, can result in significant hyperinflation resulting in diaphragmatic disadvantage and weakness. Finally, it is known that lupus and thyroid disorders can also contribute to diaphragm dysfunction.

Gene therapy protocols have been extensively described in the art. These include, but are not limited to, intramuscular injection of plasmid (naked or in liposomes), hydrodynamic gene delivery in various tissues, including muscle, interstitial injection, instillation in airways, application to endothelium, intra-hepatic parenchyme, and intravenous or intra-arterial administration. Various devices have been developed for enhancing the availability of DNA to the target cell. A simple approach is to contact the target cell physically with catheters or implantable materials containing DNA. Another approach is to utilize needle-free, jet injection devices which project a column of liquid directly into the target tissue under high pressure. These delivery paradigms can also be used to deliver vectors. Another approach to targeted gene delivery is the use of molecular conjugates, which consist of protein or synthetic ligands to which a nucleic acid- or DNA-binding agent has been attached for the specific targeting of nucleic acids to cells (Cristiano et al., 1993). In embodiments, the nucleic acid regulatory elements, the nucleic acid expression cassettes, the vectors, or the pharmaceutical compositions described herein may be for use as a vaccine, more particularly for use as a prophylactic vaccine.

Also disclosed herein is the use of the nucleic acid regulatory elements, the nucleic acid expression cassettes, the vectors, or the pharmaceutical compositions described herein for the manufacture of medicament or a vaccine, in particular for the manufacture of a prophylactic vaccine.

Also disclosed herein is a method of vaccination, in particular prophylactic vaccination, of a subject in need of said vaccination comprising:

introducing in the subject, in particular in diaphragm-, and skeletal muscle-tissue or cells of the subject, a nucleic acid expression cassette, a vector or a pharmaceutical composition described herein, wherein the nucleic acid expression cassette, the vector or the pharmaceutical composition comprises a nucleic acid regulatory element according to any one of SEQ ID NO:1 to 7, 10 to 65, 82, and 83 (cf. Dph-CRE1 to 7, 10 to 65, 82, and 83 in Table 3), operably linked to a promoter and a transgene; and expressing an immunologically effective amount of the transgene product in the subject, in particular in diaphragm- and skeletal muscle-cells or tissue of the subject.

Also disclosed herein is a method of vaccination, in particular prophylactic vaccination, of a subject in need of said vaccination comprising:

introducing in the subject, in particular in diaphragm, skeletal muscle- and heart-tissue or cells of the subject, a nucleic acid expression cassette, a vector or a pharmaceutical composition described herein, wherein the nucleic acid expression cassette, the vector or the pharmaceutical composition comprises a nucleic acid regulatory element according to any one of SEQ ID No: 1 to 9, 66 to 81, and 84 to 89. (cf. Dph-CRE1 to 9, 66 to 81, and 84 to 89 in Table 4), operably linked to a promoter and a transgene; and expressing an immunologically effective amount of the transgene product in the subject, in particular in diaphragm-, skeletal muscle- and heart-cells or tissue of the subject.

As used herein, a phrase such as "a subject in need of treatment" includes subjects that would benefit from treatment of a recited disease or disorder. Such subjects may include, without limitation, those that have been diagnosed with said disease or disorder, those prone to contract or develop said disease or disorder and/or those in whom said disease or disorder is to be prevented.

The terms "subject" and "patient" are used interchangeably herein and refer to animals, preferably vertebrates, more preferably mammals, and specifically include human patients and non-human mammals. "Mammalian" subjects include, but are not limited to, humans, domestic animals, commercial animals, farm animals, zoo animals, sport animals, pet and experimental animals such as dogs, cats, guinea pigs, rabbits, rats, mice, horses, cattle, cows; primates such as apes, monkeys, orang-utans, and chimpanzees; canids such as dogs and wolves; felids such as cats, lions, and tigers; equids such as horses, donkeys, and zebras; food animals such as cows, pigs, and sheep; ungulates such as deer and giraffes; rodents such as mice, rats, hamsters and guinea pigs; and so on. Preferred patients or subjects are human subjects.

A 'therapeutic amount' or 'therapeutically effective amount' as used herein refers to the amount of gene product effective to treat a disease or disorder in a subject, i.e., to obtain a desired local or systemic effect. The term thus refers to the quantity of gene product that elicits the biological or medicinal response in a tissue, system, animal, or human that is being sought by a researcher, veterinarian, medical doctor or other clinician. Such amount will typically depend on the gene product and the severity of the disease, but can be decided by the skilled person, possibly through routine experimentation.

An "immunologically effective amount" as used herein refers to the amount of (trans)gene product effective to enhance the immune response of a subject against a subsequent exposure to the immunogen encoded by the (trans) gene. Levels of induced immunity can be determined, e.g.

by measuring amounts of neutralizing secretory and/or serum antibodies, e.g., by plaque neutralization, complement fixation, enzyme-linked immunosorbent, or microneutralization assay.

Typically, the amount of (trans)gene product expressed when using an expression cassette or vector as described herein (i.e., with at least one nucleic acid regulatory element) are higher than when an identical expression cassette or vector is used but without a nucleic acid regulatory element therein. More particularly, the expression is at least double as high, at least five times as high, at least ten times as high, at least 20 times as high, at least 30 times as high, at least 40 times as high, at least 50 times as high, or even at least 60 times as high as when compared to the same nucleic acid expression cassette or vector without nucleic acid regulatory element. Preferably, the higher expression remains specific to diaphragm, heart and skeletal muscle tissues or cells. Furthermore, the expression cassettes and vectors described herein direct the expression of a therapeutic amount of the gene product for an extended period. Typically, therapeutic expression is envisaged to last at least 20 days, at least 50 days, at least 100 days, at least 200 days, and in some instances 300 days or more. Expression of the gene product (e.g. polypeptide) can be measured by any art-recognized means, such as by antibody-based assays, e.g. a Western Blot or an ELISA assay, for instance to evaluate whether therapeutic expression of the gene product is achieved. Expression of the gene product may also be measured in a bioassay that detects an enzymatic or biological activity of the gene product.

Also disclosed herein is the use of the nucleic acid regulatory elements according to SEQ ID NO:1 to 7, 10 to 65, 82, and 83 (cf. Dph-CRE1 to 7, 10 to 65, 82, and 83 in Table 3), or the nucleic acid expression cassettes, or the vectors disclosed herein comprising said nucleic acid regulatory elements, for transfecting or transducing diaphragm, and/or skeletal muscle cells.

Also disclosed herein is the use of the nucleic acid regulatory elements according to SEQ ID No: 1 to 9, 66 to 81, and 84 to 89. (cf. Dph-CRE1 to 9, 66 to 81, and 84 to 89 in Table 4), or the nucleic acid expression cassettes, or the vectors disclosed herein comprising said nucleic acid regulatory elements, for transfecting or transducing diaphragm, skeletal muscle and/or heart, cells.

Further disclosed herein is the use of the nucleic acid expression cassettes or the vectors disclosed herein comprising the nucleic acid regulatory elements according to SEQ ID NO:1 to 7, 10 to 65, 82, and 83 (cf. Dph-CRE1 to 7, 10 to 65, 82, and 83 in Table 3), for expressing a transgene product in diaphragm and/or skeletal muscle cells, wherein the nucleic acid expression cassette or the vector comprises a nucleic acid regulatory element disclosed herein operably linked to a promoter and a transgene.

Further disclosed herein is the use of the nucleic acid expression cassettes or the vectors disclosed herein comprising the nucleic acid regulatory elements according to SEQ ID No: 1 to 9, 66 to 81, and 84 to 89. (cf. Dph-CRE1 to 9, 66 to 81, and 84 to 89 in Table 4), for expressing a transgene product in diaphragm, skeletal muscle, and heart cells, wherein the nucleic acid expression cassette or the vector comprises a nucleic acid regulatory element disclosed herein operably linked to a promoter and a transgene.

Further disclosed herein is a method for expressing a transgene product in diaphragm, and/or skeletal muscle cells, comprising:

transfecting or transducing said cells with a nucleic acid expression cassette or a vector disclosed herein, wherein the nucleic acid expression cassette or the vector comprises a nucleic acid regulatory element according to any one of SEQ ID NO:1 to 7, 10 to 65, 82, and 83 (cf. Dph-CRE1 to 7, 10 to 65, 82, and 83 in Table 3), operably linked to a promoter and a transgene; and expressing the transgene product in said cells.

Further disclosed herein is a method for expressing a transgene product in diaphragm, skeletal muscle and heart cells, comprising:

transfecting or transducing said cells with a nucleic acid expression cassette or a vector disclosed herein, wherein the nucleic acid expression cassette or the vector comprises a nucleic acid regulatory element according to any one of SEQ ID No: 1 to 9, 66 to 81, and 84 to 89. (cf. Dph-CRE1 to 9, 66 to 81, and 84 to 89 in Table 4) operably linked to a promoter and a transgene; and expressing the transgene product in said cells.

Non-viral transfection or viral vector-mediated transduction of diaphragm, heart, and/or skeletal muscle cells may be performed by in vitro, ex vivo or in vivo procedures. The in vitro approach requires the in vitro transfection or transduction of diaphragm, heart, and/or skeletal muscle cells, e.g. cells previously harvested from a subject, cell lines or cells differentiated from e.g. induced pluripotent stem cells or embryonic cells. The ex vivo approach requires harvesting of the diaphragm, skeletal muscle and heart, cells from a subject, in vitro transfection or transduction, and optionally re-introduction of the transfected cells into the subject. The in vivo approach requires the administration of the nucleic acid expression cassette or the vector disclosed herein into a subject. In preferred embodiments, the transfection of the diaphragm, skeletal muscle, and heart cells is performed in vitro or ex vivo.

It is understood by the skilled person that the use of the nucleic acid regulatory elements, the nucleic acid expression cassettes and vectors disclosed herein has implications beyond gene therapy, e.g. coaxed differentiation of stem cells into diaphragm, skeletal muscle, and heart cells, transgenic models for over-expression of proteins in diaphragm, skeletal muscle, and heart etc.

The invention is further explained by the following non-limiting examples

EXAMPLES

Example 1: Identification of Diaphragm-Specific Nucleic Acid Regulatory Elements To identify the diaphragm genes that are highly expressed, the gene expression profiling of the human diaphragm tissue has been investigated compared to that of other tissues such as skeletal muscle, heart, liver, spleen, and kidneys etc. The total RNA samples extracted from each tissue were purchased commercially (Table 1).

TABLE 1

| overview of RNA samples |  |
| --- | --- |
| Diaphragm RNA samples (from Biochain, #R1234169-10) | |
| Diaphragm sample 1 | Male 26 years |
| Diaphragm sample 2 | Male 24 years |

TABLE 1-continued

| overview of RNA samples |  |
| --- | --- |
| Other organs RNA samples (from Clontech, #636643) | |
| Fetal liver | pooled from 3 males/females, age 20-38 weeks |
| Bone marrow | pooled from 4 males/female, age 58-76 |
| Brain (whole) | pooled from 4 males, age 21-29 |
| Kidney | pooled from 1 female, age 40 |
| Liver | pooled from 3 males, age 24-64 |
| Lung | pooled from 3 males/females, age 32-61 |
| Skeletal muscle | pooled from 1 male, age 20 |
| Heart | pooled from 3 males, age 30, 30, 39 |
| Spleen | pooled from 15 males/females, age 22-69 |
| Testis | pooled from 7 males, age 24-87 |
| Colon | pooled from 3 males, age 24-29 |
| Spinal cord | pooled from 7 males, age 20-59 |

Gene expression profiling was performed by RNA next-generation sequencing (RNA-seq). This method provides deep coverage and base pair-level resolution. RNA sequencing quantification is proven to be an efficient alternative to microarray technique in gene expression studies, and it is a critical technology in differential expression analysis.

In this study, RNA-sequencing was achieved using Illumina™ Hiseq 4000 sequencing 50SE (20 clean reads per sample) by BGI (Hong Kong). All samples showed good to excellent quality as high RNA integrity number (RIN) index.

Figure 1:
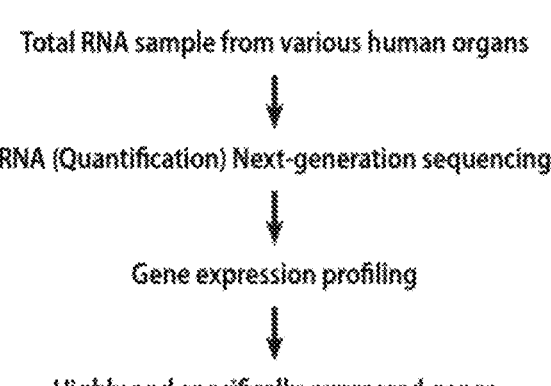
FIG. 1: Flow diagram of the identification of potential nucleic acid regulatory elements specific for diaphragm and skeletal muscle, or specific for diaphragm, skeletal muscle and heart. A computational approach was used to identify the nucleic acid regulatory elements involving the following steps: (1) gene expression profiling of total RNA samples from different human tissues, including human diaphragm tissue, by RNA (Quantification) Next-generation sequencing, (2) comparison of the gene expression profiles to identify genes that are highly and specifically expressed in i) diaphragm and skeletal muscle (17 genes), and ii) diaphragm, skeletal muscle and heart (10 genes), (3) locating the transcription start site of the identified genes using ENSEMBL, and (4) selecting candidate nucleic acid regulatory elements using UCSC Genome Browser database based on i) high DNase hypersensitivity sites; ii) high content of epigenetic markers associated with open chromatin (acetylation, methylation); iii) high content of transcription factor binding sites; iv) strong evolutionary conservation among vertebrates; and v) conserved transcription factor binding sites in 3 species (human, rat, mouse).
Figure 1:
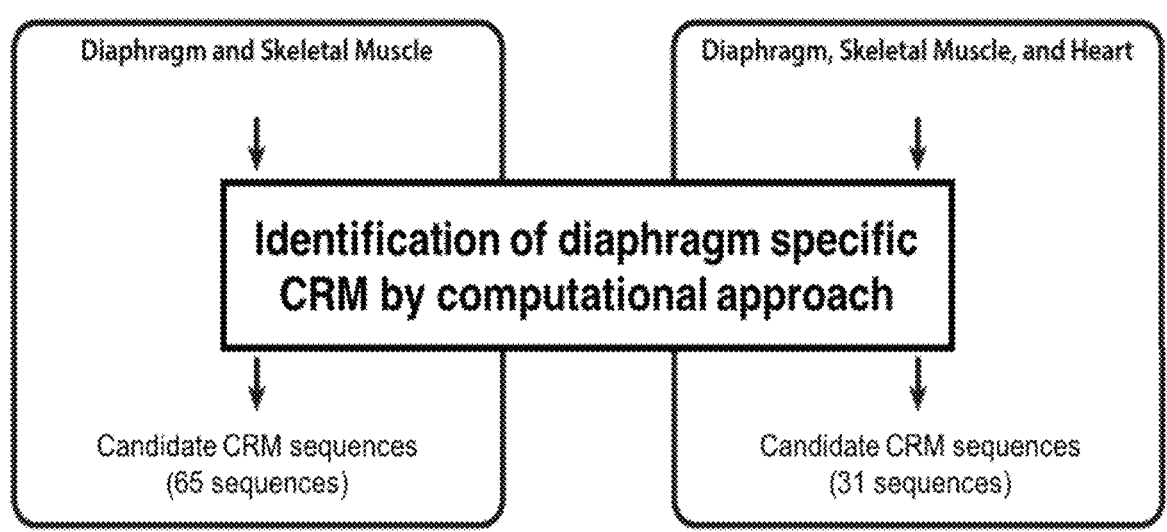
Figure 2:
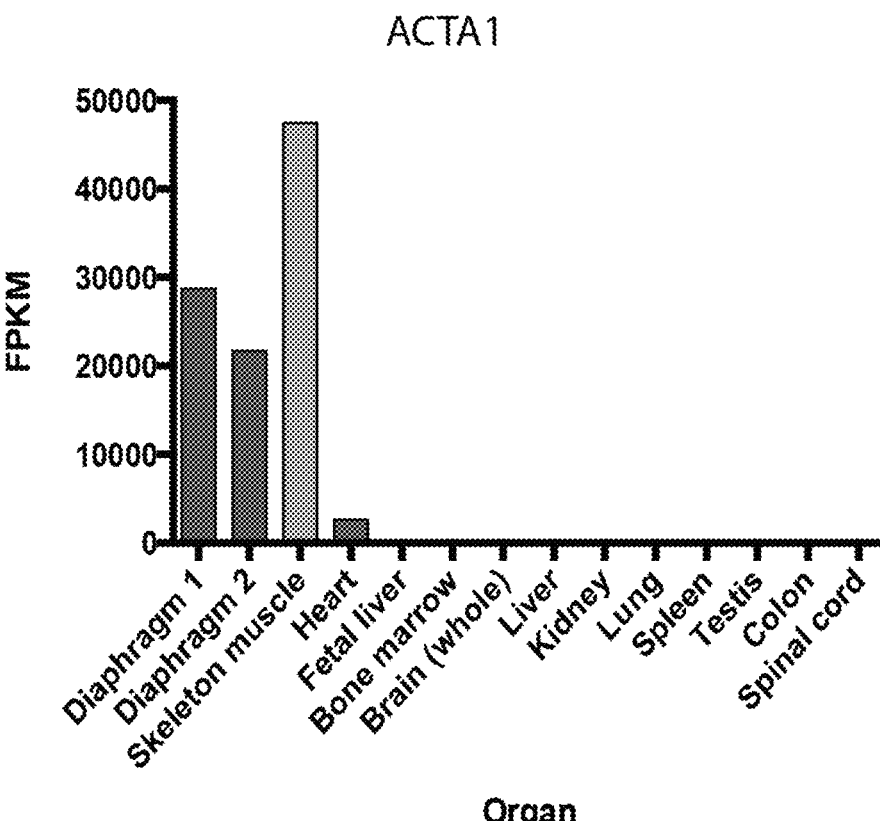
FIG. 2: Expression of the genes ACTA1 (A), CKM (B), TPM2 (C), MYL1 (D), TNNC2 (E), FHL1 (F), TNNT1 (G), TNNI2 (H), MYLPF (I), TNNT3 (J), MYH2 (K), SLN (L), MYBPC1 (M), ENO3 (N), CA3 (0), ATP2A1 (P), MYH1 (Q) in total RNA samples from the recited human tissues. Expression is indicated as Fragments Per Kilobase of transcript per Million mapped reads (FPKM).
Figure 2:
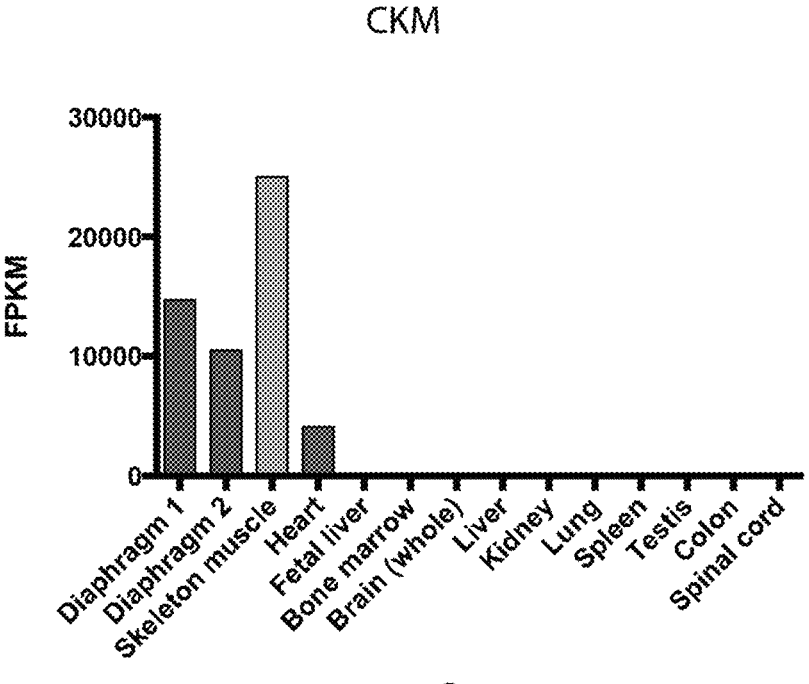
Figure 2:
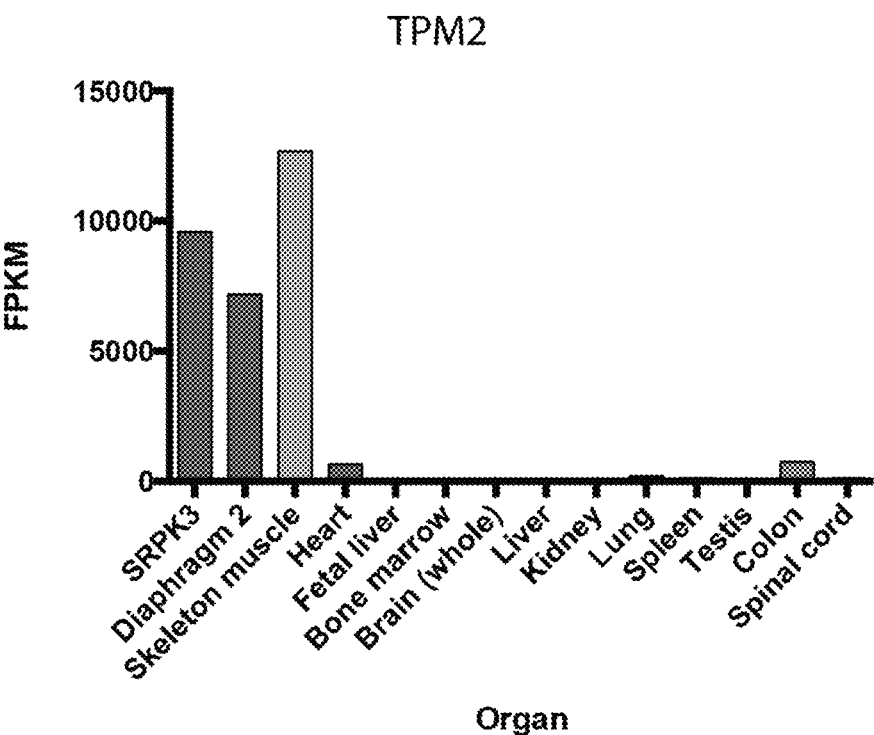
Figure 2:
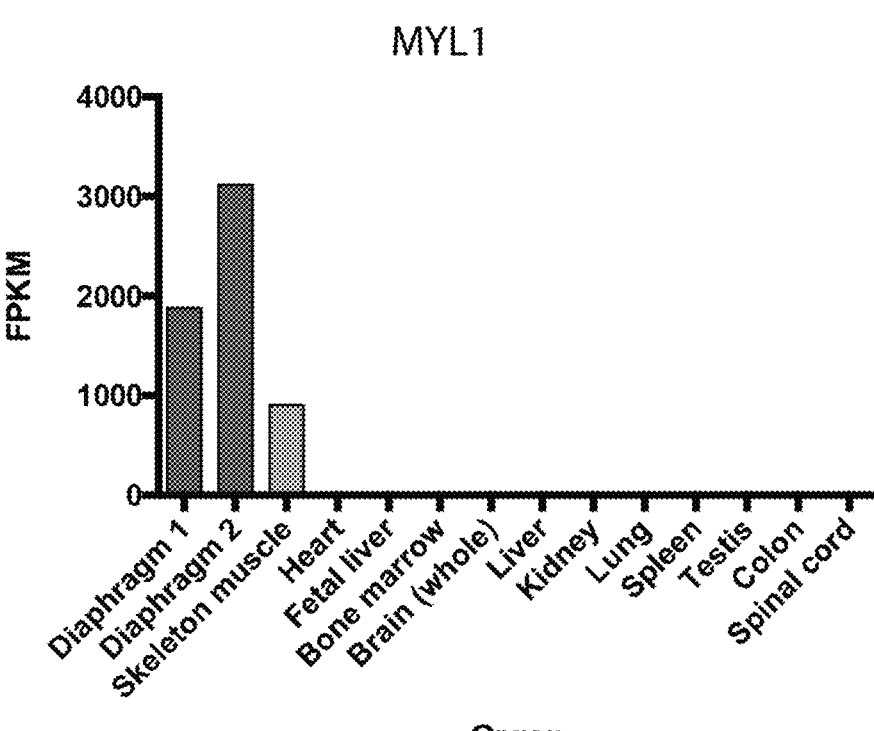
Figure 2:
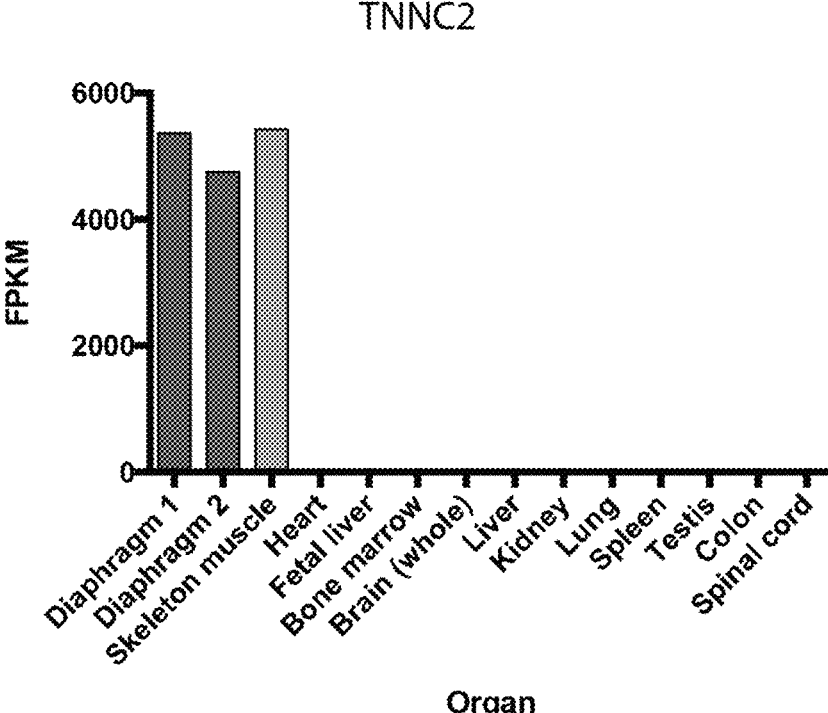
Figure 2:
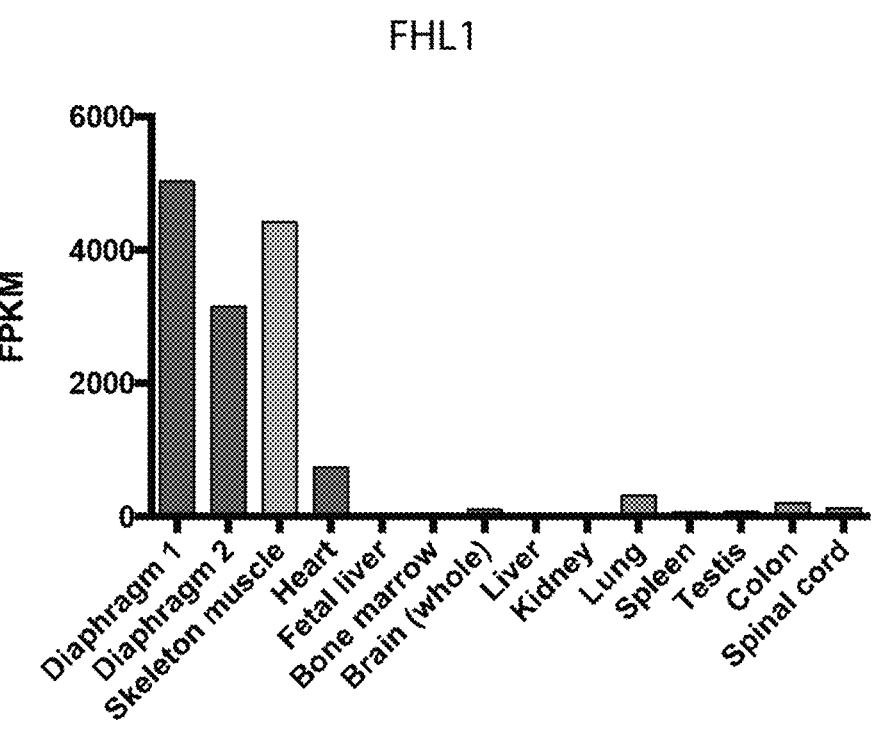
Figure 2:
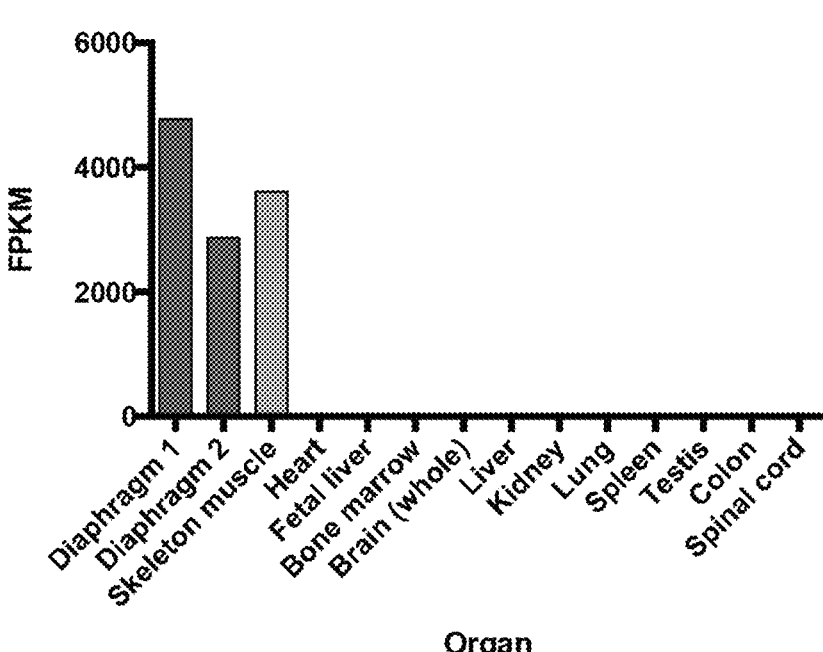
Figure 2:
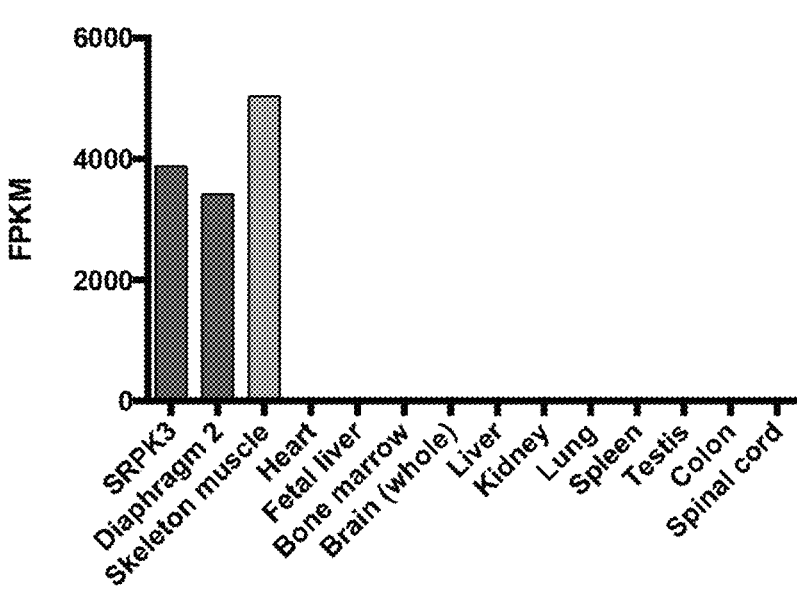
Figure 2:
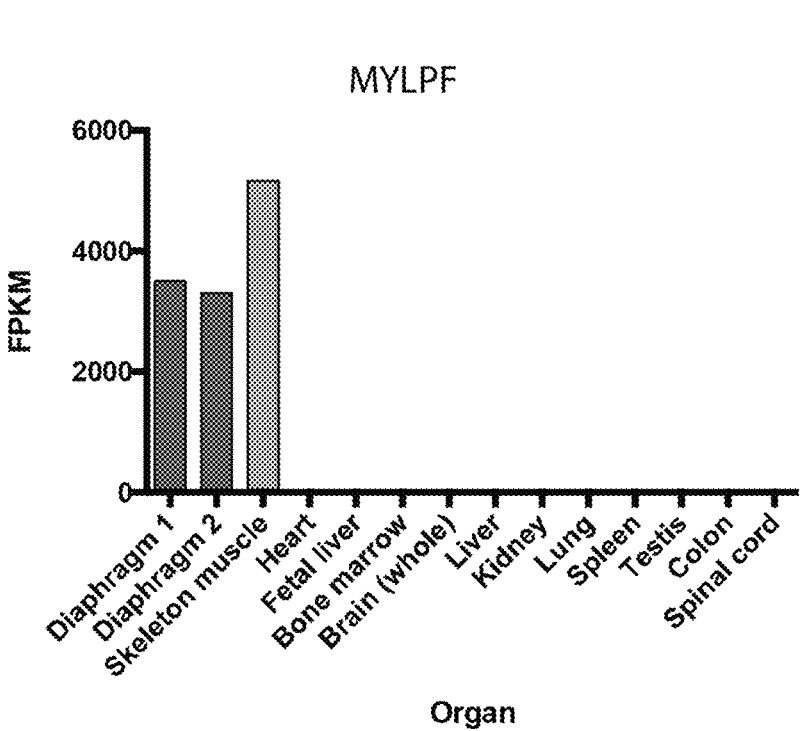
Figure 2:
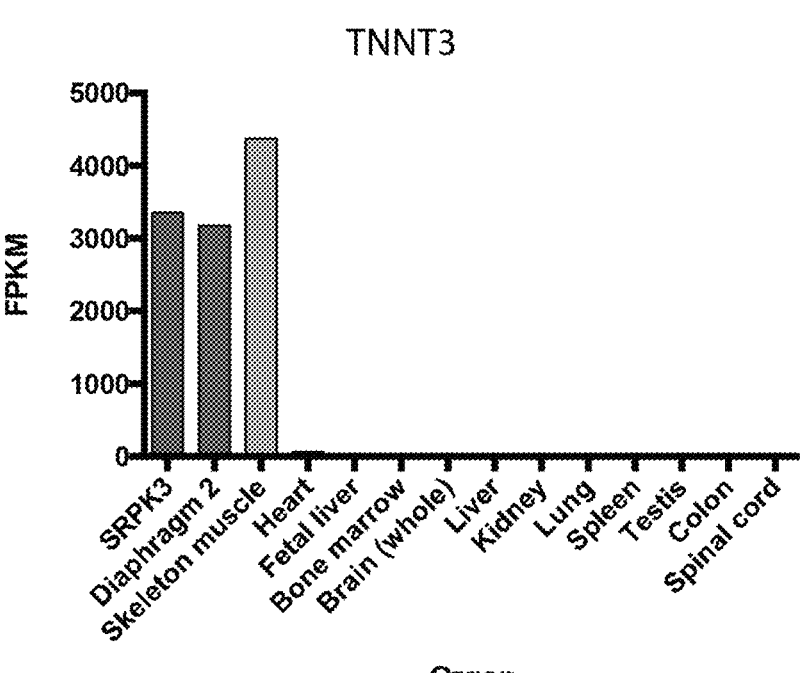
Figure 2:
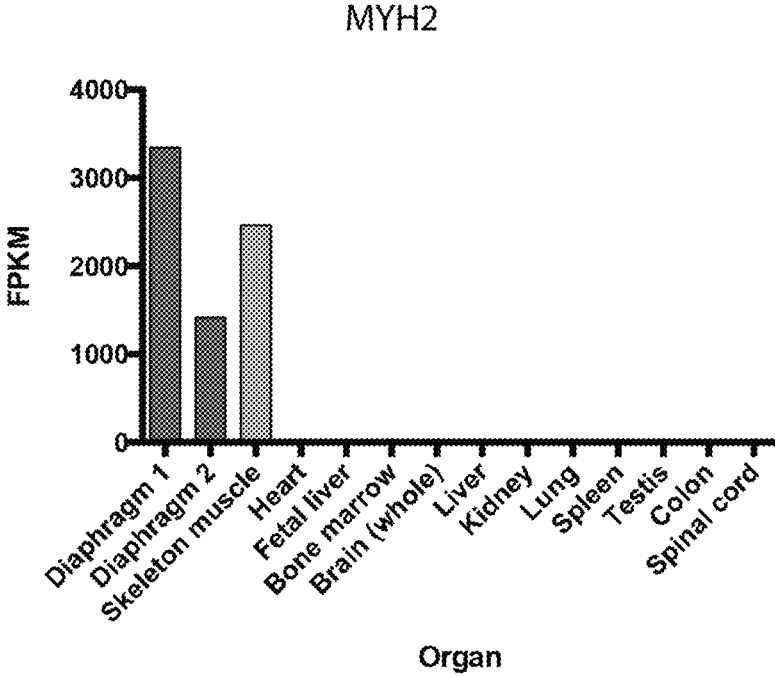
Figure 2:
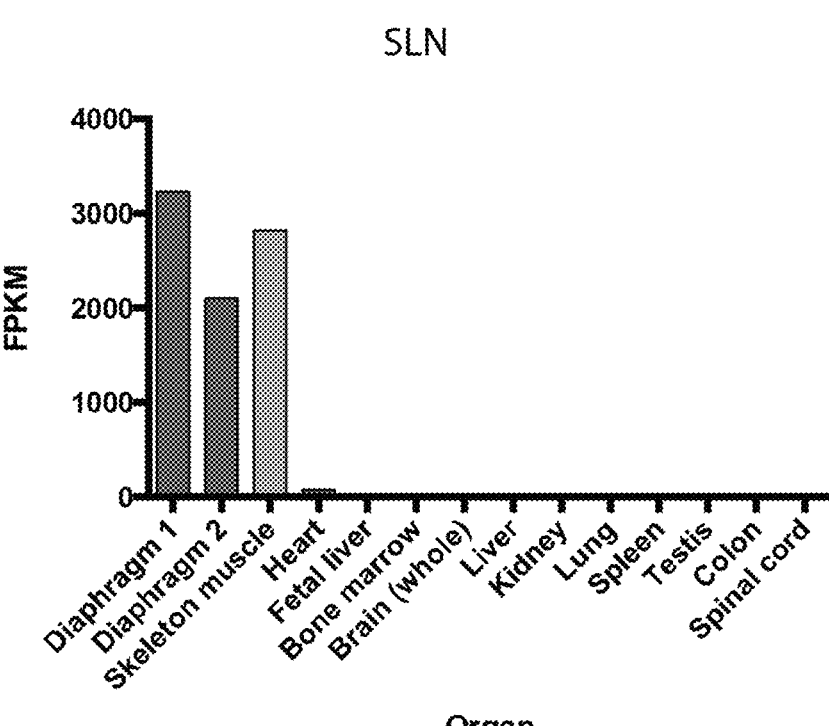
Figure 2:
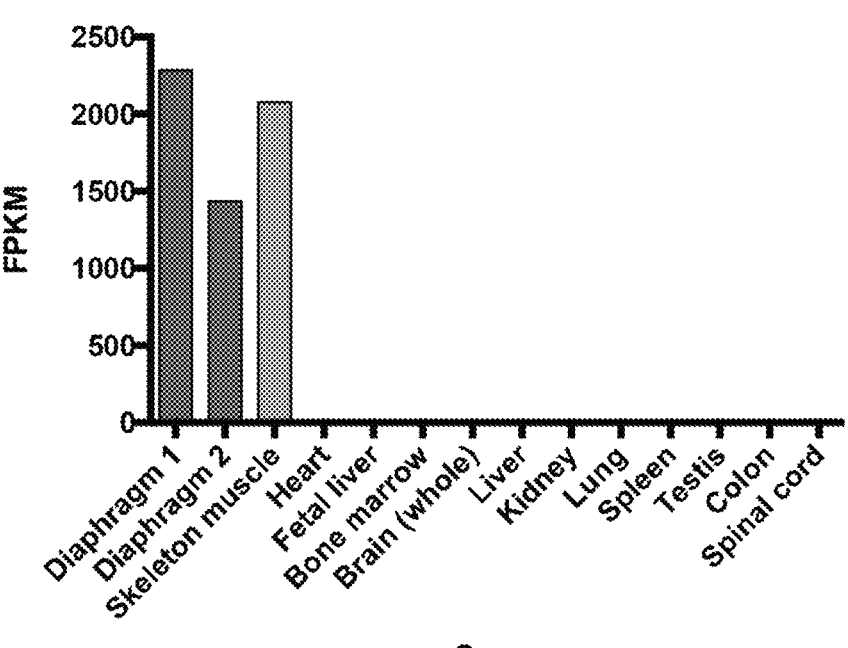
Figure 2:
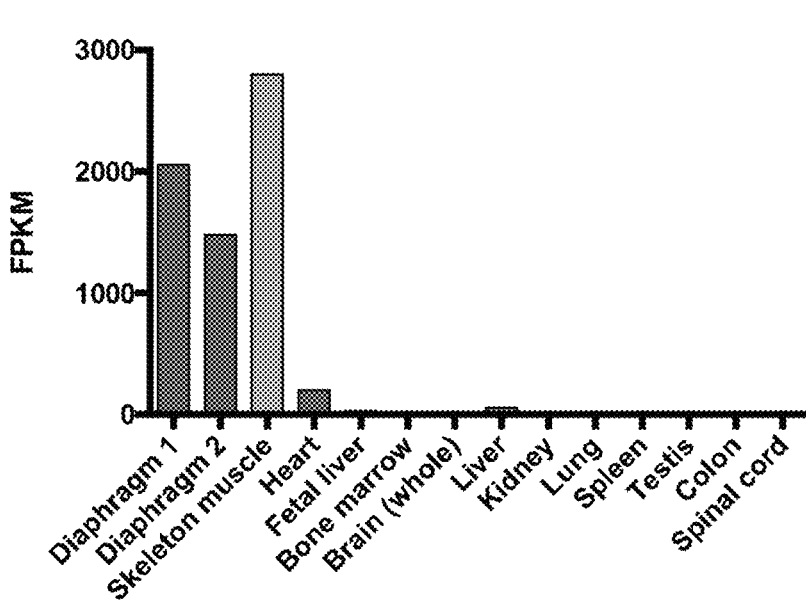
Figure 2:
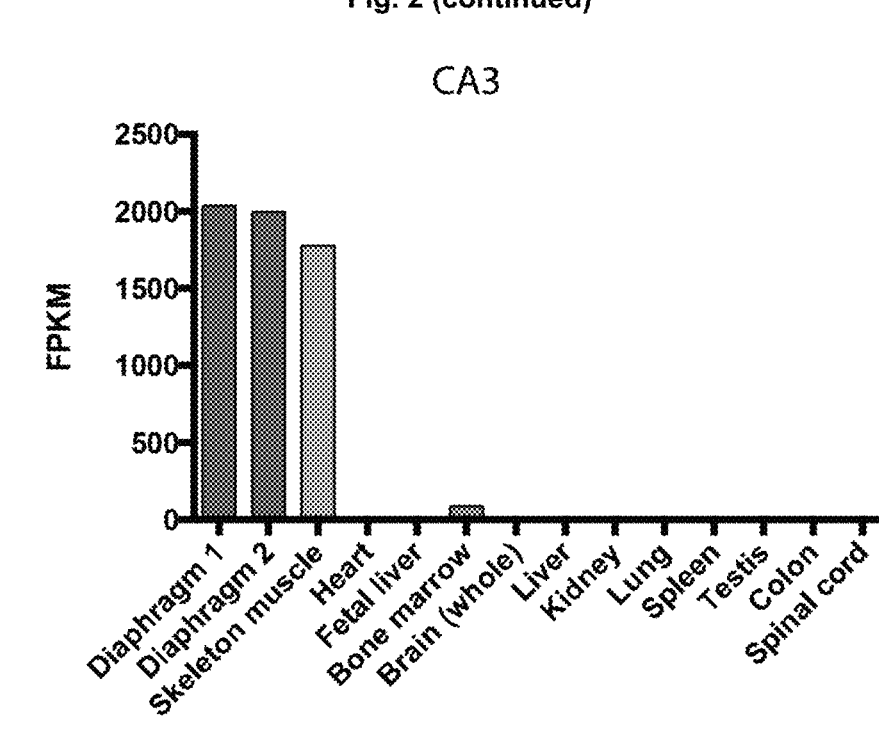
Figure 2:
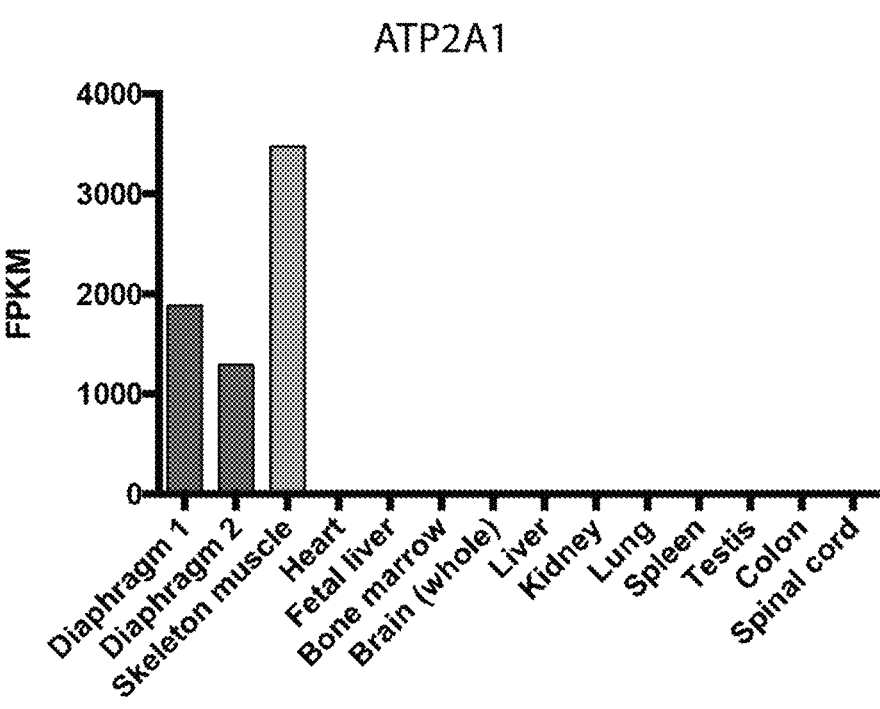
Figure 2:
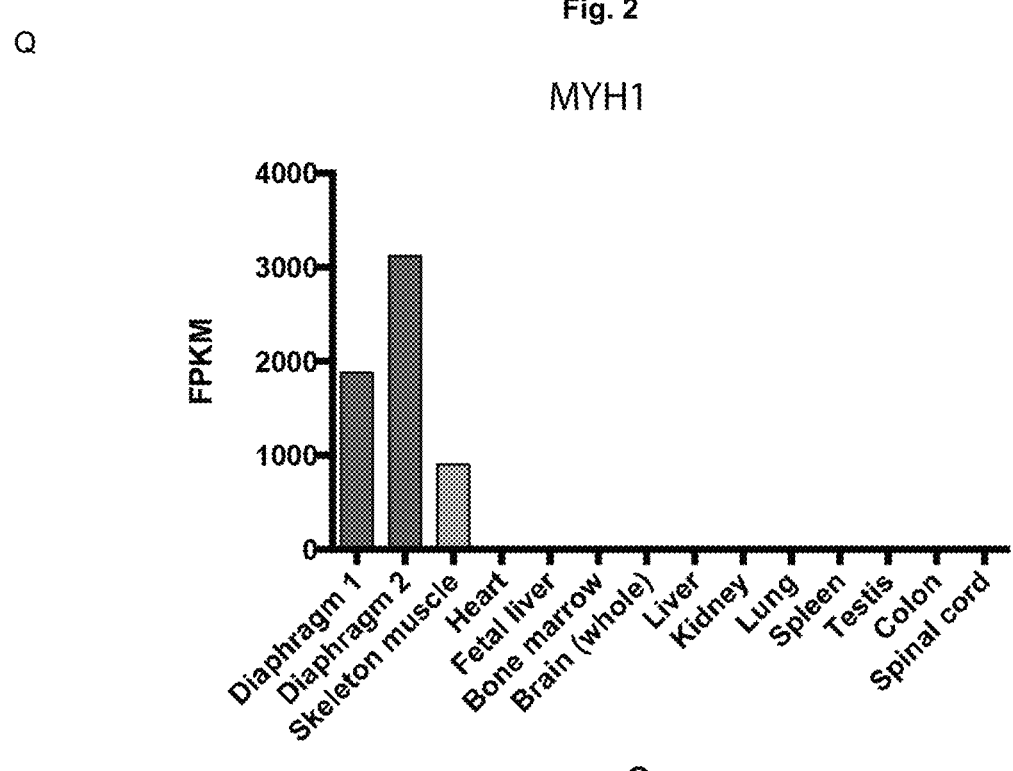
Figure 3:
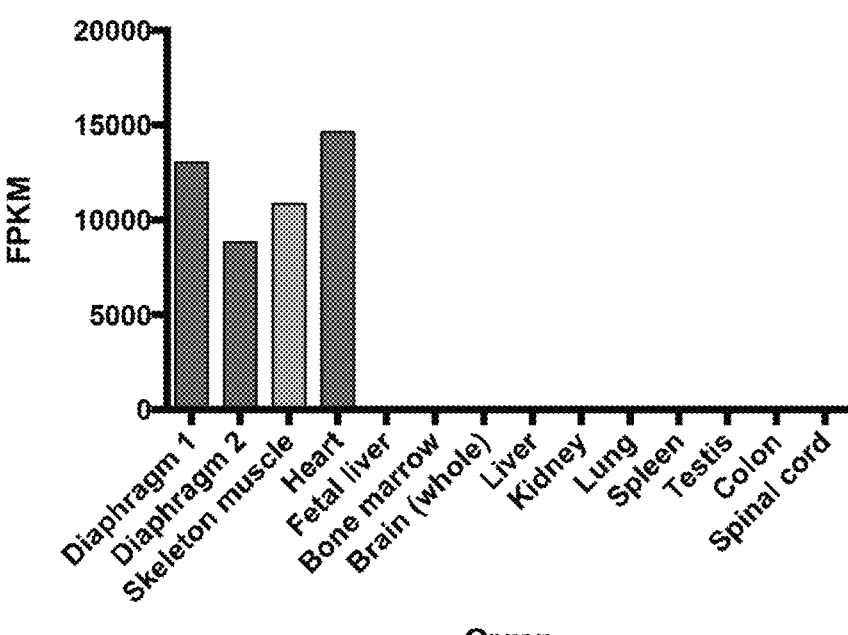
FIG. 3: Expression of the genes MYL2 (A), MB (B), DES (C), TNNC1 (D), TCAP (E), MYH7 (F), ALDOA (G), TPM1 (H) in total RNA samples from the recited human tissues. Expression is indicated as Fragments Per Kilobase of transcript per Million mapped reads (FPKM).
Figure 3:
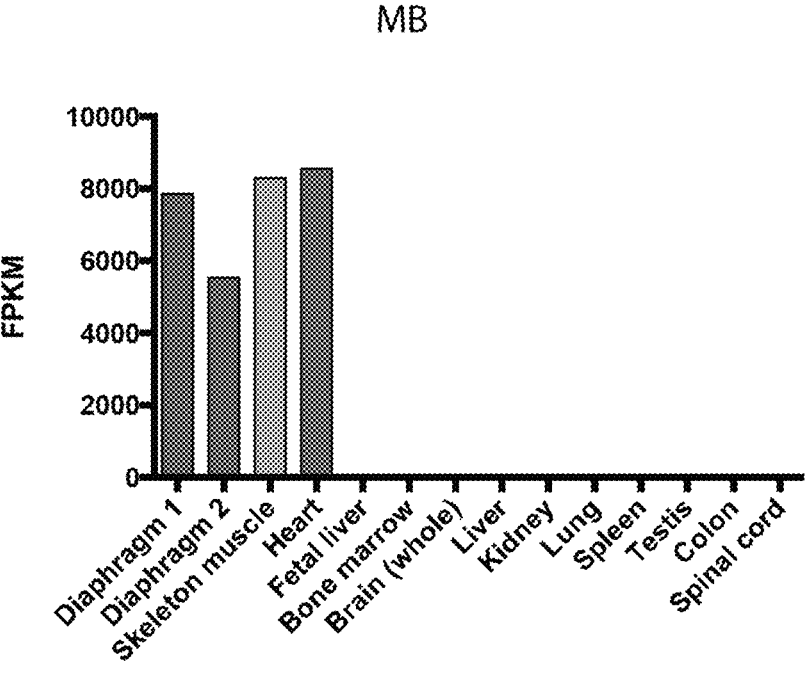
Figure 3:
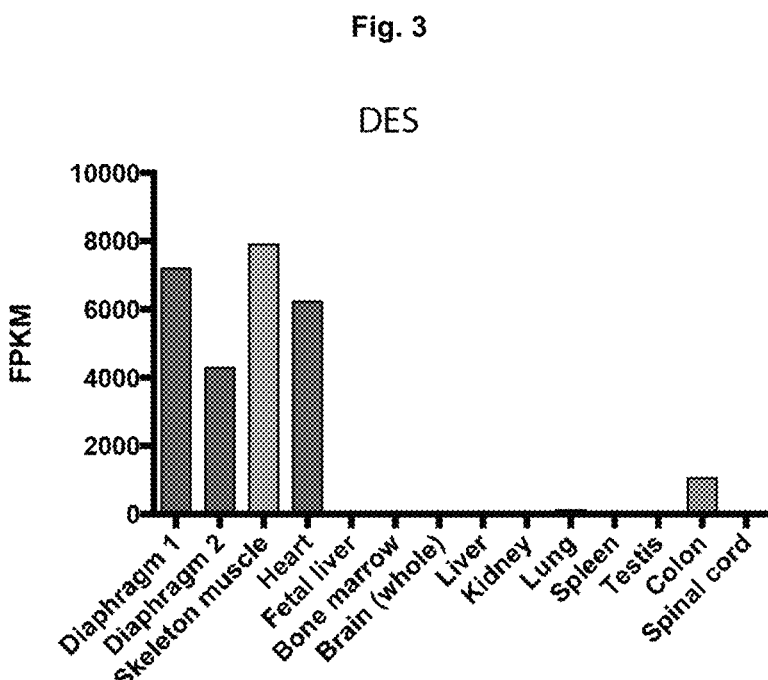
Figure 3:
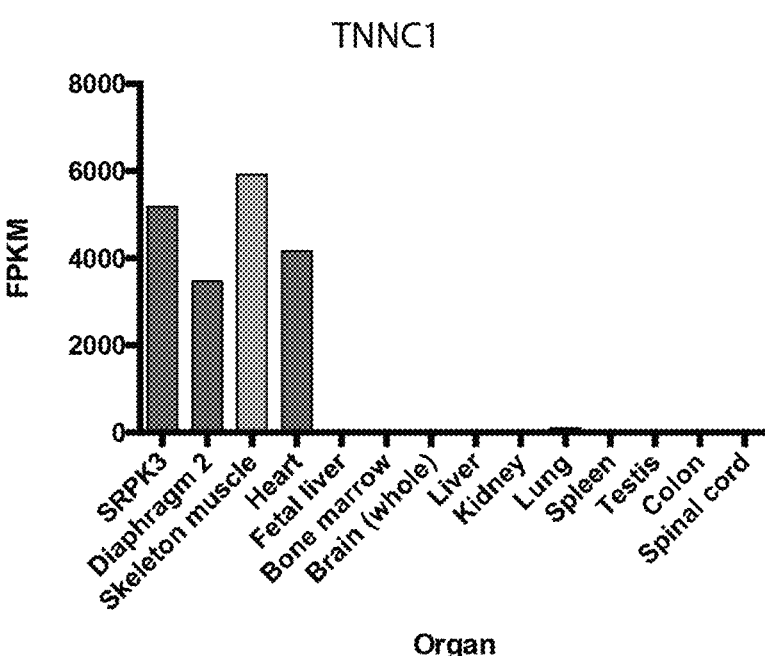
Figure 3:
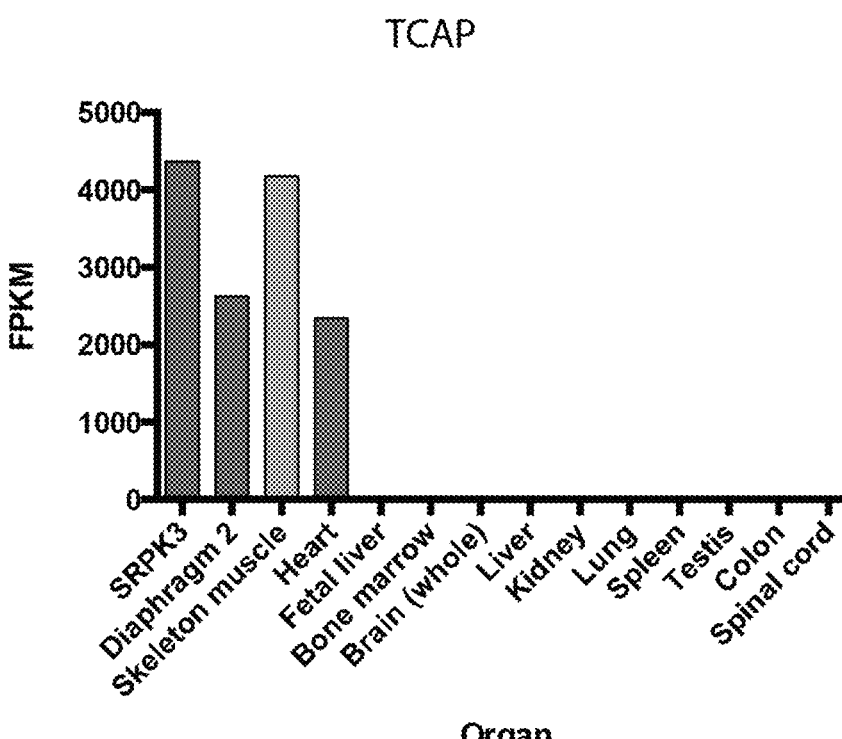
Figure 3:
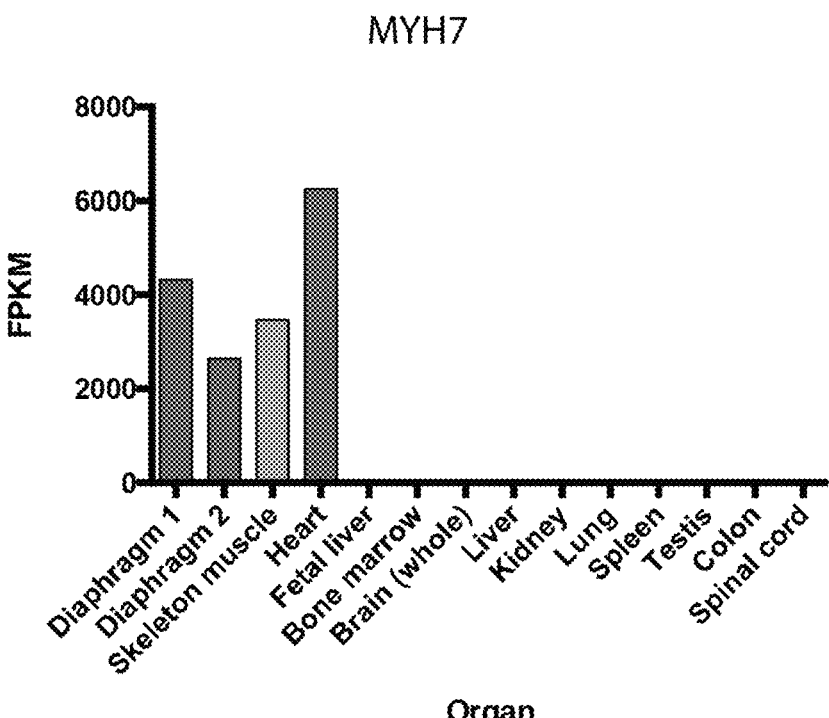
Figure 3:
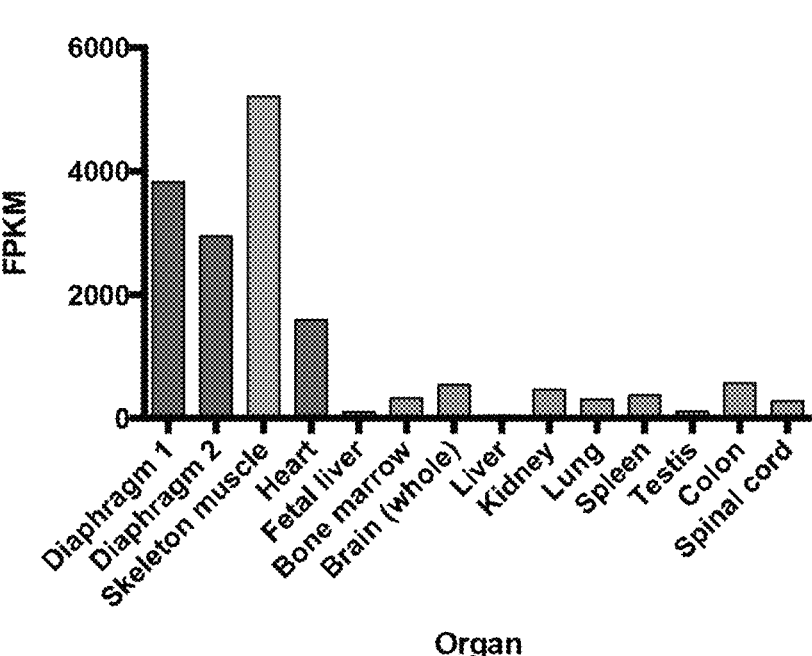
Figure 3:
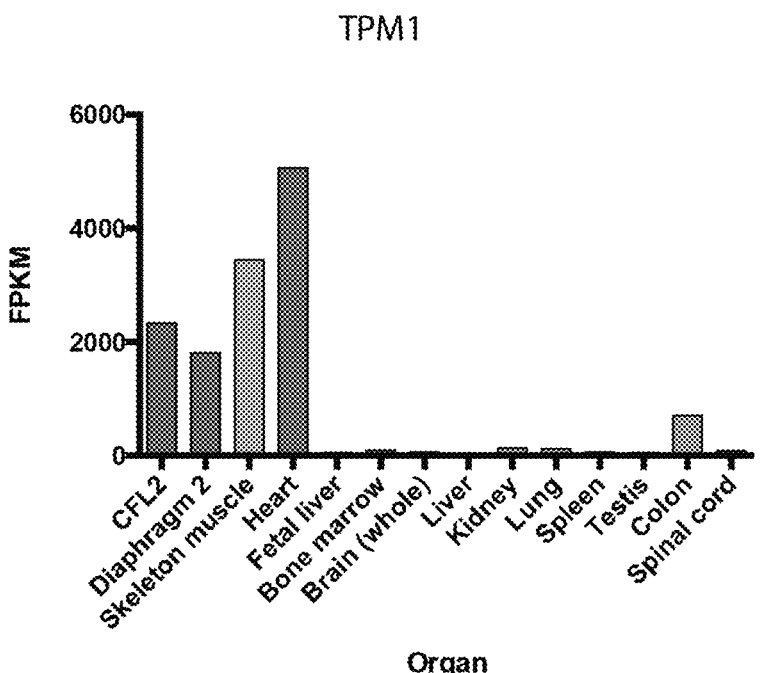

Initially, the gene expression level in diaphragm samples was ranked from highest to lowest values based on the RNA-seq data. The 25 highest expressed genes in the diaphragm were selected. The gene expression profiles were then compared between diaphragm, skeletal muscle, with or without heart versus other tissues to identify only highly and specifically expressed genes in i) diaphragm and skeletal muscle (Dph+SkM) or ii) diaphragm, skeletal muscle, and heart (Dph+SkM+Hrt). Based on this comparison, 18 genes were identified (Table 3), which are highly and specifically expressed in diaphragm and skeletal muscle and 8 genes (Table 4) that are highly expressed in diaphragm, skeletal muscle, and heart. All 25 genes (17 genes for Dph+SkM and 10 genes for Dph+SkM+Hrt: 2 genes ACTA1 and CKM are overlapping with the Dph+SkM group) were analyzed using ENSEMBL for locating the transcription start site (TSS). Subsequently, these TSS were mapped into UCSC Genome Browser Database for nucleic acid regulatory element identification. The nucleic acid regulatory elements were selected based on i) high DNase hypersentitivity sites ii) high content of epigenetic markers associated with open chromatin (i.e. acetylation, methylation) iii) high content of transcription factor binding sites iv) strong evolutionary conservation among vertebrates and v) conserved transcription factor binding sites in 3 species (human, rat, mouse) (FIG. 1). Finally, based on these 5 criteria, 89 nucleic acid regulatory elements were identified from 25 genes. 65 nucleic acid regulatory elements sequenced were identified for high expression in diaphragm and skeletal muscle (Table 3) and 31 nucleic acid regulatory elements sequenced were identified for high expression in diaphragm, skeletal muscle and heart (Table 4). 7 of these are common CREs and are therefore present in both tables.

TABLE 2

| list of genes highly expressed in Diaphragm and Skeletal Muscle or Diaphragm, Skeletal Muscle and Heart (cf. also Table 3 & 4) | |
| --- | --- |
| High expressed genes in Diaphragm and Skeletal Muscle | High expressed genes in Diaphragm and Skeletal Muscle and Heart |
| 1) ACTA1 | 1) MYL2 |
| 2) CKM | 2) MB |
| 3) TPM2 | 3) DES |
| 4) MYL1 | 4) TNNC1 |
| 5) TNNC2 | 5) TCAP |
| 6) FHL1 | 6) MYH7 |
| 7) TNNT1 | 7) ALDOA |
| 8) TNNI2 | 8) TPM1 |
| 9) MYLPF | 9) ACTA1 |
| 10) TNNT3 | 10) CKM |
| 11) MYH2 | |
| 12) SLN | |
| 13) MYBPC1 | |
| 14) CA3 | |
| 15) ATP2A1 | |
| 16) MYH1 | |
| 17) ENO3 | |

Example 2: In Vivo Comparison of Desmin Promoters

Experimental Procedures

AAV vectors comprising the muscle-specific regulatory element Sk-SH4 were generated according to the protocol described in Example 3. Briefly, the muscle-specific regulatory element Sk-SH4 was synthesized by conventional oligonucleotide synthesis and cloned upstream of the human desmin 1.4kb promoter (SEQ ID NO: 92), the human desmin 1.0kb promoter (SEQ ID NO: 91) or the murine desmin promoter (SEQ ID NO: 90) in the context of the AAV vector backbone of AAVsc-hDes1.4kb-MVM-Luc, AAVsc-hDes1.0kb-MVM-Luc or AAVsc-mDes-MVM-Luc, respectively.

Adult CB17/IcrTac/PrkdcSCID (SCID, severe combined immunodeficient) mice were intravenously injected (n=5) at a dose of $1 \times 10^{10}$ vg/mouse.

Mice were sacrificed at two weeks and four weeks after injection of the vectors and the different muscle types (biceps, diaphragm, gastrocnemius, heart, quadriceps, tibialis and triceps) were isolated and quantified using bioluminescence imaging as described in Keyaerts M1, Caveliers V, Lahoutte T. Trends Mol Med. 2012 March; 18(3):164-72. doi: 10.1016/j.molmed.2012.01.005. Epub 2012 Feb. 8. Bioluminescence imaging: looking beyond the light.

Results

Figure 4:
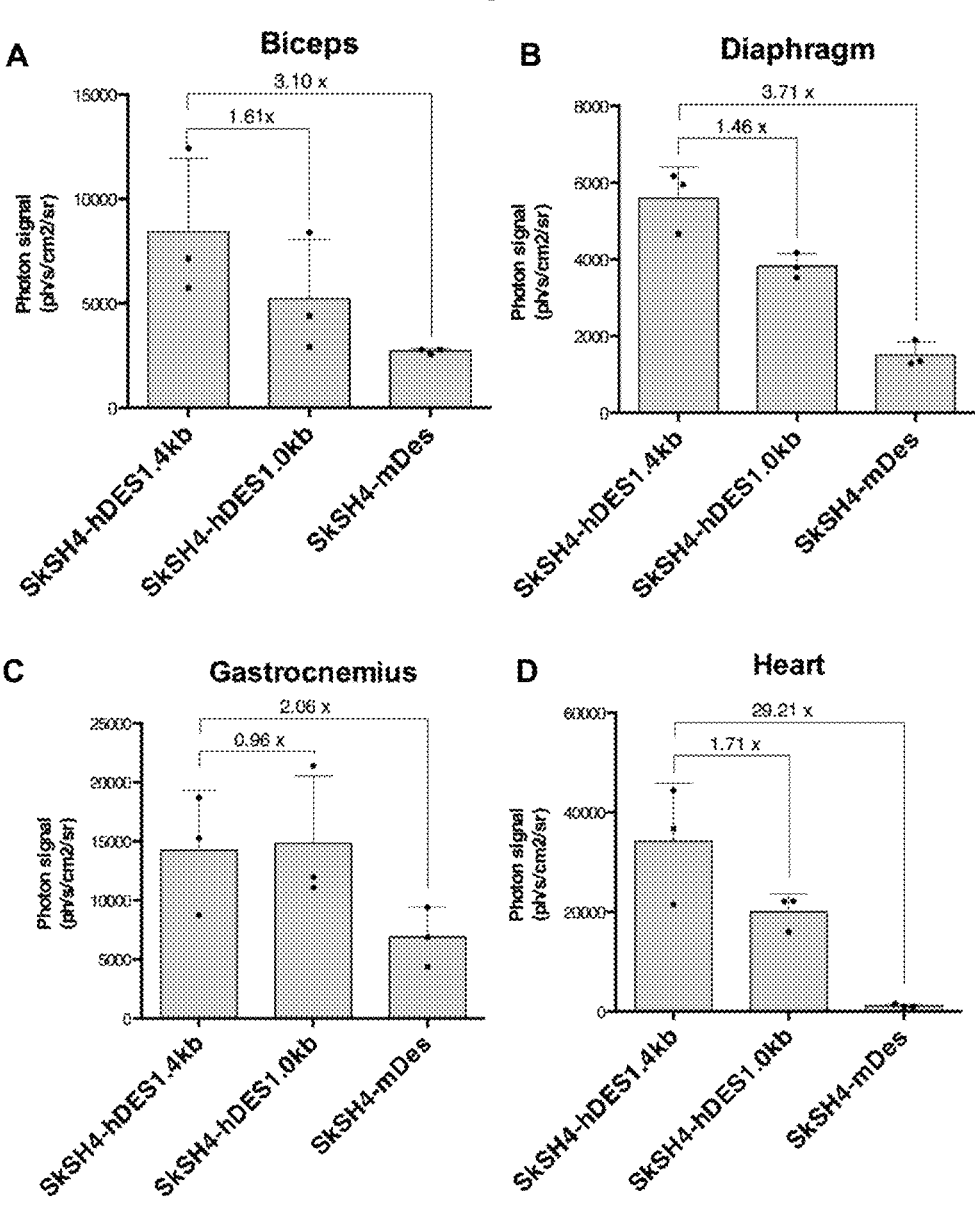
FIG. 4: In vivo comparison of desmin promoters. SCID mice were injected with $1 \times 10^{10}$ vg/mouse of AAV9-luciferase vector containing the most robust skeletal muscle specific CRE (designated as Sk-SH4) in combination with different desmin promoters: Sk-SH4-hDES1.4kb, (SEQ ID NO: 92) Sk-SH4-hDES1.0kb & (SEQ ID NO: 91) Sk-SH4-mDES (SEQ ID NO: 90), quantified as Photons signal, in murine Biceps (A), diaphragm (B), gastrocnemius (C), heart (D), quadriceps (E), tibialis (F) and triceps (G).
Figure 4:
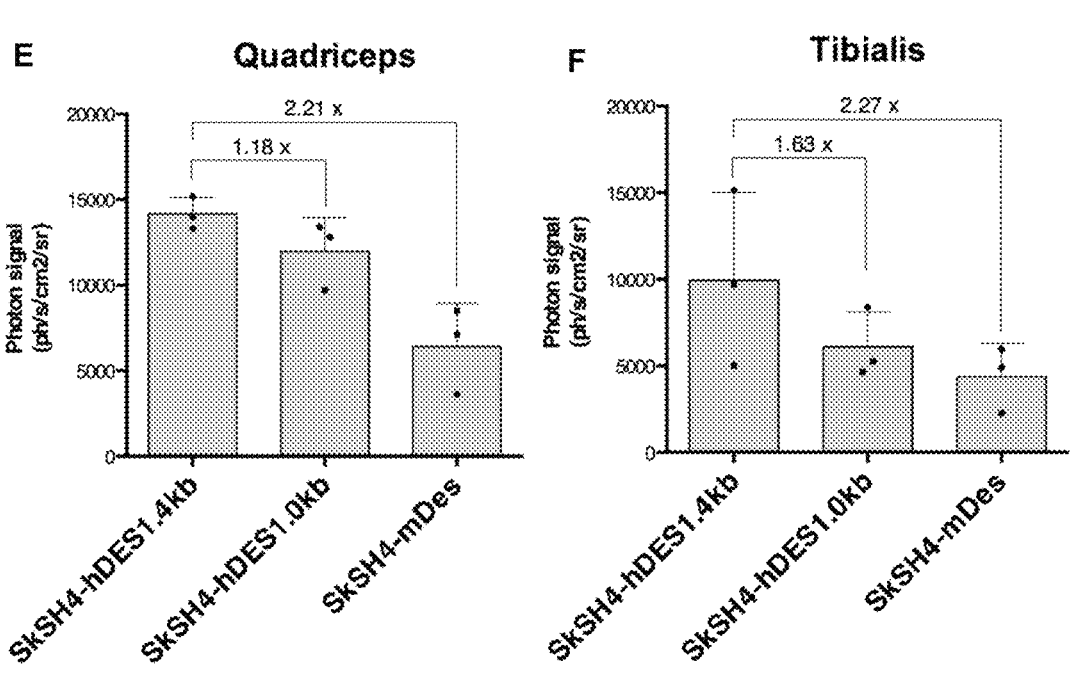
Figure 4:
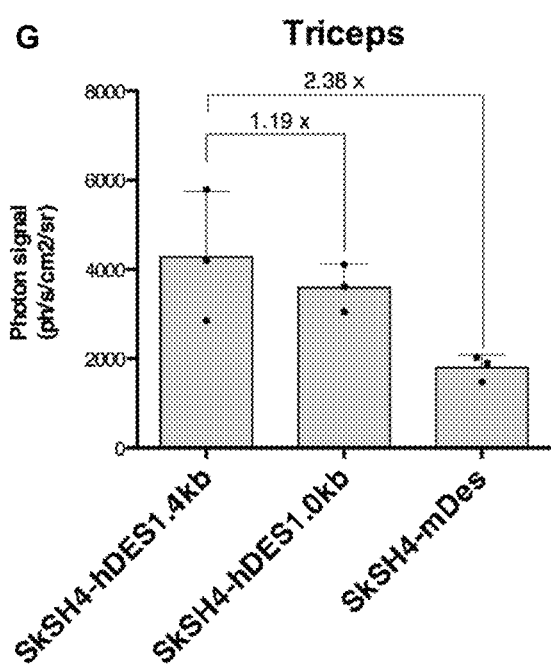

Comparison of the luciferase expression induced by the different AAV vectors quantified as Photons signal shows that the expression cassette comprising Sk-SH4-hDES1.0kb or Sk-SH4-hDES1.4kb, especially Sk-SH4-hDES1.4kb, leads to a higher luciferase expression in the different muscle types of mice (Biceps, diaphragm, gastrocnemius, heart, quadriceps, tibialis and triceps) compared to the expression cassette comprising Sk-SH4-mDES (FIG. 4).

Example 3: In Vivo Validation of Dph-CREs

The selected top diaphragm-specific nucleic acid regulatory elements (cf. Table 3 & 4) were cloned upstream of a promoter which is active in muscle, diaphragm and optionally heart tissue (e.g. mouse or human desmin promoter (DES, more preferably mDES, hDES1.0kb, or hDES1,4kb as depicted in SEQ ID NO: 90-92 respectively), or the SPc5-12 promoter (SEQ ID NO: 124), to drive expression of a reporter gene in an AAV vector backbone (e.g. pAAV$_{SC}$ or pAAV$_{SS}$). Other promotors of genes highly expressed in diaphragm can also be used. In addition, other muscle specific promoters such as muscle creatine kinase promoter (MCK) (Wang B et al., 2008) alpha-myosin heavy chain (a-MHC), myosin light chain (MLC-2) or cardiac troponin C (cTnC), myogenin MYF4 promoters ((Pacak C. A. et al; 2008) or viral promoters such as murine stem cell virus (MSCV) promoter (Suga T et al., Plos One 2011) are all potential promoters that can be used to cloned downstream of the diaphragm nucleic acid regulatory elements.

Figure 8:
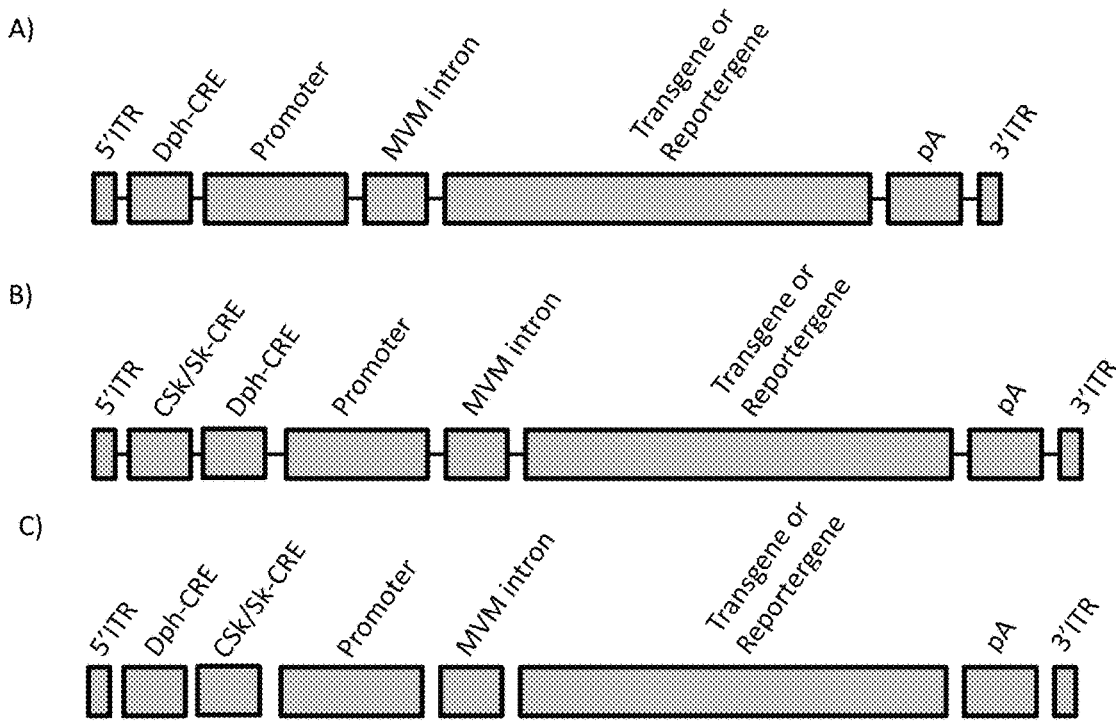
FIG. 8: Schematic view of AAV vector backbone. A) reference backbone with Dph-CREs coupled to a promotor, MVM intron, a transgene or reporter gene, and a polyA site. B-C) Same as A), but with an additional muscle CRE (Sk-CRE) or heart-muscle CRE (CSk-CRE) coupled after B) the Dph-CRE or before C) the Dph-CRE.

The plasmids also contain a Minute Virus of Mouse (MVM) intron (SEQ ID NO: 125) and a polyadenylation site (pA), e.g. the Simian Virus 40 polyadenylation site (SEQ ID NO: 126) or a synthetic poly-A site (SEQ ID NO: 127). This leads to the general AAV backbone pAAV-Dph-CRE01to89-Des/SPc-promoter-MVM-intron-Transgene/Reportergene-pA (FIG. 8 A)).

Some of these backbones were further complemented with a muscle/heart-CRE such as the ones disclosed in WO2015/110449. This leads to the AAV backbone pAAV-CSk/Sk-CRE-Dph-CRE01to89-Des/SPc-promoter-MVM-intron-Transgene/Reportergene-pA (FIG. 8 B)) or pAAV-Dph-CRE01to89-Sk/CSk-CRE-Des/SPc-promoter-MVM-intron-Transgene/Reportergene-pA (FIG. 8 C)), wherein the Sk-CRE/CSk-CRE is either one of the CRE's disclosed in WO2015/110449, preferably skeletal muscle CRE Sk-SH4 (SEQ ID NO: 121), or the skeletal muscle and cardiac CREs CSk-SH5 (SEQ ID NO: 122) and CSk-SH1 (SEQ ID NO: 123) regulatory elements.

The reporter gene is preferably a Luciferase reporter gene and the transgenes tested below are the human GAA and MTM1 genes or their codon-optimised variants (cf. example 4).

For studying the effect of the Dph-CREs on tissue specific expression, the following AAV vector backbones were used:
  for the Dph-CREs from Table 3: pAAVss-Sk-SH4-hDES1.4kb-MVM-Luciferase-pA
  for the Dph-CREs from Table 4: pAAVss-CSk-SH5-SPc5-12GTRM-MVM-Luciferase-pA, Wherein the different Dph-CREs are cloned before or after the Sk-SH4 or CSk-SH5 CRE.

Production of the AAV vector particles is achieved by transient co-transfection of AAV-reporter and AAV helper constructs, encoding AAV serotype 9 capsids into HEK293 cells, followed by a purification step based on cesium chloride (CsCl) density gradient ultracentrifugation, as described previously (Vanden Driessche et al., 2007 J Thromb Haemost 5:16-24), which is specifically incorporated by reference herein.

Briefly, two days post transfection, cells were harvested and vector particles were purified using isopycnic centrifugation methods. Harvested cells were lysed by successive freeze/thaw cycles and sonication, treated with benzonase (Novagen, Madison, WI) and deoxycholic acid (Sigma-Aldrich, St. Louis, MO) and subsequently subjected to 3 successive rounds of cesium chloride (Invitrogen Corp, Carlsbad, CA) density gradient ultracentrifugation. Fractions containing the AAV vector were collected, concentrated in 1 mM $MgCl_2$ in Dulbecco's phosphate buffered saline (PBS) (Gibco, BRL) and stored at $-80°$ C.

Vector titers (in viral genomes (vg)/ml) were determined by quantitative real-time PCR using SYBR Green mix (which included SYBR Green dye, Taqman polymerase, ROX and dNTP's all in one) and luciferase specific primers on an ABI 7500 Real-Time PCR System (Applied Biosystem, Foster city, CA, USA). The forward and reverse primers used were 5'-CCCACCGTCGTATTCGTGAG-3' (SEQ ID NO: 128) and 5'-TCAGGGCGATGGTTTTGTCCC-3' (SEQ ID NO: 129), respectively.

Typically, for all vectors titers in the range of 1.5-6.1×10$^{11}$ vg/ml were achieved from a small production batch of 20 petri dishes of producer cells. If higher number of petri dishes such as 60 dishes of producer cells were used, a higher titer typically in the range of 10$^{12}$-10$^{13}$ gc/ml of AAV particles were achieved. Known copy numbers (10$^2$-10$^7$) of the respective vector plasmids used to generate the corresponding AAV vectors, carrying the appropriate cDNAs were used to generate the standard curves.

All animal procedures were approved by the institutional animal ethics committee of the Free University of Brussels (VUB) (Brussels, Belgium). All mice were housed under specific pathogen-free conditions; food and water were provided ad libitum.

The purified AAV vectors are injected intravenously (i.v.) in 4 weeks old immunodeficient CB17-SCID mice (Janvier, France) at different vector doses, allowing the identification of the most robust diaphragm-specific nucleic acid regulatory elements by quantifying the reporter gene expression. In different muscle tissues (biceps, diaphragm, gastrocnemius, heart, quadriceps, tibialis and triceps) were quantified using bioluminescence imaging. Whole body bioluminescence was performed approx. 1 week post-AAV injection and organs bioluminescence approx. 3 weeks post-AAV injection. Luciferase expression induced by the different AAV vectors quantified as Photons signal are shown in FIGS. 5A to 5I for Dph-CRE-02, -58, -59, -60, -64, -21, -41, -18, -04, -06 for the Sk-SH4 backbone) and Dph-CRE-77, -02, -04, -06, -69, -70, -71, -66, -68, and -07 for the CSk-SH5 backbone). All 20 tested Dph-CREs show an increased expression versus the base line expression using a Sk-SH4-hDES1,4kb or CSk-SH5-SPc5-12 backbone. 100% of the diaphragm CREs tested showed enhanced luciferase expression. In particular, Dph-CRE-02, 21 and 64 show a particularly higher expression levels compared to the Sk-SH4-hDES1,4kb backbone, while Dph-CRE-04, -02 and -06 show a particularly higher expression level compared to the CSk-SH5-SPc5-12 kb backbone.

The individual screening of the 20 diaphragm CREs clearly demonstrated the successful generation of synergistic CRE combinations (Diaphragm CRE+Skeletal muscle CREs) and (Diaphragm CRE+Skeletal muscle/Heart CREs) that led to robust gene expression in the diaphragm and skeletal muscle and/or heart, higher than with any conventional vector designs that are either currently being used in clinical trials or being considered for future trials.

The experiments show that the skeletal muscle specific-CRE (Sk-SH4) leads to a robust increase in reporter (or transgene) expression in vivo when compared to control without muscle specific CRE (hDES1.4kb). In particular, the diaphragm specific CRE (Dph-CRE64, CRE02, and CRE21) coupled to the muscle specific CRE (Sk-SH4) act synergistically as a combined module, leading to an extremely high level of enhancement of luciferase expression in vivo. The other Dph CREs (60, 58, 04, 18, 41, 69, 06) also showed moderate augmentation of luciferase gene expression.

Similarly, the combined cardiac/skeletal muscle specific-CRE (CSk-SH5) led to robust increased in luciferase expression in vivo when compared to control without CSk-SH5 CRE but just the SPc5-12-GTRM promotor driving the luciferase gene. In addition, we showed that the diaphragm specific CRE (Dph-CRE04, 02, 06) when coupled to the combined cardiac/skeletal muscle specific CRE (CSk-SH5) act synergistically, leading to an extremely high level of enhancement of luciferase expression in vivo. Other Dph CREs (77, 70, 66, 71, 69, 68, 07) showed moderate level of augmentation of luciferase gene expression.

Dph-CRE64 showed the highest increase in luciferase gene expressed when combined to the Sk-SH4 muscle CRE driven from the human Desmin 1.4 kb promoter. There is a clear synergistic effect of the Diaphragm CRE in combination with the muscle CRE.

Dph-CRE04 showed the highest increase in luciferase gene expressed when combined to the CSk-SH5 muscle CRE driven from the synthetic SPc5-12 promoter. There is a clear synergistic effect of the Diaphragm CRE in combination with the muscle CRE.

This demonstrates that the CREs can act synergistically in a modular fashion.

The individual organ data confirmed the data of the whole body. In the diaphragm tissues, for the group of diaphragm CREs combined with the Sk-SH4-hDes1.4kb expression cassette, the diaphragm CREs that are the most robust are: CRE02, CRE64 CRE60 and CRE21 leading to an augmentation of 400-600 fold luciferase expression when compared to luciferase expression driven from just the human Desmin 1.4kb promoter (normalized to hDes1.4kb, fold difference depicted in lower numbers above graphs in FIG. 5A left-hand). This 400-600 fold increased in luciferase expression is the contribution of the diaphragm CRE combined with the muscle CRE (Sk-SH4). When normalized to Sk-SH4-hDes1.4kb, up to 10 fold enhancement of luciferase expression can be detected from these 4 robust diaphragm CREs (fold difference upper numbers above graphs in FIG. 5A left-hand). This 10 fold difference is the contribution of the individual diaphragm CRE driven from this expression cassette.

Similarly, for the group of diaphragm CREs combined with the CSk-SH5-SPc5-12-GTRM expression cassette, the diaphragm CREs that are the most robust are: CRE02, CRE04, CRE06) leading to an augmentation of about 300 fold luciferase expression when compared to luciferase expression driven from just the SPc5-12-GTRM promoter (normalized to SPc5-12-GTRM, fold difference depicted in lower numbers above graphs in FIG. 5A right-hand). This 300 fold increased in luciferase expression is the contribution of the diaphragm CRE combined with the muscle/heart CRE (CSk-SH5). When normalized to CSk-SH5-SPc5-12-GTRM, up to 23-25 fold enhancement of luciferase expression can be detected from these 3 robust diaphragm CREs (fold difference upper numbers above graphs in FIG. 5A right-hand). This 23-25 fold enhancement is the sole contribution from the individual diaphragm CRE.

Figure 5A:
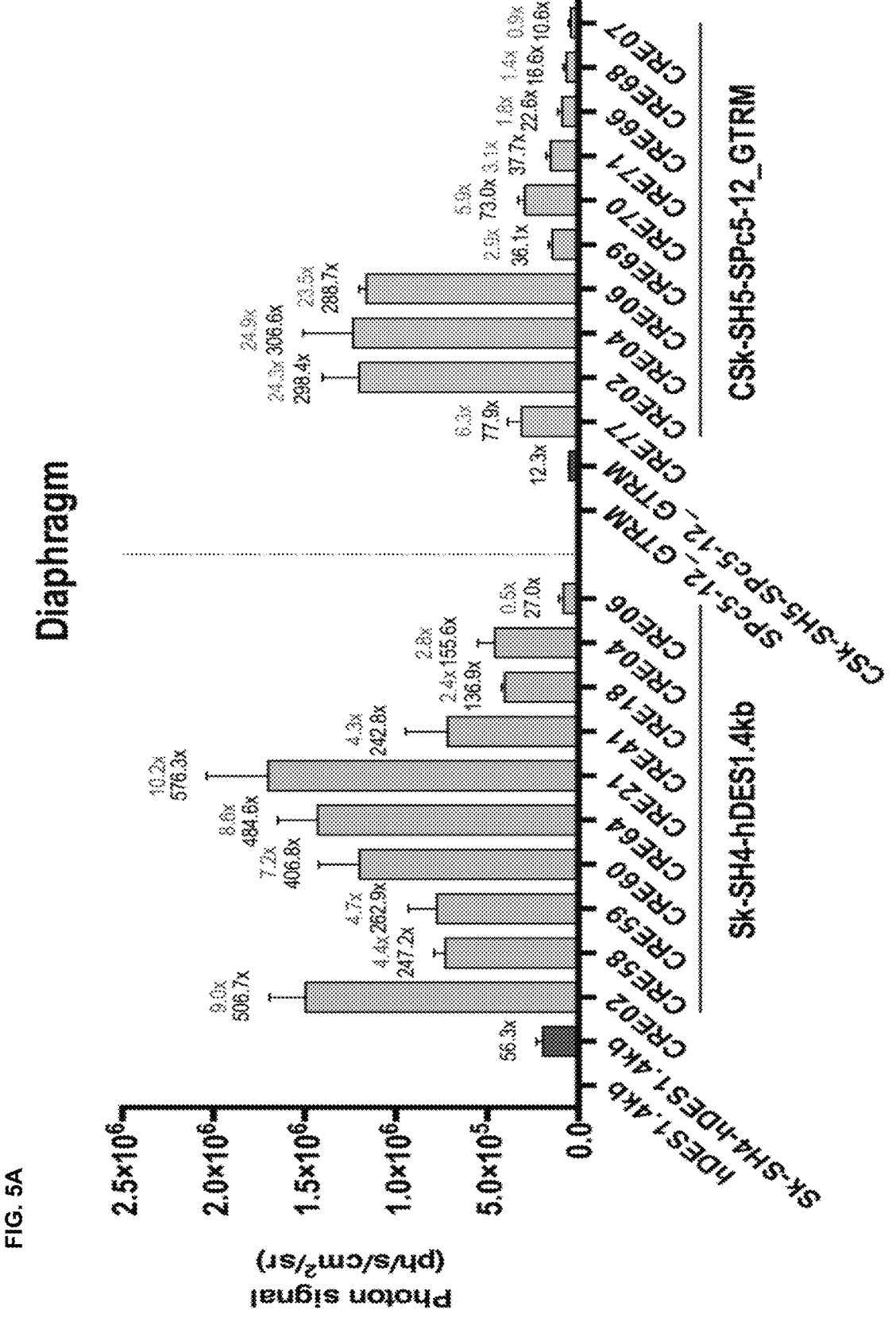
FIGS. 5A to 5I: Comparison of tissue expression levels in absence or presence of Diaphragm CREs (Dph-CREs) according to the invention.
Figure 5B:
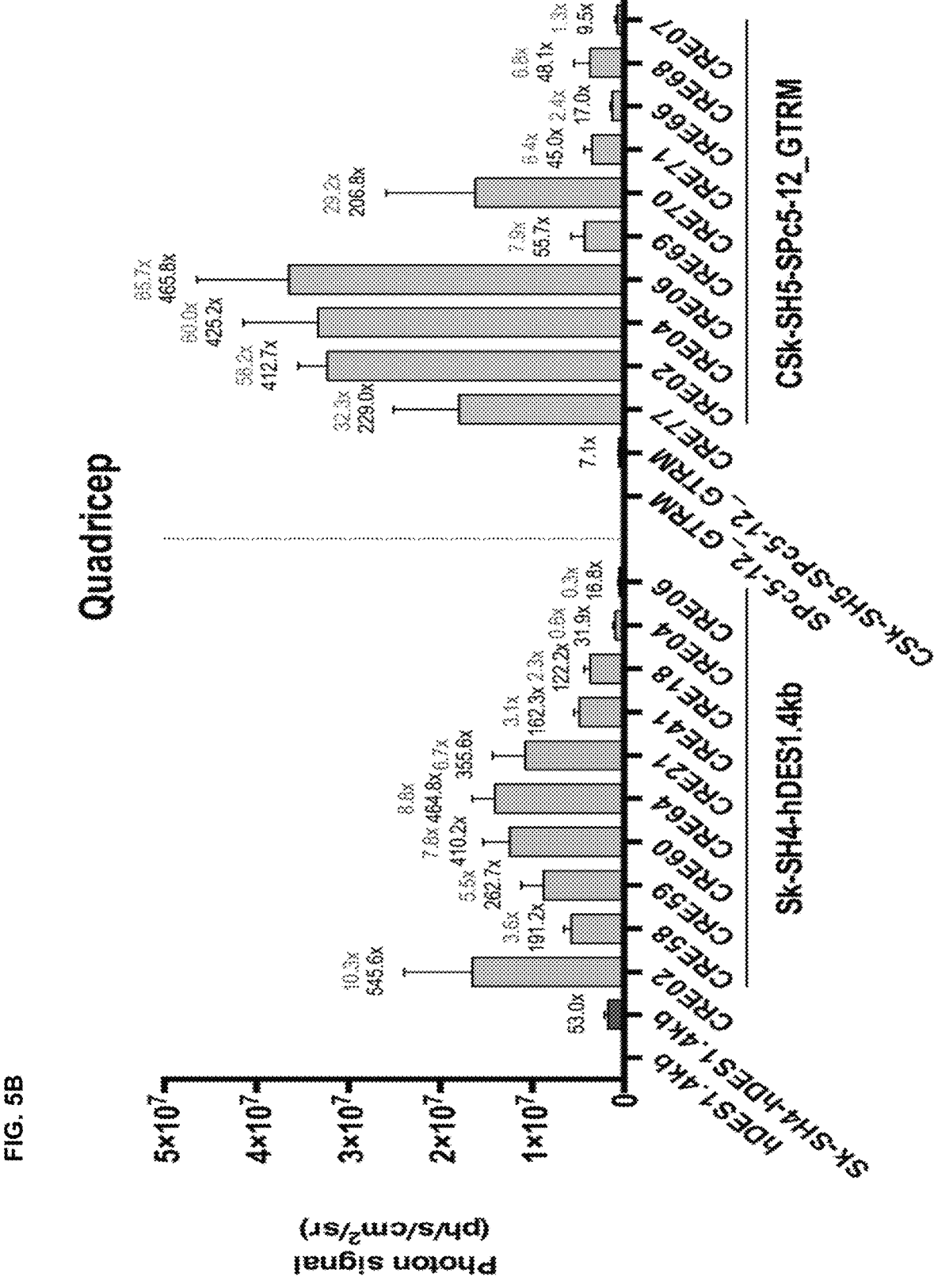
Figure 5C:
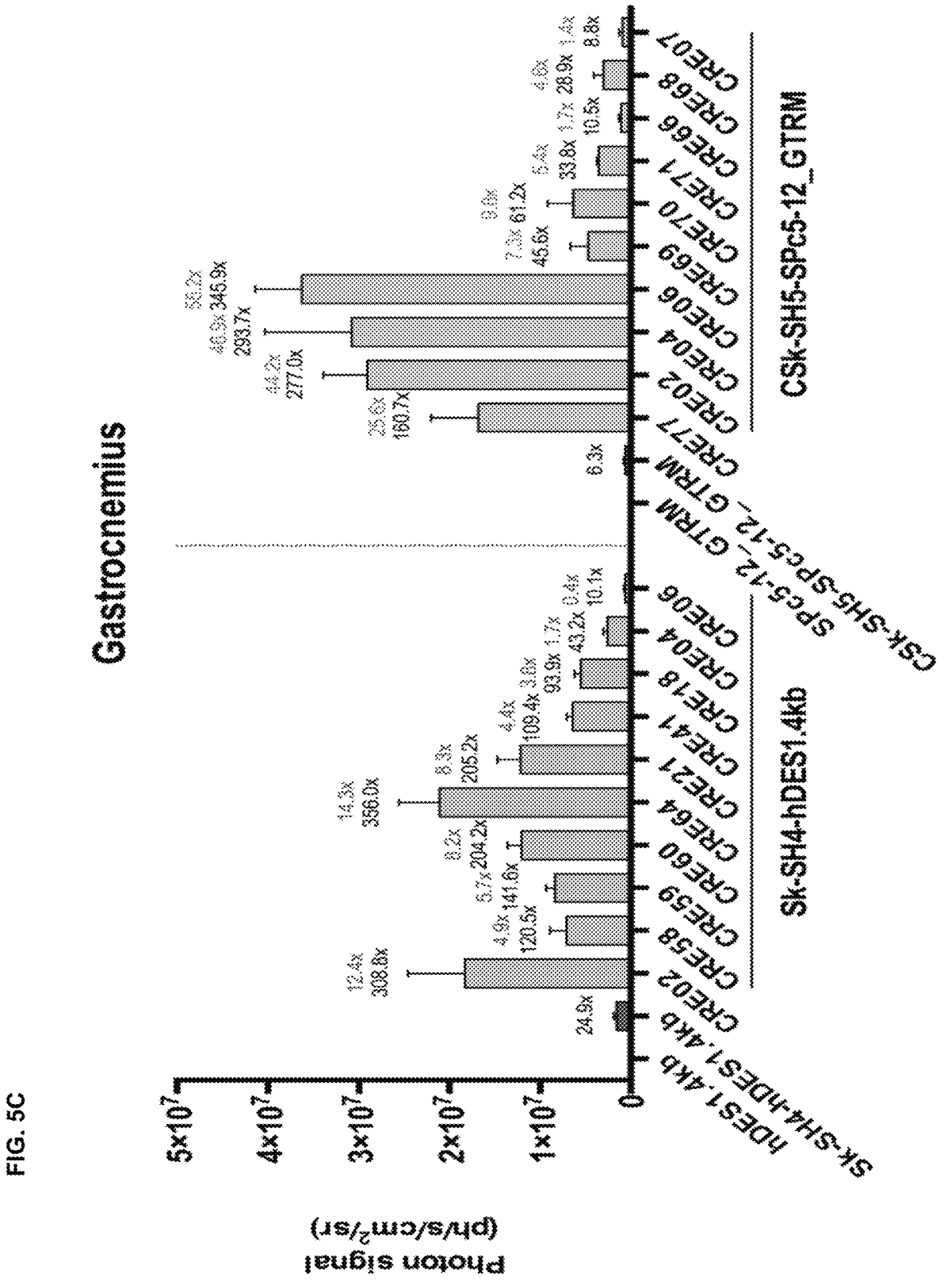
Figure 5D:
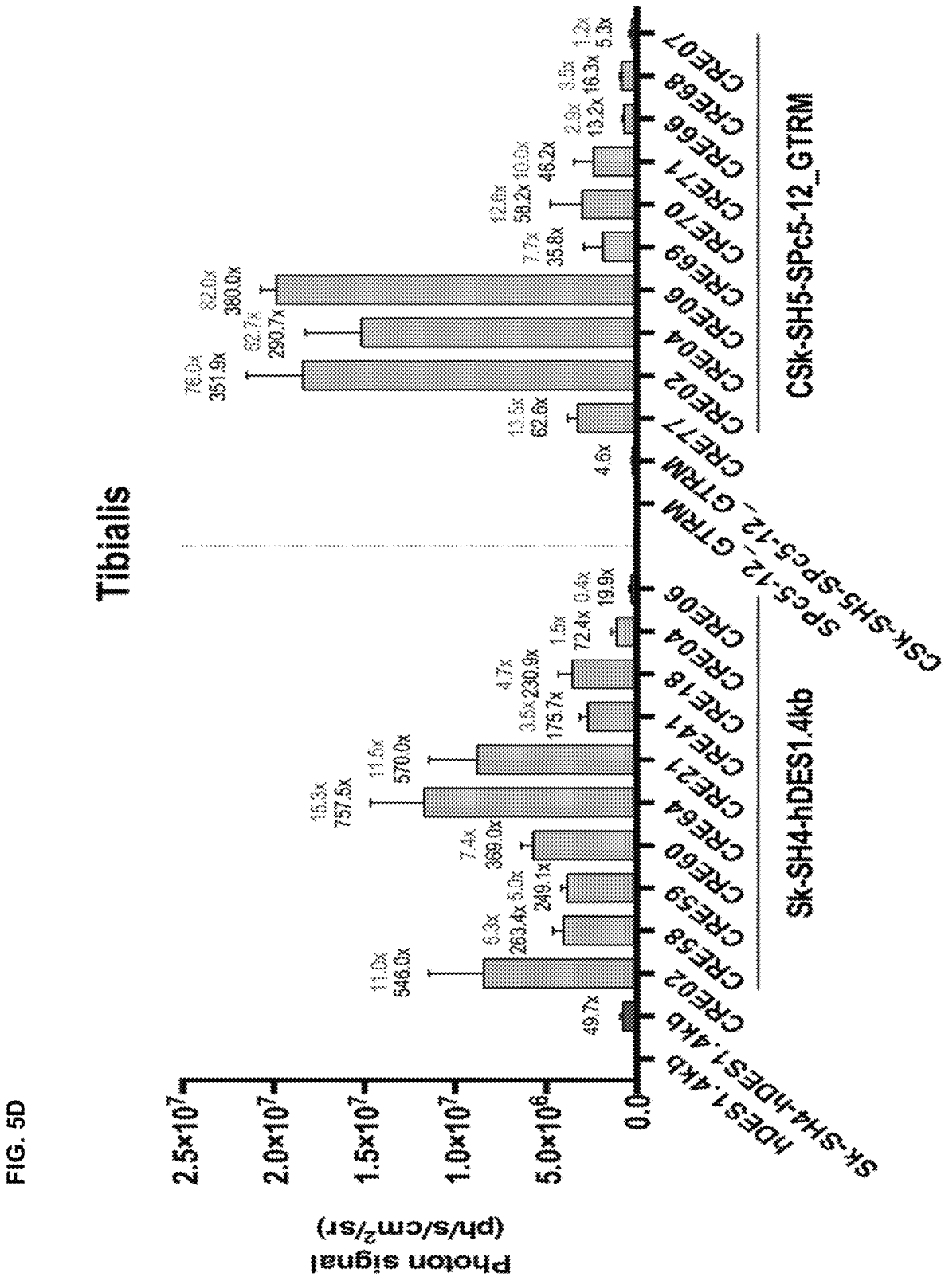
Figure 5E:
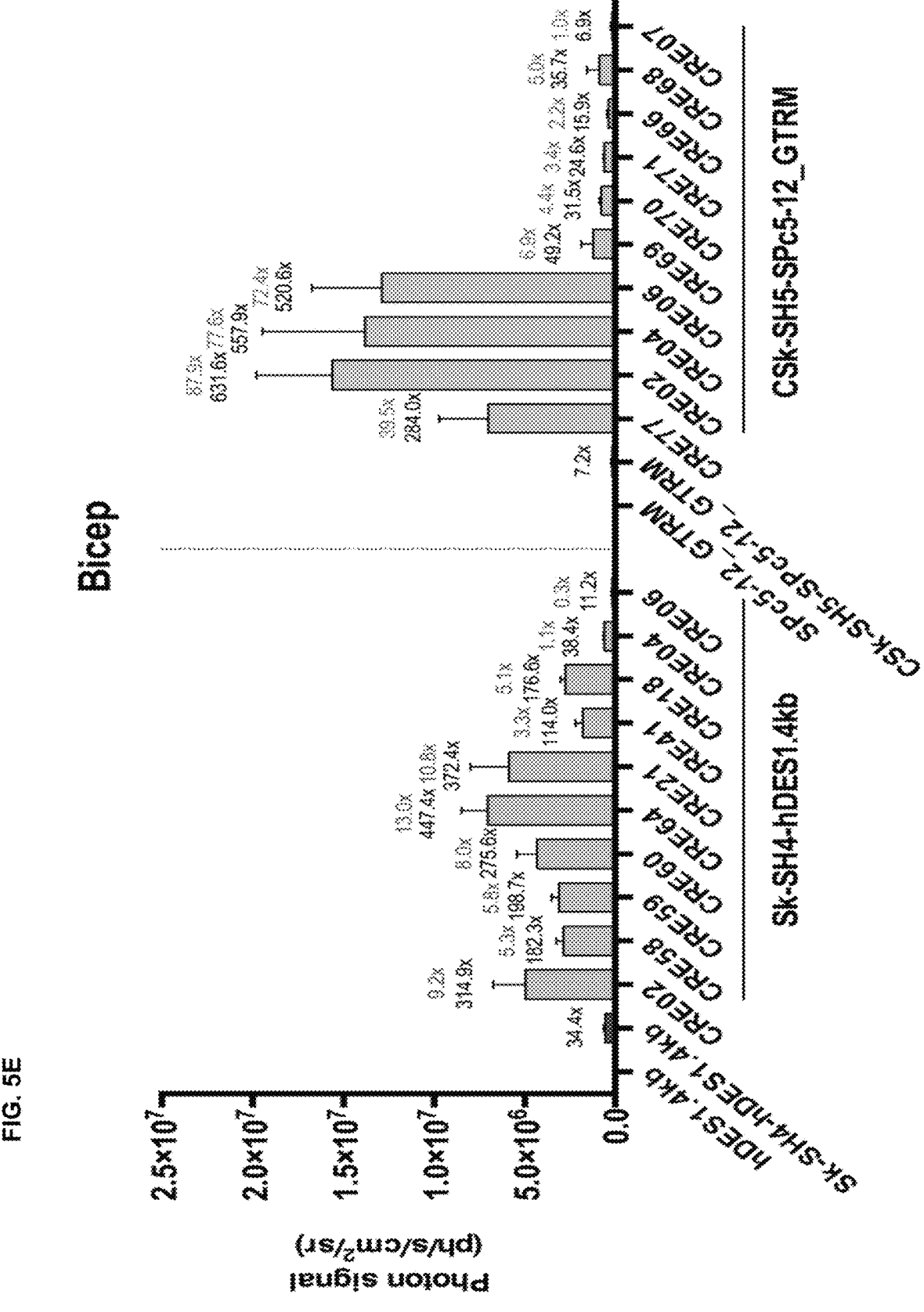
Figure 5F:
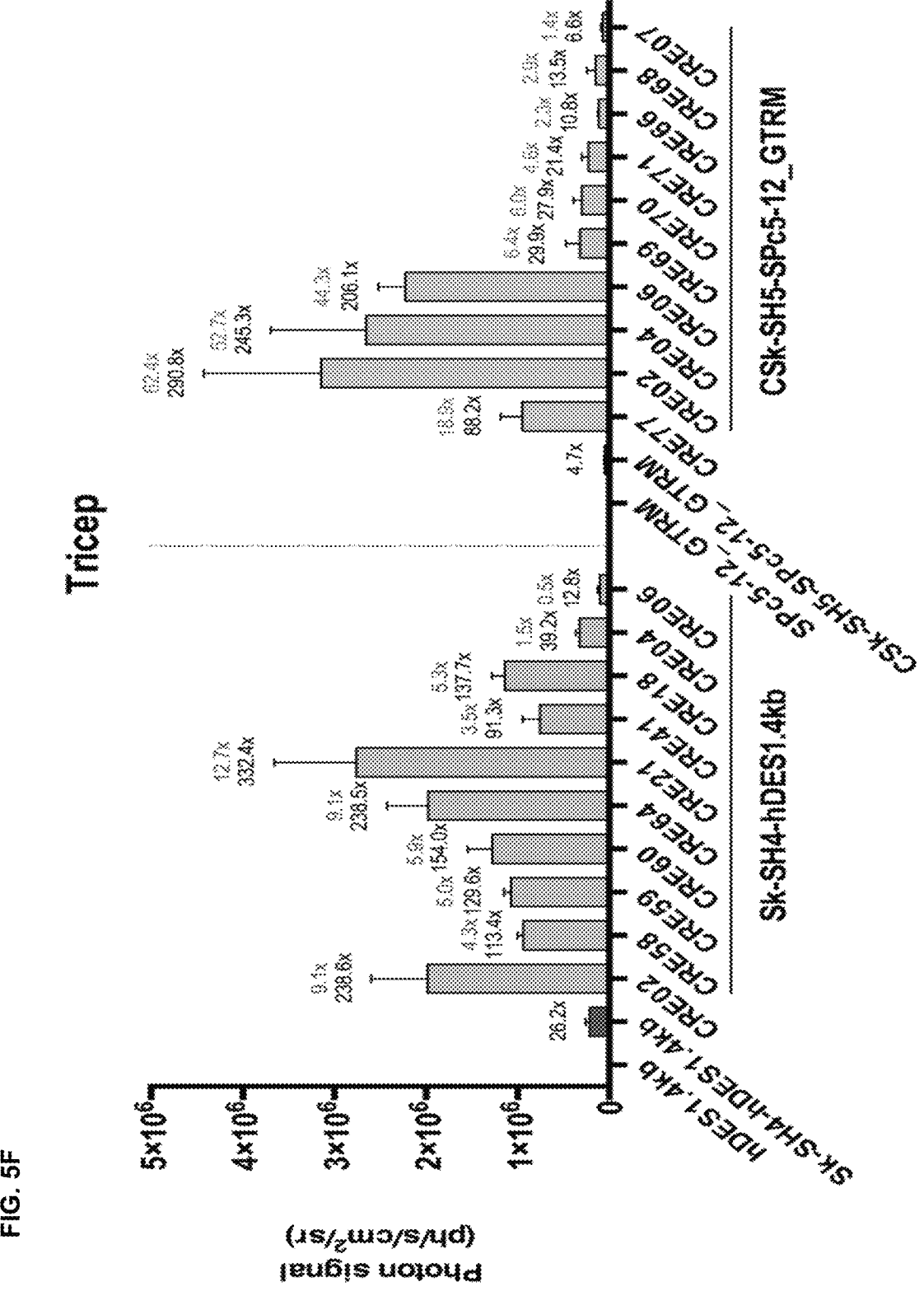
Figure 5G:
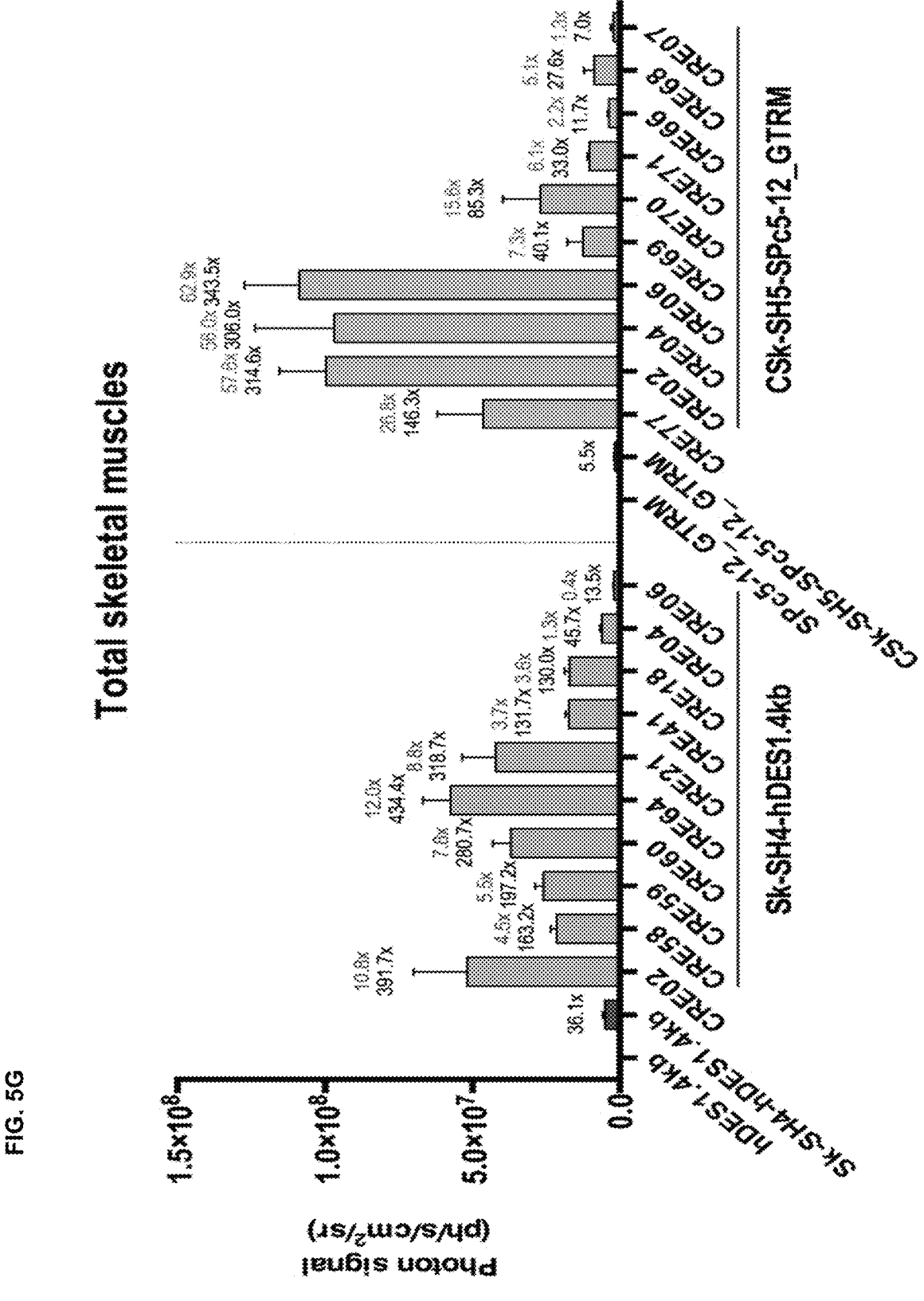
Figure 5H:
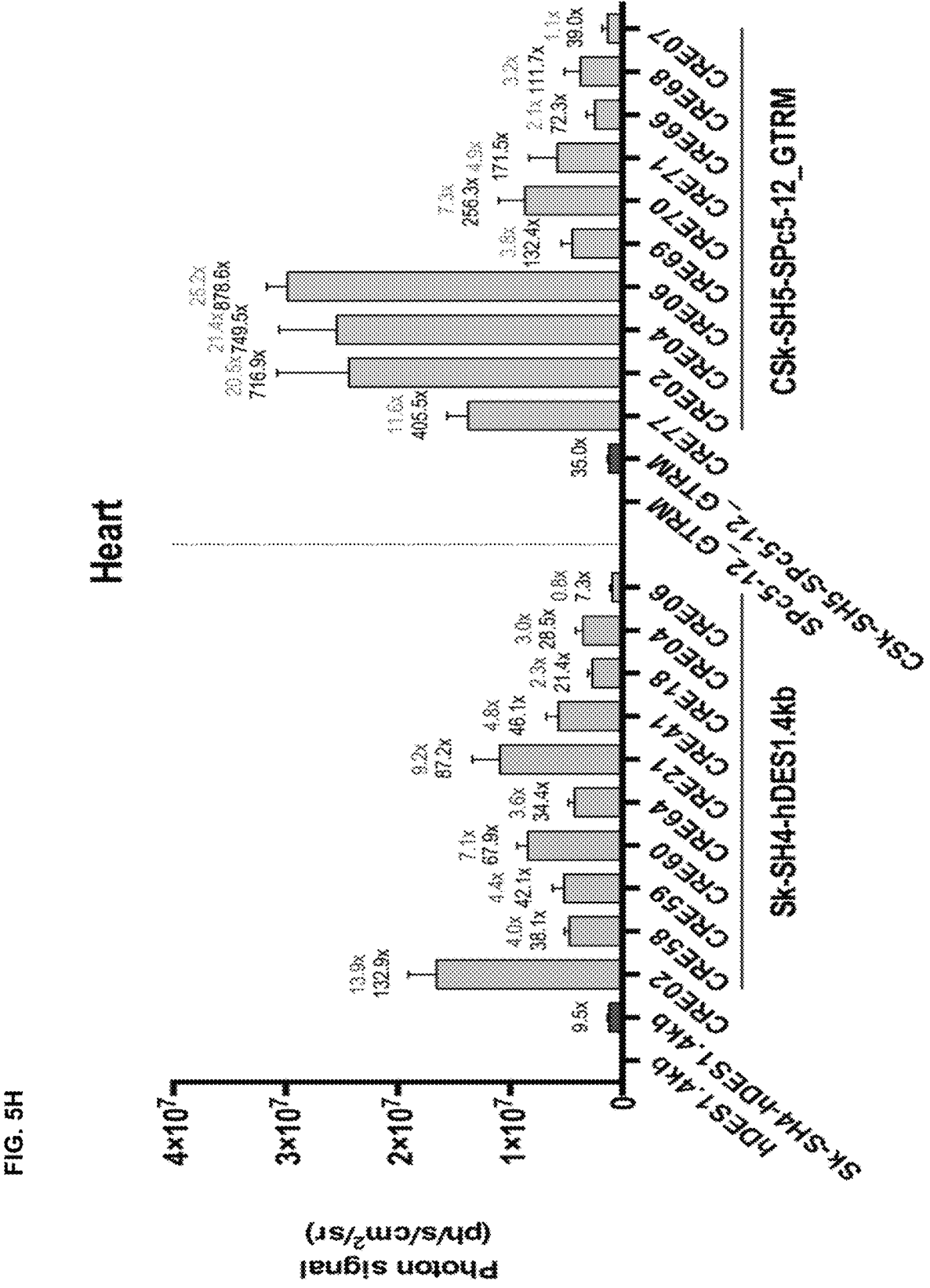
Figure 5I:
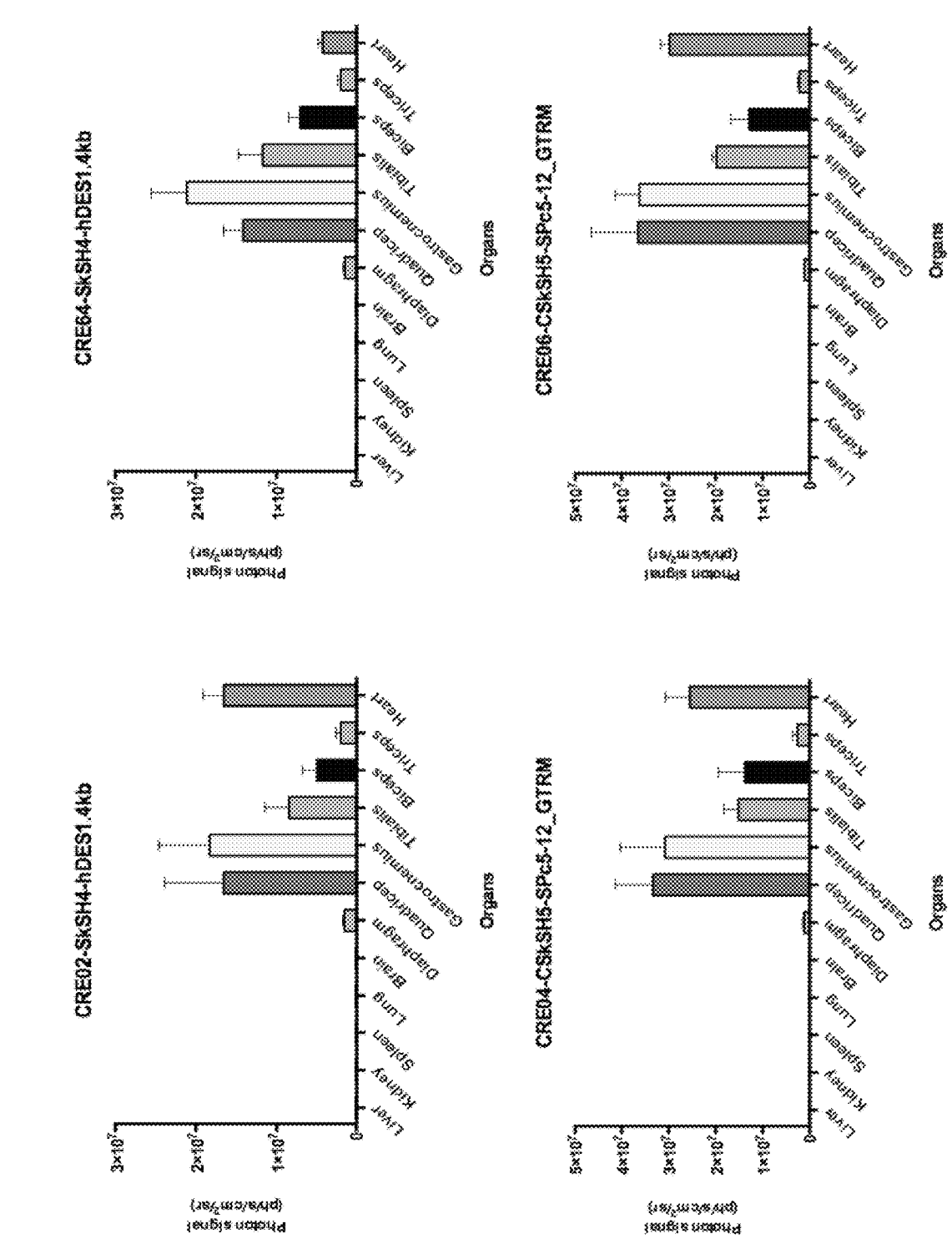

Similar comparisons are made for other muscle tissues: FIG. 5B Expression in Quadricep FIG. 5C Expression in Gastrocnemius FIG. 5D Expression in Tibialis FIG. 5E Expression in Bicep FIG. 5F Expression in Tricep FIG. 5G, Expression in heart FIG. 5H, Specificity of Diaphragm CREs (mainly expressed in diaphragm, skeletal muscle and heart but not in other tissues. The numbers of the Diaphragm CREs correspond to the numbering of Tables 3 & 4 FIG. 5I).

Example 4: Codon-Optimisation of Therapeutic Genes GAA and MTM1

Experimental Procedures

Generation of the AA V Plasmid Constructs

The human alpha-glucosidase (hGAA) gene and the human myotubularin 1 (hMTM1) gene were codon-optimized using the Gene optimizer (GeneArt, Life technologies, Germany).

The wild-type human alpha-glucosidase (hGAA; SEQ ID NO: 93) and codon-optimized hGAA genes (hGAAco; SEQ ID NO: 94) flanked by BsiWI and XmaJI restriction sites at the 5' and 3' ends, were cloned and driven from the SPc5-12 promoter, which was operably linked to the regulatory element CSk-SH5.

On the other hand, the wild-type human myotubularin 1 (hMTM1; SEQ ID NO: 95) and codon-optimized hMTM1 (hMTM1co; SEQ ID NO: 96) genes flanked by BsiWI and XmaJI restriction sites at the 5' and 3'ends were cloned and driven from the hDES1.4kb (SEQ ID NO: 92), which was operably linked to the regulatory element Sk-SH4 (SEQ ID NO: 121).

The Sk-SH4 regulatory element (SEQ ID NO: 121) operably linked to the hDES1.4kb promoter (SEQ ID NO: 92), or the CSk-SH5 regulatory element (SEQ ID NO: 122) operably linked to the SPc5-12 promoter (SEQ ID NO: 124), were cloned upstream of the MVM intron (SEQ ID NO: 125) in the context of a single stranded adeno-associated viral vector (AAVss) backbone. The vector also contained a 49 bp synthetic polyadenylation site (Levitt N et al, 1989) (SEQ ID NO: 127). The generated constructs were designated as pAAVss-Sk-SH4-hDES1.4kb-MVM-hMTM1
pAAVss-Sk-SH4-hDES1.4kb-MVM-hMTM1co
pAAVss-CSk-SH5-SPc5-12-MVM-hGAA
pAAVss-CSk-SH5-SPc5-12-MVM-hGAAco.

AA V Vector Production and Purification

AAV vector production and purification were carried out as described in Example 2.

Animal Studies

All animal procedures were approved by the institutional animal ethics committee of the Free University of Brussels (VUB) (Brussels, Belgium). All mice were housed under specific pathogen-free conditions; food and water were provided ad libitum.

The concentrated vectors ($5 \times 10^{11}$ vg/mouse) were injected into the tail-vein of 4 weeks old CB.17-SCID mice (Janvier, France). Four to five weeks post injection, the mice were euthanized and individual organs were analyzed to evaluate mRNA and protein expression.

hGAA(co) and hMTM1(co) ELISA

For all GAA and MTM1 ELISA, the protocol will follow as indicated by manufacturer's instruction. Both kits (MyBiosources) require PBS as the protein extraction cocktails. The protease inhibitor cocktail (Invitrogen, USA) is added to inhibit the protease activity and maximise the quality of the samples. For each ELISA, 50 mg of the tissue was taken from frozen storage. Then 500 uL of cold PBS with protease inhibitor were added to the tissue and then homoginized with Matrix D (MPBio) for 3 cycles of 20 s. Afterward, the lysates were centrifuged at 13,000 rpm for 5 mins at 4 C. The supernatants were collected and processed as mentioned in each ELISA kits or stored at −20 C until analysis.

mRNA Analysis

For qRT-PCR, the 30-50 mg of the samples were removed from the frozen storage. The samples were homogenised using Matrix D (MPBio) for 2 cycles of 20 s. Then the RNA were extracted using RNA Nucleospin (Macherey-Nagel). The cDNAs were synthesised using SuperScript III cDNA synthesis kit (Invitrogen, USA) according to the manufacture's protocol. Next, the cDNA was amplified by quantitative qPCR on an ABI 7700 (Applied Biosystems, USA). The primer sequences for each gene are listed table below.

| Target | Primer | Sequence | Amplicon size (bp) | SEQ ID |
|--------|--------|----------|--------------------|--------|
| hGAA | F | TGCCCTCGCA GTATATCACA G | 129 | 140 |
| | R | GAGACCCGTA GAGGTTCGC | | 141 |
| hGAAco | F | ACCCCTTCAT GCCTCCTTAT | 148 | 142 |
| | R | TCCATGTAGT CCAGGTCGTT | | 143 |
| hMTM1 | F | GTTTGAGATC CTCACGAGAT ACG | 96 | 144 |
| | R | GTCCATCCAT CCACGTTAAA CTT | | 145 |
| hMTM1co | F | GGCAAGAGAA ACAAGGACGA | 150 | 146 |
| | R | GGCATCGTCG GACTCATATC | | 147 |

Results hGAA(co) Expression

Figure 6A:
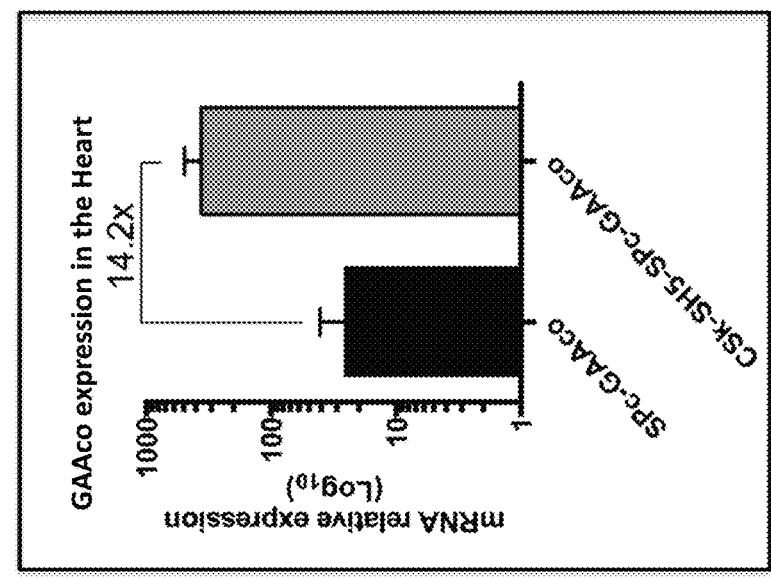
FIGS. 6A and 6B.
Figure 6A:
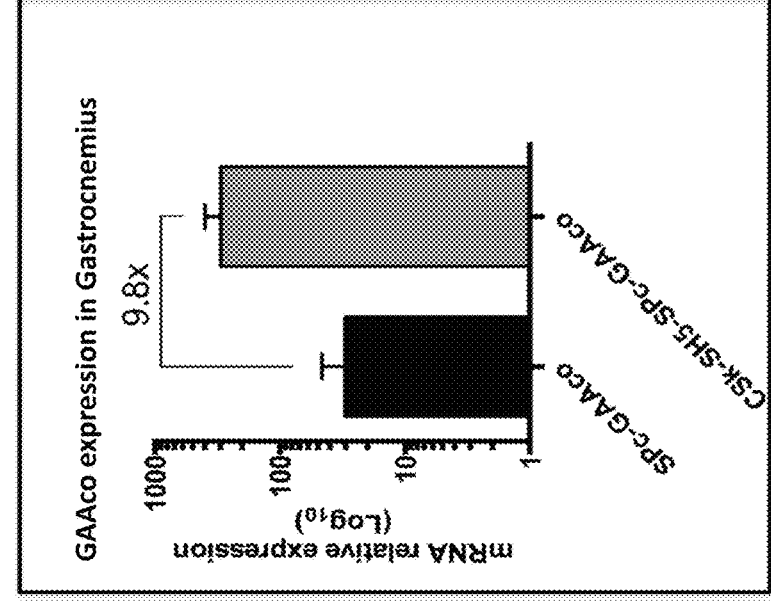
Figure 6A:
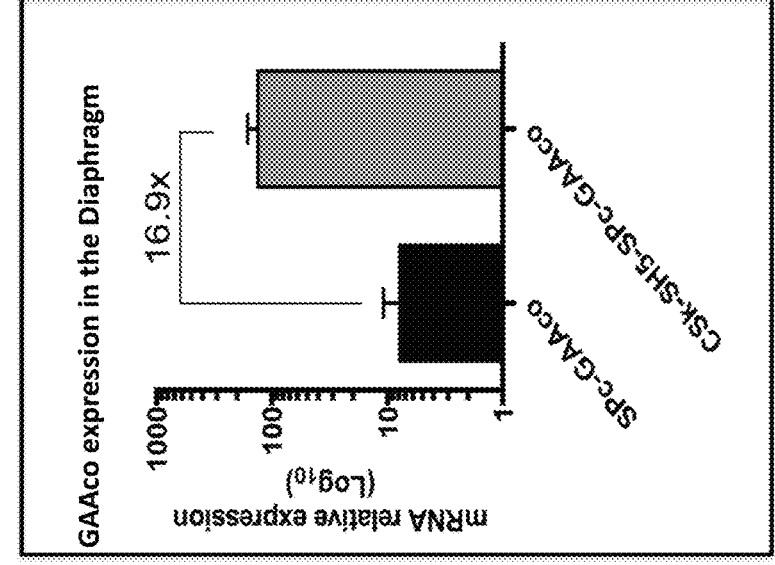
Figure 6B:
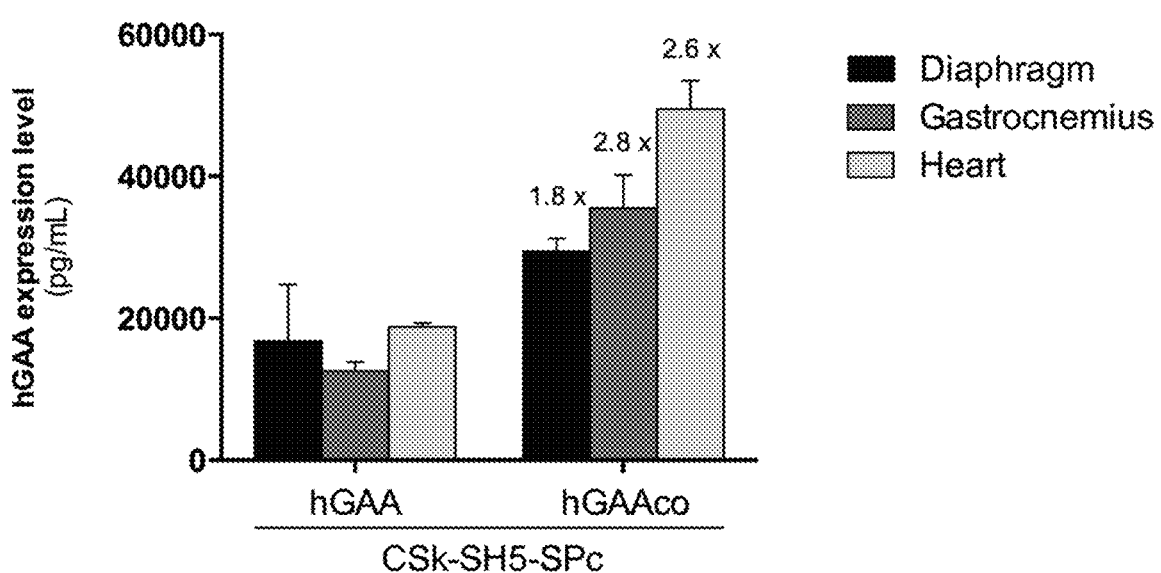

Using quantitative RT-PCR, the expression of the hGAA and hGAAco genes in diaphragm, gastrocnemius, and heart of CB.17-SCID mice injected with the SPc-hGAAco, CSk-SH5-SPc-hGAAco and CSk-SH5-SPc-hGAA constructs was assessed. The results show that CSk-SH5 can increase the hGAAco mRNA expression 16.9, 9.8, and 14.2 times respectively in diaphragm, gastrocnemius, and heart of CB.17-SCID mice (FIG. 6a) Furthermore, FIG. 6B shows that codon-optimized hGAA sequence itself improves the translation efficiency resulting in >2 folds higher hGAA protein expression in diaphragm, gastrocnemius, and heart of CB.17-SCID mice, compared to wild type hGAA.

hMTM1(co) Expression

Figure 7A:
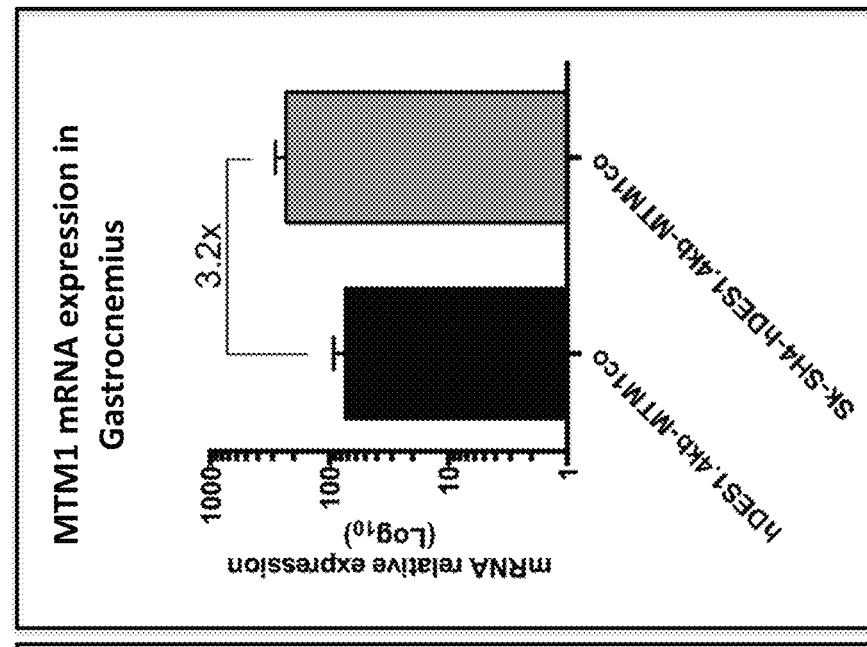
FIGS. 7A and 7B.
Figure 7A:
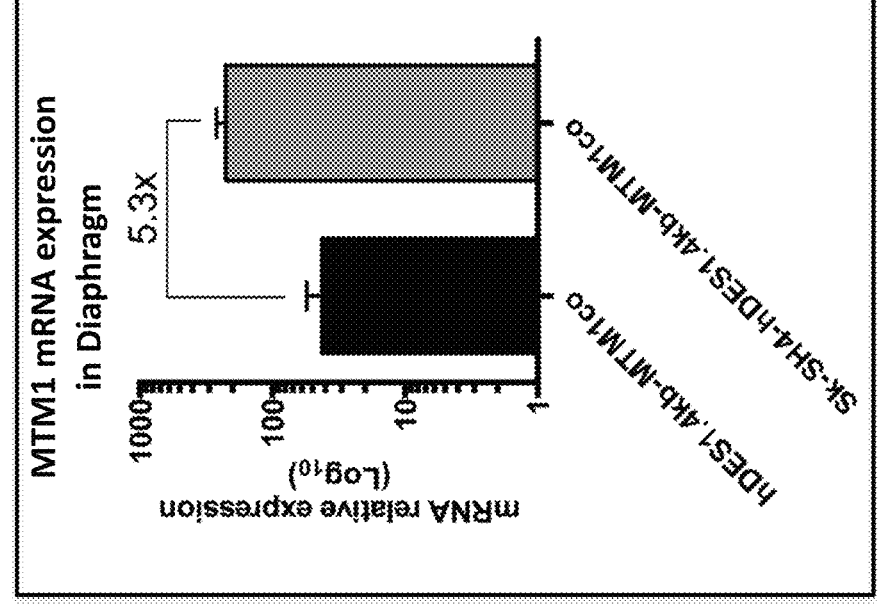
Figure 7B:
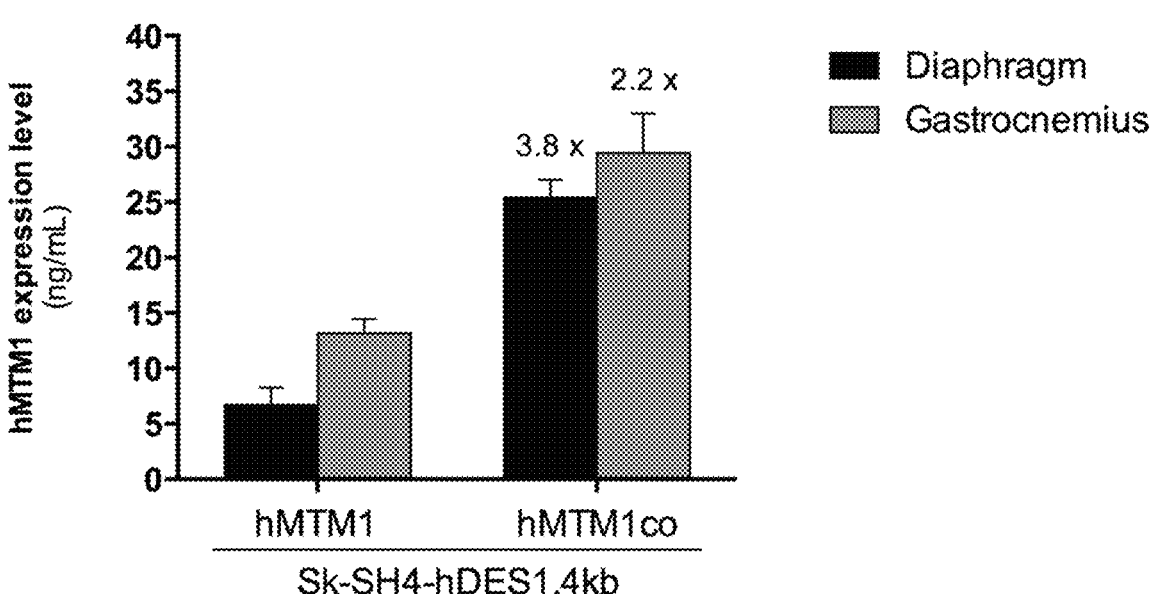

Using quantitative RT-PCR and ELISA, the expression of the hMTM1 and hMTM1co genes in diaphragm and gastrocnemius of CB.17-SCID mice injected with the hDES1.4kb-hMTM1co, Sk-SH4-hDES1.4kb-hMTM1co and Sk-SH4-hDES1.4kb-hMTM1 construct was assessed. The results show that Sk-SH4 can increase the hMTM1co mRNA expression 5.3 and 3.2 times respectively in diaphragm and gastrocnemius of CB.17-SCID mice (FIG. 7A). Furthermore, FIG. 7B shows that codon-optimized hMTM1 sequence alone can improve the translation efficiency resulting in 2-4 fold higher hMTM1 protein expression in diaphragm and gastrocnemius of CB.17-SCID mice, compared to wild type hMTM1.

Example 5: Prototype AAV Vectors for MTM and GSD-II for Potential Clinical Trial for MTM and GSD II Related Diseases The prototype AAV vector for MTM (FIG. 9 A)) was designed to maximize transcription and translation of MTM1. Transcription was enhanced by coupling the diaphragm-CRE (Dia-CRE) to the previously identified skeletal muscle CRE (Sk-SH4). These elements were cloned upstream of a 1.4 kb human desmin promoter to drive expression of a human bias codon-usage optimized human MTM1 gene (hMTM1co), in combination with the minute virus of mouse (MVM) intron and a synthetic polyadenylation site (Synth poly A).

The prototype AAV vector for GSD-II (FIG. 9 B)) was designed to maximize transcription and translation of GAA. Transcription was enhanced by coupling the diaphragm-CRE (Dia-CRE) to the previously identified cardiac/skeletal muscle CRE (CSk-SH5). These elements were cloned upstream of a synthetic SPc5-12-GTRM promoter to drive expression of a human bias codon-usage optimized human GAA gene (hGAAco), in combination with the minute virus of mouse (MVM) intron and the human acid α-glucosidase gene (hGAAco) and a synthetic polyadenylation site (Synth poly A).

The following 10 different AAV constructs have been evaluated for expressing therapeutic genes in vivo in mouse and the best performing ones will be the subject of a pre-clinical or phase I clinical trial:
1) pAAVss-hDes1.4kb-MVM-hMTM1-SynthpA (no diaphragm CRE, no muscle CRE Sk-SH4, only Desmin1.4kb promoter driving the MTM1 gene expression+MTM1) (SEQ ID NO; 135)
2) pAAVss-hDes1.4kb-MVM-hMTM1co-SynthpA (no diaphragm CRE, no muscle CRE Sk-SH4, +Des1.4kb+codon opt MTM1) (SEQ ID NO; 134)
3) pAAVss-Sk-SH4-hDes1.4kb-MVM-hMTM1-SynthpA (no diaphragm CRE, +muscle CRE Sk-SH4+Des1.4kb+MTM1) (SEQ ID NO; 137)
4) pAAVss-Sk-SH4-hDes1.4kb-MVM-hMTM1co-SynthpA (no diaphragm CRE, +muscle CRE Sk-SH4+Des1.4kb+codon opt MTM1) (SEQ ID NO; 136)
5) pAAVss-CRE64-Sk-SH4-hDes1.4kb-MVM-hMTM1co-SynthpA (contain best selected Diaphragm CRE64 combined with muscle CRE Sk-SH4) (SEQ ID NO; 131)
6) pAAVss-SPc5-12GTRM-MVM-hGAA-SynthpA (no diaphragm CRE, no muscle CRE, only SPc5-12-GTRM promoter driving the GAA gene expression)) (SEQ ID NO; 139)
7) pAAVss-SPc5-12GTRM-MVM-hGAAco-SynthpA (no diaphragm, no muscle CRE CSk-SH5, +SPc5-12-GTRM+codon opt GAA) (SEQ ID NO; 138)

8) pAAVss-CSk-SH5-SPc5-12GTRM-MVM-hGAA-SynthpA (no diaphragm CRE, +muscle CRE CSk-SH5+SPc5-12-GTRM+GAA) (SEQ ID NO; 133)
9) pAAVss-CSk-SH5-SPc-5-12GTRM-MVM-hGAAco-SynthpA ((no diaphragm CRE, +muscle CRE CSk-SH5+SPc5-12-GTRM+codon opt GAA) (SEQ ID NO; 132)
10) pAAVss-CRE04-CSK-SH5-SPc-5-12GTRM-MVM-hGAAco-SynthpA ((contain best selected Diaphragm CRE04 combined with muscle CRE CSk-SH5) (SEQ ID NO; 130)

Since Myotubular myopathy (MTM) patients do not have heart problems, it is not intended to target the heart for treating this disease. For this, the Sk-SH4 CRE with human Desmin 1,4kb promoter cassette was used in combination with Dia-CRE64 to express the MTM1 gene or codon optimised MTM1co in diaphragm and skeletal muscle tissue.

Since Pompe patients also suffer from heart problems, it is important to also target the heart. For this the CSk-SH5 CRE in combination with Dia-CRE04 is used with the synthetic SPc5-12 promoter cassette to express the therapeutic GAA gene or codon optimised GAAco gene because this combination leads to very robust expression in diaphragm, skeletal muscles and heart tissue.

Example 6: In Vivo Validation of Prototype AAV Vectors pAAVss-CRE04-CSk-SH5-SPc-5-12GTRM-MVM-hGAAco-SynthpA and pAAVss-CRE64-Sk-SH4-hDes1.4kb-MVM-hMTM1co-SynthpA AAV backbones comprising the diaphragm-specific regulatory element CRE04 (defined by SEQ ID NO:4) or CRE64 (defined by SEQ ID NO:64) combined respectively with a muscle-specific Sk-SH4 (SEQ ID NO:121) or a cardiac/muscle-specific CSk-SH5 (SEQ ID NO:122) regulatory element were injected into CB17-SCID pups at dose of $5 \times 10^{10}$ vg/mouse. At 8-week post-injection time point, the organs were removed for total RNA extraction using AllPrep DNA/RNA mini kit (Qaigen) according to manufacturer's instruction. The RNAs were reversed-transcribed using Superscript VI cDNA synthesis kit (ThermoFisher). Afterwards, cDNA from each organ was subjected to perform qRT-PCR using hGAA, hGAAco, hMTM1 or hMTM1co therapeutic gene-specific primers. The mGapdh gene was used as internal control to normalize resulting in relative expression ($2^{\Delta\Delta Ct}$).

Figure 10:
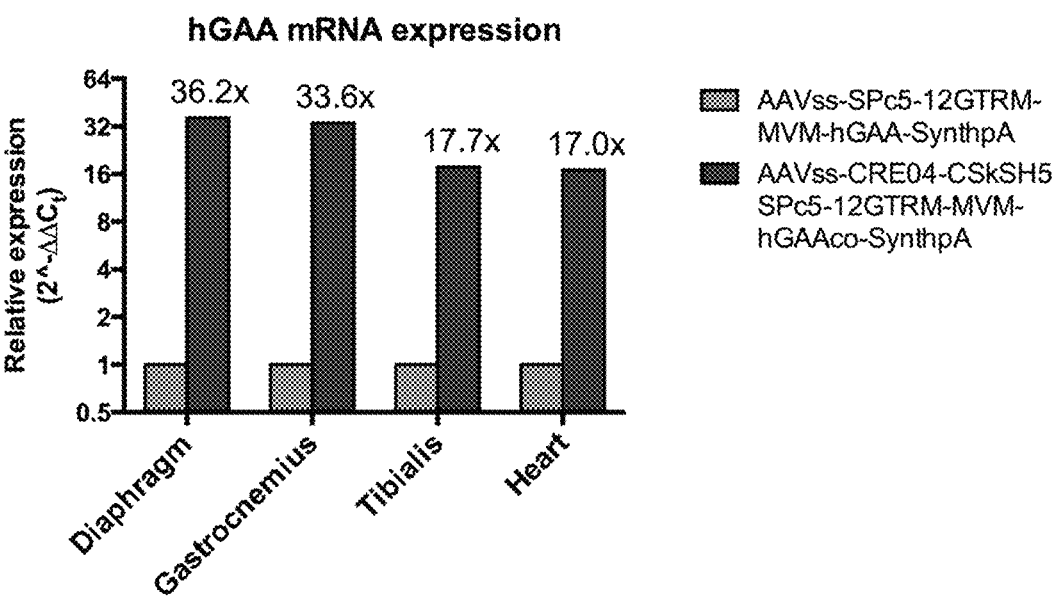
FIG. 10: Increase of GAA therapeutic gene transcription using diaphragm-specific cis-regulatory element (Dph-CRE) CRE04 (SEQ ID NO: 4) in combination with CSk-SH5 (SEQ ID NO: 122). The fold-difference indicated on the top of each bar is calculated from relative expression

AAV containing a combination of diaphragm-specific CRE04 and skeletal muscle and heart specific CSk-SH5 (AAVss-CRE04-CskSH5-SPc5-12GTRM-MVM-hGAAco-SynthpA (SEQ ID NO:130)) increased the expression of hGAAco in the diaphragm, gastrocnemius, tibialis and heart at least 17-fold compared to control (FIG. 10).

AAV containing a combination of diaphragm-specific CRE64 and Sk-SH4 (called Sk-CRM4 in the figure—AAVss-CRE64-Sk-SH4-hDes1.4kb-MVM-hMTM1co-SynthpA (SEQ ID NO:131)) increased the expression of hMTM1co in the diaphragm, gastrocnemius, tibialis and heart at least 2.6-fold compared to control (FIG. 11).

The invention claimed is:

1. A method for enhancing gene expression in diaphragm, skeletal muscle and heart tissue, comprising administering to a subject in need thereof, a nucleic acid regulatory element having a maximal length of 1000 nucleotides and comprising the sequence defined by SEQ ID NO: 2, a complement of the sequence, or a sequence hybridizing under stringent conditions to the nucleic acid regulatory element.

2. A nucleic acid expression cassette comprising at least one nucleic acid regulatory element having a maximal length of 1000 nucleotides, and comprising an isolated fragment of a naturally occurring alpha-actin-1 (ACTA-1) promoter sequence wherein said fragment is defined by the sequence SEQ ID NO: 2, a complement of the sequence, or a sequence hybridizing under stringent conditions to the nucleic acid regulatory element, operably linked to a promoter other than an ACTA-1 promoter, wherein the promoter is at least one of a diaphragm-specific promoter, a heart-specific promoter and a skeletal muscle-specific promoter.

3. The nucleic acid expression cassette according to claim 2, wherein the nucleic acid regulatory element is operably linked to the promoter and a transgene.

4. The nucleic acid expression cassette according to claim 2, wherein the promoter is selected from the group consisting of: an SPC5-12 promoter, an MYL2 promoter, an MB promoter, a DES promoter, a TNNC1 promoter, a TCAP promoter, an MYH7 promoter, an ALDA promoter, and a TPM1 promoter.

5. The nucleic acid expression cassette according to claim 3, wherein the transgene encodes a therapeutic protein or an immunogenic protein.

6. The nucleic acid expression cassette according to claim 3, wherein the transgene encodes a secretable protein or a structural protein selected from the group consisting of acid glucosidase (GAA), myotubularin (MTM1), follistatin, dystrophin, sarcoglycan, and dysferlin.

7. The nucleic acid expression cassette according to claim 3, wherein the transgene encodes acid glucosidase (GAA) as defined by SEQ ID NO: 93 or a codon-optimised human acid glucosidase gene (hGAAco) as defined by SEQ ID NO: 94.

8. The nucleic acid expression cassette according to claim 2, further comprising a Minute Virus of Mouse (MVM) intron.

9. The nucleic acid expression cassette according to claim 2, further comprising a polyadenylation signal selected from the group consisting of a synthetic polyadenylation signal (SEQ ID NO: 127) and a Simian Virus 40 (SV40) polyadenylation signal.

10. A vector comprising the nucleic acid expression cassette according to claim 2.

11. The vector according to claim 10, which is a viral vector.

12. The vector according to claim 10, which is a non-viral vector selected from the group consisting of a plasmid, a minicircle, an episomal vector, and a transposon-based vector.

13. The vector according to claim 10, further comprising a CRE CSk-SH1 regulatory element as defined in SEQ ID NO: 123, a CRE CSk-SH5 regulatory element as defined in SEQ ID NO: 122, or a CRE Sk-SH4 regulatory element as defined in SEQ ID NO: 121, positioned before or after the nucleic acid regulatory element.

14. The vector according to claim 10, comprising in addition to said nucleic acid expression cassette (a) a CRE CSk-SH1 regulatory element as defined in SEQ ID NO: 123, a CRE-CSk-SH5 regulatory element as defined in SEQ ID NO: 122, or a CRE Sk-SH4 regulatory element as defined in SEQ ID NO: 121, (b) an MVM intron, (c) an SPc5-12 promoter, (d) a human GAA transgene (SEQ ID NO: 93) or a codon-optimised variant thereof (SEQ ID NO: 94), and (e) a synthetic poly A site (SEQ ID NO: 127).

15. A pharmaceutical composition comprising the vector according to claim 10, and a pharmaceutically acceptable carrier.

16. A method of treating a disease affecting a diaphragm comprising administering a therapeutically effective amount of the pharmaceutical composition according to claim 15 to a subject in need thereof, wherein the vector comprises (a) a CRE-CSk-SH1 regulatory element (SEQ ID NO: 123), a CRE-CSk-SH5 regulatory element (SEQ ID NO: 122), or a CRE Sk-SH4 regulatory element (SEQ ID NO: 121), (b) a nucleic acid regulatory element having a maximal length of 1000 nucleotides and comprising the sequence defined by SEQ ID NO: 2, a complement of the sequence, or a sequence hybridizing under stringent conditions to the nucleic acid regulatory element, (c) an SPC5-12 promoter, and (d) a human transgene that effects a function of the diaphragm when being defective or a codon-optimized variant thereof.

17. A method of treating Pompe disease comprising administering a therapeutically effective amount of the pharmaceutical composition according to claim 15 to a subject in need thereof, wherein the vector comprises (a) a CRE-CSk-SHI regulatory element (SEQ ID NO: 123) or a CRE-CSk-SH5 regulatory element (SEQ ID NO: 122), (b) a nucleic acid regulatory element having a maximal length of 1000 nucleotides and comprising the sequence defined by SEQ ID NO: 2, a complement of the sequence, or a sequence hybridizing under stringent conditions to the nucleic acid regulatory element, (c) an SPC5-12 promoter, and (d) a human GAA transgene (SEQ ID NO: 93) or a codon-optimised variant thereof (SEQ ID NO: 94).

18. A vaccine comprising the pharmaceutical composition according to claim 15, and at least one adjuvant, wherein the nucleic acid regulatory element of the nucleic acid expression cassette operably linked to the promoter is further operably linked to an immunogenic transgene.

19. A method for expressing a transgene product in diaphragm, skeletal muscle, and heart cells, comprising:

introducing the vector according to claim 10, wherein the nucleic acid regulatory element is operably linked to the promoter and a transgene, into said cells; and expressing the transgene product in the cells.

\* \* \* \* \*